United States Patent
Doudna et al.

(10) Patent No.: US 10,570,415 B2
(45) Date of Patent: Feb. 25, 2020

(54) RNA-GUIDED NUCLEIC ACID MODIFYING ENZYMES AND METHODS OF USE THEREOF

(71) Applicant: The Regents of the University of California, Oakland, CA (US)

(72) Inventors: Jennifer A. Doudna, Berkeley, CA (US); Jillian Banfield, Berkeley, CA (US); David Burstein, Berkeley, CA (US); Lucas Benjamin Harrington, Berkeley, CA (US); Steven C. Strutt, Berkeley, CA (US)

(73) Assignee: The Regents of the University of California, Oakland, CA (US)

( * ) Notice: Subject to any disclaimer, the term of this patent is extended or adjusted under 35 U.S.C. 154(b) by 0 days.

(21) Appl. No.: 16/054,513

(22) Filed: Aug. 3, 2018

(65) Prior Publication Data

US 2018/0346927 A1 Dec. 6, 2018

Related U.S. Application Data

(63) Continuation of application No. PCT/US2017/054081, filed on Sep. 28, 2017.

(60) Provisional application No. 62/402,846, filed on Sep. 30, 2016.

(51) Int. Cl.
| | |
|---|---|
| C12N 15/85 | (2006.01) |
| C12N 9/22 | (2006.01) |
| C12N 15/113 | (2010.01) |
| C07K 19/00 | (2006.01) |
| C12N 15/52 | (2006.01) |
| C12N 15/62 | (2006.01) |
| C12N 15/88 | (2006.01) |
| C12N 9/10 | (2006.01) |
| C12N 15/74 | (2006.01) |

(52) U.S. Cl.
CPC .......... *C12N 15/8509* (2013.01); *C07K 19/00* (2013.01); *C12N 9/1007* (2013.01); *C12N 9/1025* (2013.01); *C12N 9/22* (2013.01); *C12N 15/113* (2013.01); *C12N 15/52* (2013.01); *C12N 15/62* (2013.01); *C12N 15/74* (2013.01); *C12N 15/85* (2013.01); *C12N 15/88* (2013.01); *C07K 2319/02* (2013.01); *C07K 2319/03* (2013.01); *C07K 2319/06* (2013.01); *C12N 2310/20* (2017.05); *C12N 2740/13043* (2013.01); *C12N 2740/16043* (2013.01); *C12N 2750/14143* (2013.01)

(58) Field of Classification Search
None
See application file for complete search history.

(56) References Cited

U.S. PATENT DOCUMENTS

| | | | |
|---|---|---|---|
| 9,730,967 B2 | 6/2017 | Kovarik et al. | |
| 2014/0068797 A1 | 3/2014 | Doudna et al. | |
| 2014/0273226 A1 | 9/2014 | Wu | |
| 2016/0208243 A1* | 7/2016 | Zhang | C12N 15/113 |
| 2017/0198277 A1 | 7/2017 | Kmiec et al. | |
| 2017/0233756 A1 | 8/2017 | Begemann et al. | |

FOREIGN PATENT DOCUMENTS

| | | |
|---|---|---|
| WO | WO 2015/071474 | 5/2015 |
| WO | WO 2016/123243 | 8/2016 |

OTHER PUBLICATIONS

Bautista et al. (2015) Virus-Induced Dormancy in the Archaeon Sulfolobus islandicus. mBio, 6(2):e02565-14 (Year: 2015).*
Koonin et al. (2017) Diversity, classification and evolution of CRISPR-Cas systems. Current Opinion in Microbiology, 37:37-78 (Year : 2017).*
Anantharaman et al. (2016) Thousands of microbial genomes shed light on interconnected biogeochemical processes in an aquifer system. Nature Communications, 7:13219, pp. 1-11 (Year: 2016).*
OHA03494.1 (hypothetical protein A3J58_03210 [Candidatus Sungbacteria bacterium RIFCSPHIGH02_02_FULL_52_23], NCBI Reference Sequence, priority to Oct. 21, 2016, 2 pages) (Year: 2016).*
Liu et al. (2019) CasX enzymes comprise a distinct family of RNA-guided genome editors. Nature, 566:218-223, and extended data (Year: 2019).*
Baker, et al.; "Enigmatic, ultrasmall, uncultivated Archaea"; PNAS; vol. 107, No. 19, pp. 8806-8811 (May 11, 2010).
Bautista, et al.; "Virus-Induced Dormancy in the Archaeon *Sulfolobus islandicus*"; mBio; vol. 6, No. 2, 8 pages (2015).

(Continued)

*Primary Examiner* — Neil P Hammell
(74) *Attorney, Agent, or Firm* — Bozicevic Field & Francis, LLP; Paula A. Borden

(57) ABSTRACT

The present disclosure provides CasX proteins, nucleic acids encoding the CasX proteins, and modified host cells comprising the CasX proteins and/or nucleic acids encoding same. CasX proteins are useful in a variety of applications, which are provided. The present disclosure provides CasX guide RNAs that bind to and provide sequence specificity to the CasX proteins, nucleic acids encoding the CasX guide RNAs, and modified host cells comprising the CasX guide RNAs and/or nucleic acids encoding same. CasX guide RNAs are useful in a variety of applications, which are provided. The present disclosure provides archaeal Cas9 polypeptides and nucleic acids encoding same, as well as their associated archaeal Cas9 guide RNAs and nucleic acids encoding same.

30 Claims, 58 Drawing Sheets

Specification includes a Sequence Listing.

(56) References Cited

OTHER PUBLICATIONS

Burstein, et al.; "New CRISPR-Cas systems from uncultivated microbes"; Nature; vol. 542, No. 7640, pp. 237-241 (Feb. 9, 2017).
Liu, et al.; "CasX enzymes comprise a distinct family of RNA-guided genome editors"; Nature; vol. 566, pp. 23 pages (Feb. 14, 2019).
Co-pending U.S. Appl. No. 16/335,516, filed Mar. 21, 2019.
Co-pending U.S. Appl. No. 16/422,824, filed May 24, 2019.
Choudhury, et al.; "CRISPR-dCas9 mediated TET1 targeting for selective DNA demethylation at BRCA1 promoter"; Oncotarget; vol. 7, No. 29, pp. 46545-46556 (2016).
Fonfara, et al.; "Phylogeny of Cas9 determines functional exchangeability of dual-RNA and Cas9 among orthologous type II CRISPR-Cas systems"; Nucleic Acids Research; vol. 42, No. 4, pp. 2577-2590 (2014).
Le Cong, et al.; "Multiplex Genome Engineering Using CRISPR/Cas Systems"; Science; vol. 339, pp. 819-823 (Feb. 15, 2013).
Extended European Search Report for European Patent Application No. 17857442.2 dated Jan. 1, 2020.

\* cited by examiner

FIG. 1A

```
>CasX1
MEKRINKIRKKLSADNATKPVSRSGPMKTLLVRVMTDDLKKRLEKRRKKPEVMPQVISNNAANN
LRMLLDDYTKMKEAILQVYWQEFKDDHVGLMCKFAQPASKKIDQNKLKPEMDEKGNLTTAGFAC
SQCGQPLFVYKLEQVSEKGKAYTNYFGRCNVAEHEKLILLAQLKPEKDSDEAVTYSLGKFGQRA
LDFYSIHVTKESTHPVKPLAQIAGNRYASGPVGKALSDACMGTIASFLSKYQDIIIEHQKVVKG
NQKRLESLRELAGKENLEYPSVTLPPQPHTKEGVDAYNEVIARVRMWVNLNLWQKLKLSRDDAK
PLLRLKGFPSFPVVERRENEVDWWNTINEVKKLIDAKRDMGRVFWSGVTAEKRNTILEGYNYLP
NENDHKKREGSLENPKKPAKRQFGDLLLYLEKKYAGDWGKVFDEAWERIDKKIAGLTSHIEREE
ARNAEDAQSKAVLTDWLRAKASFVLERLKEMDEKEFYACEIQLQKWYGDLRGNPFAVEAENRVV
DISGFSIGSDGHSIQYRNLLAWKYLENGKREFYLLMNYGKKGRIRFTDGTDIKKSGKWQGLLYG
GGKAKVIDLTFDPDDEQLIILPLAFGTRQGREFIWNDLLSLETGLIKLANGRVIEKTIYNKKIG
RDEPALFVALTFERREVVDPSNIKPVNLIGVDRGENIPAVIALTDPEGCPLPEFKDSSGGPTDI
LRIGEGYKEKQRAIQAAKEVEQRRAGGYSRKFASKSRNLADDMVRNSARDLFYHAVTHDAVLVF
ENLSRGFGRQGKRTFMTERQYTKMEDWLTAKLAYEGLTSKTYLSKTLAQYTSKTCSNCGFTITT
ADYDGMLVRLKKTSDGWATTLNNKELKAEGQITYYNRYKRQTVEKELSAELDRLSEESGNNDIS
KWTKGRRDEALFLLKKRFSHRPVQEQFVCLDCGHEVHADEQAALNIARSWLFLNSNSTEFKSYK
SGKQPFVGAWQAFYKRRLKEVWKPNA    (SEQ ID NO: 1)

>CasX2
MQEIKRINKIRRRLVKDSNTKKAGKTGPMKTLLVRVMTPDLRERLENLRKKPENIPQPISNTSR
ANLNKLLTDYTEMKKAILHVYWEEFQKDPVGLMSRVAQPAPKNIDQRKLIPVKDGNERLTSSGF
ACSQCCQPLYVYKLEQVNDKGKPHTNYFGRCNVSEHERLILLSPHKPEANDELVTYSLGKFGQR
ALDFYSIHVTRESNHPVKPLEQIGGNSCASGPVGKALSDACMGAVASFLTKYQDIILEHQKVIK
KNEKRLANLKDIASANGLAFPKITLPPQPHTKEGIEAYNNVVAQIVIWVNLNLWQKLKIGRDEA
KPLQRLKGFPSFPLVERQANEVDWWDMVCNVKKLINEKKEDGKVFWQNLAGYKRQEALLPYLSS
EEDRKKGKKFARYQFGDLLLHLEKKHGEDWGKVYDEAWERIDKKVEGLSKHIKLEEERRSEDAQ
SKAALTDWLRAKASFVIEGLKEADKDEFCRCELKLQKWYGDLRGKPFAIEAENSILDISGFSKQ
YNCAFIWQKDGVKKLNLYLIINYFKGGKLRFKKIKPEAFEANRFYTVINKKSGEIVPMEVNFNF
DDPNLIILPLAFGKRQGREFIWNDLLSLETGSLKLANGRVIEKTLYNRRTRQDEPALFVALTFE
RREVLDSSNIKPMNLIGIDRGENIPAVIALTDPEGCPLSRFKDSLGNPTHILRIGESYKEKQRT
IQAAKEVEQRRAGGYSRKYASKAKNLADDMVRNTARDLLYYAVTQDAMLIFENLSRGFGRQGKR
TFMAERQYTRMEDWLTAKLAYEGLPSKTYLSKTLAQYTSKTCSNCGFTITSADYDRVLEKLKKT
ATGWMTTINGKELKVEGQITYYNRYKRQNVVKDLSVELDRLSEESVNNDISSWTKGRSGEALSL
LKKRFSHRPVQEKFVCLNCGFETHADEQAALNIARSWLFLRSQEYKKYQTNKTTGNTDKRAFVE
TWQSFYRKKLKEVWKPAV    (SEQ ID NO: 2)
```

FIG. 1B

```
>CasX3
MDNANKPSTKSLVNTTRISDHFGVTPGQVTRVFSFGIIPTKRQYAIIERWFAAVEAARERLYGM
LYAHFQENPPAYLKEKFSYETFFKGRPVLNGLRDIDPTIMTSAVFTALRHKAEGAMAAFHTNHR
RLFEEARKKMREYAECLKANEALLRGAADIDWDKIVNALRTRLNTCLAPEYDAVIADFGALCAF
RALIAETNALKGAYNHALNQMLPALVKVDEPEEAEESPRLRFFNGRINDLPKFPVAERETPPDT
ETIIRQLEDMARVIPDTAEILGYIHRIRHKAARRKPGSAVPLPQRVALYCAIRMERNPEEDPST
VAGHFLGEIDRVCEKRRQGLVRTPFDSQIRARYMDIISFRATLAHPDRWTEIQFLRSNAASRRV
RAETISAPFEGFSWTSNRTNPAPQYGMALAKDANAPADAPELCICLSPSSAAFSVREKGGDLIY
MRPTGGRRGKDNPGKEITWVPGSFDEYPASGVALKLRLYFGRSQARRMLTNKTWGLLSDNPRVF
AANAELVGKKRNPQDRWKLFFHMVISGPPPVEYLDFSSDVRSRARTVIGINRGEVNPLAYAVVS
VEDGQVLEEGLLGKKEYIDQLIETRRRISEYQSREQTPPRDLRQRVRHLQDTVLGSARAKIHSL
IAFWKGILAIERLDDQFHGREQKIIPKKTYLANKTGFMNALSFSGAVRVDKKGNPWGGMIEIYP
GGISRTCTQCGTVWLARRPKNPGHRDAMVVIPDIVDDAAATGFDNVDCDAGTVDYGELFTLSRE
WVRLTPRYSRVMRGTLGDLERAIRQGDDRKSRQMLELALEPQPQWGQFFCHRCGFNGQSDVLAA
TNLARRAISLIRRLPDTDTPPTP     (SEQ ID NO: 3)
```

FIG. 2

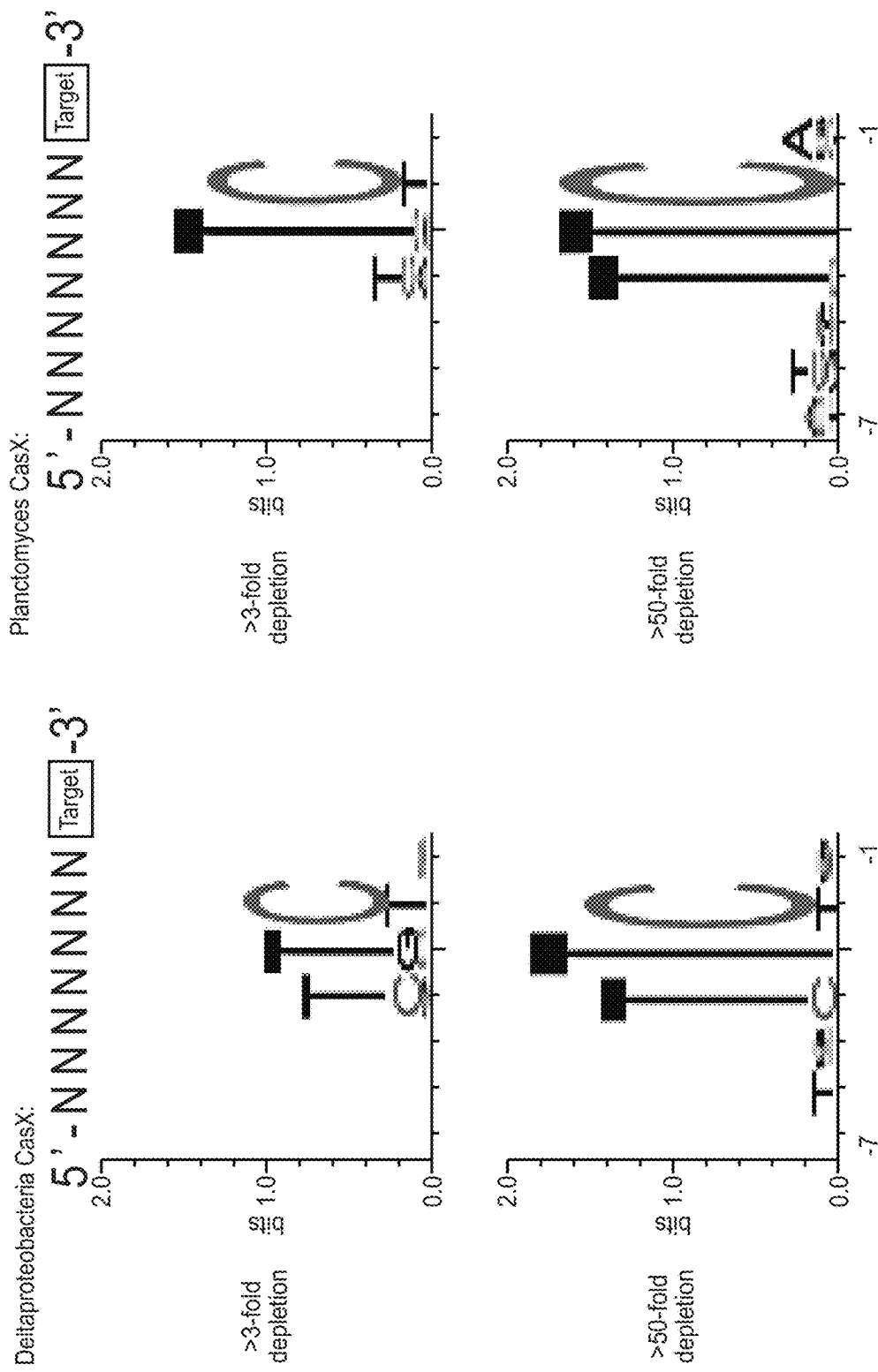

Single guide RNA

Dual guide RNA

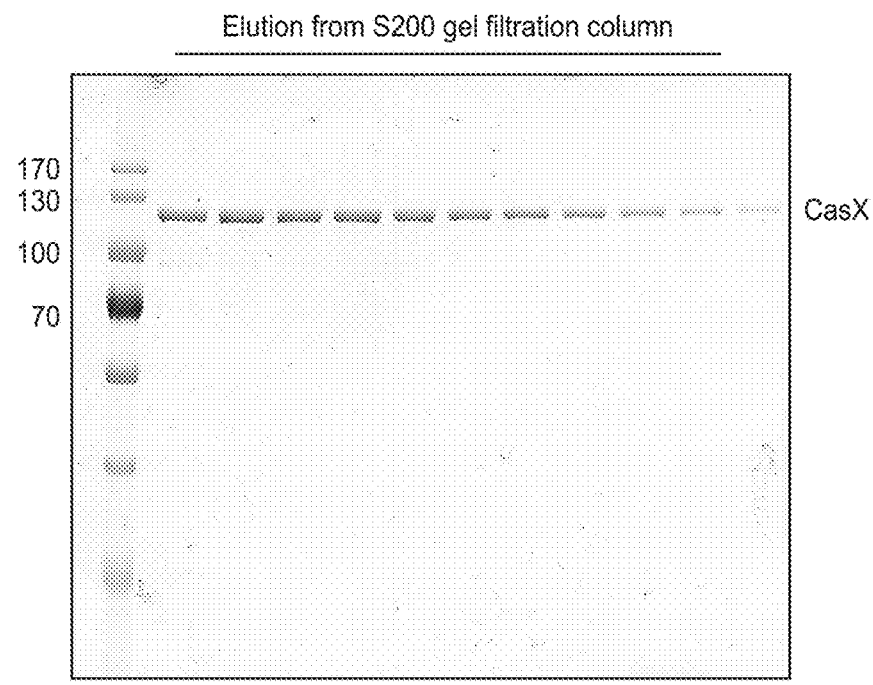
FIG. 9
FIG. 10
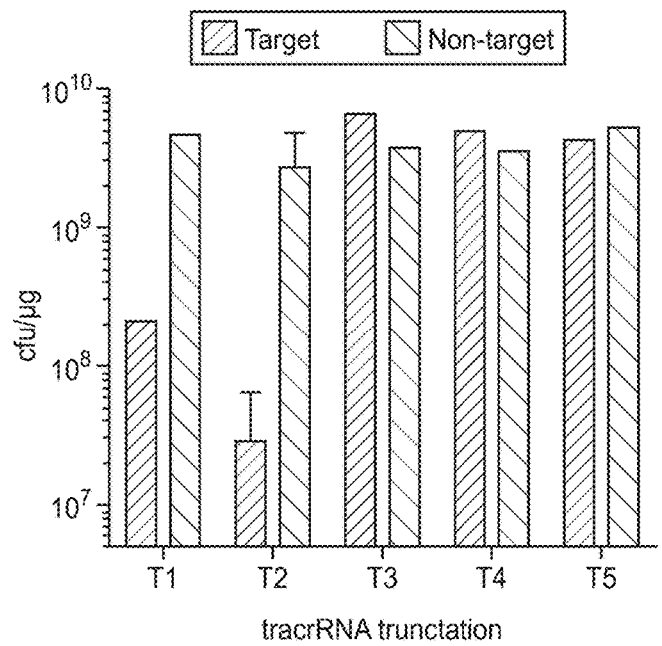
FIG. 11
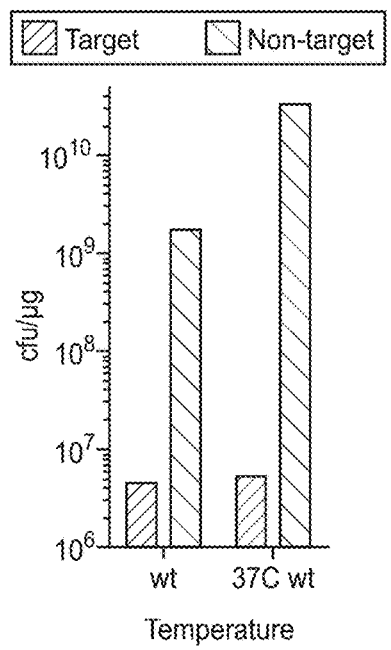

FIG. 13

>Archaeal Cas9_ARMAN-1
MRDSITAPRYSSALAARIKEFNSAFKLGIDLGTKTGGVALVKDNKVLLAK
TFLDYHKQTLEERRIHRRNRRSRLARRKRIARLRSWILRQKIYGKQLPDP
YKIKKMQLPNGVRKGENWIDLVVSGRDLSPEAFVRAITLIFQKRGQRYEE
VAKEIEEMSYKEFSTHIKALTSVTEEEFTALAAEIERRQDVVDTDKEAER
YTQLSELLSKVSESKSESKDRAQRKEDLGKVVNAFCSAHRIEDKDKWCKE
LMKLLDRPVRHARFLNKVLIRCNICDRATPKKSRPDVRELLYFDTVRNFL
KAGRVEQNPDVISYYKKIYMDAEVIRVKILNKEKLTDEDKKQKRKLASEL
NRYKNKEYVTDAQKKMQEQLKTLLFMKLTGRSRYCMAHLKERAAGKDVEE
GLHGVVQKRHDRNIAQRNHDLRVINLIESLLFDQNKSLSDAIRKNGLMYV
TIEAPEPKTKHAKKGAAVVRDPRKLKEKLFDDQNGVCIYTGLQLDKLEIS
KYEKDHIFPDSRDGPSIRDNLVLTTKEINSDKGDRTPWEWMHDNPEKWKA
FERRVAEFYKKGRINERKRELLLNKGTEYPGDNPTELARGGARVNNFITE
FNDRLKTHGVQELQTIFERNKPIVQVVRGEETQRLRRQWNALNQNFIPLK
DRAMSFNHAEDAAIAASMPPKFWREQIYRTAWHFGPSGNERPDFALAELA
PQWNDFFMTKGGPIIAVLGKTYSWKHSIIDDTIYKPFSKSAYYVGIYKK
PNAITSNAIKVLRPKLLNGEHTMSKNAKYYHQKIGNERFLMKSQKGGSII
TVKPHDGPEKVLQISPTYECAVLTKHDGKIIVKFKPIKPLRDMYARGVIK
AMDKELETSLSSMSKHAKYKELHTHDIIYLPATKKHVDGYFIITKLSAKH
GIKALPESMVKVKYTQIGSENNSEVKLTKPKPEITLDSEDITNIYNFTR >Archaeal Cas9_ARMAN-4
MLGSSRYLRYNLTSFEGKEPFLIMGYYKEYNKELSSKAQKEFNDQISEFN
SYYKLGIDLGDKTGIAIVKGNKIILAKTLIDLHSQKLDKRREARRNRRTR
LSRKKRLARLRSWVMRQKVGNQRLPDPYKIMHDNKYWSIYNKSNSANKKN
WIDLLIHSNSLSADDFVRGLTIIFRKRGYLAFKYLSRLSDKEFEKYIDNL
KPPISKYEYDEDLEELSSRVENGEIEEKKFEGLKNKLDKIDKESKDFQVK
QREEVKKELEDLVDLFAKSVDNKIDKARWKRELNNLLDKKVRKIRFDNRF
ILKCKIKGCNKNTPKKEKVRDFELKMVLNNARSDYQISDEDLNSFRNEVI
NIFQKKENLKKGELKGVTIEDLRKQLNKTFNKAKIKKGIREQIRSIVFEK
ISGRSKFCKEHLKEFSEKPAPSDRINYGVNSAREQHDFRVLNFIDKKIFK
DKLIDPSKLRYITIESPEPETEKLEKGQISEKSFETLKEKLAKETGGIDI
YTGEKLKKDFEIEHIFPRARMGPSIRENEVASNLETNKEKADRTPWEWFG
QDEKRWSEFEKRVNSLYSKKKISERKREILLNKSNEYPGLNPTELSRIPS
TLSDFVESIRKMFVKYGYEEPQTLQKGKPIIQVVRGRDTQALRWRWHAL
DSNIIPEKDRKSSFNHAEDAVIAACMPPYYLRQKIFREEAKIKRKVSNKE
KEVTRPDMPTKKIAPNWSEFMKTRNEPVIEVIGKVKPSWKNSIMDQTFYK
YLLKPFKDNLIKIPNVKNTYKWIGVNGQTDSLSLPSKVLSISNKKVDSST
VLLVHDKKGGKRNWVPKSIGGLLVYITPKDGPKRIVQVKPATQGLLIYRN
EDGRVDAVREFINPVIEMYNNGKLAFVEKENEEELLKYFNLLEKGQKFER
IRRYDMITYNSKFYYVTKINKNHRVTIQEESKIKAESDKVKSSSGKEYTR
KETEELSLQKLAELISI FIG. 15
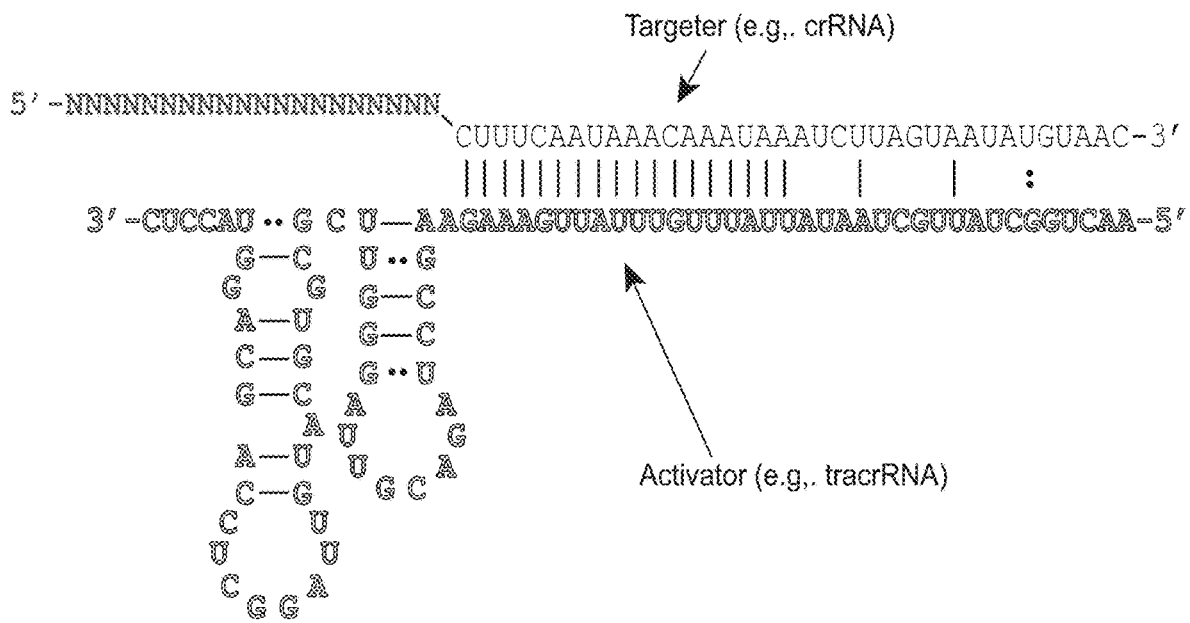
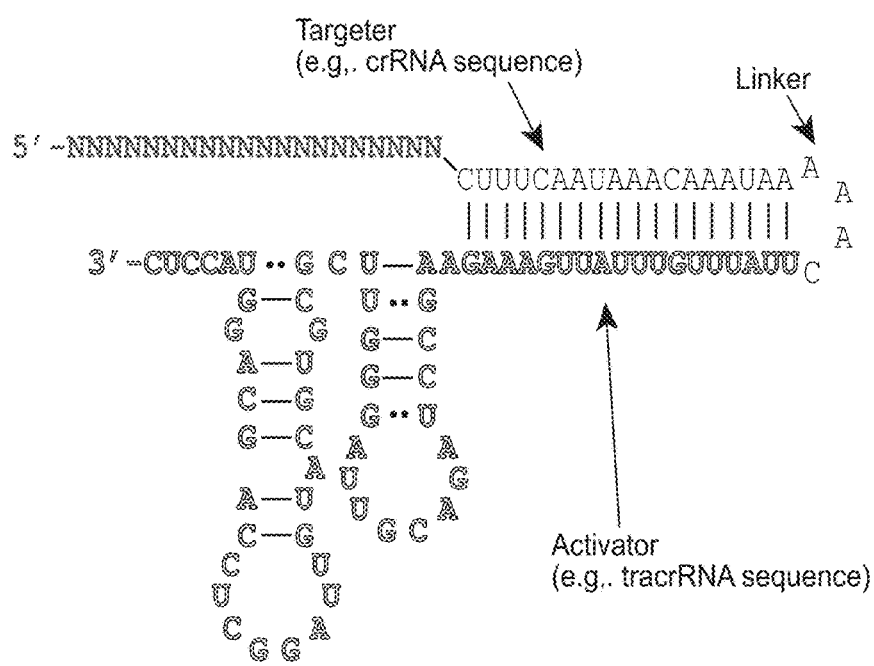

FIG. 16

```
>Lindowbacteria Cas9
VSATRKGQGSGAPISRTEAPQIALMATELEQRLNEFLDSLRLGIDFGEDYGGIALVQANRVLHAETFVDFHQAT
LKDRRRNRRGRRTRHARKMRLARLRSWILRQKLPGGQRLPDPYGVMHWPFKTKKGHTIKTGLASRQDGKRTIIQ
KCKIGTATPEEFVCSLTLLFQKRGFVWEGSDLCELSDQELAEELMTVRITEAVAAAIKEEIERRKKEPEDNKEG
EIENLETVLCDAVKRARSPRTPEHRSIVESDLKDIVDGWTRKNCPQMTDMWKKELSCLLNKHVRPARFENRIVA
GCSWCGKMVPRKSKVRELAYKVVVKNIRVEDFTSRQPLTAQEAEYFSQLWVDKEAKPPARTAIENKLKKLKASP
KMANQLYELLAPSEPKGHTNLCQQHLEMAARGAFMCNRHHAICENNNGDHQTIDSVKEGRKRAGPRNPCREDRD
RRMIRRLEQILFETPGKPGKPSHSIPRLITIEFPKPNTAQTAGCPHCKEKLSLDARVRWKMARPMKLEASNDST
PFFCPSCAAGIKITLYKKMRIKEKEIVQKYSPKDTDVLVRKTAAGGLKKLKYDMYLKETDGTCVYCGTSIGSGQ
IDHIFPQSRGGPNIDYNLISCCRTCNGNLKKNKSPWEWFGNIDQRWREFEDRVKKLPAPQRKKAILLSRESAYP
ENPTALARVGARTKEFIGRIKQMLLANGVKENEIADNYEKDKIVIQTIDGWMTSRLRGCWRTFPDGTANFPPKN
DADKRNHAQDAVLIAACPPHTWRERIFTWKPENPYFSVLQKIAPRWKDHQATMKILGRYFPRWHNQNSDIQFVH
QHKTQNGTSYTMRDTVESIDVGTDKKGGSIERIYSKSFRDFFSRTFKSLGIKMAMNEIPKLKSQWLNERRAAWM
KKNPATPVPNQRERAWEASFPRRLQFDMGYGEDVAEVNPKNGPSRFVRAQPVNDRIEVWTNDVRQAQIRTVKNR
ILFRHIQDNSPQGRTLERIFRRNDMIQLDAVQKRGRKGITGKSYEAGEYMVVKIEKGGKFTAVPAHRGKGRENQ
RQVSQREIAKLCGVSLSPKRRKPSRSTSESG (SEQ ID NO: 135)

>Deltaproteobacteria Cas9
VAAASLILQRGGLVALHPRLERKIKEFLPTYRLGVDLGEAAGGLALIHNNNILHAETFTDFHEATLETKRALRR
GRRTRHAKKMRLARLRSWILRQCIPAHVTGAEIKDSYSRLPDPYRLMKDKKYQTLPGFYEVKGQNPEKSPTWID
KAKAGEVDAEGFVIALTHILQKRGYKYDGKEFSDYDDSRLIDFIDSCAMLAEAPEMRKALEDEIMRREVGEKEK
PKLHEAFDNALNRQRERKKALPRQVREKDMEDMVDVFGRRWQLSQEIIANWKSQLTGLLNKVVREARYDNRLKS
GCSWCGKKTPRLAKPEIRELAFEAAVGNLRIRERDGRDRPISDEERNPLRGWFQRRRENHDYSRATKNTPIEER
APSEDNIRTYLEQIGVKKAWIRKKKGKEKWKFDFAMLPQLDNLINKEARKGRARLCVEHMRMQAEGKTMKDADV
DWQSMRKRNAPNPRREQHDARVLKRIERLIFNRGKKGTDAWRHGPIAVITLEVPMPVDLERAREKEQVERKPLN
LRQRLHAETEGVCIYCGENVHDRTMHLEHIVPQAKGGPDVQMNRIASCPKCNADRDTGKKDMLPSEWLTGDKWN
VFKSRVMSLNLPPLKKQLLLLEPGSKYPNDPTPLARVSARWRAFAADIMWLFDEYSVPVPTLNYEKDKPHIQVV
RGNLTSRLRRDWRWKDHEATVENFPDKRRTDLYNHAQDAAILAAIPPHTWQEQIFSDMAVRPCAKKDEQGNILK
NEKEMRPRPGIAALALAPEWADYERTQKELKRPMVHTLGKLKATWRRQIMDLSFYQNPTDNDGPLFIRKVDAKT
GKRETKEVQKGGLVVQVPHYDGTSGKRKVQIKPIQSNAIILWHDPSGRKDNLNISIERPAAIKKFVKHPVDPPI
ASDAIILGRIERASTLWLREGKGTVELKADKKSVRSSVVMPEGIYRVKELGSNGVIVVQENAVSKELANKLGIS
DDQFSKVPERALGKKELAEYFKGNQRSG (SEQ ID NO: 136)
```

```
         960         970         980         990        1,000       1,010       1,020
          |           |           |           |           |           |           |
---------------------VGIYKKPNAITSNAIKVLRP-----------------------------------------
                    746         756
-----------------------TGVNGGTDSLSLPS--KVLS------KLDNGEHTMSKNAKYYHQKIGNERFLMKSQK--
                                                765         770         780         795
--------------------------------------------------TSNKKVDSSTVLLVHDKGGKRNWVPKSI----
--------------------------------DTVESTDVGTDKKGGSIERIYSKSFRDFFSRTFKSLGIKMAMEIPKLKSQWLNERAAWMKKNPATPVPNQRER
                               820                829         832         839       843           851           861           867
 1,070       1,080       1,090       1,100       1,110       1,120       1,130       1,140
  |           |           |           |           |           |           |           |
T-YECAVLTKHD-QKII---------------VKFKPIKPLR---------MYARGVIKAMDKELETSLG---------SSMSKHA
A-TQGLIVRNEDQRVD-------------AVREFINPVL----------MYNNGKIAFVEKENEEILKYFLLEKGQ
IQSNAIIMHDPSGRKDNLNISIERPAATKKEMKHPV---------DPPIASDAIIGRIERASTIWIREGKGTVELKA
V-NDREMVTND-VRQA--------------QIRTVKNRILFRHIQD----------------------NSPQGRT
                               907         917         927         937         947         949
 1,180       1,190       1,200       1,210       1,220       1,230       1,240       1,247
  |           |           |           |           |           |           |           |
SAKHGIKALPESMVKVKYTQIGSENNSEVKLTKPKPEITLDSEDTNIYNF---------------------QR
NKNHRWTIQEESKIAESDKVKSSSGKEVT---RKETEELSLQKAELISI
GSNGVIVVQENAVSKRELANKLGISDD-IQFS-----KVPERALGKKEIAEYFKG------------NQRSG
EKGGKFTAVPAHRGK-------------GRENQRVS-----------------QREIAKLCGVSLSPKRRKPSRSTSESG
```

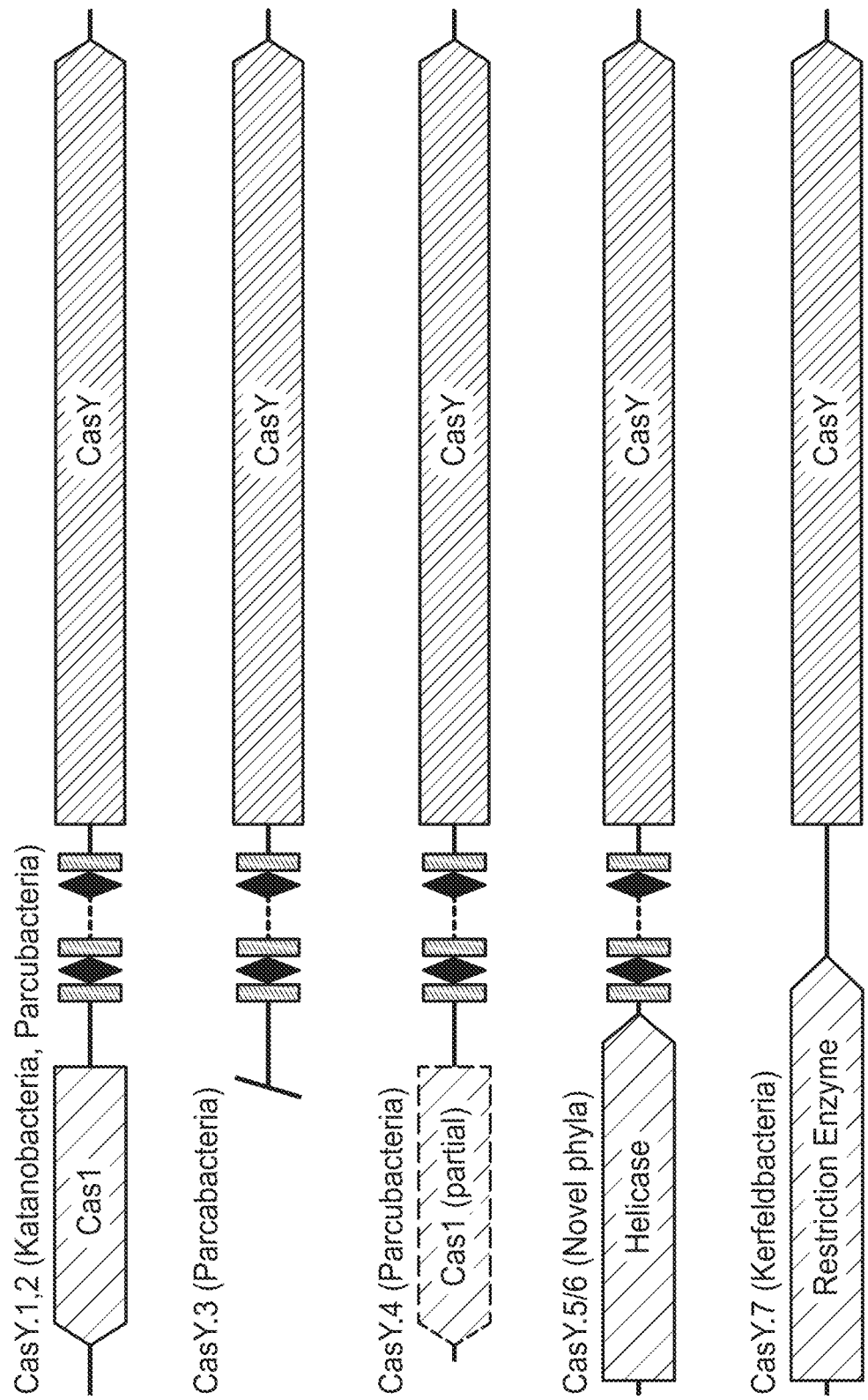

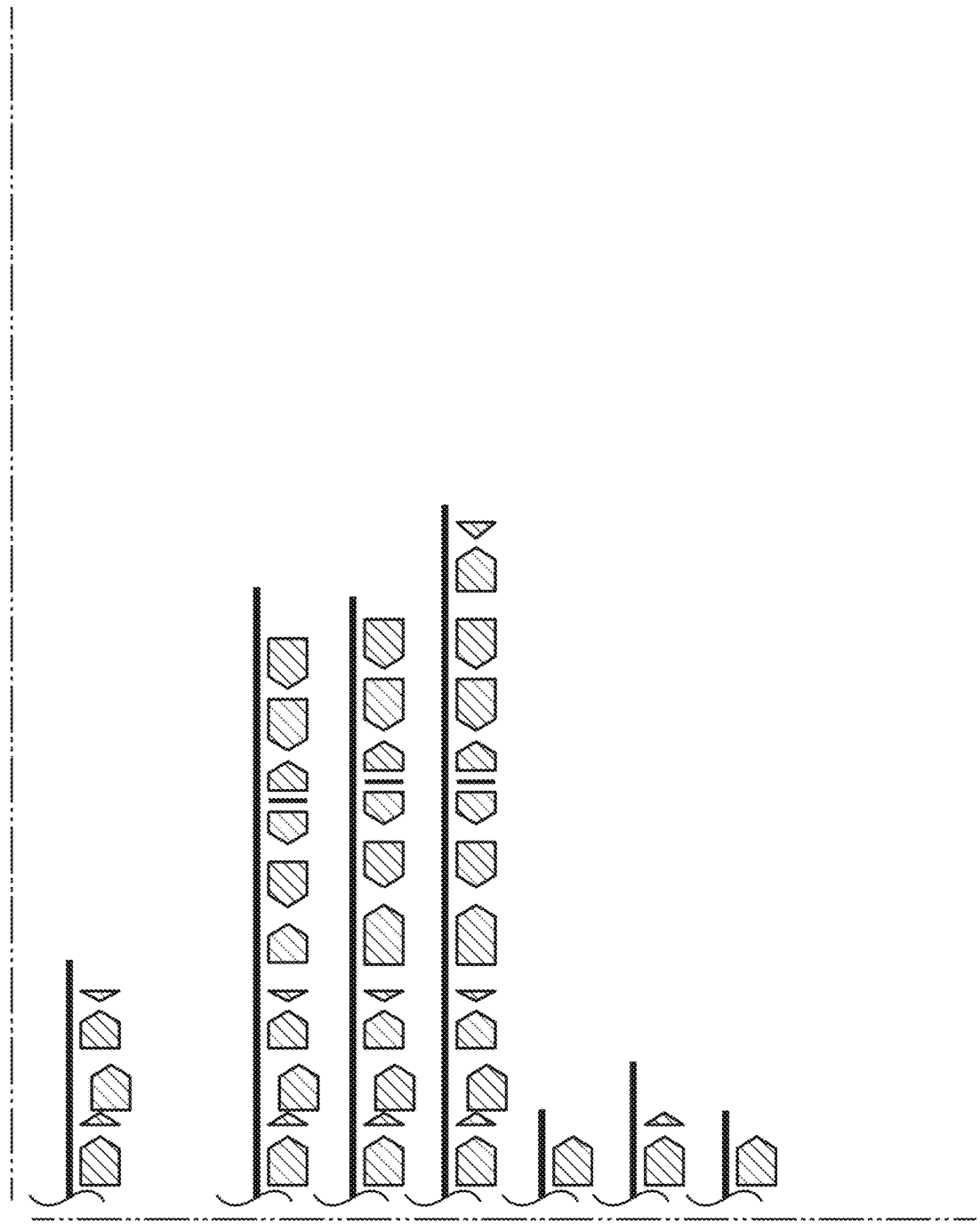

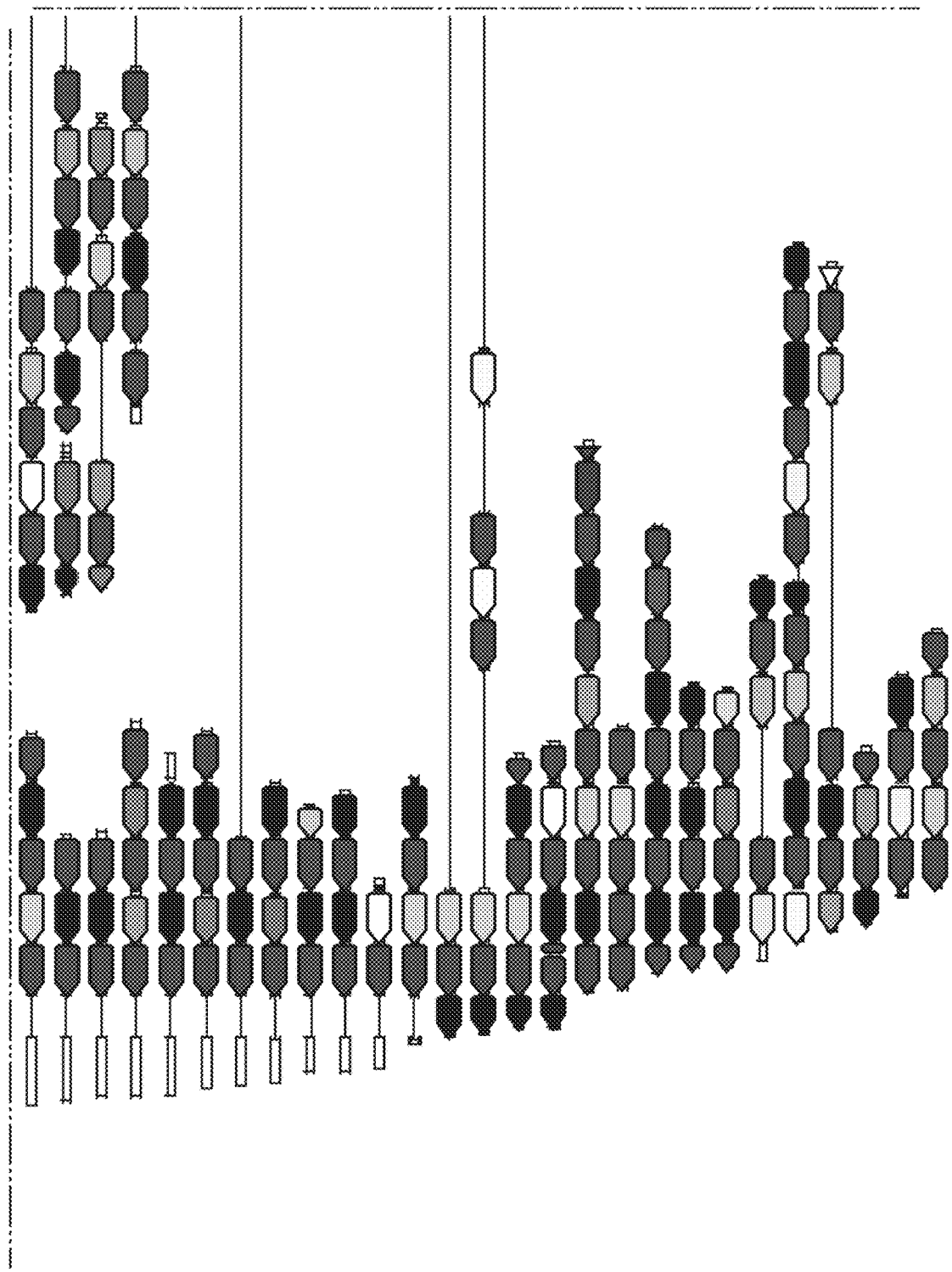

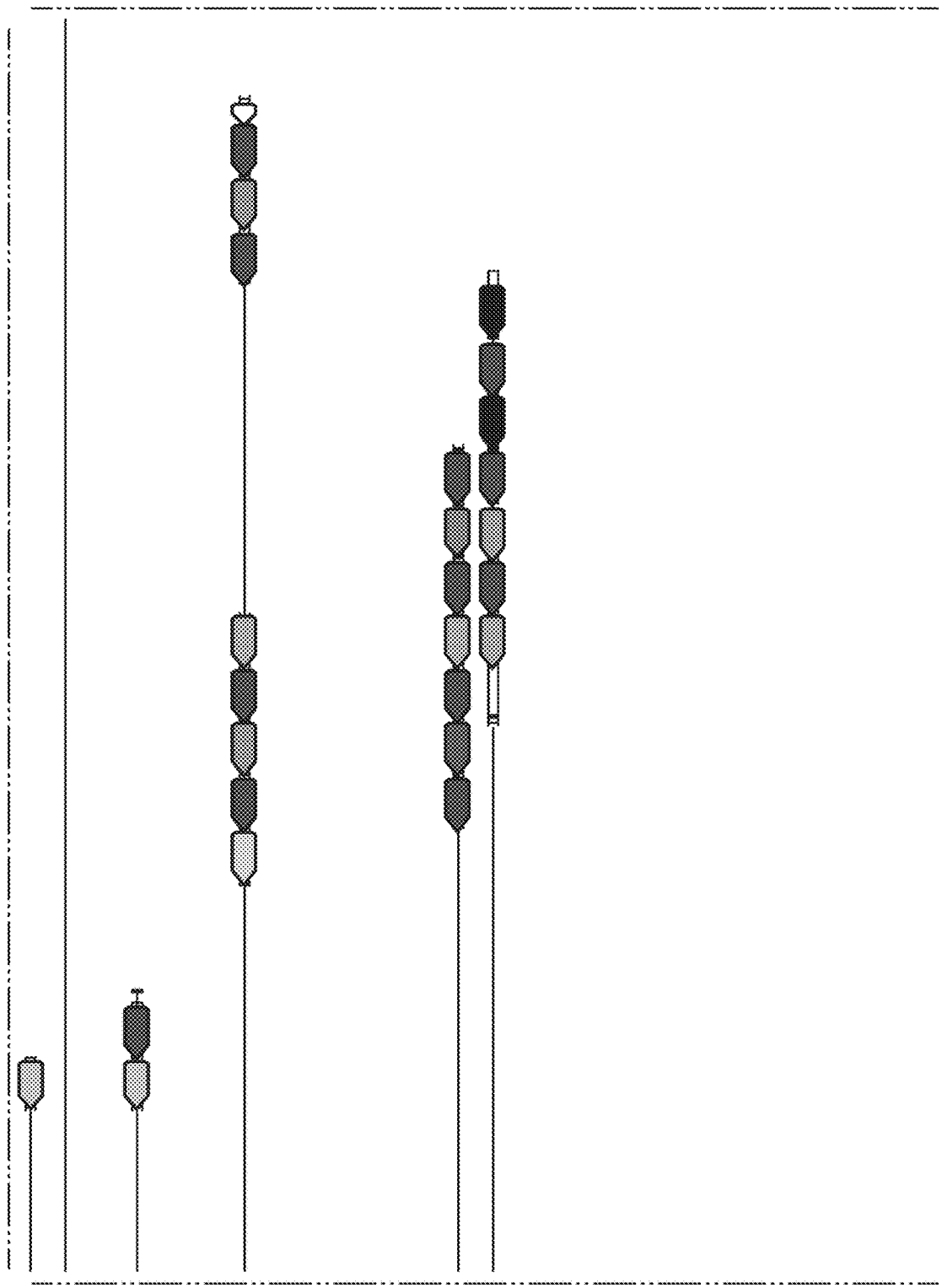

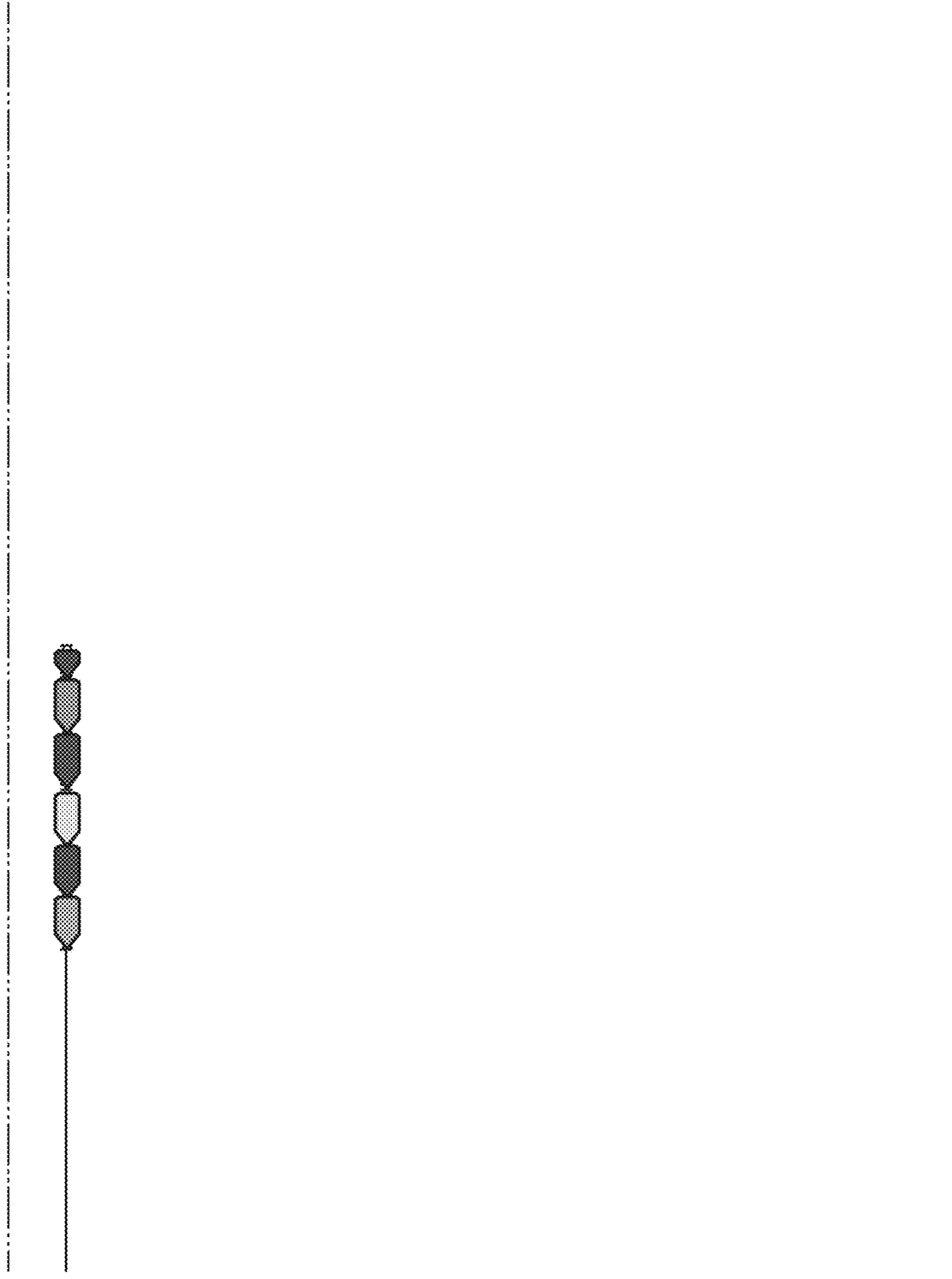

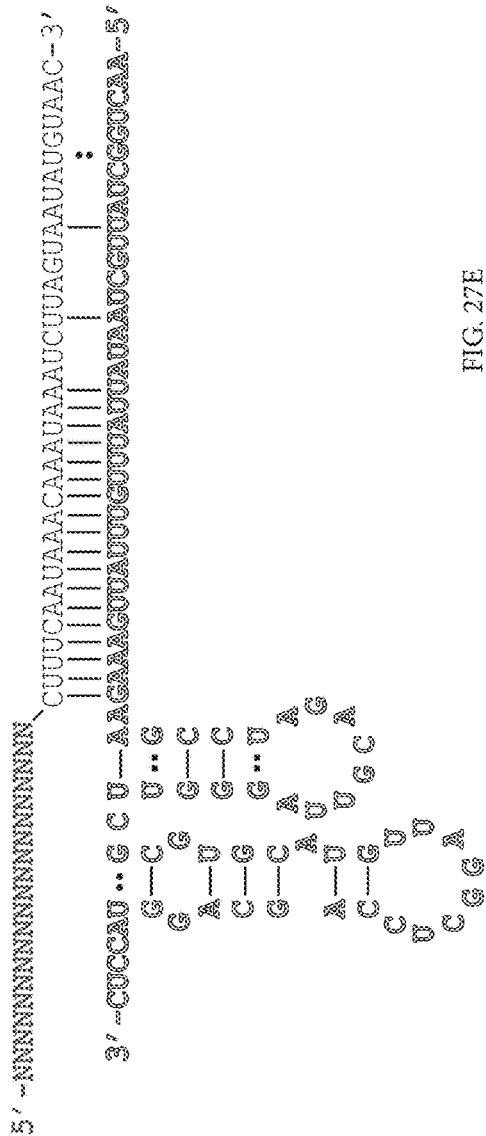
FIG. 27C
FIG. 27D
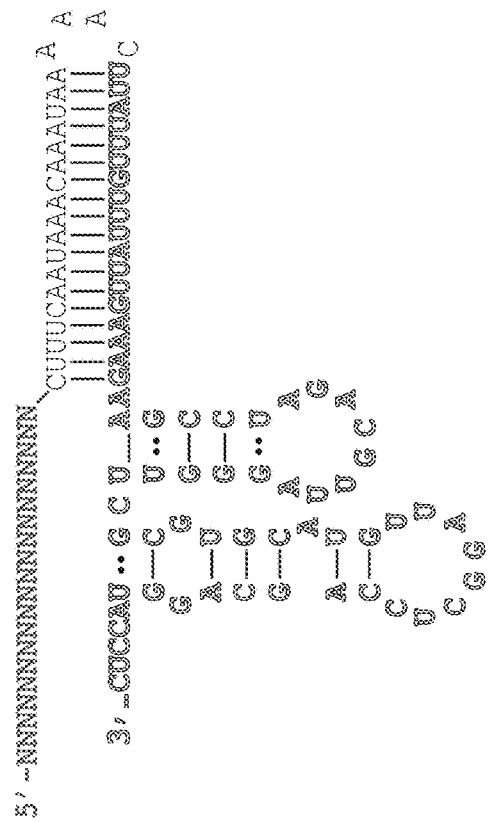
FIG. 27E

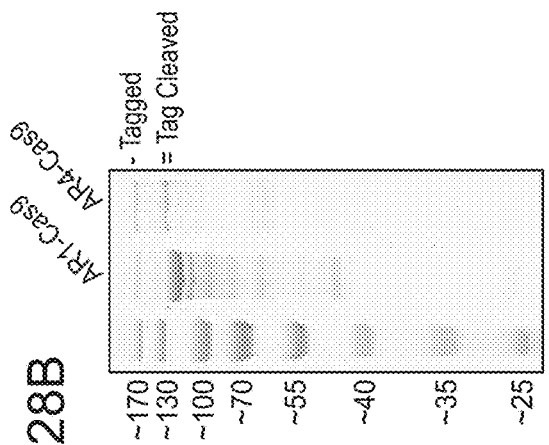
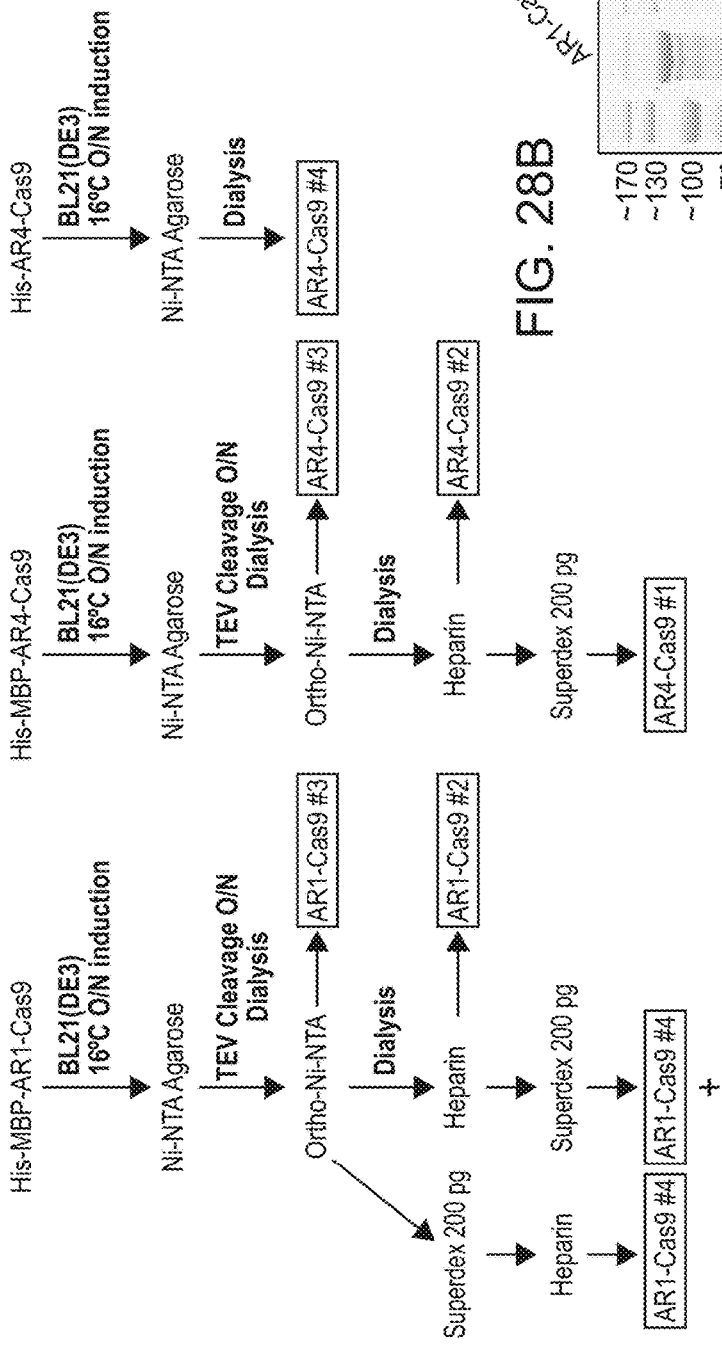
FIG. 28A
FIG. 28B

FIG. 32

*In vitro cleavage conditions assayed for Cas9 from ARMAN-1*

| Protein Purification | Buffer | Salt (mM) | Metal | Guide | Target | Temperature |
|---|---|---|---|---|---|---|
| AR1-Cas9 #1 | Tris ph 7.5 | 300 | $Mg^{2+}$ $Mn^{2+}$ $Zn^{2+}$ | crRNA cr:69 cr:69 cr:69 | dsDNA ssDNA DNA Bubble ssRNA dsDNA | 37 |
| AR1-Cas9 #1 | Tris ph 7.5 | 100-500 | $Mg^{2+}$ | cr:69 cr:104 cr:179 | dsDNA | 37 |
| AR1-Cas9 #1 | Tris ph 7.5 | 300 | $Mg^{2+}$ $Mn^{2+}$ $Zn^{2+}$ | cr:69 cr:104 cr:179 | dsDNA | 30-48 |
| AR1-Cas9 #1 | MOPS: pH 6 pH 6.5 pH 7.0 pH 7.5 | 300 | $Mg^{2+}$ | cr:69 cr:104 cr:179 | dsDNA | 37 |
| AR1-Cas9 #1 | Citrate: pH 5 pH 5.5 pH 6 | 300 | $Mg^{2+}$ | cr:69 cr:104 cr:179 | dsDNA | 37 |
| AR1-Cas9 #1 | Tris ph 7.5 | 300 | $Mg^{2+}$ $Mn^{2+}$ $Zn^{2+}$ | cr:69 cr:104 cr:179 | plasmid | 37-50 |
| AR1-Cas9 #2 | Tris ph 7.5 | 300 | $Mg^{2+}$ $Mn^{2+}$ $Zn^{2+}$ | cr:69 cr:104 cr:179 | dsDNA | 37 |
| AR1-Cas9 #3 | Tris ph 7.5 | 300 | $Mg^{2+}$ $Mn^{2+}$ $Zn^{2+}$ | cr:69 cr:104 cr:179 | dsDNA | 37 |
| AR1-Cas9 #4 | Tris ph 7.5 | 300 | $Mg^{2+}$ $Mn^{2+}$ $Zn^{2+}$ | cr:69 cr:104 cr:179 | dsDNA | 37 |
| AR1-Cas9 #5 | Tris ph 7.5 | 300 | $Mg^{2+}$ $Mn^{2+}$ $Zn^{2+}$ | cr:69 cr:104 cr:179 | dsDNA | 37 |
| AR1-Cas9 #6 | Tris ph 7.5 | 300 | $Mg^{2+}$ $Mn^{2+}$ $Zn^{2+}$ | cr:69 cr:104 cr:179 | ssDNA dsDNA | 37 |
| AR4-Cas9 #1 | Tris ph 7.5 | 300 | $Mg^{2+}$ $Mn^{2+}$ $Zn^{2+}$ | sgRNA-122 | dsDNA | 37 |
| AR4-Cas9 #2 | Tris ph 7.5 | 300 | $Mg^{2+}$ $Mn^{2+}$ $Zn^{2+}$ | sgRNA-122 | dsDNA | 37 |
| AR4-Cas9 #3 | Tris ph 7.5 | 300 | $Mg^{2+}$ $Mn^{2+}$ $Zn^{2+}$ | sgRNA-122 | dsDNA | 37 |
| AR4-Cas9 #4 | Tris ph 7.5 | 300 | $Mg^{2+}$ $Mn^{2+}$ $Zn^{2+}$ | sgRNA-122 | dsDNA | 37 |

RNA-GUIDED NUCLEIC ACID MODIFYING ENZYMES AND METHODS OF USE THEREOF

CROSS-REFERENCE

This application is a continuation of PCT/US2017/054081, filed Sep. 28, 2017, which claims the benefit of U.S. Provisional Patent Application No. 62/402,846, filed Sep. 30, 2016, each of which applications is incorporated herein by reference in its entirety.

GOVERNMENT RIGHTS

This invention was made with government support under DE-AC02-05CH11231 awarded by the Department of Energy and under 1244557 awarded by the National Science Foundation. The government has certain rights in the invention.

INCORPORATION BY REFERENCE OF SEQUENCE LISTING PROVIDED AS A TEXT FILE

A Sequence Listing is provided herewith as a text file, "BERK-342CON_SEQ_LISTING_ST25.txt" created on May 8, 2019 and having a size of 181 KB. The contents of the text file are incorporated by reference herein in their entirety.

INTRODUCTION

The CRISPR-Cas system, an example of a pathway that was unknown to science prior to the DNA sequencing era, is now understood to confer bacteria and archaea with acquired immunity against phage and viruses. Intensive research over the past decade has uncovered the biochemistry of this system. CRISPR-Cas systems consist of Cas proteins, which are involved in acquisition, targeting and cleavage of foreign DNA or RNA, and a CRISPR array, which includes direct repeats flanking short spacer sequences that guide Cas proteins to their targets. Class 2 CRISPR-Cas are streamlined versions in which a single Cas protein bound to RNA is responsible for binding to and cleavage of a targeted sequence. The programmable nature of these minimal systems has facilitated their use as a versatile technology that is revolutionizing the field of genome manipulation.

Current CRISPR-Cas technologies are based on systems from cultured bacteria, leaving untapped the vast majority of organisms that have not been isolated. To date, only a few Class 2 CRISPR/Cas systems have been discovered. There is a need in the art for additional Class 2 CRISPR/Cas systems (e.g., Cas protein plus guide RNA combinations).

SUMMARY

The present disclosure provides RNA-guided endonuclease polypeptides, referred to herein as "CasX" polypeptides (also referred to as "CasX proteins"); nucleic acids encoding the CasX polypeptides; and modified host cells comprising the CasX polypeptides and/or nucleic acids encoding same. CasX polypeptides are useful in a variety of applications, which are provided.

The present disclosure provides guide RNAs (referred to herein as "CasX guide RNAs") that bind to and provide sequence specificity to the CasX proteins; nucleic acids encoding the CasX guide RNAs; and modified host cells comprising the CasX guide RNAs and/or nucleic acids encoding same. CasX guide RNAs are useful in a variety of applications, which are provided.

The present disclosure provides archaeal Cas9 polypeptides and nucleic acids encoding same, as well as their associated guide RNAs (archaeal Cas9 guide RNAs) and nucleic acids encoding same.

BRIEF DESCRIPTION OF THE DRAWINGS

FIGS. 1A-1B depict three naturally occurring CasX protein sequences.

FIG. 2 depicts an alignment of the two identified naturally occurring CasX protein sequences.

FIGS. 5A-5C depict experiments performed (PAM dependent plasmid interference by CasX) to determine a PAM sequence for CasX.

FIG. 9 presents data showing recombinant expression and purification of CasX.

FIG. 10 presents data using various different tracrRNA sequences (different sequence lengths) for cleavage activity.

FIG. 11 presents data related to CasX functioning at room temperature versus 37° C.

FIG. 13 presents example archaeal Cas9 proteins (ARMAN-1 and ARMAN-4, SEQ ID NOs: 71 and 72, respectively). Catalytic residues that correspond to D10 and H840 of *S. pyogenes* are bold and underlined.

FIG. 15 present example dual guide (top panel)(top RNA-SEQ ID NO: 74, bottom RNA-SEQ ID NO: 78) and single guide (bottom panel)(SEQ ID NO: 80) formats that can be used with an archaeal Cas9 protein (e.g., ARMAN-4 Cas9).

FIG. 16 present two newly identified non-archaeal Cas9 proteins.

Figure 17B:
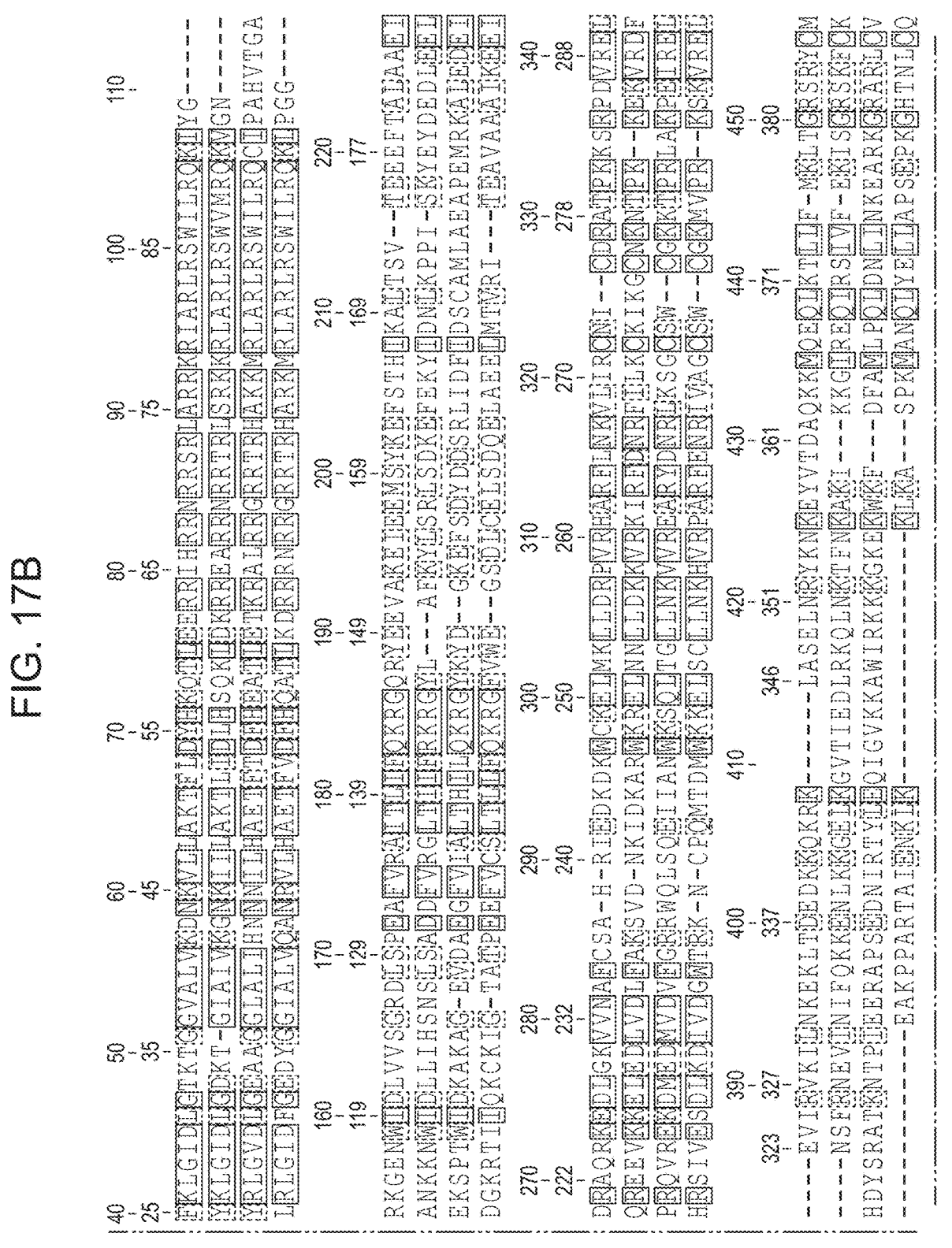
Figure 17D:
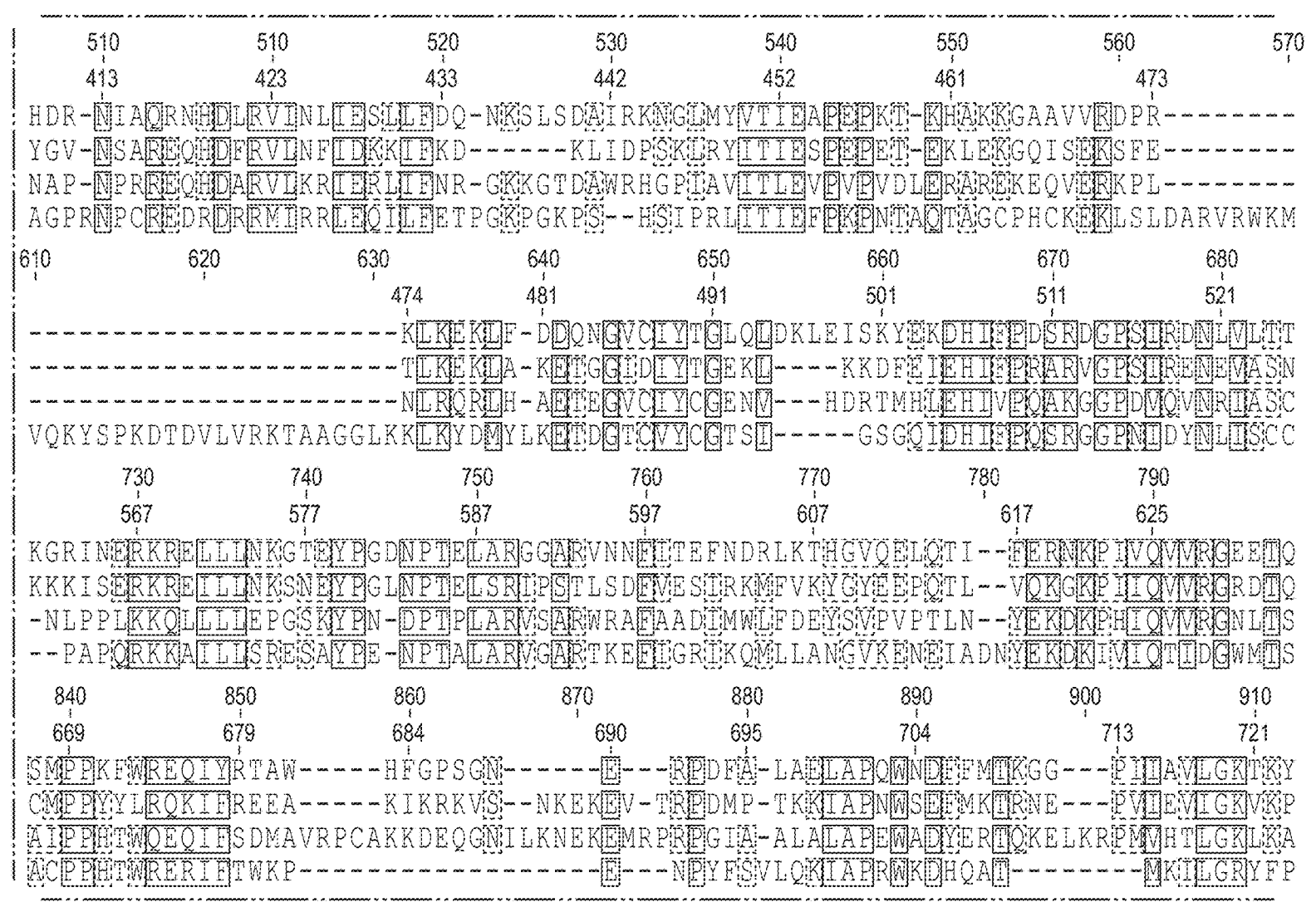

FIGS. 17A-17F present (i) an alignment of two newly identified non-archaeal Cas9 proteins with ARMAN-1 and ARMAN-4 Cas9 proteins; and (ii) an alignment of Cas9 proteins from ARMAN-1 and ARMAN-4, as well as two closely related Cas9 proteins from uncultivated bacteria, to the *Actinomyces naeslundii* Cas9, whose structure has been solved. Sequences from top to bottom: SEQ ID NOs: 151-154.

FIG. 18A, Ratio of major lineages with and without isolated representatives in all bacteria and archaea, based on data of Hug et al.[32]. The results highlight the massive scale of as yet little investigated biology in these domains. Archaeal Cas9 and the novel CRISPR-CasY were found exclusively in lineages with no isolated representatives. FIG. 18A, Locus organization of the newly discovered CRISPR-Cas systems.

FIG. 19A, CRISPR arrays reconstructed from 15 different AMD samples. White boxes indicate repeats and colored diamonds indicate spacers (identical spacers are similarly colored; unique spacers are in black). The conserved region of the array is highlighted (on the right). The diversity of recently acquired spacers (on the left) indicates the system is active. An analysis that also includes CRISPR fragments from the read data is presented in 25. FIG. 19B, A single putative viral contig reconstructed from AMD metagenomic data contains 56 protospacers (red vertical bars) from the ARMAN-1 CRISPR arrays. FIG. 19C, Sequence analysis revealed a conserved 'NGG' PAM motif downstream of the protospacers on the non-target strand.

FIG. 20A, Diagram of CasX plasmid interference assays. *E. coli* expressing a minimal CasX locus is transformed with a plasmid containing a spacer matching the sequence in the CRISPR array (target) or plasmid containing a non-matching spacer (non-target). After being transformed, cultures are plated and colony forming units (cfu) quantified. FIG. 20B, Serial dilution of *E. coli* expressing the Planctomycetes CasX locus targeting spacer 1 (sX.1) and transformed with the specified target (sX1, CasX spacer 1; sX2, CasX spacer 2; NT, non-target). FIG. 20C, Plasmid interference by Deltaproteobacteria CasX. Experiments were conducted in triplicate and mean±s.d. is shown. FIG. 20D, PAM depletion assays for the Planctomycetes CasX locus expressed in *E. coli*. PAM sequences depleted greater than 30-fold compared to a control library were used to generate the WebLogo.

FIG. 21A, Mapping of environmental RNA sequences (metatranscriptomic data) to the CasX CRISPR locus diagramed below (red arrow, putative tracrRNA; white boxes, repeat sequences; green diamonds, spacer sequences). Inset shows detailed view of the first repeat and spacer. FIG. 21B, Diagram of CasX double-stranded DNA interference. The site of RNA processing is indicated by black arrows. FIG. 21C, Results of. plasmid interference assays with the putative tracrRNA knocked out of the CasX locus and CasX coexpressed with a crRNA alone, a truncated sgRNA or a full length sgRNA (T, target; NT, non-target). Experiments were conducted in triplicate and mean±s.d. is shown.

FIGS. 22A-22C present data showing expression of a CasY locus in *E. coli* is sufficient for DNA interference. FIG. 22A, Diagrams of CasY loci and neighboring proteins. FIG. 22B, WebLogo of 5' PAM sequences depleted greater than 3-fold by CasY relative to a control library. FIG. 22C, Plasmid interference by *E. coli* expressing CasY.1 and transformed with targets containing the indicated PAM. Experiments were conducted in triplicate and mean±s.d is shown.

FIG. 23A, Simplified phylogenetic tree of the universal Cas1 protein. CRISPR types of known systems are noted on the wedges and branches; the newly described systems are in bold. Detailed Cas1 phylogeny is presented in Supplementary Data 2.

FIGS. 24A-24D present shows that archaeal Cas9 from ARMAN-4 is found on numerous contigs with a degenerate CRISPR array. Cas9 from ARMAN-4 is highlighted in dark red on 16 different contigs. Proteins with putative domains or functions are labeled whereas hypothetical proteins are unlabeled. Fifteen of the contigs contain two degenerate direct repeats (one bp mismatch) and a single, conserved spacer. The remaining contig contains only one direct repeat. Unlike ARMAN-1, no additional Cas proteins are found adjacent to Cas9 in ARMAN-4.

FIGS. 25A-25F present a full reconstruction of ARMAN-1 CRISPR arrays. Reconstruction of CRISPR arrays, that include reference assembled sequences, as well as array segments reconstructed from the short DNA reads. Green arrows indicate repeats and colored arrows indicate CRISPR spacers (identical spacers are colored the same whereas unique spacers are colored in black). In CRISPR systems, spacers are typically added unidirectionally, so the high variety of spacers on the left side is attributed to recent acquisition.

FIG. 26A, Protospacers (red arrows) from ARMAN-1 map to the genome of ARMAN-2, a nanoarchaeon from the same environment. Six protospacers map uniquely to a portion of the genome flanked by two long-terminal repeats (LTRs), and two additional protospacers match perfectly within the LTRs (blue and green). This region is likely a transposon, suggesting the CRISPR-Cas system of ARMAN-1 plays a role in suppressing mobilization of this element. FIG. 26B, Protospacers also map to a *Thermoplasmatales* archaeon (I-plasma), another member of the Richmond Mine ecosystem that is found in the same samples as ARMAN organisms. The protospacers cluster within a region of the genome encoding short, hypothetical proteins, suggesting this might also represent a mobile element.

FIGS. 27A-27E presents predicted secondary structure of ARMAN-1 crRNA and tracrRNA. FIG. 27A, The CRISPR repeat and tracrRNA anti-repeat are depicted in black whereas the spacer-derived sequence is shown as a series of green N's. No clear termination signal can be predicted from the locus, so three different tracrRNA lengths were tested based on their secondary structure—69, 104, and 179 in red, blue, and pink, respectively. Sequences from top to bottom: SEQ ID Nos:145-146. FIG. 21B, Engineered single-guide RNA (SEQ ID NO:147) corresponding to dual-guide in FIG. 27A. FIG. 27C, Dual-guide for ARMAN-4 Cas9 with two different hairpins on 3' end of tracrRNA (75 and 122). Sequences from top to bottom: SEQ ID Nos:148-149. FIG. 27D, Engineered single-guide RNA (SEQ ID NO:150) corresponding to dual-guide in FIG. 27C. FIG. 27E, Conditions tested in *E. coli* in vivo targeting assay.

FIGS. 28A-28B present purification schema for in vitro biochemistry studies. FIG. 28A, ARMAN-1 (AR1) and ARMAN-4 (AR4) Cas9 were expressed and purified under a variety of conditions as outlined in the Supplementary Materials. Proteins outlined in blue boxes were tested for cleavage activity in vitro. FIG. 28B, Fractions of AR1-Cas9 and AR4-Cas9 purifications were separated on a 10% SDS-PAGE gel.

FIG. 30A, Plasmid interference assays for CasX2 (Planctomycetes) and CasX1 (Deltaproteobacteria), continued from FIG. 20C (sX1, CasX spacer 1; sX2, CasX spacer 2; NT, non-target). Experiments were conducted in triplicate and mean±s.d. is shown. FIG. 30B, Serial dilution of *E. coli* expressing a CasX locus and transformed with the specified target, continued from FIG. 20B-20C. FIG. 30C, PAM depletion assays for the Deltaproteobacteria CasX and FIG. 30D, Planctomycetes CasX expressed in *E. coli*. PAM sequences depleted greater than the indicated PAM depletion value threshold (PDVT) compared to a control library were used to generate the WebLogo. FIG. 30E, Diagram depicting the location of Northern blot probes for CasX.1. FIG. 30F, Northern blots for CasX.1 tracrRNA in total RNA extracted from *E. coli* expressing the CasX.1 locus.

FIG. 32 presents a table of cleavage conditions assayed for Cas9 from ARMAN-1 and ARMAN-4.

DEFINITIONS

Figure 3A:
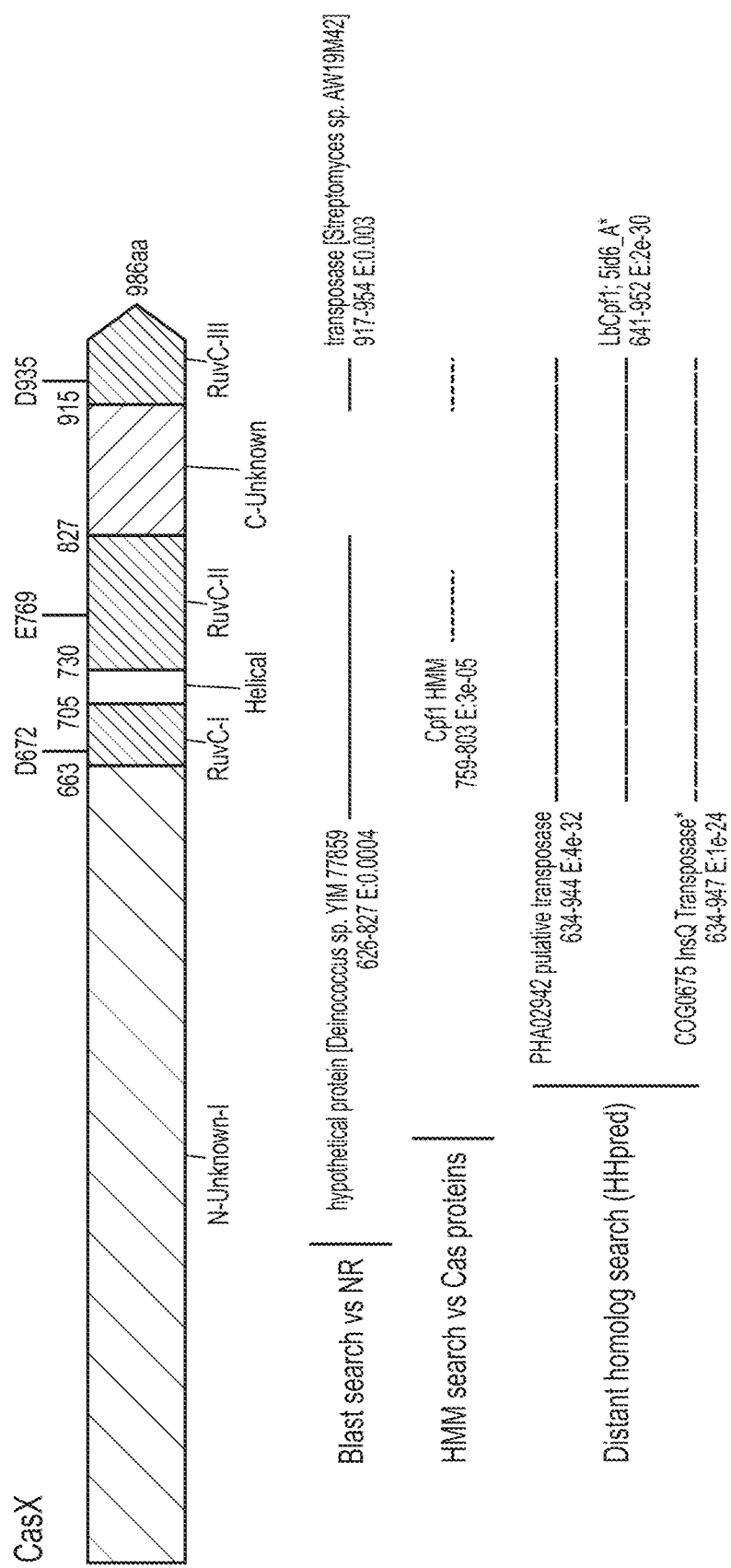
FIGS. 3A-3B depict a schematic domain representation for CasX. Also shown are results from various searches attempting to identify homologs of CasX. Also depicted are portions of the CasX-containing CRISPR loci there were identified from two different species.

"Heterologous," as used herein, means a nucleotide or polypeptide sequence that is not found in the native nucleic acid or protein, respectively. For example, relative to a CasX polypeptide, a heterologous polypeptide comprises an amino acid sequence from a protein other than the CasX polypeptide. In some cases, a portion of a CasX protein from one species is fused to a portion of a CasX protein from a different species. The CasX sequence from each species could therefor be considered to be heterologous relative to one another. As another example, a CasX protein (e.g., a dCasX protein) can be fused to an active domain from a non-CasX protein (e.g., a histone deacetylase), and the sequence of the active domain could be considered a heterologous polypeptide (it is heterologous to the CasX protein).

The terms "polynucleotide" and "nucleic acid," used interchangeably herein, refer to a polymeric form of nucleotides of any length, either ribonucleotides or deoxynucleotides. Thus, this term includes, but is not limited to, single-, double-, or multi-stranded DNA or RNA, genomic DNA, cDNA, DNA-RNA hybrids, or a polymer comprising purine and pyrimidine bases or other natural, chemically or biochemically modified, non-natural, or derivatized nucleotide bases. The terms "polynucleotide" and "nucleic acid" should be understood to include, as applicable to the embodiment being described, single-stranded (such as sense or antisense) and double-stranded polynucleotides.

The terms "polypeptide," "peptide," and "protein", are used interchangeably herein, refer to a polymeric form of amino acids of any length, which can include genetically coded and non-genetically coded amino acids, chemically or biochemically modified or derivatized amino acids, and polypeptides having modified peptide backbones. The term includes fusion proteins, including, but not limited to, fusion proteins with a heterologous amino acid sequence, fusions with heterologous and homologous leader sequences, with or without N-terminal methionine residues; immunologically tagged proteins; and the like.

The term "naturally-occurring" as used herein as applied to a nucleic acid, a protein, a cell, or an organism, refers to a nucleic acid, cell, protein, or organism that is found in nature.

As used herein the term "isolated" is meant to describe a polynucleotide, a polypeptide, or a cell that is in an environment different from that in which the polynucleotide, the polypeptide, or the cell naturally occurs. An isolated genetically modified host cell may be present in a mixed population of genetically modified host cells.

As used herein, the term "exogenous nucleic acid" refers to a nucleic acid that is not normally or naturally found in and/or produced by a given bacterium, organism, or cell in nature. As used herein, the term "endogenous nucleic acid" refers to a nucleic acid that is normally found in and/or produced by a given bacterium, organism, or cell in nature. An "endogenous nucleic acid" is also referred to as a "native nucleic acid" or a nucleic acid that is "native" to a given bacterium, organism, or cell.

"Recombinant," as used herein, means that a particular nucleic acid (DNA or RNA) is the product of various combinations of cloning, restriction, and/or ligation steps resulting in a construct having a structural coding or non-coding sequence distinguishable from endogenous nucleic acids found in natural systems. Generally, DNA sequences encoding the structural coding sequence can be assembled from cDNA fragments and short oligonucleotide linkers, or from a series of synthetic oligonucleotides, to provide a synthetic nucleic acid which is capable of being expressed from a recombinant transcriptional unit contained in a cell or in a cell-free transcription and translation system. Such sequences can be provided in the form of an open reading frame uninterrupted by internal non-translated sequences, or introns, which are typically present in eukaryotic genes. Genomic DNA comprising the relevant sequences can also be used in the formation of a recombinant gene or transcriptional unit. Sequences of non-translated DNA may be present 5' or 3' from the open reading frame, where such sequences do not interfere with manipulation or expression of the coding regions, and may indeed act to modulate production of a desired product by various mechanisms (see "DNA regulatory sequences", below).

Thus, e.g., the term "recombinant" polynucleotide or "recombinant" nucleic acid refers to one which is not naturally occurring, e.g., is made by the artificial combination of two otherwise separated segments of sequence through human intervention. This artificial combination is often accomplished by either chemical synthesis means, or by the artificial manipulation of isolated segments of nucleic acids, e.g., by genetic engineering techniques. Such is usually done to replace a codon with a redundant codon encoding the same or a conservative amino acid, while typically introducing or removing a sequence recognition site. Alternatively, it is performed to join together nucleic acid segments of desired functions to generate a desired combination of functions. This artificial combination is often accomplished by either chemical synthesis means, or by the artificial manipulation of isolated segments of nucleic acids, e.g., by genetic engineering techniques.

Similarly, the term "recombinant" polypeptide refers to a polypeptide which is not naturally occurring, e.g., is made by the artificial combination of two otherwise separated segments of amino sequence through human intervention. Thus, e.g., a polypeptide that comprises a heterologous amino acid sequence is recombinant.

By "construct" or "vector" is meant a recombinant nucleic acid, generally recombinant DNA, which has been generated for the purpose of the expression and/or propagation of a specific nucleotide sequence(s), or is to be used in the construction of other recombinant nucleotide sequences.

The terms "DNA regulatory sequences," "control elements," and "regulatory elements," used interchangeably herein, refer to transcriptional and translational control sequences, such as promoters, enhancers, polyadenylation signals, terminators, protein degradation signals, and the like, that provide for and/or regulate expression of a coding sequence and/or production of an encoded polypeptide in a host cell.

The term "transformation" is used interchangeably herein with "genetic modification" and refers to a permanent or transient genetic change induced in a cell following introduction of new nucleic acid (e.g., DNA exogenous to the cell) into the cell. Genetic change ("modification") can be accomplished either by incorporation of the new nucleic acid into the genome of the host cell, or by transient or stable maintenance of the new nucleic acid as an episomal element. Where the cell is a eukaryotic cell, a permanent genetic change is generally achieved by introduction of new DNA into the genome of the cell. In prokaryotic cells, permanent changes can be introduced into the chromosome or via extrachromosomal elements such as plasmids and expression vectors, which may contain one or more selectable markers to aid in their maintenance in the recombinant host cell. Suitable methods of genetic modification include viral infection, transfection, conjugation, protoplast fusion, electroporation, particle gun technology, calcium phosphate precipitation, direct microinjection, and the like. The choice of method is generally dependent on the type of cell being transformed and the circumstances under which the transformation is taking place (i.e. in vitro, ex vivo, or in vivo). A general discussion of these methods can be found in Ausubel, et al, Short Protocols in Molecular Biology, 3rd ed., Wiley & Sons, 1995.

"Operably linked" refers to a juxtaposition wherein the components so described are in a relationship permitting them to function in their intended manner. For instance, a promoter is operably linked to a coding sequence if the promoter affects its transcription or expression. As used herein, the terms "heterologous promoter" and "heterologous control regions" refer to promoters and other control regions that are not normally associated with a particular nucleic acid in nature. For example, a "transcriptional control region heterologous to a coding region" is a transcriptional control region that is not normally associated with the coding region in nature.

A "host cell," as used herein, denotes an in vivo or in vitro eukaryotic cell, a prokaryotic cell, or a cell from a multicellular organism (e.g., a cell line) cultured as a unicellular entity, which eukaryotic or prokaryotic cells can be, or have been, used as recipients for a nucleic acid (e.g., an expression vector), and include the progeny of the original cell which has been genetically modified by the nucleic acid. It is understood that the progeny of a single cell may not necessarily be completely identical in morphology or in genomic or total DNA complement as the original parent, due to natural, accidental, or deliberate mutation. A "recombinant host cell" (also referred to as a "genetically modified host cell") is a host cell into which has been introduced a heterologous nucleic acid, e.g., an expression vector. For example, a subject prokaryotic host cell is a genetically modified prokaryotic host cell (e.g., a bacterium), by virtue of introduction into a suitable prokaryotic host cell of a heterologous nucleic acid, e.g., an exogenous nucleic acid that is foreign to (not normally found in nature in) the prokaryotic host cell, or a recombinant nucleic acid that is not normally found in the prokaryotic host cell; and a subject eukaryotic host cell is a genetically modified eukaryotic host cell, by virtue of introduction into a suitable eukaryotic host cell of a heterologous nucleic acid, e.g., an exogenous nucleic acid that is foreign to the eukaryotic host cell, or a recombinant nucleic acid that is not normally found in the eukaryotic host cell.

The term "conservative amino acid substitution" refers to the interchangeability in proteins of amino acid residues having similar side chains. For example, a group of amino acids having aliphatic side chains consists of glycine, alanine, valine, leucine, and isoleucine; a group of amino acids having aliphatic-hydroxyl side chains consists of serine and threonine; a group of amino acids having amide-containing side chains consists of asparagine and glutamine; a group of amino acids having aromatic side chains consists of phenylalanine, tyrosine, and tryptophan; a group of amino acids having basic side chains consists of lysine, arginine, and histidine; and a group of amino acids having sulfur-containing side chains consists of cysteine and methionine. Exemplary conservative amino acid substitution groups are: valine-leucine-isoleucine, phenylalanine-tyrosine, lysine-arginine, alanine-valine, and asparagine-glutamine.

A polynucleotide or polypeptide has a certain percent "sequence identity" to another polynucleotide or polypeptide, meaning that, when aligned, that percentage of bases or amino acids are the same, and in the same relative position, when comparing the two sequences. Sequence similarity can be determined in a number of different manners. To determine sequence identity, sequences can be aligned using the methods and computer programs, including BLAST, available over the world wide web at ncbi.nlm.nih.gov/BLAST. See, e.g., Altschul et al. (1990), *J. Mol. Biol.* 215:403-10. Another alignment algorithm is FASTA, available in the Genetics Computing Group (GCG) package, from Madison, Wis., USA, a wholly owned subsidiary of Oxford Molecular Group, Inc. Other techniques for alignment are described in Methods in Enzymology, vol. 266: Computer Methods for Macromolecular Sequence Analysis (1996), ed. Doolittle, Academic Press, Inc., a division of Harcourt Brace & Co., San Diego, Calif., USA. Of particular interest are alignment programs that permit gaps in the sequence. The Smith-Waterman is one type of algorithm that permits gaps in sequence alignments. See *Meth. Mol. Biol.* 70: 173-187 (1997). Also, the GAP program using the Needleman and Wunsch alignment method can be utilized to align sequences. See *J. Mol. Biol.* 48: 443-453 (1970).

As used herein, the terms "treatment," "treating," and the like, refer to obtaining a desired pharmacologic and/or physiologic effect. The effect may be prophylactic in terms of completely or partially preventing a disease or symptom thereof and/or may be therapeutic in terms of a partial or complete cure for a disease and/or adverse effect attributable to the disease. "Treatment," as used herein, covers any treatment of a disease in a mammal, e.g., in a human, and includes: (a) preventing the disease from occurring in a subject which may be predisposed to the disease but has not yet been diagnosed as having it; (b) inhibiting the disease, i.e., arresting its development; and (c) relieving the disease, i.e., causing regression of the disease.

The terms "individual," "subject," "host," and "patient," used interchangeably herein, refer to an individual organism, e.g., a mammal, including, but not limited to, murines, simians, humans, mammalian farm animals, mammalian sport animals, and mammalian pets.

Before the present invention is further described, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges, and are also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, the preferred methods and materials are now described. All publications mentioned herein are incorporated herein by reference to disclose and describe the methods and/or materials in connection with which the publications are cited.

It must be noted that as used herein and in the appended claims, the singular forms "a," "an," and "the" include plural referents unless the context clearly dictates otherwise. Thus, for example, reference to "a CasX polypeptide" includes a plurality of such polypeptides and reference to "the guide RNA" includes reference to one or more guide RNAs and equivalents thereof known to those skilled in the art, and so forth. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable sub-combination. All combinations of the embodiments pertaining to the invention are specifically embraced by the present invention and are disclosed herein just as if each and every combination was individually and explicitly disclosed. In addition, all sub-combinations of the various embodiments and elements thereof are also specifically embraced by the present invention and are disclosed herein just as if each and every such sub-combination was individually and explicitly disclosed herein.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

DETAILED DESCRIPTION

The present disclosure provides RNA-guided endonuclease polypeptides, referred to herein as "CasX" polypeptides (also referred to as "CasX proteins"); nucleic acids encoding the CasX polypeptides; and modified host cells comprising the CasX polypeptides and/or nucleic acids encoding same. CasX polypeptides are useful in a variety of applications, which are provided.

The present disclosure provides guide RNAs (referred to herein as "CasX guide RNAs") that bind to and provide sequence specificity to the CasX proteins; nucleic acids encoding the CasX guide RNAs; and modified host cells comprising the CasX guide RNAs and/or nucleic acids encoding same. CasX guide RNAs are useful in a variety of applications, which are provided.

The present disclosure provides archaeal Cas9 polypeptides and nucleic acids encoding same, as well as their associated guide RNAs (archaeal Cas9 guide RNAs) and nucleic acids encoding same.

Compositions

CRISPR/CasX Proteins and Guide RNAs

A CRISPR/Cas endonuclease (e.g., a CasX protein) interacts with (binds to) a corresponding guide RNA (e.g., a CasX guide RNA) to form a ribonucleoprotein (RNP) complex that is targeted to a particular site in a target nucleic acid via base pairing between the guide RNA and a target sequence within the target nucleic acid molecule. A guide RNA includes a nucleotide sequence (a guide sequence) that is complementary to a sequence (the target site) of a target nucleic acid. Thus, a CasX protein forms a complex with a CasX guide RNA and the guide RNA provides sequence specificity to the RNP complex via the guide sequence. The CasX protein of the complex provides the site-specific activity. In other words, the CasX protein is guided to a target site (e.g., stabilized at a target site) within a target nucleic acid sequence (e.g. a chromosomal sequence or an extrachromosomal sequence, e.g., an episomal sequence, a minicircle sequence, a mitochondrial sequence, a chloroplast sequence, etc.) by virtue of its association with the guide RNA.

The present disclosure provides compositions comprising a CasX polypeptide (and/or a nucleic acid encoding the CasX polypeptide) (e.g., where the CasX polypeptide can be a naturally existing protein, a nickase CasX protein, a dCasX protein, a chimeric CasX protein, etc.). The present disclosure provides compositions comprising a CasX guide RNA (and/or a nucleic acid encoding the CasX guide RNA) (e.g., where the CasX guide RNA can be in dual or single guide format). The present disclosure provides compositions comprising (a) a CasX polypeptide (and/or a nucleic acid encoding the CasX polypeptide) (e.g., where the CasX polypeptide can be a naturally existing protein, a nickase CasX protein, a dCasX protein, a chimeric CasX protein, etc.) and (b) a CasX guide RNA (and/or a nucleic acid encoding the CasX guide RNA) (e.g., where the CasX guide RNA can be in dual or single guide format). The present disclosure provides a nucleic acid/protein complex (RNP complex)

comprising: (a) a CasX polypeptide of the present disclosure (e.g., where the CasX polypeptide can be a naturally existing protein, a nickase CasX protein, a dCasX protein, a chimeric CasX protein, etc.); and (b) a CasX guide RNA (e.g., where the CasX guide RNA can be in dual or single guide format).

CasX Protein

A CasX polypeptide (this term is used interchangeably with the term "CasX protein") can bind and/or modify (e.g., cleave, nick, methylate, demethylate, etc.) a target nucleic acid and/or a polypeptide associated with target nucleic acid (e.g., methylation or acetylation of a histone tail) (e.g., in some cases the CasX protein includes a fusion partner with an activity, and in some cases the CasX protein provides nuclease activity). In some cases, the CasX protein is a naturally-occurring protein (e.g., naturally occurs in prokaryotic cells). In other cases, the CasX protein is not a naturally-occurring polypeptide (e.g., the CasX protein is a variant CasX protein, a chimeric protein, and the like).

Assays to determine whether given protein interacts with a CasX guide RNA can be any convenient binding assay that tests for binding between a protein and a nucleic acid. Suitable binding assays (e.g., gel shift assays) will be known to one of ordinary skill in the art (e.g., assays that include adding a CasX guide RNA and a protein to a target nucleic acid). Assays to determine whether a protein has an activity (e.g., to determine if the protein has nuclease activity that cleaves a target nucleic acid and/or some heterologous activity) can be any convenient assay (e.g., any convenient nucleic acid cleavage assay that tests for nucleic acid cleavage). Suitable assays (e.g., cleavage assays) will be known to one of ordinary skill in the art.

A naturally occurring CasX protein functions as an endonuclease that catalyzes a double strand break at a specific sequence in a targeted double stranded DNA (dsDNA). The sequence specificity is provided by the associated guide RNA, which hybridizes to a target sequence within the target DNA. The naturally occurring guide RNA includes a tracrRNA hybridized to a crRNA, where the crRNA includes a guide sequence that hybridizes to a target sequence in the target DNA.

Figure 2:
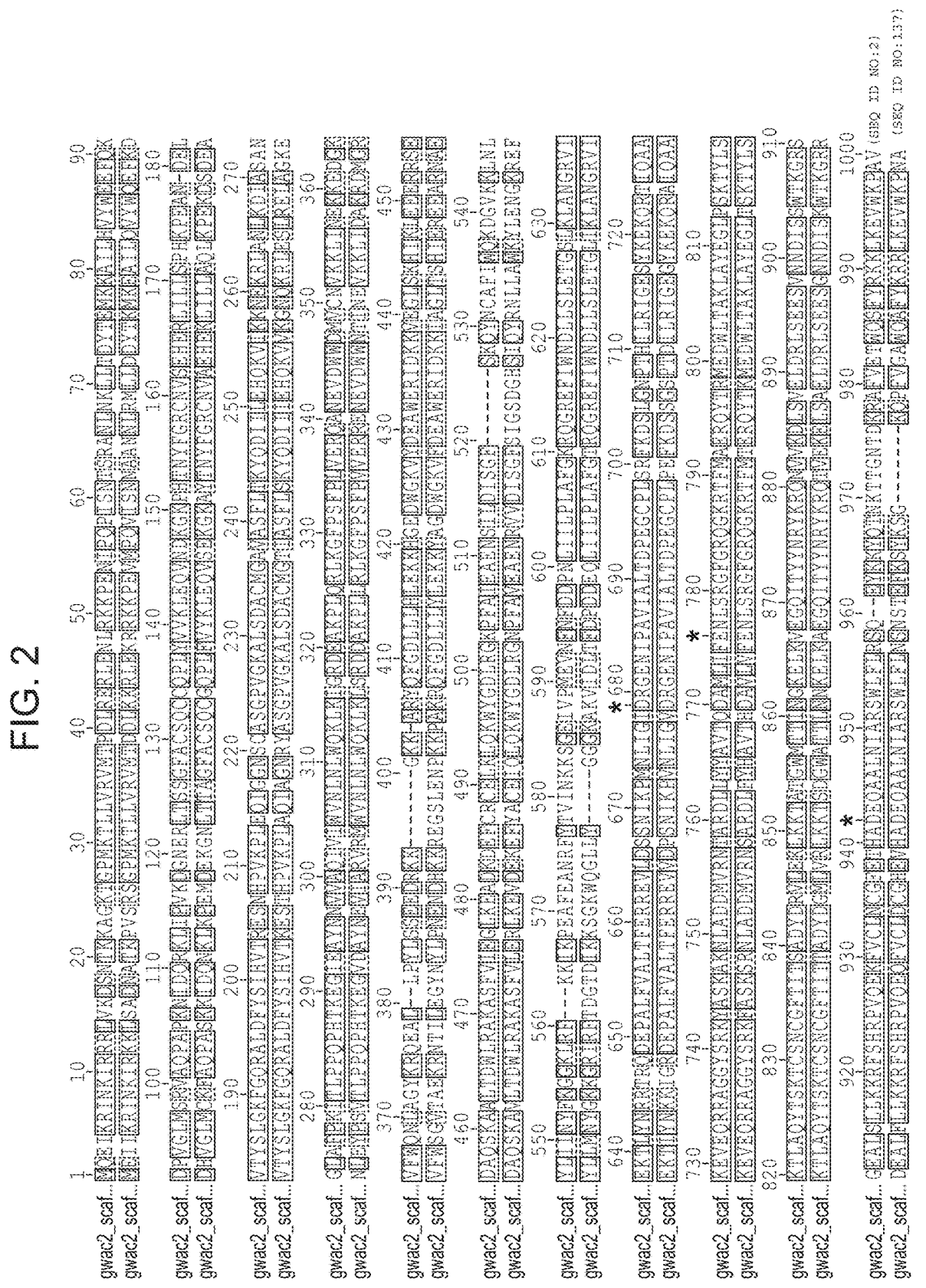

In some embodiments, the CasX protein of the subject methods and/or compositions is (or is derived from) a naturally occurring (wild type) protein. Examples of naturally occurring CasX proteins are depicted in FIGS. 1A-1B and are set forth as SEQ ID NOs: 1-3. An alignment of two naturally occurring CasX proteins is presented in FIG. 2 ('gwa2' is CasX1 and 'gwc2' is CasX2). A partial DNA scaffold of the CRISPR locus assembled from sequencing data (from a Deltaproteobacter (gwc2 scaffold) and from a Planctomycetes (gwc2 scaffold)) is set forth as SEQ ID NOs: 51 and 52, respectively. It is important to note that this newly discovered protein (CasX) is short compared to previously identified CRISPR-Cas endonucleases, and thus use of this protein as an alternative provides the advantage that the nucleotide sequence encoding the protein is relatively short. This is useful, for example, in cases where a nucleic acid encoding the CasX protein is desirable, e.g., in situations that employ a viral vector (e.g., an AAV vector), for delivery to a cell such as a eukaryotic cell (e.g., mammalian cell, human cell, mouse cell, in vitro, ex vivo, in vivo) for research and/or clinical applications. It is also noted herein that bacteria harboring CasX CRISPR loci were present in environmental samples that were collected at low temperature (e.g., 10-17° C.). Thus, CasX is expected to be able to function well at low temperatures (e.g., 10-14° C., 10-17° C., 10-20° C.) (e.g., better than other Cas endonucleases discovered to date).

In some cases, a CasX protein (of the subject compositions and/or methods) includes an amino acid sequence having 20% or more sequence identity (e.g., 30% or more, 40% or more, 50% or more, 60% or more, 70% or more, 80% or more, 85% or more, 90% or more, 95% or more, 97% or more, 98% or more, 99% or more, or 100% sequence identity) with the CasX protein sequence set forth as SEQ ID NO: 1. For example, in some cases, a CasX protein includes an amino acid sequence having 50% or more sequence identity (e.g., 60% or more, 70% or more, 80% or more, 85% or more, 90% or more, 95% or more, 97% or more, 98% or more, 99% or more, or 100% sequence identity) with the CasX protein sequence set forth as SEQ ID NO: 1. In some cases, a CasX protein includes an amino acid sequence having 80% or more sequence identity (e.g., 85% or more, 90% or more, 95% or more, 97% or more, 98% or more, 99% or more, or 100% sequence identity) with the CasX protein sequence set forth as SEQ ID NO: 1. In some cases, a CasX protein includes an amino acid sequence having 90% or more sequence identity (e.g., 95% or more, 97% or more, 98% or more, 99% or more, or 100% sequence identity) with the CasX protein sequence set forth as SEQ ID NO: 1. In some cases, a CasX protein includes an amino acid sequence having the CasX protein sequence set forth as SEQ ID NO: 1. In some cases, a CasX protein includes an amino acid sequence having the CasX protein sequence set forth as SEQ ID NO: 1, with the exception that the sequence includes an amino acid substitution (e.g., 1, 2, or 3 amino acid substitutions) that reduces the naturally occurring catalytic activity of the protein (e.g., such as at amino acid positions described below).

In some cases, a CasX protein includes an amino acid sequence having 20% or more sequence identity (e.g., 30% or more, 40% or more, 50% or more, 60% or more, 70% or more, 80% or more, 85% or more, 90% or more, 95% or more, 97% or more, 98% or more, 99% or more, or 100% sequence identity) with the CasX protein sequence set forth as SEQ ID NO: 2. In some cases, a CasX protein includes an amino acid sequence having 50% or more sequence identity (e.g., 60% or more, 70% or more, 80% or more, 85% or more, 90% or more, 95% or more, 97% or more, 98% or more, 99% or more, or 100% sequence identity) with the CasX protein sequence set forth as SEQ ID NO: 2. In some cases, a CasX protein includes an amino acid sequence having 80% or more sequence identity (e.g., 85% or more, 90% or more, 95% or more, 97% or more, 98% or more, 99% or more, or 100% sequence identity) with the CasX protein sequence set forth as SEQ ID NO: 2. In some cases, a CasX protein includes an amino acid sequence having 90% or more sequence identity (e.g., 95% or more, 97% or more, 98% or more, 99% or more, or 100% sequence identity) with the CasX protein sequence set forth as SEQ ID NO: 2. In some cases, a CasX protein includes an amino acid sequence having the CasX protein sequence set forth as SEQ ID NO: 2. In some cases, a CasX protein includes an amino acid sequence having the CasX protein sequence set forth as SEQ ID NO: 2, with the exception that the sequence includes an amino acid substitution (e.g., 1, 2, or 3 amino acid substitutions) that reduces the naturally occurring catalytic activity of the protein (e.g., such as at amino acid positions described below).

In some cases, a CasX protein includes an amino acid sequence having 20% or more sequence identity (e.g., 30% or more, 40% or more, 50% or more, 60% or more, 70% or more, 80% or more, 85% or more, 90% or more, 95% or more, 97% or more, 98% or more, 99% or more, or 100% sequence identity) with the CasX protein sequence set forth as SEQ ID NO: 3. In some cases, a CasX protein includes an amino acid sequence having 50% or more sequence identity (e.g., 60% or more, 70% or more, 80% or more, 85% or more, 90% or more, 95% or more, 97% or more, 98% or more, 99% or more, or 100% sequence identity) with the CasX protein sequence set forth as SEQ ID NO: 3. In some cases, a CasX protein includes an amino acid sequence having 80% or more sequence identity (e.g., 85% or more, 90% or more, 95% or more, 97% or more, 98% or more, 99% or more, or 100% sequence identity) with the CasX protein sequence set forth as SEQ ID NO: 3. In some cases, a CasX protein includes an amino acid sequence having 90% or more sequence identity (e.g., 95% or more, 97% or more, 98% or more, 99% or more, or 100% sequence identity) with the CasX protein sequence set forth as SEQ ID NO: 3. In some cases, a CasX protein includes an amino acid sequence having the CasX protein sequence set forth as SEQ ID NO: 3. In some cases, a CasX protein includes an amino acid sequence having the CasX protein sequence set forth as SEQ ID NO: 3, with the exception that the sequence includes an amino acid substitution (e.g., 1, 2, or 3 amino acid substitutions) that reduces the naturally occurring catalytic activity of the protein (e.g., such as at amino acid positions described below).

In some cases, a CasX protein includes an amino acid sequence having 20% or more sequence identity (e.g., 30% or more, 40% or more, 50% or more, 60% or more, 70% or more, 80% or more, 85% or more, 90% or more, 95% or more, 97% or more, 98% or more, 99% or more, or 100% sequence identity) with any one of the CasX protein sequences set forth as SEQ ID NOs: 1 and 2. In some cases, a CasX protein includes an amino acid sequence having 50% or more sequence identity (e.g., 60% or more, 70% or more, 80% or more, 85% or more, 90% or more, 95% or more, 97% or more, 98% or more, 99% or more, or 100% sequence identity) with any one of the CasX protein sequences set forth as SEQ ID NOs: 1 and 2. In some cases, a CasX protein includes an amino acid sequence having 80% or more sequence identity (e.g., 85% or more, 90% or more, 95% or more, 97% or more, 98% or more, 99% or more, or 100% sequence identity) with any one of the CasX protein sequences set forth as SEQ ID NOs: 1 and 2. In some cases, a CasX protein includes an amino acid sequence having 90% or more sequence identity (e.g., 95% or more, 97% or more, 98% or more, 99% or more, or 100% sequence identity) with any one of the CasX protein sequences set forth as SEQ ID NOs: 1 and 2. In some cases, a CasX protein includes an amino acid sequence having the CasX protein sequence set forth in any one of SEQ ID NOs: 1 and 2. In some cases, a CasX protein includes an amino acid sequence having the CasX protein sequence set forth in any one of SEQ ID NOs: 1 and 2, with the exception that the sequence includes an amino acid substitution (e.g., 1, 2, or 3 amino acid substitutions) that reduces the naturally occurring catalytic activity of the protein (e.g., such as at amino acid positions described below).

In some cases, a CasX protein includes an amino acid sequence having 20% or more sequence identity (e.g., 30% or more, 40% or more, 50% or more, 60% or more, 70% or more, 80% or more, 85% or more, 90% or more, 95% or more, 97% or more, 98% or more, 99% or more, or 100% sequence identity) with any one of the CasX protein sequences set forth as SEQ ID NOs: 1-3. In some cases, a CasX protein includes an amino acid sequence having 50% or more sequence identity (e.g., 60% or more, 70% or more, 80% or more, 85% or more, 90% or more, 95% or more, 97% or more, 98% or more, 99% or more, or 100% sequence identity) with any one of the CasX protein sequences set forth as SEQ ID NOs: 1-3. In some cases, a CasX protein includes an amino acid sequence having 80% or more sequence identity (e.g., 85% or more, 90% or more, 95% or more, 97% or more, 98% or more, 99% or more, or 100% sequence identity) with any one of the CasX protein sequences set forth as SEQ ID NOs: 1-3. In some cases, a CasX protein includes an amino acid sequence having 90% or more sequence identity (e.g., 95% or more, 97% or more, 98% or more, 99% or more, or 100% sequence identity) with any one of the CasX protein sequences set forth as SEQ ID NOs: 1-3. In some cases, a CasX protein includes an amino acid sequence having the CasX protein sequence set forth in any one of SEQ ID NOs: 1-3. In some cases, a CasX protein includes an amino acid sequence having the CasX protein sequence set forth in any one of SEQ ID NOs: 1-3, with the exception that the sequence includes an amino acid substitution (e.g., 1, 2, or 3 amino acid substitutions) that reduces the naturally occurring catalytic activity of the protein (e.g., such as at amino acid positions described below).

CasX Protein Domains

Figure 3B:
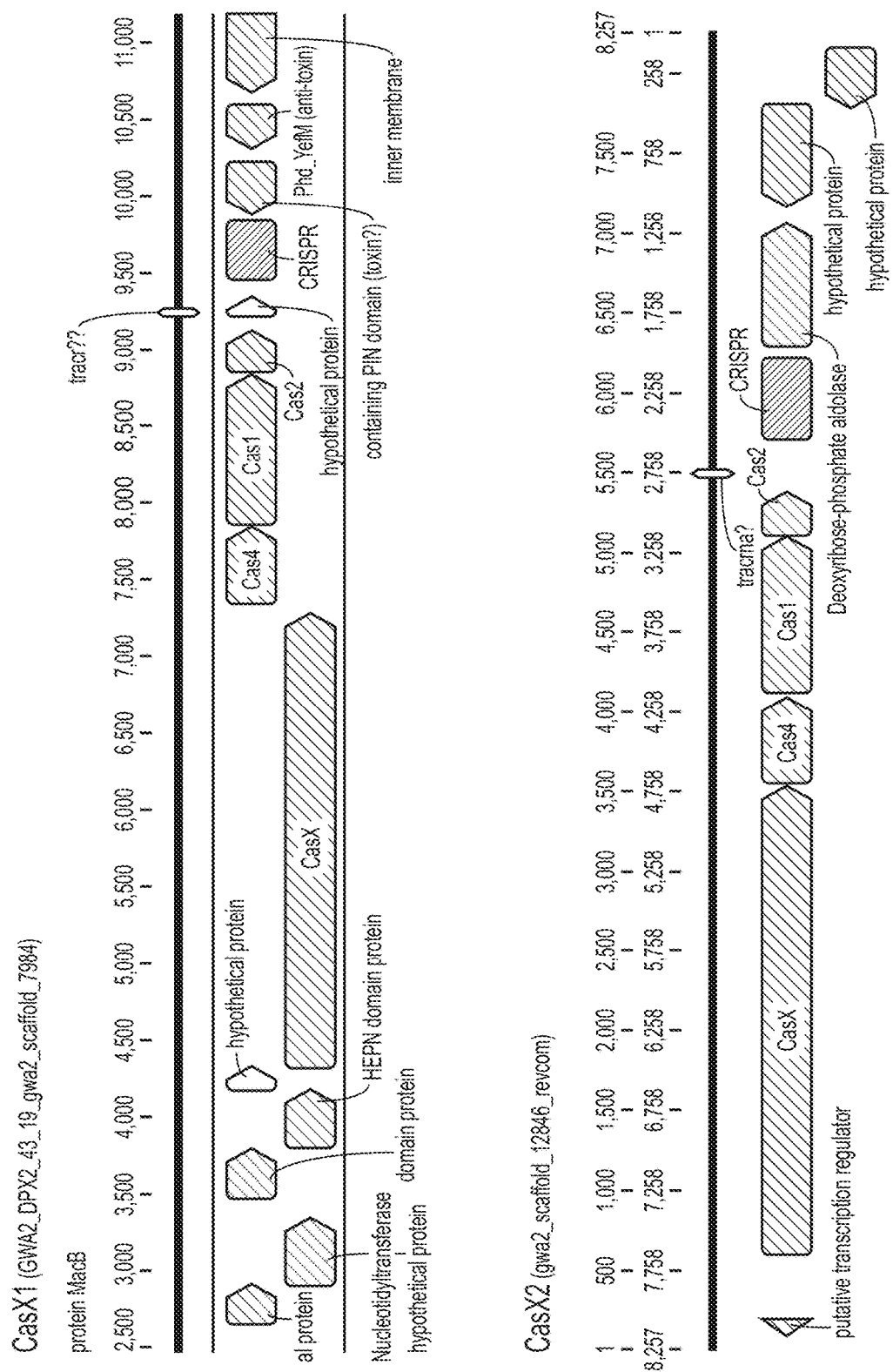

The domains of a CasX protein are depicted in FIGS. 3A-3B. As can be seen in the schematic representation of FIGS. 3A-3B (amino acids are numbered based on the CasX1 protein (SEQ ID NO: 1)), a CasX protein includes an N-terminal domain roughly 650 amino acids in length (e.g., 663 for CasX1 and 650 for CasX2), and a C-terminal domain that includes 3 partial RuvC domains (RuvC-I, RuvC-II, and RuvC-III, also referred to herein as subdomains) that are not contiguous with respect to the primary amino acid sequence of the CasX protein, but form a RuvC domain once the protein is produced and folds. Thus, in some cases, a CasX protein (of the subject compositions and/or methods) includes an amino acid sequence with an N-terminal domain (e.g., not including any fused heterologous sequence such as an NLS and/or a domain with a catalytic activity) having a length in a range of from 500-750 amino acids (e.g, from 550-750, 600-750, 640-750, 650-750, 500-700, 550-700, 600-700, 640-700, 650-700, 500-680, 550-680, 600-680, 640-680, 650-680, 500-670, 550-670, 600-670, 640-670, or 650-670 amino acids). In some cases, a CasX protein (of the subject compositions and/or methods) includes an amino acid sequence having a length (e.g., not including any fused heterologous sequence such as an NLS and/or a domain with a catalytic activity) in a range of from 500-750 amino acids (e.g, from 550-750, 600-750, 640-750, 650-750, 500-700, 550-700, 600-700, 640-700, 650-700, 500-680, 550-680, 600-680, 640-680, 650-680, 500-670, 550-670, 600-670, 640-670, or 650-670 amino acids) that is N-terminal to a split Ruv C domain (e.g., 3 partial RuvC domains—RuvC-I, RuvC-II, and RuvC-III).

In some cases, a CasX protein (of the subject compositions and/or methods) includes an amino acid sequence having 20% or more sequence identity (e.g., 30% or more, 40% or more, 50% or more, 60% or more, 70% or more, 80% or more, 85% or more, 90% or more, 95% or more, 97% or more, 98% or more, 99% or more, or 100% sequence identity) with the N-terminal domain (e.g., the domain depicted as amino acids 1-663 for CasX1 in FIG. 3A) of the CasX protein sequence set forth as SEQ ID NO: 1. For example, in some cases, a CasX protein includes an amino acid sequence having 50% or more sequence identity (e.g., 60% or more, 70% or more, 80% or more, 85% or more, 90% or more, 95% or more, 97% or more, 98% or more, 99% or more, or 100% sequence identity) with the N-terminal domain (e.g., the domain depicted as amino acids 1-663 for CasX1 in FIG. 3A) of the CasX protein sequence set forth as SEQ ID NO: 1. In some cases, a CasX protein includes an amino acid sequence having 80% or more sequence identity (e.g., 85% or more, 90% or more, 95% or more, 97% or more, 98% or more, 99% or more, or 100% sequence identity) with the N-terminal domain (e.g., the domain depicted as amino acids 1-663 for CasX1 in FIG. 3A) of the CasX protein sequence set forth as SEQ ID NO: 1. In some cases, a CasX protein includes an amino acid sequence having 90% or more sequence identity (e.g., 95% or more, 97% or more, 98% or more, 99% or more, or 100% sequence identity) with the N-terminal domain (e.g., the domain depicted as amino acids 1-663 for CasX1 in FIG. 3A) of the CasX protein sequence set forth as SEQ ID NO: 1. In some cases, a CasX protein includes an amino acid sequence having amino acids 1-663 of the CasX protein sequence set forth as SEQ ID NO: 1.

In some cases, a CasX protein (of the subject compositions and/or methods) includes an amino acid sequence having 20% or more sequence identity (e.g., 30% or more, 40% or more, 50% or more, 60% or more, 70% or more, 80% or more, 85% or more, 90% or more, 95% or more, 97% or more, 98% or more, 99% or more, or 100% sequence identity) with the N-terminal domain (e.g., the domain depicted as amino acids 1-663 for CasX1 in FIG. 3A) of the CasX protein sequence set forth as SEQ ID NO: 2. For example, in some cases, a CasX protein includes an amino acid sequence having 50% or more sequence identity (e.g., 60% or more, 70% or more, 80% or more, 85% or more, 90% or more, 95% or more, 97% or more, 98% or more, 99% or more, or 100% sequence identity) with the N-terminal domain (e.g., the domain depicted as amino acids 1-663 for CasX1 in FIG. 3A) of the CasX protein sequence set forth as SEQ ID NO: 2. In some cases, a CasX protein includes an amino acid sequence having 80% or more sequence identity (e.g., 85% or more, 90% or more, 95% or more, 97% or more, 98% or more, 99% or more, or 100% sequence identity) with the N-terminal domain (e.g., the domain depicted as amino acids 1-663 for CasX1 in FIG. 3A) of the CasX protein sequence set forth as SEQ ID NO: 2. In some cases, a CasX protein includes an amino acid sequence having 90% or more sequence identity (e.g., 95% or more, 97% or more, 98% or more, 99% or more, or 100% sequence identity) with the N-terminal domain (e.g., the domain depicted as amino acids 1-663 for CasX1 in FIG. 3A) of the CasX protein sequence set forth as SEQ ID NO: 2. In some cases, a CasX protein includes an amino acid sequence of SEQ ID NO: 2 corresponding to amino acids 1-663 of the CasX protein sequence set forth as SEQ ID NO: 1.

In some cases, a CasX protein (of the subject compositions and/or methods) includes an amino acid sequence having 20% or more sequence identity (e.g., 30% or more, 40% or more, 50% or more, 60% or more, 70% or more, 80% or more, 85% or more, 90% or more, 95% or more, 97% or more, 98% or more, 99% or more, or 100% sequence identity) with the N-terminal domain (e.g., the domain depicted as amino acids 1-663 for CasX1 in FIG. 3A) of the CasX protein sequence set forth as SEQ ID NO: 3. For example, in some cases, a CasX protein includes an amino acid sequence having 50% or more sequence identity (e.g., 60% or more, 70% or more, 80% or more, 85% or more, 90% or more, 95% or more, 97% or more, 98% or more, 99% or more, or 100% sequence identity) with the N-terminal domain (e.g., the domain depicted as amino acids 1-663 for CasX1 in FIG. 3A) of the CasX protein sequence set forth as SEQ ID NO: 3. In some cases, a CasX protein includes an amino acid sequence having 80% or more sequence identity (e.g., 85% or more, 90% or more, 95% or more, 97% or more, 98% or more, 99% or more, or 100% sequence identity) with the N-terminal domain (e.g., the domain depicted as amino acids 1-663 for CasX1 in FIG. 3A) of the CasX protein sequence set forth as SEQ ID NO: 3. In some cases, a CasX protein includes an amino acid sequence having 90% or more sequence identity (e.g., 95% or more, 97% or more, 98% or more, 99% or more, or 100% sequence identity) with the N-terminal domain (e.g., the domain depicted as amino acids 1-663 for CasX1 in FIG. 3A) of the CasX protein sequence set forth as SEQ ID NO: 3. In some cases, a CasX protein includes an amino acid sequence of SEQ ID NO: 3 corresponding to amino acids 1-663 of the CasX protein sequence set forth as SEQ ID NO: 1.

In some cases, a CasX protein (of the subject compositions and/or methods) includes an amino acid sequence having 20% or more sequence identity (e.g., 30% or more, 40% or more, 50% or more, 60% or more, 70% or more, 80% or more, 85% or more, 90% or more, 95% or more, 97% or more, 98% or more, 99% or more, or 100% sequence identity) with the N-terminal domain (e.g., the domain depicted as amino acids 1-663 for CasX1 in FIG. 3A) of any one of the CasX protein sequences set forth as SEQ ID NOs: 1 and 2. For example, in some cases, a CasX protein includes an amino acid sequence having 50% or more sequence identity (e.g., 60% or more, 70% or more, 80% or more, 85% or more, 90% or more, 95% or more, 97% or more, 98% or more, 99% or more, or 100% sequence identity) with the N-terminal domain (e.g., the domain depicted as amino acids 1-663 for CasX1 in FIG. 3A) of any one of the CasX protein sequences set forth as SEQ ID NOs: 1 and 2. In some cases, a CasX protein includes an amino acid sequence having 80% or more sequence identity (e.g., 85% or more, 90% or more, 95% or more, 97% or more, 98% or more, 99% or more, or 100% sequence identity) with the N-terminal domain (e.g., the domain depicted as amino acids 1-663 for CasX1 in FIG. 3A) of any one of the CasX protein sequences set forth as SEQ ID NOs: 1 and 2. In some cases, a CasX protein includes an amino acid sequence having 90% or more sequence identity (e.g., 95% or more, 97% or more, 98% or more, 99% or more, or 100% sequence identity) with the N-terminal domain (e.g., the domain depicted as amino acids 1-663 for CasX1 in FIG. 3A) of any one of the CasX protein sequences set forth as SEQ ID NOs: 1 and 2. In some cases, a CasX protein includes an amino acid sequence corresponding to amino acids 1-663 of the CasX protein sequence set forth as SEQ ID NO: 1.

In some cases, a CasX protein (of the subject compositions and/or methods) includes a first amino acid sequence having 20% or more sequence identity (e.g., 30% or more, 40% or more, 50% or more, 60% or more, 70% or more, 80% or more, 85% or more, 90% or more, 95% or more, 97% or more, 98% or more, 99% or more, or 100% sequence identity) with the N-terminal domain (e.g., the domain depicted as amino acids 1-663 for CasX1 in FIG. 3A) of any one of the CasX protein sequences set forth as SEQ ID NOs: 1 and 2; and a second amino acid sequence, C-terminal to the first amino acid sequence, that includes a split Ruv C domain (e.g., 3 partial RuvC domains—RuvC-I, RuvC-II, and RuvC-III). For example, in some cases, a CasX protein includes a first amino acid sequence having 50% or more sequence identity (e.g., 60% or more, 70% or more, 80% or more, 85% or more, 90% or more, 95% or more, 97% or more, 98% or more, 99% or more, or 100% sequence identity) with the N-terminal domain (e.g., the domain depicted as amino acids 1-663 for CasX1 in FIG. 3A) of any one of the CasX protein sequences set forth as SEQ ID NOs: 1 and 2; and a second amino acid sequence, C-terminal to the first amino acid sequence, that includes a split Ruv C domain (e.g., 3 partial RuvC domains—RuvC-I, RuvC-II, and RuvC-III). In some cases, a CasX protein includes a first amino acid sequence having 80% or more sequence identity (e.g., 85% or more, 90% or more, 95% or more, 97% or more, 98% or more, 99% or more, or 100% sequence identity) with the N-terminal domain (e.g., the domain depicted as amino acids 1-663 for CasX1 in FIG. 3A) of any one of the CasX protein sequences set forth as SEQ ID NOs: 1 and 2; and a second amino acid sequence, C-terminal to the first amino acid sequence, that includes a split Ruv C domain (e.g., 3 partial RuvC domains—RuvC-I, RuvC-II, and RuvC-III). In some cases, a CasX protein includes a first amino acid sequence having 90% or more sequence identity (e.g., 95% or more, 97% or more, 98% or more, 99% or more, or 100% sequence identity) with the N-terminal domain (e.g., the domain depicted as amino acids 1-663 for CasX1 in FIG. 3A) of any one of the CasX protein sequences set forth as SEQ ID NOs: 1 and 2; and a second amino acid sequence, C-terminal to the first amino acid sequence, that includes a split Ruv C domain (e.g., 3 partial RuvC domains—RuvC-I, RuvC-II, and RuvC-III). In some cases, a CasX protein includes an amino acid sequence corresponding to amino acids 1-663 of the CasX protein sequence set forth as SEQ ID NO: 1 (e.g., amino acids 1-650 of the CasX protein sequence set forth as SEQ ID NO: 2); and a second amino acid sequence, C-terminal to the first amino acid sequence, that includes a split Ruv C domain (e.g., 3 partial RuvC domains—RuvC-I, RuvC-II, and RuvC-III).

In some cases, a CasX protein (of the subject compositions and/or methods) includes an amino acid sequence having 20% or more sequence identity (e.g., 30% or more, 40% or more, 50% or more, 60% or more, 70% or more, 80% or more, 85% or more, 90% or more, 95% or more, 97% or more, 98% or more, 99% or more, or 100% sequence identity) with the N-terminal domain (e.g., the domain depicted as amino acids 1-663 for CasX1 in FIG. 3A) of any one of the CasX protein sequences set forth as SEQ ID NOs: 1-3. For example, in some cases, a CasX protein includes an amino acid sequence having 50% or more sequence identity (e.g., 60% or more, 70% or more, 80% or more, 85% or more, 90% or more, 95% or more, 97% or more, 98% or more, 99% or more, or 100% sequence identity) with the N-terminal domain (e.g., the domain depicted as amino acids 1-663 for CasX1 in FIG. 3A) of any one of the CasX protein sequences set forth as SEQ ID NOs: 1-3. In some cases, a CasX protein includes an amino acid sequence having 80% or more sequence identity (e.g., 85% or more, 90% or more, 95% or more, 97% or more, 98% or more, 99% or more, or 100% sequence identity) with the N-terminal domain (e.g., the domain depicted as amino acids 1-663 for CasX1 in FIG. 3A) of any one of the CasX protein sequences set forth as SEQ ID NOs: 1-3. In some cases, a CasX protein includes an amino acid sequence having 90% or more sequence identity (e.g., 95% or more, 97% or more, 98% or more, 99% or more, or 100% sequence identity) with the N-terminal domain (e.g., the domain depicted as amino acids 1-663 for CasX1 in FIG. 3A) of any one of the CasX protein sequences set forth as SEQ ID NOs: 1-3. In some cases, a CasX protein includes an amino acid sequence corresponding to amino acids 1-663 of the CasX protein sequence set forth as SEQ ID NO: 1.

In some cases, a CasX protein (of the subject compositions and/or methods) includes a first amino acid sequence having 20% or more sequence identity (e.g., 30% or more, 40% or more, 50% or more, 60% or more, 70% or more, 80% or more, 85% or more, 90% or more, 95% or more, 97% or more, 98% or more, 99% or more, or 100% sequence identity) with the N-terminal domain (e.g., the domain depicted as amino acids 1-663 for CasX1 in FIG. 3A) of any one of the CasX protein sequences set forth as SEQ ID NOs: 1-3; and a second amino acid sequence, C-terminal to the first amino acid sequence, that includes a split Ruv C domain (e.g., 3 partial RuvC domains—RuvC-I, RuvC-II, and RuvC-III). For example, in some cases, a CasX protein includes a first amino acid sequence having 50% or more sequence identity (e.g., 60% or more, 70% or more, 80% or more, 85% or more, 90% or more, 95% or more, 97% or more, 98% or more, 99% or more, or 100% sequence identity) with the N-terminal domain (e.g., the domain depicted as amino acids 1-663 for CasX1 in FIG. 3A) of any one of the CasX protein sequences set forth as SEQ ID NOs: 1-3; and a second amino acid sequence, C-terminal to the first amino acid sequence, that includes a split Ruv C domain (e.g., 3 partial RuvC domains—RuvC-I, RuvC-II, and RuvC-III). In some cases, a CasX protein includes a first amino acid sequence having 80% or more sequence identity (e.g., 85% or more, 90% or more, 95% or more, 97% or more, 98% or more, 99% or more, or 100% sequence identity) with the N-terminal domain (e.g., the domain depicted as amino acids 1-663 for CasX1 in FIG. 3A) of any one of the CasX protein sequences set forth as SEQ ID NOs: 1-3; and a second amino acid sequence, C-terminal to the first amino acid sequence, that includes a split Ruv C domain (e.g., 3 partial RuvC domains—RuvC-I, RuvC-II, and RuvC-III). In some cases, a CasX protein includes a first amino acid sequence having 90% or more sequence identity (e.g., 95% or more, 97% or more, 98% or more, 99% or more, or 100% sequence identity) with the N-terminal domain (e.g., the domain depicted as amino acids 1-663 for CasX1 in FIG. 3A) of any one of the CasX protein sequences set forth as SEQ ID NOs: 1-3; and a second amino acid sequence, C-terminal to the first amino acid sequence, that includes a split Ruv C domain (e.g., 3 partial RuvC domains—RuvC-I, RuvC-II, and RuvC-III). In some cases, a CasX protein includes an amino acid sequence corresponding to amino acids 1-663 of the CasX protein sequence set forth as SEQ ID NO: 1 (e.g., amino acids 1-650 of the CasX protein sequence set forth as SEQ ID NO: 2); and a second amino acid sequence, C-terminal to the first amino acid sequence, that includes a split Ruv C domain (e.g., 3 partial RuvC domains—RuvC-I, RuvC-II, and RuvC-III).

In some embodiments, the split RuvC domain of a CasX protein (of the subject compositions and/or methods) includes a region between the RuvC-II and RuvC-III subdomains that is larger than the RuvC-III subdomain. For example, in some cases, the ratio of the length of the region between the RuvC-II and RuvC-III subdomains over the length of the RuvC-III subdomain is 1.1 or greater (e.g., 1.2). In some cases, the ratio of the length of the region between the RuvC-II and RuvC-III subdomains over the length of the RuvC-III subdomain is greater than 1.). In some cases, the ratio of the length of the region between the RuvC-II and RuvC-III subdomains over the length of the RuvC-III subdomain is greater than 1and between 1 and 1.3 (e.g., 1 and 1.2).

In some embodiments (for a CasX protein of the subject compositions and/or methods), the ratio of the length of the RuvC-II subdomain over the length of the RuvC-III subdomain is 2 or less (e.g., 1.8 or less, 1.7 or less, 1.6 or less, 1.5 or less, or 1.4 or less). For example, in some cases, the ratio of the length of the RuvC-II subdomain over the length of the RuvC-III subdomain is 1.5 or less (e.g., 1.4 or less). In some embodiments, the ratio of the length of the RuvC-II subdomain over the length of the RuvC-III subdomain is in a range of from 1 to 2 (e.g., from 1.1 to 2, 1.2 to 2, 1 to 1.8, 1.1 to 1.8, 1.2 to 1.8, 1 to 1.6, 1.1 to 1.6, 1.2 to 1.6, 1 to 14, 1.1 to 1.4, or 1.2 to 1.4).

In some cases (for a CasX protein of the subject compositions and/or methods), the ratio of the length of the region between the RuvC-II and RuvC-III subdomains over the length of the RuvC-III subdomain is greater than 1. In some cases, the ratio of the length of the region between the RuvC-II and RuvC-III subdomains over the length of the RuvC-III subdomain is greater than l and between 1 and 1.3 (e.g., 1 and 1.2).

In some cases (for a CasX protein of the subject compositions and/or methods), the region between the RuvC-II and RuvC-III subdomains is at least 73 amino acids in length (e.g., at least 75, 77, 80, 85, or 87 amino acids in length). For example, in some cases, the region between the RuvC-II and RuvC-III subdomains is at least 78 amino acids in length (e.g., at least 80, 85, or 87 amino acids in length). In some cases, the region between the RuvC-II and RuvC-III subdomains is at least 85 amino acids in length. In some cases, the region between the RuvC-II and RuvC-III subdomains has a length in a range of from 75-100 amino acids (e.g., a range of from 75-95, 75-90, 75-88, 78-100, 78-95, 78-90, 78-88, 80-100, 80-95, 80-90, 80-88, 83-100, 83-95, 83-90, 83-88, 85-100, 85-95, 85-90, or 85-88 amino acids). In some cases, the region between the RuvC-II and RuvC-III subdomains has a length in a range of from 80-95 amino acids (e.g., a range of from 80-90, 80-88, 83-95, 83-90, 83-88, 85-95, 85-90, or 85-88 amino acids).

In some cases, a CasX protein (of the subject compositions and/or methods) includes a first amino acid sequence having 20% or more sequence identity (e.g., 30% or more, 40% or more, 50% or more, 60% or more, 70% or more, 80% or more, 85% or more, 90% or more, 95% or more, 97% or more, 98% or more, 99% or more, or 100% sequence identity) with the N-terminal domain (e.g., the domain depicted as amino acids 1-663 for CasX1 in FIG. 3A) of any one of the CasX protein sequences set forth as SEQ ID NOs: 1 and 2; and a second amino acid sequence, C-terminal to the first amino acid sequence, that includes 3 partial RuvC domains—RuvC-I, RuvC-II, and RuvC-III—where: (i) the ratio of the length of the region between the RuvC-II and RuvC-III subdomains over the length of the RuvC-III subdomain is 1.1 or greater (e.g., 1.2); (ii) the ratio of the length of the region between the RuvC-II and RuvC-III subdomains over the length of the RuvC-III subdomain is greater than 1; (iii) the ratio of the length of the region between the RuvC-II and RuvC-III subdomains over the length of the RuvC-III subdomain is greater than l and between 1 and 1.3 (e.g., 1 and 1.2); (iv) the ratio of the length of the RuvC-II subdomain over the length of the RuvC-III subdomain is 2 or less (e.g., 1.8 or less, 1.7 or less, 1.6 or less, 1.5 or less, or 1.4 or less); (v) the ratio of the length of the RuvC-II subdomain over the length of the RuvC-III subdomain is 1.5 or less (e.g., 1.4 or less); (vi) the ratio of the length of the RuvC-II subdomain over the length of the RuvC-III subdomain is in a range of from 1 to 2 (e.g., from 1.1 to 2, 1.2 to 2, 1 to 1.8, 1.1 to 1.8, 1.2 to 1.8, 1 to 1.6, 1.1 to 1.6, 1.2 to 1.6, 1 to 14, 1.1 to 1.4, or 1.2 to 1.4); (vii) the ratio of the length of the region between the RuvC-II and RuvC-III subdomains over the length of the RuvC-III subdomain is greater than 1; (viii) the ratio of the length of the region between the RuvC-II and RuvC-III subdomains over the length of the RuvC-III subdomain is greater than l and between 1 and 1.3 (e.g., 1 and 1.2); (ix) the region between the RuvC-II and RuvC-III subdomains is at least 73 amino acids in length (e.g., at least 75, 77, 80, 85, or 87 amino acids in length); (x) the region between the RuvC-II and RuvC-III subdomains is at least 78 amino acids in length (e.g., at least 80, 85, or 87 amino acids in length); (xi) the region between the RuvC-II and RuvC-III subdomains is at least 85 amino acids in length; (x) the region between the RuvC-II and RuvC-III subdomains has a length in a range of from 75-100 amino acids (e.g., a range of from 75-95, 75-90, 75-88, 78-100, 78-95, 78-90, 78-88, 80-100, 80-95, 80-90, 80-88, 83-100, 83-95, 83-90, 83-88, 85-100, 85-95, 85-90, or 85-88 amino acids); or (xi) the region between the RuvC-II and RuvC-III subdomains has a length in a range of from 80-95 amino acids (e.g., a range of from 80-90, 80-88, 83-95, 83-90, 83-88, 85-95, 85-90, or 85-88 amino acids).

For example, in some cases, a CasX protein includes a first amino acid sequence having 50% or more sequence identity (e.g., 60% or more, 70% or more, 80% or more, 85% or more, 90% or more, 95% or more, 97% or more, 98% or more, 99% or more, or 100% sequence identity) with the N-terminal domain (e.g., the domain depicted as amino acids 1-663 for CasX1 in FIG. 3A) of any one of the CasX protein sequences set forth as SEQ ID NOs: 1 and 2; and a second amino acid sequence, C-terminal to the first amino acid sequence, that includes 3 partial RuvC domains—RuvC-I, RuvC-II, and RuvC-III—where: (i) the ratio of the length of the region between the RuvC-II and RuvC-III subdomains over the length of the RuvC-III subdomain is 1.1 or greater (e.g., 1.2); (ii) the ratio of the length of the region between the RuvC-II and RuvC-III subdomains over the length of the RuvC-III subdomain is greater than 1; (iii) the ratio of the length of the region between the RuvC-II and RuvC-III subdomains over the length of the RuvC-III subdomain is greater than l and between 1 and 1.3 (e.g., 1 and 1.2); (iv) the ratio of the length of the RuvC-II subdomain over the length of the RuvC-III subdomain is 2 or less (e.g., 1.8 or less, 1.7 or less, 1.6 or less, 1.5 or less, or 1.4 or less); (v) the ratio of the length of the RuvC-II subdomain over the length of the RuvC-III subdomain is 1.5 or less (e.g., 1.4 or less); (vi) the ratio of the length of the RuvC-II subdomain over the length of the RuvC-III subdomain is in a range of from 1 to 2 (e.g., from 1.1 to 2, 1.2 to 2, 1 to 1.8, 1.1 to 1.8, 1.2 to 1.8, 1 to 1.6, 1.1 to 1.6, 1.2 to 1.6, 1 to 14, 1.1 to 1.4, or 1.2 to 1.4); (vii) the ratio of the length of the region between the RuvC-II and RuvC-III subdomains over the length of the RuvC-III subdomain is greater than 1; (viii) the ratio of the length of the region between the RuvC-II and RuvC-III subdomains over the length of the RuvC-III subdomain is greater than l and between 1 and 1.3 (e.g., 1 and 1.2); (ix) the region between the RuvC-II and RuvC-III subdomains is at least 73 amino acids in length (e.g., at least 75, 77, 80, 85, or 87 amino acids in length); (x) the region between the RuvC-II and RuvC-III subdomains is at least 78 amino acids in length (e.g., at least 80, 85, or 87 amino acids in length); (xi) the region between the RuvC-II and RuvC-III subdomains is at least 85 amino acids in length; (x) the region between the RuvC-II and RuvC-III subdomains has a length in a range of from 75-100 amino acids (e.g., a range of from 75-95, 75-90, 75-88, 78-100, 78-95, 78-90, 78-88, 80-100, 80-95, 80-90, 80-88, 83-100, 83-95, 83-90, 83-88, 85-100, 85-95, 85-90, or 85-88 amino acids); or (xi) the region between the RuvC-II and RuvC-III subdomains has a length in a range of from 80-95 amino acids (e.g., a range of from 80-90, 80-88, 83-95, 83-90, 83-88, 85-95, 85-90, or 85-88 amino acids).

In some cases, a CasX protein includes a first amino acid sequence having 80% or more sequence identity (e.g., 85% or more, 90% or more, 95% or more, 97% or more, 98% or more, 99% or more, or 100% sequence identity) with the N-terminal domain (e.g., the domain depicted as amino acids 1-663 for CasX1 in FIG. 3A) of any one of the CasX protein sequences set forth as SEQ ID NOs: 1 and 2; and a second amino acid sequence, C-terminal to the first amino acid sequence, that includes 3 partial RuvC domains—RuvC-I, RuvC-II, and RuvC-III—where: (i) the ratio of the length of the region between the RuvC-II and RuvC-III subdomains over the length of the RuvC-III subdomain is 1.1 or greater (e.g., 1.2); (ii) the ratio of the length of the region between the RuvC-II and RuvC-III subdomains over the length of the RuvC-III subdomain is greater than 1; (iii) the ratio of the length of the region between the RuvC-II and RuvC-III subdomains over the length of the RuvC-III subdomain is greater than 1 and between 1 and 1.3 (e.g., 1 and 1.2); (iv) the ratio of the length of the RuvC-II subdomain over the length of the RuvC-III subdomain is 2 or less (e.g., 1.8 or less, 1.7 or less, 1.6 or less, 1.5 or less, or 1.4 or less); (v) the ratio of the length of the RuvC-II subdomain over the length of the RuvC-III subdomain is 1.5 or less (e.g., 1.4 or less); (vi) the ratio of the length of the RuvC-II subdomain over the length of the RuvC-III subdomain is in a range of from 1 to 2 (e.g., from 1.1 to 2, 1.2 to 2, 1 to 1.8, 1.1 to 1.8, 1.2 to 1.8, 1 to 1.6, 1.1 to 1.6, 1.2 to 1.6, 1 to 14, 1.1 to 1.4, or 1.2 to 1.4); (vii) the ratio of the length of the region between the RuvC-II and RuvC-III subdomains over the length of the RuvC-III subdomain is greater than 1; (viii) the ratio of the length of the region between the RuvC-II and RuvC-III subdomains over the length of the RuvC-III subdomain is greater than 1 and between 1 and 1.3 (e.g., 1 and 1.2); (ix) the region between the RuvC-II and RuvC-III subdomains is at least 73 amino acids in length (e.g., at least 75, 77, 80, 85, or 87 amino acids in length); (x) the region between the RuvC-II and RuvC-III subdomains is at least 78 amino acids in length (e.g., at least 80, 85, or 87 amino acids in length); (xi) the region between the RuvC-II and RuvC-III subdomains is at least 85 amino acids in length; (x) the region between the RuvC-II and RuvC-III subdomains has a length in a range of from 75-100 amino acids (e.g., a range of from 75-95, 75-90, 75-88, 78-100, 78-95, 78-90, 78-88, 80-100, 80-95, 80-90, 80-88, 83-100, 83-95, 83-90, 83-88, 85-100, 85-95, 85-90, or 85-88 amino acids); or (xi) the region between the RuvC-II and RuvC-III subdomains has a length in a range of from 80-95 amino acids (e.g., a range of from 80-90, 80-88, 83-95, 83-90, 83-88, 85-95, 85-90, or 85-88 amino acids).

In some cases, a CasX protein includes a first amino acid sequence having 90% or more sequence identity (e.g., 95% or more, 97% or more, 98% or more, 99% or more, or 100% sequence identity) with the N-terminal domain (e.g., the domain depicted as amino acids 1-663 for CasX1 in 3A) of any one of the CasX protein sequences set forth as SEQ ID NOs: 1 and 2; and a second amino acid sequence, C-terminal to the first amino acid sequence, that includes 3 partial RuvC domains—RuvC-I, RuvC-II, and RuvC-III—where: (i) the ratio of the length of the region between the RuvC-II and RuvC-III subdomains over the length of the RuvC-III subdomain is 1.1 or greater (e.g., 1.2); (ii) the ratio of the length of the region between the RuvC-II and RuvC-III subdomains over the length of the RuvC-III subdomain is greater than 1; (iii) the ratio of the length of the region between the RuvC-II and RuvC-III subdomains over the length of the RuvC-III subdomain is greater than 1 and between 1 and 1.3 (e.g., 1 and 1.2); (iv) the ratio of the length of the RuvC-II subdomain over the length of the RuvC-III subdomain is 2 or less (e.g., 1.8 or less, 1.7 or less, 1.6 or less, 1.5 or less, or 1.4 or less); (v) the ratio of the length of the RuvC-II subdomain over the length of the RuvC-III subdomain is 1.5 or less (e.g., 1.4 or less); (vi) the ratio of the length of the RuvC-II subdomain over the length of the RuvC-III subdomain is in a range of from 1 to 2 (e.g., from 1.1 to 2, 1.2 to 2, 1 to 1.8, 1.1 to 1.8, 1.2 to 1.8, 1 to 1.6, 1.1 to 1.6, 1.2 to 1.6, 1 to 14, 1.1 to 1.4, or 1.2 to 1.4); (vii) the ratio of the length of the region between the RuvC-II and RuvC-III subdomains over the length of the RuvC-III subdomain is greater than 1; (viii) the ratio of the length of the region between the RuvC-II and RuvC-III subdomains over the length of the RuvC-III subdomain is greater than 1 and between 1 and 1.3 (e.g., 1 and 1.2); (ix) the region between the RuvC-II and RuvC-III subdomains is at least 73 amino acids in length (e.g., at least 75, 77, 80, 85, or 87 amino acids in length); (x) the region between the RuvC-II and RuvC-III subdomains is at least 78 amino acids in length (e.g., at least 80, 85, or 87 amino acids in length); (xi) the region between the RuvC-II and RuvC-III subdomains is at least 85 amino acids in length; (x) the region between the RuvC-II and RuvC-III subdomains has a length in a range of from 75-100 amino acids (e.g., a range of from 75-95, 75-90, 75-88, 78-100, 78-95, 78-90, 78-88, 80-100, 80-95, 80-90, 80-88, 83-100, 83-95, 83-90, 83-88, 85-100, 85-95, 85-90, or 85-88 amino acids); or (xi) the region between the RuvC-II and RuvC-III subdomains has a length in a range of from 80-95 amino acids (e.g., a range of from 80-90, 80-88, 83-95, 83-90, 83-88, 85-95, 85-90, or 85-88 amino acids).

In some cases, a CasX protein (of the subject compositions and/or methods) includes a first amino acid sequence having 20% or more sequence identity (e.g., 30% or more, 40% or more, 50% or more, 60% or more, 70% or more, 80% or more, 85% or more, 90% or more, 95% or more, 97% or more, 98% or more, 99% or more, or 100% sequence identity) with the N-terminal domain (e.g., the domain depicted as amino acids 1-663 for CasX1 in FIG. 3A) of any one of the CasX protein sequences set forth as SEQ ID NOs: 1-3; and a second amino acid sequence, C-terminal to the first amino acid sequence, that includes 3 partial RuvC domains—RuvC-I, RuvC-II, and RuvC-III—where: (i) the ratio of the length of the region between the RuvC-II and RuvC-III subdomains over the length of the RuvC-III subdomain is 1.1 or greater (e.g., 1.2); (ii) the ratio of the length of the region between the RuvC-II and RuvC-III subdomains over the length of the RuvC-III subdomain is greater than 1; (iii) the ratio of the length of the region between the RuvC-II and RuvC-III subdomains over the length of the RuvC-III subdomain is greater than 1 and between 1 and 1.3 (e.g., 1 and 1.2); (iv) the ratio of the length of the RuvC-II subdomain over the length of the RuvC-III subdomain is 2 or less (e.g., 1.8 or less, 1.7 or less, 1.6 or less, 1.5 or less, or 1.4 or less); (v) the ratio of the length of the RuvC-II subdomain over the length of the RuvC-III subdomain is 1.5 or less (e.g., 1.4 or less); (vi) the ratio of the length of the RuvC-II subdomain over the length of the RuvC-III subdomain is in a range of from 1 to 2 (e.g., from 1.1 to 2, 1.2 to 2, 1 to 1.8, 1.1 to 1.8, 1.2 to 1.8, 1 to 1.6, 1.1 to 1.6, 1.2 to 1.6, 1 to 14, 1.1 to 1.4, or 1.2 to 1.4); (vii) the ratio of the length of the region between the RuvC-II and RuvC-III subdomains over the length of the RuvC-III subdomain is greater than 1; (viii) the ratio of the length of the region between the RuvC-II and RuvC-III subdomains over the length of the RuvC-III subdomain is greater than 1 and between 1 and 1.3 (e.g., 1 and 1.2); (ix) the region between the RuvC-II and RuvC-III subdomains is at least 73 amino acids in length (e.g., at least 75, 77, 80, 85, or 87 amino acids in length); (x) the region between the RuvC-II and RuvC-III subdomains is at least 78 amino acids in length (e.g., at least 80, 85, or 87 amino acids in length); (xi) the region between the RuvC-II and RuvC-III subdomains is at least 85 amino acids in length; (x) the region between the RuvC-II and RuvC-III subdomains has a length in a range of from 75-100 amino acids (e.g., a range of from 75-95, 75-90, 75-88, 78-100, 78-95, 78-90, 78-88, 80-100, 80-95, 80-90, 80-88, 83-100, 83-95, 83-90, 83-88, 85-100, 85-95, 85-90, or 85-88 amino acids); or (xi) the region between the RuvC-II and RuvC-III subdomains has a length in a range of from 80-95 amino acids (e.g., a range of from 80-90, 80-88, 83-95, 83-90, 83-88, 85-95, 85-90, or 85-88 amino acids).

For example, in some cases, a CasX protein includes a first amino acid sequence having 50% or more sequence identity (e.g., 60% or more, 70% or more, 80% or more, 85% or more, 90% or more, 95% or more, 97% or more, 98% or more, 99% or more, or 100% sequence identity) with the N-terminal domain (e.g., the domain depicted as amino acids 1-663 for CasX1 in FIG. 3A) of any one of the CasX protein sequences set forth as SEQ ID NOs: 1-3; and a second amino acid sequence, C-terminal to the first amino acid sequence, that includes 3 partial RuvC domains—RuvC-I, RuvC-II, and RuvC-III—where: (i) the ratio of the length of the region between the RuvC-II and RuvC-III subdomains over the length of the RuvC-III subdomain is 1.1 or greater (e.g., 1.2); (ii) the ratio of the length of the region between the RuvC-II and RuvC-III subdomains over the length of the RuvC-III subdomain is greater than 1; (iii) the ratio of the length of the region between the RuvC-II and RuvC-III subdomains over the length of the RuvC-III subdomain is greater than 1 and between 1 and 1.3 (e.g., 1 and 1.2); (iv) the ratio of the length of the RuvC-II subdomain over the length of the RuvC-III subdomain is 2 or less (e.g., 1.8 or less, 1.7 or less, 1.6 or less, 1.5 or less, or 1.4 or less); (v) the ratio of the length of the RuvC-II subdomain over the length of the RuvC-III subdomain is 1.5 or less (e.g., 1.4 or less); (vi) the ratio of the length of the RuvC-II subdomain over the length of the RuvC-III subdomain is in a range of from 1 to 2 (e.g., from 1.1 to 2, 1.2 to 2, 1 to 1.8, 1.1 to 1.8, 1.2 to 1.8, 1 to 1.6, 1.1 to 1.6, 1.2 to 1.6, 1 to 14, 1.1 to 1.4, or 1.2 to 1.4); (vii) the ratio of the length of the region between the RuvC-II and RuvC-III subdomains over the length of the RuvC-III subdomain is greater than 1; (viii) the ratio of the length of the region between the RuvC-II and RuvC-III subdomains over the length of the RuvC-III subdomain is greater than 1 and between 1 and 1.3 (e.g., 1 and 1.2); (ix) the region between the RuvC-II and RuvC-III subdomains is at least 73 amino acids in length (e.g., at least 75, 77, 80, 85, or 87 amino acids in length); (x) the region between the RuvC-II and RuvC-III subdomains is at least 78 amino acids in length (e.g., at least 80, 85, or 87 amino acids in length); (xi) the region between the RuvC-II and RuvC-III subdomains is at least 85 amino acids in length; (x) the region between the RuvC-II and RuvC-III subdomains has a length in a range of from 75-100 amino acids (e.g., a range of from 75-95, 75-90, 75-88, 78-100, 78-95, 78-90, 78-88, 80-100, 80-95, 80-90, 80-88, 83-100, 83-95, 83-90, 83-88, 85-100, 85-95, 85-90, or 85-88 amino acids); or (xi) the region between the RuvC-II and RuvC-III subdomains has a length in a range of from 80-95 amino acids (e.g., a range of from 80-90, 80-88, 83-95, 83-90, 83-88, 85-95, 85-90, or 85-88 amino acids).

In some cases, a CasX protein includes a first amino acid sequence having 80% or more sequence identity (e.g., 85% or more, 90% or more, 95% or more, 97% or more, 98% or more, 99% or more, or 100% sequence identity) with the N-terminal domain (e.g., the domain depicted as amino acids 1-663 for CasX1 in FIG. 3A) of any one of the CasX protein sequences set forth as SEQ ID NOs: 1-3; and a second amino acid sequence, C-terminal to the first amino acid sequence, that includes 3 partial RuvC domains—RuvC-I, RuvC-II, and RuvC-III—where: (i) the ratio of the length of the region between the RuvC-II and RuvC-III subdomains over the length of the RuvC-III subdomain is 1.1 or greater (e.g., 1.2); (ii) the ratio of the length of the region between the RuvC-II and RuvC-III subdomains over the length of the RuvC-III subdomain is greater than 1; (iii) the ratio of the length of the region between the RuvC-II and RuvC-III subdomains over the length of the RuvC-III subdomain is greater than 1 and between 1 and 1.3 (e.g., 1 and 1.2); (iv) the ratio of the length of the RuvC-II subdomain over the length of the RuvC-III subdomain is 2 or less (e.g., 1.8 or less, 1.7 or less, 1.6 or less, 1.5 or less, or 1.4 or less); (v) the ratio of the length of the RuvC-II subdomain over the length of the RuvC-III subdomain is 1.5 or less (e.g., 1.4 or less); (vi) the ratio of the length of the RuvC-II subdomain over the length of the RuvC-III subdomain is in a range of from 1 to 2 (e.g., from 1.1 to 2, 1.2 to 2, 1 to 1.8, 1.1 to 1.8, 1.2 to 1.8, 1 to 1.6, 1.1 to 1.6, 1.2 to 1.6, 1 to 14, 1.1 to 1.4, or 1.2 to 1.4); (vii) the ratio of the length of the region between the RuvC-II and RuvC-III subdomains over the length of the RuvC-III subdomain is greater than 1; (viii) the ratio of the length of the region between the RuvC-II and RuvC-III subdomains over the length of the RuvC-III subdomain is greater than 1 and between 1 and 1.3 (e.g., 1 and 1.2); (ix) the region between the RuvC-II and RuvC-III subdomains is at least 73 amino acids in length (e.g., at least 75, 77, 80, 85, or 87 amino acids in length); (x) the region between the RuvC-II and RuvC-III subdomains is at least 78 amino acids in length (e.g., at least 80, 85, or 87 amino acids in length); (xi) the region between the RuvC-II and RuvC-III subdomains is at least 85 amino acids in length; (x) the region between the RuvC-II and RuvC-III subdomains has a length in a range of from 75-100 amino acids (e.g., a range of from 75-95, 75-90, 75-88, 78-100, 78-95, 78-90, 78-88, 80-100, 80-95, 80-90, 80-88, 83-100, 83-95, 83-90, 83-88, 85-100, 85-95, 85-90, or 85-88 amino acids); or (xi) the region between the RuvC-II and RuvC-III subdomains has a length in a range of from 80-95 amino acids (e.g., a range of from 80-90, 80-88, 83-95, 83-90, 83-88, 85-95, 85-90, or 85-88 amino acids).

In some cases, a CasX protein includes a first amino acid sequence having 90% or more sequence identity (e.g., 95% or more, 97% or more, 98% or more, 99% or more, or 100% sequence identity) with the N-terminal domain (e.g., the domain depicted as amino acids 1-663 for CasX1 in 3A) of any one of the CasX protein sequences set forth as SEQ ID NOs: 1-3; and a second amino acid sequence, C-terminal to the first amino acid sequence, that includes 3 partial RuvC domains—RuvC-I, RuvC-II, and RuvC-III—where: (i) the ratio of the length of the region between the RuvC-II and RuvC-III subdomains over the length of the RuvC-III subdomain is 1.1 or greater (e.g., 1.2); (ii) the ratio of the length of the region between the RuvC-II and RuvC-III subdomains over the length of the RuvC-III subdomain is greater than 1; (iii) the ratio of the length of the region between the RuvC-II and RuvC-III subdomains over the length of the RuvC-III subdomain is greater than 1 and between 1 and 1.3 (e.g., 1 and 1.2); (iv) the ratio of the length of the RuvC-II subdomain over the length of the RuvC-III subdomain is 2 or less (e.g., 1.8 or less, 1.7 or less, 1.6 or less, 1.5 or less, or 1.4 or less); (v) the ratio of the length of the RuvC-II subdomain over the length of the RuvC-III subdomain is 1.5 or less (e.g., 1.4 or less); (vi) the ratio of the length of the RuvC-II subdomain over the length of the RuvC-III subdomain is in a range of from 1 to 2 (e.g., from 1.1 to 2, 1.2 to 2, 1 to 1.8, 1.1 to 1.8, 1.2 to 1.8, 1 to 1.6, 1.1 to 1.6, 1.2 to 1.6, 1 to 14, 1.1 to 1.4, or 1.2 to 1.4); (vii) the ratio of the length of the region between the RuvC-II and RuvC-III subdomains over the length of the RuvC-III subdomain is greater than 1; (viii) the ratio of the length of the region between the RuvC-II and RuvC-III subdomains over the length of the RuvC-III subdomain is greater than land between 1 and 1.3 (e.g., 1 and 1.2); (ix) the region between the RuvC-II and RuvC-III subdomains is at least 73 amino acids in length (e.g., at least 75, 77, 80, 85, or 87 amino acids in length); (x) the region between the RuvC-II and RuvC-III subdomains is at least 78 amino acids in length (e.g., at least 80, 85, or 87 amino acids in length); (xi) the region between the RuvC-II and RuvC-III subdomains is at least 85 amino acids in length; (x) the region between the RuvC-II and RuvC-III subdomains has a length in a range of from 75-100 amino acids (e.g., a range of from 75-95, 75-90, 75-88, 78-100, 78-95, 78-90, 78-88, 80-100, 80-95, 80-90, 80-88, 83-100, 83-95, 83-90, 83-88, 85-100, 85-95, 85-90, or 85-88 amino acids); or (xi) the region between the RuvC-II and RuvC-III subdomains has a length in a range of from 80-95 amino acids (e.g., a range of from 80-90, 80-88, 83-95, 83-90, 83-88, 85-95, 85-90, or 85-88 amino acids).

In some cases, a CasX protein includes an amino acid sequence corresponding to amino acids 1-663 of the CasX protein sequence set forth as SEQ ID NO: 1 (e.g., amino acids 1-650 of the CasX protein sequence set forth as SEQ ID NO: 2); and a second amino acid sequence, C-terminal to the first amino acid sequence, that includes 3 partial RuvC domains—RuvC-I, RuvC-II, and RuvC-III—where: (i) the ratio of the length of the region between the RuvC-II and RuvC-III subdomains over the length of the RuvC-III subdomain is 1.1 or greater (e.g., 1.2); (ii) the ratio of the length of the region between the RuvC-II and RuvC-III subdomains over the length of the RuvC-III subdomain is greater than 1; (iii) the ratio of the length of the region between the RuvC-II and RuvC-III subdomains over the length of the RuvC-III subdomain is greater than land between 1 and 1.3 (e.g., 1 and 1.2); (iv) the ratio of the length of the RuvC-II subdomain over the length of the RuvC-III subdomain is 2 or less (e.g., 1.8 or less, 1.7 or less, 1.6 or less, 1.5 or less, or 1.4 or less); (v) the ratio of the length of the RuvC-II subdomain over the length of the RuvC-III subdomain is 1.5 or less (e.g., 1.4 or less); (vi) the ratio of the length of the RuvC-II subdomain over the length of the RuvC-III subdomain is in a range of from 1 to 2 (e.g., from 1.1 to 2, 1.2 to 2, 1 to 1.8, 1.1 to 1.8, 1.2 to 1.8, 1 to 1.6, 1.1 to 1.6, 1.2 to 1.6, 1 to 14, 1.1 to 1.4, or 1.2 to 1.4); (vii) the ratio of the length of the region between the RuvC-II and RuvC-III subdomains over the length of the RuvC-III subdomain is greater than 1; (viii) the ratio of the length of the region between the RuvC-II and RuvC-III subdomains over the length of the RuvC-III subdomain is greater than land between 1 and 1.3 (e.g., 1 and 1.2); (ix) the region between the RuvC-II and RuvC-III subdomains is at least 73 amino acids in length (e.g., at least 75, 77, 80, 85, or 87 amino acids in length); (x) the region between the RuvC-II and RuvC-III subdomains is at least 78 amino acids in length (e.g., at least 80, 85, or 87 amino acids in length); (xi) the region between the RuvC-II and RuvC-III subdomains is at least 85 amino acids in length; (x) the region between the RuvC-II and RuvC-III subdomains has a length in a range of from 75-100 amino acids (e.g., a range of from 75-95, 75-90, 75-88, 78-100, 78-95, 78-90, 78-88, 80-100, 80-95, 80-90, 80-88, 83-100, 83-95, 83-90, 83-88, 85-100, 85-95, 85-90, or 85-88 amino acids); or (xi) the region between the RuvC-II and RuvC-III subdomains has a length in a range of from 80-95 amino acids (e.g., a range of from 80-90, 80-88, 83-95, 83-90, 83-88, 85-95, 85-90, or 85-88 amino acids).

In some cases, a CasX protein (of the subject compositions and/or methods) includes a first amino acid sequence with an N-terminal domain (e.g., not including any fused heterologous sequence such as an NLS and/or a domain with a catalytic activity) having a length in a range of from 500-750 amino acids (e.g, from 550-750, 600-750, 640-750, 650-750, 500-700, 550-700, 600-700, 640-700, 650-700, 500-680, 550-680, 600-680, 640-680, 650-680, 500-670, 550-670, 600-670, 640-670, or 650-670 amino acids); and a second amino acid sequence (C-terminal to the first) having a split Ruv C domain with 3 partial RuvC domains—RuvC-I, RuvC-II, and RuvC-III, where: (i) the ratio of the length of the region between the RuvC-II and RuvC-III subdomains over the length of the RuvC-III subdomain is 1.1 or greater (e.g., 1.2); (ii) the ratio of the length of the region between the RuvC-II and RuvC-III subdomains over the length of the RuvC-III subdomain is greater than 1; (iii) the ratio of the length of the region between the RuvC-II and RuvC-III subdomains over the length of the RuvC-III subdomain is greater than land between 1 and 1.3 (e.g., 1 and 1.2); (iv) the ratio of the length of the RuvC-II subdomain over the length of the RuvC-III subdomain is 2 or less (e.g., 1.8 or less, 1.7 or less, 1.6 or less, 1.5 or less, or 1.4 or less); (v) the ratio of the length of the RuvC-II subdomain over the length of the RuvC-III subdomain is 1.5 or less (e.g., 1.4 or less); (vi) the ratio of the length of the RuvC-II subdomain over the length of the RuvC-III subdomain is in a range of from 1 to 2 (e.g., from 1.1 to 2, 1.2 to 2, 1 to 1.8, 1.1 to 1.8, 1.2 to 1.8, 1 to 1.6, 1.1 to 1.6, 1.2 to 1.6, 1 to 14, 1.1 to 1.4, or 1.2 to 1.4); (vii) the ratio of the length of the region between the RuvC-II and RuvC-III subdomains over the length of the RuvC-III subdomain is greater than 1; (viii) the ratio of the length of the region between the RuvC-II and RuvC-III subdomains over the length of the RuvC-III subdomain is greater than land between 1 and 1.3 (e.g., 1 and 1.2); (ix) the region between the RuvC-II and RuvC-III subdomains is at least 73 amino acids in length (e.g., at least 75, 77, 80, 85, or 87 amino acids in length); (x) the region between the RuvC-II and RuvC-III subdomains is at least 78 amino acids in length (e.g., at least 80, 85, or 87 amino acids in length); (xi) the region between the RuvC-II and RuvC-III subdomains is at least 85 amino acids in length; (x) the region between the RuvC-II and RuvC-III subdomains has a length in a range of from 75-100 amino acids (e.g., a range of from 75-95, 75-90, 75-88, 78-100, 78-95, 78-90, 78-88, 80-100, 80-95, 80-90, 80-88, 83-100, 83-95, 83-90, 83-88, 85-100, 85-95, 85-90, or 85-88 amino acids); or (xi) the region between the RuvC-II and RuvC-III subdomains has a length in a range of from 80-95 amino acids (e.g., a range of from 80-90, 80-88, 83-95, 83-90, 83-88, 85-95, 85-90, or 85-88 amino acids).

In some cases, a CasX protein (of the subject compositions and/or methods) includes a first amino acid sequence having a length (e.g., not including any fused heterologous sequence such as an NLS and/or a domain with a catalytic activity) in a range of from 500-750 amino acids (e.g, from 550-750, 600-750, 640-750, 650-750, 500-700, 550-700, 600-700, 640-700, 650-700, 500-680, 550-680, 600-680, 640-680, 650-680, 500-670, 550-670, 600-670, 640-670, or 650-670 amino acids) that is N-terminal to a split Ruv C domain with 3 partial RuvC domains—RuvC-I, RuvC-II, and RuvC-III, where: (i) the ratio of the length of the region between the RuvC-II and RuvC-III subdomains over the length of the RuvC-III subdomain is 1.1 or greater (e.g., 1.2); (ii) the ratio of the length of the region between the RuvC-II and RuvC-III subdomains over the length of the RuvC-III subdomain is greater than 1; (iii) the ratio of the length of the region between the RuvC-II and RuvC-III subdomains over the length of the RuvC-III subdomain is greater than 1 and between 1 and 1.3 (e.g., 1 and 1.2); (iv) the ratio of the length of the RuvC-II subdomain over the length of the RuvC-III subdomain is 2 or less (e.g., 1.8 or less, 1.7 or less, 1.6 or less, 1.5 or less, or 1.4 or less); (v) the ratio of the length of the RuvC-II subdomain over the length of the RuvC-III subdomain is 1.5 or less (e.g., 1.4 or less); (vi) the ratio of the length of the RuvC-II subdomain over the length of the RuvC-III subdomain is in a range of from 1 to 2 (e.g., from 1.1 to 2, 1.2 to 2, 1 to 1.8, 1.1 to 1.8, 1.2 to 1.8, 1 to 1.6, 1.1 to 1.6, 1.2 to 1.6, 1 to 14, 1.1 to 1.4, or 1.2 to 1.4); (vii) the ratio of the length of the region between the RuvC-II and RuvC-III subdomains over the length of the RuvC-III subdomain is greater than 1; (viii) the ratio of the length of the region between the RuvC-II and RuvC-III subdomains over the length of the RuvC-III subdomain is greater than 1 and between 1 and 1.3 (e.g., 1 and 1.2); (ix) the region between the RuvC-II and RuvC-III subdomains is at least 73 amino acids in length (e.g., at least 75, 77, 80, 85, or 87 amino acids in length); (x) the region between the RuvC-II and RuvC-III subdomains is at least 78 amino acids in length (e.g., at least 80, 85, or 87 amino acids in length); (xi) the region between the RuvC-II and RuvC-III subdomains is at least 85 amino acids in length; (x) the region between the RuvC-II and RuvC-III subdomains has a length in a range of from 75-100 amino acids (e.g., a range of from 75-95, 75-90, 75-88, 78-100, 78-95, 78-90, 78-88, 80-100, 80-95, 80-90, 80-88, 83-100, 83-95, 83-90, 83-88, 85-100, 85-95, 85-90, or 85-88 amino acids); or (xi) the region between the RuvC-II and RuvC-III subdomains has a length in a range of from 80-95 amino acids (e.g., a range of from 80-90, 80-88, 83-95, 83-90, 83-88, 85-95, 85-90, or 85-88 amino acids).

In some cases, a CasX protein (of the subject compositions and/or methods) includes an amino acid sequence having 20% or more sequence identity (e.g., 30% or more, 40% or more, 50% or more, 60% or more, 70% or more, 80% or more, 85% or more, 90% or more, 95% or more, 97% or more, 98% or more, 99% or more, or 100% sequence identity) with the C-terminal domain (e.g., the domain depicted as amino acids 664-986 for CasX1 in FIG. 3A) of the CasX protein sequence set forth as SEQ ID NO: 1. For example, in some cases, a CasX protein includes an amino acid sequence having 50% or more sequence identity (e.g., 60% or more, 70% or more, 80% or more, 85% or more, 90% or more, 95% or more, 97% or more, 98% or more, 99% or more, or 100% sequence identity) with the C-terminal domain (e.g., the domain depicted as amino acids 664-986 for CasX1 in FIG. 3A) of the CasX protein sequence set forth as SEQ ID NO: 1. In some cases, a CasX protein includes an amino acid sequence having 80% or more sequence identity (e.g., 85% or more, 90% or more, 95% or more, 97% or more, 98% or more, 99% or more, or 100% sequence identity) with the C-terminal domain (e.g., the domain depicted as amino acids 664-986 for CasX1 in FIG. 3A) of the CasX protein sequence set forth as SEQ ID NO: 1. In some cases, a CasX protein includes an amino acid sequence having 90% or more sequence identity (e.g., 95% or more, 97% or more, 98% or more, 99% or more, or 100% sequence identity) with the C-terminal domain (e.g., the domain depicted as amino acids 664-986 for CasX1 in FIG. 3A) of the CasX protein sequence set forth as SEQ ID NO: 1. In some cases, a CasX protein includes an amino acid sequence having amino acids 664-986 of the CasX protein sequence set forth as SEQ ID NO: 1.

In some cases, a CasX protein (of the subject compositions and/or methods) includes an amino acid sequence having 20% or more sequence identity (e.g., 30% or more, 40% or more, 50% or more, 60% or more, 70% or more, 80% or more, 85% or more, 90% or more, 95% or more, 97% or more, 98% or more, 99% or more, or 100% sequence identity) with the C-terminal domain (e.g., the domain depicted as amino acids 664-986 for CasX1 in FIG. 3A) of the CasX protein sequence set forth as SEQ ID NO: 2. For example, in some cases, a CasX protein includes an amino acid sequence having 50% or more sequence identity (e.g., 60% or more, 70% or more, 80% or more, 85% or more, 90% or more, 95% or more, 97% or more, 98% or more, 99% or more, or 100% sequence identity) with the C-terminal domain (e.g., the domain depicted as amino acids 664-986 for CasX1 in FIG. 3A) of the CasX protein sequence set forth as SEQ ID NO: 2. In some cases, a CasX protein includes an amino acid sequence having 80% or more sequence identity (e.g., 85% or more, 90% or more, 95% or more, 97% or more, 98% or more, 99% or more, or 100% sequence identity) with the C-terminal domain (e.g., the domain depicted as amino acids 664-986 for CasX1 in FIG. 3A) of the CasX protein sequence set forth as SEQ ID NO: 2. In some cases, a CasX protein includes an amino acid sequence having 90% or more sequence identity (e.g., 95% or more, 97% or more, 98% or more, 99% or more, or 100% sequence identity) with the C-terminal domain (e.g., the domain depicted as amino acids 664-986 for CasX1 in FIG. 3A) of the CasX protein sequence set forth as SEQ ID NO: 2. In some cases, a CasX protein includes an amino acid sequence of SEQ ID NO: 2 corresponding to amino acids 664-986 of the CasX protein sequence set forth as SEQ ID NO: 1.

In some cases, a CasX protein (of the subject compositions and/or methods) includes an amino acid sequence having 20% or more sequence identity (e.g., 30% or more, 40% or more, 50% or more, 60% or more, 70% or more, 80% or more, 85% or more, 90% or more, 95% or more, 97% or more, 98% or more, 99% or more, or 100% sequence identity) with the C-terminal domain (e.g., the domain depicted as amino acids 664-986 for CasX1 in FIG. 3A) of the CasX protein sequence set forth as SEQ ID NO: 3. For example, in some cases, a CasX protein includes an amino acid sequence having 50% or more sequence identity (e.g., 60% or more, 70% or more, 80% or more, 85% or more, 90% or more, 95% or more, 97% or more, 98% or more, 99% or more, or 100% sequence identity) with the C-terminal domain (e.g., the domain depicted as amino acids 664-986 for CasX1 in FIG. 3A) of the CasX protein sequence set forth as SEQ ID NO: 3. In some cases, a CasX protein includes an amino acid sequence having 80% or more sequence identity (e.g., 85% or more, 90% or more, 95% or more, 97% or more, 98% or more, 99% or more, or 100% sequence identity) with the C-terminal domain (e.g., the domain depicted as amino acids 664-986 for CasX1 in FIG. 3A) of the CasX protein sequence set forth as SEQ ID NO: 3. In some cases, a CasX protein includes an amino acid sequence having 90% or more sequence identity (e.g., 95% or more, 97% or more, 98% or more, 99% or more, or 100% sequence identity) with the C-terminal domain (e.g., the domain depicted as amino acids 664-986 for CasX1 in FIG. 3A) of the CasX protein sequence set forth as SEQ ID NO:

3. In some cases, a CasX protein includes an amino acid sequence of SEQ ID NO: 3 corresponding to amino acids 664-986 of the CasX protein sequence set forth as SEQ ID NO: 1.

In some cases, a CasX protein (of the subject compositions and/or methods) includes an amino acid sequence having 20% or more sequence identity (e.g., 30% or more, 40% or more, 50% or more, 60% or more, 70% or more, 80% or more, 85% or more, 90% or more, 95% or more, 97% or more, 98% or more, 99% or more, or 100% sequence identity) with the C-terminal domain (e.g., the domain depicted as amino acids 664-986 for CasX1 in FIG. 3A) of any one of the CasX protein sequences set forth as SEQ ID NOs: 1 and 2 (e.g., amino acids 651-978 for the CasX protein sequence set forth as SEQ ID NO: 2). For example, in some cases, a CasX protein includes an amino acid sequence having 50% or more sequence identity (e.g., 60% or more, 70% or more, 80% or more, 85% or more, 90% or more, 95% or more, 97% or more, 98% or more, 99% or more, or 100% sequence identity) with the C-terminal domain (e.g., the domain depicted as amino acids 664-986 for CasX1 in FIG. 3A) of any one of the CasX protein sequences set forth as SEQ ID NOs: 1 and 2. In some cases, a CasX protein includes an amino acid sequence having 80% or more sequence identity (e.g., 85% or more, 90% or more, 95% or more, 97% or more, 98% or more, 99% or more, or 100% sequence identity) with the C-terminal domain (e.g., the domain depicted as amino acids 664-986 for CasX1 in FIG. 3A) of any one of the CasX protein sequences set forth as SEQ ID NOs: 1 and 2. In some cases, a CasX protein includes an amino acid sequence having 90% or more sequence identity (e.g., 95% or more, 97% or more, 98% or more, 99% or more, or 100% sequence identity) with the C-terminal domain (e.g., the domain depicted as amino acids 664-986 for CasX1 in FIG. 3A) of any one of the CasX protein sequences set forth as SEQ ID NOs: 1 and 2. In some cases, a CasX protein includes an amino acid sequence corresponding to amino acids 664-986 of the CasX protein sequence set forth as SEQ ID NO: 1 (e.g., amino acids 651-978 of the CasX protein sequence set forth as SEQ ID NO: 2).

In some cases, a CasX protein (of the subject compositions and/or methods) includes a first amino acid sequence (an N-terminal domain) (e.g., not including any fused heterologous sequence such as an NLS and/or a domain with a catalytic activity) having a length in a range of from 500-750 amino acids (e.g, from 550-750, 600-750, 640-750, 650-750, 500-700, 550-700, 600-700, 640-700, 650-700, 500-680, 550-680, 600-680, 640-680, 650-680, 500-670, 550-670, 600-670, 640-670, or 650-670 amino acids); and a second amino acid sequence, positioned C-terminal to the first amino acid sequence, having 20% or more sequence identity (e.g., 30% or more, 40% or more, 50% or more, 60% or more, 70% or more, 80% or more, 85% or more, 90% or more, 95% or more, 97% or more, 98% or more, 99% or more, or 100% sequence identity) with the C-terminal domain (e.g., the domain depicted as amino acids 664-986 for CasX1 in FIG. 3A) of any one of the CasX protein sequences set forth as SEQ ID NOs: 1 and 2 (e.g., amino acids 651-978 for the CasX protein sequence set forth as SEQ ID NO: 2). For example, in some cases, a CasX protein includes a first amino acid sequence (an N-terminal domain) (e.g., not including any fused heterologous sequence such as an NLS and/or a domain with a catalytic activity) having a length in a range of from 500-750 amino acids (e.g, from 550-750, 600-750, 640-750, 650-750, 500-700, 550-700, 600-700, 640-700, 650-700, 500-680, 550-680, 600-680, 640-680, 650-680, 500-670, 550-670, 600-670, 640-670, or 650-670 amino acids); and a second amino acid sequence, positioned C-terminal to the first amino acid sequence, having 50% or more sequence identity (e.g., 60% or more, 70% or more, 80% or more, 85% or more, 90% or more, 95% or more, 97% or more, 98% or more, 99% or more, or 100% sequence identity) with the C-terminal domain (e.g., the domain depicted as amino acids 664-986 for CasX1 in FIG. 3A) of any one of the CasX protein sequences set forth as SEQ ID NOs: 1 and 2. In some cases, a CasX protein includes a first amino acid sequence (an N-terminal domain) (e.g., not including any fused heterologous sequence such as an NLS and/or a domain with a catalytic activity) having a length in a range of from 500-750 amino acids (e.g, from 550-750, 600-750, 640-750, 650-750, 500-700, 550-700, 600-700, 640-700, 650-700, 500-680, 550-680, 600-680, 640-680, 650-680, 500-670, 550-670, 600-670, 640-670, or 650-670 amino acids); and a second amino acid sequence, positioned C-terminal to the first amino acid sequence, having 80% or more sequence identity (e.g., 85% or more, 90% or more, 95% or more, 97% or more, 98% or more, 99% or more, or 100% sequence identity) with the C-terminal domain (e.g., the domain depicted as amino acids 664-986 for CasX1 in FIG. 3A) of any one of the CasX protein sequences set forth as SEQ ID NOs: 1 and 2. In some cases, a CasX protein includes a first amino acid sequence (an N-terminal domain) (e.g., not including any fused heterologous sequence such as an NLS and/or a domain with a catalytic activity) having a length in a range of from 500-750 amino acids (e.g, from 550-750, 600-750, 640-750, 650-750, 500-700, 550-700, 600-700, 640-700, 650-700, 500-680, 550-680, 600-680, 640-680, 650-680, 500-670, 550-670, 600-670, 640-670, or 650-670 amino acids); and a second amino acid sequence, positioned C-terminal to the first amino acid sequence, having 90% or more sequence identity (e.g., 95% or more, 97% or more, 98% or more, 99% or more, or 100% sequence identity) with the C-terminal domain (e.g., the domain depicted as amino acids 664-986 for CasX1 in FIG. 3A) of any one of the CasX protein sequences set forth as SEQ ID NOs: 1 and 2. In some cases, a CasX protein includes a first amino acid sequence (an N-terminal domain) (e.g., not including any fused heterologous sequence such as an NLS and/or a domain with a catalytic activity) having a length in a range of from 500-750 amino acids (e.g, from 550-750, 600-750, 640-750, 650-750, 500-700, 550-700, 600-700, 640-700, 650-700, 500-680, 550-680, 600-680, 640-680, 650-680, 500-670, 550-670, 600-670, 640-670, or 650-670 amino acids); and a second amino acid sequence, positioned C-terminal to the first amino acid sequence, having an amino acid sequence corresponding to amino acids 664-986 of the CasX protein sequence set forth as SEQ ID NO: 1 (e.g. amino acids 651-978 of the CasX protein sequence set forth as SEQ ID NO: 2).

In some cases, a CasX protein (of the subject compositions and/or methods) includes an amino acid sequence having 20% or more sequence identity (e.g., 30% or more, 40% or more, 50% or more, 60% or more, 70% or more, 80% or more, 85% or more, 90% or more, 95% or more, 97% or more, 98% or more, 99% or more, or 100% sequence identity) with the C-terminal domain (e.g., the domain depicted as amino acids 664-986 for CasX1 in FIG. 3A) of any one of the CasX protein sequences set forth as SEQ ID NOs: 1-3 (e.g., amino acids 651-978 for the CasX protein sequence set forth as SEQ ID NO: 2). For example, in some cases, a CasX protein includes an amino acid sequence having 50% or more sequence identity (e.g., 60% or more, 70% or more, 80% or more, 85% or more, 90% or more, 95% or more, 97% or more, 98% or more, 99% or more, or 100% sequence identity) with the C-terminal domain (e.g., the domain depicted as amino acids 664-986 for CasX1 in FIG. 3A) of any one of the CasX protein sequences set forth as SEQ ID NOs: 1-3. In some cases, a CasX protein includes an amino acid sequence having 80% or more sequence identity (e.g., 85% or more, 90% or more, 95% or more, 97% or more, 98% or more, 99% or more, or 100% sequence identity) with the C-terminal domain (e.g., the domain depicted as amino acids 664-986 for CasX1 in FIG. 3A) of any one of the CasX protein sequences set forth as SEQ ID NOs: 1-3. In some cases, a CasX protein includes an amino acid sequence having 90% or more sequence identity (e.g., 95% or more, 97% or more, 98% or more, 99% or more, or 100% sequence identity) with the C-terminal domain (e.g., the domain depicted as amino acids 664-986 for CasX1 in FIG. 3A) of any one of the CasX protein sequences set forth as SEQ ID NOs: 1-3. In some cases, a CasX protein includes an amino acid sequence corresponding to amino acids 664-986 of the CasX protein sequence set forth as SEQ ID NO: 1 (e.g., amino acids 651-978 of the CasX protein sequence set forth as SEQ ID NO: 2).

In some cases, a CasX protein (of the subject compositions and/or methods) includes a first amino acid sequence (an N-terminal domain) (e.g., not including any fused heterologous sequence such as an NLS and/or a domain with a catalytic activity) having a length in a range of from 500-750 amino acids (e.g, from 550-750, 600-750, 640-750, 650-750, 500-700, 550-700, 600-700, 640-700, 650-700, 500-680, 550-680, 600-680, 640-680, 650-680, 500-670, 550-670, 600-670, 640-670, or 650-670 amino acids); and a second amino acid sequence, positioned C-terminal to the first amino acid sequence, having 20% or more sequence identity (e.g., 30% or more, 40% or more, 50% or more, 60% or more, 70% or more, 80% or more, 85% or more, 90% or more, 95% or more, 97% or more, 98% or more, 99% or more, or 100% sequence identity) with the C-terminal domain (e.g., the domain depicted as amino acids 664-986 for CasX1 in FIG. 3A) of any one of the CasX protein sequences set forth as SEQ ID NOs: 1-3 (e.g., amino acids 651-978 for the CasX protein sequence set forth as SEQ ID NO: 2). For example, in some cases, a CasX protein includes a first amino acid sequence (an N-terminal domain) (e.g., not including any fused heterologous sequence such as an NLS and/or a domain with a catalytic activity) having a length in a range of from 500-750 amino acids (e.g, from 550-750, 600-750, 640-750, 650-750, 500-700, 550-700, 600-700, 640-700, 650-700, 500-680, 550-680, 600-680, 640-680, 650-680, 500-670, 550-670, 600-670, 640-670, or 650-670 amino acids); and a second amino acid sequence, positioned C-terminal to the first amino acid sequence, having 50% or more sequence identity (e.g., 60% or more, 70% or more, 80% or more, 85% or more, 90% or more, 95% or more, 97% or more, 98% or more, 99% or more, or 100% sequence identity) with the C-terminal domain (e.g., the domain depicted as amino acids 664-986 for CasX1 in FIG. 3A) of any one of the CasX protein sequences set forth as SEQ ID NOs: 1-3. In some cases, a CasX protein includes a first amino acid sequence (an N-terminal domain) (e.g., not including any fused heterologous sequence such as an NLS and/or a domain with a catalytic activity) having a length in a range of from 500-750 amino acids (e.g, from 550-750, 600-750, 640-750, 650-750, 500-700, 550-700, 600-700, 640-700, 650-700, 500-680, 550-680, 600-680, 640-680, 650-680, 500-670, 550-670, 600-670, 640-670, or 650-670 amino acids); and a second amino acid sequence, positioned C-terminal to the first amino acid sequence, having 80% or more sequence identity (e.g., 85% or more, 90% or more, 95% or more, 97% or more, 98% or more, 99% or more, or 100% sequence identity) with the C-terminal domain (e.g., the domain depicted as amino acids 664-986 for CasX1 in FIG. 3A) of any one of the CasX protein sequences set forth as SEQ ID NOs: 1-3. In some cases, a CasX protein includes a first amino acid sequence (an N-terminal domain) (e.g., not including any fused heterologous sequence such as an NLS and/or a domain with a catalytic activity) having a length in a range of from 500-750 amino acids (e.g, from 550-750, 600-750, 640-750, 650-750, 500-700, 550-700, 600-700, 640-700, 650-700, 500-680, 550-680, 600-680, 640-680, 650-680, 500-670, 550-670, 600-670, 640-670, or 650-670 amino acids); and a second amino acid sequence, positioned C-terminal to the first amino acid sequence, having 90% or more sequence identity (e.g., 95% or more, 97% or more, 98% or more, 99% or more, or 100% sequence identity) with the C-terminal domain (e.g., the domain depicted as amino acids 664-986 for CasX1 in FIG. 3A) of any one of the CasX protein sequences set forth as SEQ ID NOs: 1-3. In some cases, a CasX protein includes a first amino acid sequence (an N-terminal domain) (e.g., not including any fused heterologous sequence such as an NLS and/or a domain with a catalytic activity) having a length in a range of from 500-750 amino acids (e.g, from 550-750, 600-750, 640-750, 650-750, 500-700, 550-700, 600-700, 640-700, 650-700, 500-680, 550-680, 600-680, 640-680, 650-680, 500-670, 550-670, 600-670, 640-670, or 650-670 amino acids); and a second amino acid sequence, positioned C-terminal to the first amino acid sequence, having an amino acid sequence corresponding to amino acids 664-986 of the CasX protein sequence set forth as SEQ ID NO: 1 (e.g., amino acids 651-978 of the CasX protein sequence set forth as SEQ ID NO: 2).

CasX Variants

A variant CasX protein has an amino acid sequence that is different by at least one amino acid (e.g., has a deletion, insertion, substitution, fusion) when compared to the amino acid sequence of the corresponding wild type CasX protein. A CasX protein that cleaves one strand but not the other of a double stranded target nucleic acid is referred to herein as a "nickase" (e.g., a "nickase CasX"). A CasX protein that has substantially no nuclease activity is referred to herein as a dead CasX protein ("dCasX") (with the caveat that nuclease activity can be provided by a heterologous polypeptide—a fusion partner—in the case of a chimeric CasX protein, which is described in more detail below). For any of the CasX variant proteins described herein (e.g., nickase CasX, dCasX, chimeric CasX), the CasX variant can include a CasX protein sequence with the same parameters described above (e.g., domains that are present, percent identity, and the like).

Variants—Catalytic Activity

In some cases, the CasX protein is a variant CasX protein, e.g., mutated relative to the naturally occurring catalytically active sequence, and exhibits reduced cleavage activity (e.g., exhibits 90%, or less, 80% or less, 70% or less, 60% or less, 50% or less, 40% or less, or 30% or less cleavage activity) when compared to the corresponding naturally occurring sequence. In some cases, such a variant CasX protein is a catalytically 'dead' protein (has substantially no cleavage activity) and can be referred to as a 'dCasX.' In some cases, the variant CasX protein is a nickase (cleaves only one strand of a double stranded target nucleic acid, e.g., a double stranded target DNA). As described in more detail herein, in some cases, a CasX protein (in some case a CasX protein with wild type cleavage activity and in some cases a variant CasX with reduced cleavage activity, e.g., a dCasX or a nickase CasX) is fused (conjugated) to a heterologous polypeptide that has an activity of interest (e.g., a catalytic activity of interest) to form a fusion protein (a chimeric CasX protein).

Conserved catalytic residues of CasX include D672, E769, D935 when numbered according to CasX1 (SEQ ID NO: 1) and 659D, 756E, and 922D when numbered according to CasX2 (SEQ ID NO: 2) (these residues are underlined in FIGS. 1A-1B). (Note, in the alignment of FIG. 2, the numbering does not track with either CasX protein but instead tracks with the alignment itself. The conserved residues noted above in this paragraph are marked in the FIG., CasX2 is the top sequence ('gwc2') and CasX1 is the bottom sequence ('gwa2')).

Thus, in some cases, the CasX protein has reduced activity and one or more of the above described amino acids (or one or more corresponding amino acids of any CasX protein) are mutated (e.g., substituted with an alanine). In some cases, the variant CasX protein is a catalytically 'dead' protein (is catalytically inactive) and is referred to as 'dCasX.' A dCasX protein can be fused to a fusion partner that provides an activity, and in some cases, the dCasX (e.g., one without a fusion partner that provides catalytic activity—but which can have an NLS when expressed in a eukaryotic cell) can bind to target DNA and can block RNA polymerase from translating from a target DNA. In some cases, the variant CasX protein is a nickase (cleaves only one strand of a double stranded target nucleic acid, e.g., a double stranded target DNA).

Variants—Chimeric CasX (i.e., Fusion Proteins)

As noted above, in some cases, a CasX protein (in some cases a CasX protein with wild type cleavage activity and in some cases a variant CasX with reduced cleavage activity, e.g., a dCasX or a nickase CasX) is fused (conjugated) to a heterologous polypeptide that has an activity of interest (e.g., a catalytic activity of interest) to form a fusion protein (a chimeric CasX protein). A heterologous polypeptide to which a CasX protein can be fused is referred to herein as a 'fusion partner.'

In some cases the fusion partner can modulate transcription (e.g., inhibit transcription, increase transcription) of a target DNA. For example, in some cases the fusion partner is a protein (or a domain from a protein) that inhibits transcription (e.g., a transcriptional repressor, a protein that functions via recruitment of transcription inhibitor proteins, modification of target DNA such as methylation, recruitment of a DNA modifier, modulation of histones associated with target DNA, recruitment of a histone modifier such as those that modify acetylation and/or methylation of histones, and the like). In some cases the fusion partner is a protein (or a domain from a protein) that increases transcription (e.g., a transcription activator, a protein that acts via recruitment of transcription activator proteins, modification of target DNA such as demethylation, recruitment of a DNA modifier, modulation of histones associated with target DNA, recruitment of a histone modifier such as those that modify acetylation and/or methylation of histones, and the like).

In some cases, a chimeric CasX protein includes a heterologous polypeptide that has enzymatic activity that modifies a target nucleic acid (e.g., nuclease activity, methyltransferase activity, demethylase activity, DNA repair activity, DNA damage activity, deamination activity, dismutase activity, alkylation activity, depurination activity, oxidation activity, pyrimidine dimer forming activity, integrase activity, transposase activity, recombinase activity, polymerase activity, ligase activity, helicase activity, photolyase activity or glycosylase activity).

In some cases, a chimeric CasX protein includes a heterologous polypeptide that has enzymatic activity that modifies a polypeptide (e.g., a histone) associated with a target nucleic acid (e.g., methyltransferase activity, demethylase activity, acetyltransferase activity, deacetylase activity, kinase activity, phosphatase activity, ubiquitin ligase activity, deubiquitinating activity, adenylation activity, deadenylation activity, SUMOylating activity, deSUMOylating activity, ribosylation activity, deribosylation activity, myristoylation activity or demyristoylation activity).

Examples of proteins (or fragments thereof) that can be used in increase transcription include but are not limited to: transcriptional activators such as VP16, VP64, VP48, VP160, p65 subdomain (e.g., from NFkB), and activation domain of EDLL and/or TAL acitvation domain (e.g., for activity in plants); histone lysine methyltransferases such as SET1A, SET1B, MLL1 to 5, ASH1, SYMD2, NSD1, and the like; histone lysine demethylases such as JHDM2a/b, UTX, JMJD3, and the like; histone acetyltransferases such as GCN5, PCAF, CBP, p300, TAF1, TIP60/PLIP, MOZ/MYST3, MORF/MYST4, SRC1, ACTR, P160, CLOCK, and the like; and DNA demethylases such as Ten-Eleven Translocation (TET) dioxygenase 1 (TET1CD), TET1, DME, DML1, DML2, ROS1, and the like.

Examples of proteins (or fragments thereof) that can be used in decrease transcription include but are not limited to: transcriptional repressors such as the Krüppel associated box (KRAB or SKD); KOX1 repression domain; the Mad mSIN3 interaction domain (SID); the ERF repressor domain (ERD), the SRDX repression domain (e.g., for repression in plants), and the like; histone lysine methyltransferases such as Pr-SET7/8, SUV4-20H1, RIZ1, and the like; histone lysine demethylases such as JMJD2A/JHDM3A, JMJD2B, JMJD2C/GASC1, JMJD2D, JARID1A/RBP2, JARID1B/PLU-1, JARID1C/SMCX, JARID1D/SMCY, and the like; histone lysine deacetylases such as HDAC1, HDAC2, HDAC3, HDAC8, HDAC4, HDAC5, HDAC7, HDAC9, SIRT1, SIRT2, HDAC11, and the like; DNA methylases such as HhaI DNA m5c-methyltransferase (M.HhaI), DNA methyltransferase 1 (DNMT1), DNA methyltransferase 3a (DNMT3a), DNA methyltransferase 3b (DNMT3b), METI, DRM3 (plants), ZMET2, CMT1, CMT2 (plants), and the like; and periphery recruitment elements such as Lamin A, Lamin B, and the like.

In some cases the fusion partner has enzymatic activity that modifies the target nucleic acid (e.g., ssRNA, dsRNA, ssDNA, dsDNA). Examples of enzymatic activity that can be provided by the fusion partner include but are not limited to: nuclease activity such as that provided by a restriction enzyme (e.g., FokI nuclease), methyltransferase activity such as that provided by a methyltransferase (e.g., HhaI DNA m5c-methyltransferase (M.HhaI), DNA methyltransferase 1 (DNMT1), DNA methyltransferase 3a (DNMT3a), DNA methyltransferase 3b (DNMT3b), METI, DRM3 (plants), ZMET2, CMT1, CMT2 (plants), and the like); demethylase activity such as that provided by a demethylase (e.g., Ten-Eleven Translocation (TET) dioxygenase 1 (TET1CD), TET1, DME, DML1, DML2, ROS1, and the like), DNA repair activity, DNA damage activity, deamination activity such as that provided by a deaminase (e.g., a cytosine deaminase enzyme such as rat APOBEC1), dismutase activity, alkylation activity, depurination activity, oxidation activity, pyrimidine dimer forming activity, integrase activity such as that provided by an integrase and/or resolvase (e.g., Gin invertase such as the hyperactive mutant of the Gin invertase, GinH106Y; human immunodeficiency virus type 1 integrase (IN); Tn3 resolvase; and the like), transposase activity, recombinase activity such as that provided by a recombinase (e.g., catalytic domain of Gin recombinase), polymerase activity, ligase activity, helicase activity, photolyase activity, and glycosylase activity).

In some cases the fusion partner has enzymatic activity that modifies a protein associated with the target nucleic acid (e.g., ssRNA, dsRNA, ssDNA, dsDNA) (e.g., a histone, an RNA binding protein, a DNA binding protein, and the like). Examples of enzymatic activity (that modifies a protein associated with a target nucleic acid) that can be provided by the fusion partner include but are not limited to: methyltransferase activity such as that provided by a histone methyltransferase (HMT) (e.g., suppressor of variegation 3-9 homolog 1 (SUV39H1, also known as KMT1A), euchromatic histone lysine methyltransferase 2 (G9A, also known as KMT1C and EHMT2), SUV39H2, ESET/SETDB1, and the like, SET1A, SET1B, MLL1 to 5, ASH1, SYMD2, NSD1, DOT1L, Pr-SET7/8, SUV4-20H1, EZH2, RIZ1), demethylase activity such as that provided by a histone demethylase (e.g., Lysine Demethylase 1A (KDM1A also known as LSD1), JHDM2a/b, JMJD2A/JHDM3A, JMJD2B, JMJD2C/GASC1, JMJD2D, JARID1A/RBP2, JARID1B/PLU-1, JARID1C/SMCX, JARID1D/SMCY, UTX, JMJD3, and the like), acetyltransferase activity such as that provided by a histone acetylase transferase (e.g., catalytic core/fragment of the human acetyltransferase p300, GCN5, PCAF, CBP, TAF1, TIP60/PLIP, MOZ/MYST3, MORF/MYST4, HBO1/MYST2, HMOF/MYST1, SRC1, ACTR, P160, CLOCK, and the like), deacetylase activity such as that provided by a histone deacetylase (e.g., HDAC1, HDAC2, HDAC3, HDAC8, HDAC4, HDAC5, HDAC7, HDAC9, SIRT1, SIRT2, HDAC11, and the like), kinase activity, phosphatase activity, ubiquitin ligase activity, deubiquitinating activity, adenylation activity, deadenylation activity, SUMOylating activity, deSUMOylating activity, ribosylation activity, deribosylation activity, myristoylation activity, and demyristoylation activity.

An additional examples of a suitable fusion partners are dihydrofolate reductase (DHFR) destabilization domain (e.g., to generate a chemically controllable chimeric CasX protein), and a chloroplast transit peptide. Suitable chloroplast transit peptides include, but are not limited to:

```
                                          (SEQ ID NO: 83)
MASMISSSAVTTVSRASRGQSAAMAPFGGLKSMTGFPVRKVNTDITSITS
NGGRVKCMQVWPPIGKKKFETLSYLPPLTRDSRA;

(SEQ ID NO: 84)
MASMISSSAVTTVSRASRGQSAAMAPFGGLKSMTGFPVRKVNTDITSITS
NGGRVKS;

(SEQ ID NO: 85)
MASSMLSSATMVASPAQATMVAPFNGLKSSAAFPATRKANNDITSITSNG
GRVNCMQVWPPIEKKKFETLSYLPDLTDSGGRVNC;

(SEQ ID NO: 86)
MAQVSRICNGVQNPSLISNLSKSSQRKSPLSVSLKTQQHPRAYPISSSWG
LKKSGMTLIGSELRPLKVMSSVSTAC;

(SEQ ID NO: 87)
MAQVSRICNGVWNPSLISNLSKSSQRKSPLSVSLKTQQHPRAYPISSSWG
LKKSGMTLIGSELRPLKVMSSVSTAC;

(SEQ ID NO: 88)
MAQINNMAQGIQTLNPNSNFHKPQVPKSSSFLVFGSKKLKNSANSMLVLK
KDSIFMQLFCSFRISASVATAC;
```

```
                                          (SEQ ID NO: 89)
MAALVTSQLATSGTVLSVTDRFRRPGFQGLRPRNPADAALGMRTVGASAA
PKQSRKPHRFDRRCLSMVV;

(SEQ ID NO: 90)
MAALTTSQLATSATGFGIADRSAPSSLLRHGFQGLKPRSPAGGDATSLSV
TTSARATPKQQRSVQRGSRRFPSVVVC;

(SEQ ID NO: 91)
MASSVLSSAAVATRSNVAQANMVAPFTGLKSAASFPVSRKQNLDITSIAS
NGGRVQC;

(SEQ ID NO: 92)
MESLAATSVFAPSRVAVPAARALVRAGTVVPTRRTSSTSGTSGVKCSAAV
TPQASPVISRSAAAA;
and (SEQ ID NO: 93)
MGAAATSMQSLKFSNRLVPPSRRLSPVPNNVTCNNLPKSAAPVRTVKCCA
SSWNSTINGAAATTNGASAASS.
```

In some case, a CasX fusion polypeptide of the present disclosure comprises: a) a CasX polypeptide of the present disclosure; and b) a chloroplast transit peptide. Thus, for example, a CRISPR-CasX complex can be targeted to the chloroplast. In some cases, this targeting may be achieved by the presence of an N-terminal extension, called a chloroplast transit peptide (CTP) or plastid transit peptide. Chromosomal transgenes from bacterial sources must have a sequence encoding a CTP sequence fused to a sequence encoding an expressed polypeptide if the expressed polypeptide is to be compartmentalized in the plant plastid (e.g. chloroplast). Accordingly, localization of an exogenous polypeptide to a chloroplast is often 1 accomplished by means of operably linking a polynucleotide sequence encoding a CTP sequence to the 5' region of a polynucleotide encoding the exogenous polypeptide. The CTP is removed in a processing step during translocation into the plastid. Processing efficiency may, however, be affected by the amino acid sequence of the CTP and nearby sequences at the NH 2 terminus of the peptide. Other options for targeting to the chloroplast which have been described are the maize cab-m7 signal sequence (U.S. Pat. No. 7,022,896, WO 97/41228) a pea glutathione reductase signal sequence (WO 97/41228) and the CTP described in US2009029861.

In some cases, a CasX fusion polypeptide of the present disclosure can comprise: a) a CasX polypeptide of the present disclosure; and b) an endosomal escape peptide. In some cases, an endosomal escape polypeptide comprises the amino acid sequence GLFXALLXLLXSLWXLLLXA (SEQ ID NO:94), wherein each X is independently selected from lysine, histidine, and arginine. In some cases, an endosomal escape polypeptide comprises the amino acid sequence GLFHALLHLLHSLWHLLLHA (SEQ ID NO:95).

For examples of some of the above fusion partners (and more) used in the context of fusions with Cas9, Zinc Finger, and/or TALE proteins (for site specific target nucleic modification, modulation of transcription, and/or target protein modification, e.g., histone modification), see, e.g.: Nomura et al, J Am Chem Soc. 2007 Jul. 18; 129(28):8676-7; Rivenbark et al., Epigenetics. 2012 April; 7(4):350-60; Nucleic Acids Res. 2016 Jul. 8; 44(12):5615-28; Gilbert et. al., Cell. 2013 Jul. 18; 154(2):442-51; Kearns et al., Nat Methods. 2015 May; 12(5):401-3; Mendenhall et. al., Nat Biotechnol. 2013 December; 31(12):1133-6; Hilton et. al., Nat Biotechnol. 2015 May; 33(5):510-7; Gordley et. al., Proc Natl Acad Sci USA. 2009 Mar. 31; 106(13):5053-8; Akopian et. al., Proc Natl Acad Sci USA. 2003 Jul. 22;

100(15):8688-91; Tan et., al., J Virol. 2006 February; 80(4): 1939-48; Tan et. al., Proc Natl Acad Sci USA. 2003 Oct. 14; 100(21):11997-2002; Papworth et. al., Proc Natl Acad Sci USA. 2003 Feb. 18; 100(4):1621-6; Sanjana et. al., Nat Protoc. 2012 Jan. 5; 7(1):171-92; Beerli et. al., Proc Natl Acad Sci USA. 1998 Dec. 8; 95(25):14628-33; Snowden et. al., Curr Biol. 2002 Dec. 23; 12(24):2159-66; Xu et. al., Xu et. al., Cell Discov. 2016 May 3; 2:16009; Komor et al., Nature. 2016 Apr. 20; 533(7603):420-4; Chaikind et. al., Nucleic Acids Res. 2016 Aug. 11; Choudhury at. al., Oncotarget. 2016 Jun. 23; Du et. al., Cold Spring Harb Protoc. 2016 Jan. 4; Pham et. al., Methods Mol Biol. 2016; 1358: 43-57; Balboa et al., Stem Cell Reports. 2015 Sep. 8; 5(3):448-59; Hara et. al., Sci Rep. 2015 Jun. 9; 5:11221; Piatek et. al., Plant Biotechnol J. 2015 May; 13(4):578-89; Hu et al., Nucleic Acids Res. 2014 April; 42(7):4375-90; Cheng et. al., Cell Res. 2013 October; 23(10):1163-71; cheng et. al., Cell Res. 2013 October; 23(10):1163-71; and Maeder et. al., Nat Methods. 2013 October; 10(10):977-9.

Additional suitable heterologous polypeptide include, but are not limited to, a polypeptide that directly and/or indirectly provides for increased transcription and/or translation of a target nucleic acid (e.g., a transcription activator or a fragment thereof, a protein or fragment thereof that recruits a transcription activator, a small molecule/drug-responsive transcription and/or translation regulator, a translation-regulating protein, etc.). Non-limiting examples of heterologous polypeptides to accomplish increased or decreased transcription include transcription activator and transcription repressor domains. In some such cases, a chimeric CasX polypeptide is targeted by the guide nucleic acid (guide RNA) to a specific location (i.e., sequence) in the target nucleic acid and exerts locus-specific regulation such as blocking RNA polymerase binding to a promoter (which selectively inhibits transcription activator function), and/or modifying the local chromatin status (e.g., when a fusion sequence is used that modifies the target nucleic acid or modifies a polypeptide associated with the target nucleic acid). In some cases, the changes are transient (e.g., transcription repression or activation). In some cases, the changes are inheritable (e.g., when epigenetic modifications are made to the target nucleic acid or to proteins associated with the target nucleic acid, e.g., nucleosomal histones).

Non-limiting examples of heterologous polypeptides for use when targeting ssRNA target nucleic acids include (but are not limited to): splicing factors (e.g., RS domains); protein translation components (e.g., translation initiation, elongation, and/or release factors; e.g., eIF4G); RNA methylases; RNA editing enzymes (e.g., RNA deaminases, e.g., adenosine deaminase acting on RNA (ADAR), including A to I and/or C to U editing enzymes); helicases; RNA-binding proteins; and the like. It is understood that a heterologous polypeptide can include the entire protein or in some cases can include a fragment of the protein (e.g., a functional domain).

The heterologous polypeptide of a subject chimeric CasX polypeptide can be any domain capable of interacting with ssRNA (which, for the purposes of this disclosure, includes intramolecular and/or intermolecular secondary structures, e.g., double-stranded RNA duplexes such as hairpins, stem-loops, etc.), whether transiently or irreversibly, directly or indirectly, including but not limited to an effector domain selected from the group comprising; Endonucleases (for example RNase III, the CRR22 DYW domain, Dicer, and PIN (PilT N-terminus) domains from proteins such as SMG5 and SMG6); proteins and protein domains responsible for stimulating RNA cleavage (for example CPSF, CstF, CFIm and CFIIm); Exonucleases (for example XRN-1 or Exonuclease T); Deadenylases (for example HNT3); proteins and protein domains responsible for nonsense mediated RNA decay (for example UPF1, UPF2, UPF3, UPF3b, RNP S1, Y14, DEK, REF2, and SRm160); proteins and protein domains responsible for stabilizing RNA (for example PABP); proteins and protein domains responsible for repressing translation (for example Ago2 and Ago4); proteins and protein domains responsible for stimulating translation (for example Staufen); proteins and protein domains responsible for (e.g., capable of) modulating translation (e.g., translation factors such as initiation factors, elongation factors, release factors, etc., e.g., eIF4G); proteins and protein domains responsible for polyadenylation of RNA (for example PAP1, GLD-2, and Star-PAP); proteins and protein domains responsible for polyuridinylation of RNA (for example CI D1 and terminal uridylate transferase); proteins and protein domains responsible for RNA localization (for example from IMP1, ZBP1, She2p, She3p, and Bicaudal-D); proteins and protein domains responsible for nuclear retention of RNA (for example Rrp6); proteins and protein domains responsible for nuclear export of RNA (for example TAP, NXF1, THO, TREX, REF, and Aly); proteins and protein domains responsible for repression of RNA splicing (for example PTB, Sam68, and hnRNP A1); proteins and protein domains responsible for stimulation of RNA splicing (for example Serine/Arginine-rich (SR) domains); proteins and protein domains responsible for reducing the efficiency of transcription (for example FUS (TLS)); and proteins and protein domains responsible for stimulating transcription (for example CDK7 and HIV Tat). Alternatively, the effector domain may be selected from the group comprising Endonucleases; proteins and protein domains capable of stimulating RNA cleavage; Exonucleases; Deadenylases; proteins and protein domains having nonsense mediated RNA decay activity; proteins and protein domains capable of stabilizing RNA; proteins and protein domains capable of repressing translation; proteins and protein domains capable of stimulating translation; proteins and protein domains capable of modulating translation (e.g., translation factors such as initiation factors, elongation factors, release factors, etc., e.g., eIF4G); proteins and protein domains capable of polyadenylation of RNA; proteins and protein domains capable of polyuridinylation of RNA; proteins and protein domains having RNA localization activity; proteins and protein domains capable of nuclear retention of RNA; proteins and protein domains having RNA nuclear export activity; proteins and protein domains capable of repression of RNA splicing; proteins and protein domains capable of stimulation of RNA splicing; proteins and protein domains capable of reducing the efficiency of transcription; and proteins and protein domains capable of stimulating transcription. Another suitable heterologous polypeptide is a PUF RNA-binding domain, which is described in more detail in WO2012068627, which is hereby incorporated by reference in its entirety.

Some RNA splicing factors that can be used (in whole or as fragments thereof) as heterologous polypeptides for a chimeric CasX polypeptide have modular organization, with separate sequence-specific RNA binding modules and splicing effector domains. For example, members of the Serine/Arginine-rich (SR) protein family contain N-terminal RNA recognition motifs (RRMs) that bind to exonic splicing enhancers (ESEs) in pre-mRNAs and C-terminal RS domains that promote exon inclusion. As another example, the hnRNP protein hnRNP A1 binds to exonic splicing silencers (ESSs) through its RRM domains and inhibits exon inclusion through a C-terminal Glycine-rich domain Some splicing factors can regulate alternative use of splice site (ss) by binding to regulatory sequences between the two alternative sites. For example, ASF/SF2 can recognize ESEs and promote the use of intron proximal sites, whereas hnRNP A1 can bind to ESSs and shift splicing towards the use of intron distal sites. One application for such factors is to generate ESFs that modulate alternative splicing of endogenous genes, particularly disease associated genes. For example, Bcl-x pre-mRNA produces two splicing isoforms with two alternative 5' splice sites to encode proteins of opposite functions. The long splicing isoform Bcl-xL is a potent apoptosis inhibitor expressed in long-lived postmitotic cells and is up-regulated in many cancer cells, protecting cells against apoptotic signals. The short isoform Bcl-xS is a pro-apoptotic isoform and expressed at high levels in cells with a high turnover rate (e.g., developing lymphocytes). The ratio of the two Bcl-x splicing isoforms is regulated by multiple cω-elements that are located in either the core exon region or the exon extension region (i.e., between the two alternative 5' splice sites). For more examples, see WO2010075303, which is hereby incorporated by reference in its entirety.

Further suitable fusion partners include, but are not limited to proteins (or fragments thereof) that are boundary elements (e.g., CTCF), proteins and fragments thereof that provide periphery recruitment (e.g., Lamin A, Lamin B, etc.), protein docking elements (e.g., FKBP/FRB, Pil1/Aby1, etc.).

Examples of various additional suitable heterologous polypeptide (or fragments thereof) for a subject chimeric CasX polypeptide include, but are not limited to those described in the following applications (which publications are related to other CRISPR endonucleases such as Cas9, but the described fusion partners can also be used with CasX instead): PCT patent applications: WO2010075303, WO2012068627, and WO2013155555, and can be found, for example, in U.S. patents and patent applications: U.S. Pat. Nos. 8,906,616; 8,895,308; 8,889,418; 8,889,356; 8,871,445; 8,865,406; 8,795,965; 8,771,945; 8,697,359; 20140068797; 20140170753; 20140179006; 20140179770; 20140186843; 20140186919; 20140186958; 20140189896; 20140227787; 20140234972; 20140242664; 20140242699; 20140242700; 20140242702; 20140248702; 20140256046; 20140273037; 20140273226; 20140273230; 20140273231; 20140273232; 20140273233; 20140273234; 20140273235; 20140287938; 20140295556; 20140295557; 20140298547; 20140304853; 20140309487; 20140310828; 20140310830; 20140315985; 20140335063; 20140335620; 20140342456; 20140342457; 20140342458; 20140349400; 20140349405; 20140356867; 20140356956; 20140356958; 20140356959; 20140357523; 20140357530; 20140364333; and 20140377868; all of which are hereby incorporated by reference in their entirety.

In some cases, a heterologous polypeptide (a fusion partner) provides for subcellular localization, i.e., the heterologous polypeptide contains a subcellular localization sequence (e.g., a nuclear localization signal (NLS) for targeting to the nucleus, a sequence to keep the fusion protein out of the nucleus, e.g., a nuclear export sequence (NES), a sequence to keep the fusion protein retained in the cytoplasm, a mitochondrial localization signal for targeting to the mitochondria, a chloroplast localization signal for targeting to a chloroplast, an ER retention signal, and the like). In some embodiments, a CasX fusion polypeptide does not include a NLS so that the protein is not targeted to the nucleus (which can be advantageous, e.g., when the target nucleic acid is an RNA that is present in the cyosol). In some embodiments, the heterologous polypeptide can provide a tag (i.e., the heterologous polypeptide is a detectable label) for ease of tracking and/or purification (e.g., a fluorescent protein, e.g., green fluorescent protein (GFP), YFP, RFP, CFP, mCherry, tdTomato, and the like; a histidine tag, e.g., a 6×His tag; a hemagglutinin (HA) tag; a FLAG tag; a Myc tag; and the like).

In some cases a CasX protein (e.g., a wild type CasX protein, a variant CasX protein, a chimeric CasX protein, a dCasX protein, a chimeric CasX protein where the CasX portion has reduced nuclease activity—such as a dCasX protein fused to a fusion partner, and the like) includes (is fused to) a nuclear localization signal (NLS) (e.g, in some cases 2 or more, 3 or more, 4 or more, or 5 or more NLSs). Thus, in some cases, a CasX polypeptide includes one or more NLSs (e.g., 2 or more, 3 or more, 4 or more, or 5 or more NLSs). In some cases, one or more NLSs (2 or more, 3 or more, 4 or more, or 5 or more NLSs) are positioned at or near (e.g., within 50 amino acids of) the N-terminus and/or the C-terminus. In some cases, one or more NLSs (2 or more, 3 or more, 4 or more, or 5 or more NLSs) are positioned at or near (e.g., within 50 amino acids of) the N-terminus. In some cases, one or more NLSs (2 or more, 3 or more, 4 or more, or 5 or more NLSs) are positioned at or near (e.g., within 50 amino acids of) the C-terminus. In some cases, one or more NLSs (3 or more, 4 or more, or 5 or more NLSs) are positioned at or near (e.g., within 50 amino acids of) both the N-terminus and the C-terminus. In some cases, an NLS is positioned at the N-terminus and an NLS is positioned at the C-terminus.

In some cases a CasX protein (e.g., a wild type CasX protein, a variant CasX protein, a chimeric CasX protein, a dCasX protein, a chimeric CasX protein where the CasX portion has reduced nuclease activity—such as a dCasX protein fused to a fusion partner, and the like) includes (is fused to) between 1 and 10 NLSs (e.g., 1-9, 1-8, 1-7, 1-6, 1-5, 2-10, 2-9, 2-8, 2-7, 2-6, or 2-5 NLSs). In some cases a CasX protein (e.g., a wild type CasX protein, a variant CasX protein, a chimeric CasX protein, a dCasX protein, a chimeric CasX protein where the CasX portion has reduced nuclease activity—such as a dCasX protein fused to a fusion partner, and the like) includes (is fused to) between 2 and 5 NLSs (e.g., 2-4, or 2-3 NLSs).

Non-limiting examples of NLSs include an NLS sequence derived from: the NLS of the SV40 virus large T-antigen, having the amino acid sequence PKKKRKV (SEQ ID NO: 96); the NLS from nucleoplasmin (e.g., the nucleoplasmin bipartite NLS with the sequence KRPAATKKAGQAKKKK (SEQ ID NO: 97)); the c-myc NLS having the amino acid sequence PAAKRVKLD (SEQ ID NO: 98) or RQRR-NELKRSP (SEQ ID NO: 99); the hRNPA1 M9 NLS having the sequence NQSSNFGPMKGGNFGGRSS-GPYGGGGQYFAKPRNQGGY (SEQ ID NO: 100); the sequence RMRIZFKNKGKDTAELRRRRVEVSVEL-RKAKKDEQILKRRNV (SEQ ID NO: 101) of the IBB domain from importin-alpha; the sequences VSRKRPRP (SEQ ID NO: 102) and PPKKARED (SEQ ID NO: 103) of the myoma T protein; the sequence PQPKKKPL (SEQ ID NO: 104) of human p53; the sequence SALIKKKKKMAP (SEQ ID NO: 105) of mouse c-abl IV; the sequences DRLRR (SEQ ID NO: 106) and PKQKKRK (SEQ ID NO: 107) of the influenza virus NS1; the sequence RKLKK-KIKKL (SEQ ID NO: 108) of the Hepatitis virus delta antigen; the sequence REKKKFLKRR (SEQ ID NO: 109) of the mouse Mx1 protein; the sequence KRK-GDEVDGVDEVAKKKSKK (SEQ ID NO: 110) of the human poly(ADP-ribose) polymerase; and the sequence RKCLQAGMNLEARKTKK (SEQ ID NO: 111) of the steroid hormone receptors (human) glucocorticoid. In general, NLS (or multiple NLSs) are of sufficient strength to drive accumulation of the CasX protein in a detectable amount in the nucleus of a eukaryotic cell. Detection of accumulation in the nucleus may be performed by any suitable technique. For example, a detectable marker may be fused to the CasX protein such that location within a cell may be visualized. Cell nuclei may also be isolated from cells, the contents of which may then be analyzed by any suitable process for detecting protein, such as immunohistochemistry, Western blot, or enzyme activity assay. Accumulation in the nucleus may also be determined indirectly.

In some cases, a CasX fusion polypeptide includes a "Protein Transduction Domain" or PTD (also known as a CPP—cell penetrating peptide), which refers to a polypeptide, polynucleotide, carbohydrate, or organic or inorganic compound that facilitates traversing a lipid bilayer, micelle, cell membrane, organelle membrane, or vesicle membrane. A PTD attached to another molecule, which can range from a small polar molecule to a large macromolecule and/or a nanoparticle, facilitates the molecule traversing a membrane, for example going from extracellular space to intracellular space, or cytosol to within an organelle. In some embodiments, a PTD is covalently linked to the amino terminus a polypeptide (e.g., linked to a wild type CasX to generate a fusino protein, or linked to a variant CasX protein such as a dCasX, nickase CasX, or chimeric CasX protein to generate a fusion protein). In some embodiments, a PTD is covalently linked to the carboxyl terminus of a polypeptide (e.g., linked to a wild type CasX to generate a fusino protein, or linked to a variant CasX protein such as a dCasX, nickase CasX, or chimeric CasX protein to generate a fusion protein). In some cases, the PTD is inserted interally in the CasX fusion polypeptide (i.e., is not at the N- or C-terminus of the CasX fusion polypeptide) at a suitable insertion site. In some cases, a subject CasX fusion polypeptide includes (is conjugated to, is fused to) one or more PTDs (e.g., two or more, three or more, four or more PTDs). In some cases a PTD includes a nuclear localization signal (NLS) (e.g, in some cases 2 or more, 3 or more, 4 or more, or 5 or more NLSs). Thus, in some cases, a CasX fusion polypeptide includes one or more NLSs (e.g., 2 or more, 3 or more, 4 or more, or 5 or more NLSs). In some embodiments, a PTD is covalently linked to a nucleic acid (e.g., a CasX guide nucleic acid, a polynucleotide encoding a CasX guide nucleic acid, a polynucleotide encoding a CasX fusion polypeptide, a donor polynucleotide, etc.). Examples of PTDs include but are not limited to a minimal undecapeptide protein transduction domain (corresponding to residues 47-57 of HIV-1 TAT comprising YGRKKRRQRRR; SEQ ID NO:112); a polyarginine sequence comprising a number of arginines sufficient to direct entry into a cell (e.g., 3, 4, 5, 6, 7, 8, 9, 10, or 10-50 arginines); a VP22 domain (Zender et al. (2002) *Cancer Gene Ther.* 9(6):489-96); an *Drosophila* Antennapedia protein transduction domain (Noguchi et al. (2003) *Diabetes* 52(7):1732-1737); a truncated human calcitonin peptide (Trehin et al. (2004) *Pharm. Research* 21:1248-1256); polylysine (Wender et al. (2000) *Proc. Natl. Acad. Sci. USA* 97:13003-13008); RRQRRTSKLMKR (SEQ ID NO:113); Transportan GWTLNSAGYLLGKINL-KALAALAKKIL (SEQ ID NO:114); KALAWEAKLAKA-LAKALAKHLAKALAKALKCEA (SEQ ID NO:115); and RQIKIWFQNRRMKWKK (SEQ ID NO:116). Exemplary PTDs include but are not limited to, YGRKKRRQRRR (SEQ ID NO:117), RKKRRQRRR (SEQ ID NO:118); an arginine homopolymer of from 3 arginine residues to 50 arginine residues; Exemplary PTD domain amino acid sequences include, but are not limited to, any of the following: YGRKKRRQRRR (SEQ ID NO:119); RKKRRQRRR (SEQ ID NO:120); YARAAARQARA (SEQ ID NO:121); THRLPRRRRRR (SEQ ID NO:122); and GGRRAR-RRRRR (SEQ ID NO:123). In some embodiments, the PTD is an activatable CPP (ACPP) (Aguilera et al. (2009) *Integr Biol* (*Camb*) June; 1(5-6): 371-381). ACPPs comprise a polycationic CPP (e.g., Arg9 or "R9") connected via a cleavable linker to a matching polyanion (e.g., Glu9 or "E9"), which reduces the net charge to nearly zero and thereby inhibits adhesion and uptake into cells. Upon cleavage of the linker, the polyanion is released, locally unmasking the polyarginine and its inherent adhesiveness, thus "activating" the ACPP to traverse the membrane.

Linkers (e.g., for Fusion Partners)

In some embodiments, a subject CasX protein can fused to a fusion partner via a linker polypeptide (e.g., one or more linker polypeptides). The linker polypeptide may have any of a variety of amino acid sequences. Proteins can be joined by a spacer peptide, generally of a flexible nature, although other chemical linkages are not excluded. Suitable linkers include polypeptides of between 4 amino acids and 40 amino acids in length, or between 4 amino acids and 25 amino acids in length. These linkers can be produced by using synthetic, linker-encoding oligonucleotides to couple the proteins, or can be encoded by a nucleic acid sequence encoding the fusion protein. Peptide linkers with a degree of flexibility can be used. The linking peptides may have virtually any amino acid sequence, bearing in mind that the preferred linkers will have a sequence that results in a generally flexible peptide. The use of small amino acids, such as glycine and alanine, are of use in creating a flexible peptide. The creation of such sequences is routine to those of skill in the art. A variety of different linkers are commercially available and are considered suitable for use.

Examples of linker polypeptides include glycine polymers (G)$_n$, glycine-serine polymers (including, for example, (GS)$_n$, GSGGS$_n$ (SEQ ID NO: 124), GGSGGS$_n$ (SEQ ID NO: 125), and GGGS$_n$ (SEQ ID NO: 126), where n is an integer of at least one), glycine-alanine polymers, alanine-serine polymers. Exemplary linkers can comprise amino acid sequences including, but not limited to, GGSG (SEQ ID NO: 127), GGSGG (SEQ ID NO: 128), GSGSG (SEQ ID NO: 129), GSGGG (SEQ ID NO: 130), GGGSG (SEQ ID NO: 131), GSSSG (SEQ ID NO: 132), and the like. The ordinarily skilled artisan will recognize that design of a peptide conjugated to any desired element can include linkers that are all or partially flexible, such that the linker can include a flexible linker as well as one or more portions that confer less flexible structure.

Detectable Labels

In some cases, a CasX polypeptide of the present disclosure comprises a detectable label. Suitable detectable labels and/or moieties that can provide a detectable signal can include, but are not limited to, an enzyme, a radioisotope, a member of a specific binding pair; a fluorophore; a fluorescent protein; a quantum dot; and the like.

Suitable fluorescent proteins include, but are not limited to, green fluorescent protein (GFP) or variants thereof, blue fluorescent variant of GFP (BFP), cyan fluorescent variant of GFP (CFP), yellow fluorescent variant of GFP (YFP), enhanced GFP (EGFP), enhanced CFP (ECFP), enhanced YFP (EYFP), GFPS65T, Emerald, Topaz (TYFP), Venus, Citrine, mCitrine, GFPuv, destabilised EGFP (dEGFP), destabilised ECFP (dECFP), destabilised EYFP (dEYFP), mCFPm, Cerulean, T-Sapphire, CyPet, YPet, mKO, HcRed, t-HcRed, DsRed, DsRed2, DsRed-monomer, J-Red, dimer2, t-dimer2(12), mRFP1, pocilloporin, *Renilla* GFP, Monster GFP, paGFP, Kaede protein and kindling protein, Phycobiliproteins and Phycobiliprotein conjugates including B-Phycoerythrin, R-Phycoerythrin and Allophycocyanin. Other examples of fluorescent proteins include mHoneydew, mBanana, mOrange, dTomato, tdTomato, mTangerine, mStrawberry, mCherry, mGrape1, mRaspberry, mGrape2, mPlum (Shaner et al. (2005) *Nat. Methods* 2:905-909), and the like. Any of a variety of fluorescent and colored proteins from Anthozoan species, as described in, e.g., Matz et al. (1999) *Nature Biotechnol.* 17:969-973, is suitable for use.

Suitable enzymes include, but are not limited to, horse radish peroxidase (HRP), alkaline phosphatase (AP), beta-galactosidase (GAL), glucose-6-phosphate dehydrogenase, beta-N-acetylglucosaminidase, β-glucuronidase, invertase, Xanthine Oxidase, firefly luciferase, glucose oxidase (GO), and the like.

Protospacer Adjacent Motif (PAM)

A CasX protein binds to target DNA at a target sequence defined by the region of complementarity between the DNA-targeting RNA and the target DNA. As is the case for many CRISPR endonucleases, site-specific binding and/or cleavage) of a double stranded target DNA occurs at locations determined by both (i) base-pairing complementarity between the guide RNA and the target DNA; and (ii) a short motif [referred to as the protospacer adjacent motif (PAM)] in the target DNA.

In some embodiments, the PAM for a CasX protein is immediately 5' of the target sequence of the non-complementary strand of the target DNA (the complementary strand hybridizes to the guide sequence of the guide RNA while the non-complementary strand does not directly hybridize with the guide RNA and is the reverse complement of the non-complementary strand). In some embodiments (e.g., when CasX1 as described herein is used), the PAM sequence of the non-complementary strand is 5'-TCN-3' (and in some cases TTCN), where N is any DNA nucleotide. As an example, see FIG. 6C, and FIG. 7, in which the PAM (TCN) (on the non-complementary strand) is TCA (and in the FIG. PAM shown is TTCA), and the PAM is 5' of the target sequence.

In some cases, different CasX proteins (i.e., CasX proteins from various species) may be advantageous to use in the various provided methods in order to capitalize on various enzymatic characteristics of the different CasX proteins (e.g., for different PAM sequence preferences; for increased or decreased enzymatic activity; for an increased or decreased level of cellular toxicity; to change the balance between NHEJ, homology-directed repair, single strand breaks, double strand breaks, etc.; to take advantage of a short total sequence; and the like). CasX proteins from different species may require different PAM sequences in the target DNA. Thus, for a particular CasX protein of choice, the PAM sequence requirement may be different than the 5'-TCN-3' sequence described above. Various methods (including in silico and/or wet lab methods) for identification of the appropriate PAM sequence are known in the art and are routine, and any convenient method can be used. The TCN PAM sequence described herein was identified using a PAM depletion assay (e.g., see FIGS. 5A-5C of the working examples below).

CasX Guide RNA

A nucleic acid molecule that binds to a CasX protein, forming a ribonucleoprotein complex (RNP), and targets the complex to a specific location within a target nucleic acid (e.g., a target DNA) is referred to herein as a "CasX guide RNA" or simply as a "guide RNA." It is to be understood that in some cases, a hybrid DNA/RNA can be made such that a CasX guide RNA includes DNA bases in addition to RNA bases, but the term "CasX guide RNA" is still used to encompass such a molecule herein.

A CasX guide RNA can be said to include two segments, a targeting segment and a protein-binding segment. The targeting segment of a CasX guide RNA includes a nucleotide sequence (a guide sequence) that is complementary to (and therefore hybridizes with) a specific sequence (a target site) within a target nucleic acid (e.g., a target ssRNA, a target ssDNA, the complementary strand of a double stranded target DNA, etc.). The protein-binding segment (or "protein-binding sequence") interacts with (binds to) a CasX polypeptide. The protein-binding segment of a subject CasX guide RNA includes two complementary stretches of nucleotides that hybridize to one another to form a double stranded RNA duplex (dsRNA duplex). Site-specific binding and/or cleavage of a target nucleic acid (e.g., genomic DNA) can occur at locations (e.g., target sequence of a target locus) determined by base-pairing complementarity between the CasX guide RNA (the guide sequence of the CasX guide RNA) and the target nucleic acid.

A CasX guide RNA and a CasX protein, e.g., a fusion CasX polypeptide, form a complex (e.g., bind via non-covalent interactions). The CasX guide RNA provides target specificity to the complex by including a targeting segment, which includes a guide sequence (a nucleotide sequence that is complementary to a sequence of a target nucleic acid). The CasX protein of the complex provides the site-specific activity (e.g., cleavage activity provided by the CasX protein and/or an activity provided by the fusion partner in the case of a chimeric CasX protein). In other words, the CasX protein is guided to a target nucleic acid sequence (e.g. a target sequence) by virtue of its association with the CasX guide RNA.

The "guide sequence" also referred to as the "targeting sequence" of a CasX guide RNA can be modified so that the CasX guide RNA can target a CasX protein (e.g., a naturally occurring CasX protein, a fusion CasX polypeptide (chimeric CasX), and the like) to any desired sequence of any desired target nucleic acid, with the exception (e.g., as described herein) that the PAM sequence can be taken into account. Thus, for example, a CasX guide RNA can have a guide sequence with complementarity to (e.g., can hybridize to) a sequence in a nucleic acid in a eukaryotic cell, e.g., a viral nucleic acid, a eukaryotic nucleic acid (e.g., a eukaryotic chromosome, chromosomal sequence, a eukaryotic RNA, etc.), and the like.

A subject CasX guide RNA can also be said to include an "activator" and a "targeter" (e.g., an "activator-RNA" and a "targeter-RNA," respectively). When the "activator" and a "targeter" are two separate molecules the guide RNA is referred to herein as a "dual guide RNA", a "dgRNA," a "double-molecule guide RNA", or a "two-molecule guide RNA." (e.g., a "CasX dual guide RNA"). In some embodiments, the activator and targeter are covalently linked to one another (e.g., via intervening nucleotides) and the guide RNA is referred to herein as a "single guide RNA", an "sgRNA," a "single-molecule guide RNA," or a "one-molecule guide RNA" (e.g., a "CasX single guide RNA"). Thus, a subject CasX single guide RNA comprises a targeter (e.g., targeter-RNA) and an activator (e.g., activator-RNA) that are linked to one another (e.g., by intervening nucleotides), and hybridize to one another to form the double stranded RNA duplex (dsRNA duplex) of the protein-binding segment of the guide RNA, thus resulting in a stem-loop structure (FIG. 6C). Thus, the targeter and the activator each have a duplex-forming segment, where the duplex forming segment of the targeter and the duplex-forming segment of the activator have complementarity with one another and hybridize to one another.

In some embodiments, the linker of a CasX single guide RNA is a stretch of nucleotides (depicted as GAAA in FIG. 6C). In some cases, the targeter and activator of a CasX single guide RNA are linked to one another by intervening nucleotides and the linker can have a length of from 3 to 20 nucleotides (nt) (e.g., from 3 to 15, 3 to 12, 3 to 10, 3 to 8, 3 to 6, 3 to 5, 3 to 4, 4 to 20, 4 to 15, 4 to 12, 4 to 10, 4 to 8, 4 to 6, or 4 to 5 nt). In some embodiments, the linker of a CasX single guide RNA can have a length of from 3 to 100 nucleotides (nt) (e.g., from 3 to 80, 3 to 50, 3 to 30, 3 to 25, 3 to 20, 3 to 15, 3 to 12, 3 to 10, 3 to 8, 3 to 6, 3 to 5, 3 to 4, 4 to 100, 4 to 80, 4 to 50, 4 to 30, 4 to 25, 4 to 20, 4 to 15, 4 to 12, 4 to 10, 4 to 8, 4 to 6, or 4 to 5 nt). In some embodiments, the linker of a CasX single guide RNA can have a length of from 3 to 10 nucleotides (nt) (e.g., from 3 to 9, 3 to 8, 3 to 7, 3 to 6, 3 to 5, 3 to 4, 4 to 10, 4 to 9, 4 to 8, 4 to 7, 4 to 6, or 4 to 5 nt).

Guide Sequence of a CasX Guide RNA

The targeting segment of a subject CasX guide RNA includes a guide sequence (i.e., a targeting sequence), which is a nucleotide sequence that is complementary to a sequence (a target site) in a target nucleic acid. In other words, the targeting segment of a CasX guide RNA can interact with a target nucleic acid (e.g., double stranded DNA (dsDNA), single stranded DNA (ssDNA), single stranded RNA (ssRNA), or double stranded RNA (dsRNA)) in a sequence-specific manner via hybridization (i.e., base pairing). The guide sequence of a CasX guide RNA can be modified (e.g., by genetic engineering)/designed to hybridize to any desired target sequence (e.g., while taking the PAM into account, e.g., when targeting a dsDNA target) within a target nucleic acid (e.g., a eukaryotic target nucleic acid such as genomic DNA).

In some embodiments, the percent complementarity between the guide sequence and the target site of the target nucleic acid is 60% or more (e.g., 65% or more, 70% or more, 75% or more, 80% or more, 85% or more, 90% or more, 95% or more, 97% or more, 98% or more, 99% or more, or 100%). In some cases, the percent complementarity between the guide sequence and the target site of the target nucleic acid is 80% or more (e.g., 85% or more, 90% or more, 95% or more, 97% or more, 98% or more, 99% or more, or 100%). In some cases, the percent complementarity between the guide sequence and the target site of the target nucleic acid is 90% or more (e.g., 95% or more, 97% or more, 98% or more, 99% or more, or 100%). In some cases, the percent complementarity between the guide sequence and the target site of the target nucleic acid is 100%.

In some cases, the percent complementarity between the guide sequence and the target site of the target nucleic acid is 100% over the seven contiguous 3'-most nucleotides of the target site of the target nucleic acid.

In some cases, the percent complementarity between the guide sequence and the target site of the target nucleic acid is 60% or more (e.g., 70% or more, 75% or more, 80% or more, 85% or more, 90% or more, 95% or more, 97% or more, 98% or more, 99% or more, or 100%) over 19 or more (e.g., 20 or more, 21 or more, 22 or more) contiguous nucleotides. In some cases, the percent complementarity between the guide sequence and the target site of the target nucleic acid is 80% or more (e.g., 85% or more, 90% or more, 95% or more, 97% or more, 98% or more, 99% or more, or 100%) over 19 or more (e.g., 20 or more, 21 or more, 22 or more) contiguous nucleotides. In some cases, the percent complementarity between the guide sequence and the target site of the target nucleic acid is 90% or more (e.g., 95% or more, 97% or more, 98% or more, 99% or more, or 100%) over 19 or more (e.g., 20 or more, 21 or more, 22 or more) contiguous nucleotides. In some cases, the percent complementarity between the guide sequence and the target site of the target nucleic acid is 100% over 19 or more (e.g., 20 or more, 21 or more, 22 or more) contiguous nucleotides.

In some cases, the percent complementarity between the guide sequence and the target site of the target nucleic acid is 60% or more (e.g., 70% or more, 75% or more, 80% or more, 85% or more, 90% or more, 95% or more, 97% or more, 98% or more, 99% or more, or 100%) over 19-25 contiguous nucleotides. In some cases, the percent complementarity between the guide sequence and the target site of the target nucleic acid is 80% or more (e.g., 85% or more, 90% or more, 95% or more, 97% or more, 98% or more, 99% or more, or 100%) over 19-25 contiguous nucleotides. In some cases, the percent complementarity between the guide sequence and the target site of the target nucleic acid is 90% or more (e.g., 95% or more, 97% or more, 98% or more, 99% or more, or 100%) over 19-25 contiguous nucleotides. In some cases, the percent complementarity between the guide sequence and the target site of the target nucleic acid is 100% over 19-25 contiguous nucleotides.

In some cases, the guide sequence has a length in a range of from 19-30 nucleotides (nt) (e.g., from 19-25, 19-22, 19-20, 20-30, 20-25, or 20-22 nt). In some cases, the guide sequence has a length in a range of from 19-25 nucleotides (nt) (e.g., from 19-22, 19-20, 20-25, 20-25, or 20-22 nt). In some cases, the guide sequence has a length of 19 or more nt (e.g., 20 or more, 21 or more, or 22 or more nt; 19 nt, 20 nt, 21 nt, 22 nt, 23 nt, 24 nt, 25 nt, etc.). In some cases the guide sequence has a length of 19 nt. In some cases the guide sequence has a length of 20 nt. In some cases the guide sequence has a length of 21 nt. In some cases the guide sequence has a length of 22 nt. In some cases the guide sequence has a length of 23 nt.

Protein-Binding Segment of a CasX Guide RNA

The protein-binding segment of a subject CasX guide RNA interacts with a CasX protein. The CasX guide RNA guides the bound CasX protein to a specific nucleotide sequence within target nucleic acid via the above mentioned guide sequence. The protein-binding segment of a CasX guide RNA comprises two stretches of nucleotides (the duplex-forming segment of the activator and the duplex-forming segment of the targeter) that are complementary to one another and hybridize to form a double stranded RNA duplex (dsRNA duplex). Thus, the protein-binding segment includes a dsRNA duplex.

In some cases, the dsRNA duplex region formed between the activator and targeter (i.e., the activator/targeter dsRNA duplex) (e.g., in dual or single guide RNA format) includes a range of from 8-25 base pairs (bp) (e.g., from 8-22, 8-18, 8-15, 8-12, 12-25, 12-22, 12-18, 12-15, 13-25, 13-22, 13-18, 13-15, 14-25, 14-22, 14-18, 14-15, 15-25, 15-22, 15-18, 17-25, 17-22, or 17-18 bp, e.g., 15 bp, 16 bp, 17 bp, 18 bp, 19 bp, 20 bp, 21 bp, etc.). In some cases, the duplex region (e.g., in dual or single guide RNA format) includes 8 or more bp (e.g., 10 or more, 12 or more, 15 or more, or 17 or more bp). In some cases, not all nucleotides of the duplex region are paired, and therefore the duplex forming region can include a bulge (e.g., see FIG. 6C, and FIG. 7). The term "bulge" herein is used to mean a stretch of nucleotides (which can be one nucleotide) that do not contribute to a double stranded duplex, but which are surround 5' and 3' by nucleotides that do contribute, and as such a bulge is considered part of the duplex region. In some cases, the dsRNA duplex formed between the activator and targeter (i.e., the activator/targeter dsRNA duplex) includes 1 or more bulges (e.g., 2 or more, 3 or more, 4 or more bulges). In some cases, the dsRNA duplex formed between the activator and targeter (i.e., the activator/targeter dsRNA duplex) includes 2 or more bulges (e.g., 3 or more, 4 or more bulges). In some cases, the dsRNA duplex formed between the activator and targeter (i.e., the activator/targeter dsRNA duplex) includes 1-5 bulges (e.g., 1-4, 1-3, 2-5, 2-4, or 2-3 bulges).

Thus, in some cases, the duplex-forming segments of the activator and targeter have 70%-100% complementarity (e.g., 75%-100%, 80%-10%, 85%-100%, 90%-100%, 95%-100% complementarity) with one another. In some cases, the duplex-forming segments of the activator and targeter have 70%-100% complementarity (e.g., 75%-100%, 80%-10%, 85%-100%, 90%-100%, 95%-100% complementarity) with one another. In some cases, the duplex-forming segments of the activator and targeter have 85%-100% complementarity (e.g., 90%-100%, 95%-100% complementarity) with one another. In some cases, the duplex-forming segments of the activator and targeter have 70%-95% complementarity (e.g., 75%-95%, 80%-95%, 85%-95%, 90%-95% complementarity) with one another.

In other words, in some embodiments, the dsRNA duplex formed between the activator and targeter (i.e., the activator/targeter dsRNA duplex) includes two stretches of nucleotides that have 70%-100% complementarity (e.g., 75%-100%, 80%-10%, 85%-100%, 90%-100%, 95%-100% complementarity) with one another. In some cases, the activator/targeter dsRNA duplex includes two stretches of nucleotides that have 85%-100% complementarity (e.g., 90%-100%, 95%-100% complementarity) with one another. In some cases, the activator/targeter dsRNA duplex includes two stretches of nucleotides that have 70%-95% complementarity (e.g., 75%-95%, 80%-95%, 85%-95%, 90%-95% complementarity) with one another.

The duplex region of a subject CasX guide RNA (in dual guide or single guide RNA format) can include one or more (1, 2, 3, 4, 5, etc) mutations relative to a naturally occurring duplex region. For example, in some cases a base pair can be maintained while the nucleotides contributing to the base pair from each segment (targeter and activator) can be different. In some cases, the duplex region of a subject CasX guide RNA includes more paired bases, less paired bases, a smaller bulge, a larger bulge, fewer bulges, more bulges, or any convenient combination thereof, as compared to a naturally occurring duplex region (of a naturally occurring CasX guide RNA).

In some cases, the activator (e.g., activator-RNA) of a subject CasX guide RNA (in dual or single guide RNA format) includes at least two internal RNA duplexes (i.e., two internal hairpins in addition to the activator/targeter dsRNA). The internal RNA duplexes (hairpins) of the activator can be positioned 5' of the activator/targeter dsRNA duplex (e.g., see FIG. 6C, and FIG. 7, both of which include an activator with 2 internal hairpins positioned 5' of the activator/targeter dsRNA duplex). In some cases, the activator includes one hairpin positioned 5' of the activator/targeter dsRNA duplex. In some cases, the activator includes two hairpins positioned 5' of the activator/targeter dsRNA duplex. In some cases, the activator includes three hairpins positioned 5' of the activator/targeter dsRNA duplex. In some cases, the activator includes two or more hairpins (e.g., 3 or more or 4 or more hairpins) positioned 5' of the activator/targeter dsRNA duplex. In some cases, the activator includes 2 to 5 hairpins (e.g., 2 to 4, or 2 to 3 hairpins) positioned 5' of the activator/targeter dsRNA duplex.

In some cases, the activator-RNA (e.g., in dual or single guide RNA format) comprises at least 2 nucleotides (nt) (e.g., at least 3 or at least 4 nt) 5' of the 5'-most hairpin stem, e.g., as depicted in the tracrRNA of FIGS. 6A-6C and FIG. 7. In some cases, the activator-RNA (e.g., in dual or single guide RNA format) comprises at least 4 nt 5' of the 5'-most hairpin stem, e.g., as depicted in the tracrRNA of FIGS. 6A-6C and FIG. 7.

In some cases, the activator-RNA (e.g., in dual or single guide format) has a length of 65 nucleotides (nt) or more (e.g., 66 or more, 67 or more, 68 or more, 69 or more, 70 or more, or 75 or more nt). In some cases, the activator-RNA (e.g., in dual or single guide format) has a length of 66 nt or more (e.g., 67 or more, 68 or more, 69 or more, 70 or more, or 75 or more nt). In some cases, the activator-RNA (e.g., in dual or single guide format) has a length of 67 nt or more (e.g., 68 or more, 69 or more, 70 or more, or 75 or more nt).

In some cases, the activator-RNA (e.g., in dual or single guide format) includes 45 or more nucleotides (nt) (e.g., 46 or more, 47 or more, 48 or more, 49 or more, 50 or more, 51 or more, 52 or more, 53 or more, 54 or more, or 55 or more nt) 5' of the dsRNA duplex formed between the activator and the targeter (the activator/targeter dsRNA duplex). In some cases, the activator is truncated at the 5' end relative to a naturally occurring CasX activator. In some cases, the activator is extended at the 5' end relative to a naturally occurring CasX activator.

Examples of various Cas9 guide RNAs can be found in the art, and in some cases variations similar to those introduced into Cas9 guide RNAs can also be introduced into CasX guide RNAs of the present disclosure. For example, see Jinek et al., Science. 2012 Aug. 17; 337(6096):816-21; Chylinski et al., RNA Biol. 2013 May; 10(5):726-37; Ma et al., Biomed Res Int. 2013; 2013:270805; Hou et al., Proc Natl Acad Sci USA. 2013 Sep. 24; 110(39):15644-9; Jinek et al., Elife. 2013; 2:e00471; Pattanayak et al., Nat Biotechnol. 2013 September; 31(9):839-43; Qi et al, Cell. 2013 Feb. 28; 152(5):1173-83; Wang et al., Cell. 2013 May 9; 153(4):910-8; Auer et. al., Genome Res. 2013 Oct. 31; Chen et. al., Nucleic Acids Res. 2013 Nov. 1; 41(20):e19; Cheng et. al., Cell Res. 2013 October; 23(10):1163-71; Cho et. al., Genetics. 2013 November; 195(3):1177-80; DiCarlo et al., Nucleic Acids Res. 2013 April; 41(7):4336-43; Dickinson et. al., Nat Methods. 2013 October; 10(10):1028-34; Ebina et. al., Sci Rep. 2013; 3:2510; Fujii et. al, Nucleic Acids Res. 2013 Nov. 1; 41(20):e187; Hu et. al., Cell Res. 2013 November; 23(11):1322-5; Jiang et. al., Nucleic Acids Res. 2013 Nov. 1; 41(20):e188; Larson et. al., Nat Protoc. 2013 November; 8(11):2180-96; Mali et. at., Nat Methods. 2013 October; 10(10):957-63; Nakayama et. al., Genesis. 2013 December; 51(12):835-43; Ran et. al., Nat Protoc. 2013 November; 8(11):2281-308; Ran et. al., Cell. 2013 Sep. 12; 154(6):1380-9; Upadhyay et. al., G3 (Bethesda). 2013 Dec. 9; 3(12):2233-8; Walsh et. al., Proc Natl Acad Sci USA. 2013 Sep. 24; 110(39):15514-5; Xie et. al., Mol Plant. 2013 Oct. 9; Yang et. al., Cell. 2013 Sep. 12; 154(6):1370-9; Briner et al., Mol Cell. 2014 Oct. 23; 56(2):333-9; and U.S. patents and patent applications: U.S. Pat. Nos. 8,906,616; 8,895,308; 8,889,418; 8,889,356; 8,871,445; 8,865,406; 8,795,965; 8,771,945; 8,697,359; 20140068797; 20140170753; 20140179006; 20140179770; 20140186843;

20140186919; 20140186958; 20140189896; 20140227787; 20140234972; 20140242664; 20140242699; 20140242700; 20140242702; 20140248702; 20140256046; 20140273037; 20140273226; 20140273230; 20140273231; 20140273232; 20140273233; 20140273234; 20140273235; 20140287938; 20140295556; 20140295557; 20140298547; 20140304853; 20140309487; 20140310828; 20140310830; 20140315985; 20140335063; 20140335620; 20140342456; 20140342457; 20140342458; 20140349400; 20140349405; 20140356867; 20140356956; 20140356958; 20140356959; 20140357523; 20140357530; 20140364333; and 20140377868; all of which are hereby incorporated by reference in their entirety.

The term "activator" or "activator RNA" is used herein to mean a tracrRNA-like molecule (tracrRNA: "trans-acting CRISPR RNA") of a CasX dual guide RNA (and therefore of a CasX single guide RNA when the "activator" and the "targeter" are linked together by, e.g., intervening nucleotides). Thus, for example, a CasX guide RNA (dgRNA or sgRNA) comprises an activator sequence (e.g., a tracrRNA sequence). A tracr molecule (a tracrRNA) is a naturally existing molecule that hybridizes with a CRISPR RNA molecule (a crRNA) to form a CasX dual guide RNA. The term "activator" is used herein to encompass naturally existing tracrRNAs, but also to encompass tracrRNAs with modifications (e.g., truncations, extensions, sequence variations, base modifications, backbone modifications, linkage modifications, etc.) where the activator retains at least one function of a tracrRNA (e.g., contributes to the dsRNA duplex to which CasX protein binds). In some cases the activator provides one or more stem loops that can interact with CasX protein. An activator can be referred to as having a tracr sequence (tracrRNA sequence) and in some cases is a tracrRNA, but the term "activator" is not limited to naturally existing tracrRNAs.

In some cases (e.g., in some cases where the guide RNA is in single guide format), the activator-RNA is truncated (shorter) relative to the corresponding wild type tracrRNA. In some cases (e.g., in some cases where the guide RNA is in single guide format) the activator-RNA is not truncated (shorter) relative to the corresponding wild type tracrRNA. In some cases (e.g., in some cases where the guide RNA is in single guide format) the activator-RNA has a length that is greater than 50 nt (e.g., greater than 55 nt, greater than 60 nt, greater than 65 nt, greater than 70 nt, greater than 75 nt, greater than 80 nt). In some cases (e.g., in some cases where the guide RNA is in single guide format) the activator-RNA has a length that is greater than 80 nt. In some cases (e.g., in some cases where the guide RNA is in single guide format) the activator-RNA has a length in a range of from 51 to 90 nt (e.g., from 51-85, 51-84, 55-90, 55-85, 55-84, 60-90, 60-85, 60-84, 65-90, 65-85, 65-84, 70-90, 70-85, 70-84, 75-90, 75-85, 75-84, 80-90, 80-85, or 80-84 nt). In some cases (e.g., in some cases where the guide RNA is in single guide format) the activator-RNA has a length in a range of from 80-90 nt.

The term "targeter" or "targeter RNA" is used herein to refer to a crRNA-like molecule (crRNA: "CRISPR RNA") of a CasX dual guide RNA (and therefore of a CasX single guide RNA when the "activator" and the "targeter" are linked together, e.g., by intervening nucleotides). Thus, for example, a CasX guide RNA (dgRNA or sgRNA) comprises a guide sequences and a duplex-forming segment (e.g., a duplex forming segment of a crRNA, which can also be referred to as a crRNA repeat). Because the sequence of a targeting segment (the segment that hybridizes with a target sequence of a target nucleic acid) of a targeter is modified by a user to hybridize with a desired target nucleic acid, the sequence of a targeter will often be a non-naturally occurring sequence. However, the duplex-forming segment of a targeter (described in more detail herein), which hybridizes with the duplex-forming segment of an activator, can include a naturally existing sequence (e.g., can include the sequence of a duplex-forming segment of a naturally existing crRNA, which can also be referred to as a crRNA repeat). Thus, the term targeter is used herein to distinguish from naturally occurring crRNAs, despite the fact that part of a targeter (e.g., the duplex-forming segment) often includes a naturally occurring sequence from a crRNA. However, the term "targeter" encompasses naturally occurring crRNAs.

As noted above, a targeter comprises both the guide sequence of the CasX guide RNA and a stretch (a "duplex-forming segment") of nucleotides that forms one half of the dsRNA duplex of the protein-binding segment of the CasX guide RNA. A corresponding tracrRNA-like molecule (activator) comprises a stretch of nucleotides (a duplex-forming segment) that forms the other half of the dsRNA duplex of the protein-binding segment of the CasX guide RNA. In other words, a stretch of nucleotides of the targeter is complementary to and hybridizes with a stretch of nucleotides of the activator to form the dsRNA duplex of the protein-binding segment of a CasX guide RNA. As such, each targeter can be said to have a corresponding activator (which has a region that hybridizes with the targeter). The targeter molecule additionally provides the guide sequence. Thus, a targeter and an activator (as a corresponding pair) hybridize to form a CasX guide RNA. The particular sequence of a given naturally existing crRNA or tracrRNA molecule can be characteristic of the species in which the RNA molecules are found. Examples of suitable activators and targeters are provided herein.

Example Guide RNA Sequences

Figure 6A:
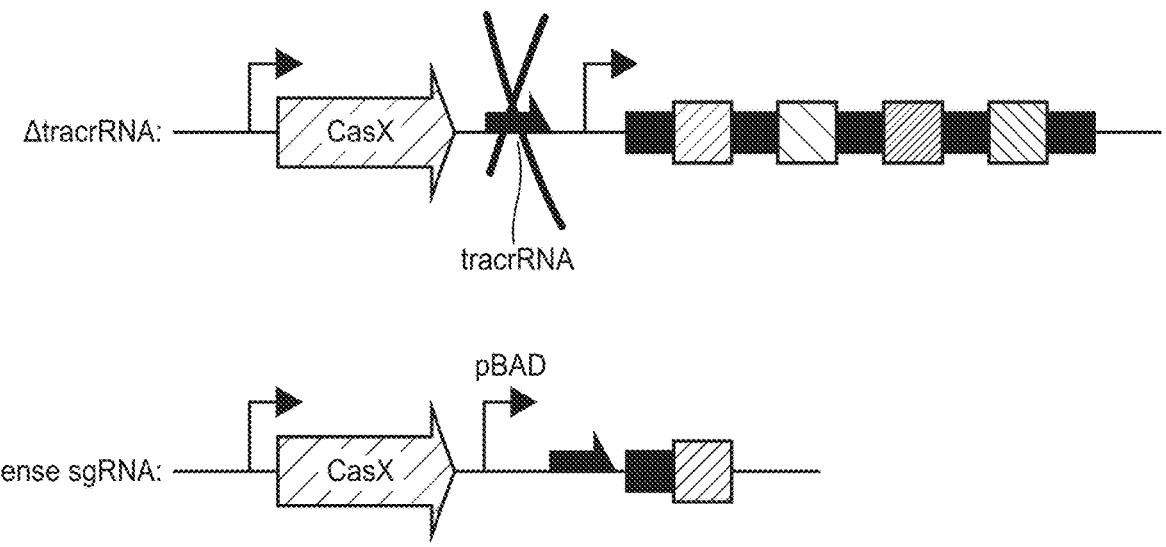
FIGS. 6A-6C depict experiments performed to determine that CasX is a dual-guided CRISPR-Cas effector complex. Sequences depicted from top to bottom: SEQ ID NOs:138-140.
Figure 6B:
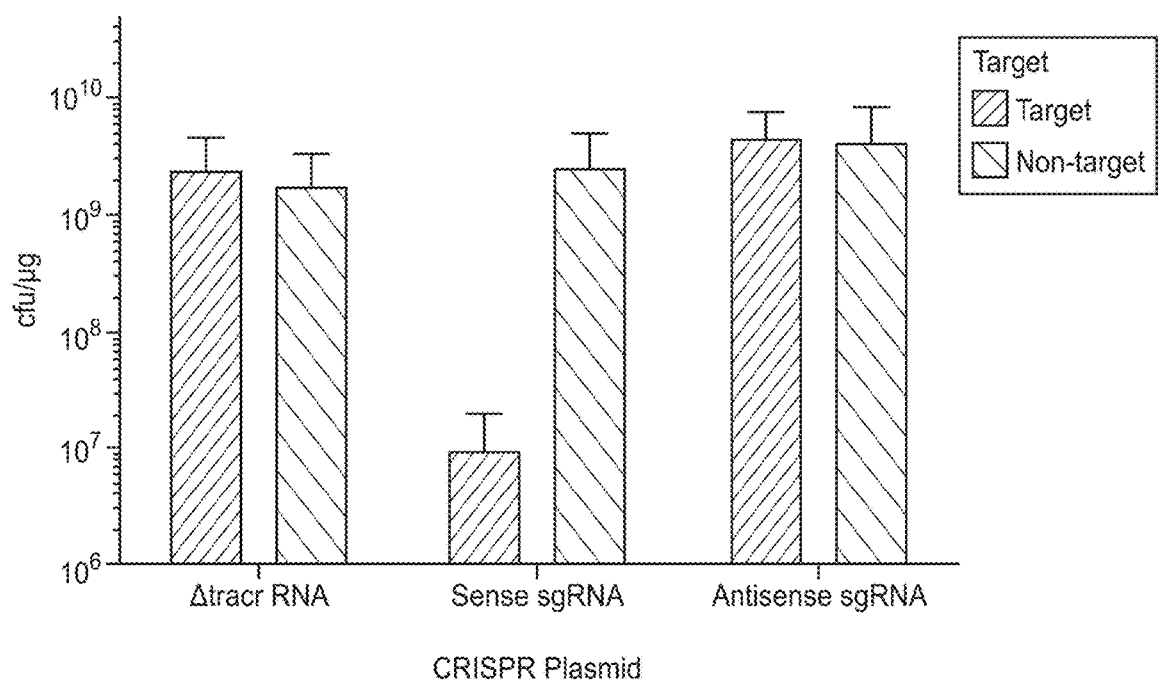
Figure 6C:
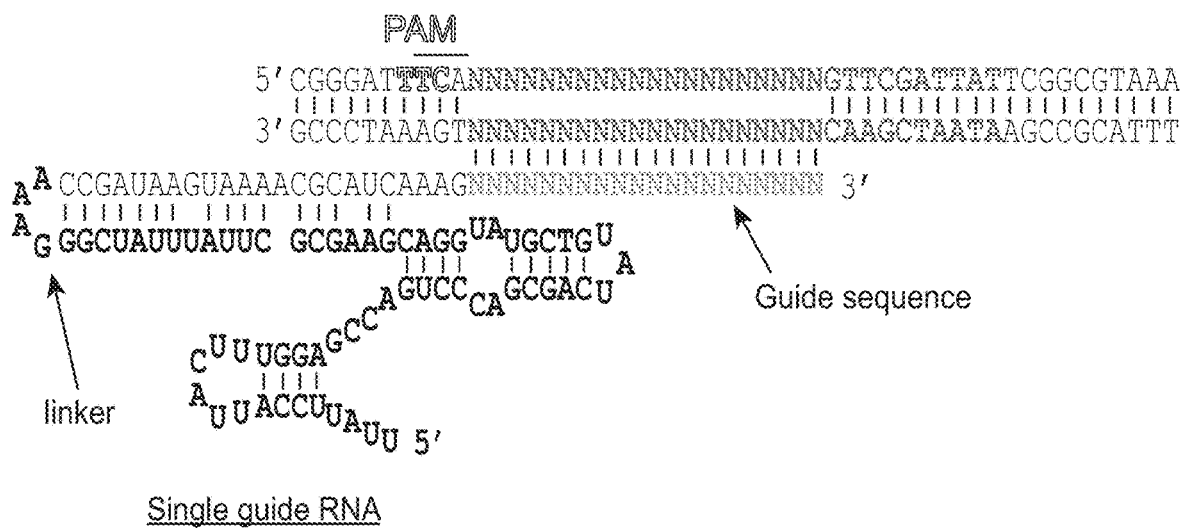
Figure 7:
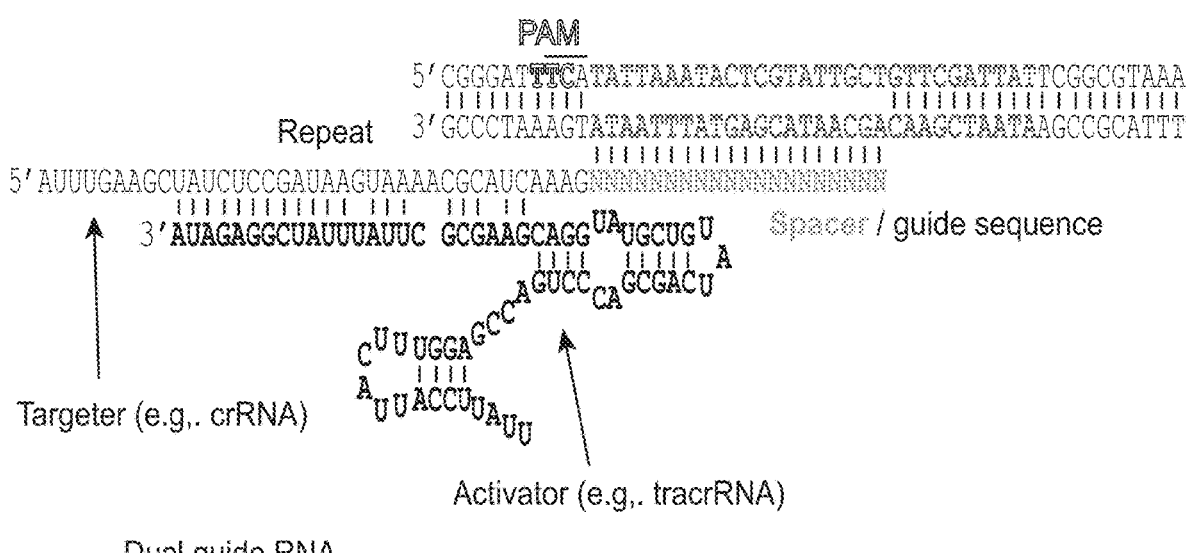
FIG. 7 presents a schematic of CasX RNA guided DNA interference. Sequences depicted from top to bottom: SEQ ID NOs:141-144.

The guide RNAs depicted in FIGS. 6A-6C (dual guide format) and FIG. 7 (dual guide format) are from the natural locus for CasX1. For the sequences discussed in the paragraphs below, and for the sequences described and tested in the working examples below, the tracrRNA and crRNA sequences were from the CasX1 locus. The same parameters and sets of possible targeter-RNAs and activator-RNAs are expected and can be derived from comparing the sequences for the CasX1 locus with those of the CasX2 locus. For example, CasX1 tracrRNA sequences:

```
                                        (SEQ ID NO: 25)
UUAUUCCAUUACUUUGGAGCCAGUCCCAGCGACUAUGUCGUAUGGACGAA
GCGCUUAUUUAUCGGAGA
```
and
```
                                        (SEQ ID NO: 23)
UUAUUCCAUUACUUUGGAGCCAGUCCCAGCGACUAUGUCGUAUGGACGAA
GCGCUUAUUUAUCGG
``` can be compared to the CasX2 tracrRNA sequences:

```
                                        (SEQ ID NO: 26)
UUAUCUCAUUACUUUGAGAGCCAUCACCAGCGACUAUGUCGUAUGGGUAA
AGCGCUUAUUUAUCGGAGA
```
and
```
                                        (SEQ ID NO: 27)
UUAUCUCAUUACUUUGAGAGCCAUCACCAGCGACUAUGUCGUAUGGGUAA
AGCGCUUAUUUAUCGG.
```

For the CasX3 locus, tracr is likely within these 230 nt (complementary region is underlined):

(SEQ ID NO: 28)
UAAAUUUUUUGAGCCCUAUCUCCGCGAGGAAGACAGGGCUCUUUUCAUG
AGAGGAAGCUUUUAUACCCGACCGGUAAUCCGGUCGGGGAUUGGCCGU
UGAAACGAUUUUAAAGCGGCCAAUGGGCCCCUCUAUAUGGAUACUACUU
AUAUAAGGAGCUUGGGGAAGAAGAUAGCUUAAUCCCGCUAUCUUGUCAA
GGGGUUGGGGGAGUAUCAGUAUCCGGCAGGCGCC.

Likewise, the CasX1 crRNA sequence CCGAUAAGUAAAACGCAU-CAAAGNNNNNNNNNNNNNNNNNNNNN (SEQ ID NO: 11 without the Ns, SEQ ID NO: 61 with the Ns) can be compared to the CasX2 crRNA sequence UCUC-CGAUAAAUAAGAAGCAU-CAAAGNNNNNNNNNNNNNNNNNNNNN (SEQ ID NO: 13 without the Ns, SEQ ID NO: 69 with the Ns).

crRNA repeats from the CasX3 locus are GTTTACA-CACTCCCTCTCATAGGGT (SEQ ID NO: 54), GTTTA-CACACTCCCTCTCATGAGGT (SEQ ID NO: 55), TTT-TACATACCCCCTCTCATGGGAT (SEQ ID NO: 56), and GTTTACACACTCCCTCTCATGGGGG (SEQ ID NO: 57). Therefore crRNA sequences (e.g., from the CasX3 locus) can include GUUUACACACUCCCUCUCAUAGG-GUNNNNNNNNNNNNNNNNNNNNN (SEQ ID NO: 14 without the Ns, SEQ ID NO: 31 with the Ns), GUUUACA-CACUCCCUCUCAUGAG-GUNNNNNNNNNNNNNNNNNNNNN (SEQ ID NO: 15 without the Ns, SEQ ID NO: 32 with the Ns), UUUUA-CAUACCCCUCU-CAUGGGAUNNNNNNNNNNNNNNNNNNNNN (SEQ ID NO: 16 without the Ns, SEQ ID NO: 33 with the Ns), and/or GUUUACACACUCCCUCU-CAUGGGGGNNNNNNNNNNNNNNNNNNNNN (SEQ ID NO: 17 without the Ns, SEQ ID NO: 34 with the Ns).

Example Targeter-RNA (e.g., crRNA) Sequences

In some cases, the targeter-RNA (e.g., in dual or single guide RNA format) comprises (e.g., in addition to a guide sequence) the crRNA sequence CCGAUAAGUAAAACG-CAUCAAAG (SEQ ID NO: 11) (e.g., see the sgRNA of FIG. 6C). In some cases, the targeter-RNA (e.g., in dual or single guide RNA format) comprises a nucleotide sequence having 80% or more identity (e.g., 85% or more, 90% or more, 93% or more, 95% or more, 97% or more, 98% or more, or 100% identity) with the crRNA sequence CCGAUAAGUAAAACGCAUCAAAG (SEQ ID NO: 11).

In some cases, the targeter-RNA comprises (e.g., in addition to a guide sequence) the crRNA sequence AUUUGAAGGUAUCUCCGAUAAGUAAAACGCAU-CAAAG (SEQ ID NO: 12). In some cases, the targeter-RNA comprises a nucleotide sequence having 80% or more identity (e.g., 85% or more, 90% or more, 93% or more, 95% or more, 97% or more, 98% or more, or 100% identity) with the crRNA sequence AUUUGAAGGUAUCUC-CGAUAAGUAAAACGCAUCAAAG (SEQ ID NO: 12).

In some cases, the targeter-RNA (e.g., in dual or single guide RNA format) comprises (e.g., in addition to a guide sequence) the crRNA sequence UCUC-CGAUAAAUAAGAAGCAUCAAAG (SEQ ID NO: 13). In some cases, the targeter-RNA (e.g., in dual or single guide RNA format) comprises a nucleotide sequence having 80% or more identity (e.g., 85% or more, 90% or more, 93% or more, 95% or more, 97% or more, 98% or more, or 100% identity) with the crRNA sequence (SEQ ID NO: 13)
UCUCCGAUAAAUAAGAAGCAUCAAAG.

In some cases, the targeter-RNA (e.g., in dual or single guide RNA format) comprises (e.g., in addition to a guide sequence) the crRNA sequence GUUUACACACUCCCU-CUCAUAGGGU (SEQ ID NO: 14). In some cases, the targeter-RNA (e.g., in dual or single guide RNA format) comprises a nucleotide sequence having 80% or more identity (e.g., 85% or more, 90% or more, 93% or more, 95% or more, 97% or more, 98% or more, or 100% identity) with the crRNA sequence (SEQ ID NO: 14)
GUUUACACACUCCCUCUCAUAGGGU.

In some cases, the targeter-RNA (e.g., in dual or single guide RNA format) comprises (e.g., in addition to a guide sequence) the crRNA sequence GUUUACACACUCCCU-CUCAUGAGGU (SEQ ID NO: 15). In some cases, the targeter-RNA (e.g., in dual or single guide RNA format) comprises a nucleotide sequence having 80% or more identity (e.g., 85% or more, 90% or more, 93% or more, 95% or more, 97% or more, 98% or more, or 100% identity) with the crRNA sequence (SEQ ID NO: 15)
GUUUACACACUCCCUCUCAUGAGGU.

In some cases, the targeter-RNA (e.g., in dual or single guide RNA format) comprises (e.g., in addition to a guide sequence) the crRNA sequence UUUUACAUACCCCCU-CUCAUGGGAU (SEQ ID NO: 16). In some cases, the targeter-RNA (e.g., in dual or single guide RNA format) comprises a nucleotide sequence having 80% or more identity (e.g., 85% or more, 90% or more, 93% or more, 95% or more, 97% or more, 98% or more, or 100% identity) with the crRNA sequence (SEQ ID NO: 16)
UUUUACAUACCCCCUCUCAUGGGAU.

In some cases, the targeter-RNA (e.g., in dual or single guide RNA format) comprises (e.g., in addition to a guide sequence) the crRNA sequence GUUUACACACUCCCU-CUCAUGGGGG (SEQ ID NO: 17). In some cases, the targeter-RNA (e.g., in dual or single guide RNA format) comprises a nucleotide sequence having 80% or more identity (e.g., 85% or more, 90% or more, 93% or more, 95% or more, 97% or more, 98% or more, or 100% identity) with the crRNA sequence (SEQ ID NO: 17)
GUUUACACACUCCCUCUCAUGGGGG.

In some cases, the targeter-RNA (e.g., in dual or single guide RNA format) comprises (e.g., in addition to a guide sequence) the crRNA sequence set forth in any one of SEQ ID NOs: 11 and 13. In some cases, the targeter-RNA (e.g., in dual or single guide RNA format) comprises a nucleotide sequence having 80% or more identity (e.g., 85% or more, 90% or more, 93% or more, 95% or more, 97% or more, 98% or more, or 100% identity) with the crRNA sequence set forth in any one of SEQ ID NOs: 11 and 13.

In some cases, the targeter-RNA comprises (e.g., in addition to a guide sequence) the crRNA sequence set forth in any one of SEQ ID NOs: 11-13. In some cases, the targeter-RNA comprises a nucleotide sequence having 80% or more identity (e.g., 85% or more, 90% or more, 93% or more, 95% or more, 97% or more, 98% or more, or 100% identity) with the crRNA sequence set forth in any one of SEQ ID NOs: 11-13.

In some cases, the targeter-RNA comprises (e.g., in addition to a guide sequence) the crRNA sequence set forth in any one of SEQ ID NOs: 14-17. In some cases, the targeter-RNA comprises a nucleotide sequence having 80% or more identity (e.g., 85% or more, 90% or more, 93% or more, 95% or more, 97% or more, 98% or more, or 100% identity) with the crRNA sequence set forth in any one of SEQ ID NOs: 14-17.

In some cases, the targeter-RNA comprises (e.g., in addition to a guide sequence) the crRNA sequence set forth in any one of SEQ ID NOs: 11-17. In some cases, the targeter-RNA comprises a nucleotide sequence having 80% or more identity (e.g., 85% or more, 90% or more, 93% or more, 95% or more, 97% or more, 98% or more, or 100% identity) with the crRNA sequence set forth in any one of SEQ ID NOs: 11-17.

Example Activator-RNA (e.g., tracrRNA) Sequences

In some cases, the activator-RNA (e.g., in dual or single guide RNA format) comprises the tracrRNA sequence ACAUCUGGCGCGUUUAUUCCAUUACUUUGGAGCCAGUCCCAGCGACUAUGUCGUAUGGACGAAGCGCUUAUUUAUCGGAGA (SEQ ID NO: 21). In some cases, the targeter-RNA (e.g., in dual or single guide RNA format) comprises a nucleotide sequence having 80% or more identity (e.g., 85% or more, 90% or more, 93% or more, 95% or more, 97% or more, 98% or more, 99% or more, or 100% identity) with the tracrRNA sequence (SEQ ID NO: 21)
ACAUCUGGCGCGUUUAUUCCAUUACUUUGGAGCCAGUCCCAGCGACUAUGUCGUAUGGACGAAGCGCUUAUUUAUCGGAGA.

In some cases, the activator-RNA (e.g., in dual or single guide RNA format) comprises the tracrRNA sequence ACAUCUGGCGCGUUUAUUCCAUUACUUUGGAGCCAGUCCCAGCGACUAUGUCGUAUGGACGAAGCGCUUAUUUAUCGG (SEQ ID NO: 22). In some cases, the targeter-RNA (e.g., in dual or single guide RNA format) comprises a nucleotide sequence having 80% or more identity (e.g., 85% or more, 90% or more, 93% or more, 95% or more, 97% or more, 98% or more, 99% or more, or 100% identity) with the tracrRNA sequence (SEQ ID NO: 22)
ACAUCUGGCGCGUUUAUUCCAUUACUUUGGAGCCAGUCCCAGCGACUAUGUCGUAUGGACGAAGCGCUUAUUUAUCGG.

In some cases, the activator-RNA (e.g., in dual or single guide RNA format) comprises the tracrRNA sequence UUAUUCCAUUACUUUGGAGCCAGUCCCAGCGACUAUGUCGUAUGGACGAAGCGCUUAUU UAUCGG (SEQ ID NO: 23) (e.g., see the sgRNA of FIG. 6). In some cases, the targeter-RNA (e.g., in dual or single guide RNA format) comprises a nucleotide sequence having 80% or more identity (e.g., 85% or more, 90% or more, 93% or more, 95% or more, 97% or more, 98% or more, 99% or more, or 100% identity) with the tracrRNA sequence (SEQ ID NO: 23)
UUAUUCCAUUACUUUGGAGCCAGUCCCAGCGACUAUGUCGUAUGGACGAAGCGCUUAUUUAUCGG.

In some cases, the activator-RNA (e.g., in dual or single guide RNA format) comprises the tracrRNA sequence AAGUAGUAAAUUACAUCUGGCGCGUUUAUUCCAUUACUUUGGAGCCAGUCCCAGCGACU AUGUCGUAUGGACGAAGCGCUUAUUUAUCGGAGA (SEQ ID NO: 24) (e.g., see the sgRNA of 6). In some cases, the targeter-RNA (e.g., in dual or single guide RNA format) comprises a nucleotide sequence having 80% or more identity (e.g., 85% or more, 90% or more, 93% or more, 95% or more, 97% or more, 98% or more, 99% or more, or 100% identity) with the tracrRNA sequence (SEQ ID NO: 24)
AAGUAGUAAAUUACAUCUGGCGCGUUUAUUCCAUUACUUUGGAGCCAGUCCAGCGACUAUGUCGUAUGGACGAAGCGCUUAUUUAUCGGAGA.

In some cases, the activator-RNA (e.g., in dual or single guide RNA format) comprises the tracrRNA sequence UUAUUCCAUUACUUUGGAGCCAGUCCCAGCGACUAUGUCGUAUGGACGAAGCGCUUAUU UAUCGGAGA (SEQ ID NO: 25) (e.g., see the sgRNA of FIGS. 6A-6C). In some cases, the targeter-RNA (e.g., in dual or single guide RNA format) comprises a nucleotide sequence having 80% or more identity (e.g., 85% or more, 90% or more, 93% or more, 95% or more, 97% or more, 98% or more, 99% or more, or 100% identity) with the tracrRNA sequence (SEQ ID NO: 25)
UUAUUCCAUUACUUUGGAGCCAGUCCCAGCGACUAUGUCGUAUGGACGAAGCGCUUAUUUAUCGGAGA.

In some cases, the activator-RNA (e.g., in dual or single guide RNA format) comprises the tracrRNA sequence UUAUCUCAUUACUUUGAGAGCCAUCACCAGCGACUAUGUCGUAUGGGUAAAGCGCUUAU UUAUCGGAGA (SEQ ID NO: 26). In some cases, the targeter-RNA (e.g., in dual or single guide RNA format) comprises a nucleotide sequence having 80% or more identity (e.g., 85% or more, 90% or more, 93% or more, 95% or more, 97% or more, 98% or more, 99% or more, or 100% identity) with the tracrRNA sequence (SEQ ID NO: 26)
UUAUCUCAUUACUUUGAGAGCCAUCACCAGCGACUAUGUCGUAUGGGUAAAGCGCUUAUUUAUCGGAGA.

In some cases, the activator-RNA (e.g., in dual or single guide RNA format) comprises the tracrRNA sequence UUAUCUCAUUACUUUGAGAGCCAUCACCAGCGACUAUGUCGUAUGGGUAAAGCGCUUAU UUAUCGG (SEQ ID NO: 27). In some cases, the targeter-RNA (e.g., in dual or single guide RNA format) comprises a nucleotide sequence having 80% or more identity (e.g., 85% or more, 90% or more, 93% or more, 95% or more, 97% or more, 98% or more, 99% or more, or 100% identity) with the tracrRNA sequence (SEQ ID NO: 27)
UUAUCUCAUUACUUUGAGAGCCAUCACCAGCGACUAUGUCGUAUGGGUAA

AGCGCUUAUUUAUCGG.

In some cases, the activator-RNA (e.g., in dual or single guide RNA format) comprises a tracrRNA sequence from within the following sequence: UAAAUUUUUUGAGC-CCUAUCUCCGCGAGGAAGACAGGGCUCUUU UCAUGAGAGGAAGCU UUUAUACCCGACCG-GUAAUCCGGUCGGGGGAUUGGCCGUUGAAAC-GAUUUUAAAGCGGC CAAUGGGCCCCUCUAUAUG-GAUACUACUUAUAUAAGGAGCUUGGGGAAGAAGAUAGCUU AAUCCCGCUAUCUUGUCAAGGGGUUGGGGGA-GUAUCAGUAUCCGGCAGGCGCC (SEQ ID NO: 28). In some cases, the targeter-RNA (e.g., in dual or single guide RNA format) comprises a nucleotide sequence having 80% or more identity (e.g., 85% or more, 90% or more, 93% or more, 95% or more, 97% or more, 98% or more, 99% or more, or 100% identity) with the a tracrRNA sequence from within:

(SEQ ID NO: 28)
UAAAUUUUUUGAGCCCUAUCUCCGCGAGGAAGACAGGGCUCUUUUCAUG

AGAGGAAGCUUUUAUACCCGACCGGUAAUCCGGUCGGGGGAUUGGCCGU

UGAAACGAUUUUAAAGCGGCCAAUGGGCCCCUCUAUAUGGAUACUACUU

AUAUAAGGAGCUUGGGGAAGAAGAUAGCUUAAUCCCGCUAUCUUGUCAA

GGGGUUGGGGGAGUAUCAGUAUCCGGCAGGCGCC.

In some cases, the activator-RNA (e.g., in dual or single guide RNA format) comprises the tracrRNA sequence set forth in any one of SEQ ID NOs: 21-27. In some cases, the targeter-RNA (e.g., in dual or single guide RNA format) comprises a nucleotide sequence having 80% or more identity (e.g., 85% or more, 90% or more, 93% or more, 95% or more, 97% or more, 98% or more, 99% or more, or 100% identity) with the tracrRNA sequence set forth in any one of SEQ ID NOs: 21-27.

In some cases, the activator-RNA (e.g., in dual or single guide RNA format) comprises the tracrRNA sequence set forth in any one of SEQ ID NOs: 21-27. In some cases, the targeter-RNA (e.g., in dual or single guide RNA format) comprises a nucleotide sequence having 80% or more identity (e.g., 85% or more, 90% or more, 93% or more, 95% or more, 97% or more, 98% or more, 99% or more, or 100% identity) with the tracrRNA sequence set forth in any one of SEQ ID NOs: 21-28.

In some cases, a CasX single guide RNA comprises the sequence UUAUUCCAUUACUUUGGAGCCAGUCCCA-GCGACUAUGUCGUAUGGACGAAGCGCUUAUU UAUCGGgaaaCCGAUAAGUAAAACGCAUCAAAG (SEQ ID NO: 41). In some cases, the targeter-RNA comprises a nucleotide sequence having 80% or more identity (e.g., 85% or more, 90% or more, 93% or more, 95% or more, 97% or more, 98% or more, 99% or more, or 100% identity) with the tracrRNA sequence (SEQ ID NO: 41)
UUAUUCCAUUACUUUGGAGCCAGUCCCAGCGACUAUGUCGUAUGGACGAA
GCGCUUAUUUAUCGGgaaaCCGAUAAGUAAAACGCAUCAAAG.

In some cases, a CasX single guide RNA comprises the sequence ACAUCUGGCGCGUUUAUUCCAUUAC-UUUGGAGCCAGUCCCAGCGACUAUGUCGUAUG- GAC GAAGCGCUUAUUUAUCGGAGAgaaaC-CGAUAAGUAAAACGCAUCAAAG (SEQ ID NO: 42). In some cases, the targeter-RNA comprises a nucleotide sequence having 80% or more identity (e.g., 85% or more, 90% or more, 93% or more, 95% or more, 97% or more, 98% or more, 99% or more, or 100% identity) with the tracrRNA sequence (SEQ ID NO: 42)
ACAUCUGGCGCGUUUAUUCCAUUACUUUGGAGCCAGUCCCAGCGACUAUG UCGUAUGGACGAAGCGCUUAUUUAUCGGAGAgaaaCCGAUAAGUAAAACG

CAUCAAAG.

In some cases, a CasX single guide RNA comprises the sequence UUAUCUCAUUACUUUGAGAGCCAUCAC-CAGCGACUAUGUCGUAUGGGUAAAGCGCUUAU UUAUCGGgaaaUCUCCGAUAAAUAAGAAGCAU-CAAAG (SEQ ID NO: 43). In some cases, the targeter-RNA comprises a nucleotide sequence having 80% or more identity (e.g., 85% or more, 90% or more, 93% or more, 95% or more, 97% or more, 98% or more, 99% or more, or 100% identity) with the tracrRNA sequence (SEQ ID NO: 43)
UUAUCUCAUUACUUUGAGAGCCAUCACCAGCGACUAUGUCGUAUGGGUAA AGCGCUUAUUUAUCGGgaaaUCUCCGAUAAAUAAGAAGCAUCAAAG.

In some cases, a CasX single guide RNA comprises the sequence set forth in any one of SEQ ID NOs: 41-43. In some cases, the targeter-RNA comprises a nucleotide sequence having 80% or more identity (e.g., 85% or more, 90% or more, 93% or more, 95% or more, 97% or more, 98% or more, 99% or more, or 100% identity) with the tracrRNA sequence set forth in any one of SEQ ID NOs: 41-43.

CasX Systems

The present disclosure provides a CasX system. A CasX system of the present disclosure can comprise: a) a CasX polypeptide of the present disclosure and a CasX guide RNA; b) a CasX polypeptide of the present disclosure, a CasX guide RNA, and a donor template nucleic acid; c) a CasX fusion polypeptide of the present disclosure and a CasX guide RNA; d) a CasX fusion polypeptide of the present disclosure, a CasX guide RNA, and a donor template nucleic acid; e) an mRNA encoding a CasX polypeptide of the present disclosure; and a CasX guide RNA; f) an mRNA encoding a CasX polypeptide of the present disclosure, a CasX guide RNA, and a donor template nucleic acid; g) an mRNA encoding a CasX fusion polypeptide of the present disclosure; and a CasX guide RNA; h) an mRNA encoding a CasX fusion polypeptide of the present disclosure, a CasX guide RNA, and a donor template nucleic acid; i) a recombinant expression vector comprising a nucleotide sequence encoding a CasX polypeptide of the present disclosure and a nucleotide sequence encoding a CasX guide RNA; j) a recombinant expression vector comprising a nucleotide sequence encoding a CasX polypeptide of the present disclosure, a nucleotide sequence encoding a CasX guide RNA, and a nucleotide sequence encoding a donor template nucleic acid; k) a recombinant expression vector comprising a nucleotide sequence encoding a CasX fusion polypeptide of the present disclosure and a nucleotide sequence encoding a CasX guide RNA; l) a recombinant expression vector comprising a nucleotide sequence encoding a CasX fusion polypeptide of the present disclosure, a nucleotide sequence encoding a CasX guide RNA, and a nucleotide sequence encoding a donor template nucleic acid; m) a first recombinant expression vector comprising a nucleotide sequence encoding a CasX polypeptide of the present disclosure, and a second recombinant expression vector comprising a nucleotide sequence encoding a CasX guide RNA; n) a first recombinant expression vector comprising a nucleotide sequence encoding a CasX polypeptide of the present disclosure, and a second recombinant expression vector comprising a nucleotide sequence encoding a CasX guide RNA; and a donor template nucleic acid; o) a first recombinant expression vector comprising a nucleotide sequence encoding a CasX fusion polypeptide of the present disclosure, and a second recombinant expression vector comprising a nucleotide sequence encoding a CasX guide RNA; p) a first recombinant expression vector comprising a nucleotide sequence encoding a CasX fusion polypeptide of the present disclosure, and a second recombinant expression vector comprising a nucleotide sequence encoding a CasX guide RNA; and a donor template nucleic acid; q) a recombinant expression vector comprising a nucleotide sequence encoding a CasX polypeptide of the present disclosure, a nucleotide sequence encoding a first CasX guide RNA, and a nucleotide sequence encoding a second CasX guide RNA; or r) a recombinant expression vector comprising a nucleotide sequence encoding a CasX fusion polypeptide of the present disclosure, a nucleotide sequence encoding a first CasX guide RNA, and a nucleotide sequence encoding a second CasX guide RNA; or some variation of one of (a) through (r).

Nucleic Acids

The present disclosure provides one ore more nucleic acids comprising one or more of: a donor polynucleotide sequence, a nucleotide sequence encoding a CasX polypeptide (e.g., a wild type CasX protein, a nickase CasX protein, a dCasX protein, chimeric CasX protein, and the like), a CasX guide RNA, and a nucleotide sequence encoding a CasX guide RNA (which can include two separate nucleotide sequences in the case of dual guide RNA format or which can include a singe nucleotide sequence in the case of single guide RNA format). The present disclosure provides a nucleic acid comprising a nucleotide sequence encoding a CasX fusion polypeptide. The present disclosure provides a recombinant expression vector that comprises a nucleotide sequence encoding a CasX polypeptide. The present disclosure provides a recombinant expression vector that comprises a nucleotide sequence encoding a CasX fusion polypeptide. The present disclosure provides a recombinant expression vector that comprises: a) a nucleotide sequence encoding a CasX polypeptide; and b) a nucleotide sequence encoding a CasX guide RNA(s). The present disclosure provides a recombinant expression vector that comprises: a) a nucleotide sequence encoding a CasX fusion polypeptide; and b) a nucleotide sequence encoding a CasX guide RNA(s). In some cases, the nucleotide sequence encoding the CasX protein and/or the nucleotide sequence encoding the CasX guide RNA is operably linked to a promoter that is operable in a cell type of choice (e.g., a prokarytoic cell, a eukaryotic cell, a plant cell, an animal cell, a mammalian cell, a primate cell, a rodent cell, a human cell, etc.).

In some cases, a nucleotide sequence encoding a CasX polypeptide of the present disclosure is codon optimized. This type of optimization can entail a mutation of a CasX-encoding nucleotide sequence to mimic the codon preferences of the intended host organism or cell while encoding the same protein. Thus, the codons can be changed, but the encoded protein remains unchanged. For example, if the intended target cell was a human cell, a human codon-optimized CasX-encoding nucleotide sequence could be used. As another non-limiting example, if the intended host cell were a mouse cell, then a mouse codon-optimized CasX-encoding nucleotide sequence could be generated. As another non-limiting example, if the intended host cell were a plant cell, then a plant codon-optimized CasX-encoding nucleotide sequence could be generated. As another non-limiting example, if the intended host cell were an insect cell, then an insect codon-optimized CasX-encoding nucleotide sequence could be generated.

The present disclosure provides one or more recombinant expression vectors that include (in different recombinant expression vectors in some cases, and in the same recombinant expression vector in some cases): (i) a nucleotide sequence of a donor template nucleic acid (where the donor template comprises a nucleotide sequence having homology to a target sequence of a target nucleic acid (e.g., a target genome)); (ii) a nucleotide sequence that encodes a CasX guide RNA that hybridizes to a target sequence of the target locus of the targeted genome (e.g., a single or dual guide RNA) (e.g., operably linked to a promoter that is operable in a target cell such as a eukaryotic cell); and (iii) a nucleotide sequence encoding a CasX protein (e.g., operably linked to a promoter that is operable in a target cell such as a eukaryotic cell). The present disclosure provides one or more recombinant expression vectors that include (in different recombinant expression vectors in some cases, and in the same recombinant expression vector in some cases): (i) a nucleotide sequence of a donor template nucleic acid (where the donor template comprises a nucleotide sequence having homology to a target sequence of a target nucleic acid (e.g., a target genome)); and (ii) a nucleotide sequence that encodes a CasX guide RNA that hybridizes to a target sequence of the target locus of the targeted genome (e.g., a single or dual guide RNA) (e.g., operably linked to a promoter that is operable in a target cell such as a eukaryotic cell). The present disclosure provides one or more recombinant expression vectors that include (in different recombinant expression vectors in some cases, and in the same recombinant expression vector in some cases): (i) a nucleotide sequence that encodes a CasX guide RNA that hybridizes to a target sequence of the target locus of the targeted genome (e.g., a single or dual guide RNA) (e.g., operably linked to a promoter that is operable in a target cell such as a eukaryotic cell); and (ii) a nucleotide sequence encoding a CasX protein (e.g., operably linked to a promoter that is operable in a target cell such as a eukaryotic cell).

Suitable expression vectors include viral expression vectors (e.g. viral vectors based on vaccinia virus; poliovirus; adenovirus (see, e.g., Li et al., Invest Opthalmol Vis Sci 35:2543 2549, 1994; Borras et al., Gene Ther 6:515 524, 1999; Li and Davidson, PNAS 92:7700 7704, 1995; Sakamoto et al., H Gene Ther 5:1088 1097, 1999; WO 94/12649, WO 93/03769; WO 93/19191; WO 94/28938; WO 95/11984 and WO 95/00655); adeno-associated virus (AAV) (see, e.g., Ali et al., Hum Gene Ther 9:81 86, 1998, Flannery et al., PNAS 94:6916 6921, 1997; Bennett et al., Invest Opthalmol Vis Sci 38:2857 2863, 1997; Jomary et al., Gene Ther 4:683 690, 1997, Rolling et al., Hum Gene Ther 10:641 648, 1999; Ali et al., Hum Mol Genet 5:591 594, 1996; Srivastava in WO 93/09239, Samulski et al., J. Vir. (1989) 63:3822-3828; Mendelson et al., Virol. (1988) 166:154-165; and Flotte et al., PNAS (1993) 90:10613-10617); SV40; herpes simplex virus; human immunodeficiency virus (see, e.g., Miyoshi et al., PNAS 94:10319 23, 1997; Takahashi et al., J Virol 73:7812 7816, 1999); a retroviral vector (e.g., Murine Leukemia Virus, spleen necrosis virus, and vectors derived from retroviruses such as Rous Sarcoma Virus, Harvey Sarcoma Virus, avian leukosis virus, a lentivirus, human immunodeficiency virus, myeloproliferative sarcoma virus, and mammary tumor virus); and the like. In some cases, a recombinant expression vector of the present disclosure is a recombinant adeno-associated virus (AAV) vector. In some cases, a recombinant expression vector of the present disclosure is a recombinant lentivirus vector. In some cases, a recombinant expression vector of the present disclosure is a recombinant retroviral vector.

Depending on the host/vector system utilized, any of a number of suitable transcription and translation control elements, including constitutive and inducible promoters, transcription enhancer elements, transcription terminators, etc. may be used in the expression vector.

In some embodiments, a nucleotide sequence encoding a CasX guide RNA is operably linked to a control element, e.g., a transcriptional control element, such as a promoter. In some embodiments, a nucleotide sequence encoding a CasX protein or a CasX fusion polypeptide is operably linked to a control element, e.g., a transcriptional control element, such as a promoter.

The transcriptional control element can be a promoter. In some cases, the promoter is a constitutively active promoter. In some cases, the promoter is a regulatable promoter. In some cases, the promoter is an inducible promoter. In some cases, the promoter is a tissue-specific promoter. In some cases, the promoter is a cell type-specific promoter. In some cases, the transcriptional control element (e.g., the promoter) is functional in a targeted cell type or targeted cell population. For example, in some cases, the transcriptional control element can be functional in eukaryotic cells, e.g., hematopoietic stem cells (e.g., mobilized peripheral blood (mPB) CD34(+) cell, bone marrow (BM) CD34(+) cell, etc.).

Non-limiting examples of eukaryotic promoters (promoters functional in a eukaryotic cell) include EF1α, those from cytomegalovirus (CMV) immediate early, herpes simplex virus (HSV) thymidine kinase, early and late SV40, long terminal repeats (LTRs) from retrovirus, and mouse metallothionein-I. Selection of the appropriate vector and promoter is well within the level of ordinary skill in the art. The expression vector may also contain a ribosome binding site for translation initiation and a transcription terminator. The expression vector may also include appropriate sequences for amplifying expression. The expression vector may also include nucleotide sequences encoding protein tags (e.g., 6×His tag, hemagglutinin tag, fluorescent protein, etc.) that can be fused to the CasX protein, thus resulting in a chimeric CasX polypeptide.

In some embodiments, a nucleotide sequence encoding a CasX guide RNA and/or a CasX fusion polypeptide is operably linked to an inducible promoter. In some embodiments, a nucleotide sequence encoding a CasX guide RNA and/or a CasX fusion protein is operably linked to a constitutive promoter.

A promoter can be a constitutively active promoter (i.e., a promoter that is constitutively in an active/"ON" state), it may be an inducible promoter (i.e., a promoter whose state, active/"ON" or inactive/"OFF", is controlled by an external stimulus, e.g., the presence of a particular temperature, compound, or protein.), it may be a spatially restricted promoter (i.e., transcriptional control element, enhancer, etc.)(e.g., tissue specific promoter, cell type specific promoter, etc.), and it may be a temporally restricted promoter (i.e., the promoter is in the "ON" state or "OFF" state during specific stages of embryonic development or during specific stages of a biological process, e.g., hair follicle cycle in mice).

Suitable promoters can be derived from viruses and can therefore be referred to as viral promoters, or they can be derived from any organism, including prokaryotic or eukaryotic organisms. Suitable promoters can be used to drive expression by any RNA polymerase (e.g., pol I, pol II, pol III). Exemplary promoters include, but are not limited to the SV40 early promoter, mouse mammary tumor virus long terminal repeat (LTR) promoter; adenovirus major late promoter (Ad MLP); a herpes simplex virus (HSV) promoter, a cytomegalovirus (CMV) promoter such as the CMV immediate early promoter region (CMVIE), a rous sarcoma virus (RSV) promoter, a human U6 small nuclear promoter (U6) (Miyagishi et al., Nature Biotechnology 20, 497-500 (2002)), an enhanced U6 promoter (e.g., Xia et al., Nucleic Acids Res. 2003 Sep. 1; 31(17)), a human H1 promoter (H1), and the like.

In some cases, a nucleotide sequence encoding a CasX guide RNA is operably linked to (under the control of) a promoter operable in a eukaryotic cell (e.g., a U6 promoter, an enhanced U6 promoter, an H1 promoter, and the like). As would be understood by one of ordinary skill in the art, when expressing an RNA (e.g., a guide RNA) from a nucleic acid (e.g., an expression vector) using a U6 promoter (e.g., in a eukaryotic cell), or another PolIII promoter, the RNA may need to be mutated if there are several Ts in a row (coding for Us in the RNA). This is because a string of Ts (e.g., 5 Ts) in DNA can act as a terminator for polymerase III (PolIII). Thus, in order to ensure transcription of a guide RNA (e.g., the activator portion and/or targeter portion, in dual guide or single guide format) in a eukaryotic cell it may sometimes be necessary to modify the sequence encoding the guide RNA to eliminate runs of Ts. In some cases, a nucleotide sequence encoding a CasX protein (e.g., a wild type CasX protein, a nickase CasX protein, a dCasX protein, a chimeric CasX protein and the like) is operably linked to a promoter operable in a eukaryotic cell (e.g., a CMV promoter, an EF1α promoter, an estrogen receptor-regulated promoter, and the like).

Examples of inducible promoters include, but are not limited to T7 RNA polymerase promoter, T3 RNA polymerase promoter, Isopropyl-beta-D-thiogalactopyranoside (IPTG)-regulated promoter, lactose induced promoter, heat shock promoter, Tetracycline-regulated promoter, Steroid-regulated promoter, Metal-regulated promoter, estrogen receptor-regulated promoter, etc. Inducible promoters can therefore be regulated by molecules including, but not limited to, doxycycline; estrogen and/or an estrogen analog; IPTG; etc.

Inducible promoters suitable for use include any inducible promoter described herein or known to one of ordinary skill in the art. Examples of inducible promoters include, without limitation, chemically/biochemically-regulated and physically-regulated promoters such as alcohol-regulated promoters, tetracycline-regulated promoters (e.g., anhydrotetracycline (aTc)-responsive promoters and other tetracycline-responsive promoter systems, which include a tetracycline repressor protein (tetR), a tetracycline operator sequence (tetO) and a tetracycline transactivator fusion protein (tTA)), steroid-regulated promoters (e.g., promoters based on the rat glucocorticoid receptor, human estrogen receptor, moth ecdysone receptors, and promoters from the steroid/retinoid/thyroid receptor superfamily), metal-regulated promoters (e.g., promoters derived from metallothionein (proteins that bind and sequester metal ions) genes from yeast, mouse and human), pathogenesis-regulated promoters (e.g., induced by salicylic acid, ethylene or benzothiadiazole (BTH)), temperature/heat-inducible promoters (e.g., heat shock promoters), and light-regulated promoters (e.g., light responsive promoters from plant cells).

In some cases, the promoter is a spatially restricted promoter (i.e., cell type specific promoter, tissue specific promoter, etc.) such that in a multi-cellular organism, the promoter is active (i.e., "ON") in a subset of specific cells. Spatially restricted promoters may also be referred to as enhancers, transcriptional control elements, control sequences, etc. Any convenient spatially restricted promoter may be used as long as the promoter is functional in the targeted host cell (e.g., eukaryotic cell; prokaryotic cell).

In some cases, the promoter is a reversible promoter. Suitable reversible promoters, including reversible inducible promoters are known in the art. Such reversible promoters may be isolated and derived from many organisms, e.g., eukaryotes and prokaryotes. Modification of reversible promoters derived from a first organism for use in a second organism, e.g., a first prokaryote and a second a eukaryote, a first eukaryote and a second a prokaryote, etc., is well known in the art. Such reversible promoters, and systems based on such reversible promoters but also comprising additional control proteins, include, but are not limited to, alcohol regulated promoters (e.g., alcohol dehydrogenase I (alcA) gene promoter, promoters responsive to alcohol transactivator proteins (AlcR), etc.), tetracycline regulated promoters, (e.g., promoter systems including TetActivators, TetON, TetOFF, etc.), steroid regulated promoters (e.g., rat glucocorticoid receptor promoter systems, human estrogen receptor promoter systems, retinoid promoter systems, thyroid promoter systems, ecdysone promoter systems, mifepristone promoter systems, etc.), metal regulated promoters (e.g., metallothionein promoter systems, etc.), pathogenesis-related regulated promoters (e.g., salicylic acid regulated promoters, ethylene regulated promoters, benzothiadiazole regulated promoters, etc.), temperature regulated promoters (e.g., heat shock inducible promoters (e.g., HSP-70, HSP-90, soybean heat shock promoter, etc.), light regulated promoters, synthetic inducible promoters, and the like.

Methods of introducing a nucleic acid (e.g., a nucleic acid comprising a donor polynucleotide sequence, one or more nucleic acids encoding a CasX protein and/or a CasX guide RNA, and the like) into a host cell are known in the art, and any convenient method can be used to introduce a nucleic acid (e.g., an expression construct) into a cell. Suitable methods include e.g., viral infection, transfection, lipofection, electroporation, calcium phosphate precipitation, polyethyleneimine (PEI)-mediated transfection, DEAE-dextran mediated transfection, liposome-mediated transfection, particle gun technology, calcium phosphate precipitation, direct microinjection, nanoparticle-mediated nucleic acid delivery, and the like.

Introducing the recombinant expression vector into cells can occur in any culture media and under any culture conditions that promote the survival of the cells. Introducing the recombinant expression vector into a target cell can be carried out in vivo or ex vivo. Introducing the recombinant expression vector into a target cell can be carried out in vitro.

In some embodiments, a CasX protein can be provided as RNA. The RNA can be provided by direct chemical synthesis or may be transcribed in vitro from a DNA (e.g., encoding the CasX protein). Once synthesized, the RNA may be introduced into a cell by any of the well-known techniques for introducing nucleic acids into cells (e.g., microinjection, electroporation, transfection, etc.).

Nucleic acids may be provided to the cells using well-developed transfection techniques; see, e.g. Angel and Yanik (2010) PLoS ONE 5(7): e11756, and the commercially available TransMessenger® reagents from Qiagen, Stemfect™ RNA Transfection Kit from Stemgent, and TransIT®-mRNA Transfection Kit from Minis Bio LLC. See also Beumer et al. (2008) PNAS 105(50):19821-19826.

Vectors may be provided directly to a target host cell. In other words, the cells are contacted with vectors comprising the subject nucleic acids (e.g., recombinant expression vectors having the donor template sequence and encoding the CasX guide RNA; recombinant expression vectors encoding the CasX protein; etc.) such that the vectors are taken up by the cells. Methods for contacting cells with nucleic acid vectors that are plasmids, include electroporation, calcium chloride transfection, microinjection, and lipofection are well known in the art. For viral vector delivery, cells can be contacted with viral particles comprising the subject viral expression vectors.

Retroviruses, for example, lentiviruses, are suitable for use in methods of the present disclosure. Commonly used retroviral vectors are "defective", i.e. unable to produce viral proteins required for productive infection. Rather, replication of the vector requires growth in a packaging cell line. To generate viral particles comprising nucleic acids of interest, the retroviral nucleic acids comprising the nucleic acid are packaged into viral capsids by a packaging cell line. Different packaging cell lines provide a different envelope protein (ecotropic, amphotropic or xenotropic) to be incorporated into the capsid, this envelope protein determining the specificity of the viral particle for the cells (ecotropic for murine and rat; amphotropic for most mammalian cell types including human, dog and mouse; and xenotropic for most mammalian cell types except murine cells). The appropriate packaging cell line may be used to ensure that the cells are targeted by the packaged viral particles. Methods of introducing subject vector expression vectors into packaging cell lines and of collecting the viral particles that are generated by the packaging lines are well known in the art. Nucleic acids can also introduced by direct micro-injection (e.g., injection of RNA).

Vectors used for providing the nucleic acids encoding CasX guide RNA and/or a CasX polypeptide to a target host cell can include suitable promoters for driving the expression, that is, transcriptional activation, of the nucleic acid of interest. In other words, in some cases, the nucleic acid of interest will be operably linked to a promoter. This may include ubiquitously acting promoters, for example, the CMV-β-actin promoter, or inducible promoters, such as promoters that are active in particular cell populations or that respond to the presence of drugs such as tetracycline. By transcriptional activation, it is intended that transcription will be increased above basal levels in the target cell by 10 fold, by 100 fold, more usually by 1000 fold. In addition, vectors used for providing a nucleic acid encoding a CasX guide RNA and/or a CasX protein to a cell may include nucleic acid sequences that encode for selectable markers in the target cells, so as to identify cells that have taken up the CasX guide RNA and/or CasX protein.

A nucleic acid comprising a nucleotide sequence encoding a CasX polypeptide, or a CasX fusion polypeptide, is in some cases an RNA. Thus, a CasX fusion protein can be introduced into cells as RNA. Methods of introducing RNA into cells are known in the art and may include, for example, direct injection, transfection, or any other method used for the introduction of DNA. A CasX protein may instead be provided to cells as a polypeptide. Such a polypeptide may optionally be fused to a polypeptide domain that increases solubility of the product. The domain may be linked to the polypeptide through a defined protease cleavage site, e.g. a TEV sequence, which is cleaved by TEV protease. The linker may also include one or more flexible sequences, e.g. from 1 to 10 glycine residues. In some embodiments, the cleavage of the fusion protein is performed in a buffer that maintains solubility of the product, e.g. in the presence of from 0.5 to 2 M urea, in the presence of polypeptides and/or polynucleotides that increase solubility, and the like. Domains of interest include endosomolytic domains, e.g. influenza HA domain; and other polypeptides that aid in production, e.g. IF2 domain, GST domain, GRPE domain, and the like. The polypeptide may be formulated for improved stability. For example, the peptides may be PEGylated, where the polyethyleneoxy group provides for enhanced lifetime in the blood stream.

Additionally or alternatively, a CasX polypeptide of the present disclosure may be fused to a polypeptide permeant domain to promote uptake by the cell. A number of permeant domains are known in the art and may be used in the non-integrating polypeptides of the present disclosure, including peptides, peptidomimetics, and non-peptide carriers. For example, a permeant peptide may be derived from the third alpha helix of Drosophila melanogaster transcription factor Antennapaedia, referred to as penetratin, which comprises the amino acid sequence RQIKIWFQNRRMKWKK (SEQ ID NO: 133). As another example, the permeant peptide comprises the HIV-1 tat basic region amino acid sequence, which may include, for example, amino acids 49-57 of naturally-occurring tat protein. Other permeant domains include poly-arginine motifs, for example, the region of amino acids 34-56 of HIV-1 rev protein, nona-arginine, octa-arginine, and the like. (See, for example, Futaki et al. (2003) Curr Protein Pept Sci. 2003 April; 4(2): 87-9 and 446; and Wender et al. (2000) Proc. Natl. Acad. Sci. U.S.A 2000 Nov. 21; 97(24):13003-8; published U.S. Patent applications 20030220334; 20030083256; 20030032593; and 20030022831, herein specifically incorporated by reference for the teachings of translocation peptides and peptoids). The nona-arginine (R9) sequence is one of the more efficient PTDs that have been characterized (Wender et al. 2000; Uemura et al. 2002). The site at which the fusion is made may be selected in order to optimize the biological activity, secretion or binding characteristics of the polypeptide. The optimal site will be determined by routine experimentation.

A CasX polypeptide of the present disclosure may be produced in vitro or by eukaryotic cells or by prokaryotic cells, and it may be further processed by unfolding, e.g. heat denaturation, dithiothreitol reduction, etc. and may be further refolded, using methods known in the art.

Modifications of interest that do not alter primary sequence include chemical derivatization of polypeptides, e.g., acylation, acetylation, carboxylation, amidation, etc. Also included are modifications of glycosylation, e.g. those made by modifying the glycosylation patterns of a polypeptide during its synthesis and processing or in further processing steps; e.g. by exposing the polypeptide to enzymes which affect glycosylation, such as mammalian glycosylating or deglycosylating enzymes. Also embraced are sequences that have phosphorylated amino acid residues, e.g. phosphotyrosine, phosphoserine, or phosphothreonine.

Also suitable for inclusion in embodiments of the present disclosure are nucleic acids (e.g., encoding a CasX guide RNA, encoding a CasX fusion protein, etc.) and proteins (e.g., a CasX fusion protein derived from a wild type protein or a variant protein) that have been modified using ordinary molecular biological techniques and synthetic chemistry so as to improve their resistance to proteolytic degradation, to change the target sequence specificity, to optimize solubility properties, to alter protein activity (e.g., transcription modulatory activity, enzymatic activity, etc.) or to render them more suitable. Analogs of such polypeptides include those containing residues other than naturally occurring L-amino acids, e.g. D-amino acids or non-naturally occurring synthetic amino acids. D-amino acids may be substituted for some or all of the amino acid residues.

A CasX polypeptide of the present disclosure may be prepared by in vitro synthesis, using conventional methods as known in the art. Various commercial synthetic apparatuses are available, for example, automated synthesizers by Applied Biosystems, Inc., Beckman, etc. By using synthesizers, naturally occurring amino acids may be substituted with unnatural amino acids. The particular sequence and the manner of preparation will be determined by convenience, economics, purity required, and the like.

If desired, various groups may be introduced into the peptide during synthesis or during expression, which allow for linking to other molecules or to a surface. Thus cysteines can be used to make thioethers, histidines for linking to a metal ion complex, carboxyl groups for forming amides or esters, amino groups for forming amides, and the like.

A CasX polypeptide of the present disclosure may also be isolated and purified in accordance with conventional methods of recombinant synthesis. A lysate may be prepared of the expression host and the lysate purified using high performance liquid chromatography (HPLC), exclusion chromatography, gel electrophoresis, affinity chromatography, or other purification technique. For the most part, the compositions which are used will comprise 20% or more by weight of the desired product, more usually 75% or more by weight, preferably 95% or more by weight, and for therapeutic purposes, usually 99.5% or more by weight, in relation to contaminants related to the method of preparation of the product and its purification. Usually, the percentages will be based upon total protein. Thus, in some cases, a CasX polypeptide, or a CasX fusion polypeptide, of the present disclosure is at least 80% pure, at least 85% pure, at least 90% pure, at least 95% pure, at least 98% pure, or at least 99% pure (e.g., free of contaminants, non-CasX proteins or other macromolecules, etc.).

To induce cleavage or any desired modification to a target nucleic acid (e.g., genomic DNA), or any desired modification to a polypeptide associated with target nucleic acid, the CasX guide RNA and/or the CasX polypeptide of the present disclosure and/or the donor template sequence, whether they be introduced as nucleic acids or polypeptides, are provided to the cells for about 30 minutes to about 24 hours, e.g., 1 hour, 1.5 hours, 2 hours, 2.5 hours, 3 hours, 3.5 hours 4 hours, 5 hours, 6 hours, 7 hours, 8 hours, 12 hours, 16 hours, 18 hours, 20 hours, or any other period from about 30 minutes to about 24 hours, which may be repeated with a frequency of about every day to about every 4 days, e.g., every 1.5 days, every 2 days, every 3 days, or any other frequency from about every day to about every four days. The agent(s) may be provided to the subject cells one or more times, e.g. one time, twice, three times, or more than three times, and the cells allowed to incubate with the agent(s) for some amount of time following each contacting event e.g. 16-24 hours, after which time the media is replaced with fresh media and the cells are cultured further.

In cases in which two or more different targeting complexes are provided to the cell (e.g., two different CasX guide RNAs that are complementary to different sequences within the same or different target nucleic acid), the complexes may be provided simultaneously (e.g. as two polypeptides and/or nucleic acids), or delivered simultaneously. Alternatively, they may be provided consecutively, e.g. the targeting complex being provided first, followed by the second targeting complex, etc. or vice versa.

To improve the delivery of a DNA vector into a target cell, the DNA can be protected from damage and its entry into the cell facilitated, for example, by using lipoplexes and polyplexes. Thus, in some cases, a nucleic acid of the present disclosure (e.g., a recombinant expression vector of the present disclosure) can be covered with lipids in an organized structure like a micelle or a liposome. When the organized structure is complexed with DNA it is called a lipoplex. There are three types of lipids, anionic (negatively-charged), neutral, or cationic (positively-charged). Lipoplexes that utilize cationic lipids have proven utility for gene transfer. Cationic lipids, due to their positive charge, naturally complex with the negatively charged DNA. Also as a result of their charge, they interact with the cell membrane. Endocytosis of the lipoplex then occurs, and the DNA is released into the cytoplasm. The cationic lipids also protect against degradation of the DNA by the cell.

Complexes of polymers with DNA are called polyplexes. Most polyplexes consist of cationic polymers and their production is regulated by ionic interactions. One large difference between the methods of action of polyplexes and lipoplexes is that polyplexes cannot release their DNA load into the cytoplasm, so to this end, co-transfection with endosome-lytic agents (to lyse the endosome that is made during endocytosis) such as inactivated adenovirus must occur. However, this is not always the case; polymers such as polyethylenimine have their own method of endosome disruption as does chitosan and trimethylchitosan.

Dendrimers, a highly branched macromolecule with a spherical shape, may be also be used to genetically modify stem cells. The surface of the dendrimer particle may be functionalized to alter its properties. In particular, it is possible to construct a cationic dendrimer (i.e., one with a positive surface charge). When in the presence of genetic material such as a DNA plasmid, charge complementarity leads to a temporary association of the nucleic acid with the cationic dendrimer. On reaching its destination, the dendrimer-nucleic acid complex can be taken up into a cell by endocytosis.

In some cases, a nucleic acid of the disclosure (e.g., an expression vector) includes an insertion site for a guide sequence of interest. For example, a nucleic acid can include an insertion site for a guide sequence of interest, where the insertion site is immediately adjacent to a nucleotide sequence encoding the portion of a CasX guide RNA that does not change when the guide sequence is changed to hybrized to a desired target sequence (e.g., sequences that contribute to the CasX binding aspect of the guide RNA, e.g., the sequences that contribute to the dsRNA duplex(es) of the CasX guide RNA—this portion of the guide RNA can also be referred to as the 'scaffold' or 'constant region' of the guide RNA). Thus, in some cases, a subject nucleic acid (e.g., an expression vector) includes a nucleotide sequence encoding a CasX guide RNA, except that the portion encoding the guide sequence portion of the guide RNA is an insertion sequence (an insertion site). An insertion site is any nucleotide sequence used for the insertion of a desired sequence. "Insertion sites" for use with various technologies are known to those of ordinary skill in the art and any convenient insertion site can be used. An insertion site can be for any method for manipulating nucleic acid sequences. For example, in some cases the insertion site is a multiple cloning site (MCS) (e.g., a site including one or more restriction enzyme recognition sequences), a site for ligation independent cloning, a site for recombination based cloning (e.g., recombination based on att sites), a nucleotide sequence recognized by a CRISPR/Cas (e.g. Cas9) based technology, and the like.

An insertion site can be any desirable length, and can depend on the type of insertion site (e.g., can depend on whether (and how many) the site includes one or more restriction enzyme recognition sequences, whether the site includes a target site for a CRISPR/Cas protein, etc.). In some cases, an insertion site of a subject nucleic acid is 3 or more nucleotides (nt) in length (e.g., 5 or more, 8 or more, 10 or more, 15 or more, 17 or more, 18 or more, 19 or more, 20 or more or 25 or more, or 30 or more nt in length). In some cases, the length of an insertion site of a subject nucleic acid has a length in a range of from 2 to 50 nucleotides (nt) (e.g., from 2 to 40 nt, from 2 to 30 nt, from 2 to 25 nt, from 2 to 20 nt, from 5 to 50 nt, from 5 to 40 nt, from 5 to 30 nt, from 5 to 25 nt, from 5 to 20 nt, from 10 to 50 nt, from 10 to 40 nt, from 10 to 30 nt, from 10 to 25 nt, from 10 to 20 nt, from 17 to 50 nt, from 17 to 40 nt, from 17 to 30 nt, from 17 to 25 nt). In some cases, the length of an insertion site of a subject nucleic acid has a length in a range of from 5 to 40 nt.

Nucleic Acid Modifications

In some embodiments, a subject nucleic acid (e.g., a CasX guide RNA) has one or more modifications, e.g., a base modification, a backbone modification, etc., to provide the nucleic acid with a new or enhanced feature (e.g., improved stability). A nucleoside is a base-sugar combination. The base portion of the nucleoside is normally a heterocyclic base. The two most common classes of such heterocyclic bases are the purines and the pyrimidines. Nucleotides are nucleosides that further include a phosphate group covalently linked to the sugar portion of the nucleoside. For those nucleosides that include a pentofuranosyl sugar, the phosphate group can be linked to the 2', the 3', or the 5' hydroxyl moiety of the sugar. In forming oligonucleotides, the phosphate groups covalently link adjacent nucleosides to one another to form a linear polymeric compound. In turn, the respective ends of this linear polymeric compound can be further joined to form a circular compound, however, linear compounds are suitable. In addition, linear compounds may have internal nucleotide base complementarity and may therefore fold in a manner as to produce a fully or partially double-stranded compound. Within oligonucleotides, the phosphate groups are commonly referred to as forming the internucleoside backbone of the oligonucleotide. The normal linkage or backbone of RNA and DNA is a 3' to 5' phosphodiester linkage.

Suitable nucleic acid modifications include, but are not limited to: 2'Omethyl modified nucleotides, 2' Fluoro modified nucleotides, locked nucleic acid (LNA) modified nucleotides, peptide nucleic acid (PNA) modified nucleotides, nucleotides with phosphorothioate linkages, and a 5' cap (e.g., a 7-methylguanylate cap (m7G)). Additional details and additional modifications are described below.

A 2'-O-Methyl modified nucleotide (also referred to as 2'-O-Methyl RNA) is a naturally occurring modification of RNA found in tRNA and other small RNAs that arises as a post-transcriptional modification. Oligonucleotides can be directly synthesized that contain 2'-O-Methyl RNA. This modification increases Tm of RNA:RNA duplexes but results in only small changes in RNA:DNA stability. It is stabile with respect to attack by single-stranded ribonucleases and is typically 5 to 10-fold less susceptible to DNases than DNA. It is commonly used in antisense oligos as a means to increase stability and binding affinity to the target message.

2' Fluoro modified nucleotides (e.g., 2' Fluoro bases) have a fluorine modified ribose which increases binding affinity (Tm) and also confers some relative nuclease resistance when compared to native RNA. These modifications are commonly employed in ribozymes and siRNAs to improve stability in serum or other biological fluids.

LNA bases have a modification to the ribose backbone that locks the base in the C3'-endo position, which favors RNA A-type helix duplex geometry. This modification significantly increases Tm and is also very nuclease resistant. Multiple LNA insertions can be placed in an oligo at any position except the 3'-end. Applications have been described ranging from antisense oligos to hybridization probes to SNP detection and allele specific PCR. Due to the large increase in Tm conferred by LNAs, they also can cause an increase in primer dimer formation as well as self-hairpin formation. In some cases, the number of LNAs incorporated into a single oligo is 10 bases or less.

The phosphorothioate (PS) bond (i.e., a phosphorothioate linkage) substitutes a sulfur atom for a non-bridging oxygen in the phosphate backbone of a nucleic acid (e.g., an oligo). This modification renders the internucleotide linkage resistant to nuclease degradation. Phosphorothioate bonds can be introduced between the last 3-5 nucleotides at the 5'- or 3'-end of the oligo to inhibit exonuclease degradation. Including phosphorothioate bonds within the oligo (e.g., throughout the entire oligo) can help reduce attack by endonucleases as well.

In some embodiments, a subject nucleic acid has one or more nucleotides that are 2'-O-Methyl modified nucleotides. In some embodiments, a subject nucleic acid (e.g., a dsRNA, a siNA, etc.) has one or more 2' Fluoro modified nucleotides. In some embodiments, a subject nucleic acid (e.g., a dsRNA, a siNA, etc.) has one or more LNA bases. In some embodiments, a subject nucleic acid (e.g., a dsRNA, a siNA, etc.) has one or more nucleotides that are linked by a phosphorothioate bond (i.e., the subject nucleic acid has one or more phosphorothioate linkages). In some embodiments, a subject nucleic acid (e.g., a dsRNA, a siNA, etc.) has a 5' cap (e.g., a 7-methylguanylate cap (m7G)). In some embodiments, a subject nucleic acid (e.g., a dsRNA, a siNA, etc.) has a combination of modified nucleotides. For example, a subject nucleic acid (e.g., a dsRNA, a siNA, etc.) can have a 5' cap (e.g., a 7-methylguanylate cap (m7G)) in addition to having one or more nucleotides with other modifications (e.g., a 2'-O-Methyl nucleotide and/or a 2' Fluoro modified nucleotide and/or a LNA base and/or a phosphorothioate linkage).

Modified Backbones and Modified Internucleoside Linkages

Examples of suitable nucleic acids (e.g., a CasX guide RNA) containing modifications include nucleic acids containing modified backbones or non-natural internucleoside linkages. Nucleic acids having modified backbones include those that retain a phosphorus atom in the backbone and those that do not have a phosphorus atom in the backbone.

Suitable modified oligonucleotide backbones containing a phosphorus atom therein include, for example, phosphorothioates, chiral phosphorothioates, phosphorodithioates, phosphotriesters, aminoalkylphosphotriesters, methyl and other alkyl phosphonates including 3'-alkylene phosphonates, 5'-alkylene phosphonates and chiral phosphonates, phosphinates, phosphoramidates including 3'-amino phosphoramidate and aminoalkylphosphoramidates, phosphorodiamidates, thionophosphoramidates, thionoalkylphosphonates, thionoalkylphosphotriesters, selenophosphates and boranophosphates having normal 3'-5' linkages, 2'-5' linked analogs of these, and those having inverted polarity wherein one or more internucleotide linkages is a 3' to 3', 5' to 5' or 2' to 2' linkage. Suitable oligonucleotides having inverted polarity comprise a single 3' to 3' linkage at the 3'-most internucleotide linkage i.e. a single inverted nucleoside residue which may be a basic (the nucleobase is missing or has a hydroxyl group in place thereof). Various salts (such as, for example, potassium or sodium), mixed salts and free acid forms are also included.

In some embodiments, a subject nucleic acid comprises one or more phosphorothioate and/or heteroatom internucleoside linkages, in particular —CH$_2$—NH—O—CH$_2$—, —CH$_2$—N(CH$_3$)—O—CH$_2$— (known as a methylene (methylimino) or MMI backbone), —CH$_2$—O—N(CH$_3$)—CH$_2$—, —CH$_2$—N(CH$_3$)—N(CH$_3$)—CH$_2$— and —O—N(CH$_3$)—CH$_2$—CH$_2$— (wherein the native phosphodiester internucleotide linkage is represented as —O—P(=O)(OH)—O—CH$_2$—). MMI type internucleoside linkages are disclosed in the above referenced U.S. Pat. No. 5,489,677, the disclosure of which is incorporated herein by reference in its entirety. Suitable amide internucleoside linkages are disclosed in U.S. Pat. No. 5,602,240, the disclosure of which is incorporated herein by reference in its entirety.

Also suitable are nucleic acids having morpholino backbone structures as described in, e.g., U.S. Pat. No. 5,034,506. For example, in some embodiments, a subject nucleic acid comprises a 6-membered morpholino ring in place of a ribose ring. In some of these embodiments, a phosphorodiamidate or other non-phosphodiester internucleoside linkage replaces a phosphodiester linkage.

Suitable modified polynucleotide backbones that do not include a phosphorus atom therein have backbones that are formed by short chain alkyl or cycloalkyl internucleoside linkages, mixed heteroatom and alkyl or cycloalkyl internucleoside linkages, or one or more short chain heteroatomic or heterocyclic internucleoside linkages. These include those having morpholino linkages (formed in part from the sugar portion of a nucleoside); siloxane backbones; sulfide, sulfoxide and sulfone backbones; formacetyl and thioformacetyl backbones; methylene formacetyl and thioformacetyl backbones; riboacetyl backbones; alkene containing backbones; sulfamate backbones; methyleneimino and methylenehydrazino backbones; sulfonate and sulfonamide backbones; amide backbones; and others having mixed N, O, S and CH$_2$ component parts.

Mimetics

A subject nucleic acid can be a nucleic acid mimetic. The term "mimetic" as it is applied to polynucleotides is intended to include polynucleotides wherein only the furanose ring or both the furanose ring and the internucleotide linkage are replaced with non-furanose groups, replacement of only the furanose ring is also referred to in the art as being a sugar surrogate. The heterocyclic base moiety or a modified heterocyclic base moiety is maintained for hybridization with an appropriate target nucleic acid. One such nucleic acid, a polynucleotide mimetic that has been shown to have excellent hybridization properties, is referred to as a peptide nucleic acid (PNA). In PNA, the sugar-backbone of a polynucleotide is replaced with an amide containing backbone, in particular an aminoethylglycine backbone. The nucleotides are retained and are bound directly or indirectly to aza nitrogen atoms of the amide portion of the backbone.

One polynucleotide mimetic that has been reported to have excellent hybridization properties is a peptide nucleic acid (PNA). The backbone in PNA compounds is two or more linked aminoethylglycine units which gives PNA an amide containing backbone. The heterocyclic base moieties are bound directly or indirectly to aza nitrogen atoms of the amide portion of the backbone. Representative U.S. patents that describe the preparation of PNA compounds include, but are not limited to: U.S. Pat. Nos. 5,539,082; 5,714,331; and 5,719,262, the disclosures of which are incorporated herein by reference in their entirety.

Another class of polynucleotide mimetic that has been studied is based on linked morpholino units (morpholino nucleic acid) having heterocyclic bases attached to the morpholino ring. A number of linking groups have been reported that link the morpholino monomeric units in a morpholino nucleic acid. One class of linking groups has been selected to give a non-ionic oligomeric compound. The non-ionic morpholino-based oligomeric compounds are less likely to have undesired interactions with cellular proteins. Morpholino-based polynucleotides are non-ionic mimics of oligonucleotides which are less likely to form undesired interactions with cellular proteins (Dwaine A. Braasch and David R. Corey, *Biochemistry*, 2002, 41(14), 4503-4510). Morpholino-based polynucleotides are disclosed in U.S. Pat. No. 5,034,506, the disclosure of which is incorporated herein by reference in its entirety. A variety of compounds within the morpholino class of polynucleotides have been prepared, having a variety of different linking groups joining the monomeric subunits.

A further class of polynucleotide mimetic is referred to as cyclohexenyl nucleic acids (CeNA). The furanose ring normally present in a DNA/RNA molecule is replaced with a cyclohexenyl ring. CeNA DMT protected phosphoramidite monomers have been prepared and used for oligomeric compound synthesis following classical phosphoramidite chemistry. Fully modified CeNA oligomeric compounds and oligonucleotides having specific positions modified with CeNA have been prepared and studied (see Wang et al., *J. Am. Chem. Soc.*, 2000, 122, 8595-8602, the disclosure of which is incorporated herein by reference in its entirety). In general the incorporation of CeNA monomers into a DNA chain increases its stability of a DNA/RNA hybrid. CeNA oligoadenylates formed complexes with RNA and DNA complements with similar stability to the native complexes. The study of incorporating CeNA structures into natural nucleic acid structures was shown by NMR and circular dichroism to proceed with easy conformational adaptation.

A further modification includes Locked Nucleic Acids (LNAs) in which the 2'-hydroxyl group is linked to the 4' carbon atom of the sugar ring thereby forming a 2'-C,4'-C-oxymethylene linkage thereby forming a bicyclic sugar moiety. The linkage can be a methylene ($-CH_2-$), group bridging the 2' oxygen atom and the 4' carbon atom wherein n is 1 or 2 (Singh et al., *Chem. Commun.*, 1998, 4, 455-456, the disclosure of which is incorporated herein by reference in its entirety). LNA and LNA analogs display very high duplex thermal stabilities with complementary DNA and RNA (Tm=+3 to +10° C.), stability towards 3'-exonucleolytic degradation and good solubility properties. Potent and nontoxic antisense oligonucleotides containing LNAs have been described (e.g., Wahlestedt et al., *Proc. Natl. Acad. Sci. U.S.A.*, 2000, 97, 5633-5638, the disclosure of which is incorporated herein by reference in its entirety).

The synthesis and preparation of the LNA monomers adenine, cytosine, guanine, 5-methylcytosine, thymine and uracil, along with their oligomerization, and nucleic acid recognition properties have been described (e.g., Koshkin et al., *Tetrahedron*, 1998, 54, 3607-3630, the disclosure of which is incorporated herein by reference in its entirety). LNAs and preparation thereof are also described in WO 98/39352 and WO 99/14226, as well as U.S. applications 20120165514, 20100216983, 20090041809, 20060117410, 20040014959, 20020094555, and 20020086998, the disclosures of which are incorporated herein by reference in their entirety.

Modified Sugar Moieties

A subject nucleic acid can also include one or more substituted sugar moieties. Suitable polynucleotides comprise a sugar substituent group selected from: OH; F; O-, S-, or N-alkyl; O-, S-, or N-alkenyl; O-, S- or N-alkynyl; or O-alkyl-O-alkyl, wherein the alkyl, alkenyl and alkynyl may be substituted or unsubstituted $C_1$ to $C_{10}$ alkyl or $C_2$ to $C_{10}$ alkenyl and alkynyl. Particularly suitable are $O((CH_2)_nO)_mCH_3$, $O(CH_2)_nOCH_3$, $O(CH_2)_nNH_2$, $O(CH_2)_nCH_3$, $O(CH_2)_nONH_2$, and $O(CH_2)_nON((CH_2)_nCH_3)_2$, where n and m are from 1 to about 10. Other suitable polynucleotides comprise a sugar substituent group selected from: $C_1$ to $C_{10}$ lower alkyl, substituted lower alkyl, alkenyl, alkynyl, alkaryl, aralkyl, O-alkaryl or O-aralkyl, SH, $SCH_3$, OCN, Cl, Br, CN, $CF_3$, $OCF_3$, $SOCH_3$, $SO_2CH_3$, $ONO_2$, $NO_2$, $N_3$, $NH_2$, heterocycloalkyl, heterocycloalkaryl, aminoalkylamino, polyalkylamino, substituted silyl, an RNA cleaving group, a reporter group, an intercalator, a group for improving the pharmacokinetic properties of an oligonucleotide, or a group for improving the pharmacodynamic properties of an oligonucleotide, and other substituents having similar properties. A suitable modification includes 2'-methoxyethoxy (2'-O—$CH_2$ $CH_2OCH_3$, also known as 2'-O-(2-methoxyethyl) or 2'-MOE) (Martin et al., *Helv. Chim. Acta*, 1995, 78, 486-504, the disclosure of which is incorporated herein by reference in its entirety) i.e., an alkoxyalkoxy group. A further suitable modification includes 2'-dimethylaminooxyethoxy, i.e., a $O(CH_2)_2ON(CH_3)_2$ group, also known as 2'-DMAOE, as described in examples hereinbelow, and 2'-dimethylaminoethoxyethoxy (also known in the art as 2'-O-dimethyl-amino-ethoxy-ethyl or 2'-DMAEOE), i.e., 2'-O—$CH_2$—O—$CH_2$—$N(CH_3)_2$.

Other suitable sugar substituent groups include methoxy (—O—$CH_3$), aminopropoxy $CH_2$ $CH_2$ $CH_2NH_2$), allyl (—$CH_2$—CH=$CH_2$), —O-allyl (—O—$CH_2$—CH=$CH_2$) and fluoro (F). 2'-sugar substituent groups may be in the arabin (up) position or ribo (down) position. A suitable 2'-arabino modification is 2'-F. Similar modifications may also be made at other positions on the oligomeric compound, particularly the 3' position of the sugar on the 3' terminal nucleoside or in 2'-5' linked oligonucleotides and the 5' position of 5' terminal nucleotide. Oligomeric compounds may also have sugar mimetics such as cyclobutyl moieties in place of the pentofuranosyl sugar.

Base Modifications and Substitutions

A subject nucleic acid may also include nucleobase (often referred to in the art simply as "base") modifications or substitutions. As used herein, "unmodified" or "natural" nucleobases include the purine bases adenine (A) and guanine (G), and the pyrimidine bases thymine (T), cytosine (C) and uracil (U). Modified nucleobases include other synthetic and natural nucleobases such as 5-methylcytosine (5-me-C), 5-hydroxymethyl cytosine, xanthine, hypoxanthine, 2-aminoadenine, 6-methyl and other alkyl derivatives of adenine and guanine, 2-propyl and other alkyl derivatives of adenine and guanine, 2-thiouracil, 2-thiothymine and 2-thiocytosine, 5-halouracil and cytosine, 5-propynyl (—C≡C—CH₃) uracil and cytosine and other alkynyl derivatives of pyrimidine bases, 6-azo uracil, cytosine and thymine, 5-uracil (pseudouracil), 4-thiouracil, 8-halo, 8-amino, 8-thiol, 8-thioalkyl, 8-hydroxyl and other 8-substituted adenines and guanines, 5-halo particularly 5-bromo, 5-trifluoromethyl and other 5-substituted uracils and cytosines, 7-methylguanine and 7-methyladenine, 2-F-adenine, 2-amino-adenine, 8-azaguanine and 8-azaadenine, 7-deazaguanine and 7-deazaadenine and 3-deazaguanine and 3-deazaadenine. Further modified nucleobases include tricyclic pyrimidines such as phenoxazine cytidine(1H-pyrimido(5,4-b)(1,4)benzoxazin-2(3H)-one), phenothiazine cytidine (1H-pyrimido(5,4-b)(1,4)benzothiazin-2(3H)-one), G-clamps such as a substituted phenoxazine cytidine (e.g. 9-(2-aminoethoxy)-H-pyrimido (5,4-(b) (1,4)benzoxazin-2(3H)-one), carbazole cytidine (2H-pyrimido(4,5-b)indol-2-one), pyridoindole cytidine (H-pyrido(3',2':4,5)pyrrolo(2,3-d)pyrimidin-2-one).

Heterocyclic base moieties may also include those in which the purine or pyrimidine base is replaced with other heterocycles, for example 7-deaza-adenine, 7-deazaguanosine, 2-aminopyridine and 2-pyridone. Further nucleobases include those disclosed in U.S. Pat. No. 3,687,808, those disclosed in *The Concise Encyclopedia Of Polymer Science And Engineering*, pages 858-859, Kroschwitz, J. I., ed. John Wiley & Sons, 1990, those disclosed by Englisch et al., *Angewandte Chemie, International Edition*, 1991, 30, 613, and those disclosed by Sanghvi, Y. S., Chapter 15, *Antisense Research and Applications*, pages 289-302, Crooke, S. T. and Lebleu, B., ed., CRC Press, 1993; the disclosures of which are incorporated herein by reference in their entirety. Certain of these nucleobases are useful for increasing the binding affinity of an oligomeric compound. These include 5-substituted pyrimidines, 6-azapyrimidines and N-2, N-6 and 0-6 substituted purines, including 2-aminopropyladenine, 5-propynyluracil and 5-propynylcytosine. 5-methylcytosine substitutions have been shown to increase nucleic acid duplex stability by 0.6-1.2° C. (Sanghvi et al., eds., *Antisense Research and Applications*, CRC Press, Boca Raton, 1993, pp. 276-278; the disclosure of which is incorporated herein by reference in its entirety) and are suitable base substitutions, e.g., when combined with 2'-O-methoxyethyl sugar modifications.

Conjugates

Another possible modification of a subject nucleic acid involves chemically linking to the polynucleotide one or more moieties or conjugates which enhance the activity, cellular distribution or cellular uptake of the oligonucleotide. These moieties or conjugates can include conjugate groups covalently bound to functional groups such as primary or secondary hydroxyl groups. Conjugate groups include, but are not limited to, intercalators, reporter molecules, polyamines, polyamides, polyethylene glycols, polyethers, groups that enhance the pharmacodynamic properties of oligomers, and groups that enhance the pharmacokinetic properties of oligomers. Suitable conjugate groups include, but are not limited to, cholesterols, lipids, phospholipids, biotin, phenazine, folate, phenanthridine, anthraquinone, acridine, fluoresceins, rhodamines, coumarins, and dyes. Groups that enhance the pharmacodynamic properties include groups that improve uptake, enhance resistance to degradation, and/or strengthen sequence-specific hybridization with the target nucleic acid. Groups that enhance the pharmacokinetic properties include groups that improve uptake, distribution, metabolism or excretion of a subject nucleic acid.

Conjugate moieties include but are not limited to lipid moieties such as a cholesterol moiety (Letsinger et al., *Proc. Natl. Acad. Sci. USA,* 1989, 86, 6553-6556), cholic acid (Manoharan et al., *Bioorg. Med. Chem. Let.,* 1994, 4, 1053-1060), a thioether, e.g., hexyl-S-tritylthiol (Manoharan et al., *Ann. N.Y. Acad. Sci.,* 1992, 660, 306-309; Manoharan et al., *Bioorg. Med. Chem. Let.,* 1993, 3, 2765-2770), a thiocholesterol (Oberhauser et al., *Nucl. Acids Res.,* 1992, 20, 533-538), an aliphatic chain, e.g., dodecandiol or undecyl residues (Saison-Behmoaras et al., *EMBO J.,* 1991, 10, 1111-1118; Kabanov et al., *FEBS Lett.,* 1990, 259, 327-330; Svinarchuk et al., *Biochimie,* 1993, 75, 49-54), a phospholipid, e.g., di-hexadecyl-rac-glycerol or triethylammonium 1,2-di-O-hexadecyl-rac-glycero-3-H-phosphonate (Manoharan et al., *Tetrahedron Lett.,* 1995, 36, 3651-3654; Shea et al., *Nucl. Acids Res.,* 1990, 18, 3777-3783), a polyamine or a polyethylene glycol chain (Manoharan et al., *Nucleosides & Nucleotides,* 1995, 14, 969-973), or adamantane acetic acid (Manoharan et al., *Tetrahedron Lett.,* 1995, 36, 3651-3654), a palmityl moiety (Mishra et al., *Biochim. Biophys. Acta,* 1995, 1264, 229-237), or an octadecylamine or hexylamino-carbonyl-oxycholesterol moiety (Crooke et al., *J. Pharmacol. Exp. Ther.,* 1996, 277, 923-937).

A conjugate may include a "Protein Transduction Domain" or PTD (also known as a CPP—cell penetrating peptide), which may refer to a polypeptide, polynucleotide, carbohydrate, or organic or inorganic compound that facilitates traversing a lipid bilayer, micelle, cell membrane, organelle membrane, or vesicle membrane. A PTD attached to another molecule, which can range from a small polar molecule to a large macromolecule and/or a nanoparticle, facilitates the molecule traversing a membrane, for example going from extracellular space to intracellular space, or cytosol to within an organelle (e.g., the nucleus). In some embodiments, a PTD is covalently linked to the 3' end of an exogenous polynucleotide. In some embodiments, a PTD is covalently linked to the 5' end of an exogenous polynucleotide. Exemplary PTDs include but are not limited to a minimal undecapeptide protein transduction domain (corresponding to residues 47-57 of HIV-1 TAT comprising YGRKKRRQRRR; SEQ ID NO:112); a polyarginine sequence comprising a number of arginines sufficient to direct entry into a cell (e.g., 3, 4, 5, 6, 7, 8, 9, 10, or 10-50 arginines); a VP22 domain (Zender et al. (2002) *Cancer Gene Ther.* 9(6):489-96); an *Drosophila* Antennapedia protein transduction domain (Noguchi et al. (2003) *Diabetes* 52(7):1732-1737); a truncated human calcitonin peptide (Trehin et al. (2004) *Pharm. Research* 21:1248-1256); polylysine (Wender et al. (2000) *Proc. Natl. Acad. Sci. USA* 97:13003-13008); RRQRRTSKLMKR SEQ ID NO:113); Transportan GWTLNSAGYLLGKINLKALAALAKKIL SEQ ID NO:114); KALAWEAKLAKALAKA-LAKHLAKALAKALKCEA SEQ ID NO:115); and RQIKI-WFQNRRMKWKK SEQ ID NO:116). Exemplary PTDs include but are not limited to, YGRKKRRQRRR SEQ ID NO:117), RKKRRQRRR SEQ ID NO:118); an arginine homopolymer of from 3 arginine residues to 50 arginine residues; Exemplary PTD domain amino acid sequences include, but are not limited to, any of the following: YGRK-KRRQRRR SEQ ID NO:119); RKKRRQRR SEQ ID NO:120); YARAAARQARA SEQ ID NO:121); THRL-PRRRRRR SEQ ID NO:122); and GGRRARRRRRR SEQ ID NO:123). In some embodiments, the PTD is an activatable CPP (ACPP) (Aguilera et al. (2009) *Integr Biol (Camb)* June; 1(5-6): 371-381). ACPPs comprise a polycationic CPP (e.g., Arg9 or "R9") connected via a cleavable linker to a matching polyanion (e.g., Glu9 or "E9"), which reduces the net charge to nearly zero and thereby inhibits adhesion and uptake into cells. Upon cleavage of the linker, the polyanion is released, locally unmasking the polyarginine and its inherent adhesiveness, thus "activating" the ACPP to traverse the membrane.

Introducing Components into a Target Cell

A CasX guide RNA (or a nucleic acid comprising a nucleotide sequence encoding same) and/or a CasX polypeptide of the present disclosure (or a nucleic acid comprising a nucleotide sequence encoding same) and/or a CasX fusion polypeptide of the present disclosure (or a nucleic acid that includes a nucleotide sequence encoding a CasX fusion polypeptide of the present disclosure) and/or a donor polynucleotide (donor template) can be introduced into a host cell by any of a variety of well-known methods.

Any of a variety of compounds and methods can be used to deliver to a target cell a CasX system of the present disclosure (e.g., where a CasX system comprises: a) a CasX polypeptide of the present disclosure and a CasX guide RNA; b) a CasX polypeptide of the present disclosure, a CasX guide RNA, and a donor template nucleic acid; c) a CasX fusion polypeptide of the present disclosure and a CasX guide RNA; d) a CasX fusion polypeptide of the present disclosure, a CasX guide RNA, and a donor template nucleic acid; e) an mRNA encoding a CasX polypeptide of the present disclosure; and a CasX guide RNA; f) an mRNA encoding a CasX polypeptide of the present disclosure, a CasX guide RNA, and a donor template nucleic acid; g) an mRNA encoding a CasX fusion polypeptide of the present disclosure; and a CasX guide RNA; h) an mRNA encoding a CasX fusion polypeptide of the present disclosure, a CasX guide RNA, and a donor template nucleic acid; i) a recombinant expression vector comprising a nucleotide sequence encoding a CasX polypeptide of the present disclosure and a nucleotide sequence encoding a CasX guide RNA; j) a recombinant expression vector comprising a nucleotide sequence encoding a CasX polypeptide of the present disclosure, a nucleotide sequence encoding a CasX guide RNA, and a nucleotide sequence encoding a donor template nucleic acid; k) a recombinant expression vector comprising a nucleotide sequence encoding a CasX fusion polypeptide of the present disclosure and a nucleotide sequence encoding a CasX guide RNA; 1) a recombinant expression vector comprising a nucleotide sequence encoding a CasX fusion polypeptide of the present disclosure, a nucleotide sequence encoding a CasX guide RNA, and a nucleotide sequence encoding a donor template nucleic acid; m) a first recombinant expression vector comprising a nucleotide sequence encoding a CasX polypeptide of the present disclosure, and a second recombinant expression vector comprising a nucleotide sequence encoding a CasX guide RNA; n) a first recombinant expression vector comprising a nucleotide sequence encoding a CasX polypeptide of the present disclosure, and a second recombinant expression vector comprising a nucleotide sequence encoding a CasX guide RNA; and a donor template nucleic acid; o) a first recombinant expression vector comprising a nucleotide sequence encoding a CasX fusion polypeptide of the present disclosure, and a second recombinant expression vector comprising a nucleotide sequence encoding a CasX guide RNA; p) a first recombinant expression vector comprising a nucleotide sequence encoding a CasX fusion polypeptide of the present disclosure, and a second recombinant expression vector comprising a nucleotide sequence encoding a CasX guide RNA; and a donor template nucleic acid; q) a recombinant expression vector comprising a nucleotide sequence encoding a CasX polypeptide of the present disclosure, a nucleotide sequence encoding a first CasX guide RNA, and a nucleotide sequence encoding a second CasX guide RNA; or r) a recombinant expression vector comprising a nucleotide sequence encoding a CasX fusion polypeptide of the present disclosure, a nucleotide sequence encoding a first CasX guide RNA, and a nucleotide sequence encoding a second CasX guide RNA; or some variation of one of (a) through (r). As a non-limiting example, a CasX system of the present disclosure can be combined with a lipid. As another non-limiting example, a CasX system of the present disclosure can be combined with a particle, or formulated into a particle.

Methods of introducing a nucleic acid into a host cell are known in the art, and any convenient method can be used to introduce a subject nucleic acid (e.g., an expression construct/vector) into a target cell (e.g., prokaryotic cell, eukaryotic cell, plant cell, animal cell, mammalian cell, human cell, and the like). Suitable methods include, e.g., viral infection, transfection, conjugation, protoplast fusion, lipofection, electroporation, calcium phosphate precipitation, polyethyleneimine (PEI)-mediated transfection, DEAE-dextran mediated transfection, liposome-mediated transfection, particle gun technology, calcium phosphate precipitation, direct micro injection, nanoparticle-mediated nucleic acid delivery (see, e.g., Panyam et., al Adv Drug Deliv Rev. 2012 Sep. 13. pii: 50169-409X(12)00283-9. doi: 10.1016/j.addr.2012.09.023), and the like.

In some cases, a CasX polypeptide of the present disclosure is provided as a nucleic acid (e.g., an mRNA, a DNA, a plasmid, an expression vector, a viral vector, etc.) that encodes the CasX polypeptide. In some cases, the CasX polypeptide of the present disclosure is provided directly as a protein (e.g., without an associated guide RNA or with an associate guide RNA, i.e., as a ribonucleoprotein complex). A CasX polypeptide of the present disclosure can be introduced into a cell (provided to the cell) by any convenient method; such methods are known to those of ordinary skill in the art. As an illustrative example, a CasX polypeptide of the present disclosure can be injected directly into a cell (e.g., with or without a CasX guide RNA or nucleic acid encoding a CasX guide RNA, and with or without a donor polynucleotide). As another example, a preformed complex of a CasX polypeptide of the present disclosure and a CasX guide RNA (an RNP) can be introduced into a cell (e.g, eukaryotic cell) (e.g., via injection, via nucleofection; via a protein transduction domain (PTD) conjugated to one or more components, e.g., conjugated to the CasX protein, conjugated to a guide RNA, conjugated to a CasX polypeptide of the present disclosure and a guide RNA; etc.).

In some cases, a CasX fusion polypeptide (e.g., dCasX fused to a fusion partner, nickase CasX fused to a fusion partner, etc.) of the present disclosure is provided as a nucleic acid (e.g., an mRNA, a DNA, a plasmid, an expression vector, a viral vector, etc.) that encodes the CasX fusion polypeptide. In some cases, the CasX fusion polypeptide of the present disclosure is provided directly as a protein (e.g., without an associated guide RNA or with an associate guide RNA, i.e., as a ribonucleoprotein complex). A CasX fusion polypeptide of the present disclosure can be introduced into a cell (provided to the cell) by any convenient method; such methods are known to those of ordinary skill in the art. As an illustrative example, a CasX fusion polypeptide of the present disclosure can be injected directly into a cell (e.g., with or without nucleic acid encoding a CasX guide RNA and with or without a donor polynucleotide). As another example, a preformed complex of a CasX fusion polypeptide of the present disclosure and a CasX guide RNA (an RNP) can be introduced into a cell (e.g., via injection, via nucleofection; via a protein transduction domain (PTD) conjugated to one or more components, e.g., conjugated to the CasX fusion protein, conjugated to a guide RNA, conjugated to a CasX fusion polypeptide of the present disclosure and a guide RNA; etc.).

In some cases, a nucleic acid (e.g., a CasX guide RNA; a nucleic acid comprising a nucleotide sequence encoding a CasX polypeptide of the present disclosure; etc.) is delivered to a cell (e.g., a target host cell) and/or a polypeptide (e.g., a CasX polypeptide; a CasX fusion polypeptide) in a particle, or associated with a particle. In some cases, a CasX system of the present disclosure is delivered to a cell in a particle, or associated with a particle. The terms "particle" and nanoparticle" can be used interchangeable, as appropriate. A recombinant expression vector comprising a nucleotide sequence encoding a CasX polypeptide of the present disclosure and/or a CasX guide RNA, an mRNA comprising a nucleotide sequence encoding a CasX polypeptide of the present disclosure, and guide RNA may be delivered simultaneously using particles or lipid envelopes; for instance, a CasX polypeptide and a CasX guide RNA, e.g., as a complex (e.g., a ribonucleoprotein (RNP) complex), can be delivered via a particle, e.g., a delivery particle comprising lipid or lipidoid and hydrophilic polymer, e.g., a cationic lipid and a hydrophilic polymer, for instance wherein the cationic lipid comprises 1,2-dioleoyl-3-trimethylammonium-propane (DOTAP) or 1,2-ditetradecanoyl-sn-glycero-3-phosphocholine (DMPC) and/or wherein the hydrophilic polymer comprises ethylene glycol or polyethylene glycol (PEG); and/or wherein the particle further comprises cholesterol (e.g., particle from formulation 1=DOTAP 100, DMPC 0, PEG 0, Cholesterol 0; formulation number 2=DOTAP 90, DMPC 0, PEG 10, Cholesterol 0; formulation number 3=DOTAP 90, DMPC 0, PEG 5, Cholesterol 5). For example, a particle can be formed using a multistep process in which a CasX polypeptide and a CasX guideRNA are mixed together, e.g., at a 1:1 molar ratio, e.g., at room temperature, e.g., for 30 minutes, e.g., in sterile, nuclease free 1× phosphate-buffered saline (PBS); and separately, DOTAP, DMPC, PEG, and cholesterol as applicable for the formulation are dissolved in alcohol, e.g., 100% ethanol; and, the two solutions are mixed together to form particles containing the complexes).

A CasX polypeptide of the present disclosure (or an mRNA comprising a nucleotide sequence encoding a CasX polypeptide of the present disclosure; or a recombinant expression vector comprising a nucleotide sequence encoding a CasX polypeptide of the present disclosure) and/or CasX guide RNA (or a nucleic acid such as one or more expression vectors encoding the CasX guide RNA) may be delivered simultaneously using particles or lipid envelopes. For example, a biodegradable core-shell structured nanoparticle with a poly (β-amino ester) (PBAE) core enveloped by a phospholipid bilayer shell can be used. In some cases, particles/nanoparticles based on self assembling bioadhesive polymers are used; such particles/nanoparticles may be applied to oral delivery of peptides, intravenous delivery of peptides and nasal delivery of peptides, e.g., to the brain. Other embodiments, such as oral absorption and ocular delivery of hydrophobic drugs are also contemplated. A molecular envelope technology, which involves an engineered polymer envelope which is protected and delivered to the site of the disease, can be used. Doses of about 5 mg/kg can be used, with single or multiple doses, depending on various factors, e.g., the target tissue.

Lipidoid compounds (e.g., as described in US patent application 20110293703) are also useful in the administration of polynucleotides, and can be used to deliver a CasX polypeptide of the present disclosure, a CasX fusion polypeptide of the present disclosure, an RNP of the present disclosure, a nucleic acid of the present disclosure, or a CasX system of the present disclosure (e.g., where a CasX system comprises: a) a CasX polypeptide of the present disclosure and a CasX guide RNA; b) a CasX polypeptide of the present disclosure, a CasX guide RNA, and a donor template nucleic acid; c) a CasX fusion polypeptide of the present disclosure and a CasX guide RNA; d) a CasX fusion polypeptide of the present disclosure, a CasX guide RNA, and a donor template nucleic acid; e) an mRNA encoding a CasX polypeptide of the present disclosure; and a CasX guide RNA; f) an mRNA encoding a CasX polypeptide of the present disclosure, a CasX guide RNA, and a donor template nucleic acid; g) an mRNA encoding a CasX fusion polypeptide of the present disclosure; and a CasX guide RNA; h) an mRNA encoding a CasX fusion polypeptide of the present disclosure, a CasX guide RNA, and a donor template nucleic acid; i) a recombinant expression vector comprising a nucleotide sequence encoding a CasX polypeptide of the present disclosure and a nucleotide sequence encoding a CasX guide RNA; j) a recombinant expression vector comprising a nucleotide sequence encoding a CasX polypeptide of the present disclosure, a nucleotide sequence encoding a CasX guide RNA, and a nucleotide sequence encoding a donor template nucleic acid; k) a recombinant expression vector comprising a nucleotide sequence encoding a CasX fusion polypeptide of the present disclosure and a nucleotide sequence encoding a CasX guide RNA; l) a recombinant expression vector comprising a nucleotide sequence encoding a CasX fusion polypeptide of the present disclosure, a nucleotide sequence encoding a CasX guide RNA, and a nucleotide sequence encoding a donor template nucleic acid; m) a first recombinant expression vector comprising a nucleotide sequence encoding a CasX polypeptide of the present disclosure, and a second recombinant expression vector comprising a nucleotide sequence encoding a CasX guide RNA; n) a first recombinant expression vector comprising a nucleotide sequence encoding a CasX polypeptide of the present disclosure, and a second recombinant expression vector comprising a nucleotide sequence encoding a CasX guide RNA; and a donor template nucleic acid; o) a first recombinant expression vector comprising a nucleotide sequence encoding a CasX fusion polypeptide of the present disclosure, and a second recombinant expression vector comprising a nucleotide sequence encoding a CasX guide RNA; p) a first recombinant expression vector comprising a nucleotide sequence encoding a CasX fusion polypeptide of the present disclosure, and a second recombinant expression vector comprising a nucleotide sequence encoding a CasX guide RNA; and a donor template nucleic acid; q) a recombinant expression vector comprising a nucleotide sequence encoding a CasX polypeptide of the present disclosure, a nucleotide sequence encoding a first CasX guide RNA, and a nucleotide sequence encoding a second CasX guide RNA; or r) a recombinant expression vector comprising a nucleotide sequence encoding a CasX fusion polypeptide of the present disclosure, a nucleotide sequence encoding a first CasX guide RNA, and a nucleotide sequence encoding a second CasX guide RNA; or some variation of one of (a) through (r). In one aspect, the aminoalcohol lipidoid compounds are combined with an agent to be delivered to a cell or a subject to form microparticles, nanoparticles, liposomes, or micelles. The aminoalcohol lipidoid compounds may be combined with other aminoalcohol lipidoid compounds, polymers (synthetic or natural), surfactants, cholesterol, carbohydrates, proteins, lipids, etc. to form the particles. These particles may then optionally be combined with a pharmaceutical excipient to form a pharmaceutical composition.

A poly(beta-amino alcohol) (PBAA) can be used to deliver a CasX polypeptide of the present disclosure, a CasX fusion polypeptide of the present disclosure, an RNP of the present disclosure, a nucleic acid of the present disclosure, or a CasX system of the present disclosure, to a target cell. US Patent Publication No. 20130302401 relates to a class of poly(beta-amino alcohols) (PBAAs) that has been prepared using combinatorial polymerization.

Sugar-based particles may be used, for example GalNAc, as described with reference to WO2014118272 (incorporated herein by reference) and Nair, J K et al., 2014, Journal of the American Chemical Society 136 (49), 16958-16961) can be used to deliver a CasX polypeptide of the present disclosure, a CasX fusion polypeptide of the present disclosure, an RNP of the present disclosure, a nucleic acid of the present disclosure, or a CasX system of the present disclosure, to a target cell.

In some cases, lipid nanoparticles (LNPs) are used to deliver a CasX polypeptide of the present disclosure, a CasX fusion polypeptide of the present disclosure, an RNP of the present disclosure, a nucleic acid of the present disclosure, or a CasX system of the present disclosure, to a target cell. Negatively charged polymers such as RNA may be loaded into LNPs at low pH values (e.g., pH 4) where the ionizable lipids display a positive charge. However, at physiological pH values, the LNPs exhibit a low surface charge compatible with longer circulation times. Four species of ionizable cationic lipids have been focused upon, namely 1,2-dilineoyl-3-dimethylammonium-propane (DLinDAP), 1,2-dilinoleyloxy-3-N,N-dimethylaminopropane (DLinDMA), 1,2-dilinoleyloxy-keto-N,N-dimethyl-3-aminopropane (DLinKDMA), and 1,2-dilinoleyl-4-(2-dimethylaminoethyl)-[1,3]-dioxolane (DLinKC2-DMA). Preparation of LNPs and is described in, e.g., Rosin et al. (2011) Molecular Therapy 19:1286-2200). The cationic lipids 1,2-dilineoyl-3-dimethylammonium-propane (DLinDAP), 1,2-dilinoleyloxy-3-N,N-dimethylaminopropane (DLinDMA), 1,2-dilinoleyloxyketo-N,N-dimethyl-3-aminopropane (DLinK-DMA), 1,2-dilinoleyl-4-(2-dimethylaminoethyl)-[1,3]-dioxolane (DLinKC2-DMA), (3-o-[2"-(methoxypolyethyleneglycol 2000) succinoyl]-1,2-dimyristoyl-sn-glycol (PEG-S-DMG), and R-3-[(.omega.-methoxy-poly(ethylene glycol)2000) carbamoyl]-1,2-dimyristyloxlpropyl-3-amine (PEG-C-DOMG) may be used. A nucleic acid (e.g., a CasX guide RNA; a nucleic acid of the present disclosure; etc.) may be encapsulated in LNPs containing DLinDAP, DLinDMA, DLinK-DMA, and DLinKC2-DMA (cationic lipid:DSPC:CHOL: PEGS-DMG or PEG-C-DOMG at 40:10:40:10 molar ratios). In some cases, 0.2% SP-DiOC18 is incorporated.

Spherical Nucleic Acid (SNA™) constructs and other nanoparticles (particularly gold nanoparticles) can be used to deliver a CasX polypeptide of the present disclosure, a CasX fusion polypeptide of the present disclosure, an RNP of the present disclosure, a nucleic acid of the present disclosure, or a CasX system of the present disclosure, to a target cell. See, e.g., Cutler et al., J. Am. Chem. Soc. 2011 133:9254-9257, Hao et al., Small 2011 7:3158-3162, Zhang et al., ACS Nano. 2011 5:6962-6970, Cutler et al., J. Am. Chem. Soc. 2012 134:1376-1391, Young et al., Nano Lett. 2012 12:3867-71, Zheng et al., Proc. Natl. Acad. Sci. USA. 2012 109:11975-80, Mirkin, Nanomedicine 2012 7:635-638 Zhang et al., J. Am. Chem. Soc. 2012 134:16488-1691, Weintraub, Nature 2013 495:S14-S16, Choi et al., Proc. Natl. Acad. Sci. USA. 2013 110(19): 7625-7630, Jensen et al., Sci. Transl. Med. 5, 209ra152 (2013) and Mirkin, et al., Small, 10:186-192.

Self-assembling nanoparticles with RNA may be constructed with polyethyleneimine (PEI) that is PEGylated with an Arg-Gly-Asp (RGD) peptide ligand attached at the distal end of the polyethylene glycol (PEG).

In general, a "nanoparticle" refers to any particle having a diameter of less than 1000 nm. In some cases, nanoparticles suitable for use in delivering a CasX polypeptide of the present disclosure, a CasX fusion polypeptide of the present disclosure, an RNP of the present disclosure, a nucleic acid of the present disclosure, or a CasX system of the present disclosure, to a target cell have a diameter of 500 nm or less, e.g., from 25 nm to 35 nm, from 35 nm to 50 nm, from 50 nm to 75 nm, from 75 nm to 100 nm, from 100 nm to 150 nm, from 150 nm to 200 nm, from 200 nm to 300 nm, from 300 nm to 400 nm, or from 400 nm to 500 nm. In some cases, nanoparticles suitable for use in delivering a CasX polypeptide of the present disclosure, a CasX fusion polypeptide of the present disclosure, an RNP of the present disclosure, a nucleic acid of the present disclosure, or a CasX system of the present disclosure, to a target cell have a diameter of from 25 nm to 200 nm. In some cases, nanoparticles suitable for use in delivering a CasX polypeptide of the present disclosure, a CasX fusion polypeptide of the present disclosure, an RNP of the present disclosure, a nucleic acid of the present disclosure, or a CasX system of the present disclosure, to a target cell have a diameter of 100 nm or less In some cases, nanoparticles suitable for use in delivering a CasX polypeptide of the present disclosure, a CasX fusion polypeptide of the present disclosure, an RNP of the present disclosure, a nucleic acid of the present disclosure, or a CasX system of the present disclosure, to a target cell have a diameter of from 35 nm to 60 nm.

Nanoparticles suitable for use in delivering a CasX polypeptide of the present disclosure, a CasX fusion polypeptide of the present disclosure, an RNP of the present disclosure, a nucleic acid of the present disclosure, or a CasX system of the present disclosure, to a target cell may be provided in different forms, e.g., as solid nanoparticles (e.g., metal such as silver, gold, iron, titanium), non-metal, lipid-based solids, polymers), suspensions of nanoparticles, or combinations thereof. Metal, dielectric, and semiconductor nanoparticles may be prepared, as well as hybrid structures (e.g., core-shell nanoparticles). Nanoparticles made of semiconducting material may also be labeled quantum dots if they are small enough (typically below 10 nm) that quantization of electronic energy levels occurs. Such nanoscale particles are used in biomedical applications as drug carriers or imaging agents and may be adapted for similar purposes in the present disclosure.

Semi-solid and soft nanoparticles are also suitable for use in delivering a CasX polypeptide of the present disclosure, a CasX fusion polypeptide of the present disclosure, an RNP of the present disclosure, a nucleic acid of the present disclosure, or a CasX system of the present disclosure, to a target cell. A prototype nanoparticle of semi-solid nature is the liposome.

In some cases, an exosome is used to deliver a CasX polypeptide of the present disclosure, a CasX fusion polypeptide of the present disclosure, an RNP of the present disclosure, a nucleic acid of the present disclosure, or a CasX system of the present disclosure, to a target cell.

Exosomes are endogenous nano-vesicles that transport RNAs and proteins, and which can deliver RNA to the brain and other target organs.

In some cases, a liposome is used to deliver a CasX polypeptide of the present disclosure, a CasX fusion polypeptide of the present disclosure, an RNP of the present disclosure, a nucleic acid of the present disclosure, or a CasX system of the present disclosure, to a target cell. Liposomes are spherical vesicle structures composed of a uni- or multilamellar lipid bilayer surrounding internal aqueous compartments and a relatively impermeable outer lipophilic phospholipid bilayer. Liposomes can be made from several different types of lipids; however, phospholipids are most commonly used to generate liposomes. Although liposome formation is spontaneous when a lipid film is mixed with an aqueous solution, it can also be expedited by applying force in the form of shaking by using a homogenizer, sonicator, or an extrusion apparatus. Several other additives may be added to liposomes in order to modify their structure and properties. For instance, either cholesterol or sphingomyelin may be added to the liposomal mixture in order to help stabilize the liposomal structure and to prevent the leakage of the liposomal inner cargo. A liposome formulation may be mainly comprised of natural phospholipids and lipids such as 1,2-distearoryl-sn-glycero-3-phosphatidyl choline (DSPC), sphingomyelin, egg phosphatidylcholines and monosialoganglioside.

A stable nucleic-acid-lipid particle (SNALP) can be used to deliver a CasX polypeptide of the present disclosure, a CasX fusion polypeptide of the present disclosure, an RNP of the present disclosure, a nucleic acid of the present disclosure, or a CasX system of the present disclosure, to a target cell. The SNALP formulation may contain the lipids 3-N-[(methoxypoly(ethylene glycol) 2000) carbamoyl]-1,2-dimyristyloxy-propylamine (PEG-C-DMA), 1,2-dilinoleyloxy-N,N-dimethyl-3-aminopropane (DLinDMA), 1,2-distearoyl-sn-glycero-3-phosphocholine (DSPC) and cholesterol, in a 2:40:10:48 molar percent ratio. The SNALP liposomes may be prepared by formulating D-Lin-DMA and PEG-C-DMA with distearoylphosphatidylcholine (DSPC), Cholesterol and siRNA using a 25:1 lipid/siRNA ratio and a 48/40/10/2 molar ratio of Cholesterol/D-Lin-DMA/DSPC/PEG-C-DMA. The resulting SNALP liposomes can be about 80-100 nm in size. A SNALP may comprise synthetic cholesterol (Sigma-Aldrich, St Louis, Mo., USA), dipalmitoylphosphatidylcholine (Avanti Polar Lipids, Alabaster, Ala., USA), 3-N-[(w-methoxy poly(ethylene glycol)2000) carbamoyl]-1,2-dimyrestyloxypropylamine, and cationic 1,2-dilinoleyloxy-3-N,Ndimethylaminopropane. A SNALP may comprise synthetic cholesterol (Sigma-Aldrich), 1,2-distearoyl-sn-glycero-3-phosphocholine (DSPC; Avanti Polar Lipids Inc.), PEG-cDMA, and 1,2-dilinoleyloxy-3-(N;N-dimethyl)aminopropane (DLinDMA).

Other cationic lipids, such as amino lipid 2,2-dilinoleyl-4-dimethylaminoethyl-[1,3]-dioxolane (DLin-KC2-DMA) can be used to deliver a CasX polypeptide of the present disclosure, a CasX fusion polypeptide of the present disclosure, an RNP of the present disclosure, a nucleic acid of the present disclosure, or a CasX system of the present disclosure, to a target cell. A preformed vesicle with the following lipid composition may be contemplated: amino lipid, distearoylphosphatidylcholine (DSPC), cholesterol and (R)-2,3-bis(octadecyloxy) propyl-1-(methoxy poly(ethylene glycol)2000)propylcarbamate (PEG-lipid) in the molar ratio 40/10/40/10, respectively, and a FVII siRNA/total lipid ratio of approximately 0.05 (w/w). To ensure a narrow particle size distribution in the range of 70-90 nm and a low polydispersity index of 0.11.+−0.04 (n=56), the particles may be extruded up to three times through 80 nm membranes prior to adding the guide RNA. Particles containing the highly potent amino lipid 16 may be used, in which the molar ratio of the four lipid components 16, DSPC, cholesterol and PEG-lipid (50/10/38.5/1.5) which may be further optimized to enhance in vivo activity.

Lipids may be formulated with a CasX system of the present disclosure or component(s) thereof or nucleic acids encoding the same to form lipid nanoparticles (LNPs). Suitable lipids include, but are not limited to, DLin-KC2-DMA4, C12-200 and colipids distearoylphosphatidyl choline, cholesterol, and PEG-DMG may be formulated with a CasX system, or component thereof, of the present disclosure, using a spontaneous vesicle formation procedure. The component molar ratio may be about 50/10/38.5/1.5 (DLin-KC2-DMA or C12-200/disteroylphosphatidyl choline/cholesterol/PEG-DMG).

A CasX system of the present disclosure, or a component thereof, may be delivered encapsulated in PLGA microspheres such as that further described in US published applications 20130252281 and 20130245107 and 20130244279.

Supercharged proteins can be used to deliver a CasX polypeptide of the present disclosure, a CasX fusion polypeptide of the present disclosure, an RNP of the present disclosure, a nucleic acid of the present disclosure, or a CasX system of the present disclosure, to a target cell. Supercharged proteins are a class of engineered or naturally occurring proteins with unusually high positive or negative net theoretical charge. Both supernegatively and superpositively charged proteins exhibit the ability to withstand thermally or chemically induced aggregation. Superpositively charged proteins are also able to penetrate mammalian cells. Associating cargo with these proteins, such as plasmid DNA, RNA, or other proteins, can facilitate the functional delivery of these macromolecules into mammalian cells both in vitro and in vivo.

Cell Penetrating Peptides (CPPs) can be used to deliver a CasX polypeptide of the present disclosure, a CasX fusion polypeptide of the present disclosure, an RNP of the present disclosure, a nucleic acid of the present disclosure, or a CasX system of the present disclosure, to a target cell. CPPs typically have an amino acid composition that either contains a high relative abundance of positively charged amino acids such as lysine or arginine or has sequences that contain an alternating pattern of polar/charged amino acids and non-polar, hydrophobic amino acids.

An implantable device can be used to deliver a CasX polypeptide of the present disclosure, a CasX fusion polypeptide of the present disclosure, an RNP of the present disclosure, a nucleic acid of the present disclosure (e.g., a CasX guide RNA, a nucleic acid encoding a CasX guide RNA, a nucleic acid encoding CasX polypeptide, a donor template, and the like), or a CasX system of the present disclosure, to a target cell (e.g., a target cell in vivo, where the target cell is a target cell in circulation, a target cell in a tissue, a target cell in an organ, etc.). An implantable device suitable for use in delivering a CasX polypeptide of the present disclosure, a CasX fusion polypeptide of the present disclosure, an RNP of the present disclosure, a nucleic acid of the present disclosure, or a CasX system of the present disclosure, to a target cell (e.g., a target cell in vivo, where the target cell is a target cell in circulation, a target cell in a tissue, a target cell in an organ, etc.) can include a container (e.g., a reservoir, a matrix, etc.) that comprises the CasX polypeptide, the CasX fusion polypeptide, the RNP, or the CasX system (or component thereof, e.g., a nucleic acid of the present disclosure).

A suitable implantable device can comprise a polymeric substrate, such as a matrix for example, that is used as the device body, and in some cases additional scaffolding materials, such as metals or additional polymers, and materials to enhance visibility and imaging. An implantable delivery device can be advantageous in providing release locally and over a prolonged period, where the polypeptide and/or nucleic acid to be delivered is released directly to a target site, e.g., the extracellular matrix (ECM), the vasculature surrounding a tumor, a diseased tissue, etc. Suitable implantable delivery devices include devices suitable for use in delivering to a cavity such as the abdominal cavity and/or any other type of administration in which the drug delivery system is not anchored or attached, comprising a biostable and/or degradable and/or bioabsorbable polymeric substrate, which may for example optionally be a matrix. In some cases, a suitable implantable drug delivery device comprises degradable polymers, wherein the main release mechanism is bulk erosion. In some cases, a suitable implantable drug delivery device comprises non degradable, or slowly degraded polymers, wherein the main release mechanism is diffusion rather than bulk erosion, so that the outer part functions as membrane, and its internal part functions as a drug reservoir, which practically is not affected by the surroundings for an extended period (for example from about a week to about a few months). Combinations of different polymers with different release mechanisms may also optionally be used. The concentration gradient at the can be maintained effectively constant during a significant period of the total releasing period, and therefore the diffusion rate is effectively constant (termed "zero mode" diffusion). By the term "constant" it is meant a diffusion rate that is maintained above the lower threshold of therapeutic effectiveness, but which may still optionally feature an initial burst and/or may fluctuate, for example increasing and decreasing to a certain degree. The diffusion rate can be so maintained for a prolonged period, and it can be considered constant to a certain level to optimize the therapeutically effective period, for example the effective silencing period.

In some cases, the implantable delivery system is designed to shield the nucleotide based therapeutic agent from degradation, whether chemical in nature or due to attack from enzymes and other factors in the body of the subject.

The site for implantation of the device, or target site, can be selected for maximum therapeutic efficacy. For example, a delivery device can be implanted within or in the proximity of a tumor environment, or the blood supply associated with a tumor. The target location can be, e.g.: 1) the brain at degenerative sites like in Parkinson or Alzheimer disease at the basal ganglia, white and gray matter; 2) the spine, as in the case of amyotrophic lateral sclerosis (ALS); 3) uterine cervix; 4) active and chronic inflammatory joints; 5) dermis as in the case of psoriasis; 7) sympathetic and sensoric nervous sites for analgesic effect; 7) a bone; 8) a site of acute or chronic infection; 9) Intra vaginal; 10) Inner ear— auditory system, labyrinth of the inner ear, vestibular system; 11) Intra tracheal; 12) Intra-cardiac; coronary, epicardiac; 13) urinary tract or bladder; 14) biliary system; 15) parenchymal tissue including and not limited to the kidney, liver, spleen; 16) lymph nodes; 17) salivary glands; 18) dental gums; 19) Intra-articular (into joints); 20) Intra-ocular; 21) Brain tissue; 22) Brain ventricles; 23) Cavities, including abdominal cavity (for example but without limitation, for ovary cancer); 24) Intra esophageal; and 25) Intra rectal; and 26) into the vasculature.

The method of insertion, such as implantation, may optionally already be used for other types of tissue implantation and/or for insertions and/or for sampling tissues, optionally without modifications, or alternatively optionally only with non-major modifications in such methods. Such methods optionally include but are not limited to brachytherapy methods, biopsy, endoscopy with and/or without ultrasound, such as stereotactic methods into the brain tissue, laparoscopy, including implantation with a laparoscope into joints, abdominal organs, the bladder wall and body cavities.

Modified Host Cells

The present disclosure provides a modified cell comprising a CasX polypeptide of the present disclosure and/or a nucleic acid comprising a nucleotide sequence encoding a CasX polypeptide of the present disclosure. The present disclosure provides a modified cell comprising a CasX polypeptide of the present disclosure, where the modified cell is a cell that does not normally comprise a CasX polypeptide of the present disclosure. The present disclosure provides a modified cell (e.g., a genetically modified cell) comprising nucleic acid comprising a nucleotide sequence encoding a CasX polypeptide of the present disclosure. The present disclosure provides a genetically modified cell that is genetically modified with an mRNA comprising a nucleotide sequence encoding a CasX polypeptide of the present disclosure. The present disclosure provides a genetically modified cell that is genetically modified with a recombinant expression vector comprising a nucleotide sequence encoding a CasX polypeptide of the present disclosure. The present disclosure provides a genetically modified cell that is genetically modified with a recombinant expression vector comprising: a) a nucleotide sequence encoding a CasX polypeptide of the present disclosure; and b) a nucleotide sequence encoding a CasX guide RNA of the present disclosure. The present disclosure provides a genetically modified cell that is genetically modified with a recombinant expression vector comprising: a) a nucleotide sequence encoding a CasX polypeptide of the present disclosure; b) a nucleotide sequence encoding a CasX guide RNA of the present disclosure; and c) a nucleotide sequence encoding a donor template.

A cell that serves as a recipient for a CasX polypeptide of the present disclosure and/or a nucleic acid comprising a nucleotide sequence encoding a CasX polypeptide of the present disclosure and/or a CasX guide RNA of the present disclosure, can be any of a variety of cells, including, e.g., in vitro cells; in vivo cells; ex vivo cells; primary cells; cancer cells; animal cells; plant cells; algal cells; fungal cells; etc. A cell that serves as a recipient for a CasX polypeptide of the present disclosure and/or a nucleic acid comprising a nucleotide sequence encoding a CasX polypeptide of the present disclosure and/or a CasX guide RNA of the present disclosure is referred to as a "host cell" or a "target cell." A host cell or a target cell can be a recipient of a CasX system of the present disclosure. A host cell or a target cell can be a recipient of a CasX RNP of the present disclosure. A host cell or a target cell can be a recipient of a single component of a CasX system of the present disclosure.

Non-limiting examples of cells (target cells) include: a prokaryotic cell, eukaryotic cell, a bacterial cell, an archaeal cell, a cell of a single-cell eukaryotic organism, a protozoa cell, a cell from a plant (e.g., cells from plant crops, fruits, vegetables, grains, soy bean, corn, maize, wheat, seeds, tomatoes, rice, cassava, sugarcane, pumpkin, hay, potatos, cotton, *cannabis*, tobacco, flowering plants, conifers, gymnosperms, angiosperms, ferns, clubmosses, hornworts, liverworts, mosses, dicotyledons, monocyledons, etc.), an algal cell, (e.g., *Botryococcus braunii, Chlamydomonas reinhardtii, Nannochloropsis gaditana, Chlorella pyrenoidosa, Sargassum patens, C. agardh*, and the like), seaweeds (e.g. kelp) a fungal cell (e.g., a yeast cell, a cell from a mushroom), an animal cell, a cell from an invertebrate animal (e.g., fruit fly, cnidarian, echinoderm, nematode, etc.), a cell from a vertebrate animal (e.g., fish, amphibian, reptile, bird, mammal), a cell from a mammal (e.g., an ungulate (e.g., a pig, a cow, a goat, a sheep); a rodent (e.g., a rat, a mouse); a non-human primate; a human; a feline (e.g., a cat); a canine (e.g., a dog); etc.), and the like. In some cases, the cell is a cell that does not originate from a natural organism (e.g., the cell can be a synthetically made cell; also referred to as an artificial cell).

A cell can be an in vitro cell (e.g., established cultured cell line). A cell can be an ex vivo cell (cultured cell from an individual). A cell can be and in vivo cell (e.g., a cell in an individual). A cell can be an isolated cell. A cell can be a cell inside of an organism. A cell can be an organism. A cell can be a cell in a cell culture (e.g., in vitro cell culture). A cell can be one of a collection of cells. A cell can be a prokaryotic cell or derived from a prokaryotic cell. A cell can be a bacterial cell or can be derived from a bacterial cell. A cell can be an archaeal cell or derived from an archaeal cell. A cell can be a eukaryotic cell or derived from a eukaryotic cell. A cell can be a plant cell or derived from a plant cell. A cell can be an animal cell or derived from an animal cell. A cell can be an invertebrate cell or derived from an invertebrate cell. A cell can be a vertebrate cell or derived from a vertebrate cell. A cell can be a mammalian cell or derived from a mammalian cell. A cell can be a rodent cell or derived from a rodent cell. A cell can be a human cell or derived from a human cell. A cell can be a microbe cell or derived from a microbe cell. A cell can be a fungi cell or derived from a fungi cell. A cell can be an insect cell. A cell can be an arthropod cell. A cell can be a protozoan cell. A cell can be a helminth cell.

Suitable cells include a stem cell (e.g. an embryonic stem (ES) cell, an induced pluripotent stem (iPS) cell; a germ cell (e.g., an oocyte, a sperm, an oogonia, a spermatogonia, etc.); a somatic cell, e.g. a fibroblast, an oligodendrocyte, a glial cell, a hematopoietic cell, a neuron, a muscle cell, a bone cell, a hepatocyte, a pancreatic cell, etc.

Suitable cells include human embryonic stem cells, fetal cardiomyocytes, myofibroblasts, mesenchymal stem cells, autotransplated expanded cardiomyocytes, adipocytes, totipotent cells, pluripotent cells, blood stem cells, myoblasts, adult stem cells, bone marrow cells, mesenchymal cells, embryonic stem cells, parenchymal cells, epithelial cells, endothelial cells, mesothelial cells, fibroblasts, osteoblasts, chondrocytes, exogenous cells, endogenous cells, stem cells, hematopoietic stem cells, bone-marrow derived progenitor cells, myocardial cells, skeletal cells, fetal cells, undifferentiated cells, multipotent progenitor cells, unipotent progenitor cells, monocytes, cardiac myoblasts, skeletal myoblasts, macrophages, capillary endothelial cells, xenogenic cells, allogenic cells, and post-natal stem cells.

In some cases, the cell is an immune cell, a neuron, an epithelial cell, and endothelial cell, or a stem cell. In some cases, the immune cell is a T cell, a B cell, a monocyte, a natural killer cell, a dendritic cell, or a macrophage. In some cases, the immune cell is a cytotoxic T cell. In some cases, the immune cell is a helper T cell. In some cases, the immune cell is a regulatory T cell (Treg).

In some cases, the cell is a stem cell. Stem cells include adult stem cells. Adult stem cells are also referred to as somatic stem cells.

Adult stem cells are resident in differentiated tissue, but retain the properties of self-renewal and ability to give rise to multiple cell types, usually cell types typical of the tissue in which the stem cells are found. Numerous examples of somatic stem cells are known to those of skill in the art, including muscle stem cells; hematopoietic stem cells; epithelial stem cells; neural stem cells; mesenchymal stem cells; mammary stem cells; intestinal stem cells; mesodermal stem cells; endothelial stem cells; olfactory stem cells; neural crest stem cells; and the like.

Stem cells of interest include mammalian stem cells, where the term "mammalian" refers to any animal classified as a mammal, including humans; non-human primates; domestic and farm animals; and zoo, laboratory, sports, or pet animals, such as dogs, horses, cats, cows, mice, rats, rabbits, etc. In some cases, the stem cell is a human stem cell. In some cases, the stem cell is a rodent (e.g., a mouse; a rat) stem cell. In some cases, the stem cell is a non-human primate stem cell.

Stem cells can express one or more stem cell markers, e.g., SOX9, KRT19, KRT7, LGR5, CA9, FXYD2, CDH6, CLDN18, TSPAN8, BPIFB1, OLFM4, CDH17, and PPARGC1A.

In some embodiments, the stem cell is a hematopoietic stem cell (HSC). HSCs are mesoderm-derived cells that can be isolated from bone marrow, blood, cord blood, fetal liver and yolk sac. HSCs are characterized as $CD34^+$ and $CD3^-$. HSCs can repopulate the erythroid, neutrophil-macrophage, megakaryocyte and lymphoid hematopoietic cell lineages in vivo. In vitro, HSCs can be induced to undergo at least some self-renewing cell divisions and can be induced to differentiate to the same lineages as is seen in vivo. As such, HSCs can be induced to differentiate into one or more of erythroid cells, megakaryocytes, neutrophils, macrophages, and lymphoid cells.

In other embodiments, the stem cell is a neural stem cell (NSC). Neural stem cells (NSCs) are capable of differentiating into neurons, and glia (including oligodendrocytes, and astrocytes). A neural stem cell is a multipotent stem cell which is capable of multiple divisions, and under specific conditions can produce daughter cells which are neural stem cells, or neural progenitor cells that can be neuroblasts or glioblasts, e.g., cells committed to become one or more types of neurons and glial cells respectively. Methods of obtaining NSCs are known in the art.

In other embodiments, the stem cell is a mesenchymal stem cell (MSC). MSCs originally derived from the embryonal mesoderm and isolated from adult bone marrow, can differentiate to form muscle, bone, cartilage, fat, marrow stroma, and tendon. Methods of isolating MSC are known in the art; and any known method can be used to obtain MSC. See, e.g., U.S. Pat. No. 5,736,396, which describes isolation of human MSC.

A cell is in some cases a plant cell. A plant cell can be a cell of a monocotyledon. A cell can be a cell of a dicotyledon.

In some cases, the cell is a plant cell. For example, the cell can be a cell of a major agricultural plant, e.g., Barley, Beans (Dry Edible), Canola, Corn, Cotton (Pima), Cotton (Upland), Flaxseed, Hay (Alfalfa), Hay (Non-Alfalfa), Oats, Peanuts, Rice, Sorghum, Soybeans, Sugarbeets, Sugarcane, Sunflowers (Oil), Sunflowers (Non-Oil), Sweet Potatoes, Tobacco (Burley), Tobacco (Flue-cured), Tomatoes, Wheat (Durum), Wheat (Spring), Wheat (Winter), and the like. As another example, the cell is a cell of a vegetable crops which include but are not limited to, e.g., alfalfa sprouts, aloe leaves, arrow root, arrowhead, artichokes, asparagus, bamboo shoots, banana flowers, bean sprouts, beans, beet tops, beets, bittermelon, bok choy, broccoli, broccoli rabe (*rappini*), brussels sprouts, cabbage, cabbage sprouts, cactus leaf (nopales), calabaza, cardoon, carrots, cauliflower, celery, chayote, chinese artichoke (crosnes), chinese cabbage, chinese celery, chinese chives, choy sum, *chrysanthemum* leaves (tung ho), collard greens, corn stalks, corn-sweet, cucumbers, daikon, dandelion greens, dasheen, dau mue (pea tips), donqua (winter melon), eggplant, endive, escarole, fiddle head ferns, field cress, frisee, gai choy (chinese mustard), gailon, galanga (siam, thai ginger), garlic, ginger root, gobo, greens, hanover salad greens, huauzontle, jerusalem artichokes, jicama, kale greens, kohlrabi, lamb's quarters (quilete), lettuce (bibb), lettuce (boston), lettuce (boston red), lettuce (green leaf), lettuce (iceberg), lettuce (lolla rossa), lettuce (oak leaf—green), lettuce (oak leaf—red), lettuce (processed), lettuce (red leaf), lettuce (romaine), lettuce (ruby romaine), lettuce (russian red mustard), linkok, lo bok, long beans, lotus root, mache, maguey (agave) leaves, malanga, mesculin mix, mizuna, moap (smooth luffa), moo, moqua (fuzzy squash), mushrooms, mustard, nagaimo, okra, ong choy, onions green, opo (long squash), ornamental corn, ornamental gourds, parsley, parsnips, peas, peppers (bell type), peppers, pumpkins, radicchio, radish sprouts, radishes, rape greens, rape greens, rhubarb, romaine (baby red), rutabagas, salicornia (sea bean), sinqua (angled/ridged luffa), spinach, squash, straw bales, sugarcane, sweet potatoes, swiss chard, tamarindo, taro, taro leaf, taro shoots, tatsoi, tepeguaje (guaje), tindora, tomatillos, tomatoes, tomatoes (cherry), tomatoes (grape type), tomatoes (plum type), tumeric, turnip tops greens, turnips, water chestnuts, yampi, yams (names), yu choy, yuca (cassava), and the like.

A cell is in some cases an arthropod cell. For example, the cell can be a cell of a sub-order, a family, a sub-family, a group, a sub-group, or a species of, e.g., Chelicerata, Myriapodia, Hexipodia, Arachnida, Insecta, Archaeognatha, Thysanura, Palaeoptera, Ephemeroptera, Odonata, Anisoptera, Zygoptera, Neoptera, Exopterygota, Plecoptera, Embioptera, Orthoptera, Zoraptera, Dermaptera, Dictyoptera, Notoptera, Grylloblattidae, Mantophasmatidae, Phasmatodea, Blattaria, Isoptera, Mantodea, Parapneuroptera, Psocoptera, Thysanoptera, Phthiraptera, Hemiptera, Endopterygota or Holometabola, Hymenoptera, Coleoptera, Strepsiptera, Raphidioptera, Megaloptera, Neuroptera, Mecoptera, Siphonaptera, Diptera, Trichoptera, or Lepidoptera.

A cell is in some cases an insect cell. For example, in some cases, the cell is a cell of a mosquito, a grasshopper, a true bug, a fly, a flea, a bee, a wasp, an ant, a louse, a moth, or a beetle.

Kits

The present disclosure provides a kit comprising a CasX system of the present disclosure, or a component of a CasX system of the present disclosure.

A kit of the present disclosure can comprise: a) a CasX polypeptide of the present disclosure and a CasX guide RNA; b) a CasX polypeptide of the present disclosure, a CasX guide RNA, and a donor template nucleic acid; c) a CasX fusion polypeptide of the present disclosure and a CasX guide RNA; d) a CasX fusion polypeptide of the present disclosure, a CasX guide RNA, and a donor template nucleic acid; e) an mRNA encoding a CasX polypeptide of the present disclosure; and a CasX guide RNA; f) an mRNA encoding a CasX polypeptide of the present disclosure, a CasX guide RNA, and a donor template nucleic acid; g) an mRNA encoding a CasX fusion polypeptide of the present disclosure; and a CasX guide RNA; h) an mRNA encoding a CasX fusion polypeptide of the present disclosure, a CasX guide RNA, and a donor template nucleic acid; i) a recombinant expression vector comprising a nucleotide sequence encoding a CasX polypeptide of the present disclosure and a nucleotide sequence encoding a CasX guide RNA; j) a recombinant expression vector comprising a nucleotide sequence encoding a CasX polypeptide of the present disclosure, a nucleotide sequence encoding a CasX guide RNA, and a nucleotide sequence encoding a donor template nucleic acid; k) a recombinant expression vector comprising a nucleotide sequence encoding a CasX fusion polypeptide of the present disclosure and a nucleotide sequence encoding a CasX guide RNA; 1) a recombinant expression vector comprising a nucleotide sequence encoding a CasX fusion polypeptide of the present disclosure, a nucleotide sequence encoding a CasX guide RNA, and a nucleotide sequence encoding a donor template nucleic acid; m) a first recombinant expression vector comprising a nucleotide sequence encoding a CasX polypeptide of the present disclosure, and a second recombinant expression vector comprising a nucleotide sequence encoding a CasX guide RNA; n) a first recombinant expression vector comprising a nucleotide sequence encoding a CasX polypeptide of the present disclosure, and a second recombinant expression vector comprising a nucleotide sequence encoding a CasX guide RNA; and a donor template nucleic acid; o) a first recombinant expression vector comprising a nucleotide sequence encoding a CasX fusion polypeptide of the present disclosure, and a second recombinant expression vector comprising a nucleotide sequence encoding a CasX guide RNA; p) a first recombinant expression vector comprising a nucleotide sequence encoding a CasX fusion polypeptide of the present disclosure, and a second recombinant expression vector comprising a nucleotide sequence encoding a CasX guide RNA; and a donor template nucleic acid; q) a recombinant expression vector comprising a nucleotide sequence encoding a CasX polypeptide of the present disclosure, a nucleotide sequence encoding a first CasX guide RNA, and a nucleotide sequence encoding a second CasX guide RNA; or r) a recombinant expression vector comprising a nucleotide sequence encoding a CasX fusion polypeptide of the present disclosure, a nucleotide sequence encoding a first CasX guide RNA, and a nucleotide sequence encoding a second CasX guide RNA; or some variation of one of (a) through (r).

A kit of the present disclosure can comprise: a) a component, as described above, of a CasX system of the present disclosure, or can comprise a CasX system of the present disclosure; and b) one or more additional reagents, e.g., i) a buffer; ii) a protease inhibitor; iii) a nuclease inhibitor; iv) a reagent required to develop or visualize a detectable label; v) a positive and/or negative control target DNA; vi) a positive and/or negative control CasX guide RNA; and the like. A kit of the present disclosure can comprise: a) a component, as described above, of a CasX system of the present disclosure, or can comprise a CasX system of the present disclosure; and b) a therapeutic agent.

A kit of the present disclosure can comprise a recombinant expression vector comprising: a) an insertion site for inserting a nucleic acid comprising a nucleotide sequence encoding a portion of a CasX guide RNA that hybridizes to a target nucleotide sequence in a target nucleic acid; and b)

a nucleotide sequence encoding the CasX-binding portion of a CasX guide RNA. A kit of the present disclosure can comprise a recombinant expression vector comprising: a) an insertion site for inserting a nucleic acid comprising a nucleotide sequence encoding a portion of a CasX guide RNA that hybridizes to a target nucleotide sequence in a target nucleic acid; b) a nucleotide sequence encoding the CasX-binding portion of a CasX guide RNA; and c) a nucleotide sequence encoding a CasX polypeptide of the present disclosure.

Utility

A CasX polypeptide of the present disclosure, or a CasX fusion polypeptide of the present disclosure, finds use in a variety of methods (e.g., in combination with a CasX guide RNA and in some cases further in combination with a donor template). For example, a CasX polypeptide of the present disclosure can be used to (i) modify (e.g., cleave, e.g., nick; methylate; etc.) target nucleic acid (DNA or RNA; single stranded or double stranded); (ii) modulate transcription of a target nucleic acid; (iii) label a target nucleic acid; (iv) bind a target nucleic acid (e.g., for purposes of isolation, labeling, imaging, tracking, etc.); (v) modify a polypeptide (e.g., a histone) associated with a target nucleic acid; and the like. Thus, the present disclosure provides a method of modifying a target nucleic acid. In some cases, a method of the present disclosure for modifying a target nucleic acid comprises contacting the target nucleic acid with: a) a CasX polypeptide of the present disclosure; and b) one or more (e.g., two) CasX guide RNAs. In some cases, a method of the present disclosure for modifying a target nucleic acid comprises contacting the target nucleic acid with: a) a CasX polypeptide of the present disclosure; b) a CasX guide RNA; and c) a donor nucleic acid (e.g, a donor template). In some cases, the contacting step is carried out in a cell in vitro. In some cases, the contacting step is carried out in a cell in vivo. In some cases, the contacting step is carried out in a cell ex vivo.

Because a method that uses a CasX polypeptide includes binding of the CasX polypeptide to a particular region in a target nucleic acid (by virtue of being targeted there by an associated CasX guide RNA), the methods are generally referred to herein as methods of binding (e.g., a method of binding a target nucleic acid). However, it is to be understood that in some cases, while a method of binding may result in nothing more than binding of the target nucleic acid, in other cases, the method can have different final results (e.g., the method can result in modification of the target nucleic acid, e.g., cleavage/methylation/etc., modulation of transcription from the target nucleic acid; modulation of translation of the target nucleic acid; genome editing; modulation of a protein associated with the target nucleic acid; isolation of the target nucleic acid; etc.).

For examples of suitable methods, see, for example, Jinek et al., Science. 2012 Aug. 17; 337(6096):816-21; Chylinski et al., RNA Biol. 2013 May; 10(5):726-37; Ma et al., Biomed Res Int. 2013; 2013:270805; Hou et al., Proc Natl Acad Sci USA. 2013 Sep. 24; 110(39):15644-9; Jinek et al., Elife. 2013; 2:e00471; Pattanayak et al., Nat Biotechnol. 2013 September; 31(9):839-43; Qi et al, Cell. 2013 Feb. 28; 152(5):1173-83; Wang et al., Cell. 2013 May 9; 153(4):910-8; Auer et al., Genome Res. 2013 Oct. 31; Chen et al., Nucleic Acids Res. 2013 Nov. 1; 41(20):e19; Cheng et al., Cell Res. 2013 October; 23(10):1163-71; Cho et al., Genetics. 2013 November; 195(3):1177-80; DiCarlo et al., Nucleic Acids Res. 2013 April; 41(7):4336-43; Dickinson et al., Nat Methods. 2013 October; 10(10):1028-34; Ebina et al., Sci Rep. 2013; 3:2510; Fujii et al, Nucleic Acids Res. 2013 Nov. 1; 41(20):e187; Hu et al., Cell Res. 2013 November; 23(11):1322-5; Jiang et al., Nucleic Acids Res. 2013 Nov. 1; 41(20):e188; Larson et al., Nat Protoc. 2013 November; 8(11):2180-96; Mali et. at., Nat Methods. 2013 October; 10(10):957-63; Nakayama et al., Genesis. 2013 December; 51(12):835-43; Ran et al., Nat Protoc. 2013 November; 8(11):2281-308; Ran et al., Cell. 2013 Sep. 12; 154(6):1380-9; Upadhyay et al., G3 (Bethesda). 2013 Dec. 9; 3(12):2233-8; Walsh et al., Proc Natl Acad Sci USA. 2013 Sep. 24; 110(39):15514-5; Xie et al., Mol Plant. 2013 Oct. 9; Yang et al., Cell. 2013 Sep. 12; 154(6):1370-9; and U.S. patents and patent applications: U.S. Pat. Nos. 8,906,616; 8,895,308; 8,889,418; 8,889,356; 8,871,445; 8,865,406; 8,795,965; 8,771,945; 8,697,359; 20140068797; 20140170753; 20140179006; 20140179770; 20140186843; 20140186919; 20140186958; 20140189896; 20140227787; 20140234972; 20140242664; 20140242699; 20140242700; 20140242702; 20140248702; 20140256046; 20140273037; 20140273226; 20140273230; 20140273231; 20140273232; 20140273233; 20140273234; 20140273235; 20140287938; 20140295556; 20140295557; 20140298547; 20140304853; 20140309487; 20140310828; 20140310830; 20140315985; 20140335063; 20140335620; 20140342456; 20140342457; 20140342458; 20140349400; 20140349405; 20140356867; 20140356956; 20140356958; 20140356959; 20140357523; 20140357530; 20140364333; and 20140377868; each of which is hereby incorporated by reference in its entirety.

For example, the present disclosure provides (but is not limited to) methods of cleaving a target nucleic acid; methods of editing a target nucleic acid; methods of modulating transcription from a target nucleic acid; methods of isolating a target nucleic acid, methods of binding a target nucleic acid, methods of imaging a target nucleic acid, methods of modifying a target nucleic acid, and the like.

As used herein, the terms/phrases "contact a target nucleic acid" and "contacting a target nucleic acid", for example, with a CasX polypeptide or with a CasX fusion polypeptide, etc., encompass all methods for contacting the target nucleic acid. For example, a CasX polypeptide can be provided to a cell as protein, RNA (encoding the CasX polypeptide), or DNA (encoding the CasX polypeptide); while a CasX guide RNA can be provided as a guide RNA or as a nucleic acid encoding the guide RNA. As such, when, for example, performing a method in a cell (e.g., inside of a cell in vitro, inside of a cell in vivo, inside of a cell ex vivo), a method that includes contacting the target nucleic acid encompasses the introduction into the cell of any or all of the components in their active/final state (e.g., in the form of a protein(s) for CasX polypeptide; in the form of a protein for a CasX fusion polypeptide; in the form of an RNA in some cases for the guide RNA), and also encompasses the introduction into the cell of one or more nucleic acids encoding one or more of the components (e.g., nucleic acid(s) comprising nucleotide sequence(s) encoding a CasX polypeptide or a CasX fusion polypeptide, nucleic acid(s) comprising nucleotide sequence(s) encoding guide RNA(s), nucleic acid comprising a nucleotide sequence encoding a donor template, and the like). Because the methods can also be performed in vitro outside of a cell, a method that includes contacting a target nucleic acid, (unless otherwise specified) encompasses contacting outside of a cell in vitro, inside of a cell in vitro, inside of a cell in vivo, inside of a cell ex vivo, etc.

In some cases, a method of the present disclosure for modifying a target nucleic acid comprises contacting a target nucleic acid with a CasX polypeptide of the present disclosure, or with a CasX fusion polypeptide of the present disclosure. In some cases, abmethod of the present disclosure for modifying a target nucleic acid comprises contacting a target nucleic acid with a CasX polypeptide and a CasX guide RNA. In some cases, abmethod of the present disclosure for modifying a target nucleic acid comprises contacting a target nucleic acid with a CasX polypeptidel, a first CasX guide RNA, and a second CasX guide RNA In some cases, a method of the present disclosure for modifying a target nucleic acid comprises contacting a target nucleic acid with a CasX polypeptide of the present disclosure and a CasX guide RNA and a donor DNA template.

Target Nucleic Acids and Target Cells of Interest

A CasX polypeptide of the present disclosure, or a CasX fusion polypeptide of the present disclosure, when bound to a CasX guide RNA, can bind to a target nucleic acid, and in some cases, can bind to and modify a target nucleic acid. A target nucleic acid can be any nucleic acid (e.g., DNA, RNA), can be double stranded or single stranded, can be any type of nucleic acid (e.g., a chromosome (genomic DNA), derived from a chromosome, chromosomal DNA, plasmid, viral, extracellular, intracellular, mitochondrial, chloroplast, linear, circular, etc.) and can be from any organism (e.g., as long as the CasX guide RNA comprises a nucleotide sequence that hybridizes to a target sequence in a target nucleic acid, such that the target nucleic acid can be targeted).

A target nucleic acid can be DNA or RNA. A target nucleic acid can be double stranded (e.g., dsDNA, dsRNA) or single stranded (e.g., ssRNA, ssDNA). In some cases, a target nucleic acid is single stranded. In some cases, a target nucleic acid is a single stranded RNA (ssRNA). In some cases, a target ssRNA (e.g., a target cell ssRNA, a viral ssRNA, etc.) is selected from: mRNA, rRNA, tRNA, non-coding RNA (ncRNA), long non-coding RNA (lncRNA), and microRNA (miRNA). In some cases, a target nucleic acid is a single stranded DNA (ssDNA) (e.g., a viral DNA). As noted above, in some cases, a target nucleic acid is single stranded.

A target nucleic acid can be located anywhere, for example, outside of a cell in vitro, inside of a cell in vitro, inside of a cell in vivo, inside of a cell ex vivo. Suitable target cells (which can comprise target nucleic acids such as genomic DNA) include, but are not limited to: a bacterial cell; an archaeal cell; a cell of a single-cell eukaryotic organism; a plant cell; an algal cell, e.g., *Botryococcus braunii, Chlamydomonas reinhardtii, Nannochloropsis gaditana, Chlorella pyrenoidosa, Sargassum patens, C. agardh*, and the like; a fungal cell (e.g., a yeast cell); an animal cell; a cell from an invertebrate animal (e.g. fruit fly, a cnidarian, an echinoderm, a nematode, etc.); a cell of an insect (e.g., a mosquito; a bee; an agricultural pest; etc.); a cell of an arachnid (e.g., a spider; a tick; etc.); a cell from a vertebrate animal (e.g., a fish, an amphibian, a reptile, a bird, a mammal); a cell from a mammal (e.g., a cell from a rodent; a cell from a human; a cell of a non-human mammal; a cell of a rodent (e.g., a mouse, a rat); a cell of a lagomorph (e.g., a rabbit); a cell of an ungulate (e.g., a cow, a horse, a camel, a llama, a vicuña, a sheep, a goat, etc.); a cell of a marine mammal (e.g., a whale, a seal, an elephant seal, a dolphin, a sea lion; etc.) and the like. Any type of cell may be of interest (e.g. a stem cell, e.g. an embryonic stem (ES) cell, an induced pluripotent stem (iPS) cell, a germ cell (e.g., an oocyte, a sperm, an oogonia, a spermatogonia, etc.), an adult stem cell, a somatic cell, e.g. a fibroblast, a hematopoietic cell, a neuron, a muscle cell, a bone cell, a hepatocyte, a pancreatic cell; an in vitro or in vivo embryonic cell of an embryo at any stage, e.g., a 1-cell, 2-cell, 4-cell, 8-cell, etc. stage zebrafish embryo; etc.).

Cells may be from established cell lines or they may be primary cells, where "primary cells", "primary cell lines", and "primary cultures" are used interchangeably herein to refer to cells and cells cultures that have been derived from a subject and allowed to grow in vitro for a limited number of passages, i.e. splittings, of the culture. For example, primary cultures are cultures that may have been passaged 0 times, 1 time, 2 times, 4 times, 5 times, 10 times, or 15 times, but not enough times go through the crisis stage. Typically, the primary cell lines are maintained for fewer than 10 passages in vitro. Target cells can be unicellular organisms and/or can be grown in culture. If the cells are primary cells, they may be harvest from an individual by any convenient method. For example, leukocytes may be conveniently harvested by apheresis, leukocytapheresis, density gradient separation, etc., while cells from tissues such as skin, muscle, bone marrow, spleen, liver, pancreas, lung, intestine, stomach, etc. can be conveniently harvested by biopsy.

In some of the above applications, the subject methods may be employed to induce target nucleic acid cleavage, target nucleic acid modification, and/or to bind target nucleic acids (e.g., for visualization, for collecting and/or analyzing, etc.) in mitotic or post-mitotic cells in vivo and/or ex vivo and/or in vitro (e.g., to disrupt production of a protein encoded by a targeted mRNA, to cleave or otherwise modify target DNA, to generically modify a target cell, and the like). Because the guide RNA provides specificity by hybridizing to target nucleic acid, a mitotic and/or post-mitotic cell of interest in the disclosed methods may include a cell from any organism (e.g. a bacterial cell, an archaeal cell, a cell of a single-cell eukaryotic organism, a plant cell, an algal cell, e.g., *Botryococcus braunii, Chlamydomonas reinhardtii, Nannochloropsis gaditana, Chlorella pyrenoidosa, Sargassum patens, C. agardh*, and the like, a fungal cell (e.g., a yeast cell), an animal cell, a cell from an invertebrate animal (e.g. fruit fly, cnidarian, echinoderm, nematode, etc.), a cell from a vertebrate animal (e.g., fish, amphibian, reptile, bird, mammal), a cell from a mammal, a cell from a rodent, a cell from a human, etc.). In some cases, a subject CasX protein (and/or nucleic acid encoding the protein such as DNA and/or RNA), and/or CasX guide RNA (and/or a DNA encoding the guide RNA), and/or donor template, and/or RNP can be introduced into an individual (i.e., the target cell can be in vivo) (e.g., a mammal, a rat, a mouse, a pig, a primate, a non-human primate, a human, etc.). In some case, such an administration can be for the purpose of treating and/or preventing a disease, e.g., by editing the genome of targeted cells.

Plant cells include cells of a monocotyledon, and cells of a dicotyledon. The cells can be root cells, leaf cells, cells of the xylem, cells of the phloem, cells of the cambium, apical meristem cells, parenchyma cells, collenchyma cells, sclerenchyma cells, and the like. Plant cells include cells of agricultural crops such as wheat, corn, rice, sorghum, millet, soybean, etc. Plant cells include cells of agricultural fruit and nut plants, e.g., plant that produce apricots, oranges, lemons, apples, plums, pears, almonds, etc.

Additional examples of target cells are listed above in the section titled "Modified cells." Non-limiting examples of cells (target cells) include: a prokaryotic cell, eukaryotic cell, a bacterial cell, an archaeal cell, a cell of a single-cell eukaryotic organism, a protozoa cell, a cell from a plant (e.g., cells from plant crops, fruits, vegetables, grains, soy bean, corn, maize, wheat, seeds, tomatoes, rice, cassava, sugarcane, pumpkin, hay, potatos, cotton, *cannabis*, tobacco, flowering plants, conifers, gymnosperms, angiosperms, ferns, clubmosses, hornworts, liverworts, mosses, dicotyledons, monocotyledons, etc.), an algal cell, (e.g., *Botryococcus braunii, Chlamydomonas reinhardtii, Nannochloropsis gaditana, Chlorella pyrenoidosa, Sargassum patens, C. agardh*, and the like), seaweeds (e.g. kelp) a fungal cell (e.g., a yeast cell, a cell from a mushroom), an animal cell, a cell from an invertebrate animal (e.g., fruit fly, cnidarian, echinoderm, nematode, etc.), a cell from a vertebrate animal (e.g., fish, amphibian, reptile, bird, mammal), a cell from a mammal (e.g., an ungulate (e.g., a pig, a cow, a goat, a sheep); a rodent (e.g., a rat, a mouse); a non-human primate; a human; a feline (e.g., a cat); a canine (e.g., a dog); etc.), and the like. In some cases, the cell is a cell that does not originate from a natural organism (e.g., the cell can be a synthetically made cell; also referred to as an artificial cell).

A cell can be an in vitro cell (e.g., established cultured cell line). A cell can be an ex vivo cell (cultured cell from an individual). A cell can be and in vivo cell (e.g., a cell in an individual). A cell can be an isolated cell. A cell can be a cell inside of an organism. A cell can be an organism. A cell can be a cell in a cell culture (e.g., in vitro cell culture). A cell can be one of a collection of cells. A cell can be a prokaryotic cell or derived from a prokaryotic cell. A cell can be a bacterial cell or can be derived from a bacterial cell. A cell can be an archaeal cell or derived from an archaeal cell. A cell can be a eukaryotic cell or derived from a eukaryotic cell. A cell can be a plant cell or derived from a plant cell. A cell can be an animal cell or derived from an animal cell. A cell can be an invertebrate cell or derived from an invertebrate cell. A cell can be a vertebrate cell or derived from a vertebrate cell. A cell can be a mammalian cell or derived from a mammalian cell. A cell can be a rodent cell or derived from a rodent cell. A cell can be a human cell or derived from a human cell. A cell can be a microbe cell or derived from a microbe cell. A cell can be a fungi cell or derived from a fungi cell. A cell can be an insect cell. A cell can be an arthropod cell. A cell can be a protozoan cell. A cell can be a helminth cell.

Suitable cells include a stem cell (e.g. an embryonic stem (ES) cell, an induced pluripotent stem (iPS) cell; a germ cell (e.g., an oocyte, a sperm, an oogonia, a spermatogonia, etc.); a somatic cell, e.g. a fibroblast, an oligodendrocyte, a glial cell, a hematopoietic cell, a neuron, a muscle cell, a bone cell, a hepatocyte, a pancreatic cell, etc.

Suitable cells include human embryonic stem cells, fetal cardiomyocytes, myofibroblasts, mesenchymal stem cells, autotransplated expanded cardiomyocytes, adipocytes, totipotent cells, pluripotent cells, blood stem cells, myoblasts, adult stem cells, bone marrow cells, mesenchymal cells, embryonic stem cells, parenchymal cells, epithelial cells, endothelial cells, mesothelial cells, fibroblasts, osteoblasts, chondrocytes, exogenous cells, endogenous cells, stem cells, hematopoietic stem cells, bone-marrow derived progenitor cells, myocardial cells, skeletal cells, fetal cells, undifferentiated cells, multipotent progenitor cells, unipotent progenitor cells, monocytes, cardiac myoblasts, skeletal myoblasts, macrophages, capillary endothelial cells, xenogenic cells, allogenic cells, and post-natal stem cells.

In some cases, the cell is an immune cell, a neuron, an epithelial cell, and endothelial cell, or a stem cell. In some cases, the immune cell is a T cell, a B cell, a monocyte, a natural killer cell, a dendritic cell, or a macrophage. In some cases, the immune cell is a cytotoxic T cell. In some cases, the immune cell is a helper T cell. In some cases, the immune cell is a regulatory T cell (Treg).

In some cases, the cell is a stem cell. Stem cells include adult stem cells. Adult stem cells are also referred to as somatic stem cells.

Adult stem cells are resident in differentiated tissue, but retain the properties of self-renewal and ability to give rise to multiple cell types, usually cell types typical of the tissue in which the stem cells are found. Numerous examples of somatic stem cells are known to those of skill in the art, including muscle stem cells; hematopoietic stem cells; epithelial stem cells; neural stem cells; mesenchymal stem cells; mammary stem cells; intestinal stem cells; mesodermal stem cells; endothelial stem cells; olfactory stem cells; neural crest stem cells; and the like.

Stem cells of interest include mammalian stem cells, where the term "mammalian" refers to any animal classified as a mammal, including humans; non-human primates; domestic and farm animals; and zoo, laboratory, sports, or pet animals, such as dogs, horses, cats, cows, mice, rats, rabbits, etc. In some cases, the stem cell is a human stem cell. In some cases, the stem cell is a rodent (e.g., a mouse; a rat) stem cell. In some cases, the stem cell is a non-human primate stem cell.

Stem cells can express one or more stem cell markers, e.g., SOX9, KRT19, KRT7, LGR5, CA9, FXYD2, CDH6, CLDN18, TSPAN8, BPIFB1, OLFM4, CDH17, and PPARGC1A.

In some embodiments, the stem cell is a hematopoietic stem cell (HSC). HSCs are mesoderm-derived cells that can be isolated from bone marrow, blood, cord blood, fetal liver and yolk sac. HSCs are characterized as $CD34^+$ and $CD3^-$. HSCs can repopulate the erythroid, neutrophil-macrophage, megakaryocyte and lymphoid hematopoietic cell lineages in vivo. In vitro, HSCs can be induced to undergo at least some self-renewing cell divisions and can be induced to differentiate to the same lineages as is seen in vivo. As such, HSCs can be induced to differentiate into one or more of erythroid cells, megakaryocytes, neutrophils, macrophages, and lymphoid cells.

In other embodiments, the stem cell is a neural stem cell (NSC). Neural stem cells (NSCs) are capable of differentiating into neurons, and glia (including oligodendrocytes, and astrocytes). A neural stem cell is a multipotent stem cell which is capable of multiple divisions, and under specific conditions can produce daughter cells which are neural stem cells, or neural progenitor cells that can be neuroblasts or glioblasts, e.g., cells committed to become one or more types of neurons and glial cells respectively. Methods of obtaining NSCs are known in the art.

In other embodiments, the stem cell is a mesenchymal stem cell (MSC). MSCs originally derived from the embryonal mesoderm and isolated from adult bone marrow, can differentiate to form muscle, bone, cartilage, fat, marrow stroma, and tendon. Methods of isolating MSC are known in the art; and any known method can be used to obtain MSC. See, e.g., U.S. Pat. No. 5,736,396, which describes isolation of human MSC.

A cell is in some cases a plant cell. A plant cell can be a cell of a monocotyledon. A cell can be a cell of a dicotyledon.

In some cases, the cell is a plant cell. For example, the cell can be a cell of a major agricultural plant, e.g., Barley, Beans (Dry Edible), Canola, Corn, Cotton (Pima), Cotton (Upland), Flaxseed, Hay (Alfalfa), Hay (Non-Alfalfa), Oats, Peanuts, Rice, Sorghum, Soybeans, Sugarbeets, Sugarcane, Sunflowers (Oil), Sunflowers (Non-Oil), Sweet Potatoes, Tobacco (Burley), Tobacco (Flue-cured), Tomatoes, Wheat (Durum), Wheat (Spring), Wheat (Winter), and the like. As another example, the cell is a cell of a vegetable crops which include but are not limited to, e.g., alfalfa sprouts, aloe leaves, arrow root, arrowhead, artichokes, asparagus, bamboo shoots, banana flowers, bean sprouts, beans, beet tops, beets, bittermelon, bok choy, broccoli, broccoli rabe (rappini), brussels sprouts, cabbage, cabbage sprouts, cactus leaf (nopales), calabaza, cardoon, carrots, cauliflower, celery, chayote, chinese artichoke (crosnes), chinese cabbage, chinese celery, chinese chives, choy sum, *chrysanthemum* leaves (tung ho), collard greens, corn stalks, corn-sweet, cucumbers, daikon, dandelion greens, dasheen, dau mue (pea tips), donqua (winter melon), eggplant, endive, escarole, fiddle head ferns, field cress, frisee, gai choy (chinese mustard), gailon, galanga (siam, thai ginger), garlic, ginger root, gobo, greens, hanover salad greens, huauzontle, jerusalem artichokes, jicama, kale greens, kohlrabi, lamb's quarters (quilete), lettuce (bibb), lettuce (boston), lettuce (boston red), lettuce (green leaf), lettuce (iceberg), lettuce (lolla rossa), lettuce (oak leaf—green), lettuce (oak leaf—red), lettuce (processed), lettuce (red leaf), lettuce (romaine), lettuce (ruby romaine), lettuce (russian red mustard), linkok, lo bok, long beans, lotus root, mache, maguey (agave) leaves, malanga, mesculin mix, mizuna, moap (smooth luffa), moo, moqua (fuzzy squash), mushrooms, mustard, nagaimo, okra, ong choy, onions green, opo (long squash), ornamental corn, ornamental gourds, parsley, parsnips, peas, peppers (bell type), peppers, pumpkins, radicchio, radish sprouts, radishes, rape greens, rape greens, rhubarb, romaine (baby red), rutabagas, salicornia (sea bean), sinqua (angled/ridged luffa), spinach, squash, straw bales, sugarcane, sweet potatoes, swiss chard, tamarindo, taro, taro leaf, taro shoots, tatsoi, tepeguaje (guaje), tindora, tomatillos, tomatoes, tomatoes (cherry), tomatoes (grape type), tomatoes (plum type), tumeric, turnip tops greens, turnips, water chestnuts, yampi, yams (names), yu choy, yuca (cassava), and the like.

A cell is in some cases an arthropod cell. For example, the cell can be a cell of a sub-order, a family, a sub-family, a group, a sub-group, or a species of, e.g., Chelicerata, Myriapodia, Hexipodia, Arachnida, Insecta, Archaeognatha, Thysanura, Palaeoptera, Ephemeroptera, Odonata, Anisoptera, Zygoptera, Neoptera, Exopterygota, Plecoptera, Embioptera, Orthoptera, Zoraptera, Dermaptera, Dictyoptera, Notoptera, Grylloblattidae, Mantophasmatidae, Phasmatodea, Blattaria, Isoptera, Mantodea, Parapneuroptera, Psocoptera, Thysanoptera, Phthiraptera, Hemiptera, Endopterygota or Holometabola, Hymenoptera, Coleoptera, Strepsiptera, Raphidioptera, Megaloptera, Neuroptera, Mecoptera, Siphonaptera, Diptera, Trichoptera, or Lepidoptera.

A cell is in some cases an insect cell. For example, in some cases, the cell is a cell of a mosquito, a grasshopper, a true bug, a fly, a flea, a bee, a wasp, an ant, a louse, a moth, or a beetle.

Introducing Components into a Target Cell

A Cas9 guide RNA (or a nucleic acid comprising a nucleotide sequence encoding same), and/or a Cas9 fusion polypeptide (or a nucleic acid comprising a nucleotide sequence encoding same) and/or a donor polynucleotide can be introduced into a host cell by any of a variety of well-known methods.

Methods of introducing a nucleic acid into a cell are known in the art, and any convenient method can be used to introduce a nucleic acid (e.g., an expression construct) into a target cell (e.g., eukaryotic cell, human cell, stem cell, progenitor cell, and the like). Suitable methods are described in more detail elsewhere herein and include e.g., viral or bacteriophage infection, transfection, conjugation, protoplast fusion, lipofection, electroporation, calcium phosphate precipitation, polyethyleneimine (PEI)-mediated transfection, DEAE-dextran mediated transfection, liposome-mediated transfection, particle gun technology, calcium phosphate precipitation, direct micro injection, nanoparticle-mediated nucleic acid delivery (see, e.g., Panyam et., al Adv Drug Deliv Rev. 2012 Sep. 13. pii: 50169-409X(12)00283-9. doi: 10.1016/j.addr.2012.09.023), and the like. Any or all of the components can be introduced into a cell as a composition (e.g., including any convenient combination of: a a CasX polypeptide, a CasX guide RNA, a donor polynucleotide, etc.) using known methods, e.g., such as nucleofection.

Donor Polynucleotide (Donor Template)

Guided by a CasX dual or single guide RNA, a CasX protein in some cases generates site-specific double strand breaks (DSBs) or single strand breaks (SSBs) (e.g., when the CasX protein is a nickase variant) within double-stranded DNA (dsDNA) target nucleic acids, which are repaired either by non-homologous end joining (NHEJ) or homology-directed recombination (HDR).

In some cases, contacting a target DNA (with a CasX protein and a CasX guide RNA) occurs under conditions that are permissive for nonhomologous end joining or homology-directed repair. Thus, in some cases, a subject method includes contacting the target DNA with a donor polynucleotide (e.g., by introducing the donor polynucleotide into a cell), wherein the donor polynucleotide, a portion of the donor polynucleotide, a copy of the donor polynucleotide, or a portion of a copy of the donor polynucleotide integrates into the target DNA. In some cases, the method does not comprise contacting a cell with a donor polynucleotide, and the target DNA is modified such that nucleotides within the target DNA are deleted.

In some cases, CasX guide RNA (or DNA encoding same) and a CasX protein (or a nucleic acid encoding same, such as an RNA or a DNA, e.g, one or more expression vectors) are coadministered (e.g., contacted with a target nucleic acid, administered to cells, etc.) with a donor polynucleotide sequence that includes at least a segment with homology to the target DNA sequence, the subject methods may be used to add, i.e. insert or replace, nucleic acid material to a target DNA sequence (e.g. to "knock in" a nucleic acid, e.g., one that encodes for a protein, an siRNA, an miRNA, etc.), to add a tag (e.g., 6xHis, a fluorescent protein (e.g., a green fluorescent protein; a yellow fluorescent protein, etc.), hemagglutinin (HA), FLAG, etc.), to add a regulatory sequence to a gene (e.g. promoter, polyadenylation signal, internal ribosome entry sequence (IRES), 2A peptide, start codon, stop codon, splice signal, localization signal, etc.), to modify a nucleic acid sequence (e.g., introduce a mutation, remove a disease causing mutation by introducing a correct sequence), and the like. As such, a complex comprising a CasX guide RNA and CasX protein is useful in any in vitro or in vivo application in which it is desirable to modify DNA in a site-specific, i.e. "targeted", way, for example gene knock-out, gene knock-in, gene editing, gene tagging, etc., as used in, for example, gene therapy, e.g. to treat a disease or as an antiviral, antipathogenic, or anticancer therapeutic, the production of genetically modified organisms in agriculture, the large scale production of proteins by cells for therapeutic, diagnostic, or research purposes, the induction of iPS cells, biological research, the targeting of genes of pathogens for deletion or replacement, etc.

In applications in which it is desirable to insert a polynucleotide sequence into he genome where a target sequence is cleaved, a donor polynucleotide (a nucleic acid comprising a donor sequence) can also be provided to the cell. By a "donor sequence" or "donor polynucleotide" or "donor template" it is meant a nucleic acid sequence to be inserted at the site cleaved by the CasX protein (e.g., after dsDNA cleavage, after nicking a target DNA, after dual nicking a target DNA, and the like). The donor polynucleotide can contain sufficient homology to a genomic sequence at the target site, e.g. 70%, 80%, 85%, 90%, 95%, or 100% homology with the nucleotide sequences flanking the target site, e.g. within about 50 bases or less of the target site, e.g. within about 30 bases, within about 15 bases, within about 10 bases, within about 5 bases, or immediately flanking the target site, to support homology-directed repair between it and the genomic sequence to which it bears homology. Approximately 25, 50, 100, or 200 nucleotides, or more than 200 nucleotides, of sequence homology between a donor and a genomic sequence (or any integral value between 10 and 200 nucleotides, or more) can support homology-directed repair. Donor polynucleotides can be of any length, e.g. 10 nucleotides or more, 50 nucleotides or more, 100 nucleotides or more, 250 nucleotides or more, 500 nucleotides or more, 1000 nucleotides or more, 5000 nucleotides or more, etc.

The donor sequence is typically not identical to the genomic sequence that it replaces. Rather, the donor sequence may contain at least one or more single base changes, insertions, deletions, inversions or rearrangements with respect to the genomic sequence, so long as sufficient homology is present to support homology-directed repair (e.g., for gene correction, e.g., to convert a disease-causing base pair of a non disease-causing base pair). In some embodiments, the donor sequence comprises a non-homologous sequence flanked by two regions of homology, such that homology-directed repair between the target DNA region and the two flanking sequences results in insertion of the non-homologous sequence at the target region. Donor sequences may also comprise a vector backbone containing sequences that are not homologous to the DNA region of interest and that are not intended for insertion into the DNA region of interest. Generally, the homologous region(s) of a donor sequence will have at least 50% sequence identity to a genomic sequence with which recombination is desired. In certain embodiments, 60%, 70%, 80%, 90%, 95%, 98%, 99%, or 99.9% sequence identity is present. Any value between 1% and 100% sequence identity can be present, depending upon the length of the donor polynucleotide.

The donor sequence may comprise certain sequence differences as compared to the genomic sequence, e.g. restriction sites, nucleotide polymorphisms, selectable markers (e.g., drug resistance genes, fluorescent proteins, enzymes etc.), etc., which may be used to assess for successful insertion of the donor sequence at the cleavage site or in some cases may be used for other purposes (e.g., to signify expression at the targeted genomic locus). In some cases, if located in a coding region, such nucleotide sequence differences will not change the amino acid sequence, or will make silent amino acid changes (i.e., changes which do not affect the structure or function of the protein). Alternatively, these sequences differences may include flanking recombination sequences such as FLPs, loxP sequences, or the like, that can be activated at a later time for removal of the marker sequence.

In some cases, the donor sequence is provided to the cell as single-stranded DNA. In some cases, the donor sequence is provided to the cell as double-stranded DNA. It may be introduced into a cell in linear or circular form. If introduced in linear form, the ends of the donor sequence may be protected (e.g., from exonucleolytic degradation) by any convenient method and such methods are known to those of skill in the art. For example, one or more dideoxynucleotide residues can be added to the 3' terminus of a linear molecule and/or self-complementary oligonucleotides can be ligated to one or both ends. See, for example, Chang et al. (1987) Proc. Natl. Acad Sci USA 84:4959-4963; Nehls et al. (1996) Science 272:886-889. Additional methods for protecting exogenous polynucleotides from degradation include, but are not limited to, addition of terminal amino group(s) and the use of modified internucleotide linkages such as, for example, phosphorothioates, phosphoramidates, and O-methyl ribose or deoxyribose residues. As an alternative to protecting the termini of a linear donor sequence, additional lengths of sequence may be included outside of the regions of homology that can be degraded without impacting recombination. A donor sequence can be introduced into a cell as part of a vector molecule having additional sequences such as, for example, replication origins, promoters and genes encoding antibiotic resistance. Moreover, donor sequences can be introduced as naked nucleic acid, as nucleic acid complexed with an agent such as a liposome or poloxamer, or can be delivered by viruses (e.g., adenovirus, AAV), as described elsewhere herein for nucleic acids encoding a CasX guide RNA and/or a CasX fusion polypeptide and/or donor polynucleotide.

Transgenic, Non-Human Organisms

As described above, in some cases, a nucleic acid (e.g., a recombinant expression vector) of the present disclosure (e.g., a nucleic acid comprising a nucleotide sequence encoding a CasX polypeptide of the present disclosure; a nucleic acid comprising a nucleotide sequence encoding a CasX fusion polypeptide of the present disclosure; etc.), is used as a transgene to generate a transgenic non-human organism that produces a CasX polypeptide, or a CasX fusion polypeptide, of the present disclosure. The present disclosure provides a transgenic-non-human organism comprising a nucleotide sequence encoding a CasX polypeptide, or a CasX fusion polypeptide, of the present disclosure.

Transgenic, Non-Human Animals

The present disclosure provides a transgenic non-human animal, which animal comprises a transgene comprising a nucleic acid comprising a nucleotide sequence encoding a CasX polypeptide or a CasX fusion polypeptide. In some embodiments, the genome of the transgenic non-human animal comprises a nucleotide sequence encoding a CasX polypeptide,e or a CasX fusion polypeptide, of the present disclosure. In some cases, the transgenic non-human animal is homozygous for the genetic modification. In some cases, the transgenic non-human animal is heterozygous for the genetic modification. In some embodiments, the transgenic non-human animal is a vertebrate, for example, a fish (e.g., salmon, trout, zebra fish, gold fish, puffer fish, cave fish, etc.), an amphibian (frog, newt, salamander, etc.), a bird (e.g., chicken, turkey, etc.), a reptile (e.g., snake, lizard, etc.), a non-human mammal (e.g., an ungulate, e.g., a pig, a cow, a goat, a sheep, etc.; a lagomorph (e.g., a rabbit); a rodent (e.g., a rat, a mouse); a non-human primate; etc.), etc. In some cases, the transgenic non-human animal is an invertebrate. In some cases, the transgenic non-human animal is an insect (e.g., a mosquito; an agricultural pest; etc.). In some cases, the transgenic non-human animal is an arachnid.

Nucleotide sequences encoding a a CasX polypeptide,e or a CasX fusion polypeptide, of the present disclosure can be under the control of (i.e., operably linked to) an unknown promoter (e.g., when the nucleic acid randomly integrates into a host cell genome) or can be under the control of (i.e., operably linked to) a known promoter. Suitable known promoters can be any known promoter and include constitutively active promoters (e.g., CMV promoter), inducible promoters (e.g., heat shock promoter, tetracycline-regulated promoter, steroid-regulated promoter, metal-regulated promoter, estrogen receptor-regulated promoter, etc.), spatially restricted and/or temporally restricted promoters (e.g., a tissue specific promoter, a cell type specific promoter, etc.), etc.

Transgenic Plants

As described above, in some cases, a nucleic acid (e.g., a recombinant expression vector) of the present disclosure (e.g., a nucleic acid comprising a nucleotide sequence encoding a CasX polypeptide of the present disclosure; a nucleic acid comprising a nucleotide sequence encoding a CasX fusion polypeptide of the present disclosure; etc.), is used as a transgene to generate a transgenic plant that produces a CasX polypeptide, or a CasX fusion polypeptide, of the present disclosure. The present disclosure provides a transgenic plant comprising a nucleotide sequence encoding a CasX polypeptide, or a CasX fusion polypeptide, of the present disclosure. In some embodiments, the genome of the transgenic plant comprises a subject nucleic acid. In some embodiments, the transgenic plant is homozygous for the genetic modification. In some embodiments, the transgenic plant is heterozygous for the genetic modification.

Methods of introducing exogenous nucleic acids into plant cells are well known in the art. Such plant cells are considered "transformed," as defined above. Suitable methods include viral infection (such as double stranded DNA viruses), transfection, conjugation, protoplast fusion, electroporation, particle gun technology, calcium phosphate precipitation, direct microinjection, silicon carbide whiskers technology, Agrobacterium-mediated transformation and the like. The choice of method is generally dependent on the type of cell being transformed and the circumstances under which the transformation is taking place (i.e. in vitro, ex vivo, or in vivo).

Transformation methods based upon the soil bacterium Agrobacterium tumefaciens are particularly useful for introducing an exogenous nucleic acid molecule into a vascular plant. The wild type form of Agrobacterium contains a Ti (tumor-inducing) plasmid that directs production of tumorigenic crown gall growth on host plants. Transfer of the tumor-inducing T-DNA region of the Ti plasmid to a plant genome requires the Ti plasmid-encoded virulence genes as well as T-DNA borders, which are a set of direct DNA repeats that delineate the region to be transferred. An Agrobacterium-based vector is a modified form of a Ti plasmid, in which the tumor inducing functions are replaced by the nucleic acid sequence of interest to be introduced into the plant host.

Agrobacterium-mediated transformation generally employs cointegrate vectors or binary vector systems, in which the components of the Ti plasmid are divided between a helper vector, which resides permanently in the Agrobacterium host and carries the virulence genes, and a shuttle vector, which contains the gene of interest bounded by T-DNA sequences. A variety of binary vectors is well known in the art and are commercially available, for example, from Clontech (Palo Alto, Calif.). Methods of coculturing Agrobacterium with cultured plant cells or wounded tissue such as leaf tissue, root explants, hypocotyledons, stem pieces or tubers, for example, also are well known in the art. See, e.g., Glick and Thompson, (eds.), Methods in Plant Molecular Biology and Biotechnology, Boca Raton, Fla.: CRC Press (1993).

Microprojectile-mediated transformation also can be used to produce a subject transgenic plant. This method, first described by Klein et al. (Nature 327:70-73 (1987)), relies on microprojectiles such as gold or tungsten that are coated with the desired nucleic acid molecule by precipitation with calcium chloride, spermidine or polyethylene glycol. The microprojectile particles are accelerated at high speed into an angiosperm tissue using a device such as the BIOLISTIC PD-1000 (Biorad; Hercules Calif.).

A nucleic acid of the present disclosure (e.g., a nucleic acid (e.g., a recombinant expression vector) comprising a nucleotide sequence encoding a CasX polypeptide, or a CasX fusion polypeptide, of the present disclosure) may be introduced into a plant in a manner such that the nucleic acid is able to enter a plant cell(s), e.g., via an in vivo or ex vivo protocol. By "in vivo," it is meant in the nucleic acid is administered to a living body of a plant e.g. infiltration. By "ex vivo" it is meant that cells or explants are modified outside of the plant, and then such cells or organs are regenerated to a plant. A number of vectors suitable for stable transformation of plant cells or for the establishment of transgenic plants have been described, including those described in Weissbach and Weissbach, (1989) Methods for Plant Molecular Biology Academic Press, and Gelvin et al., (1990) Plant Molecular Biology Manual, Kluwer Academic Publishers. Specific examples include those derived from a Ti plasmid of Agrobacterium tumefaciens, as well as those disclosed by Herrera-Estrella et al. (1983) Nature 303: 209, Bevan (1984) Nucl Acid Res. 12: 8711-8721, Klee (1985) Bio/Technolo 3: 637-642. Alternatively, non-Ti vectors can be used to transfer the DNA into plants and cells by using free DNA delivery techniques. By using these methods transgenic plants such as wheat, rice (Christou (1991) Bio/Technology 9:957-9 and 4462) and corn (Gordon-Kamm (1990) Plant Cell 2: 603-618) can be produced. An immature embryo can also be a good target tissue for monocots for direct DNA delivery techniques by using the particle gun (Weeks et al. (1993) Plant Physiol 102: 1077-1084; Vasil (1993) Bio/Technolo 10: 667-674; Wan and Lemeaux (1994) Plant Physiol 104: 37-48 and for Agrobacterium-mediated DNA transfer (Ishida et al. (1996) Nature Biotech 14: 745-750). Exemplary methods for introduction of DNA into chloroplasts are biolistic bombardment, polyethylene glycol transformation of protoplasts, and microinjection (Danieli et al Nat. Biotechnol 16:345-348, 1998; Staub et al Nat. Biotechnol 18: 333-338, 2000; O'Neill et al Plant J. 3:729-738, 1993; Knoblauch et al Nat. Biotechnol 17: 906-909; U.S. Pat. Nos. 5,451,513, 5,545,817, 5,545,818, and 5,576, 198; in Intl. Application No. WO 95/16783; and in Boynton et al., Methods in Enzymology 217: 510-536 (1993), Svab et al., Proc. Natl. Acad. Sci. USA 90: 913-917 (1993), and McBride et al., Proc. Natl. Acad. Sci. USA 91: 7301-7305 (1994)). Any vector suitable for the methods of biolistic bombardment, polyethylene glycol transformation of protoplasts and microinjection will be suitable as a targeting vector for chloroplast transformation. Any double stranded DNA vector may be used as a transformation vector, especially when the method of introduction does not utilize Agrobacterium.

Plants which can be genetically modified include grains, forage crops, fruits, vegetables, oil seed crops, palms, forestry, and vines. Specific examples of plants which can be modified follow: maize, banana, peanut, field peas, sunflower, tomato, canola, tobacco, wheat, barley, oats, potato, soybeans, cotton, carnations, sorghum, lupin and rice.

The present disclosure provides transformed plant cells, tissues, plants and products that contain the transformed plant cells. A feature of the subject transformed cells, and tissues and products that include the same is the presence of a subject nucleic acid integrated into the genome, and production by plant cells of a CasX polypeptide, or a CasX fusion polypeptide, of the present disclosure. Recombinant plant cells of the present invention are useful as populations of recombinant cells, or as a tissue, seed, whole plant, stem, fruit, leaf, root, flower, stem, tuber, grain, animal feed, a field of plants, and the like.

Nucleotide sequences encoding a CasX polypeptide, or a CasX fusion polypeptide, of the present disclosure can be under the control of (i.e., operably linked to) an unknown promoter (e.g., when the nucleic acid randomly integrates into a host cell genome) or can be under the control of (i.e., operably linked to) a known promoter. Suitable known promoters can be any known promoter and include constitutively active promoters, inducible promoters, spatially restricted and/or temporally restricted promoters, etc.

Archaeal Cas9 Polypeptides and Guide RNAs

The inventors have discovered a type II CRISPR/Cas locus in archaeal cells for the first time. It was previously thought that archaeal cells include only type I and/or type III CRISPR/cas systems, but not type II systems, and Cas9 is the signature protein of type II CRISPR systems. In other words, prior to this disclosure the art has taught that organisms that belong to the archaea do not include Cas9 proteins. Provided are methods and compositions that include an archaeal Cas9 protein (or a nucleic acid encoding same) (e.g., an ARMAN-1 Cas9 protein, an ARMAN-4 Cas9 protein, variants thereof, and the like), and/or an archaeal Cas9 guide RNA (dual or single guide RNA format) (or DNA encoding same, e.g., one or more expression vectors), and/or a donor template.

The term ARMAN refers to "archaeal Richmond Mine acidophilic nanoorganisms", see, e.g., Baker et. al., Proc Natl Acad Sci USA. 2010 May 11; 107(19): 8806-8811; Baker et. al., Science. 2006 Dec. 22; 314(5807):1933-5. ARMAN-1 can also be referred to as "Candidatus Micrarchaeum acidiphilum ARMAN-1"; while ARMAN-4 can also be referred to as "Candidatus Parvarchaeum acidiphilum ARMAN-4." ARMAN-2 and ARMAN-5 have also been identified and can be referred to as "Candidatus Micrarchaeum acidiphilum ARMAN-2" while ARMAN-5 can be referred to as "Candidatus Parvarchaeum acidiphilum ARMAN-5." Thus, the term "Candidatus Micrarchaeum acidiphilum" is a generic term encompassing at least Candidatus Micrarchaeum acidiphilum ARMAN-1 and Candidatus Micrarchaeum acidiphilum ARMAN-2, while the term "Candidatus Parvarchaeum acidiphilum" is a generic term encompassing at least Candidatus Parvarchaeum acidiphilum ARMAN-4 and Candidatus Parvarchaeum acidiphilum ARMAN-5. Thus, provided are methods and compositions that include an archaeal Cas9 protein (or a nucleic acid encoding same) (e.g., a Candidatus Micrarchaeum acidiphilum Cas9 protein, a Candidatus Parvarchaeum acidiphilum Cas9 protein, an ARMAN-1 Cas9 protein, an ARMAN-4 Cas9 protein, variants thereof, and the like), and/or an archaeal Cas9 guide RNA (dual or single guide RNA format) (or DNA encoding same, e.g., one or more expression vectors), and/or a donor template.

Figure 14A:
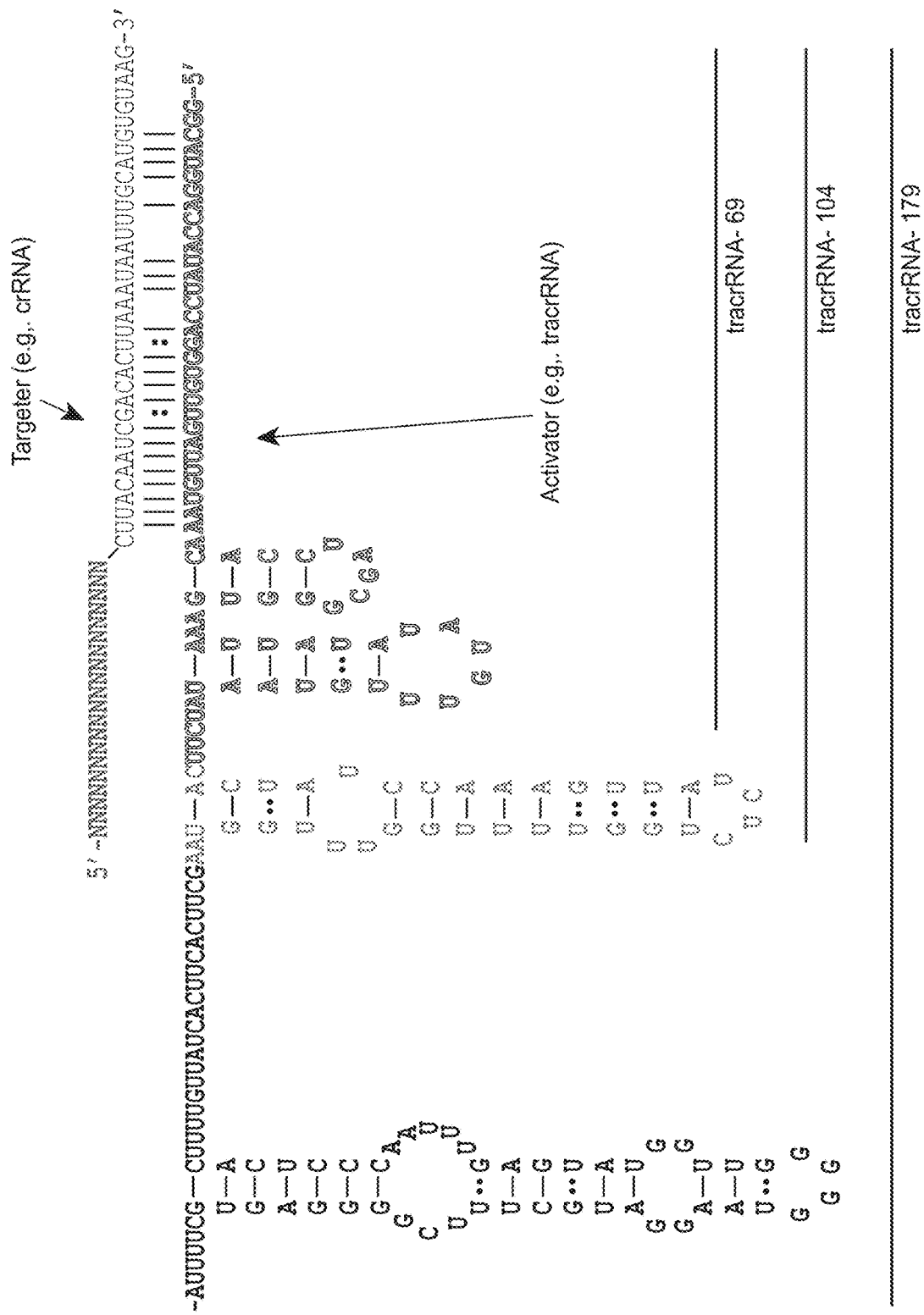
FIGS. 14A-14B present-example dual guide (top panel) (top RNA-SEQ ID NO: 73, bottom RNA-SEQ ID NO: 77) and single guide (bottom panel)(SEQ ID NO: 79) formats that can be used with an archaeal Cas9 protein (e.g., ARMAN-1 Cas9).
Figure 14B:
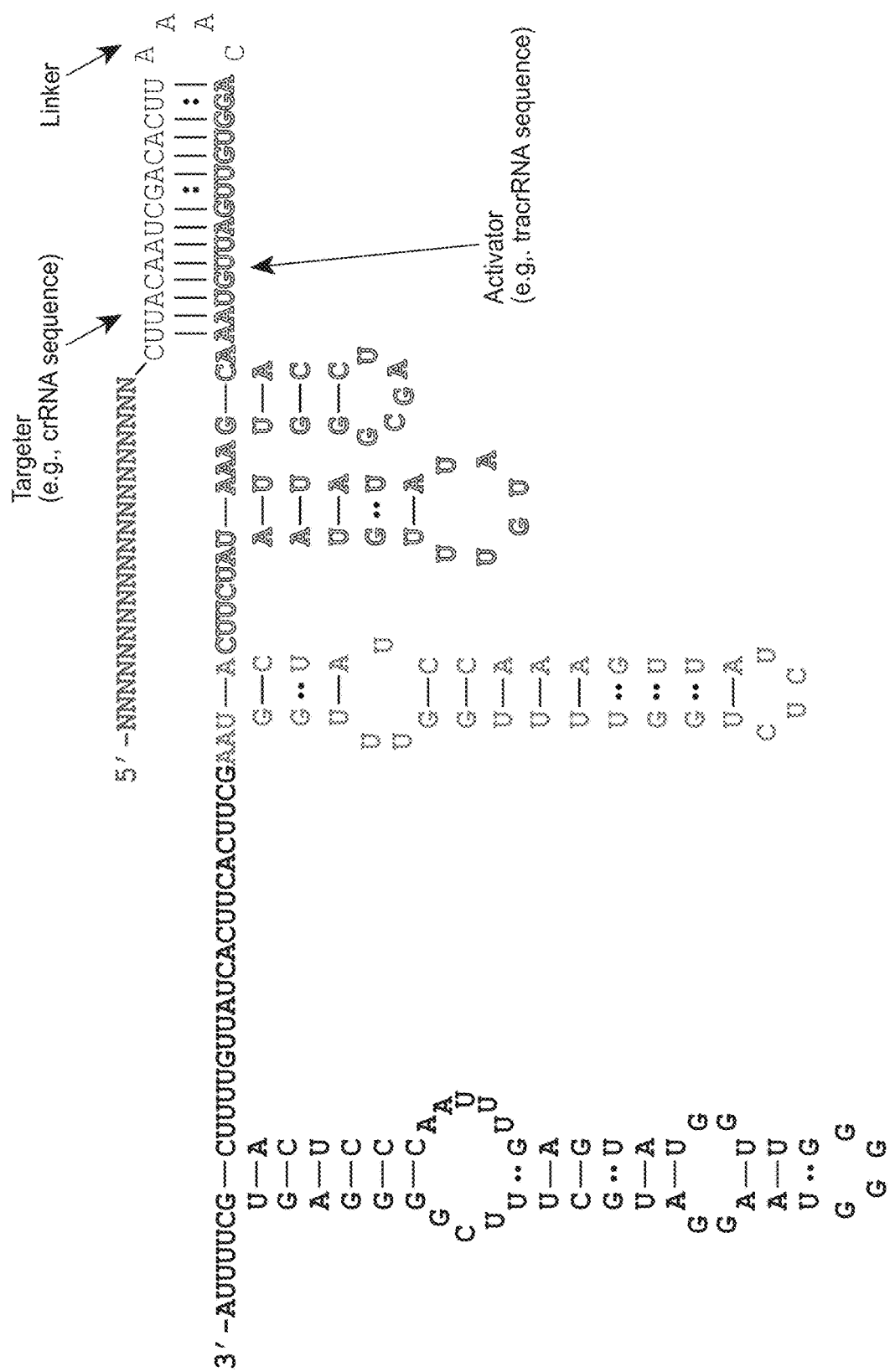
Figure 17A:
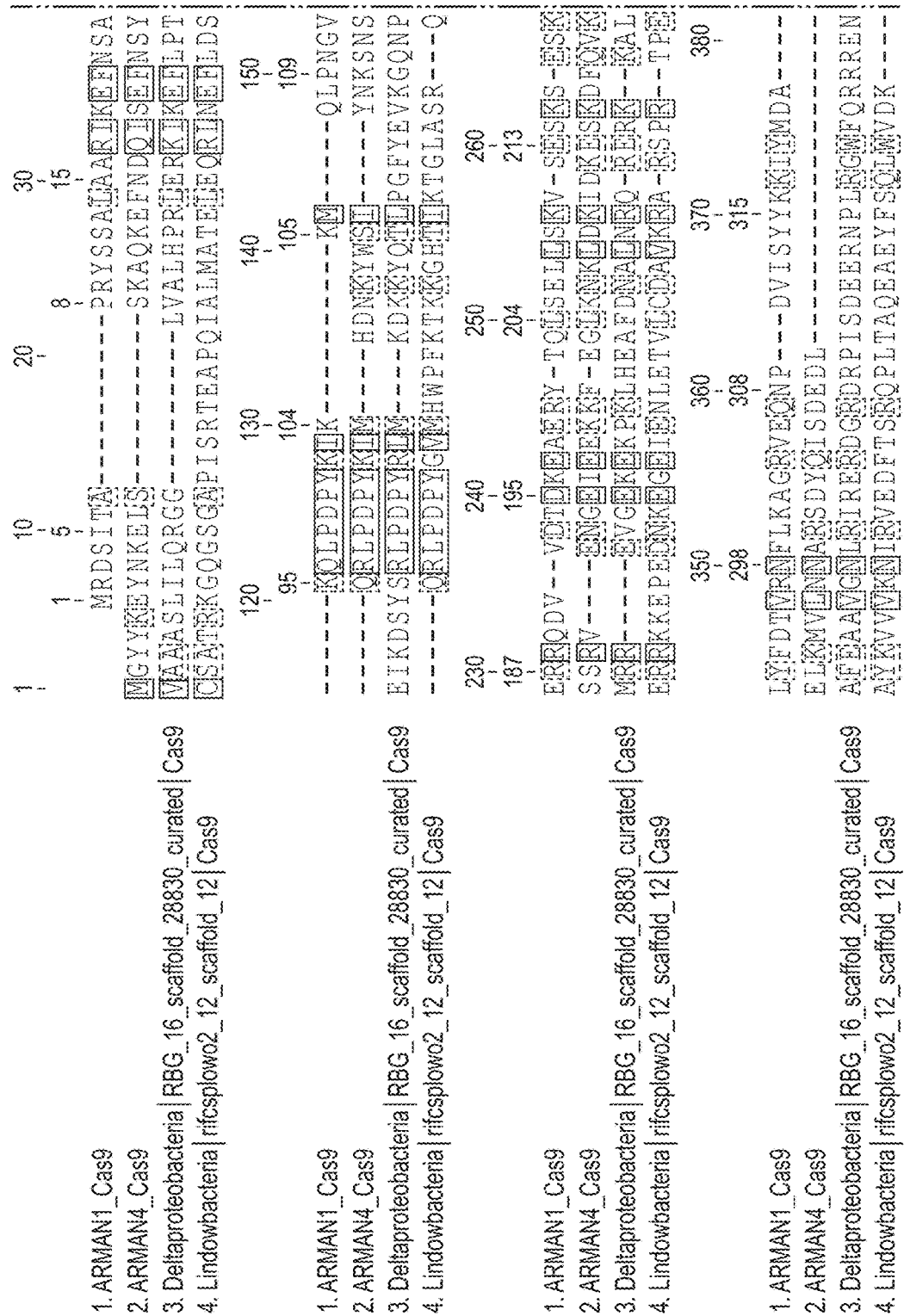
Figure 17C:
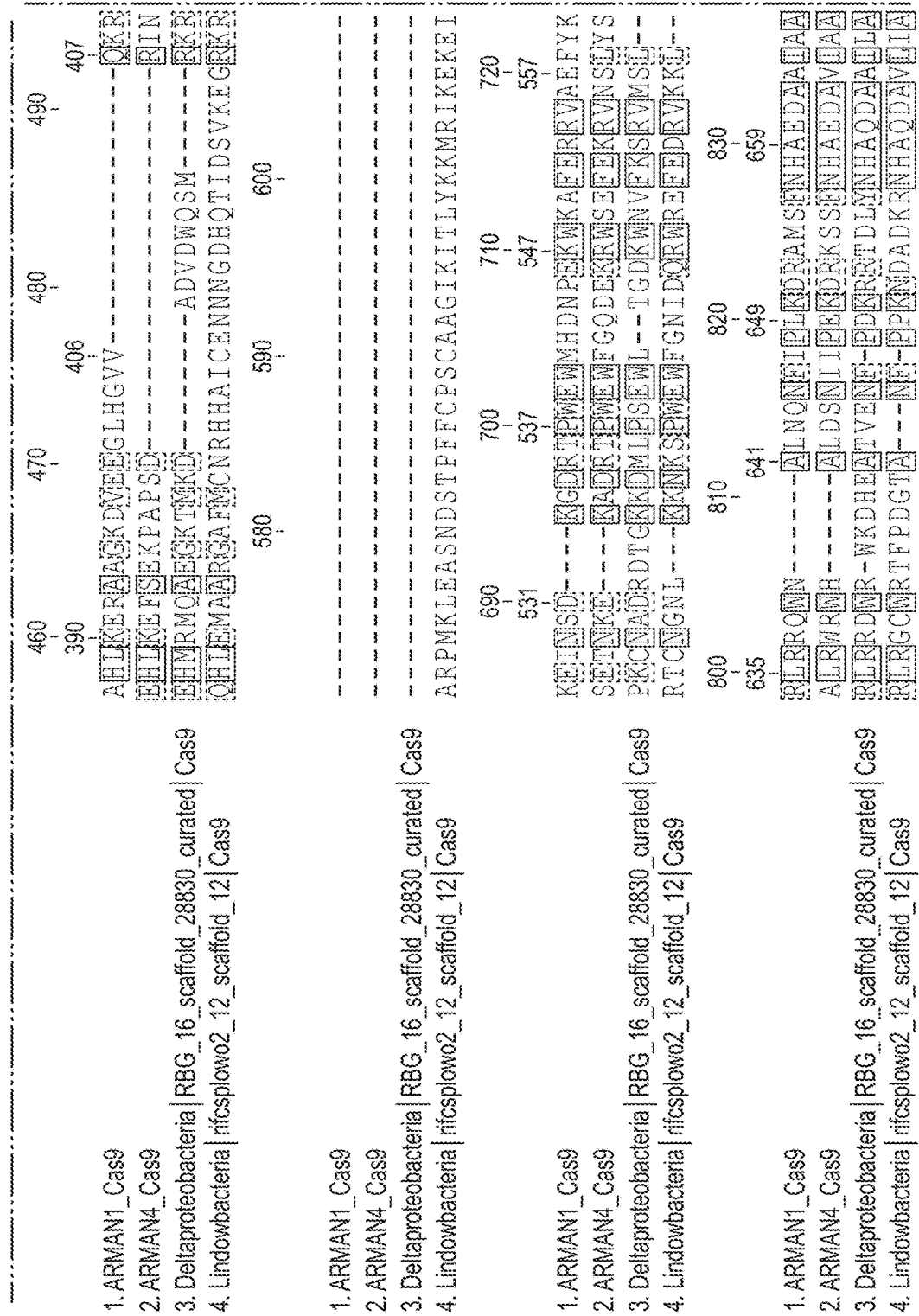
Figure 17E:
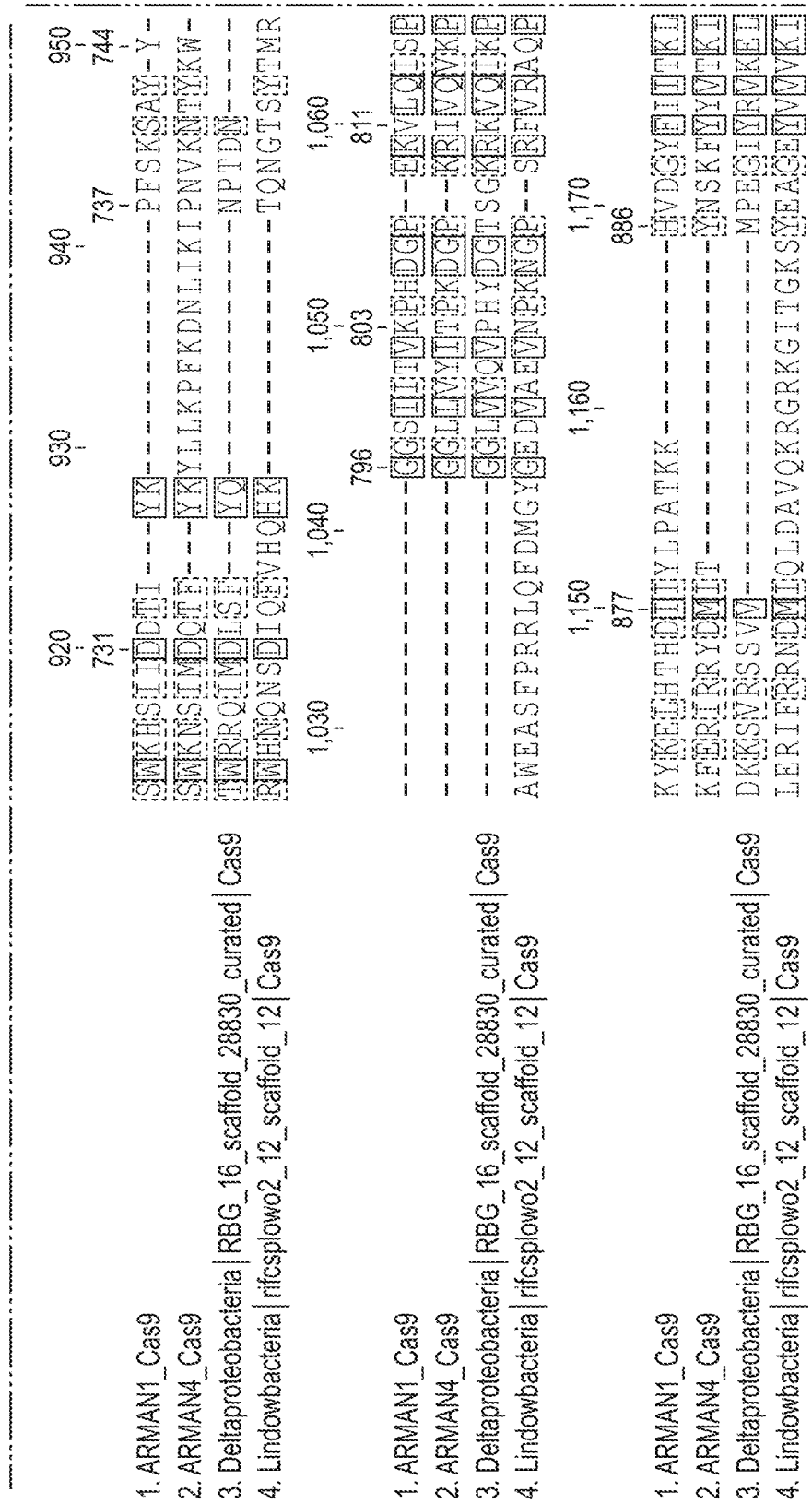

In any of the embodiments described herein (e.g., including all described compositions and methods, e.g., nucleic acids, methods of binding, methods of imaging, methods of modifying, genome editing, etc.), instead of a CasX protein, an archaeal Cas9 protein (e.g., an ARMAN-1 Cas9 protein, an ARMAN-4 Cas9 protein, and the like) can be used. In other words, an archaeal Cas9 protein (e.g., an ARMAN-1 Cas9 protein, an ARMAN-4 Cas9 protein, and the like) can substitute for a CasX protein. In such cases, where appropriate, the corresponding guide RNA (an archael Cas9 guide RNA, e.g., in either dual or single guide format) should be used instead of a CasX guide RNA. Examples of archaeal Cas9 proteins and archael Cas9 guide RNAs are illustrated in FIG. 13 (ARMAN-1 and ARMAN-4 Cas9 proteins), FIGS. 14A-14B (ARMAN-1 Cas9 guide RNAs), and FIG. 15 (ARMAN-4 Cas9 guide RNAs). Note that the orientation of the guide sequence of an archaeal Cas9 guide RNA relative to the rest of the guide RNA (e.g., relative to the duplex-forming segment of the targeter) is the opposite of a CasX guide RNA (e.g., compare the Ns of FIG. 6 and FIG. 7 where the guide sequence is at the 3' end for a CasX guide RNA to the Ns of FIGS. 14 A-14B and FIG. 15 where the guide sequence is at the 5' end for an archaeal Cas9 guide RNA); while the location of a PAM on a target dsDNA is also opposite for archael Cas9 proteins compared to CasX proteins (see below for more details).

Archaeal Cas9 Protein

Non-archaeal Cas9 proteins (i.e., Cas9 proteins from bacteria, but not from archaea) are known in the art, and a subject archaeal Cas9 protein has similar domain structure. However, the overall sequence of archaeal Cas9 proteins are highly divergent and share very little overall sequence homology.

A naturally occurring archaeal Cas9 protein functions as an endonuclease that catalyzes a double strand break at a specific sequence in a targeted double stranded DNA (dsDNA). The sequence specificity is provided by the associated guide RNA, which hybridizes to a target sequence within the target DNA. The naturally occurring guide RNA includes a tracrRNA hybridized to a crRNA, where the crRNA includes a guide sequence that hybridizes to a target sequence in the target DNA.

In some embodiments, the archaeal Cas9 protein of the subject methods and/or compositions is (or is derived from) a naturally occurring (wild type) protein. Examples of naturally occurring archaeal Cas9 proteins are depicted in FIG. 13 and are set forth as SEQ ID NOs: 71 and 72. It is important to note that the newly discovered archaeal Cas9 proteins (e.g., see FIG. 13) are short compared to previously identified CRISPR-Cas endonucleases (e.g., they are among the smallest known Cas9 proteins), and thus use of archaeal Cas9 proteins as an alternative provides the advantage that the nucleotide sequence encoding the protein is relatively short. This is useful, for example, in cases where a nucleic acid encoding the CasX protein is desirable, e.g., in situations that employ a viral vector (e.g., an AAV vector), for delivery to a cell such as a eukaryotic cell (e.g., mammalian cell, human cell, mouse cell, in vitro, ex vivo, in vivo) for research and/or clinical applications.

Figure 12A:
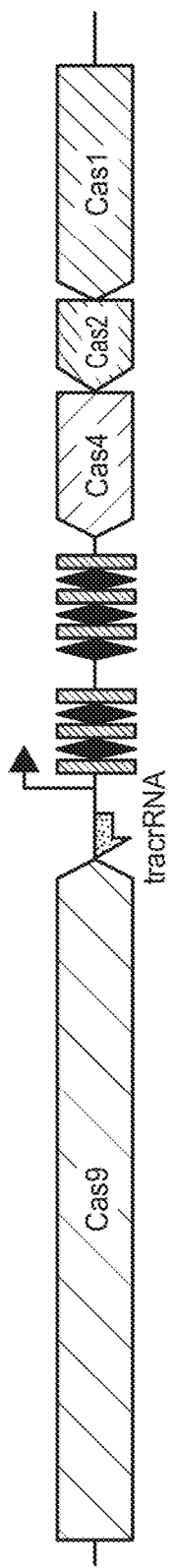
FIGS. 12A-12E present a information related to an archaeal Cas9 CRISPR system (the ARMAN-1 type II CRISPR-cas system).
Figure 12B:
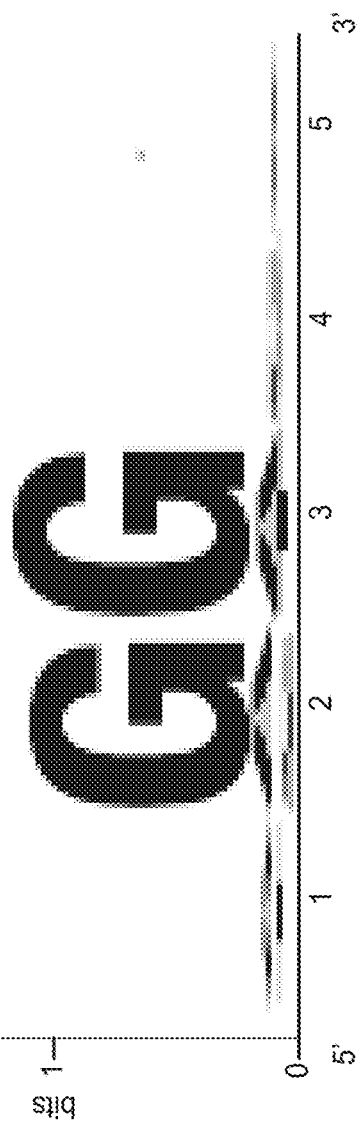
Figure 12C:
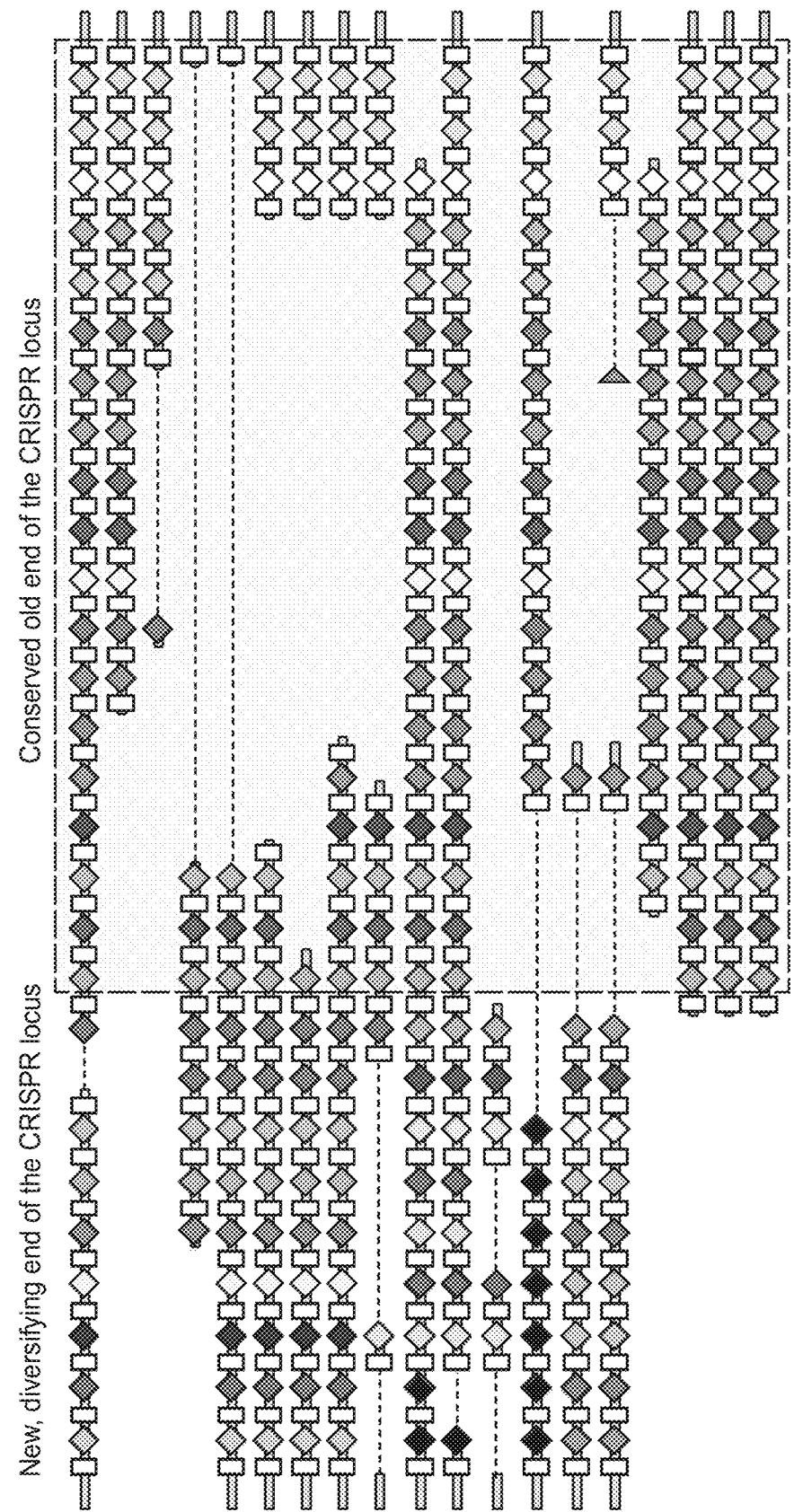
Figure 12D:
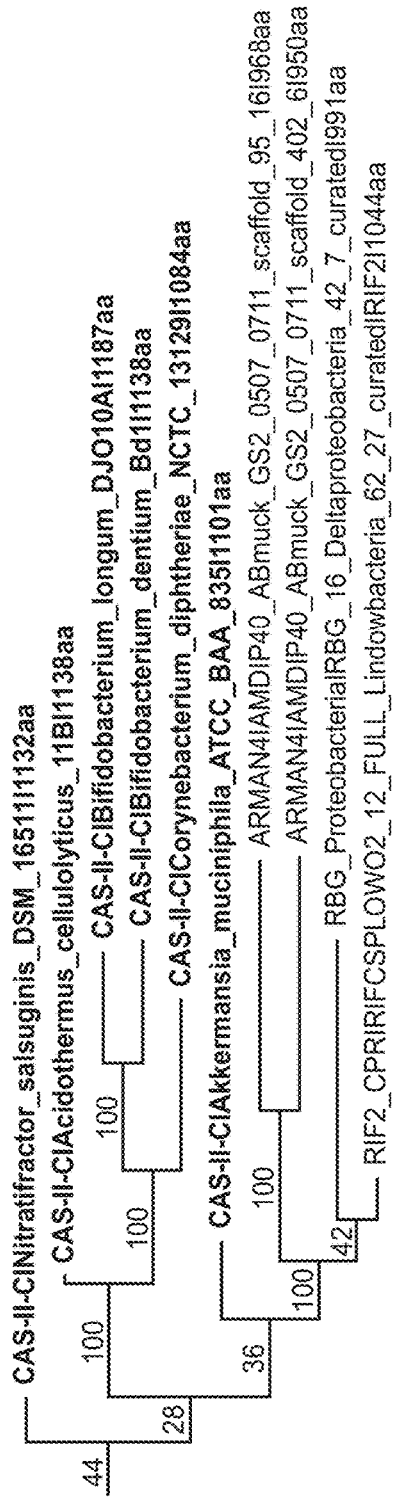

Two additional Cas9 proteins (see FIG. 16) were identified by the inventors that are non-archaeal Cas9 proteins, but cluster with archaeal Cas9s on phylogeny trees, and thus are related in sequence to archaeal Cas9s (e.g, Deltaproteobacteria Cas9 of FIG. 16 appears in the tree of FIG. 12D, as RBG_ProteobacterialRBG_16_Deltaproteobacteria_42_7_ curated|991aa; while Lindowbacteria Cas9 of FIG. 16 appears in the tree of FIG. 12D as RIF2_CPR|RIFCSPLOWO2_12_FULL_Lindowbacteria_62_27_curated|RIF2|1044aa). An alignment of the sequences of FIG. 16 to ARMAN-1 Cas9 and ARMAN-4 Cas9 is provided in FIGS. 17A-17F.

In some cases, a subject Cas9 protein (e.g., archaeal Cas9 protein) includes an amino acid sequence having 50% or more sequence identity (e.g., 60% or more, 70% or more, 80% or more, 90% or more, 95% or more, 98% or more, 99% or more, or 100% sequence identity) with the amino acid sequence set forth as SEQ ID NO: 71 (ARMAN-1). In some cases, a subject Cas9 protein (e.g., archaeal Cas9 protein) includes an amino acid sequence having 70% or more sequence identity (e.g., 80% or more, 90% or more, 95% or more, 98% or more, 99% or more, or 100% sequence identity) with the amino acid sequence set forth as SEQ ID NO: 71 (ARMAN-1). In some cases, a subject Cas9 protein (e.g., archaeal Cas9 protein) includes an amino acid sequence having 80% or more sequence identity (e.g., 90% or more, 95% or more, 98% or more, 99% or more, or 100% sequence identity) with the amino acid sequence set forth as SEQ ID NO: 71 (ARMAN-1). In some cases, a subject Cas9 protein (e.g., archaeal Cas9 protein) includes an amino acid sequence having 95% or more sequence identity (e.g., 98% or more, 99% or more, or 100% sequence identity) with the amino acid sequence set forth as SEQ ID NO: 71 (ARMAN-1). In some cases, a subject Cas9 protein (e.g., archaeal Cas9 protein) includes the amino acid sequence set forth as SEQ ID NO: 71. In some cases, a subject Cas9 protein (e.g., archaeal Cas9 protein) is a Candidatus Micrarchaeum acidiphilum Cas9 protein. In some cases, a subject Cas9 protein (e.g., archaeal Cas9 protein) is an ARMAN-1 Cas9 protein.

In some cases, a subject Cas9 protein (e.g., archaeal Cas9 protein) includes an amino acid sequence having 50% or more sequence identity (e.g., 60% or more, 70% or more, 80% or more, 90% or more, 95% or more, 98% or more, 99% or more, or 100% sequence identity) with the amino acid sequence set forth as SEQ ID NO: 72 (ARMAN-4). In some cases, a subject Cas9 protein (e.g., archaeal Cas9 protein) includes an amino acid sequence having 70% or more sequence identity (e.g., 80% or more, 90% or more, 95% or more, 98% or more, 99% or more, or 100% sequence identity) with the amino acid sequence set forth as SEQ ID NO: 72 (ARMAN-4). In some cases, a subject Cas9 protein (e.g., archaeal Cas9 protein) includes an amino acid sequence having 80% or more sequence identity (e.g., 90% or more, 95% or more, 98% or more, 99% or more, or 100% sequence identity) with the amino acid sequence set forth as SEQ ID NO: 72 (ARMAN-4). In some cases, a subject Cas9 protein (e.g., archaeal Cas9 protein) includes an amino acid sequence having 95% or more sequence identity (e.g., 98% or more, 99% or more, or 100% sequence identity) with the amino acid sequence set forth as SEQ ID NO: 72 (ARMAN-4). In some cases, a subject Cas9 protein (e.g., archaeal Cas9 protein) includes the amino acid sequence set forth as SEQ ID NO: 72. In some cases, a subject Cas9 protein (e.g., archaeal Cas9 protein) is a Candidatus Parvarchaeum acidiphilum Cas9 protein. In some cases, a subject Cas9 protein (e.g., archaeal Cas9 protein) is an ARMAN-4 Cas9 protein.

In some cases, a subject Cas9 protein (e.g., archaeal Cas9 protein) includes an amino acid sequence having 50% or more sequence identity (e.g., 60% or more, 70% or more, 80% or more, 90% or more, 95% or more, 98% or more, 99% or more, or 100% sequence identity) with the amino acid sequence set forth in any one of SEQ ID NOs: 71 and 72 (ARMAN-1 AND ARMAN-4, respectively). In some cases, a subject Cas9 protein (e.g., archaeal Cas9 protein) includes an amino acid sequence having 70% or more sequence identity (e.g., 80% or more, 90% or more, 95% or more, 98% or more, 99% or more, or 100% sequence identity) with the amino acid sequence set forth in any one of SEQ ID NOs: 71 and 72 (ARMAN-1 AND ARMAN-4, respectively). In some cases, a subject Cas9 protein (e.g., archaeal Cas9 protein) includes an amino acid sequence having 80% or more sequence identity (e.g., 90% or more, 95% or more, 98% or more, 99% or more, or 100% sequence identity) with the amino acid sequence set forth in any one of SEQ ID NOs: 71 and 72 (ARMAN-1 AND ARMAN-4, respectively). In some cases, a subject Cas9 protein (e.g.,
archaeal Cas9 protein) includes an amino acid sequence having 95% or more sequence identity (e.g., 98% or more, 99% or more, or 100% sequence identity) with the amino acid sequence set forth in any one of SEQ ID NOs: 71 and 72 (ARMAN-1 AND ARMAN-4, respectively). In some cases, a subject Cas9 protein (e.g., archaeal Cas9 protein) includes the amino acid sequence set forth in any one of SEQ ID NOs: 71 and 72. In some cases, a subject Cas9 protein (e.g., archaeal Cas9 protein) is a Candidatus Micrarchaeum acidiphilum Cas9 protein (e.g., an ARMAN-1 Cas9 protein) or a Candidatus Parvarchaeum acidiphilum Cas9 protein (e.g., an ARMAN-4 Cas9 protein).

In some cases, a subject Cas9 protein includes an amino acid sequence having 50% or more sequence identity (e.g., 60% or more, 70% or more, 80% or more, 90% or more, 95% or more, 98% or more, 99% or more, or 100% sequence identity) with the amino acid sequence set forth as SEQ ID NO: 135. In some cases, a subject Cas9 protein includes an amino acid sequence having 70% or more sequence identity (e.g., 80% or more, 90% or more, 95% or more, 98% or more, 99% or more, or 100% sequence identity) with the amino acid sequence set forth as SEQ ID NO: 135. In some cases, a subject Cas9 protein includes an amino acid sequence having 80% or more sequence identity (e.g., 90% or more, 95% or more, 98% or more, 99% or more, or 100% sequence identity) with the amino acid sequence set forth as SEQ ID NO: 135. In some cases, a subject Cas9 protein includes an amino acid sequence having 95% or more sequence identity (e.g., 98% or more, 99% or more, or 100% sequence identity) with the amino acid sequence set forth as SEQ ID NO: 135. In some cases, a subject Cas9 protein includes the amino acid sequence set forth as SEQ ID NO: 135.

In some cases, a subject Cas9 protein includes an amino acid sequence having 50% or more sequence identity (e.g., 60% or more, 70% or more, 80% or more, 90% or more, 95% or more, 98% or more, 99% or more, or 100% sequence identity) with the amino acid sequence set forth as SEQ ID NO: 136. In some cases, a subject Cas9 protein includes an amino acid sequence having 70% or more sequence identity (e.g., 80% or more, 90% or more, 95% or more, 98% or more, 99% or more, or 100% sequence identity) with the amino acid sequence set forth as SEQ ID NO: 136. In some cases, a subject Cas9 protein includes an amino acid sequence having 80% or more sequence identity (e.g., 90% or more, 95% or more, 98% or more, 99% or more, or 100% sequence identity) with the amino acid sequence set forth as SEQ ID NO: 136. In some cases, a subject Cas9 protein includes an amino acid sequence having 95% or more sequence identity (e.g., 98% or more, 99% or more, or 100% sequence identity) with the amino acid sequence set forth as SEQ ID NO: 136. In some cases, a subject Cas9 protein includes the amino acid sequence set forth as SEQ ID NO: 136.

In some cases, a subject Cas9 protein includes an amino acid sequence having 50% or more sequence identity (e.g., 60% or more, 70% or more, 80% or more, 90% or more, 95% or more, 98% or more, 99% or more, or 100% sequence identity) with the amino acid sequence set forth in any one of SEQ ID NOs: 135 and 136. In some cases, a subject Cas9 protein includes an amino acid sequence having 70% or more sequence identity (e.g., 80% or more, 90% or more, 95% or more, 98% or more, 99% or more, or 100% sequence identity) with the amino acid sequence set forth in any one of SEQ ID NOs: 135 and 136. In some cases, a subject Cas9 protein includes an amino acid sequence having 80% or more sequence identity (e.g., 90% or more, 95% or more, 98% or more, 99% or more, or 100% sequence identity) with the amino acid sequence set forth in any one of SEQ ID NOs: 135 and 136. In some cases, a subject Cas9 protein includes an amino acid sequence having 95% or more sequence identity (e.g., 98% or more, 99% or more, or 100% sequence identity) with the amino acid sequence in any one of SEQ ID NOs: 135 and 136. In some cases, a subject Cas9 protein includes the amino acid sequence set forth in any one of SEQ ID NOs: 135 and 136.

In some cases, a subject Cas9 protein includes an amino acid sequence having 50% or more sequence identity (e.g., 60% or more, 70% or more, 80% or more, 90% or more, 95% or more, 98% or more, 99% or more, or 100% sequence identity) with the amino acid sequence set forth in any one of SEQ ID NOs: 71, 72, 135, and 136. In some cases, a subject Cas9 protein includes an amino acid sequence having 70% or more sequence identity (e.g., 80% or more, 90% or more, 95% or more, 98% or more, 99% or more, or 100% sequence identity) with the amino acid sequence set forth in any one of SEQ ID NOs: 71, 72, 135, and 136. In some cases, a subject Cas9 protein includes an amino acid sequence having 80% or more sequence identity (e.g., 90% or more, 95% or more, 98% or more, 99% or more, or 100% sequence identity) with the amino acid sequence set forth in any one of SEQ ID NOs: 71, 72, 135, and 136. In some cases, a subject Cas9 protein includes an amino acid sequence having 95% or more sequence identity (e.g., 98% or more, 99% or more, or 100% sequence identity) with the amino acid sequence in any one of SEQ ID NOs: 71, 72, 135, and 136. In some cases, a subject Cas9 protein includes the amino acid sequence set forth in any one of SEQ ID NOs: 71, 72, 135, and 136.

Variants (Including Nickases, dCas9, and Chimeric Cas9 Proteins)

Please refer to the section on variants of of CasX proteins for nomenclature and uses, etc., for variants that can be used (e.g., swap in archaeal Cas9 proteins for CasX proteins, swap in either of the two newly identified non-archaeal Cas9 proteins for CasX proteins, etc.). Any of the above parameters for a subject Cas9 protein (e.g., archaeal Cas9 protein) can be swapped in, e.g., including the % identity parameters above, ARMAN-1 Cas9 protein, ARMAN-4 Cas9 protein, Candidatus Micrarchaeum acidiphilum Cas9 protein, Candidatus Parvarchaeum acidiphilum Cas9 protein, and the like).

Catalytic residues of Cas9 proteins (e.g., archaeal Cas9 proteins) are readily identifiable despite the extremely low overall sequence identity with non-carchaeal Cas9 proteins. For example, D30 (RuvC domain) and H506 (HNH domain) of the archaeal Cas9 set forth as SEQ ID NO: 71 (ARMAN-1) correspond to D10 and H840 of S. pyogenes Cas9, respectively; while D58 (RuvC domain) and H514 (HNH domain) of the archaeal Cas9 set forth as SEQ ID NO: 72 (ARMAN-4) correspond to D10 and H840 of S. pyogenes Cas9, respectively. These residues are bold and underlined in FIG. 13.

A Cas9 nickase (e.g., archaeal Cas9 nickase) can be generated by removing the catalytic activity (e.g., by mutating a catalytic residue) of either the RuvC domain (e.g., by mutating D30 of ARMAN-1 Cas9; D58 of ARMAN-4 Cas9 protein) or the HNH domain (e.g., by mutating H506 of ARMAN-1 Cas9; H514 of ARMAN-4 Cas9 protein) (e.g., each domain cleaves one strand of a target double stranded DNA). A dead version of a Cas9 protein (e.g., archaeal Cas9 protein) (e.g., dCas9, archaeal dCas9) can be generated by removing the catalytic activity (e.g., by mutating catalytic residues) of both the RuvC domain and the HNH domain.

All of the same fusion proteins can be used, except that archaeal Cas9 (or one of the newly identified non-archaeal Cas9s) can be swapped in for CasX. Non-limiting examples include: archaeal Cas9 or dCas9 or nickase Cas9 with an NLS(s), archaeal Cas9 or dCas9 or nickase Cas9 with a fusion partner that has catalytic activity and/or transcription repression or activation activity (e.g., to modify a target DNA, to modify a protein such as a histone associated with a target DNA, to modulate transcription from a target DNA, and the like), archaeal Cas9 or dCas9 or nickase Cas9 with a detectable label, and the like. The list of fusion partners that can be used for an archaeal Cas9 is the same as the list that can be used for a CasX protein (discussed in more detail herein).

Protospacer Adjacent Motif (PAM) for Archaeal Cas9 Protein

The PAM for an archaeal Cas9 protein is immediately 3' of the target sequence of the non-complementary strand of the target DNA (the complementary strand hybridizes to the guide sequence of the guide RNA while the non-complementary strand does not directly hybridize with the guide RNA and is the reverse complement of the non-complementary strand). Thus, the PAM for an archaeal Cas9 protein is on the opposite side of the target sequence compared to a PAM for a CasX protein (e.g., see FIG. 6C, and FIG. 7, which shows the 5' orientation of a PAM for a CasX protein). In some embodiments (e.g., when an archaeal Cas9 protein as described herein is used), the PAM sequence of the non-complementary strand is 5'-NGG-3', where N is any DNA nucleotide.

In some cases, different archaeal Cas9 proteins (i.e., archaeal Cas9 proteins from various archaeal species, variants of archaeal Cas9 proteins where the PAM preferences have changed) may be advantageous to use in the various provided methods in order to capitalize on various enzymatic characteristics of the different archaeal Cas9 proteins (e.g., for different PAM sequence preferences; for increased or decreased enzymatic activity; for an increased or decreased level of cellular toxicity; to change the balance between NHEJ, homology-directed repair, single strand breaks, double strand breaks, etc.; to take advantage of a short total sequence; and the like). Archaeal Cas9 proteins from different species (or variant thereof) may prefer different PAM sequences in the target DNA. Thus, for a particular archaeal Cas9 protein of choice, the PAM sequence preference may be different than the 5'-NGG-3' sequence described above. Various methods (including in silico and/or wet lab methods) for identification of the appropriate PAM sequence are known in the art and are routine, and any convenient method can be used. The NGG PAM sequence described herein was identified using in silico sequence analysis techniques (e.g., see FIG. 12B of the working examples below).

Archaeal Cas9 Guide RNA

Non-archaeal Cas9 guide RNAs (i.e., Cas9 guide RNAs from bacteria, but not from archaea) are known in the art, and a subject archaeal Cas9 guide RNA has similar structure as non-archaeal Cas9 guide RNAs. Note that for an archaeal Cas9 guide RNA, the guide sequence is located 5' of the duplex-forming segment of the targeter RNA, while it is located 3' of the duplex-forming segment in a CasX guide RNA (e.g., compare FIGS. 14A-14B and FIG. 15, which depict example archaeal Cas9 guide RNAs, to FIG. 6C, and FIG. 7, which depict example CasX guide RNAs).

In some cases, the activator (e.g., tracr sequence) of an archaeal Cas9 guide RNA (dgRNA or sgRNA) includes (i) a duplex forming segment that contributes to the dsRNA duplex of the protein-binding segment; and (ii) a stretch of nucleotides (e.g., referred to herein as a 3' tail) 3' of the duplex forming segment. In some cases, the additional nucleotides 3' of the duplex forming segment form one or more stem loops (e.g., 2 or more, 3 or more, 1, 2, or 3). In some cases, the activator (e.g., tracr sequence) of an archaeal Cas9 guide RNA (dgRNA or sgRNA) includes (i) a duplex forming segment that contributes to the dsRNA duplex of the protein-binding segment; and (ii) 5 or more nucleotides (e.g., 6 or more, 7 or more, 8 or more, 9 or more, 10 or more, 11 or more, 12 or more, 13 or more, 14 or more, 15 or more, 20 or more, 25 or more, 30 or more, 35 or more, 40 or more, 45 or more, 50 or more, 60 or more, 70 or more, or 75 or more nucleotides) 3' of the duplex forming segment. In some cases, the activator (activator RNA) of an archaeal Cas9 guide RNA (dgRNA or sgRNA) includes (i) a duplex forming segment that contributes to the dsRNA duplex of the protein-binding segment; and (ii) 5 or more nucleotides (e.g., 6 or more, 7 or more, 8 or more, 9 or more, 10 or more, 11 or more, 12 or more, 13 or more, 14 or more, 15 or more, 20 or more, 25 or more, 30 or more, 35 or more, 40 or more, 45 or more, 50 or more, 60 or more, 70 or more, or 75 or more nucleotides) 3' of the duplex forming segment.

In some cases, the activator (e.g., tracr sequence) of an archaeal Cas9 guide RNA (dgRNA or sgRNA) includes (i) a duplex forming segment that contributes to the dsRNA duplex of the protein-binding segment; and (ii) a stretch of nucleotides (e.g., referred to herein as a 3' tail) 3' of the duplex forming segment. In some cases, the stretch of nucleotides 3' of the duplex forming segment has a length in a range of from 5 to 200 nucleotides (nt) (e.g., from 5 to 150 nt, from 5 to 130 nt, from 5 to 120 nt, from 5 to 100 nt, from 5 to 80 nt, from 10 to 200 nt, from 10 to 150 nt, from 10 to 130 nt, from 10 to 120 nt, from 10 to 100 nt, from 10 to 80 nt, from 12 to 200 nt, from 12 to 150 nt, from 12 to 130 nt, from 12 to 120 nt, from 12 to 100 nt, from 12 to 80 nt, from 15 to 200 nt, from 15 to 150 nt, from 15 to 130 nt, from 15 to 120 nt, from 15 to 100 nt, from 15 to 80 nt, from 20 to 200 nt, from 20 to 150 nt, from 20 to 130 nt, from 20 to 120 nt, from 20 to 100 nt, from 20 to 80 nt, from 30 to 200 nt, from 30 to 150 nt, from 30 to 130 nt, from 30 to 120 nt, from 30 to 100 nt, or from 30 to 80 nt). In some cases, the nucleotides of the 3' tail of an activator RNA are wild type sequences.

Although a number of different alternative sequences can be used, example archaeal Cas9 guide RNA sequences can include one or more of the sequences set forth in SEQ ID NOs: 75-76 (example crRNA sequences minus the guide sequence), 77-78 (example tracrRNA sequences), and 81-82 (example single guide RNA sequences minus the guide sequence).

In some cases, the dsRNA duplex region formed between the activator and targeter (i.e., the activator/targeter dsRNA duplex) (e.g., in dual or single guide RNA format) includes a range of from 8-25 base pairs (bp) (e.g., from 8-22, 8-18, 8-15, 8-12, 12-25, 12-22, 12-18, 12-15, 13-25, 13-22, 13-18, 13-15, 14-25, 14-22, 14-18, 14-15, 15-25, 15-22, 15-18, 17-25, 17-22, or 17-18 bp, e.g., 15 bp, 16 bp, 17 bp, 18 bp, 19 bp, 20 bp, 21 bp, etc.). In some cases, the duplex region (e.g., in dual or single guide RNA format) includes 8 or more bp (e.g., 10 or more, 12 or more, 15 or more, or 17 or more bp). In some cases, not all nucleotides of the duplex region are paired, and therefore the duplex forming region can include a bulge (e.g., see FIG. 6C, and FIG. 7). The term "bulge" herein is used to mean a stretch of nucleotides (which can be one nucleotide) that do not contribute to a double stranded duplex, but which are surround 5' and 3' by nucleotides that do contribute, and as such a bulge is considered part of the duplex region. In some cases, the dsRNA duplex formed between the activator and targeter (i.e., the activator/targeter dsRNA duplex) includes 1 or more bulges (e.g., 2 or more, 3 or more, 4 or more bulges). In some cases, the dsRNA duplex formed between the activator and targeter (i.e., the activator/targeter dsRNA duplex) includes 2 or more bulges (e.g., 3 or more, 4 or more bulges). In some cases, the dsRNA duplex formed between the activator and targeter (i.e., the activator/targeter dsRNA duplex) includes 1-5 bulges (e.g., 1-4, 1-3, 2-5, 2-4, or 2-3 bulges).

Thus, in some cases, the duplex-forming segments of the activator and targeter have 70%-100% complementarity (e.g., 75%-100%, 80%-10%, 85%-100%, 90%-100%, 95%-100% complementarity) with one another. In some cases, the duplex-forming segments of the activator and targeter have 70%-100% complementarity (e.g., 75%-100%, 80%-10%, 85%-100%, 90%-100%, 95%-100% complementarity) with one another. In some cases, the duplex-forming segments of the activator and targeter have 85%-100% complementarity (e.g., 90%-100%, 95%-100% complementarity) with one another. In some cases, the duplex-forming segments of the activator and targeter have 70%-95% complementarity (e.g., 75%-95%, 80%-95%, 85%-95%, 90%-95% complementarity) with one another.

In other words, in some embodiments, the dsRNA duplex formed between the activator and targeter (i.e., the activator/targeter dsRNA duplex) includes two stretches of nucleotides that have 70%-100% complementarity (e.g., 75%-100%, 80%-10%, 85%-100%, 90%-100%, 95%-100% complementarity) with one another. In some cases, the activator/targeter dsRNA duplex includes two stretches of nucleotides that have 85%-100% complementarity (e.g., 90%-100%, 95%-100% complementarity) with one another. In some cases, the activator/targeter dsRNA duplex includes two stretches of nucleotides that have 70%-95% complementarity (e.g., 75%-95%, 80%-95%, 85%-95%, 90%-95% complementarity) with one another.

The duplex region of a subject archaeal Cas9 guide RNA (in dual guide or single guide RNA format) can include one or more (1, 2, 3, 4, 5, etc) mutations relative to a naturally occurring duplex region. For example, in some cases a base pair can be maintained while the nucleotides contributing to the base pair from each segment (targeter and activator) can be different. In some cases, the duplex region of a subject archaeal Cas9 guide RNA includes more paired bases, less paired bases, a smaller bulge, a larger bulge, fewer bulges, more bulges, or any convenient combination thereof, as compared to a naturally occurring duplex region (of a naturally occurring archaeal Cas9 guide RNA).

Example Sequences for an Archaeal Cas9 Guide RNA

In some cases, the targeter-RNA (e.g., in dual or single guide RNA format) comprises the crRNA sequence CUUA-CAAUCGACACUUAAAUAAUUUGCAUGUGUAAG (SEQ ID NO: 75) (e.g., see the sgRNA of 6C). In some cases, the targeter-RNA (e.g., in dual or single guide RNA format) comprises a nucleotide sequence having 80% or more identity (e.g., 85% or more, 90% or more, 93% or more, 95% or more, 97% or more, 98% or more, or 100% identity) with the crRNA sequence CUUACAAUCGACA-CUUAAAUAAUUUGCAUGUGUAAG (SEQ ID NO: 75). In some cases, the targeter-RNA (e.g., in dual or single guide RNA format) comprises the crRNA sequence (SEQ ID NO: 75)
CUUACAAUCGACACUUAAAUAAUUUGCAUGUGUAAG.

In some cases, the targeter-RNA comprises the crRNA sequence CCUUUCAAUAAACAAAUAAAUCUUAGUAAUAUGUAAC (SEQ ID NO: 76). In some cases, the targeter-RNA comprises a nucleotide sequence having 80% or more identity (e.g., 85% or more, 90% or more, 93% or more, 95% or more, 97% or more, 98% or more, or 100% identity) with the crRNA sequence CUUUCAAUAAACAAAUAAAUCUUAGUAAUAUGUAAC (SEQ ID NO: 76). In some cases, the targeter-RNA (e.g., in dual or single guide RNA format) comprises the crRNA sequence (SEQ ID NO: 76)
CUUUCAAUAAACAAAUAAAUCUUAGUAAUAUGUAAC.

In some cases, the targeter-RNA comprises the crRNA sequence set forth in any one of SEQ ID NOs: 75-76. In some cases, the targeter-RNA comprises a nucleotide sequence having 80% or more identity (e.g., 85% or more, 90% or more, 93% or more, 95% or more, 97% or more, 98% or more, or 100% identity) with the crRNA sequence set forth in any one of SEQ ID NOs: 75-76.

In some cases, the activator-RNA (e.g., in dual or single guide RNA format) comprises the tracrRNA sequence GGCAUGGACCAUAUCCAGGUGUUGAUUGUAAACACCUAGCGGGGAAAUUAUAUAUGUUUGUAAUAUCUUCACUAUCCAAAGUUAUCUCUGGUUUUGGUUUGGUAAGCUUCACUUCACU AUUGUUUUCACUCCCAAUUUGAGUAUGGUUGGGGGUAAGGAUGCUUUCGGGGAGUGCUUUUA (SEQ ID NO: 77). In some cases, the targeter-RNA (e.g., in dual or single guide RNA format) comprises a nucleotide sequence having 80% or more identity (e.g., 85% or more, 90% or more, 93% or more, 95% or more, 97% or more, 98% or more, 99% or more, or 100% identity) with the tracrRNA sequence (SEQ ID NO: 77)
GGCAUGGACCAUAUCCAGGUGUUGAUUGUAAACACCUAGCGGGGAAAUUA

UAUAUGUUUGUAAUAUCUUCACUAUCCAAAGUUAUCUCUGGUUUUGGUUU

GGUAAGCUUCACUUCACUAUUGUUUUCACUCCCAAUUUGAGUAUGGUUGG

GGGUAAGGAUGCUUUCGGGGAGUGCUUUUA.

In some cases, the activator-RNA (e.g., in dual or single guide RNA format) comprises the tracrRNA sequence AACUGGCUAUUGCUAAUAUUAUUUGUUUAUUGAAAGAAGCCUAGACGUUAGGGUUCGCG UGCAUGUAGGCUCCAGCAGGUACCUC (SEQ ID NO: 78). In some cases, the targeter-RNA (e.g., in dual or single guide RNA format) comprises a nucleotide sequence having 80% or more identity (e.g., 85% or more, 90% or more, 93% or more, 95% or more, 97% or more, 98% or more, 99% or more, or 100% identity) with the tracrRNA sequence (SEQ ID NO: 78)
AACUGGCUAUUGCUAAUAUUAUUUGUUUAUUGAAAGAAGCCUAGACGUUA
GGGUUCGCGUGCAUGUAGGCUCCAGCAGGUACCUC.

In some cases, the activator-RNA (e.g., in dual or single guide RNA format) comprises the tracrRNA sequence set forth in any one of SEQ ID NOs: 77-78. In some cases, the targeter-RNA (e.g., in dual or single guide RNA format) comprises a nucleotide sequence having 80% or more identity (e.g., 85% or more, 90% or more, 93% or more, 95% or more, 97% or more, 98% or more, 99% or more, or 100% identity) with the tracrRNA sequence set forth in any one of SEQ ID NOs: 77-78.

In some cases, an archaeal Cas9 single guide RNA comprises the sequence CUUACAAUCGACACUUaaacAGGUGUUGAUUGUAAACACCUAGCGGGGAAAU UAUAUAUGU UUGUAAUAUCUUCACUAUCCAAAGUUAUCUCUGGUUUUGGUUUGGUAAGCUUCACUUCA CUAUUGUUUUCACUCCCAAUUUGAGUAUGGUUGGGGGUAAGGAUGCUUUCGGGGAG UGC UUUUA (SEQ ID NO: 81). In some cases, the targeter-RNA comprises a nucleotide sequence having 80% or more identity (e.g., 85% or more, 90% or more, 93% or more, 95% or more, 97% or more, 98% or more, 99% or more, or 100% identity) with the tracrRNA sequence (SEQ ID NO: 81)
CUUACAAUCGACACUUaaacAGGUGUUGAUUGUAAACACCUAGCGGGGAA

AUUAUAUAUGUUUGUAAUAUCUUCACUAUCCAAAGUUAUCUCUGGUUUUG

GUUUGGUAAGCUUCACUUCACUAUUGUUUUCACUCCCAAUUUGAGUAUGG

UUGGGGGUAAGGAUGCUUUCGGGGAGUGCUUUUA.

In some cases, an archaeal Cas9 single guide RNA comprises the sequence CUUUCAAUAAACAAAUAAaaacUUAUUUGUUUAUUGAAAGAAGCCUAGACGUUAGGGUUC GCGUGCAUGUAGGCUCCAGCAGGUACCUC (SEQ ID NO: 82). In some cases, the targeter-RNA comprises a nucleotide sequence having 80% or more identity (e.g., 85% or more, 90% or more, 93% or more, 95% or more, 97% or more, 98% or more, 99% or more, or 100% identity) with the tracrRNA sequence (SEQ ID NO: 82)
CUUUCAAUAAACAAAUAAaaacUUAUUUGUUUAUUGAAAGAAGCCUAGAC
GUUAGGGUUCGCGUGCAUGUAGGCUCCAGCAGGUACCUC.

In some cases, an archaeal Cas9 single guide RNA comprises the sequence set forth in any one of SEQ ID NOs: 81-82. In some cases, the targeter-RNA comprises a nucleotide sequence having 80% or more identity (e.g., 85% or more, 90% or more, 93% or more, 95% or more, 97% or more, 98% or more, 99% or more, or 100% identity) with the tracrRNA sequence set forth in any one of SEQ ID NOs: 81-82.

Guide Sequence of an Archaeal Cas9 Guide RNA

In some cases, the percent complementarity between the guide sequence and the target site of the target nucleic acid is 60% or more (e.g., 70% or more, 75% or more, 80% or more, 85% or more, 90% or more, 95% or more, 97% or more, 98% or more, 99% or more, or 100%) over 17 or more (e.g., 18 or more, 19 or more, 20 or more, 21 or more, 22 or more) contiguous nucleotides. In some cases, the percent complementarity between the guide sequence and the target site of the target nucleic acid is 80% or more (e.g., 85% or more, 90% or more, 95% or more, 97% or more, 98% or more, 99% or more, or 100%) over 17 or more (e.g., 18 or more, 19 or more, 20 or more, 21 or more, 22 or more) contiguous nucleotides. In some cases, the percent complementarity between the guide sequence and the target site of the target nucleic acid is 90% or more (e.g., 95% or more, 97% or more, 98% or more, 99% or more, or 100%) over 17 or more (e.g., 18 or more, 19 or more, 20 or more, 21 or more, 22 or more) contiguous nucleotides. In some cases, the percent complementarity between the guide sequence and the target site of the target nucleic acid is 100% over 17 or more (e.g., 18 or more, 19 or more, 20 or more, 21 or more, 22 or more) contiguous nucleotides.

In some cases, the percent complementarity between the guide sequence and the target site of the target nucleic acid is 60% or more (e.g., 70% or more, 75% or more, 80% or more, 85% or more, 90% or more, 95% or more, 97% or more, 98% or more, 99% or more, or 100%) over 17-25 contiguous nucleotides. In some cases, the percent complementarity between the guide sequence and the target site of the target nucleic acid is 80% or more (e.g., 85% or more, 90% or more, 95% or more, 97% or more, 98% or more, 99% or more, or 100%) over 17-25 contiguous nucleotides. In some cases, the percent complementarity between the guide sequence and the target site of the target nucleic acid is 90% or more (e.g., 95% or more, 97% or more, 98% or more, 99% or more, or 100%) over 17-25 contiguous nucleotides. In some cases, the percent complementarity between the guide sequence and the target site of the target nucleic acid is 100% over 17-25 contiguous nucleotides.

In some cases, the guide sequence has a length in a range of from 17-30 nucleotides (nt) (e.g., from 17-25, 17-22, 17-20, 19-30, 19-25, 19-22, 19-20, 20-30, 20-25, or 20-22 nt). In some cases, the guide sequence has a length in a range of from 17-25 nucleotides (nt) (e.g., from 17-22, 17-20, 19-25, 19-22, 19-20, 20-25, 20-25, or 20-22 nt). In some cases, the guide sequence has a length of 17 or more nt (e.g., 18 or more, 19 or more, 20 or more, 21 or more, or 22 or more nt; 17 nt, 18 nt, 19 nt, 20 nt, 21 nt, 22 nt, 23 nt, 24 nt, 25 nt, etc.). In some cases the guide sequence has a length of 17 nt. In some cases the guide sequence has a length of 18 nt. In some cases the guide sequence has a length of 19 nt. In some cases the guide sequence has a length of 20 nt. In some cases the guide sequence has a length of 21 nt. In some cases the guide sequence has a length of 22 nt. In some cases the guide sequence has a length of 23 nt.

Examples of various Cas proteins and Cas9 guide RNAs (albeit non-archeal Cas9 proteins and guide RNAs) can be found in the art, and in some cases variations similar to those introduced into non-archeal Cas9 proteins and guide RNAs can also be introduced into archeal Cas9 proteins and guide RNAs of the present disclosure, including, for example, high fidelity versions of Cas9. For example, mutations that can be introduced into previously known Cas9 proteins in order to generate a high fidelity Cas9 can also be introduced into archaeal Cas9 proteins for a same or similar purpose (e.g., a sequence and/or structural alignment can be performed to determine the appropriate amino acids to mutate in a subject archaeal Cas9 protein—e.g., amino acids N497, R661, Q695, and Q926 of a *S. pyogenes* Cas9 protein, which is not an archaeal Cas9 protein) (e.g., see Kleinstiver et al. (2016) Nature 529:490). For example, see Jinek et al., Science. 2012 Aug. 17; 337(6096):816-21; Chylinski et al., RNA Biol. 2013 May; 10(5):726-37; Ma et al., Biomed Res Int. 2013; 2013:270805; Hou et al., Proc Natl Acad Sci USA. 2013 Sep. 24; 110(39):15644-9; Jinek et al., Elife. 2013; 2:e00471; Pattanayak et al., Nat Biotechnol. 2013 September; 31(9):839-43; Qi et al, Cell. 2013 Feb. 28; 152(5):1173-83; Wang et al., Cell. 2013 May 9; 153(4):910-8; Auer et. al., Genome Res. 2013 Oct. 31; Chen et. al., Nucleic Acids Res. 2013 Nov. 1; 41(20):e19; Cheng et. al., Cell Res. 2013 October; 23(10):1163-71; Cho et. al., Genetics. 2013 November; 195(3):1177-80; DiCarlo et al., Nucleic Acids Res. 2013 April; 41(7):4336-43; Dickinson et. al., Nat Methods. 2013 October; 10(10):1028-34; Ebina et. al., Sci Rep. 2013; 3:2510; Fujii et. al, Nucleic Acids Res. 2013 Nov. 1; 41(20):e187; Hu et. al., Cell Res. 2013 November; 23(11):1322-5; Jiang et. al., Nucleic Acids Res. 2013 Nov. 1; 41(20):e188; Larson et. al., Nat Protoc. 2013 November; 8(11):2180-96; Mali et. at., Nat Methods. 2013 October; 10(10):957-63; Nakayama et. al., Genesis. 2013 December; 51(12):835-43; Ran et. al., Nat Protoc. 2013 November; 8(11):2281-308; Ran et. al., Cell. 2013 Sep. 12; 154(6): 1380-9; Upadhyay et. al., G3 (Bethesda). 2013 Dec. 9; 3(12):2233-8; Walsh et. al., Proc Natl Acad Sci USA. 2013 Sep. 24; 110(39):15514-5; Xie et. al., Mol Plant. 2013 Oct. 9; Yang et. al., Cell. 2013 Sep. 12; 154(6):1370-9; Briner et al., Mol Cell. 2014 Oct. 23; 56(2):333-9; and U.S. patents and patent applications: U.S. Pat. Nos. 8,906,616; 8,895,308; 8,889,418; 8,889,356; 8,871,445; 8,865,406; 8,795,965; 8,771,945; 8,697,359; 20140068797; 20140170753; 20140179006; 20140179770; 20140186843; 20140186919; 20140186958; 20140189896; 20140227787; 20140234972; 20140242664; 20140242699; 20140242700; 20140242702; 20140248702; 20140256046; 20140273037; 20140273226; 20140273230; 20140273231; 20140273232; 20140273233; 20140273234; 20140273235; 20140287938; 20140295556; 20140295557; 20140298547; 20140304853; 20140309487; 20140310828; 20140310830; 20140315985; 20140335063; 20140335620; 20140342456; 20140342457; 20140342458; 20140349400; 20140349405; 20140356867; 20140356956; 20140356958; 20140356959; 20140357523; 20140357530; 20140364333; and 20140377868; all of which are hereby incorporated by reference in their entirety.

EXAMPLES OF NON-LIMITING ASPECTS OF THE DISCLOSURE

Aspects, including embodiments, of the present subject matter described above may be beneficial alone or in combination, with one or more other aspects or embodiments. Without limiting the foregoing description, certain non-limiting aspects of the disclosure, (SET A—related to CasX) numbered 1-131; and (SET B—related to archaeal Cas9) numbered 1-133 are provided below. As will be apparent to those of skill in the art upon reading this disclosure, each of the individually numbered aspects may be used or combined with any of the preceding or following individually numbered aspects. This is intended to provide support for all such combinations of aspects and is not limited to combinations of aspects explicitly provided below:

Set A
Related to CasX
1. A composition comprising:
   a) a CasX polypeptide, or a nucleic acid molecule encoding the CasX polypeptide; and
   b) a CasX guide RNA, or one or more DNA molecules encoding the CasX guide RNA.
2. The composition of 1, wherein the CasX polypeptide comprises an amino acid sequence having 50% or more identity to the amino acid sequence set forth in SEQ ID NO:1 or SEQ ID NO:2 or SEQ ID NO:3.
3. The composition of 1 or 2, wherein the CasX guide RNA is a single guide RNA.
4. The composition of 1 or 2, wherein the CasX guide RNA is a dual-guide RNA.
5. The composition of any one of 1-4, wherein the composition comprises a lipid.
6. The composition of any one of 1-4, wherein a) and b) are within a liposome.

7. The composition of any one of 1-4, wherein a) and b) are within a particle.

8. The composition of any one of 1-7, comprising one or more of: a buffer, a nuclease inhibitor, and a protease inhibitor.

9. The composition of any one of 1-8, wherein the CasX polypeptide comprises an amino acid sequence having 85% or more identity to the amino acid sequence set forth in SEQ ID NO:1 or SEQ ID NO:2 or SEQ ID NO:3.

10. The composition of any one of 1-9, wherein the CasX polypeptide is a nickase that can cleave only one strand of a double-stranded target nucleic acid molecule.

11. The composition of any one of 1-9, wherein the CasX polypeptide is a catalytically inactive CasX Polypeptide (dCasX).

12. The composition of 10 or 11, wherein the CasX polypeptide comprises one or more mutations at a position corresponding to those selected from: D672, E769, and D935 of SEQ ID NO: 1.

13. The composition of any one of 1-12, further comprising a DNA donor template.

14. A CasX single guide RNA molecule, comprising:
    a) a targeter sequence comprising a guide sequence that hybridizes to a target nucleic acid, and a duplex-forming segment; and
    b) an activator sequence that hybridizes with the duplex-forming segment of the targeter sequence to form a double stranded RNA (dsRNA) duplex that can bind a CasX polypeptide.

15. The CasX single guide RNA molecule of 14, wherein the guide sequence has a length of from 19 to 30 nucleotides.

16. A DNA molecule comprising a nucleotide sequence encoding the CasX single guide RNA molecule of 14 or 15.

17. The DNA molecule of 16, wherein the nucleotide sequence encoding the CasX single guide RNA is operably linked to a promoter.

18. The DNA molecule of 17, wherein the promoter is functional in a eukaryotic cell.

19. The DNA molecule of 18, wherein the promoter is functional in one or more of: a plant cell, a fungal cell, an animal cell, cell of an invertebrate, a fly cell, a cell of a vertebrate, a mammalian cell, a primate cell, a non-human primate cell, and a human cell.

20. The DNA molecule of any one of 17-19, wherein the promoter is one or more of: a constitutive promoter, an inducible promoter, a cell type-specific promoter, and a tissue-specific promoter.

21. The DNA molecule of any one of 16-20, wherein the DNA molecule is a recombinant expression vector.

22. The DNA molecule of 21, wherein the recombinant expression vector is a recombinant adenoassociated viral vector, a recombinant retroviral vector, or a recombinant lentiviral vector.

23. The DNA molecule of 17, wherein the promoter is functional in a prokaryotic cell.

24. A CasX fusion polypeptide comprising: a CasX polypeptide fused to a heterologous polypeptide.

25. The CasX fusion polypeptide of 24, wherein the CasX polypeptide comprises an amino acid sequence having 50% or more identity to the amino acid sequence set forth in SEQ ID NO:1 or SEQ ID NO:2 or SEQ ID NO:3.

26. The CasX fusion polypeptide of 24, wherein the CasX polypeptide comprises an amino acid sequence having 85% or more identity to the amino acid sequence set forth in SEQ ID NO:1 or SEQ ID NO:2 or SEQ ID NO:3.

27. The CasX fusion polypeptide of any one of 24-27, wherein the CasX polypeptide is a nickase that can cleave only one strand of a double-stranded target nucleic acid molecule.

28. The CasX fusion polypeptide of any one of 24-27, wherein the CasX polypeptide is a catalytically inactive CasX Polypeptide (dCasX).

29. The CasX fusion polypeptide of 27 or 28, wherein the CasX polypeptide comprises one or more mutations at a position corresponding to those selected from: D672, E769, and D935 of SEQ ID NO: 1.

30. The CasX fusion polypeptide of any one of 24-29, wherein the heterologous polypeptide is fused to the N-terminus and/or the C-terminus of the CasX polypeptide.

31. The CasX fusion polypeptide of any one of 24-30, comprising an NLS.

32. The CasX fusion polypeptide of any one of 24-31, wherein the heterologous polypeptide is a targeting polypeptide that provides for binding to a cell surface moiety on a target cell or target cell type.

33. The CasX fusion polypeptide of any one of 24-31, wherein the heterologous polypeptide exhibits an enzymatic activity that modifies target DNA.

34. The CasX fusion polypeptide of 33, wherein the heterologous polypeptide exhibits an one or more enzymatic activities selected from: nuclease activity, methyltransferase activity, demethylase activity, DNA repair activity, DNA damage activity, deamination activity, dismutase activity, alkylation activity, depurination activity, oxidation activity, pyrimidine dimer forming activity, integrase activity, transposase activity, recombinase activity, polymerase activity, ligase activity, helicase activity, photolyase activity and glycosylase activity.

35. The CasX fusion polypeptide of 34, wherein the heterologous polypeptide exhibits an one or more enzymatic activities selected from: nuclease activity, methyltransferase activity, demethylase activity, deamination activity, depurination activity, integrase activity, transposase activity, and recombinase activity.

36. The CasX fusion polypeptide of any one of 24-31, wherein the heterologous polypeptide exhibits an enzymatic activity that modifies a target polypeptide associated with a target nucleic acid.

37. The CasX fusion polypeptide of 36, wherein the heterologous polypeptide exhibits histone modification activity.

38. The CasX fusion polypeptide of 36 or 37, wherein the heterologous polypeptide exhibits an one or more enzymatic activities selected from: methyltransferase activity, demethylase activity, acetyltransferase activity, deacetylase activity, kinase activity, phosphatase activity, ubiquitin ligase activity, deubiquitinating activity, adenylation activity, deadenylation activity, SUMOylating activity, deSUMOylating activity, ribosylation activity, deribosylation activity, myristoylation activity, demyristoylation activity, glycosylation activity (e.g., from O-GlcNAc transferase) and deglycosylation activity.

39. The CasX fusion polypeptide of 38, wherein the heterologous polypeptide exhibits an one or more enzymatic activities selected from: methyltransferase activity, demethylase activity, acetyltransferase activity, and deacetylase activity.

40. The CasX fusion polypeptide of any one of 24-31, wherein the heterologous polypeptide is an endosomal escape polypeptide.

41. The CasX fusion polypeptide of 40, wherein the endosomal escape polypeptide comprises an amino acid sequence selected from: GLFXALLXLLXSLWXLLLXA (SEQ ID NO:94), and GLFHALLHLLHSLWHLLLHA (SEQ ID NO:95), wherein each X is independently selected from lysine, histidine, and arginine.

42. The CasX fusion polypeptide of any one of 24-31, wherein the heterologous polypeptide is a chloroplast transit peptide.

43. The CasX fusion polypeptide of 42, wherein the chloroplast transit peptide comprises an amino acid sequence selected from

```
                                            (SEQ ID NO: 83)
MASMISSSAVTTVSRASRGQSAAMAPFGGLKSMTGFPVRKVNTDITSITS
NGGRVKCMQVWPPIGKKKFETLSYLPPLTRDSRA;

(SEQ ID NO: 84)
MASMISSSAVTTVSRASRGQSAAMAPFGGLKSMTGFPVRKVNTDITSITS
NGGRVKS;

(SEQ ID NO: 85)
MASSMLSSATMVASPAQATMVAPFNGLKSSAAFPATRKANNDITSITSNG
GRVNCMQVWPPIEKKKFETLSYLPDLTDSGGRVNC;

(SEQ ID NO: 86)
MAQVSRICNGVQNPSLISNLSKSSQRKSPLSVSLKTQQHPRAYPISSSWG
LKKSGMTLIGSELRPLKVMSSVSTAC;

(SEQ ID NO: 87)
MAQVSRICNGVWNPSLISNLSKSSQRKSPLSVSLKTQQHPRAYPISSSWG
LKKSGMTLIGSELRPLKVMSSVSTAC;

(SEQ ID NO: 88)
MAQINNMAQGIQTLNPNSNFHKPQVPKSSSFLVFGSKKLKNSANSMLVLK
KDSIFMQLFCSFRISASVATAC;

(SEQ ID NO: 89)
MAALVTSQLATSGTVLSVTDRFRRPGFQGLRPRNPADAALGMRTVGASAA
PKQSRKPHRFDRRCLSMVV;

(SEQ ID NO: 90)
MAALTTSQLATSATGFGIADRSAPSSLLRHGFQGLKPRSPAGGDATSLSV
TTSARATPKQQRSVQRGSRRFPSVVVC;

(SEQ ID NO: 91)
MASSVLSSAAVATRSNVAQANMVAPFTGLKSAASFPVSRKQNLDITSIAS
NGGRVQC;

(SEQ ID NO: 92)
MESLAATSVFAPSRVAVPAARALVRAGTVVPTRRTSSTSGTSGVKCSAAV
TPQASPVISRSAAAA;
and (SEQ ID NO: 93)
MGAAATSMQSLKFSNRLVPPSRRLSPVPNNVTCNNLPKSAAPVRTVKCCA
SSWNSTINGAAATTNGASAASS.
```

44. The CasX fusion polypeptide of any one of 24-31, wherein the heterologous polypeptide is protein that increases or decreases transcription.

45. The CasX fusion polypeptide of 44, wherein the heterologous polypeptide is a transcriptional repressor domain.

46. The CasX fusion polypeptide of 44, wherein the heterologous polypeptide is a transcriptional activation domain.

47. The CasX fusion polypeptide of any one of 24-31, wherein the heterologous polypeptide is a protein biding domain.

48. A nucleic acid molecule encoding the CasX fusion polypeptide of any one of claims 24-47.

49. The nucleic acid molecule of 48, wherein the nucleotide sequence encoding the CasX fusion polypeptide is operably linked to a promoter.

50. The nucleic acid molecule of 49, wherein the promoter is functional in a eukaryotic cell.

51. The nucleic acid molecule of 50, wherein the promoter is functional in one or more of: a plant cell, a fungal cell, an animal cell, cell of an invertebrate, a fly cell, a cell of a vertebrate, a mammalian cell, a primate cell, a non-human primate cell, and a human cell.

52. The nucleic acid molecule of any one of 49-51, wherein the promoter is one or more of: a constitutive promoter, an inducible promoter, a cell type-specific promoter, and a tissue-specific promoter.

53. The nucleic acid molecule of any one of 48-52, wherein the DNA molecule is a recombinant expression vector.

54. The nucleic acid molecule of 53, wherein the recombinant expression vector is a recombinant adenoassociated viral vector, a recombinant retroviral vector, or a recombinant lentiviral vector.

55. The nucleic acid molecule of 49, wherein the promoter is functional in a prokaryotic cell.

56. The nucleic acid molecule of 48, wherein the nucleic acid molecule is an mRNA.

57. One or more nucleic molecules encoding:
(a) a CasX guide RNA comprising an activator RNA and a targeter RNA; and
(b) a CasX polypeptide.

58. The one or more nucleic acid molecules of 57, wherein the CasX polypeptide comprises an amino acid sequence having 50% or more identity to the amino acid sequence set forth in SEQ ID NO:1 or SEQ ID NO:2 or SEQ ID NO:3.

59. The one or more nucleic acid molecules of 57, wherein the CasX polypeptide comprises an amino acid sequence having 85% or more identity to the amino acid sequence set forth in SEQ ID NO:1 or SEQ ID NO:2 or SEQ ID NO:3.

60. The one or more nucleic acid molecules of any one of 57-59, wherein the CasX guide RNA is a single guide RNA.

61. The one or more nucleic acid molecules of any one of 57-59, wherein the CasX guide RNA is a dual-guide RNA.

62. The one or more nucleic acid molecules of 61, wherein said one or more nucleic acid molecules comprises a first nucleotide sequence encoding the activator and a second nucleotide sequence encoding the targeter, and wherein said first and second nucleotide sequences are present on different DNA molecules.

63. The one or more nucleic acid molecules of any one of 57-62, wherein said one or more nucleic acid molecules comprises a nucleotide sequence encoding the CasX polypeptide that is operably linked to a promoter.

64. The one or more nucleic acid molecules of 63, wherein the promoter is functional in a eukaryotic cell.

65. The one or more nucleic acid molecules of 64, wherein the promoter is functional in one or more of: a plant cell, a fungal cell, an animal cell, cell of an invertebrate, a fly cell, a cell of a vertebrate, a mammalian cell, a primate cell, a non-human primate cell, and a human cell.

66. The one or more nucleic acid molecules of any one of 63-65, wherein the promoter is one or more of: a constitutive promoter, an inducible promoter, a cell type-specific promoter, and a tissue-specific promoter.

67. The one or more nucleic acid molecules of any one of 57-66, wherein the one or more nucleic acid molecules is one or more recombinant expression vectors.

68. The one or more nucleic acid molecules of 67, wherein the one or more recombinant expression vectors are selected from: one or more adenoassociated viral vectors, one or more recombinant retroviral vectors, or one or more recombinant lentiviral vectors.

69. The one or more nucleic acid molecules of 63, wherein the promoter is functional in a prokaryotic cell.

70. A eukaryotic cell comprising one or more of:
a) a Casx polypeptide, or a nucleic acid molecule encoding the Casx polypeptide, b) a CasX fusion polypeptide, or a nucleic acid molecule encoding the CasX fusion polypeptide, and
c) a CasX guide RNA, or a nucleic acid molecule encoding the CasX guide RNA.

71. The eukaryotic cell of 70, comprising the nucleic acid molecule encoding the Casx polypeptide, wherein said nucleic acid molecule is integrated into the genomic DNA of the cell.

72. The eukaryotic cell of 70 or 71, wherein the eukaryotic cell is a plant cell, a mammalian cell, an insect cell, an arachnid cell, a fungal cell, a bird cell, a reptile cell, an amphibian cell, an invertebrate cell, a mouse cell, a rat cell, a primate cell, a non-human primate cell, or a human cell.

73. A cell comprising a CasX fusion polypeptide, or a nucleic acid molecule encoding the CasX fusion polypeptide.

74. The cell of 73, wherein the cell is a prokaryotic cell.

75. The cell of 73 or 74, comprising the nucleic acid molecule encoding the CasX fusion polypeptide, wherein said nucleic acid molecule is integrated into the genomic DNA of the cell.

76. A method of modifying a target nucleic acid, the method comprising contacting the target nucleic acid with:
a) a CasX polypeptide; and
b) a CasX guide RNA comprising a guide sequence that hybridizes to a target sequence of the target nucleic acid, wherein said contacting results in modification of the target nucleic acid by the CasX polypeptide.

77. The method of 76, wherein said modification is cleavage of the target nucleic acid.

78. The method of 76 or 77, wherein the target nucleic acid is selected from: double stranded DNA, single stranded DNA, RNA, genomic DNA, and extrachromosomal DNA.

79. The method of any of 76-78, wherein said contacting takes place in vitro outside of a cell.

80. The method of any of 76-78, wherein said contacting takes place inside of a cell in culture.

81. The method of any of 76-78, wherein said contacting takes place inside of a cell in vivo.

82. The method of 80 or 81, wherein the cell is a eukaryotic cell.

83. The method of 82, wherein the cell is selected from: a plant cell, a fungal cell, a mammalian cell, a reptile cell, an insect cell, an avian cell, a fish cell, a parasite cell, an arthropod cell, a cell of an invertebrate, a cell of a vertebrate, a rodent cell, a mouse cell, a rat cell, a primate cell, a non-human primate cell, and a human cell.

84. The method of 80 or 81, wherein the cell is a prokaryotic cell.

85. The method of any one of 76-84, wherein said contacting results in genome editing.

86. The method of any one of 76-85, wherein said contacting comprises: introducing into a cell: (a) the CasX polypeptide, or a nucleic acid molecule encoding the the CasX polypeptide, and (b) the Casx guide RNA, or a nucleic acid molecule encoding the the CasX guide RNA.

87. The method of 86, wherein said contacting further comprises: introducing a DNA donor template into the cell.

88. The method of any one of 76-87, wherein the CasX guide RNA is a single guide RNA.

89. The method of any one of 76-87, wherein the CasX guide RNA is a dual guide RNA.

90. A method of modulating transcription from a target DNA, modifying a target nucleic acid, or modifying a protein associated with a target nucleic acid, the method comprising contacting the target nucleic acid with:
a) a CasX fusion polypeptide comprising a CasX polypeptide fused to a heterologous polypeptide; and
b) a CasX guide RNA comprising a guide sequence that hybridizes to a target sequence of the target nucleic acid.

91. The method of 90, wherein the CasX guide RNA is a single guide RNA.

92. The method of 90, wherein the CasX guide RNA is a dual guide RNA.

93. The method of any of 90-92, wherein said modification is not cleavage of the target nucleic acid.

94. The method of any of 90-93, wherein the target nucleic acid is selected from: double stranded DNA, single stranded DNA, RNA, genomic DNA, and extrachromosomal DNA.

95. The method of any of 90-94, wherein said contacting takes place in vitro outside of a cell.

96. The method of any of 90-94, wherein said contacting takes place inside of a cell in culture.

97. The method of any of 90-94, wherein said contacting takes place inside of a cell in vivo.

98. The method of 96 or 97, wherein the cell is a eukaryotic cell.

99. The method of 98, wherein the cell is selected from: a plant cell, a fungal cell, a mammalian cell, a reptile cell, an insect cell, an avian cell, a fish cell, a parasite cell, an arthropod cell, a cell of an invertebrate, a cell of a vertebrate, a rodent cell, a mouse cell, a rat cell, a primate cell, a non-human primate cell, and a human cell.

100. The method of 96 or 97, wherein the cell is a prokaryotic cell.

101. The method of any one of 90-100, wherein said contacting comprises: introducing into a cell: (a) the CasX fusion polypeptide, or a nucleic acid molecule encoding the the CasX fusion polypeptide, and (b) the Casx guide RNA, or a nucleic acid molecule encoding the the CasX guide RNA.

102. The method of any one of 90-101, wherein the CasX polypeptide is a catalytically inactive CasX Polypeptide (dCasX).

103. The method of any one of 90-102, wherein the CasX polypeptide comprises one or more mutations at a position corresponding to those selected from: D672, E769, and D935 of SEQ ID NO: 1.

104. The method of any one of 90-103, wherein the heterologous polypeptide exhibits an enzymatic activity that modifies target DNA.

105. The method of 104, wherein the heterologous polypeptide exhibits an one or more enzymatic activities selected from: nuclease activity, methyltransferase activity, demethylase activity, DNA repair activity, DNA damage activity, deamination activity, dismutase activity, alkylation activity, depurination activity, oxidation activity, pyrimidine dimer forming activity, integrase activity, transposase activity, recombinase activity, polymerase activity, ligase activity, helicase activity, photolyase activity and glycosylase activity.

106. The method of 105, wherein the heterologous polypeptide exhibits an one or more enzymatic activities selected from: nuclease activity, methyltransferase activity, demethylase activity, deamination activity, depurination activity, integrase activity, transposase activity, and recombinase activity.

107. The method of any one of 90-103, wherein the heterologous polypeptide exhibits an enzymatic activity that modifies a target polypeptide associated with a target nucleic acid.

108. The method of 107, wherein the heterologous polypeptide exhibits histone modification activity.
109. The method of 107 or 108, wherein the heterologous polypeptide exhibits an one or more enzymatic activities selected from: methyltransferase activity, demethylase activity, acetyltransferase activity, deacetylase activity, kinase activity, phosphatase activity, ubiquitin ligase activity, deubiquitinating activity, adenylation activity, deadenylation activity, SUMOylating activity, deSUMOylating activity, ribosylation activity, deribosylation activity, myristoylation activity, demyristoylation activity, glycosylation activity (e.g., from O-GlcNAc transferase) and deglycosylation activity.
110. The method of 109, wherein the heterologous polypeptide exhibits an one or more enzymatic activities selected from: methyltransferase activity, demethylase activity, acetyltransferase activity, and deacetylase activity.
111. The method of any one of 90-103, wherein the heterologous polypeptide is protein that increases or decreases transcription.
112. The method of 111, wherein the heterologous polypeptide is a transcriptional repressor domain.
113. The method of 111, wherein the heterologous polypeptide is a transcriptional activation domain.
114. The method of any one of 90-103, wherein the heterologous polypeptide is a protein biding domain.
115. A transgenic, multicellular, non-human organism whose genome comprises a transgene comprising a nucleotide sequence encoding one or more of:
  a) a Casx polypeptide,
  b) a CasX fusion polypeptide, and
  c) a CasX guide RNA.
116. The transgenic, multicellular, non-human organism of 115, wherein the CasX polypeptide comprises an amino acid sequence having 50% or more amino acid sequence identity to the amino acid sequence set forth in SEQ ID NO:1 or SEQ ID NO:2 or SEQ ID NO:3.
117. The transgenic, multicellular, non-human organism of 115, wherein the CasX polypeptide comprises an amino acid sequence having 85% or more amino acid sequence identity to the amino acid sequence set forth in SEQ ID NO:1 or SEQ ID NO:2 or SEQ ID NO:3.
118. The transgenic, multicellular, non-human organism of any one of 115-117, wherein the organism is a plant, a monocotyledon plant, a dicotyledon plant, an invertebrate animal, an insect, an arthropod, an arachnid, a parasite, a worm, a cnidarian, a vertebrate animal, a fish, a reptile, an amphibian, an ungulate, a bird, a pig, a horse, a sheep, a rodent, a mouse, a rat, or a non-human primate.
119. A system comprising:
  a) a CasX polypeptide and a CasX single guide RNA;
  b) a CasX polypeptide, a CasX guide RNA, and a DNA donor template;
  c) a CasX fusion polypeptide and a CasX guide RNA;
  d) a CasX fusion polypeptide, a CasX guide RNA, and a DNA donor template;
  e) an mRNA encoding a CasX polypeptide, and a CasX single guide RNA;
  f) an mRNA encoding a CasX polypeptide; a CasX guide RNA, and a DNA donor template;
  g) an mRNA encoding a CasX fusion polypeptide, and a CasX guide RNA;
  h) an mRNA encoding a CasX fusion polypeptide, a CasX guide RNA, and a DNA donor template;
  i) one or more recombinant expression vectors comprising: i) a nucleotide sequence encoding a CasX polypeptide; and ii) a nucleotide sequence encoding a CasX guide RNA;
  j) one or more recombinant expression vectors comprising: i) a nucleotide sequence encoding a CasX polypeptide; ii) a nucleotide sequence encoding a CasX guide RNA; and iii) a DNA donor template;
  k) one or more recombinant expression vectors comprising: i) a nucleotide sequence encoding a CasX fusion polypeptide; and ii) a nucleotide sequence encoding a CasX guide RNA; and
  l) one or more recombinant expression vectors comprising: i) a nucleotide sequence encoding a CasX fusion polypeptide; ii) a nucleotide sequence encoding a CasX guide RNA; and a DNA donor template.
120. The CasX system of 119, wherein the CasX polypeptide comprises an amino acid sequence having 50% or more amino acid sequence identity to the amino acid sequence set forth in SEQ ID NO:1 or SEQ ID NO:2 or SEQ ID NO:3.
121. The CasX system of 119, wherein the CasX polypeptide comprises an amino acid sequence having 85% or more amino acid sequence identity to the amino acid sequence set forth in SEQ ID NO:1 or SEQ ID NO:2 or SEQ ID NO:3.
122. The CasX system of any of 119-121, wherein the donor template nucleic acid has a length of from 8 nucleotides to 1000 nucleotides.
123. The CasX system of any of 119-121, wherein the donor template nucleic acid has a length of from 25 nucleotides to 500 nucleotides.
124. A kit comprising the CasX system of any one of 119-123.
125. The kit of 124, wherein the components of the kit are in the same container.
126. The kit of 124, wherein the components of the kit are in separate containers.
127. A sterile container comprising the CasX system of any one of 119-126.
128. The sterile container of 127, wherein the container is a syringe.
129. An implantable device comprising the CasX system of any one of 119-126.
130. The implantable device of 129, wherein the CasX system is within a matrix.
131. The implantable device of 129, wherein the CasX system is in a reservoir.
Set B
Related to Archaeal Cas9
1. A composition comprising:
  a) a archaeal Cas9 polypeptide, or a nucleic acid molecule encoding the archaeal Cas9 polypeptide; and
  b) a archaeal Cas9 guide RNA, or one or more DNA molecules encoding the archaeal Cas9 guide RNA.
2. The composition of 1, wherein the archaeal Cas9 polypeptide comprises an amino acid sequence having 50% or more identity to the amino acid sequence set forth in SEQ ID NO:71 or SEQ ID NO:72.
3. The composition of 1 or 2, wherein the archaeal Cas9 guide RNA is a single guide RNA.
4. The composition of 1 or 2, wherein the archaeal Cas9 guide RNA is a dual-guide RNA.
5. The composition of any one of 1-4, wherein the composition comprises a lipid.
6. The composition of any one of 1-4, wherein a) and b) are within a liposome.
7. The composition of any one of 1-4, wherein a) and b) are within a particle.

8. The composition of any one of 1-7, comprising one or more of: a buffer, a nuclease inhibitor, and a protease inhibitor.

9. The composition of any one of 1-8, wherein the archaeal Cas9 polypeptide comprises an amino acid sequence having 85% or more identity to the amino acid sequence set forth in SEQ ID NO:71 or SEQ ID NO:72.

10. The composition of any one of 1-9, wherein the archaeal Cas9 polypeptide is a nickase that can cleave only one strand of a double-stranded target nucleic acid molecule.

11. The composition of any one of 1-9, wherein the archaeal Cas9 polypeptide is a catalytically inactive archaeal Cas9 polypeptide (dead archaeal Cas9).

12. The composition of 10 or 11, wherein the archaeal Cas9 polypeptide comprises one or more mutations at a position corresponding to those selected from: D672, E769, and D935 of SEQ ID NO:71.

13. The composition of any one of 1-12, further comprising a DNA donor template.

14. A archaeal Cas9 single guide RNA molecule, comprising:
    a) a targeter sequence comprising a guide sequence that hybridizes to a target nucleic acid, and a duplex-forming segment; and
    b) an activator sequence that hybridizes with the duplex-forming segment of the targeter sequence to form a double stranded RNA (dsRNA) duplex that can bind a archaeal Cas9 polypeptide.

15. The archaeal Cas9 single guide RNA molecule of 14, wherein the guide sequence has a length of from 19 to 30 nucleotides.

16. A DNA molecule comprising a nucleotide sequence encoding the archaeal Cas9 single guide RNA molecule of 14 or 15.

17. The DNA molecule of 16, wherein the nucleotide sequence encoding the archaeal Cas9 single guide RNA is operably linked to a promoter.

18. The DNA molecule of 17, wherein the promoter is functional in a eukaryotic cell.

19. The DNA molecule of 18, wherein the promoter is functional in one or more of: a plant cell, a fungal cell, an animal cell, cell of an invertebrate, a fly cell, a cell of a vertebrate, a mammalian cell, a primate cell, a non-human primate cell, and a human cell.

20. The DNA molecule of any one of 17-19, wherein the promoter is one or more of: a constitutive promoter, an inducible promoter, a cell type-specific promoter, and a tissue-specific promoter.

21. The DNA molecule of any one of 16-20, wherein the DNA molecule is a recombinant expression vector.

22. The DNA molecule of 21, wherein the recombinant expression vector is a recombinant adenoassociated viral vector, a recombinant retroviral vector, or a recombinant lentiviral vector.

23. The DNA molecule of 17, wherein the promoter is functional in a prokaryotic cell.

24. An archaeal Cas9 fusion polypeptide comprising: a archaeal Cas9 polypeptide fused to a heterologous polypeptide.

25. The archaeal Cas9 fusion polypeptide of 24, wherein the archaeal Cas9 polypeptide comprises an amino acid sequence having 50% or more identity to the amino acid sequence set forth in SEQ ID NO:71 or SEQ ID NO:72.

26. The archaeal Cas9 fusion polypeptide of 24, wherein the archaeal Cas9 polypeptide comprises an amino acid sequence having 85% or more identity to the amino acid sequence set forth in SEQ ID NO:71 or SEQ ID NO:72.

27. The archaeal Cas9 fusion polypeptide of any one of 24-27, wherein the archaeal Cas9 polypeptide is a nickase that can cleave only one strand of a double-stranded target nucleic acid molecule.

28. The archaeal Cas9 fusion polypeptide of any one of 24-27, wherein the archaeal Cas9 polypeptide is a catalytically inactive archaeal Cas9 Polypeptide (dead archaeal Cas9).

29. The archaeal Cas9 fusion polypeptide of 27 or 28, wherein the archaeal Cas9 polypeptide comprises one or more mutations at a position corresponding to those selected from: D672, E769, and D935 of SEQ ID NO:71.

30. The archaeal Cas9 fusion polypeptide of any one of 24-29, wherein the heterologous polypeptide is fused to the N-terminus and/or the C-terminus of the archaeal Cas9 polypeptide.

31. The archaeal Cas9 fusion polypeptide of any one of 24-30, comprising an NLS.

32. The archaeal Cas9 fusion polypeptide of any one of 24-31, wherein the heterologous polypeptide is a targeting polypeptide that provides for binding to a cell surface moiety on a target cell or target cell type.

33. The archaeal Cas9 fusion polypeptide of any one of 24-31, wherein the heterologous polypeptide exhibits an enzymatic activity that modifies target DNA.

34. The archaeal Cas9 fusion polypeptide of 33, wherein the heterologous polypeptide exhibits an one or more enzymatic activities selected from: nuclease activity, methyltransferase activity, demethylase activity, DNA repair activity, DNA damage activity, deamination activity, dismutase activity, alkylation activity, depurination activity, oxidation activity, pyrimidine dimer forming activity, integrase activity, transposase activity, recombinase activity, polymerase activity, ligase activity, helicase activity, photolyase activity and glycosylase activity.

35. The archaeal Cas9 fusion polypeptide of 34, wherein the heterologous polypeptide exhibits an one or more enzymatic activities selected from: nuclease activity, methyltransferase activity, demethylase activity, deamination activity, depurination activity, integrase activity, transposase activity, and recombinase activity.

36. The archaeal Cas9 fusion polypeptide of any one of 24-31, wherein the heterologous polypeptide exhibits an enzymatic activity that modifies a target polypeptide associated with a target nucleic acid.

37. The archaeal Cas9 fusion polypeptide of 36, wherein the heterologous polypeptide exhibits histone modification activity.

38. The archaeal Cas9 fusion polypeptide of 36 or 37, wherein the heterologous polypeptide exhibits an one or more enzymatic activities selected from: methyltransferase activity, demethylase activity, acetyltransferase activity, deacetylase activity, kinase activity, phosphatase activity, ubiquitin ligase activity, deubiquitinating activity, adenylation activity, deadenylation activity, SUMOylating activity, deSUMOylating activity, ribosylation activity, deribosylation activity, myristoylation activity, demyristoylation activity, glycosylation activity (e.g., from O-GlcNAc transferase) and deglycosylation activity.

39. The archaeal Cas9 fusion polypeptide of 38, wherein the heterologous polypeptide exhibits an one or more enzymatic activities selected from: methyltransferase activity, demethylase activity, acetyltransferase activity, and deacetylase activity.

40. The archaeal Cas9 fusion polypeptide of any one of 24-31, wherein the heterologous polypeptide is an endosomal escape polypeptide.

41. The archaeal Cas9 fusion polypeptide of 40, wherein the endosomal escape polypeptide comprises an amino acid sequence selected from: GLFXALLXLLXSLWXLLLXA (SEQ ID NO:94), and GLFHALLHLLHSLWHLLLHA (SEQ ID NO:95), wherein each X is independently selected from lysine, histidine, and arginine.

42. The archaeal Cas9 fusion polypeptide of any one of 24-31, wherein the heterologous polypeptide is a chloroplast transit peptide.

43. The archaeal Cas9 fusion polypeptide of 42, wherein the chloroplast transit peptide comprises an amino acid sequence selected from (SEQ ID NO: 83)
MASMISSSAVTTVSRASRGQSAAMAPFGGLKSMTGFPVRKVNTDITSITS
NGGRVKCMQVWPPIGKKKFETLSYLPPLTRDSRA;

(SEQ ID NO: 84)
MASMISSSAVTTVSRASRGQSAAMAPFGGLKSMTGFPVRKVNTDITSITS
NGGRVKS;

(SEQ ID NO: 85)
MASSMLSSATMVASPAQATMVAPFNGLKSSAAFPATRKANNDITSITSNG
GRVNCMQVWPPIEKKKFETLSYLPDLTDSGGRVNC;

(SEQ ID NO: 86)
MAQVSRICNGVQNPSLISNLSKSSQRKSPLSVSLKTQQHPRAYPISSSWG
LKKSGMTLIGSELRPLKVMSSVSTAC;

(SEQ ID NO: 87)
MAQVSRICNGVWNPSLISNLSKSSQRKSPLSVSLKTQQHPRAYPISSSWG
LKKSGMTLIGSELRPLKVMSSVSTAC;

(SEQ ID NO: 88)
MAQINNMAQGIQTLNPNSNFHKPQVPKSSSFLVFGSKKLKNSANSMLVLK
KDSIFMQLFCSFRISASVATAC;

(SEQ ID NO: 89)
MAALVTSQLATSGTVLSVTDRFRRPGFQGLRPRNPADAALGMRTVGASAA
PKQSRKPHRFDRRCLSMVV;

(SEQ ID NO: 90)
MAALTTSQLATSATGFGIADRSAPSSLLRHGFQGLKPRSPAGGDATSLSV
TTSARATPKQQRSVQRGSRRFPSVVVC;

(SEQ ID NO: 91)
MASSVLSSAAVATRSNVAQANMVAPFTGLKSAASFPVSRKQNLDITSIAS
NGGRVQC;

(SEQ ID NO: 92)
MESLAATSVFAPSRVAVPAARALVRAGTVVPTRRTSSTSGTSGVKCSAAV
TPQASPVISRSAAAA;
and (SEQ ID NO: 93)
MGAAATSMQSLKFSNRLVPPSRRLSPVPNNVTCNNLPKSAAPVRTVKCCA
SSWNSTINGAAATTNGASAASS.

44. The archaeal Cas9 fusion polypeptide of any one of 24-31, wherein the heterologous polypeptide is protein that increases or decreases transcription.

45. The archaeal Cas9 fusion polypeptide of 44, wherein the heterologous polypeptide is a transcriptional repressor domain.

46. The archaeal Cas9 fusion polypeptide of 44, wherein the heterologous polypeptide is a transcriptional activation domain.

47. The archaeal Cas9 fusion polypeptide of any one of 24-31, wherein the heterologous polypeptide is a protein biding domain.

48. A nucleic acid molecule encoding the archaeal Cas9 fusion polypeptide of any one of claims 24-47.

49. The nucleic acid molecule of 48, wherein the nucleotide sequence encoding the archaeal Cas9 fusion polypeptide is operably linked to a promoter.

50. The nucleic acid molecule of 49, wherein the promoter is functional in a eukaryotic cell.

51. The nucleic acid molecule of 50, wherein the promoter is functional in one or more of: a plant cell, a fungal cell, an animal cell, cell of an invertebrate, a fly cell, a cell of a vertebrate, a mammalian cell, a primate cell, a non-human primate cell, and a human cell.

52. The nucleic acid molecule of any one of 49-51, wherein the promoter is one or more of: a constitutive promoter, an inducible promoter, a cell type-specific promoter, and a tissue-specific promoter.

53. The nucleic acid molecule of any one of 48-52, wherein the DNA molecule is a recombinant expression vector.

54. The nucleic acid molecule of 53, wherein the recombinant expression vector is a recombinant adenoassociated viral vector, a recombinant retroviral vector, or a recombinant lentiviral vector.

55. The nucleic acid molecule of 49, wherein the promoter is functional in a prokaryotic cell.

56. The nucleic acid molecule of 48, wherein the nucleic acid molecule is an mRNA.

57. One or more nucleic molecules encoding:
(a) a archaeal Cas9 guide RNA comprising an activator RNA and a targeter RNA; and
(b) a archaeal Cas9 polypeptide.

58. The one or more nucleic acid molecules of 57, wherein the archaeal Cas9 polypeptide comprises an amino acid sequence having 50% or more identity to the amino acid sequence set forth in SEQ ID NO:71 or SEQ ID NO:72.

59. The one or more nucleic acid molecules of 57, wherein the archaeal Cas9 polypeptide comprises an amino acid sequence having 85% or more identity to the amino acid sequence set forth in SEQ ID NO:71 or SEQ ID NO:72.

60. The one or more nucleic acid molecules of any one of 57-59, wherein the archaeal Cas9 guide RNA is a single guide RNA.

61. The one or more nucleic acid molecules of any one of 57-59, wherein the archaeal Cas9 guide RNA is a dual-guide RNA.

62. The one or more nucleic acid molecules of 61, wherein said one or more nucleic acid molecules comprises a first nucleotide sequence encoding the activator and a second nucleotide sequence encoding the targeter, and wherein said first and second nucleotide sequences are present on different DNA molecules.

63. The one or more nucleic acid molecules of any one of 57-62, wherein said one or more nucleic acid molecules comprises a nucleotide sequence encoding the archaeal Cas9 polypeptide that is operably linked to a promoter.

64. The one or more nucleic acid molecules of 63, wherein the promoter is functional in a eukaryotic cell.

65. The one or more nucleic acid molecules of 64, wherein the promoter is functional in one or more of: a plant cell, a fungal cell, an animal cell, cell of an invertebrate, a fly cell, a cell of a vertebrate, a mammalian cell, a primate cell, a non-human primate cell, and a human cell.

66. The one or more nucleic acid molecules of any one of 63-65, wherein the promoter is one or more of: a constitutive promoter, an inducible promoter, a cell type-specific promoter, and a tissue-specific promoter.

67. The one or more nucleic acid molecules of any one of 57-66, wherein the one or more nucleic acid molecules is one or more recombinant expression vectors.

68. The one or more nucleic acid molecules of 67, wherein the one or more recombinant expression vectors are selected from: one or more adenoassociated viral vectors, one or more recombinant retroviral vectors, or one or more recombinant lentiviral vectors.

69. The one or more nucleic acid molecules of 63, wherein the promoter is functional in a prokaryotic cell.

70. A eukaryotic cell comprising one or more of:
   a) a archaeal Cas9 polypeptide, or a nucleic acid molecule encoding the archaeal Cas9 polypeptide,
   b) a archaeal Cas9 fusion polypeptide, or a nucleic acid molecule encoding the archaeal Cas9 fusion polypeptide, and
   c) a archaeal Cas9 guide RNA, or a nucleic acid molecule encoding the archaeal Cas9 guide RNA.

71. The eukaryotic cell of 70, comprising the nucleic acid molecule encoding the archaeal Cas9 polypeptide, wherein said nucleic acid molecule is integrated into the genomic DNA of the cell.

72. The eukaryotic cell of 70 or 71, wherein the eukaryotic cell is a plant cell, a mammalian cell, an insect cell, an arachnid cell, a fungal cell, a bird cell, a reptile cell, an amphibian cell, an invertebrate cell, a mouse cell, a rat cell, a primate cell, a non-human primate cell, or a human cell.

73. A cell comprising a archaeal Cas9 fusion polypeptide, or a nucleic acid molecule encoding the archaeal Cas9 fusion polypeptide.

74. The cell of 73, wherein the cell is a prokaryotic cell.

75. The cell of 73 or 74, comprising the nucleic acid molecule encoding the archaeal Cas9 fusion polypeptide, wherein said nucleic acid molecule is integrated into the genomic DNA of the cell.

76. A method of modifying a target nucleic acid, the method comprising contacting the target nucleic acid with:
   a) a archaeal Cas9 polypeptide; and
   b) a archaeal Cas9 guide RNA comprising a guide sequence that hybridizes to a target sequence of the target nucleic acid, wherein said contacting results in modification of the target nucleic acid by the archaeal Cas9 polypeptide.

77. The method of 76, wherein said modification is cleavage of the target nucleic acid.

78. The method of 76 or 77, wherein the target nucleic acid is selected from: double stranded DNA, single stranded DNA, RNA, genomic DNA, and extrachromosomal DNA.

79. The method of any of 76-78, wherein said contacting takes place in vitro outside of a cell.

80. The method of any of 76-78, wherein said contacting takes place inside of a cell in culture.

81. The method of any of 76-78, wherein said contacting takes place inside of a cell in vivo.

82. The method of 80 or 81, wherein the cell is a eukaryotic cell.

83. The method of 82, wherein the cell is selected from: a plant cell, a fungal cell, a mammalian cell, a reptile cell, an insect cell, an avian cell, a fish cell, a parasite cell, an arthropod cell, a cell of an invertebrate, a cell of a vertebrate, a rodent cell, a mouse cell, a rat cell, a primate cell, a non-human primate cell, and a human cell.

84. The method of 80 or 81, wherein the cell is a prokaryotic cell.

85. The method of any one of 76-84, wherein said contacting results in genome editing.

86. The method of any one of 76-85, wherein said contacting comprises: introducing into a cell: (a) the archaeal Cas9 polypeptide, or a nucleic acid molecule encoding the the archaeal Cas9 polypeptide, and (b) the archaeal Cas9 guide RNA, or a nucleic acid molecule encoding the the archaeal Cas9 guide RNA.

87. The method of 86, wherein said contacting further comprises: introducing a DNA donor template into the cell.

88. The method of any one of 76-87, wherein the archaeal Cas9 guide RNA is a single guide RNA.

89. The method of any one of 76-87, wherein the archaeal Cas9 guide RNA is a dual guide RNA.

90. A method of modulating transcription from a target DNA, modifying a target nucleic acid, or modifying a protein associated with a target nucleic acid, the method comprising contacting the target nucleic acid with:
   a) a archaeal Cas9 fusion polypeptide comprising a archaeal Cas9 polypeptide fused to a heterologous polypeptide; and
   b) a archaeal Cas9 guide RNA comprising a guide sequence that hybridizes to a target sequence of the target nucleic acid.

91. The method of 90, wherein the archaeal Cas9 guide RNA is a single guide RNA.

92. The method of 90, wherein the archaeal Cas9 guide RNA is a dual guide RNA.

93. The method of any of 90-92, wherein said modification is not cleavage of the target nucleic acid.

94. The method of any of 90-93, wherein the target nucleic acid is selected from: double stranded DNA, single stranded DNA, RNA, genomic DNA, and extrachromosomal DNA.

95. The method of any of 90-94, wherein said contacting takes place in vitro outside of a cell.

96. The method of any of 90-94, wherein said contacting takes place inside of a cell in culture.

97. The method of any of 90-94, wherein said contacting takes place inside of a cell in vivo.

98. The method of 96 or 97, wherein the cell is a eukaryotic cell.

99. The method of 98, wherein the cell is selected from: a plant cell, a fungal cell, a mammalian cell, a reptile cell, an insect cell, an avian cell, a fish cell, a parasite cell, an arthropod cell, a cell of an invertebrate, a cell of a vertebrate, a rodent cell, a mouse cell, a rat cell, a primate cell, a non-human primate cell, and a human cell.

100. The method of 96 or 97, wherein the cell is a prokaryotic cell.

101. The method of any one of 90-100, wherein said contacting comprises: introducing into a cell: (a) the archaeal Cas9 fusion polypeptide, or a nucleic acid molecule encoding the the archaeal Cas9 fusion polypeptide, and (b) the archaeal Cas9 guide RNA, or a nucleic acid molecule encoding the the archaeal Cas9 guide RNA.

102. The method of any one of 90-101, wherein the archaeal Cas9 polypeptide is a catalytically inactive archaeal Cas9 Polypeptide (dead archaeal Cas9).

103. The method of any one of 90-102, wherein the archaeal Cas9 polypeptide comprises one or more mutations at a position corresponding to those selected from: D672, E769, and D935 of SEQ ID NO:71.

104. The method of any one of 90-103, wherein the heterologous polypeptide exhibits an enzymatic activity that modifies target DNA.

105. The method of 104, wherein the heterologous polypeptide exhibits an one or more enzymatic activities selected from: nuclease activity, methyltransferase activity, demethylase activity, DNA repair activity, DNA damage activity, deamination activity, dismutase activity, alkylation activity, depurination activity, oxidation activity, pyrimidine dimer forming activity, integrase activity, transposase activity, recombinase activity, polymerase activity, ligase activity, helicase activity, photolyase activity and glycosylase activity.

106. The method of 105, wherein the heterologous polypeptide exhibits an one or more enzymatic activities selected from: nuclease activity, methyltransferase activity, demethylase activity, deamination activity, depurination activity, integrase activity, transposase activity, and recombinase activity.

107. The method of any one of 90-103, wherein the heterologous polypeptide exhibits an enzymatic activity that modifies a target polypeptide associated with a target nucleic acid.

108. The method of 107, wherein the heterologous polypeptide exhibits histone modification activity.

109. The method of 107 or 108, wherein the heterologous polypeptide exhibits an one or more enzymatic activities selected from: methyltransferase activity, demethylase activity, acetyltransferase activity, deacetylase activity, kinase activity, phosphatase activity, ubiquitin ligase activity, deubiquitinating activity, adenylation activity, deadenylation activity, SUMOylating activity, deSUMOylating activity, ribosylation activity, deribosylation activity, myristoylation activity, demyristoylation activity, glycosylation activity (e.g., from O-GlcNAc transferase) and deglycosylation activity.

110. The method of 109, wherein the heterologous polypeptide exhibits an one or more enzymatic activities selected from: methyltransferase activity, demethylase activity, acetyltransferase activity, and deacetylase activity.

111. The method of any one of 90-103, wherein the heterologous polypeptide is protein that increases or decreases transcription.

112. The method of 111, wherein the heterologous polypeptide is a transcriptional repressor domain.

113. The method of 111, wherein the heterologous polypeptide is a transcriptional activation domain.

114. The method of any one of 90-103, wherein the heterologous polypeptide is a protein biding domain.

115. A transgenic, multicellular, non-human organism whose genome comprises a transgene comprising a nucleotide sequence encoding one or more of:
   a) a archaeal Cas9 polypeptide,
   b) a archaeal Cas9 fusion polypeptide, and
   c) a archaeal Cas9 guide RNA.

116. The transgenic, multicellular, non-human organism of 115, wherein the archaeal Cas9 polypeptide comprises an amino acid sequence having 50% or more amino acid sequence identity to the amino acid sequence set forth in SEQ ID NO:71 or SEQ ID NO:72.

117. The transgenic, multicellular, non-human organism of 115, wherein the archaeal Cas9 polypeptide comprises an amino acid sequence having 85% or more amino acid sequence identity to the amino acid sequence set forth in SEQ ID NO:71 or SEQ ID NO:72.

118. The transgenic, multicellular, non-human organism of any one of 115-117, wherein the organism is a plant, a monocotyledon plant, a dicotyledon plant, an invertebrate animal, an insect, an arthropod, an arachnid, a parasite, a worm, a cnidarian, a vertebrate animal, a fish, a reptile, an amphibian, an ungulate, a bird, a pig, a horse, a sheep, a rodent, a mouse, a rat, or a non-human primate.

119. A system comprising:
   a) a archaeal Cas9 polypeptide and a archaeal Cas9 single guide RNA;
   b) a archaeal Cas9 polypeptide, a archaeal Cas9 guide RNA, and a DNA donor template;
   c) a archaeal Cas9 fusion polypeptide and a archaeal Cas9 guide RNA;
   d) a archaeal Cas9 fusion polypeptide, a archaeal Cas9 guide RNA, and a DNA donor template;
   e) an mRNA encoding a archaeal Cas9 polypeptide, and a archaeal Cas9 single guide RNA;
   f) an mRNA encoding a archaeal Cas9 polypeptide; a archaeal Cas9 guide RNA, and a DNA donor template;
   g) an mRNA encoding a archaeal Cas9 fusion polypeptide, and a archaeal Cas9 guide RNA;
   h) an mRNA encoding a archaeal Cas9 fusion polypeptide, a archaeal Cas9 guide RNA, and a DNA donor template;
   i) one or more recombinant expression vectors comprising: i) a nucleotide sequence encoding a archaeal Cas9 polypeptide; and ii) a nucleotide sequence encoding a archaeal Cas9 guide RNA;
   j) one or more recombinant expression vectors comprising: i) a nucleotide sequence encoding a archaeal Cas9 polypeptide; ii) a nucleotide sequence encoding a archaeal Cas9 guide RNA; and iii) a DNA donor template;
   k) one or more recombinant expression vectors comprising: i) a nucleotide sequence encoding a archaeal Cas9 fusion polypeptide; and ii) a nucleotide sequence encoding a archaeal Cas9 guide RNA; and
   l) one or more recombinant expression vectors comprising: i) a nucleotide sequence encoding a archaeal Cas9 fusion polypeptide; ii) a nucleotide sequence encoding a archaeal Cas9 guide RNA; and a DNA donor template.

120. The archaeal Cas9 system of 119, wherein the archaeal Cas9 polypeptide comprises an amino acid sequence having 50% or more amino acid sequence identity to the amino acid sequence set forth in SEQ ID NO:71 or SEQ ID NO:72.

121. The archaeal Cas9 system of 119, wherein the archaeal Cas9 polypeptide comprises an amino acid sequence having 85% or more amino acid sequence identity to the amino acid sequence set forth in SEQ ID NO:71 or SEQ ID NO:72.

122. The archaeal Cas9 system of any of 119-121, wherein the donor template nucleic acid has a length of from 8 nucleotides to 1000 nucleotides.

123. The archaeal Cas9 system of any of 119-121, wherein the donor template nucleic acid has a length of from 25 nucleotides to 500 nucleotides.

124. A kit comprising the archaeal Cas9 system of any one of 119-123.

125. The kit of 124, wherein the components of the kit are in the same container.

126. The kit of 124, wherein the components of the kit are in separate containers.

127. A sterile container comprising the archaeal Cas9 system of any one of 119-126.

128. The sterile container of 127, wherein the container is a syringe.

129. An implantable device comprising the archaeal Cas9 system of any one of 119-126.

130. The implantable device of 129, wherein the archaeal Cas9 system is within a matrix.

131. The implantable device of 129, wherein the archaeal Cas9 system is in a reservoir.

132. Any one of aspects 1-131 (Set B), wherein the archaeal Cas9 protein is an ARMAN-1 Cas9 protein or an ARMAN-4 Cas9 protein.

133. Any one of aspects 1-131 (Set B), wherein the archaeal Cas9 protein is a Candidatus Micrarchaeum acidiphilum Cas9 protein or a Candidatus Parvarchaeum acidiphilum Cas9 protein.

EXAMPLES

The following examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed. Efforts have been made to ensure accuracy with respect to numbers used (e.g. amounts, temperature, etc.) but some experimental errors and deviations should be accounted for. Unless indicated otherwise, parts are parts by weight, molecular weight is weight average molecular weight, temperature is in degrees Celsius, and pressure is at or near atmospheric. Standard abbreviations may be used, e.g., bp, base pair(s); kb, kilobase(s); pl, picoliter(s); s or sec, second(s); min, minute(s); h or hr, hour(s); aa, amino acid(s); kb, kilobase(s); bp, base pair(s); nt, nucleotide(s); i.m., intramuscular(ly); i.p., intraperitoneal (ly); s.c., subcutaneous(ly); and the like.

Example 1

The work described herein includes an analysis of metagenomic samples of microbial communities from groundwater, sediments, and acid mine drainage. New Class 2 CRISPR-Cas systems were identified that are not represented among cultured organisms.

FIGS. 3A-3B. CasX Domains and Similarity Searches.

FIG. 3A Schematic domain representation for CasX inferred from distant homolog alignments with AcCpf1, using HHpred. Conserved catalytic residues are marked by red bars above the proteins. CasX contains a RuvC split domain in the C-terminal region (RuvC-I, RuvC-II, and RuvC-III), and a large novel N-terminal domain Below the schematic are displayed top hits based on the following searches: (1) BLAST search against all the proteins in NCBI (NR database, including model and environmental proteins). (2) Profile hidden markov model (HMM) search based on models built using all the Cas proteins described in Makarova et al. Nat Rev Microbiol. 2015 November; 13(11):722-36, and Shmakov et al. Mol Cell. 2015 Nov. 5; 60(3):385-97). (3) Distant homolog search based on HHpred. Hits are color-coded based on their significance, and the hit range and E-value is provided. Notably, CasX had only local hits. The 620 N-terminal amino acid of CasX had no hit in any of the search schemes. Combined, these finding indicate CasX is a new Cas protein. FIG. 3B Two different CasX-containing CRISPR loci scaffolds were constructed from sequence data, the top is from a Deltaproteobacter (CasX1) and the bottom is from a Planctomycetes (CasX2). The corresponding DNA sequence is set forth as SEQ ID NOs: 51 and 52, respectively.

Example 2

Figure 4A:
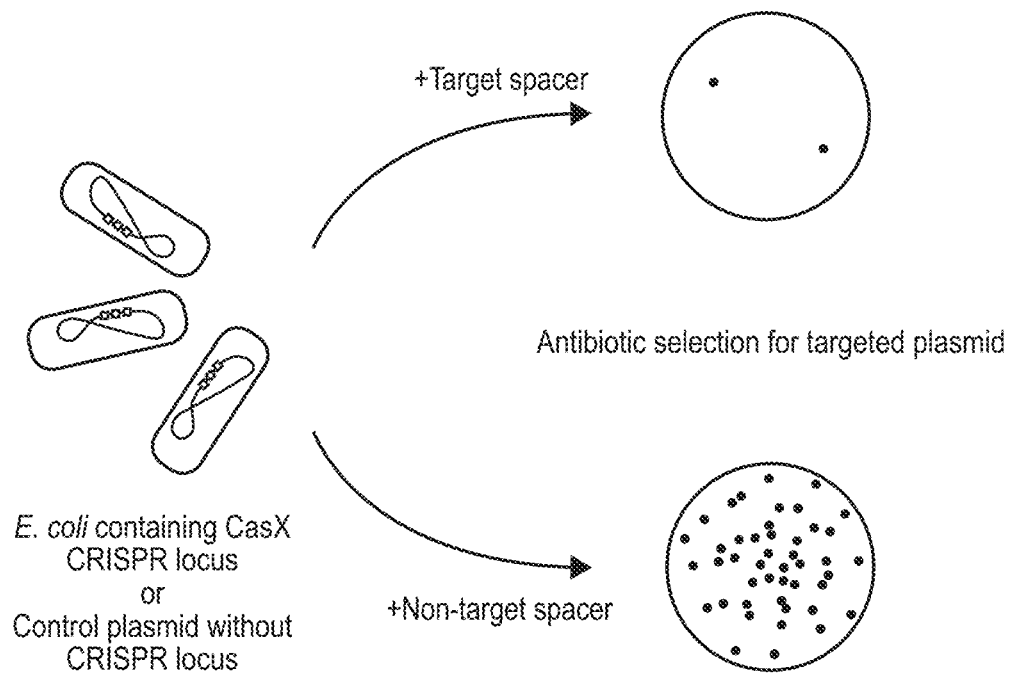
FIGS. 4A-4C depict experiments performed to demonstrate plasmid interference by CasX expressed in *Escherichia coli*.
Figure 4B:
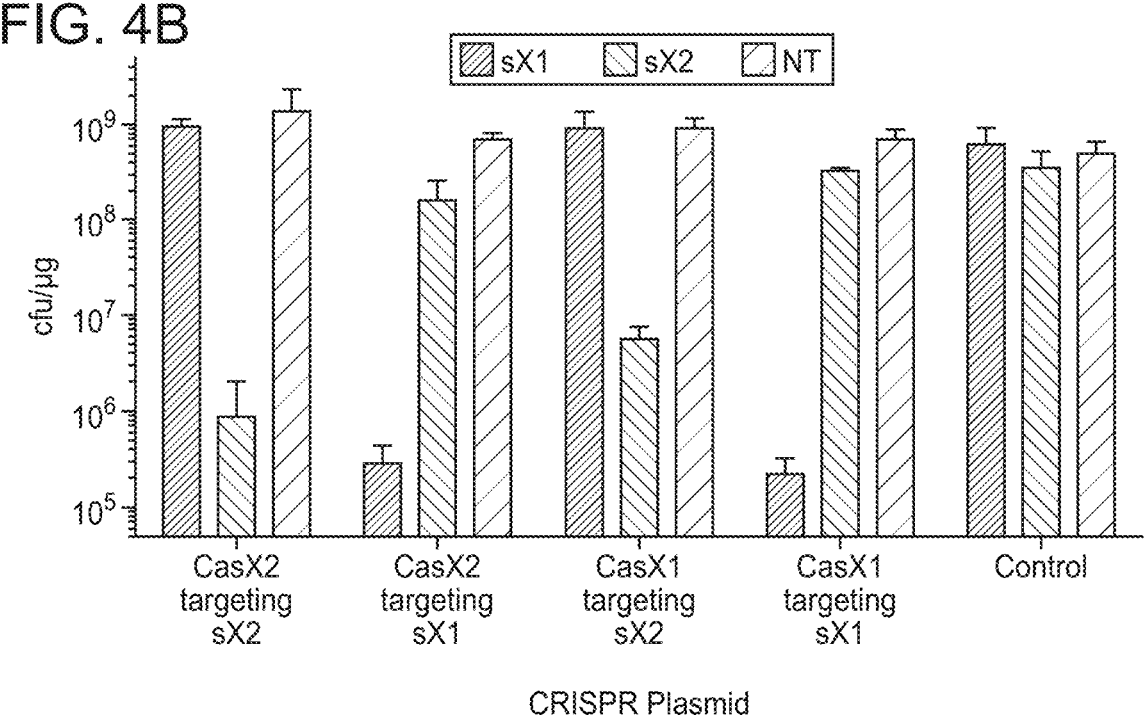
Figure 4C:
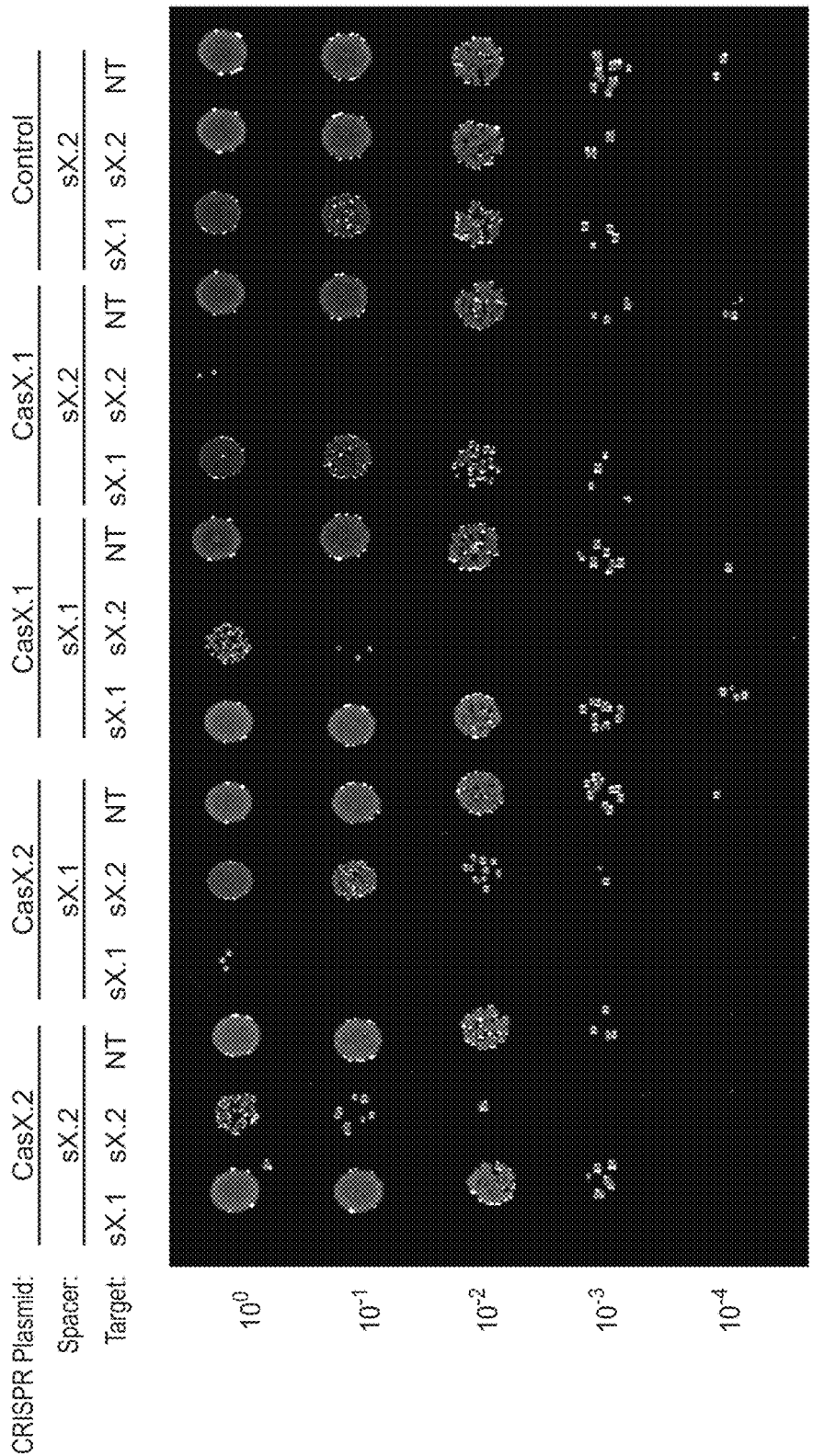

FIGS. 4A-4C. Plasmid Interference by CasX Expressed in *E. coli*.

Experimental design of CasX plasmid interference. Competent *E. coli* cells expressing the minimal interference CasX locus (acquisition proteins removed) were prepared. These cells were transformed with a plasmid containing a match to the spacer in the CasX CRISPR locus (target) or not (non-target) and plated on media containing antibiotic selection for the CRISPR and target plasmid. Successful plasmid interference results in reduced number of transformed colonies for the target plasmid. FIG. 4B cfu/ug of transformed plasmid containing spacer from CasX1 (sX1), spacer from CasX2 (sX2) or a non-target plasmid containing a random 30 nt sequence. FIG. 4C serial dilution was performed of transformants from FIG. 4B on media containing antibiotic selection for both the CRISPR and target plasmid.

Figure 5A:
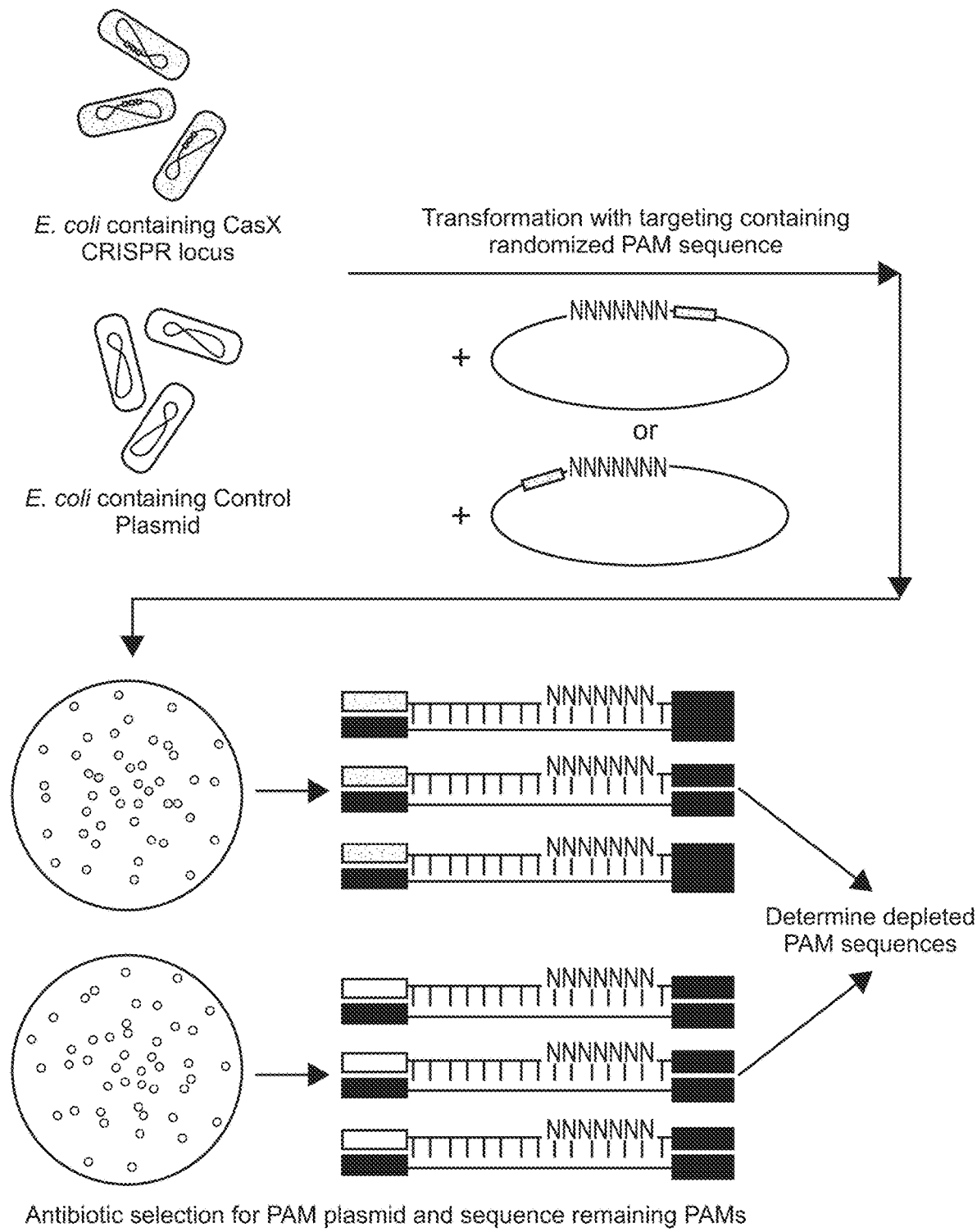

FIGS. 5A-5B PAM Dependent Plasmid Interference by CasX.

PAM depletion assays were conducted with CasX. *E. coli* containing the CasX CRISPR locus were transformed with a plasmid library with 7 nucleotides randomized 5' or 3' of the target sequence. The target plasmid was selected for and transformants were pooled. The randomized region was amplified and prepared for deep sequencing. Depleted sequences were identified and used to generate a PAM logo. FIG. 5B PAM logo generated for deltaproteobacteria CasX showed a strong preference for sequences containing a 5'-TTCN-3' flanking sequence 5' of the target. A 3' PAM was not detected. c, PAM logo generated for planctomyces CasX showed a strong preference for sequences containing a 5'-TTCN-3' flanking sequence 5' of the target with lower stringency at the first T. A 3' PAM was not detected.

FIGS. 6A-6C. CasX is a Dual-Guided CRISPR-Cas Effector Complex.

FIG. 6A CRISPR locus for tracrRNA knockout experiments and sgRNA tests. FIG. 6B colony forming units (cfu) per μg of transformed plasmid containing a target or non-target sequence. Deletion of the tracrRNA resulted in ablation of plasmid interference. Expression of a synthetic sgRNA in place of the tracrRNA and CRISPR array resulted in robust plasmid interference by CasX. FIG. 6C diagram of sgRNA design (derived from tracrRNA and crRNA sequences for CasX1). The tracrRNA (green) was joined to the crRNA (repeat, black; spacer, red) by a tetraloop (GAAA).

FIG. 7. Schematic of CasX RNA Guided DNA Interference.

CasX binds to a tracrRNA (green) and the crRNA (black, repeat; red, spacer). Base pairing of the guide RNA to the target sequence (blue) containing the correct protospacer adjacent motif (yellow) results in double stranded cleavage of the target DNA. The depicted sequences are derived from tracrRNA and crRNA sequences for CasX1.

Example 3

Figure 8:
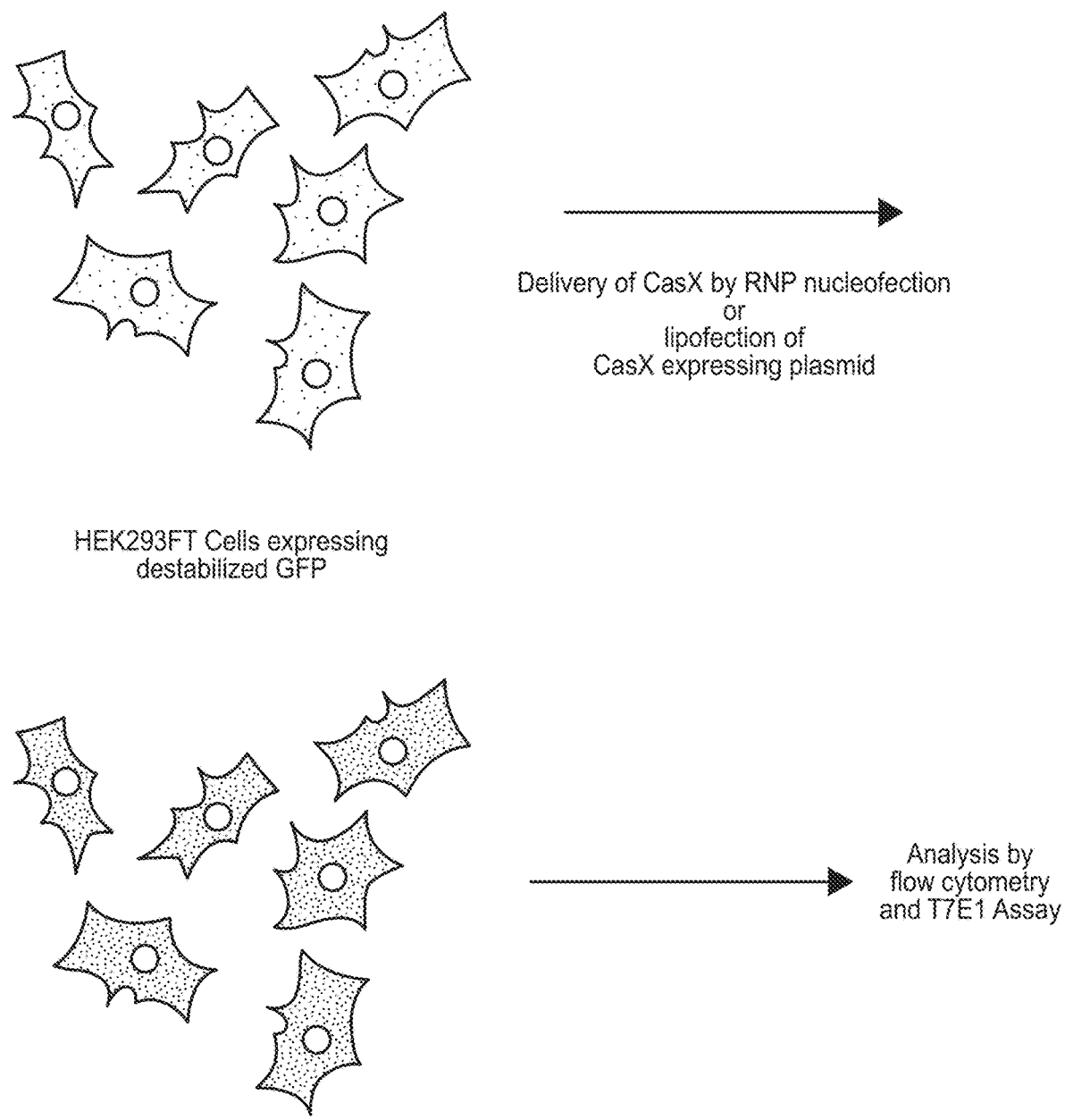
FIG. 8 presents a schematic of experimental design for one embodiment to demonstrate editing in human cells using CasX.

FIG. 8. Experimental Design for Editing Human Cells Using CasX.

HEK293 cells expressing a destabilized GFP is treated with CasX using either lipofection of plasmid expressing CasX and its guide RNA or nucleofection of CasX preassembled with its guide RNA. Successful genome cleavage will result in indels in the GFP locus causing a loss of fluorescence signal, which can be detected by flow cytometry and/or surveyor assay (e.g., T7E1 assay).

Example 4

FIG. 9. Recombinant expression and purification of CasX. CasX was fused to a maltose binding protein and was expressed in *E. coli*. The lysate was purified over Ni-NTA resin, treated with TEV, purified over a heparin column and size exclusion column. The fractions from the size exclusion column are shown with a molecular weight marker for reference. The calculated size of CasX was ~110 kDa.

Example 5

FIG. 10. Test of various tracrRNA sequences. The tracrRNA sequences tested were as follows (refer to FIG. 7 for a schematic of CasX dual guide RNA):

tracrRNA T1:
(SEQ ID NO: 24)
AAGUAGUAAAUUACAUCUGGCGCGUUUAUUCCAUUACUUUGGAGCCAGUC
CCAGCGACUAUGUCGUAUGGACGAAGCGCUUAUUUAUCGGAGA tracrRNA T2:
(SEQ ID NO: 21)
ACAUCUGGCGCGUUUAUUCCAUUACUUUGGAGCCAGUCCCAGCGACUAUG
UCGUAUGGACGAAGCGCUUAUUUAUCGGAGA tracrRNA T3:
(SEQ ID NO: 66)
UUCCAUUACUUUGGAGCCAGUCCCAGCGACUAUGUCGUAUGGACGAAGCG
CUUAUUUAUCGGAGA tracrRNA T4:
(SEQ ID NO: 67)
GUCCCAGCGACUAUGUCGUAUGGACGAAGCGCUUAUUUAUCGGAGA tracrRNA T5:
(SEQ ID NO: 68)
GAAGCGCUUAUUUAUCGGAGA In addition, the following crRNA sequences were tested for function:

crRNA 1 (Processed version of crRNA-was active in both sgRNA and dual guide format):
(SEQ ID NO: 61)
CCGAUAAGUAAAACGCAUCAAAGNNNNNNNNNNNNNNNNNNNN crRNA 2 (was active in dual guide format):
(SEQ ID NO: 62)
AUUUGAAGGUAUCUCCGAUAAGUAAAACGCAUCAAAGNNNNNNNNNNNN
NNNNNNNNNNNNNNNNNNNN In addition, the following sgRNA sequences were tested for function (refer to 6 and 7 for a schematic representation of CasX guide RNA):

sgRNA1 (was active, sense, processed):
(SEQ ID NO: 42)
ACAUCUGGCGCGUUUAUUCCAUUACUUUGGAGCCAGUCCCAGCGACUAUG UCGUAUGGACGAAGCGCUUAUUUAUCGGAGAgaaaCCGAUAAGUAAAACG

CAUCAAAGNNNNNNNNNNNNNNNNNNNN sgRNA2 (was inactive, sense, preprocessing, the underlined sequences are different relative to sgRNA1):
(SEQ ID NO: 63)
<u>AAGUAGUAAAUU</u>ACAUCUGGCGCGUUUAUUCCAUUACUUUGGAGCCAGUC CCAGCGACUAUGUCGUAUGGACGAAGCGCUUAUUUAUCGGAGA<u>UAGCUCC</u> gaaa<u>AUUUGAAGGUAUCU</u>CCGAUAAGUAAAACGCAUCAAAGNNNNNNNNNN

NNNNNNNNNNNNNNNNNNNNNN sgRNA3 (was inactive, antisense, processed):
(SEQ ID NO: 64)
NNNNNNNNNNNNNNNNNNNNCUUUGAUGCGUUUUACUUAUCGGgaaaUCU

CCGAUAAAUAAGCGCUUCGUCCAUACGACAUAGUCGCUGGGACUGGCUCC

AAAGUAAUGGAAUAAACGCGCCAGAUGU sgRNA4 (was inactive):
(SEQ ID NO: 65)
NNNNNNNNNNNNNNNNNNNNNNNNNNNNNNNNNCUUUGAUGCGUUUUACUUAU CGGAGAUACCUUCAAAUgaaaGGAGCUAUCUCCGAUAAAUAAGCGCUUCG

UCCAUACGACAUAGUCGCUGGGACUGGCUCCAAAGUAAUGGAAUAAACGC

GCCAGAUGUAAUUUACUACUU

Example 6

FIG. 11.

The CasX system (CasX protein and guide RNA) was tested for function in bacterial cells at room temperature and at 37° C. Colony forming units (cfu) per μg of transformed plasmid were assayed for plasmids containing a target or non-target sequence. The assay was performed at either room temperature or 37° C. The data show that the CasX system functioned to a similar extent at either room temperature or 37° C.

Example 7—Archaeal Cas9

FIGS. 12A-12E.

Figure 12E:
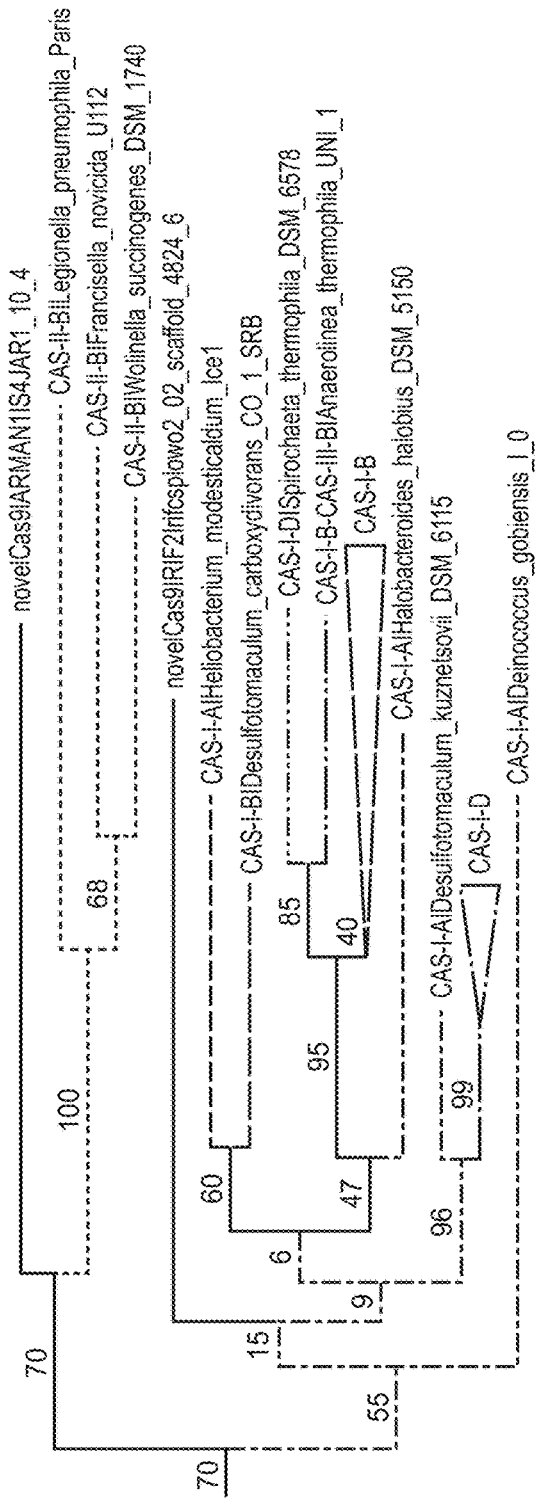

ARMAN-1 type II CRISPR-cas system. FIG. 12A, ARMAN-1 CRISPR-Cas locus outline. FIG. 12B Strong preference to NGG 3' PAM was inferred from analysis of 240 protospacers. FIG. 12C Reconstruction of CRISPR arrays in ARMAN-1 genomes sampled from Richmond Mine ecosystem. Green arrows indicate repeats and colored arrows indicate CRISPR spacers (identical spacers are colored the same whereas unique spacers are colored in black). The contigs (grey bars) are aligned based on the order of the spacers on the metagenomic contigs. The grey background indicates the conserved and presumably old region of the array. In CRISPR systems, spacers are typically added undirectionally so the high variety of spacers in the left side of the locus indicates that the left side is where recent acquisition has occurred. The presence of a diversity of recently acquired spacers as well as the preservation of repeat and spacer sequences in genome fragments assembled from datasets collected from different sites and at different times indicated that the system is active. FIG. 12D Phylogeny of the ARMAN-1 Cas9 clustered it together with the ARMAN-4 Cas9 and two new bacterial Cas9s first reported here (black). These Cas9s seem to be evolutionary related to Type II-C systems, even though the loci contain Cas4, typically found in Type II-B systems. FIG. 12E Phylogeny of the ARMAN-1 Cas1 clustered it with a different set of Type II-B. Combined, the phylogenetic trees in FIGS. 12D-12E suggest the ARMAN-1 Type II system might be the result of recombination of Type II-B and II-C CRSIPR-Cas systems.

FIGS. 14A-14B.

(TOP panel) Predicted secondary structures of crRNA:tracrRNA dual-guide RNA for ARMAN-1 Cas9. Secondary structure and base-pairing between the crRNA (top strand) and predicted tracrRNA sequences of varying lengths (bottom strand) are depicted. The "crRNA" represents the direct repeat sequence from ARMAN-1 while the $N_{20}$ in green is a user-defined sequence (guide sequence). TracrRNA-69 is shown in red while tracrRNA-104 and tracrRNA-179 are extended by the blue and pink sequences, respectively. (BOTTOM panel) Predicted structures of an example single-guide RNA for ARMAN-1 Cas9. Secondary structures of sgRNA is depicted. The "Targeter" represent a partial direct repeat (truncated) and the engineered tetraloop (linker), connecting the targeter to the activator (also truncated). The $N_{20}$ in green is a user-defined sequence (guide sequence). SgRNA including tracrRNA-69, tracrRNA-104, and tracrRNA-179 are depicted.

FIG. 15.

(TOP panel) Predicted secondary structures of crRNA: tracrRNA dual-guide RNA for ARMAN-4 Cas9. Secondary structure and base-pairing between the crRNA (top strand) and predicted tracrRNA sequences (bottom strand) are depicted. The "crRNA" represents the direct repeat sequence from ARMAN-4 while the $N_{20}$ in green is a user-defined sequence (guide sequence). (BOTTOM panel) Predicted structure of an example single-guide RNA for ARMAN-4 Cas9. Secondary structures of sgRNA is depicted. The "Targeter" represent a partial direct repeat (truncated) and the engineered tetraloop (linker), connecting the targeter to the activator (also truncated). The $N_{20}$ in green is a user-defined sequence (guide sequence).

Example 8: New CRISPR-Cas Systems from Uncultivated Microbes

CRISPR-Cas adaptive immune systems have revolutionized genome engineering by providing programmable enzymes capable of site-specific DNA cleavage. However, current CRISPR-Cas technologies are based solely on systems from cultured bacteria, leaving untapped the vast majority of enzymes from organisms that have not been isolated. The data provided herein show, using cultivation-independent genome-resolved metagenomics, identification of new CRISPR-Cas systems, including the first reported Cas9 in the archaeal domain of life. This divergent Cas9 enzyme was found in little-studied nanoarchaea as part of an active CRISPR-Cas system. In bacteria, two previously unknown systems were discovered, CRISPR-CasX and CRISPR-CasY, which are among the most streamlined systems yet identified. Notably, all required functional components were identified by metagenomics, which allowed validation of robust RNA-guided DNA interference activity in *E. coli*. The data herein show that interrogation of environmental microbial communities combined with experiments in living cells allows access to an unprecedented diversity of genomes whose content will expand the repertoire of microbe-based biotechnologies.

Results

Figure 18A:
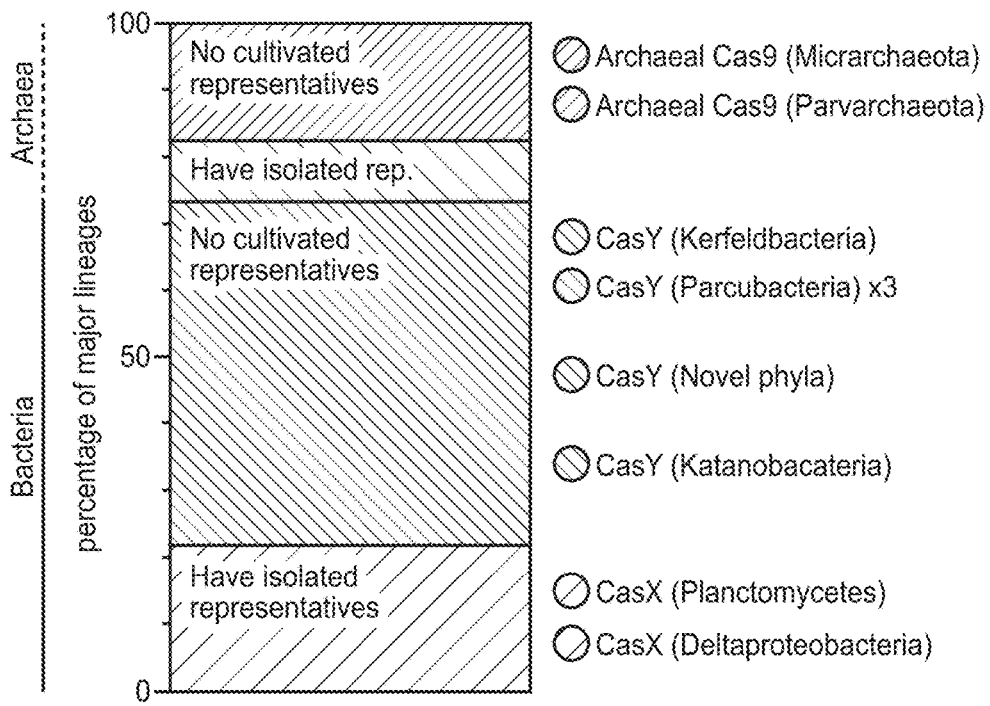
FIGS. 18A-18B present novel identified CRISPR-Cas systems from uncultivated organisms.
Figure 18B:
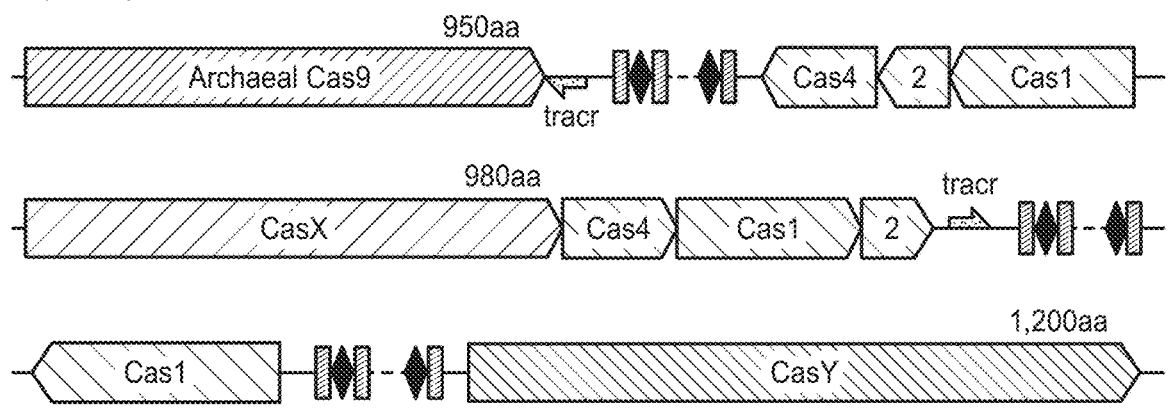

Terabase-scale metagenomic datasets from groundwater, sediment, and acid mine drainage microbial communities were analyzed, seeking class 2 CRISPR-Cas systems that are not represented among cultured organisms. The first Cas9 proteins in domain Archaea were identified and two new CRISPR-Cas systems were discovered, CRISPR-CasX and CRISPR-CasY, in uncultivated bacteria (FIGS. 18A-18B). Notably, both the archaeal Cas9 and CasY were encoded exclusively in the genomes of organisms from lineages with no known isolated representatives.

First Identification of Archaeal Cas9

One of the hallmarks of CRISPR-Cas9 was its presumed presence only in the bacterial domain. It was therefore surprising to discover Cas9 proteins encoded in genomes of the nanoarchaea ARMAN-1 (Candidatus Micrarchaeum acidiphilum ARMAN-1) and ARMAN-4 (Candidatus Parvarchaeum acidiphilum ARMAN-4) in acid-mine drainage (AMD) metagenomic datasets. These findings expand the occurrence of Cas9-containing CRISPR systems to another domain of life.

The ARMAN-4 cas9 gene was found in 16 different samples in the same genomic context, but with no other adjacent cas genes (despite being centrally located in several DNA sequence contigs >25 kbp), and with only one adjacent CRISPR repeat-spacer unit (FIGS. 24A-24D). The lack of a typical CRISPR array and cas1, which encodes the universal CRISPR integrase, points to a system with no capacity to acquire new spacers. No target could be identified for the spacer sequence, but given the conservation of the locus in samples collected over several years, its function in a "single-target" CRISPR-Cas system cannot be ruled out at this time.

Conversely, the CRISPR-Cas locus in ARMAN-1, recovered from 15 different samples, includes large CRISPR arrays adjacent to cas1, cas9, cas4 and cas9 genes. Numerous alternative ARMAN-1 CRISPR arrays with a largely conserved end (likely comprised of the oldest spacers) and a variable region into which many distinct spacers have been incorporated were reconstructed (FIG. 194a and FIGS. 25A-25F). Based on this hypervariability in spacer content, these data show that the ARMAN-1 CRISPR-Cas9 system is active in the sampled populations.

Figure 19A:
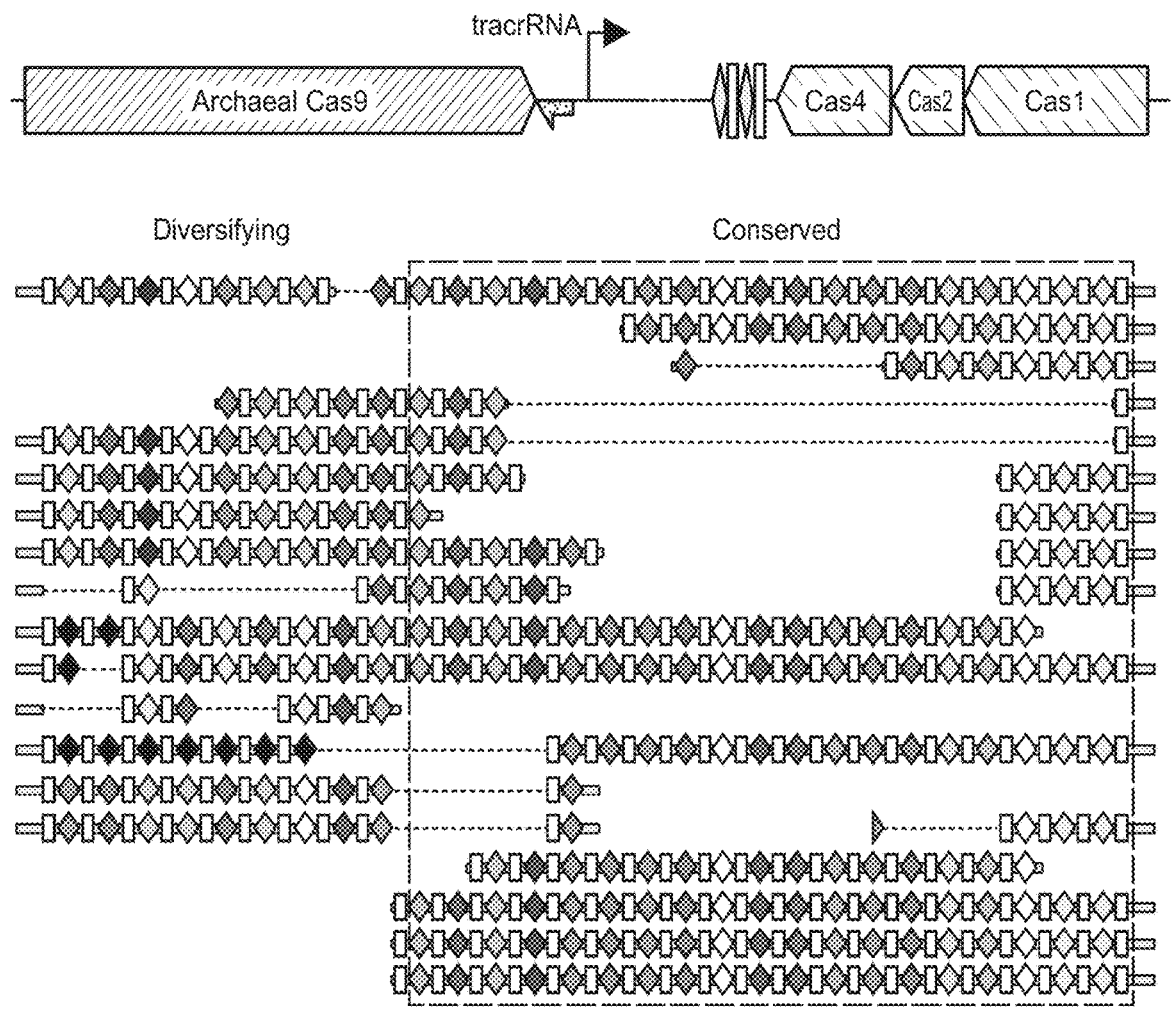
FIGS. 19A-19C present ARMAN-1 CRISPR array diversity and identification of the ARMAN-1 Cas9 PAM sequence.
Figure 19B:
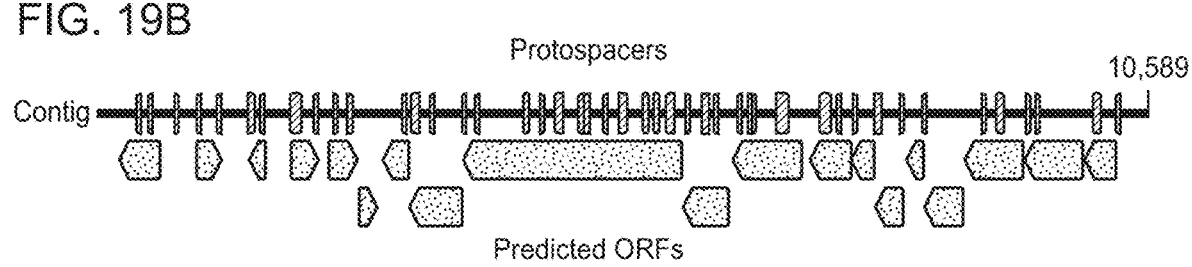
Figure 19C:
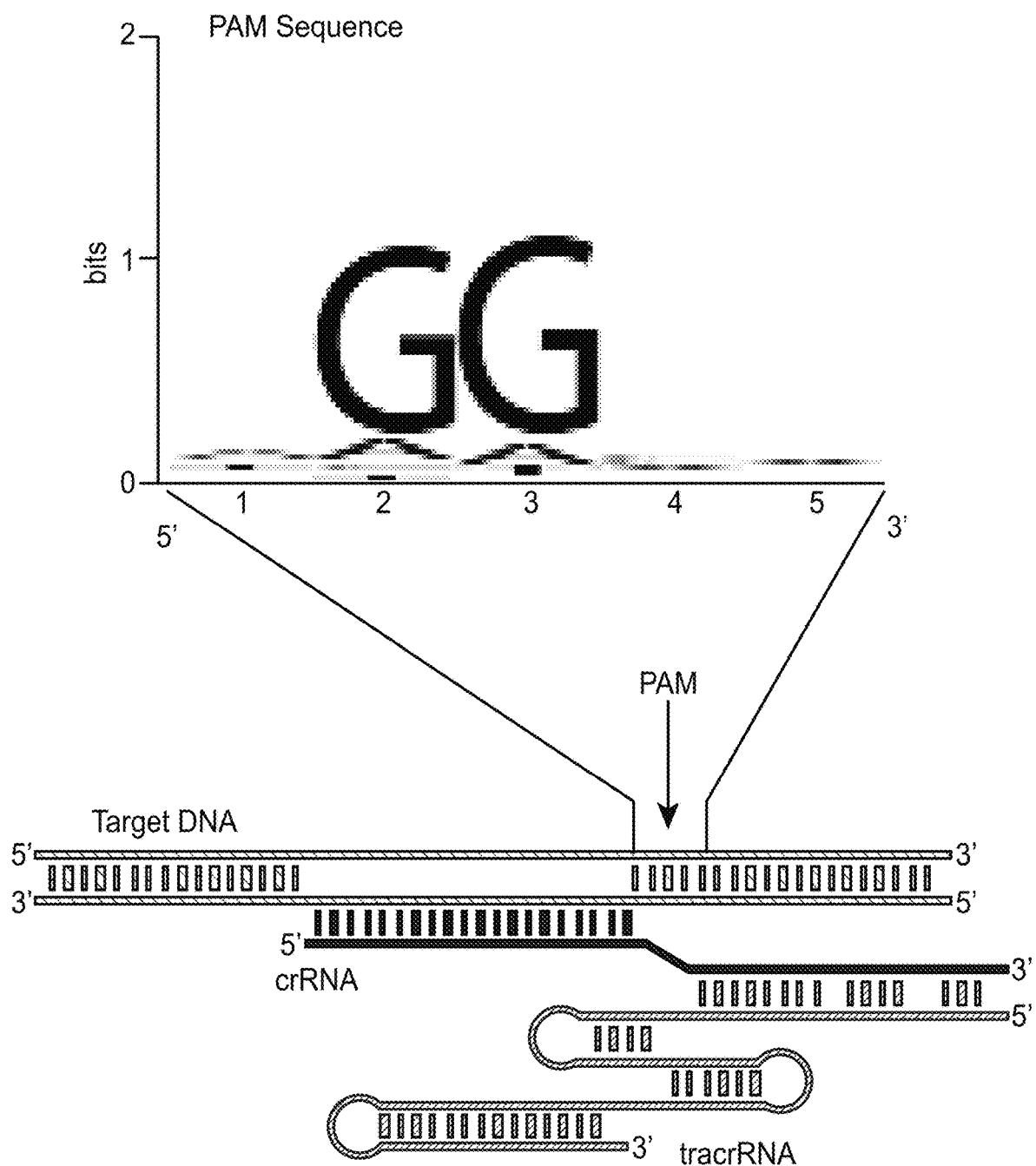
Figure 26A:
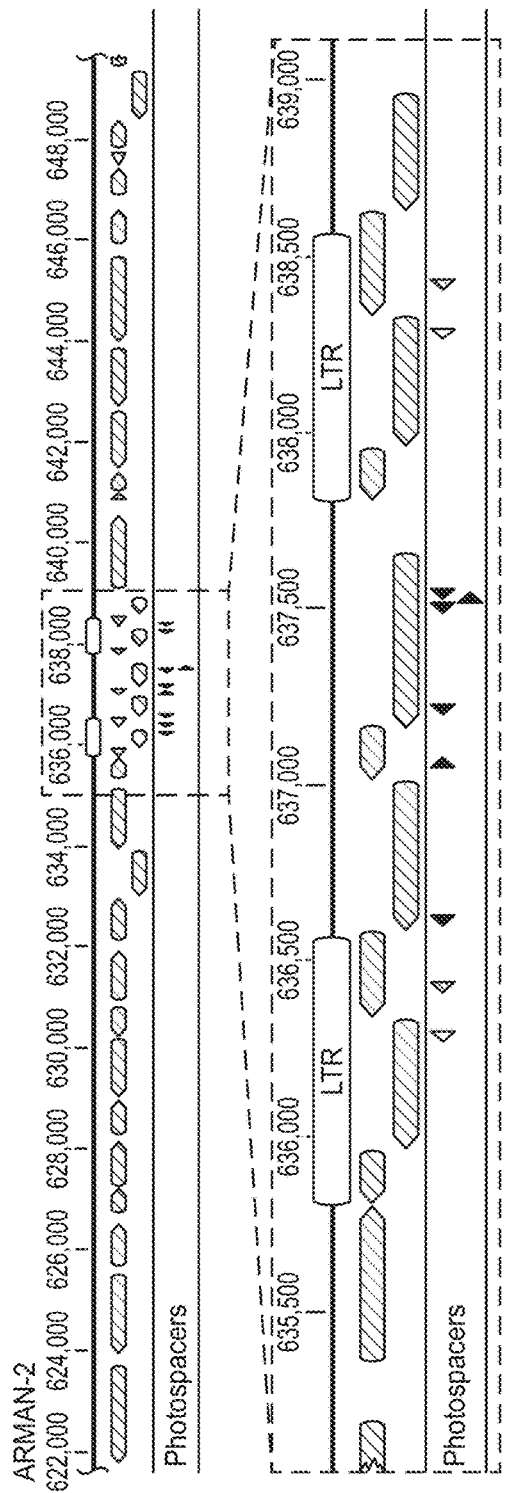
FIGS. 26A-26B show that ARMAN-1 spacers map to genomes of archaeal community members.
Figure 26B:
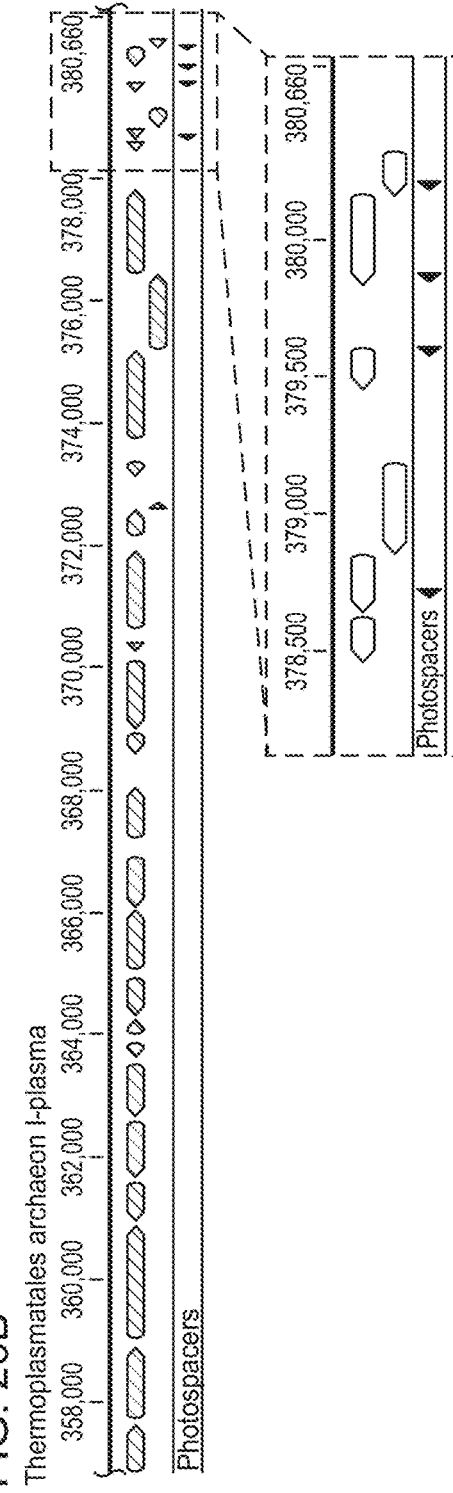

Remarkably, 56 of the putative spacer targets (protospacers) of the ARMAN-1 CRISPR-Cas9 system were located on a single 10 kbp genome fragment that is likely an ARMAN-1 virus, given that it encodes a high density of short hypothetical proteins (FIG. 19B). Indeed, cryo-electron tomographic reconstructions often identified viral particles attached to ARMAN cells. ARMAN-1 protospacers also derived from a putative transposon within the genome of ARMAN-2 (another nanoarchaeon) and a putative mobile element in the genomes of *Thermoplasmatales* archaea, including that of I-plasma from the same ecosystem (FIG. 26). Direct cytoplasmic "bridges" were observed between ARMAN and Thermoplasmatales cells, implying a close relationship between them. The ARMAN-1 CRISPR-Cas9 may thus defend against transposon propagation between these organisms, a role that is reminiscent of piRNA-mediated defense against transposition in the eukaryotic germ line.

Figure 27A:
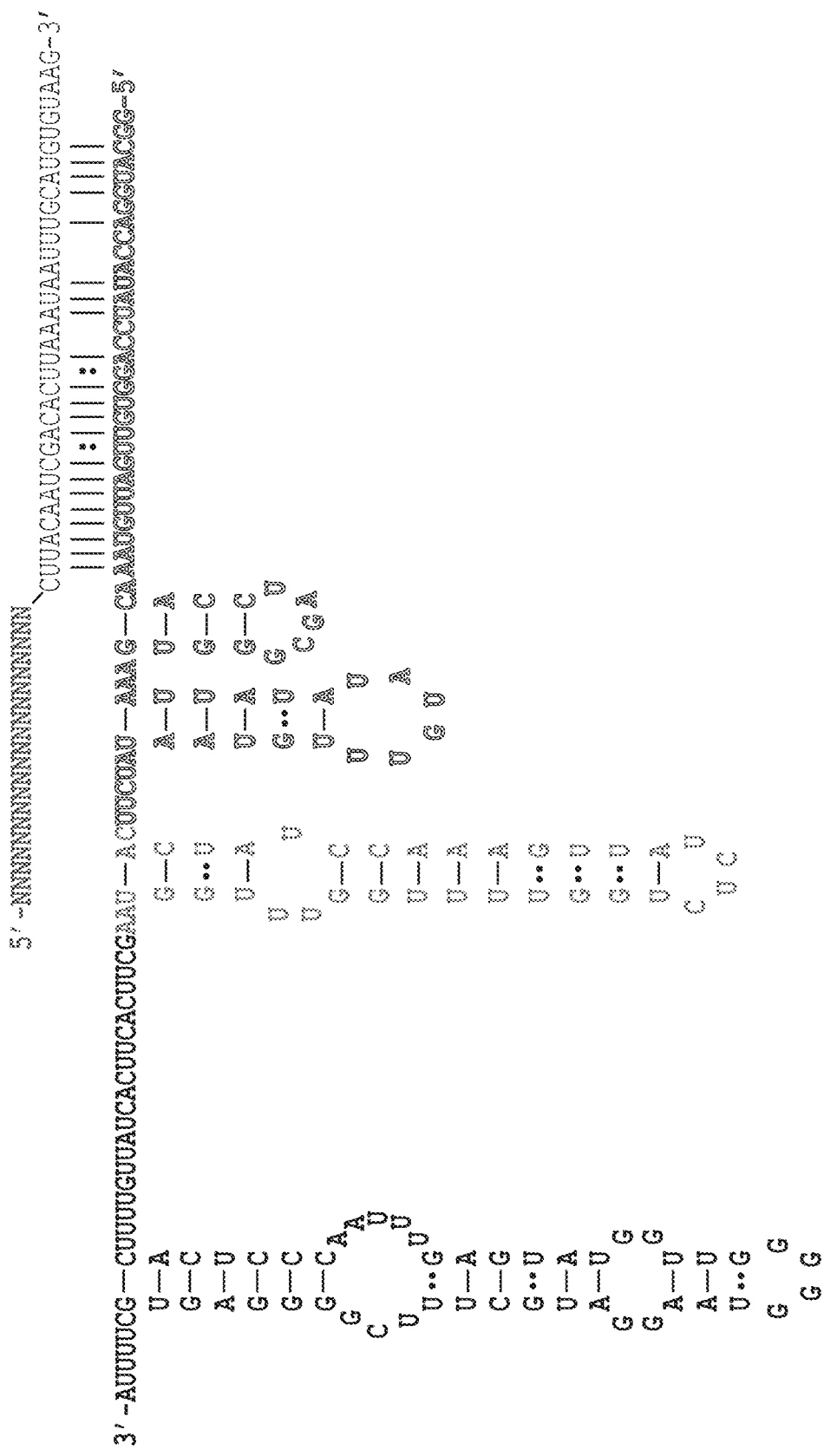
Figure 27B:
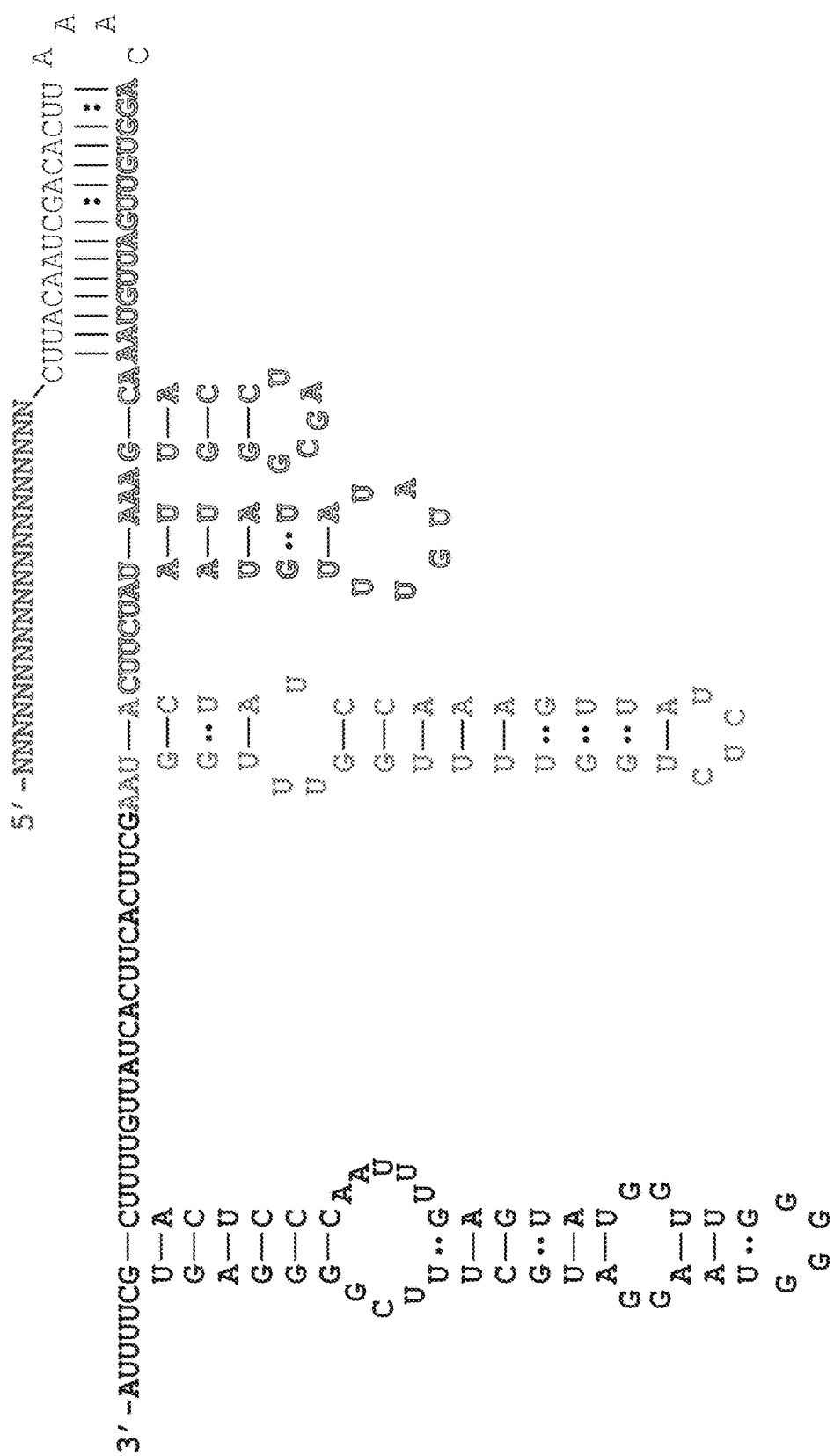

Active DNA-targeting CRISPR-Cas systems use 2 to 4 bp protospacer-adjacent motifs (PAMs) located next to target sequences for self versus non-self discrimination. Examining sequences adjacent to the genomic target sequences indeed revealed a strong 'NGG' PAM preference in ARMAN-1 (19c). Cas9 also employs two separate transcripts, CRISPR RNA (crRNA) and trans-activating CRISPR RNA (tracrRNA), for RNA-guided DNA cleavage. A putative tracrRNA was identified in the vicinity of both ARMAN-1 and ARMAN-4 CRISPR-Cas9 systems (FIG. 27). Previously, it was suggested that type II CRISPR systems were absent in archaea due to a lack of the host factor, RNase III, responsible for crRNA-tracrRNA guide complex maturation. Notably, no RNase III homologs have been identified in the ARMAN-1 genome (estimated to be 95% complete) and no internal promoters are predicted for the CRISPR array, suggesting an as-yet undetermined mechanism of guide RNA production. Biochemical experiments to test cleavage activity of ARMAN-1 and ARMAN-4 Cas9 proteins purified from both *E. coli* and yeast and in vivo *E. coli* targeting assays did not reveal any detectable activity (see FIG. 32 and FIGS. 28A-28B).

CRISPR-CasX is a New Dual-RNA-Guided CRISPR System

Figure 29:
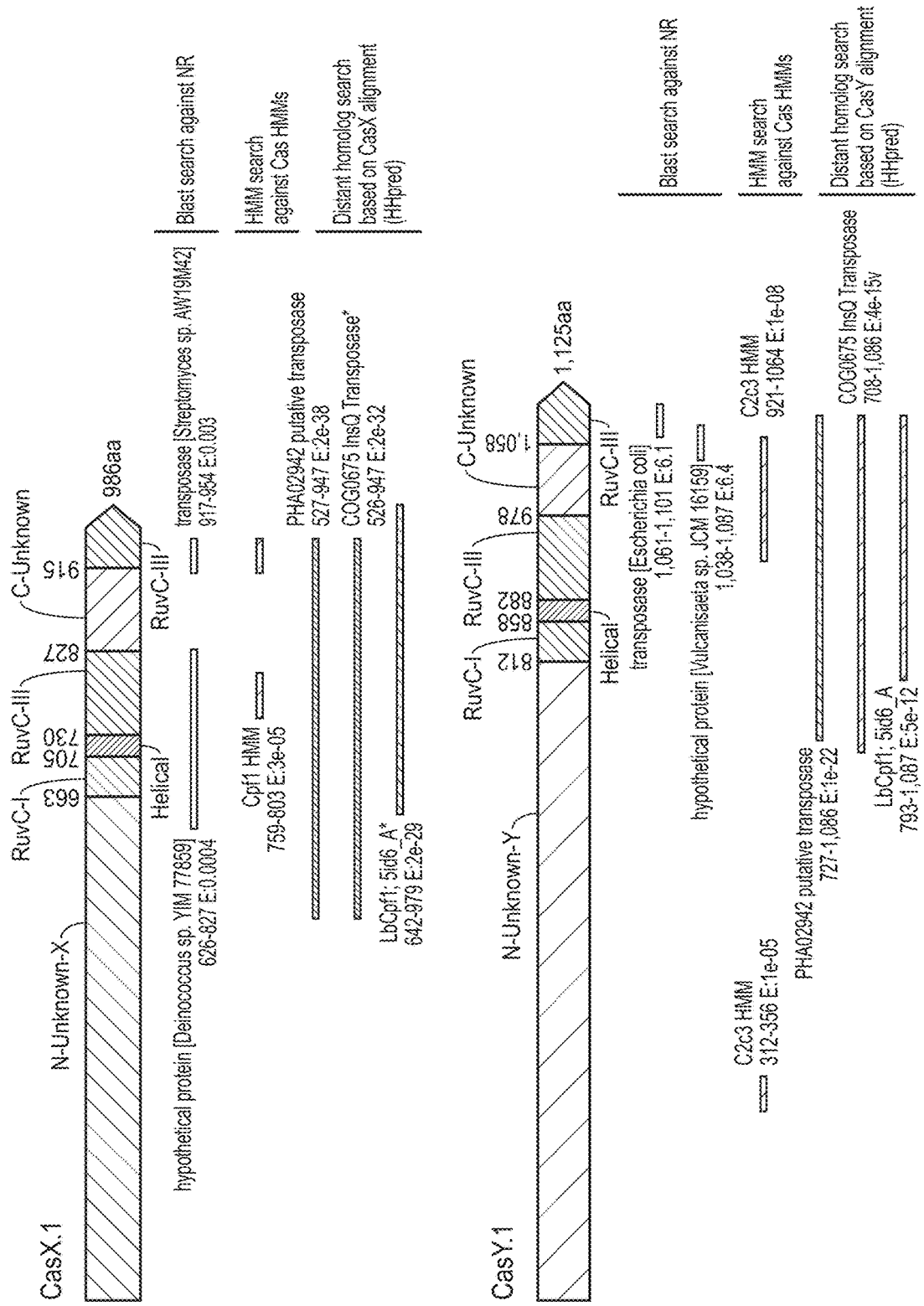
FIG. 29 presents newly identified CRISPR-Cas systems compared to known proteins. Similarity of CasX and CasY to known proteins based on the following searches: (1) Blast search against the non-redundant (NR) protein database of NCBI, (2) Hidden markov model (HMM) search against an HMM database of all known proteins and (3) distant homology search using HHpree.
Figure 30A:
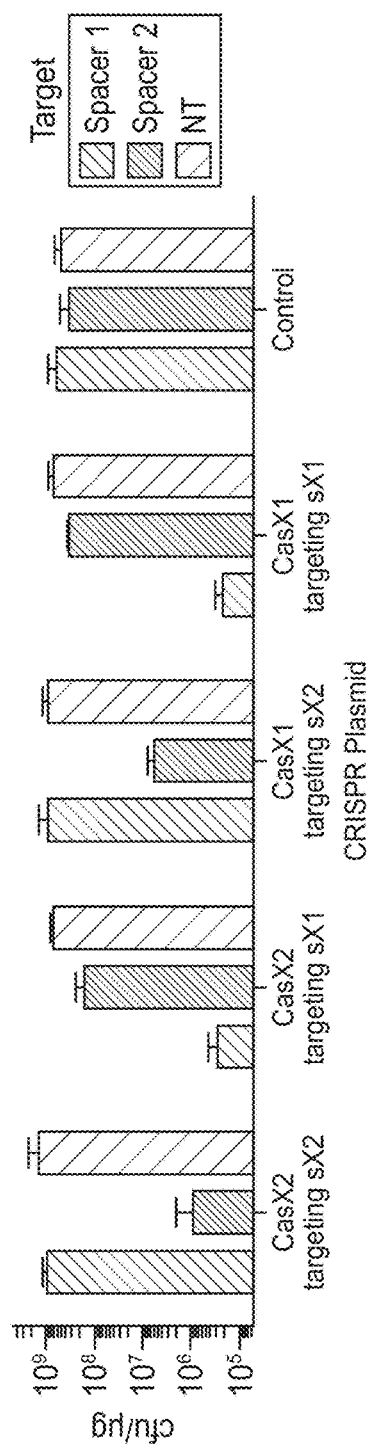
FIGS. 30A-30F presents-data related to programmed DNA interference by CasX.
Figure 30B:
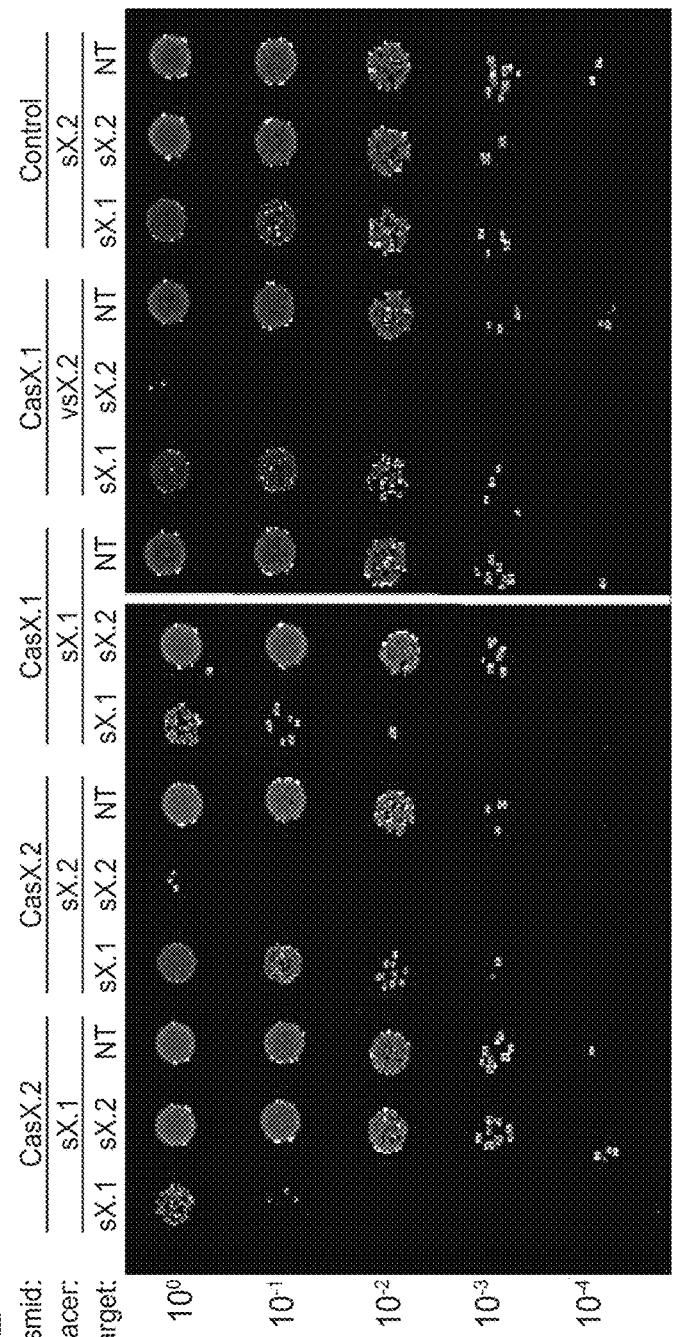
Figure 30C:
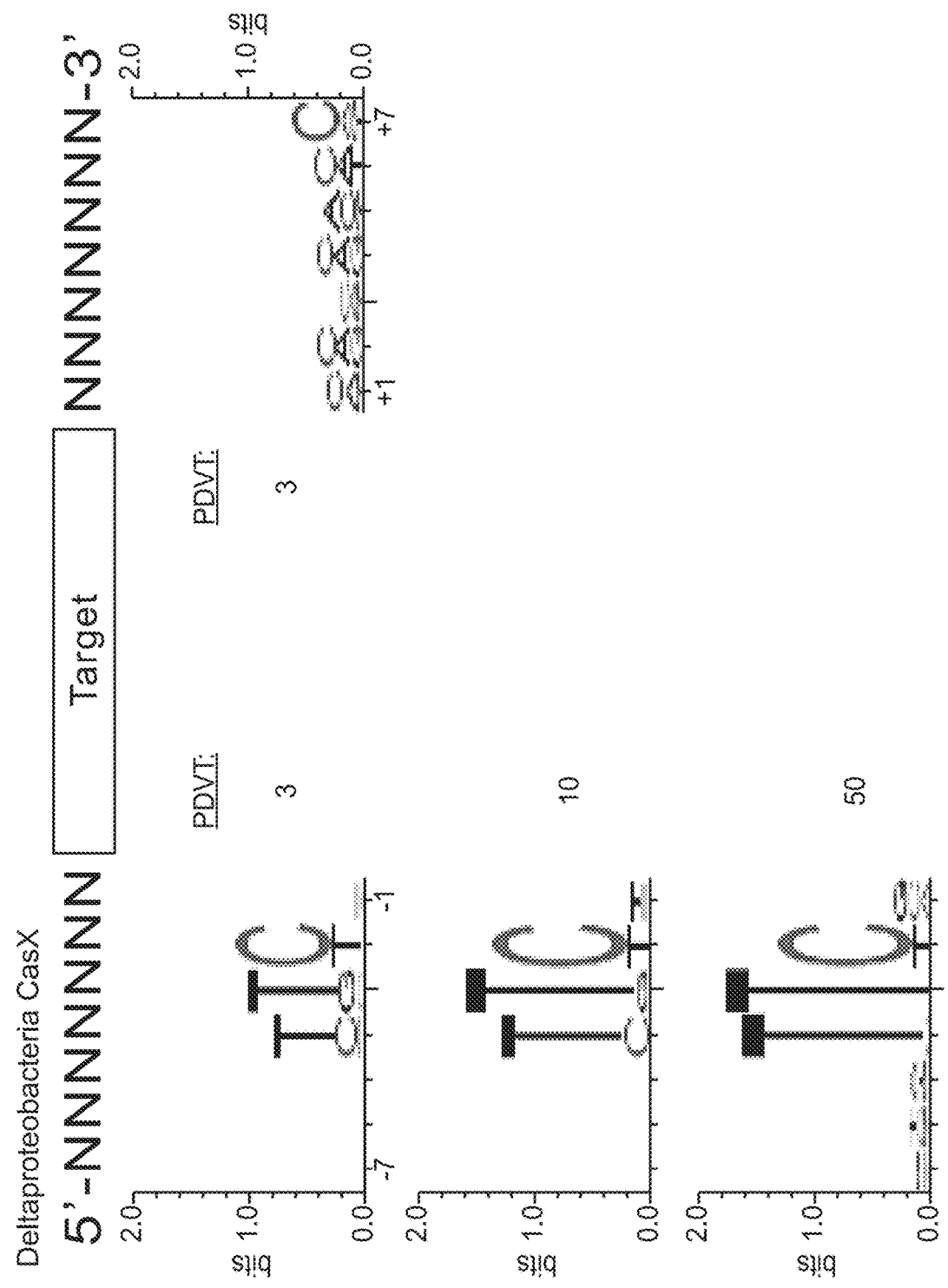
Figure 30D:
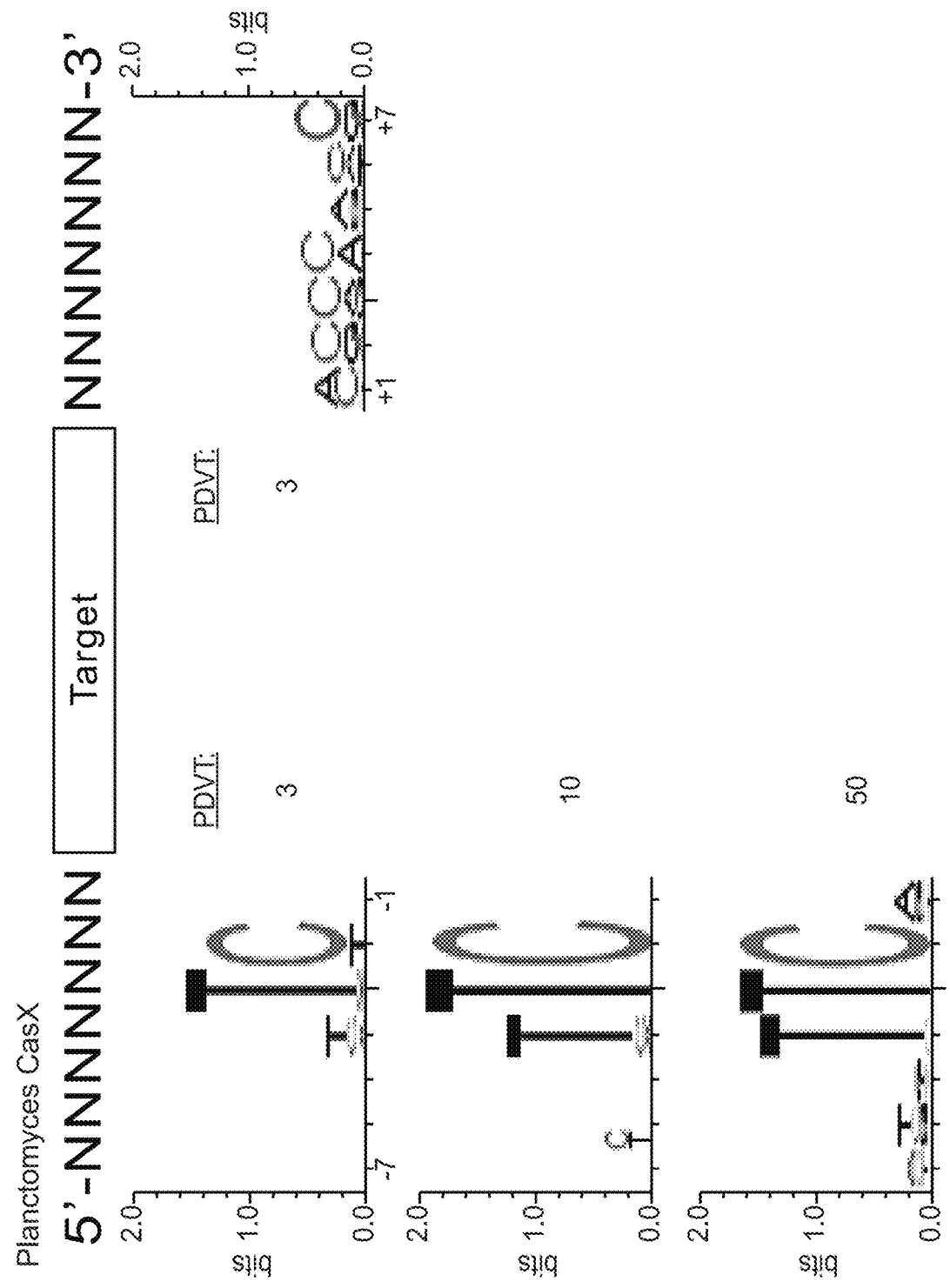
Figure 30E:
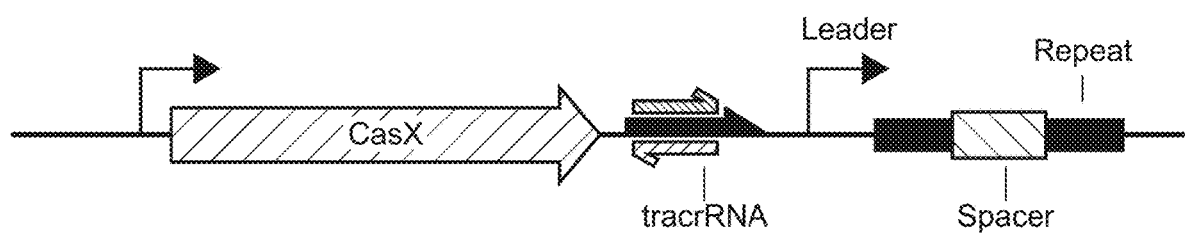
Figure 30F:
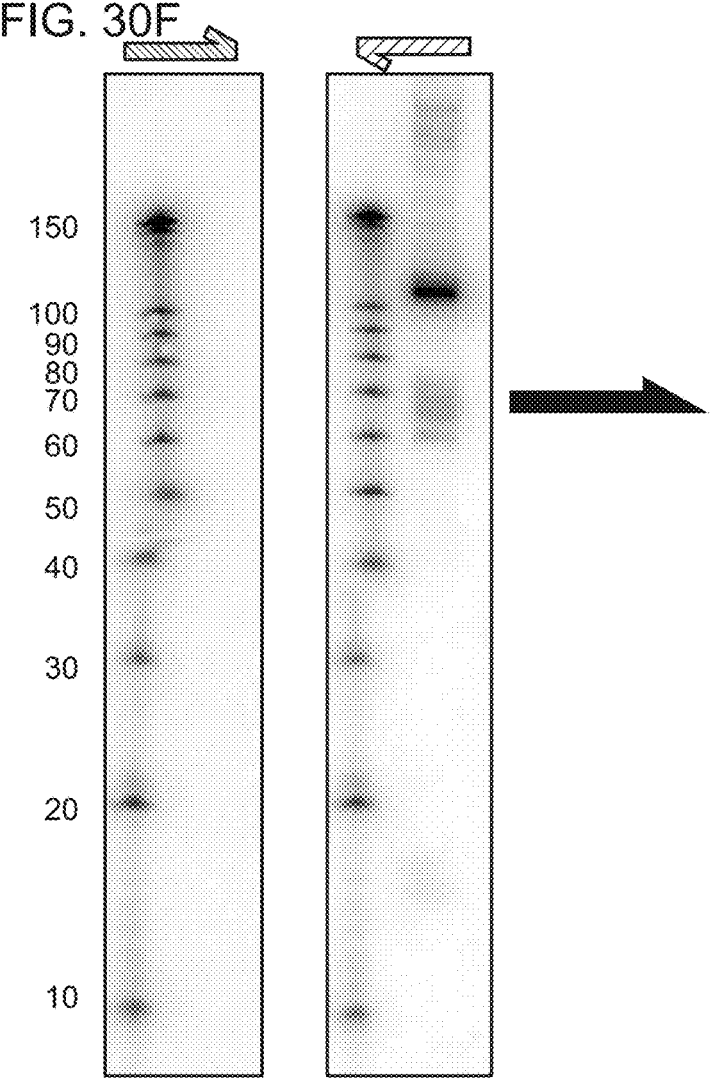

In addition to Cas9, only three families of class 2 Cas effector proteins have been discovered and experimentally validated: Cpf1, C2c1, and C2c2. Another gene, c2c3, which was identified only on small DNA fragments, has been suggested to also encode such a protein family. A new type of class 2 CRISPR-Cas system was found in the genomes of two bacteria recovered repeatedly from groundwater and sediment samples. The high conservation of this system in two organisms belonging to different phyla, Deltaproteobacteria and Planctomycetes, suggests a recent cross-phyla transfer. This newly described system includes Cas1, Cas2, Cas4 and an uncharacterized ~980 aa protein, referred to herein as CasX. The CRISPR arrays associated with each CasX had highly similar repeats of 37 base pairs, spacers of 33-34 base pairs, and a putative tracrRNA between the Cas operon and the CRISPR array (FIG. 18B). BLAST searches revealed only weak similarity (e-value >$1\times10^{-4}$) to transposases, with similarity restricted to specific regions of the CasX C-terminus. Distant homology detection and protein modeling identified a RuvC domain near the CasX C-terminal end, with organization reminiscent of that found in type V CRISPR-Cas systems (FIG. 29). The rest of the CasX protein (630 N-terminal amino acids) showed no detectable similarity to any known protein, suggesting this is a novel class 2 effector. The combination of tracrRNA and separate Cas1, Cas2 and Cas4 proteins is unique among type V systems. Further, CasX is considerably smaller than any known type V proteins: 980 aa compared to a typical size of larger than 1,200 aa for Cpf1, C2c1 and C2c3.

Figure 20B:
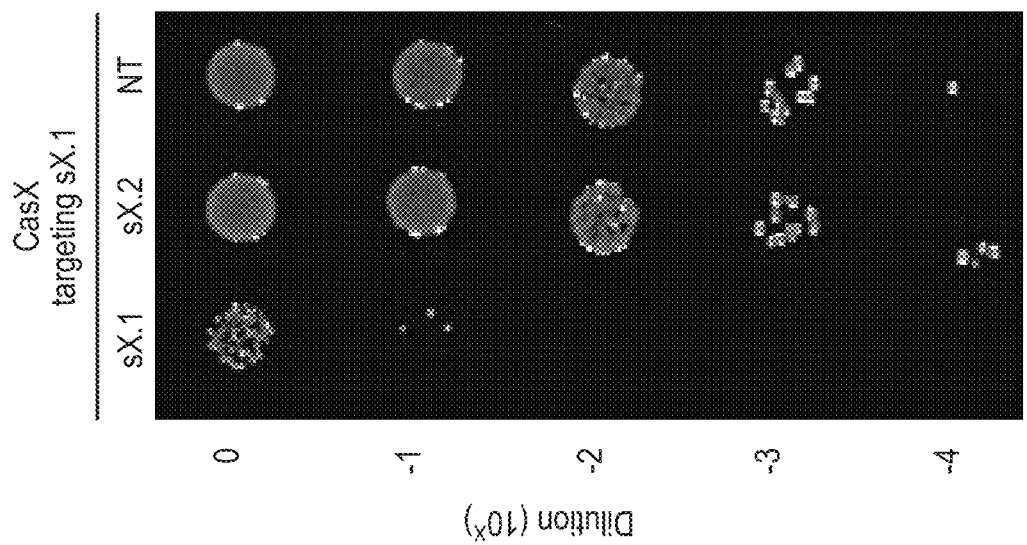
FIGS. 20A-20D present data showing that CasX mediates programmable DNA interference in *E. coli*.
Figure 20A:
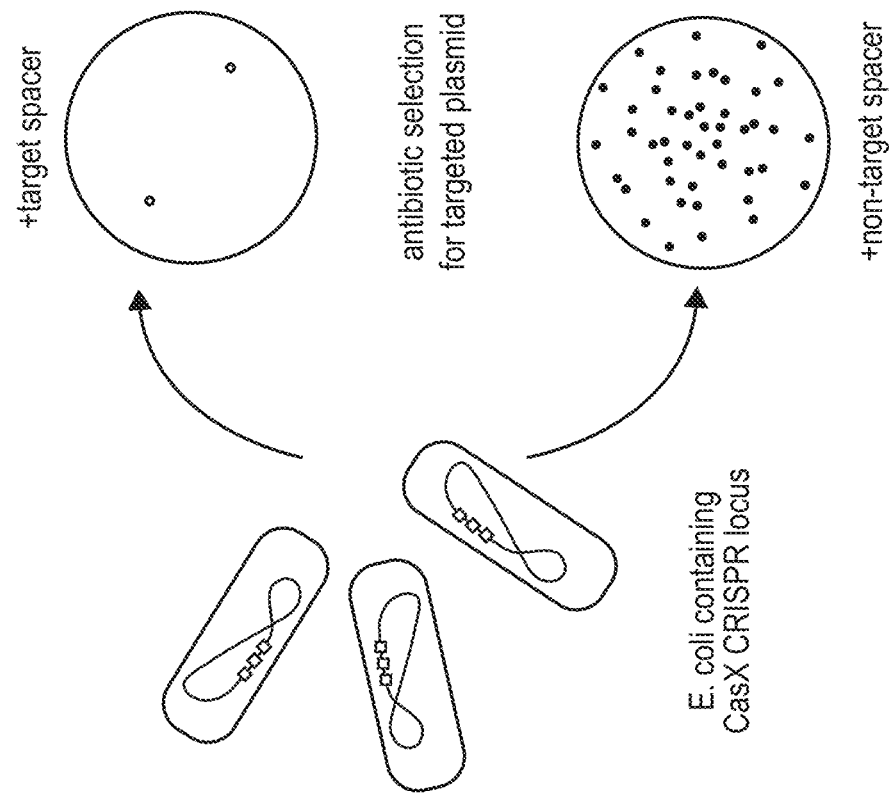
Figure 20C:
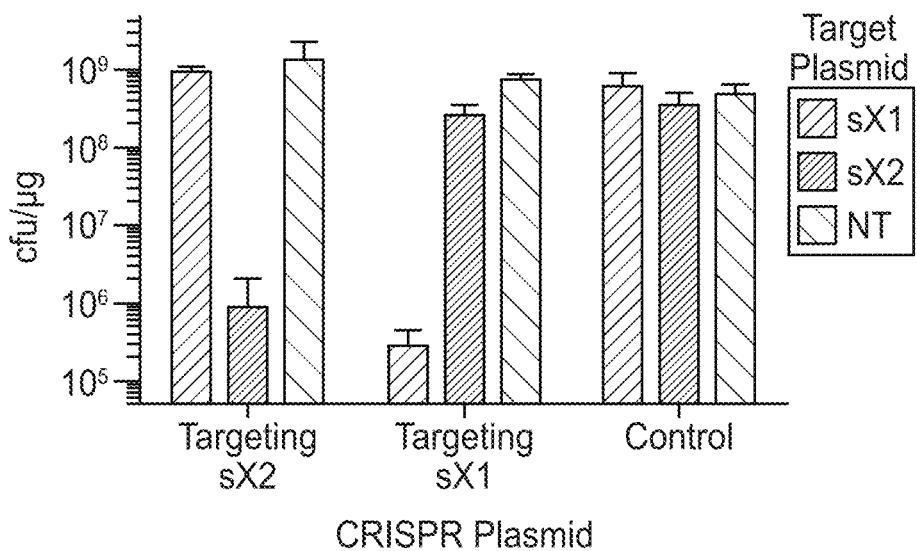
Figure 20D:
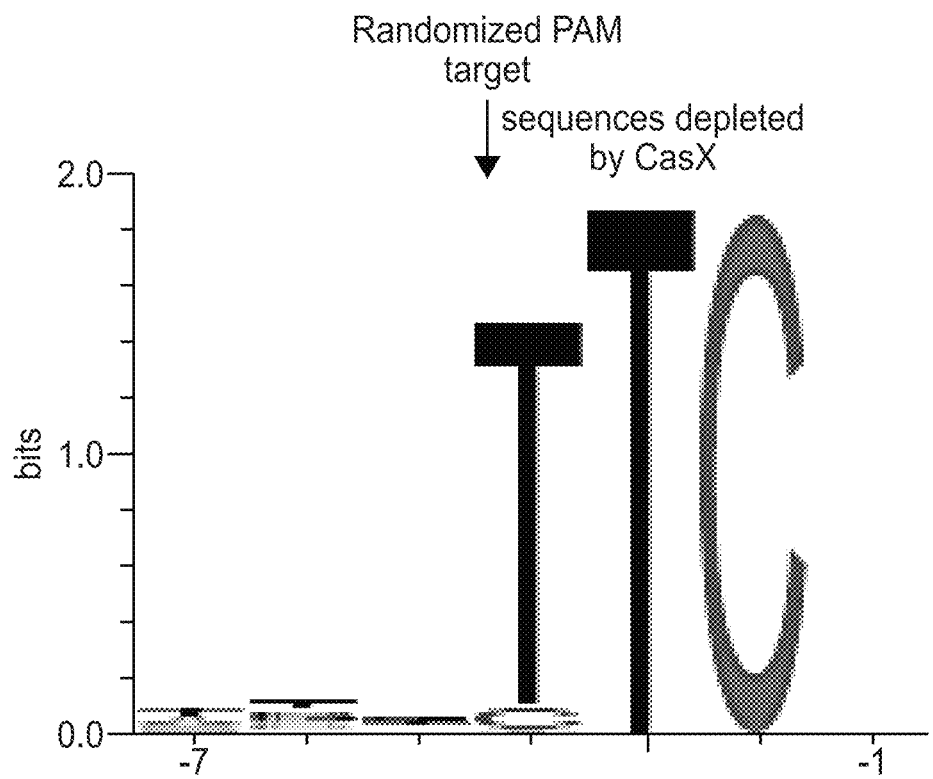

It was next wondered whether, despite its small size and non-canonical locus content, CasX would be capable of RNA-guided DNA targeting analogous to Cas9 and Cpf1 enzymes. To test this possibility, a plasmid encoding a minimal CRISPR-CasX locus including casX, a short repeat-spacer array and intervening noncoding regions was synthesized. When expressed in E. coli, this minimal locus blocked transformation by a plasmid bearing a target sequence identified by metagenomic analysis (FIG. 20A-20C, FIGS. 30A-30F). Furthermore, interference with transformation occurred only when the spacer sequence in the mini-locus matched the protospacer sequence in the plasmid target. To identify a PAM sequence for CasX, the transformation assay was repeated in E. coli using a plasmid containing either a 5' or 3' randomized sequence adjacent to the target site. This analysis revealed a stringent preference for the sequence 'TTCN' located immediately 5' of the protospacer sequence (FIG. 20D). No 3' PAM preference was observed (FIGS. 30A-30F). Consistent with this finding, 'TTCA' was the sequence found upstream of the putative Deltaproteobacteria CRISPR-CasX protospacer that was identified in the environmental samples. Notably, both CRISPR-CasX loci share the same PAM sequence, in line with their high degree of CasX protein homology.

Figure 21A:
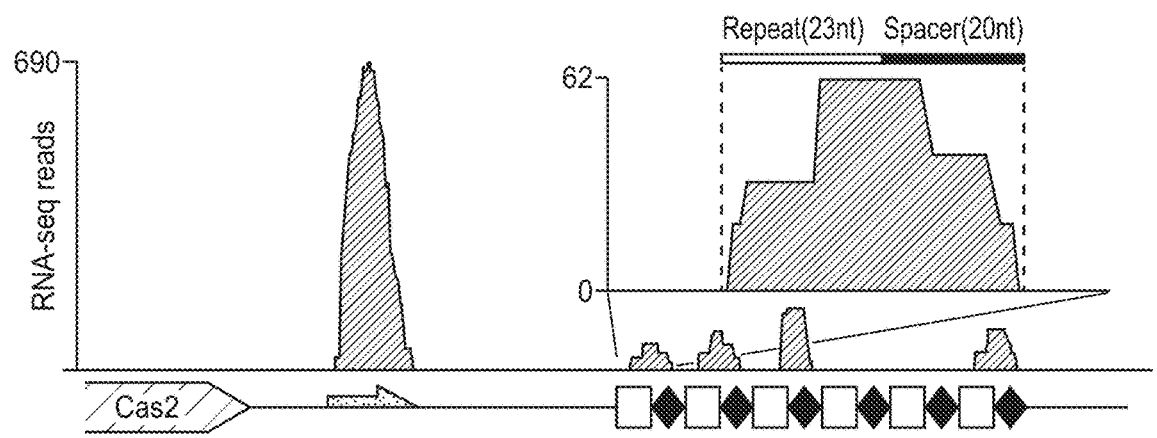
FIGS. 21A-21C present data showing CasX is a dual-guided CRISPR complex.
Figure 21B:
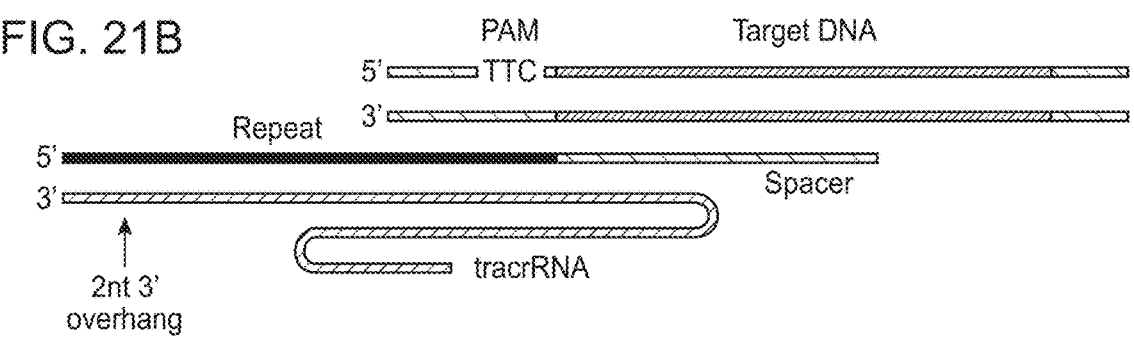
Figure 21C:
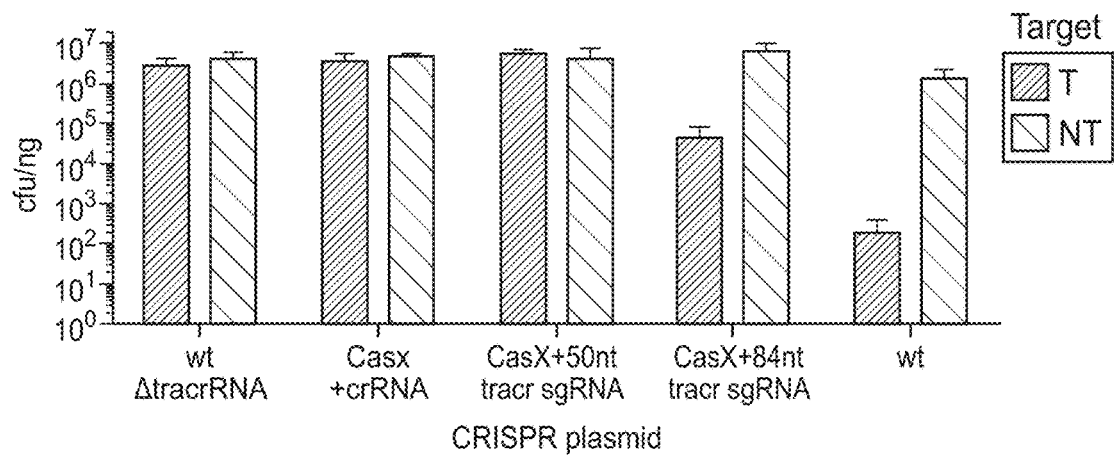

Examples of both single-RNA and dual-RNA guided systems exist among type V CRISPR loci. Environmental meta-transcriptomic data was used to determine whether CasX requires a tracrRNA for DNA targeting activity. This analysis revealed a non-coding RNA transcript with a sequence complementary to the CRISPR repeat encoded between the Cas2 open reading frame and the CRISPR array (FIG. 21A). To check for expression of this non-coding RNA in E. coli expressing the CasX locus, Northern blots were conducted against this transcript in both directions (FIGS. 30A-30F). The results showed expression of a transcript of ~110 nt encoded on the same strand as the casX gene, with a more heterogeneous transcript of ~60-70 nt, suggesting that the leader sequence for the CRISPR array lies between the tracrRNA and the array. Transcriptomic mapping further suggests that the CRISPR RNA (crRNA) is processed to include 22 nts (or about 23 nt) of the repeat and 20 nts of the adjacent spacer, similar to the crRNA processing that occurs in CRISPR-Cas9 systems (FIG. 21A). Furthermore, a 2-nt 3' overhang was identified, consistent with RNase 1E-mediated processing of the crRNA-tracrRNA duplex FIG. 21B). To determine the dependence of CasX activity on the putative tracrRNA, this region was deleted from the minimal CRISPR-CasX locus described above, and the plasmid interference assays were repeated. Deletion of the putative tracrRNA-encoding sequence from the CasX plasmid abolished the robust transformation interference observed in its presence (FIG. 21C). This putative tracrRNA was joined with the processed crRNA using a tetraloop to form a single-guide RNA (sgRNA). While expression using a heterologous promoter of the crRNA alone or a shortened version of the sgRNA did not have any significant plasmid interference, expression of the full-length sgRNA conferred resistance to plasmid transformation (FIG. 21C). Together, these results establish CasX as a new functional DNA-targeting, dual-RNA guided CRISPR enzyme. These results further demonstrate that CasX can function as a single-RNA guided CRISPR enzyme.

CRISPR-CasY, a System Found Exclusively in Bacterial Lineages Lacking Isolates

Another new class 2 Cas protein encoded in the genomes of certain candidate phyla radiation (CPR) bacteria was identified. These bacteria typically have small cell sizes (based on cryo-TEM data and enrichment via filtration), very small genomes and a limited biosynthetic capacity, indicating they are most likely symbionts. The new ~1,200 aa Cas protein, referred to herein as CasY, appears to be part of a minimal CRISPR-Cas system that includes, at most, Cas1 and a CRISPR array (FIG. 22A). Most of the CRISPR arrays have unusually short spacers of 17-19 nts, but one system, which lacks Cas1 (CasY.5), has longer spacers (27-29 nts). The six examples of CasY proteins identified had no significant sequence similarity to any protein in public databases. A sensitive search using profile models (HMMs) built from published Cas proteins[3,4] indicated that four of the six CasY proteins had local similarities (e-values $4\times10^{-11}$-$3\times10^{-18}$) to C2c3 in the C-terminal region overlapping the RuvC domains and a small region (~45 aa) of the N-terminus (see FIG. 29). C2c3 are putative type V Cas effectors that were identified on short contigs with no taxonomic affiliation, and have not been validated experimentally. Like CasY, the C2c3 were found next to arrays with short spacers and Cas1, but with no other Cas proteins. Notably, two of the CasY proteins identified in the current study had no significant similarity to C2c3, despite sharing significant sequence similarity (best Blast hits: e-values $6\times10^{-85}$, $7\times10^{75}$) with the other CasY proteins.

Figure 22B:
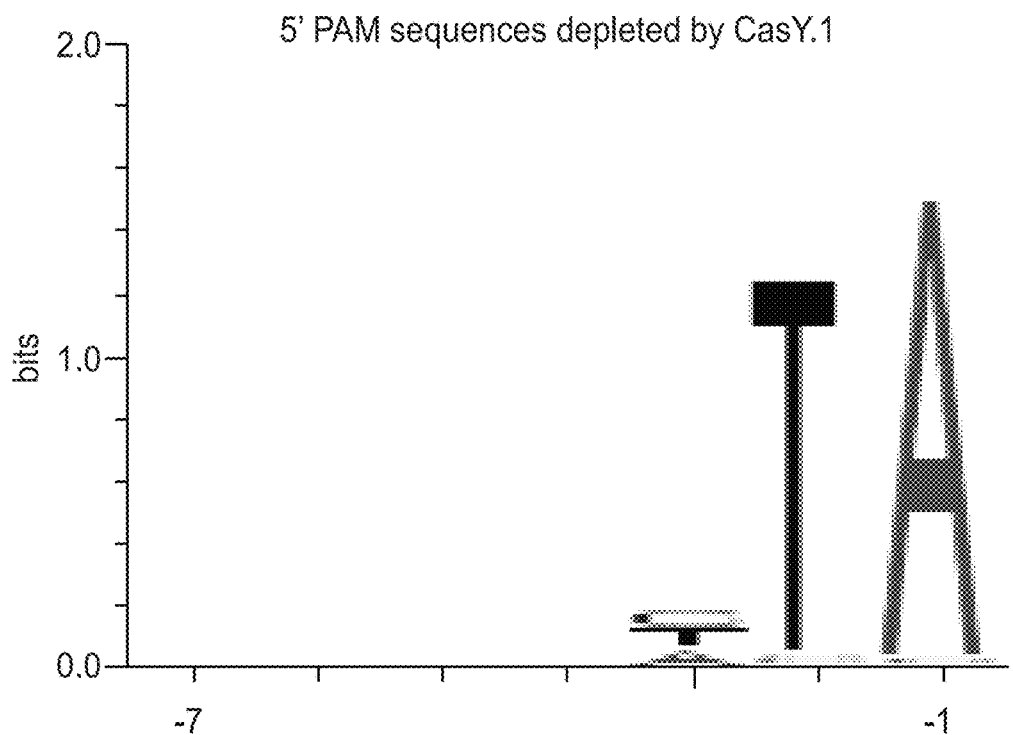
Figure 22C:
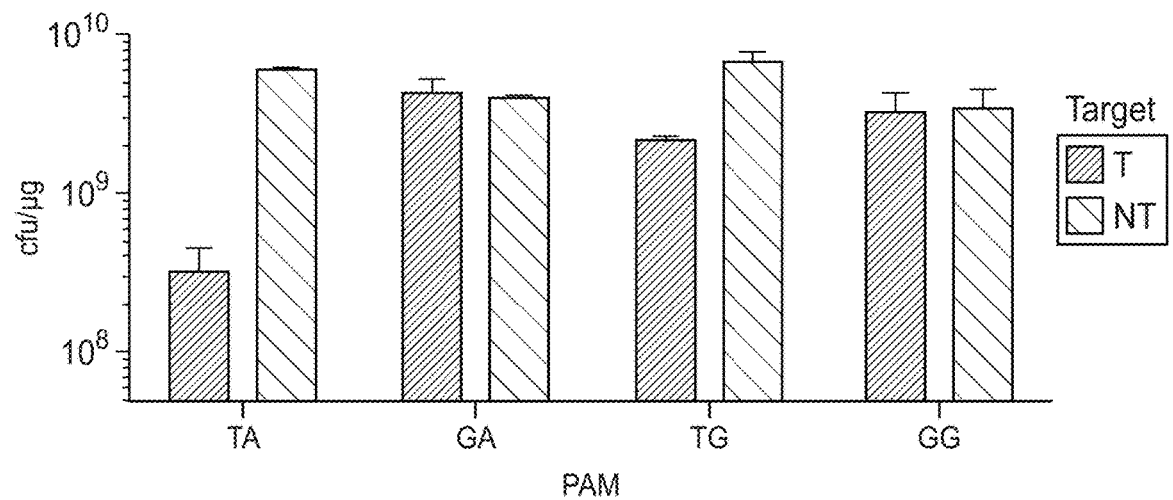

Given the low homology of CRISPR-CasY to any experimentally validated CRISPR loci, it was next wondered whether this system confers RNA-guided DNA interference, but due to the short spacer length reliable information did not exist about a possible PAM motif that might be required for such activity. To work around this, the entire CRISPR-CasY.1 locus was synthesized with a shortened CRISPR array and introduced into E. coli on a plasmid vector. These cells were then challenged in a transformation assay using a target plasmid with a sequence matching a spacer sequence in the array and containing an adjacent randomized 5' or 3' region to identify a possible PAM. Analysis of transformants revealed depletion of sequences containing a 5' TA directly adjacent to the targeted sequence (FIG. 22B). Using this identified PAM sequence, the CasY.1 locus was tested against plasmids containing a single PAM. Plasmid interference was demonstrated only in the presence of a target containing the identified 5' TA PAM sequence (FIG. 22C). Thus, these data show that CRISPR-CasY has DNA interference activity.

Discussion

Figure 23A:
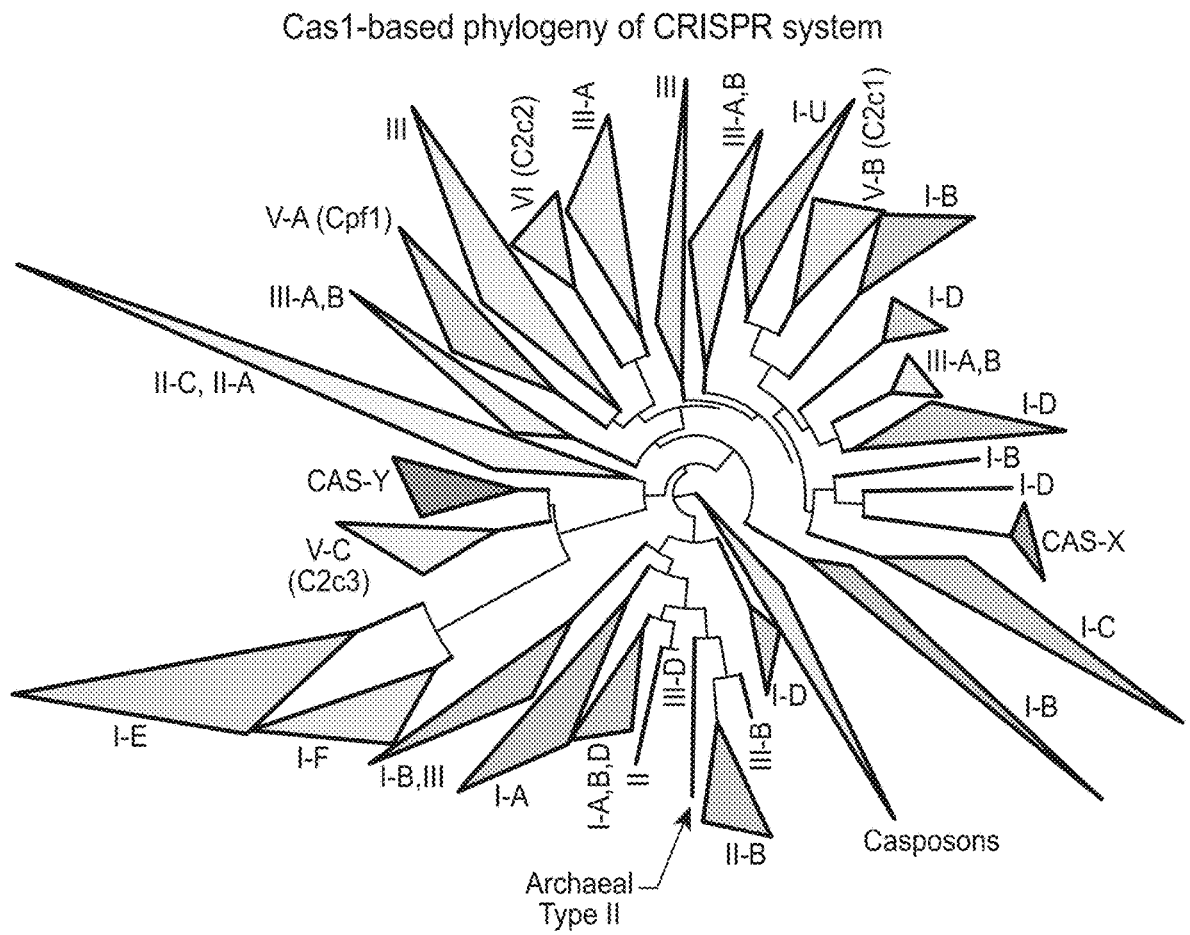
FIGS. 23A-23B present newly identified CRISPR-Cas in context of known systems.
Figure 23B:
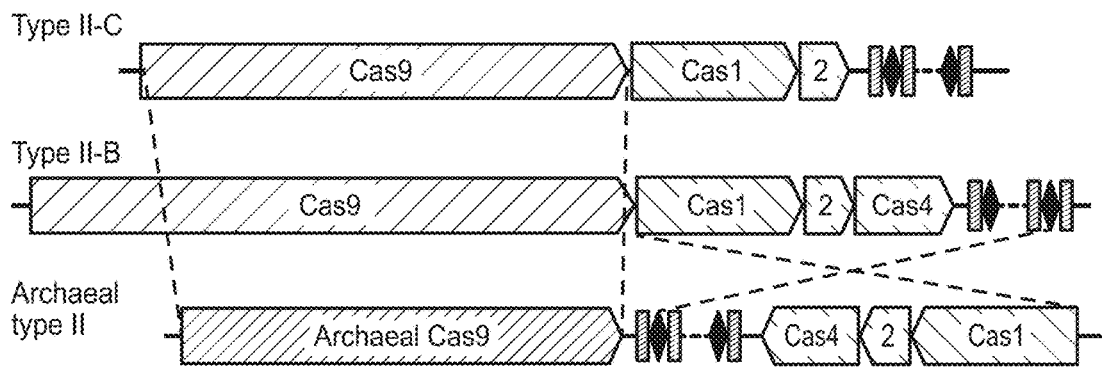
Figure 24A:
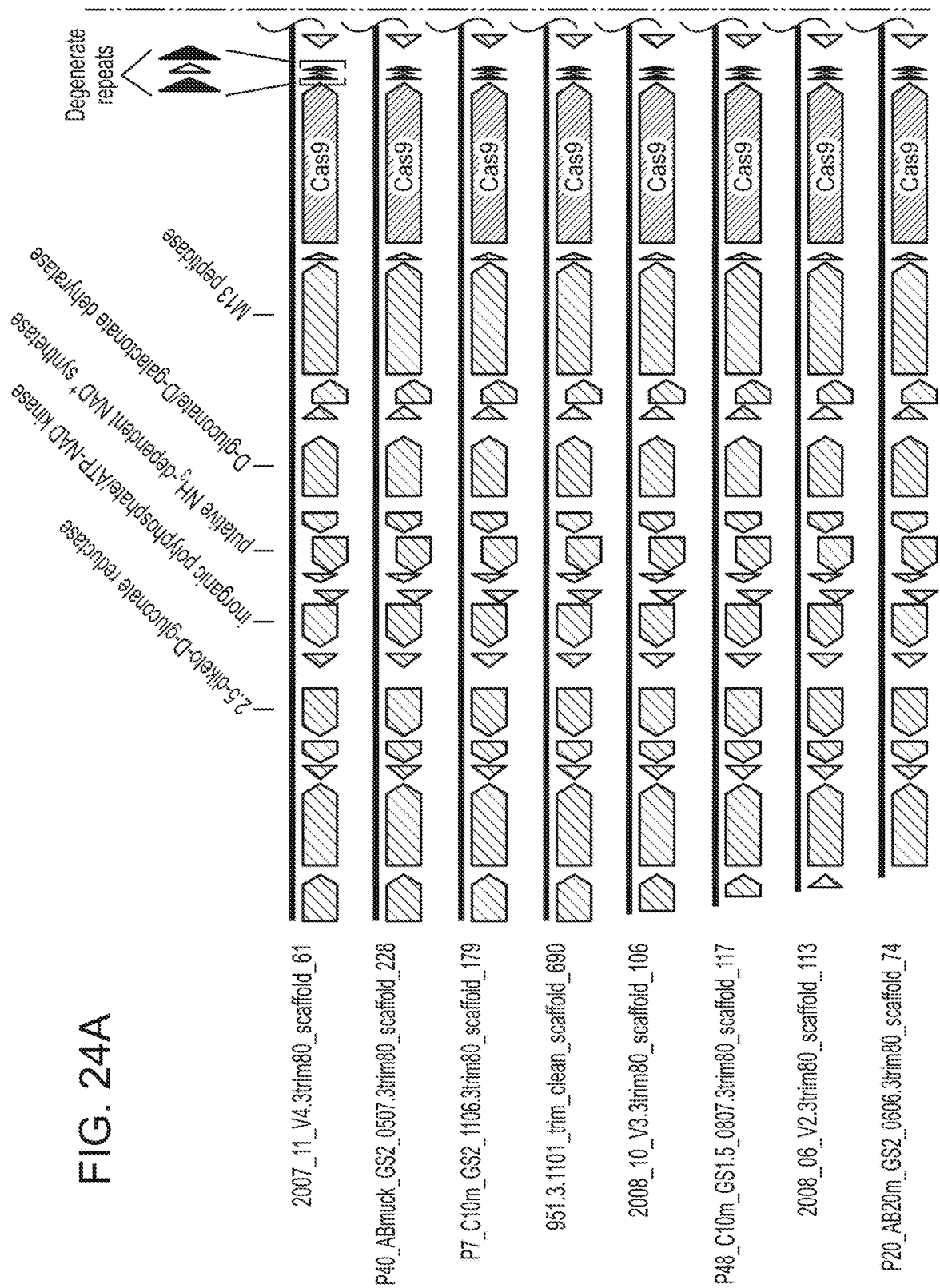
Figure 24B:
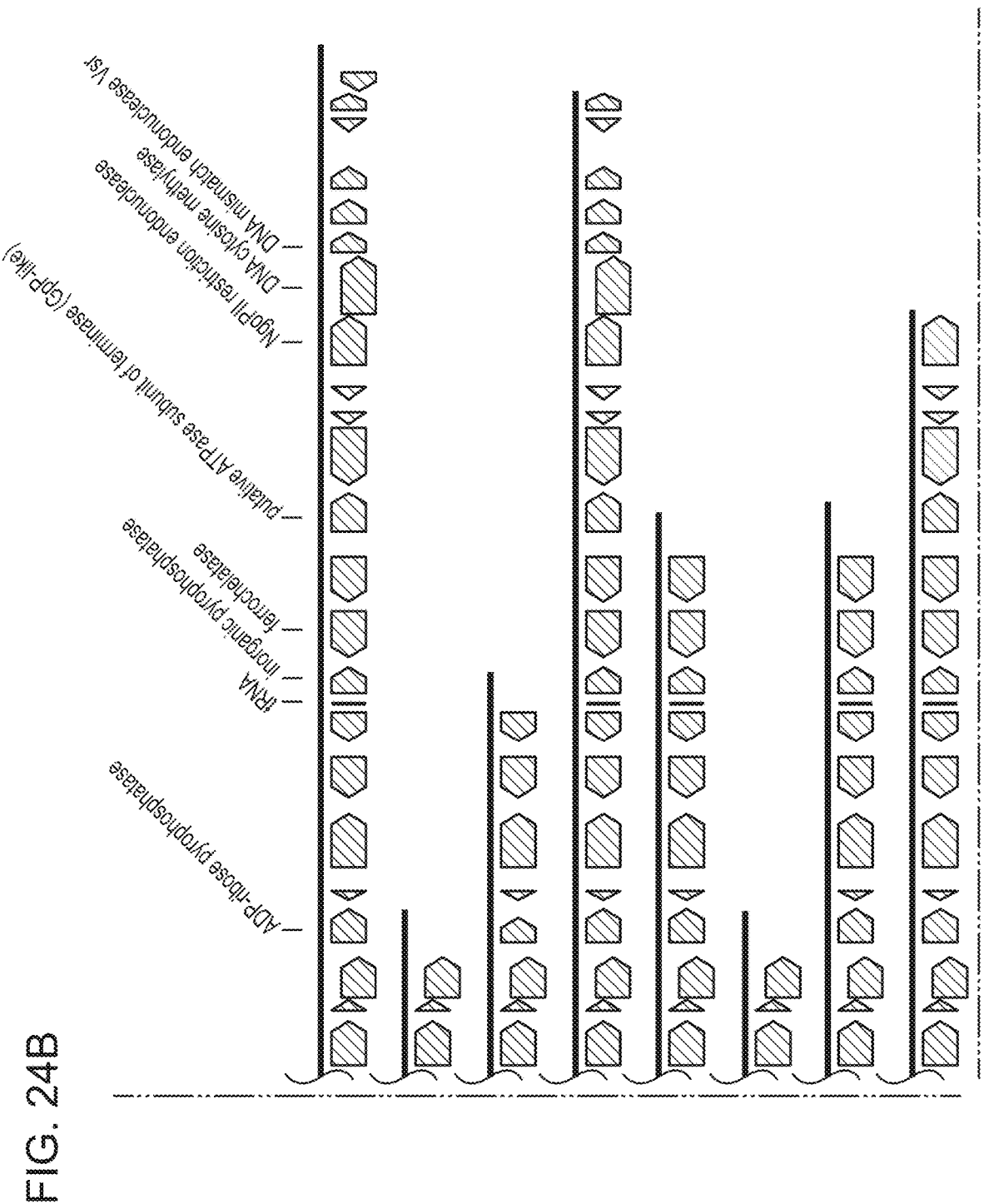
FIG. 24B, Proposed evolutionary scenario that gave rise to the archaeal type II system as a result of a recombination between type II-B and type II-C loci.
Figure 24C:
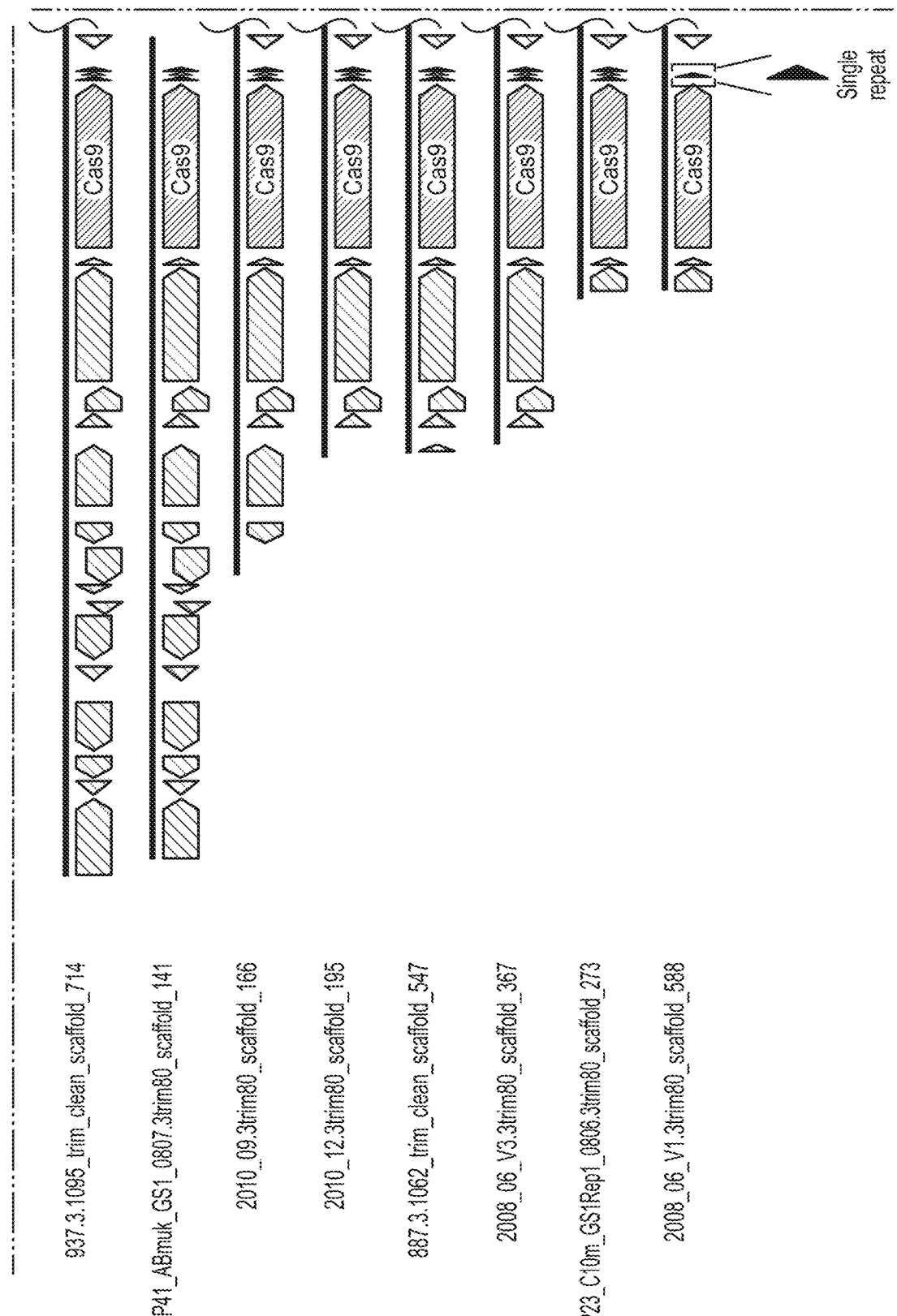
Figure 25A:
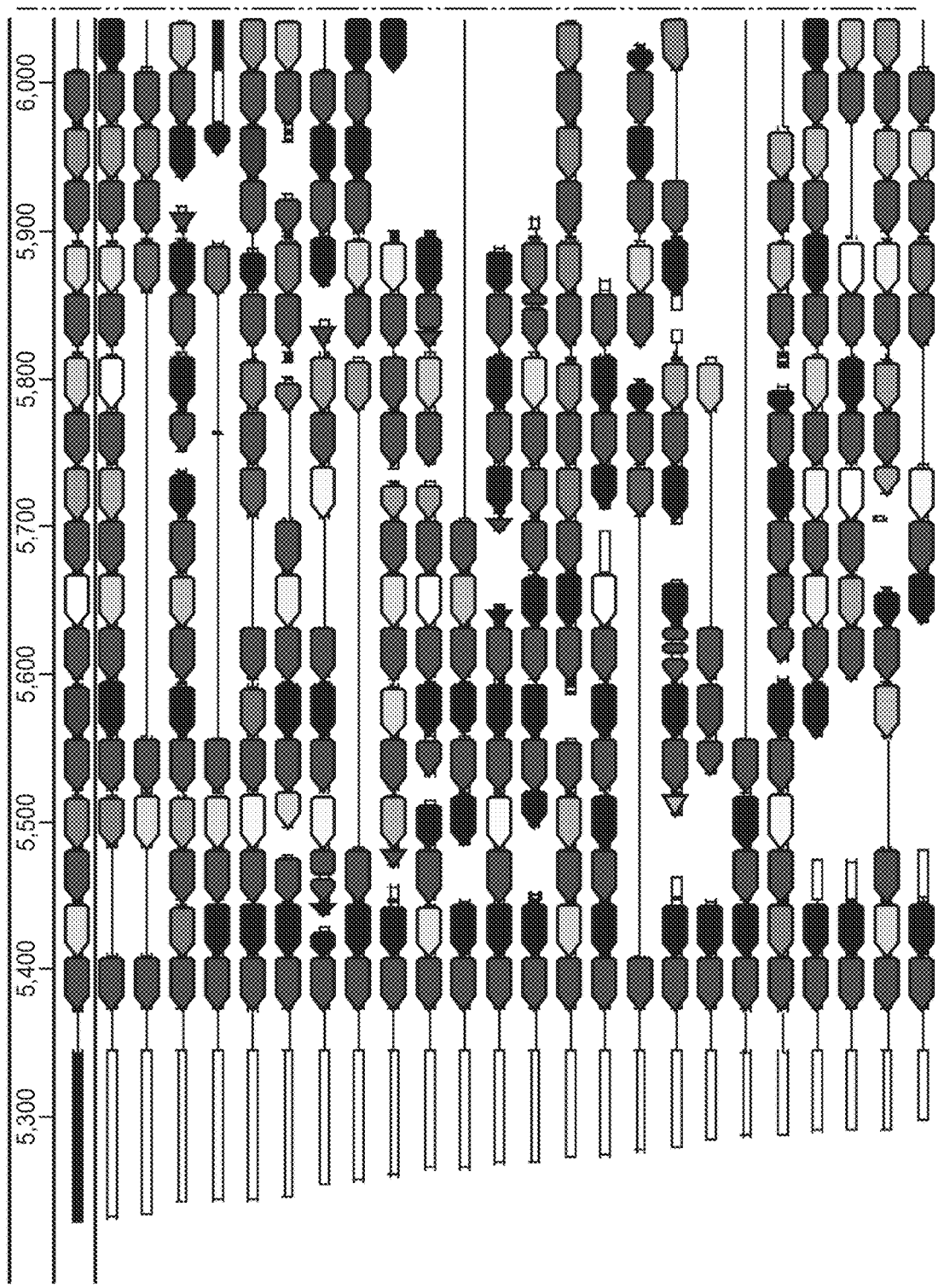
Figure 25C:
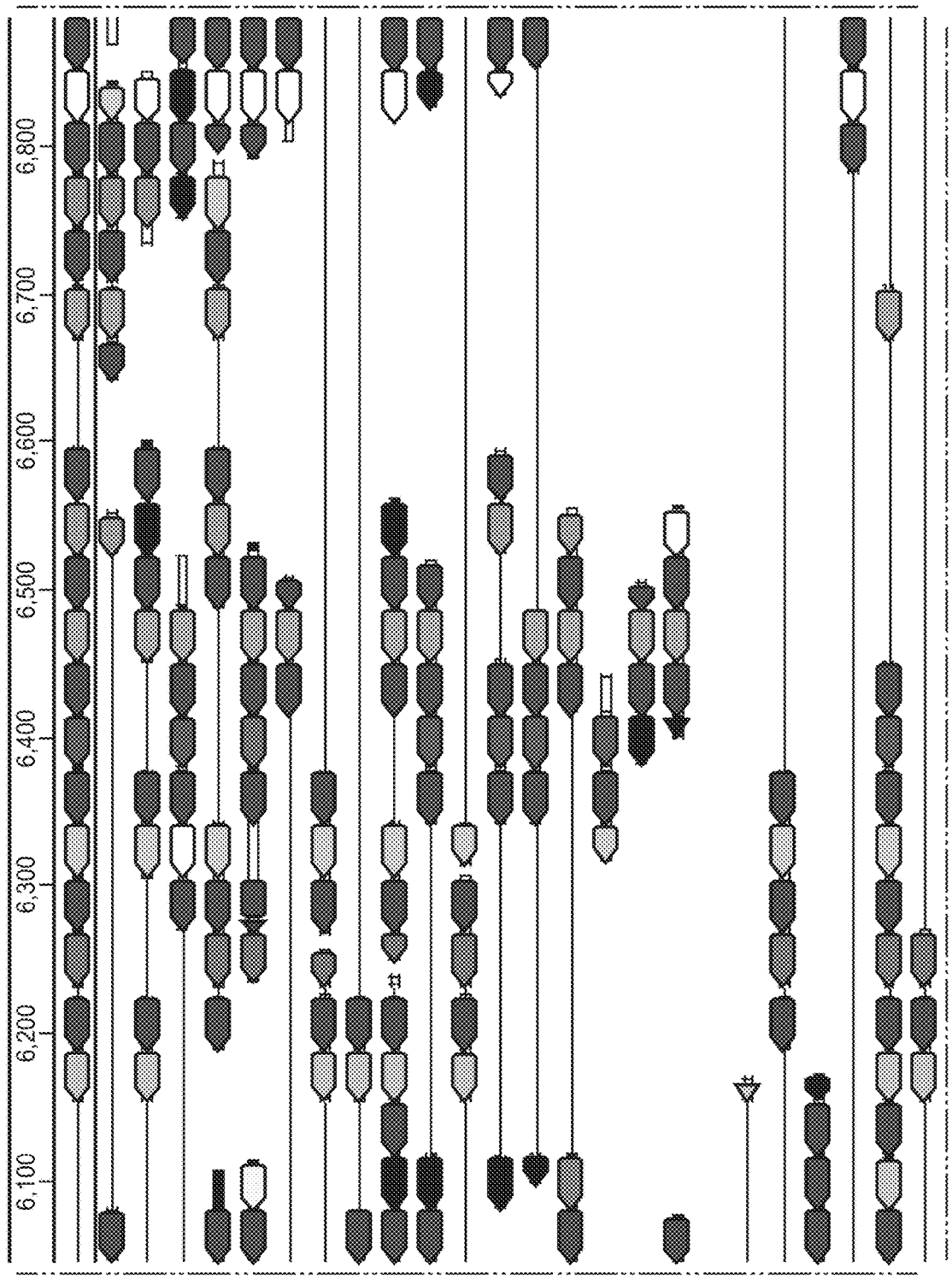
Figure 25E:
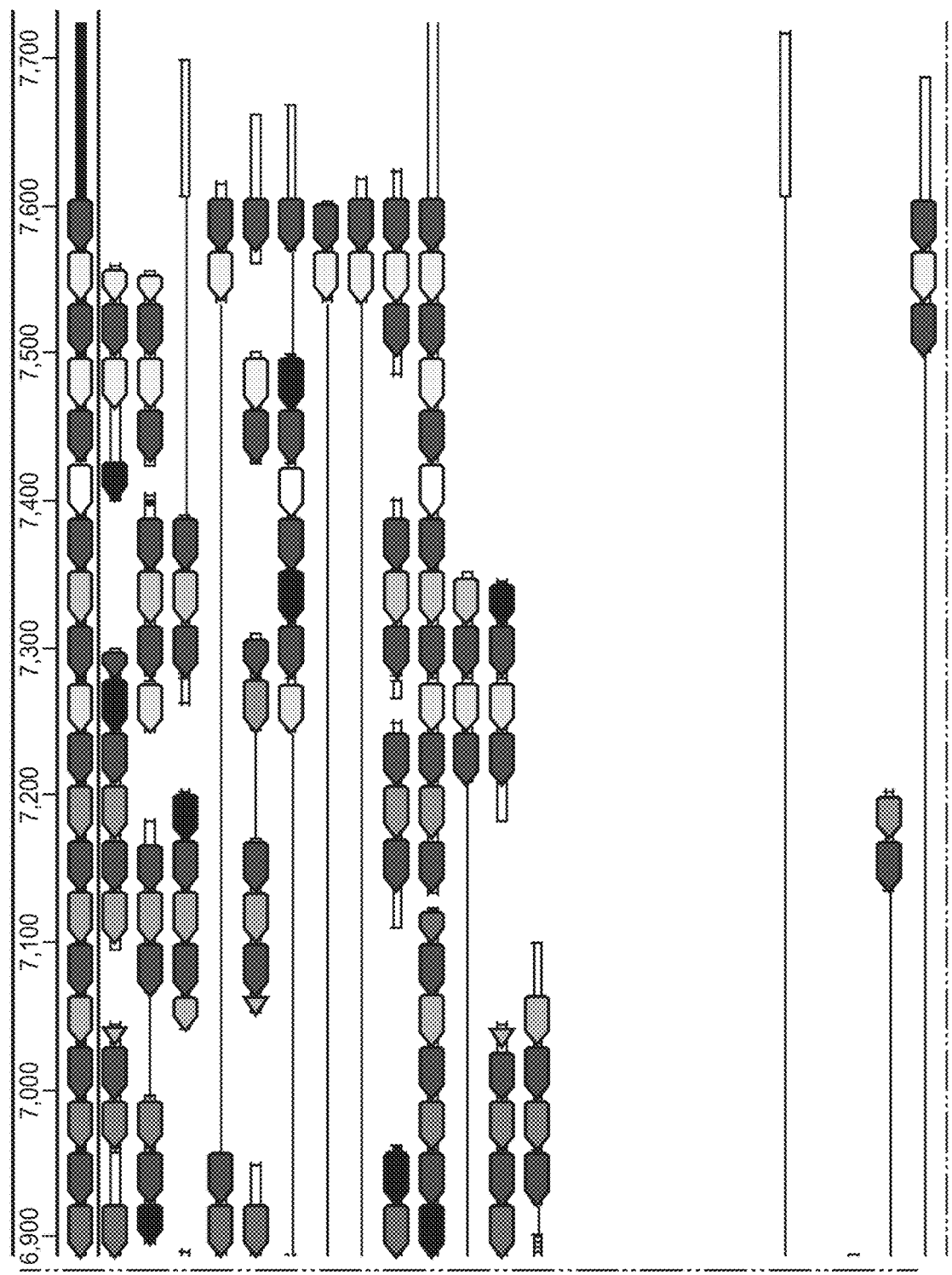
Figure 31:
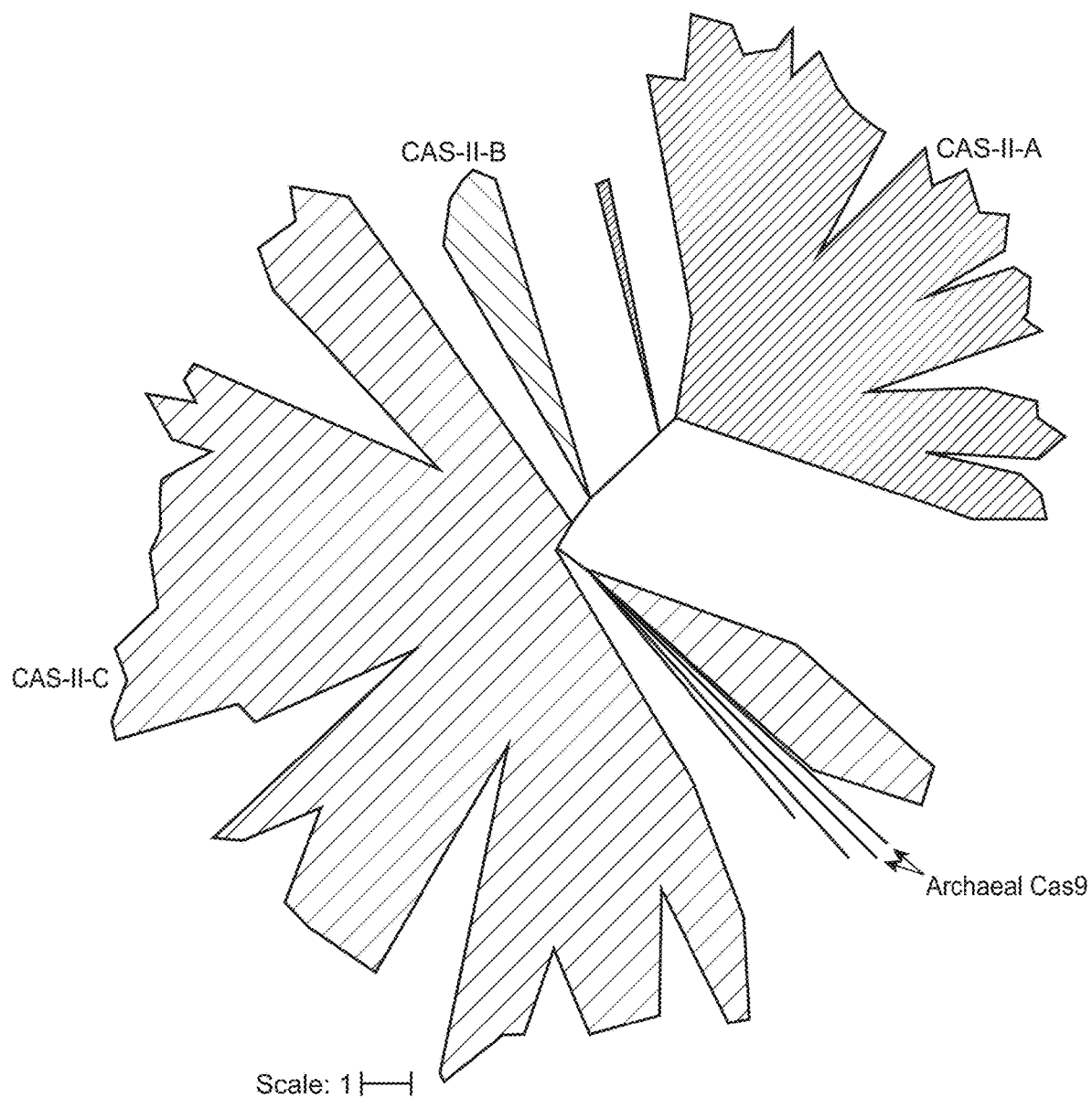
FIG. 31 presents an evolutionary tree of Cas9 homologs. Maximum-likelihood phylogenic tree of Cas9 proteins, showing the previously described systems colored based on their type: II-A in blue, II-B in green and II-C in purple. The Archaeal Cas9, cluster with type II-C CRISPR-Cas systems, together with two newly described bacterial Cas9 from uncultivated bacteria.

New class 2 CRISPR-Cas adaptive immune systems in genomes from uncultivated bacteria and archaea were identified and characterized. Evolutionary analysis of Cas1 (FIG. 23A), which is universal to active CRISPR loci, suggested that the archaeal Cas9 system described here does not clearly fall into any existing type II subtype. The Cas1 phylogeny (as well as the existence of cas4) clustered it together with type II-B systems, yet the sequence of Cas9 was more similar to type II-C proteins (FIG. 31). Thus, the archaeal type II system may have arisen as a fusion of type II-C and II-B systems (FIG. 23B). Likewise, Cas1 phylogenetic analyses indicated that the Cas1 from the CRISPR-CasX system is distant from any other known type V system. Type V systems have been suggested to be the result of the fusion of a transposon with the adaptation module (Cas1-Cas2) from an ancestral type I system. It is therefore hypothesized that the CRISPR-CasX system emerged following a fusion event different from those that gave rise to the previously described type V systems. Strikingly, both CRISPR-CasY and the putative C2c3 systems seem to lack Cas2, a protein thought to be essential for integrating DNA into the CRISPR locus. Given that all CRISPR-Cas systems are thought be descendants of an ancestral type I system that contained both Cas1 and Cas2, CRISPR-CasY and C2c3 systems may either have different ancestry than the rest of the CRISPR-Cas systems, or alternatively, Cas2 might have been lost during their evolutionary history.

The discovery described herein of Cas9 in archaea and two previously unknown CRISPR-Cas systems in bacteria used extensive DNA and RNA sequence datasets obtained from complex natural microbial communities. In the case of CasX and CasY, genome context was critical to prediction of functions that would not have been evident from unassembled sequence information. Further, the identification of a putative tracrRNA as well as targeted viral sequences uncovered through analysis of the metagenomic data guided functional testing. Interestingly, some of the most compact CRISPR-Cas loci identified to date were discovered in organisms with very small genomes. A consequence of small genome size is that these organisms likely depend on other community members for basic metabolic requirements, and thus they have remained largely outside the scope of traditional cultivation-based methods. The limited number of proteins that are required for interference make these minimal systems especially valuable for the development of new genome editing tools. Importantly, it is shown herein that metagenomic discoveries related to CRISPR-Cas systems are not restricted to in silico observations, but can be introduced into an experimental setting where their function can be tested. Given that virtually all environments where life exists can now be probed by genome-resolved metagenomic methods, it is anticipated that the combined computational-experimental approach described herein will greatly expand the diversity of known CRISPR-Cas systems, providing new technologies for biological research and clinical applications.

Methods

Metagenomics and Metatranscriptomics

Metagenomic samples from three different sites were analyzed: (1) Acid mine drainage (AMD) samples collected between 2006 and 2010 from the Richmond Mine, Iron Mountain, Calif. (2) Groundwater and sediment samples collected between 2007 and 2013 from the Rifle Integrated Field Research (IFRC) site, adjacent to the Colorado River near Rifle, Colo. (3) Groundwater collected in 2009 and 2014 from Crystal Geyser, a cold, $CO_2$-driven geyser on the Colorado Plateau in Utah.

For the AMD data, DNA extraction methods and short read sequencing were reported by Denef and Banfield (2012) and Miller et al. (2011). For the Rifle data, DNA and RNA extraction, as well as sequencing, assembly, and genomic reconstructed were described by Anantharaman et al. (2016) and Brown et al. (2015). For samples from Crystal Geyser, methods follow those described by Probst et al (2016) and Emerson et al. (2015). Briefly, DNA was extracted from samples using the PowerSoil DNA Isolation Kit (MoBio Laboratories Inc., Carlsbad, Calif., USA). RNA was extracted from 0.2 µm filters collected from six 2011 Rifle groundwater samples, as described by Brown et al. (2015). DNA was sequenced on Illumina HiSeq2000 platform, and Metatrancriptomic cDNA on 5500XL SOLiD platform. For the newly reported Crystal Geyser data and reanalysis of the AMD data, sequences were assembled using IDBA-UD. DNA and RNA (cDNA) read-mapping used to determine sequencing coverage and gene expression, respectively, was performed using Bowtie2. Open reading frames (ORFs) were predicted on assembled scaffolds using Prodigal. Scaffolds from the Crystal Geyser dataset were binned on the basis of differential coverage abundance patterns using a combination of ABAWACA, ABAWACA2 (www(dot)github(dot)com/CK7) Maxbin2, and tetranucleotide frequency using Emergent Self-Organizing Maps (ESOM). Genomes were manually curated using % GC content, taxonomic affiliation, and genome completeness. Scaffolding errors were corrected using ra2.py (www(dot)github(dot)com/christophertbrown).

CRISPR-Cas Computation Analysis

The assembled contigs from the various samples were scanned for known Cas proteins using Hidden Markov Model (HMMs) profiles, which were built using the HMMer suite, based on alignments from Makarova et al. and Shmakov et al. CRISPR arrays were identified using a local version of the CrisprFinder software. Loci that contained both Cas1 and a CRISPR array were further analyzed if one of the ten ORFs adjacent to the cas1 gene encoded for an uncharacterized protein larger than 800 aa, and no known cas interference genes were identified on the same contig. These large proteins were further analyzed as potential class 2 Cas effectors. The potential effectors were clustered to protein families based on sequence similarities using MCL. These protein families were expanded by building HMMs representing each of these families, and using them to search the metagenomic datasets for similar Cas proteins. To make sure that the protein families are indeed new, known homologs were searched using BLAST against NCBI's non-redundant (nr) and metagenomic (env_nr) protein databases, as well as HMM searches against the UniProt KnowledgeBase. Only proteins with no full-length hits (>25% of the protein's length) were considered novel proteins. Distant homology searches of the putative Cas proteins were performed using HHpred from the HH-suite. High scoring HHpred hits were used to infer domain architecture based on comparison to resolved crystal structures, and secondary structure that was predicted by JPred4. The HMM database, including the newly discovered Cas proteins are available in Supplementary Data 1.

Spacer sequences were determined from the assembled data using CrisprFinder. CRASS was used to locate additional spacers in short DNA reads of the relevant samples. Spacer targets (protospacers) were then identified by BLAST searches (using "-task blastn-short") against the relevant metagenomic assemblies for hits with ≤1 mismatch to spacers. Hits belonging to contigs that contained an associated repeat were filtered out (to avoid identifying CRISPR arrays as protospacers). Protospacer adjacent motifs (PAMs) were identified by aligning regions flanking the protospacers and visualized using WebLogo. RNA structures were predicted using mFold. CRISPR array diversity was analyzed by manually aligning spacers, repeats and flanking sequences from the assembled data. Manual alignments and contig visualizations were performed with Geneious 9.1.

For the phylogenetic analyses of Cas1 and Cas9 proteins of the newly identified systems were used along with the proteins from Makarova et al. and Shmakov et al. A non-redundant set was compiled by clustering together proteins with ≥90% identity using CD-HIT. Alignments were produced with MAFFT, and maximum-likelihood phylogenies were constructed using RAxML with PROTGAMMALG as the substitution model and 100 bootstrap samplings. Cas1 tree were rooted using the branch leading to casposons. Trees were visualized using FigTree 1.4.1 (wwwtree(dot) bio(dot)ed(dot)ac(dot)uk/software/figtree/) and iTOL v3.

Generation of Heterologous Plasmids

Metagenomic contigs were made into minimal CRISPR interference plasmids by removing proteins associated with acquisition for CasX and reducing the size of the CRISPR array for both CasX and CasY. The minimal locus was synthesized as Gblocks (Integrated DNA Technology) and assembled using Gibson Assembly.

PAM Depletion Assay

PAM depletion assays were conducted as previously described with modification. Plasmid libraries containing randomized PAM sequences were assembled by annealing a DNA oligonucleotide containing a target with a 7 nt randomized PAM region with a primer and extended with Klenow Fragment (NEB). The double stranded DNA was digested with EcoRI and NcoI and ligated into a pUC19 backbone. The ligated library was transformed into DH5α and >$10^8$ cells were harvested and the plasmids extracted and purified. 200 ng of the pooled library was transformed into electrocompetent E. coli harboring a CRISPR locus or a control plasmid with no locus. The transformed cells were plated on selective media containing carbenicillin (100 mg $L^{-1}$) and chloramphenicol (30 mg $L^{-1}$) for 30 hours at 25° C. Plasmid DNA was extracted and the PAM sequence was amplified with adapters for Illumina sequencing. The 7 nt PAM region was extracted and PAM frequencies calculated for each 7 nt sequence. PAM sequences depleted above the specified threshold were used to generate a WebLogo.

Plasmid Interference

Putative targets identified from metagenomic sequence analysis or PAM depletion assays were cloned into a pUC19 plasmid. 10 ng of target plasmid were transformed into electrocompetent E. coli (NEB Stable) containing the CRISPR loci plasmid. Cells were recovered for 2 hrs at 25° C. and an appropriate dilution was plated on selective media. Plates were incubated at 25° C. and colony forming units were counted. All plasmid interference experiments were performed in triplicate and electrocompetent cells were prepared independently for each replicate.

ARMAN-Cas9 Protein Expression and Purification

Expression constructs for Cas9 from ARMAN-1 (AR1) and ARMAN-4 (AR4) were assembled from gBlocks (Integrated DNA Technologies) that were codon-optimized for E. coli. The assembled genes were cloned into a pET-based expression vector as an N-terminal $His_6$-MBP or $His_6$ fusion protein. Expression vectors were transformed into BL21 (DE3) E. coli cells and grown in LB broth at 37° C. For protein expression, cells were induced during mid-log phase with 0.4 mM IPTG (isopropyl 13-D-1-thiogalactopyranoside) and incubated overnight at 16° C. All subsequent steps were conducted at 4° C. Cell pellets were resuspended in lysis buffer (50 mM Tris-HCl pH 8, 500 mM NaCl, 1 mM TCEP, 10 mM Imidazole) 0.5% Triton X-100 and supplemented with Complete protease inhibitor mixture (Roche) before lysis by sonication. Lysate was clarified by centrifugation at 15000 g for 40 min and applied to Superflow Ni-NTA agarose (Qiagen) in batch. The resin was washed with extensively with Wash Buffer A (50 mM Tris-HCl pH 8, 500 mM NaCl, 1 mM TCEP, 10 mM Imidazole) followed by 5 column volumes of Wash Buffer B (50 mM Tris-HCl pH 8, 1M NaCl, 1 mM TCEP, 10 mM Imidazole). Protein was eluted off of Ni-NTA resin with Elution Buffer (50 mM Tris-HCl pH 8, 500 mM NaCl, 1 mM TCEP, 300 mM Imidazole). The $His_6$-MBP tag was removed by TEV protease during overnight dialysis against Wash Buffer A. Cleaved Cas9 was removed from the affinity tag through a second Ni-NTA agarose column. The protein was dialyzed into IEX Buffer A (50 mM Tris-HCl pH 7.5, 300 mM NaCl, 1 mM TCEP, 5% glycerol) before application to a 5 mL Heparin HiTrap column (GE Life Sciences). Cas9 was eluted over a linear NaCl (0.3-1.5 M) gradient. Fractions were pooled and concentrated with a 30 kDa spin concentrator (Thermo Fisher). When applicable, Cas9 was further purified via size-exclusion chromatography on an Superdex 200 pg column (GE Life Sciences) and stored in IEX Buffer A for subsequent cleavage assays. For yeast expression, AR1-Cas9 was cloned into a Gal1/10 His6-MBP TEV Ura S. cerevisiae expression vector (Addgene plasmid #48305). The vector was transformed into a BY4741 URA3 strain and cultures were grown in MEDIA at 30° C. At an OD600 of ~0.6, protein expression was induced with 2% w/v galactose and incubated overnight at 16° C. Protein purification was performed as above.

RNA In Vitro Transcription and Oligonucleotide Purification

In vitro transcription reactions were performed as previously described[65] using synthetic DNA templates containing a T7 promoter sequence. All in vitro transcribed guide RNAs and target RNAs or DNAs were purified via denaturing PAGE. Double-stranded target RNAs and DNAs were hybridized in 20 mM Tris HCl pH 7.5 and 100 mM NaCl by incubation at 95° C. for 1 min, followed by slow-cooling to room temperature. Hybrids were purified by native PAGE.

In Vitro Cleavage Assays

Purified DNA and RNA oligonucleotides were radiolabeled using T4 polynucleotide kinase (NEB) and [γ-32P] ATP (Perkin-Elmer) in 1×PNK buffer for 30 min at 37° C. PNK was heat inactivated at 65° C. for 20 min and free ATP was removed from the labeling reactions using illustra Microspin G-25 columns (GE Life Sciences). CrRNA and tracrRNAs were mixed in equimolar quantities in 1x refolding buffer (50 mM Tris HCl pH 7.5, 300 mM NaCl, 1 mM TCEP, 5% glycerol) and incubated at 70° C. for 5 min and then slow-cooled to room temperature. The reactions were supplemented to 1 mM final metal concentration and subsequently heated at 50° C. for 5 min. After slow-cooling to room temperature, refolded guides were placed on ice. Unless noted for buffer, salt concentration, Cas9 was reconstituted with an equimolar amount of guide in 1x cleavage buffer (50 mM Tris HCl pH 7.5, 300 mM NaCl, 1 mM TCEP, 5% glycerol, 5 mM divalent metal) at 37° C. for 10 min. Cleavage reactions were conducted in 1x cleavage buffer with a 10× excess of Cas9-guide complex over radiolabeled target at 37° C. or the indicated temperature. Reactions were quenched in an equal volume of gel loading buffer supplemented with 50 mM EDTA. Cleavage products were resolved on 10% denaturing PAGE and visualized by phosphorimaging.

In Vivo E. coli Interference Assays

E. coli transformation assays for AR1- and AR4-Cas9 were conducted as previously published. Briefly, E. coli transformed with guide RNAs were made electrocompetent. Cells were then transformed with 9 fmol of plasmid encoding wild-type or catalytically inactive Cas9 (dCas9). A dilution series of recovered cells was plated on LB plates with selective antibiotics. Colonies were counted after 16 hr at 37° C.

TABLE 1

Details regarding the organisms and genomic location in which the CRISPR-Cas system were identified, as well as information on the number and average length of reconstructed spacers, and repeats length (NA, not available). ARMAN-1 spacers were reconstructed from 16 samples.

| Taxonomic group | Cas effector | NCBI Accession | Coordinates | Repeat length | # spacers | Spacers avg. length |
|---|---|---|---|---|---|---|
| ARMAN-1 | Cas9 | MOEG01000017 | 1827 . . . 7130 | 36 | 271 | 34.5 |
| ARMAN-4 | Cas9 | KY040241 | 11779 . . . 14900 | 36 | 1 | 36 |
| Deltaproteobacteria | CasX | MGPG01000094 | 4319 . . . 9866 | 37 | 5 | 33.6 |
| Planctomycetes | CasX | MHYZ01000150 | 1 . . . 5586 | 37 | 7 | 32.3 |
| Candidatus Katanobacteria | CasY.1 | MOEH01000029 | 459 . . . 5716 | 26 | 14 | 17.1 |
| Candidatus Vogelbacteria | CasY.2 | MOEJ01000028 | 7322 . . . 13087 | 26 | 18 | 17.3 |
| Candidatus Vogelbacteria | CasY.3 | MOEK01000006 | 1 . . . 4657 | 26 | 12 | 17.3 |
| Candidatus Parcubacteria | CasY.4 | KY040242 | 1 . . . 5193 | 25 | 13 | 18.4 |
| Candidatus Komeilibacteria | CasY.5 | MOEI01000022 | 2802 . . . 7242 | 36 | 8 | 26 |
| Candidatus Kerfeldbacteria | CasY.6 | MHKD01000036 | 11503 . . . 15366 | NA | NA | NA |

While the present invention has been described with reference to the specific embodiments thereof, it should be understood by those skilled in the art that various changes may be made and equivalents may be substituted without departing from the true spirit and scope of the invention. In addition, many modifications may be made to adapt a particular situation, material, composition of matter, process, process step or steps, to the objective, spirit and scope of the present invention. All such modifications are intended to be within the scope of the claims appended hereto.

What is claimed is:

1. A method of modifying a target DNA, the method comprising contacting the target DNA with:
   A) a CasX polypeptide; and
   B) a CasX guide RNA comprising a guide sequence that hybridizes to a target sequence of the target DNA,
   wherein said contacting results in modification of the target DNA by the CasX polypeptide, and
   wherein said contacting:
   a) comprises: introducing into a cell: (i) the CasX polypeptide, or a nucleic acid comprising a nucleotide sequence encoding the CasX polypeptide, and (ii) the CasX guide RNA, or a nucleic acid comprising a nucleotide sequence encoding the CasX guide RNA; or
   b) takes place in vitro outside of a cell.

2. The method of claim 1, wherein said modification is cleavage of the target DNA.

3. The method of claim 1, wherein the target DNA is selected from: double stranded DNA, single stranded DNA, genomic DNA, and extrachromosomal DNA.

4. The method of claim 1, wherein said contacting takes place in vitro outside of a cell.

5. The method of claim 1, wherein the cell of (a) is in culture in vitro.

6. The method of claim 1, wherein the cell of (a) is in vivo.

7. The method of claim 6, wherein the cell is a eukaryotic cell.

8. The method of claim 7, wherein the cell is selected from: a plant cell, a fungal cell, a mammalian cell, a reptile cell, an insect cell, an avian cell, a fish cell, a parasite cell, an arthropod cell, a cell of an invertebrate, a cell of a vertebrate, a rodent cell, a mouse cell, a rat cell, a primate cell, a non-human primate cell, and a human cell.

9. The method of claim 5, wherein the cell is a prokaryotic cell.

10. The method of claim 1, wherein the target DNA is genomic DNA.

11. The method of claim 1, wherein said contacting comprises: introducing into a cell: (a) the CasX polypeptide, or a nucleic acid comprising a nucleotide sequence encoding the CasX polypeptide, and (b) the CasX guide RNA, or a nucleic acid comprising a nucleotide sequence encoding the CasX guide RNA.

12. The method of claim 11, wherein said contacting further comprises: introducing a DNA donor template into the cell.

13. The method of claim 1, wherein the CasX guide RNA is a single guide RNA.

14. The method of claim 1, wherein the CasX guide RNA is a dual guide RNA.

15. The method of claim 1, wherein the CasX guide RNA comprises one or more of: a non-natural internucleoside linkage, a nucleic acid mimetic, a modified sugar moiety, and a modified nucleobase.

16. The method of claim 1, wherein the CasX guide RNA comprises one or more of: (i) a non-natural internucleoside linkage selected from a phosphorothioate, an inverted polarity linkage, and an abasic nucleoside linkage; (ii) a locked nucleic acid (LNA); and (iii) a modified sugar moiety selected from 2'-O-methoxyethyl, 2'-O-methyl, and 2'-fluoro.

17. The method of claim 1, wherein the CasX guide RNA comprises one or more of: a peptide nucleic acid (PNA), a morpholino nucleic acid, a cyclohexenyl nucleic acid (CeNA), and/or a locked nucleic acid (LNA).

18. The method of claim 1, wherein the CasX guide RNA comprises one or more modified sugar moieties selected from: 2'-O-(2-methoxyethyl), 2'-dimethylaminooxyethoxy, 2'-dimethylaminoethoxyethoxy, 2'-O-methyl, and 2'-fluoro.

19. The method of claim 1, wherein the CasX polypeptide compromises an amino acid sequence having at least 95% identity to the amino acid sequence set forth in SEQ ID NO:1.

20. The method of claim 1, wherein the CasX polypeptide compromises an amino acid sequence having at least 95% identity to the amino acid sequence set forth in SEQ ID NO:2.

21. The method of claim 1, wherein CasX polypeptide comprises one or more nuclear localization signal (NLS).

22. The method of claim 21, wherein the one or more NLS is at the N-terminus of the CasX polypeptide or wherein the one or more NLS is at the C-terminus of the CasX polypeptide.

23. The method of claim 21, wherein CasX polypeptide comprises an NLS at the N-terminus and an NLS at the C-terminus of the CasX polypeptide.

24. The method of claim 1, wherein said contacting comprises: introducing into a cell: (a) a nucleic acid comprising a nucleotide sequence encoding the CasX polypeptide, and (b) a nucleic acid comprising a nucleotide sequence encoding the CasX guide RNA.

25. The method of claim 24, wherein the nucleotide sequence encoding the CasX polypeptide is operably linked to a first promoter, and wherein the nucleotide sequence encoding the CasX guide RNA is operably linked to a second promoter.

26. The method of claim 25, wherein the first promoter is a CMV promoter, and wherein the second promoter is a U6 promoter.

27. The method of claim 1, wherein the target DNA is double-stranded DNA.

28. The method of claim 1, wherein the target DNA is single-stranded DNA.

29. The method of claim 1, wherein the cell of (a) is a eukaryotic cell.

30. A method of modifying a target DNA, the method comprising contacting the target DNA in a eukaryotic cell with:
A) a CasX polypeptide; and
B) a CasX guide RNA comprising a guide sequence that hybridizes to a target sequence of the target DNA,
wherein said contacting results in modification of the target DNA by the CasX polypeptide, and
wherein said contacting comprises introducing into the eukaryotic cell: (i) the CasX polypeptide, or a nucleic acid comprising a nucleotide sequence encoding the CasX polypeptide, and (ii) the CasX guide RNA, or a nucleic acid comprising a nucleotide sequence encoding the CasX guide RNA.

* * * * *

SEQUENCE LISTING

<160> NUMBER OF SEQ ID NOS: 154

<210> SEQ ID NO 1
<211> LENGTH: 986
<212> TYPE: PRT
<213> ORGANISM: Unknown
<220> FEATURE:
<223> OTHER INFORMATION: identified from meta-transcriptomics sequence
      data from unknown deltaproteobacter

<400> SEQUENCE: 1

Met Glu Lys Arg Ile Asn Lys Ile Arg Lys Lys Leu Ser Ala Asp Asn
1               5                   10                  15

Ala Thr Lys Pro Val Ser Arg Ser Gly Pro Met Lys Thr Leu Leu Val
            20                  25                  30

Arg Val Met Thr Asp Asp Leu Lys Arg Leu Glu Lys Arg Arg Lys
        35                  40                  45

Lys Pro Glu Val Met Pro Gln Val Ile Ser Asn Asn Ala Ala Asn Asn
    50                  55                  60

Leu Arg Met Leu Leu Asp Asp Tyr Thr Lys Met Lys Glu Ala Ile Leu
65                  70                  75                  80

Gln Val Tyr Trp Gln Glu Phe Lys Asp Asp His Val Gly Leu Met Cys
                85                  90                  95

Lys Phe Ala Gln Pro Ala Ser Lys Lys Ile Asp Gln Asn Lys Leu Lys
            100                 105                 110

Pro Glu Met Asp Glu Lys Gly Asn Leu Thr Thr Ala Gly Phe Ala Cys
        115                 120                 125

Ser Gln Cys Gly Gln Pro Leu Phe Val Tyr Lys Leu Glu Gln Val Ser
    130                 135                 140

Glu Lys Gly Lys Ala Tyr Thr Asn Tyr Phe Gly Arg Cys Asn Val Ala
145                 150                 155                 160

Glu His Glu Lys Leu Ile Leu Leu Ala Gln Leu Lys Pro Glu Lys Asp
                165                 170                 175

Ser Asp Glu Ala Val Thr Tyr Ser Leu Gly Lys Phe Gly Gln Arg Ala
            180                 185                 190

Leu Asp Phe Tyr Ser Ile His Val Thr Lys Glu Ser Thr His Pro Val
        195                 200                 205

Lys Pro Leu Ala Gln Ile Ala Gly Asn Arg Tyr Ala Ser Gly Pro Val
    210                 215                 220

Gly Lys Ala Leu Ser Asp Ala Cys Met Gly Thr Ile Ala Ser Phe Leu
225                 230                 235                 240

Ser Lys Tyr Gln Asp Ile Ile Glu His Gln Lys Val Val Lys Gly
                245                 250                 255

Asn Gln Lys Arg Leu Glu Ser Leu Arg Glu Leu Ala Gly Lys Glu Asn
            260                 265                 270

Leu Glu Tyr Pro Ser Val Thr Leu Pro Pro Gln Pro His Thr Lys Glu
        275                 280                 285

Gly Val Asp Ala Tyr Asn Glu Val Ile Ala Arg Val Arg Met Trp Val
    290                 295                 300

Asn Leu Asn Leu Trp Gln Lys Leu Lys Leu Ser Arg Asp Asp Ala Lys
305                 310                 315                 320

Pro Leu Leu Arg Leu Lys Gly Phe Pro Ser Phe Pro Val Val Glu Arg
                325                 330                 335

Arg Glu Asn Glu Val Asp Trp Trp Asn Thr Ile Asn Gly Val Lys Lys
            340                 345                 350

```
Leu Ile Asp Ala Lys Arg Asp Met Gly Arg Val Phe Trp Ser Gly Val
        355                 360                 365

Thr Ala Glu Lys Arg Asn Thr Ile Leu Glu Gly Tyr Asn Tyr Leu Pro
    370                 375                 380

Asn Glu Asn Asp His Lys Lys Arg Glu Gly Ser Leu Glu Asn Pro Lys
385                 390                 395                 400

Lys Pro Ala Lys Arg Gln Phe Gly Asp Leu Leu Tyr Leu Glu Lys
            405                 410                 415

Lys Tyr Ala Gly Asp Trp Gly Lys Val Phe Asp Glu Ala Trp Glu Arg
                420                 425                 430

Ile Asp Lys Lys Ile Ala Gly Leu Thr Ser His Ile Glu Arg Glu Glu
        435                 440                 445

Ala Arg Asn Ala Glu Asp Ala Gln Ser Lys Ala Val Leu Thr Asp Trp
    450                 455                 460

Leu Arg Ala Lys Ala Ser Phe Val Leu Glu Arg Leu Lys Glu Met Asp
465                 470                 475                 480

Glu Lys Glu Phe Tyr Ala Cys Glu Ile Gln Leu Gln Lys Trp Tyr Gly
                485                 490                 495

Asp Leu Arg Gly Asn Pro Phe Ala Val Glu Ala Glu Asn Arg Val Val
                500                 505                 510

Asp Ile Ser Gly Phe Ser Ile Gly Ser Asp Gly His Ser Ile Gln Tyr
        515                 520                 525

Arg Asn Leu Leu Ala Trp Lys Tyr Leu Glu Asn Gly Lys Arg Glu Phe
    530                 535                 540

Tyr Leu Met Asn Tyr Gly Lys Lys Gly Arg Ile Arg Phe Thr Asp
545                 550                 555                 560

Gly Thr Asp Ile Lys Lys Ser Gly Lys Trp Gln Gly Leu Leu Tyr Gly
                565                 570                 575

Gly Gly Lys Ala Lys Val Ile Asp Leu Thr Phe Asp Pro Asp Asp Glu
                580                 585                 590

Gln Leu Ile Ile Leu Pro Leu Ala Phe Gly Thr Arg Gln Gly Arg Glu
        595                 600                 605

Phe Ile Trp Asn Asp Leu Leu Ser Leu Glu Thr Gly Leu Ile Lys Leu
    610                 615                 620

Ala Asn Gly Arg Val Ile Glu Lys Thr Ile Tyr Asn Lys Lys Ile Gly
625                 630                 635                 640

Arg Asp Glu Pro Ala Leu Phe Val Ala Leu Thr Phe Glu Arg Arg Glu
                645                 650                 655

Val Val Asp Pro Ser Asn Ile Lys Pro Val Asn Leu Ile Gly Val Asp
                660                 665                 670

Arg Gly Glu Asn Ile Pro Ala Val Ile Ala Leu Thr Asp Pro Glu Gly
            675                 680                 685

Cys Pro Leu Pro Glu Phe Lys Asp Ser Ser Gly Gly Pro Thr Asp Ile
            690                 695                 700

Leu Arg Ile Gly Glu Gly Tyr Lys Glu Lys Gln Arg Ala Ile Gln Ala
705                 710                 715                 720

Ala Lys Glu Val Glu Gln Arg Arg Ala Gly Gly Tyr Ser Arg Lys Phe
                725                 730                 735

Ala Ser Lys Ser Arg Asn Leu Ala Asp Asp Met Val Arg Asn Ser Ala
            740                 745                 750

Arg Asp Leu Phe Tyr His Ala Val Thr His Asp Ala Val Leu Val Phe
        755                 760                 765

Glu Asn Leu Ser Arg Gly Phe Gly Arg Gln Gly Lys Arg Thr Phe Met
```

```
                770                 775                 780
Thr Glu Arg Gln Tyr Thr Lys Met Glu Asp Trp Leu Thr Ala Lys Leu
785                 790                 795                 800

Ala Tyr Glu Gly Leu Thr Ser Lys Thr Tyr Leu Ser Lys Thr Leu Ala
                805                 810                 815

Gln Tyr Thr Ser Lys Thr Cys Ser Asn Cys Gly Phe Thr Ile Thr Thr
                820                 825                 830

Ala Asp Tyr Asp Gly Met Leu Val Arg Leu Lys Lys Thr Ser Asp Gly
                835                 840                 845

Trp Ala Thr Thr Leu Asn Asn Lys Glu Leu Lys Ala Glu Gly Gln Ile
850                 855                 860

Thr Tyr Tyr Asn Arg Tyr Lys Arg Gln Thr Val Glu Lys Glu Leu Ser
865                 870                 875                 880

Ala Glu Leu Asp Arg Leu Ser Glu Glu Ser Gly Asn Asn Asp Ile Ser
                885                 890                 895

Lys Trp Thr Lys Gly Arg Arg Asp Glu Ala Leu Phe Leu Leu Lys Lys
                900                 905                 910

Arg Phe Ser His Arg Pro Val Gln Glu Gln Phe Val Cys Leu Asp Cys
                915                 920                 925

Gly His Glu Val His Ala Asp Glu Gln Ala Ala Leu Asn Ile Ala Arg
930                 935                 940

Ser Trp Leu Phe Leu Asn Ser Asn Ser Thr Glu Phe Lys Ser Tyr Lys
945                 950                 955                 960

Ser Gly Lys Gln Pro Phe Val Gly Ala Trp Gln Ala Phe Tyr Lys Arg
                965                 970                 975

Arg Leu Lys Glu Val Trp Lys Pro Asn Ala
                980                 985

<210> SEQ ID NO 2
<211> LENGTH: 978
<212> TYPE: PRT
<213> ORGANISM: Unknown
<220> FEATURE:
<223> OTHER INFORMATION: identified from meta-transcriptomics sequence
      data from unknown Planctomycetes

<400> SEQUENCE: 2

Met Gln Glu Ile Lys Arg Ile Asn Lys Ile Arg Arg Leu Val Lys
1               5                   10                  15

Asp Ser Asn Thr Lys Lys Ala Gly Lys Thr Gly Pro Met Lys Thr Leu
                20                  25                  30

Leu Val Arg Val Met Thr Pro Asp Leu Arg Glu Arg Leu Glu Asn Leu
                35                  40                  45

Arg Lys Lys Pro Glu Asn Ile Pro Gln Pro Ile Ser Asn Thr Ser Arg
50                  55                  60

Ala Asn Leu Asn Lys Leu Leu Thr Asp Tyr Thr Glu Met Lys Lys Ala
65                  70                  75                  80

Ile Leu His Val Tyr Trp Glu Glu Phe Gln Lys Asp Pro Val Gly Leu
                85                  90                  95

Met Ser Arg Val Ala Gln Pro Ala Pro Lys Asn Ile Asp Gln Arg Lys
                100                 105                 110

Leu Ile Pro Val Lys Asp Gly Asn Glu Arg Leu Thr Ser Ser Gly Phe
                115                 120                 125

Ala Cys Ser Gln Cys Cys Gln Pro Leu Tyr Val Tyr Lys Leu Glu Gln
                130                 135                 140
```

-continued

```
Val Asn Asp Lys Gly Lys Pro His Thr Asn Tyr Phe Gly Arg Cys Asn
145                 150                 155                 160

Val Ser Glu His Glu Arg Leu Ile Leu Leu Ser Pro His Lys Pro Glu
            165                 170                 175

Ala Asn Asp Glu Leu Val Thr Tyr Ser Leu Gly Lys Phe Gly Gln Arg
            180                 185                 190

Ala Leu Asp Phe Tyr Ser Ile His Val Thr Arg Glu Ser Asn His Pro
        195                 200                 205

Val Lys Pro Leu Glu Gln Ile Gly Gly Asn Ser Cys Ala Ser Gly Pro
210                 215                 220

Val Gly Lys Ala Leu Ser Asp Ala Cys Met Gly Ala Val Ala Ser Phe
225                 230                 235                 240

Leu Thr Lys Tyr Gln Asp Ile Ile Leu Glu His Gln Lys Val Ile Lys
            245                 250                 255

Lys Asn Glu Lys Arg Leu Ala Asn Leu Lys Asp Ile Ala Ser Ala Asn
            260                 265                 270

Gly Leu Ala Phe Pro Lys Ile Thr Leu Pro Pro Gln Pro His Thr Lys
        275                 280                 285

Glu Gly Ile Glu Ala Tyr Asn Asn Val Val Ala Gln Ile Val Ile Trp
290                 295                 300

Val Asn Leu Asn Leu Trp Gln Lys Leu Lys Ile Gly Arg Asp Glu Ala
305                 310                 315                 320

Lys Pro Leu Gln Arg Leu Lys Gly Phe Pro Ser Phe Pro Leu Val Glu
            325                 330                 335

Arg Gln Ala Asn Glu Val Asp Trp Trp Asp Met Val Cys Asn Val Lys
            340                 345                 350

Lys Leu Ile Asn Glu Lys Lys Glu Asp Gly Lys Val Phe Trp Gln Asn
        355                 360                 365

Leu Ala Gly Tyr Lys Arg Gln Glu Ala Leu Leu Pro Tyr Leu Ser Ser
        370                 375                 380

Glu Glu Asp Arg Lys Lys Gly Lys Lys Phe Ala Arg Tyr Gln Phe Gly
385                 390                 395                 400

Asp Leu Leu His Leu Glu Lys Lys His Gly Glu Asp Trp Gly Lys
            405                 410                 415

Val Tyr Asp Glu Ala Trp Glu Arg Ile Asp Lys Lys Val Glu Gly Leu
            420                 425                 430

Ser Lys His Ile Lys Leu Glu Glu Arg Arg Ser Glu Asp Ala Gln
        435                 440                 445

Ser Lys Ala Ala Leu Thr Asp Trp Leu Arg Ala Lys Ala Ser Phe Val
450                 455                 460

Ile Glu Gly Leu Lys Glu Ala Asp Lys Asp Glu Phe Cys Arg Cys Glu
465                 470                 475                 480

Leu Lys Leu Gln Lys Trp Tyr Gly Asp Leu Arg Gly Lys Pro Phe Ala
            485                 490                 495

Ile Glu Ala Glu Asn Ser Ile Leu Asp Ile Ser Gly Phe Ser Lys Gln
            500                 505                 510

Tyr Asn Cys Ala Phe Ile Trp Gln Lys Asp Gly Val Lys Lys Leu Asn
        515                 520                 525

Leu Tyr Leu Ile Ile Asn Tyr Phe Lys Gly Gly Lys Leu Arg Phe Lys
        530                 535                 540

Lys Ile Lys Pro Glu Ala Phe Glu Ala Asn Arg Phe Tyr Thr Val Ile
545                 550                 555                 560

Asn Lys Lys Ser Gly Glu Ile Val Pro Met Glu Val Asn Phe Asn Phe
```

```
                565                 570                 575
Asp Asp Pro Asn Leu Ile Ile Leu Pro Leu Ala Phe Gly Lys Arg Gln
            580                 585                 590

Gly Arg Glu Phe Ile Trp Asn Asp Leu Leu Ser Leu Glu Thr Gly Ser
        595                 600                 605

Leu Lys Leu Ala Asn Gly Arg Val Ile Glu Lys Thr Leu Tyr Asn Arg
    610                 615                 620

Arg Thr Arg Gln Asp Glu Pro Ala Leu Phe Val Ala Leu Thr Phe Glu
625                 630                 635                 640

Arg Arg Glu Val Leu Asp Ser Ser Asn Ile Lys Pro Met Asn Leu Ile
            645                 650                 655

Gly Ile Asp Arg Gly Glu Asn Ile Pro Ala Val Ile Ala Leu Thr Asp
            660                 665                 670

Pro Glu Gly Cys Pro Leu Ser Arg Phe Lys Asp Ser Leu Gly Asn Pro
        675                 680                 685

Thr His Ile Leu Arg Ile Gly Glu Ser Tyr Lys Glu Lys Gln Arg Thr
    690                 695                 700

Ile Gln Ala Ala Lys Glu Val Glu Gln Arg Arg Ala Gly Gly Tyr Ser
705                 710                 715                 720

Arg Lys Tyr Ala Ser Lys Ala Lys Asn Leu Ala Asp Asp Met Val Arg
                725                 730                 735

Asn Thr Ala Arg Asp Leu Leu Tyr Tyr Ala Val Thr Gln Asp Ala Met
            740                 745                 750

Leu Ile Phe Glu Asn Leu Ser Arg Gly Phe Gly Arg Gln Gly Lys Arg
        755                 760                 765

Thr Phe Met Ala Glu Arg Gln Tyr Thr Arg Met Glu Asp Trp Leu Thr
    770                 775                 780

Ala Lys Leu Ala Tyr Glu Gly Leu Pro Ser Lys Thr Tyr Leu Ser Lys
785                 790                 795                 800

Thr Leu Ala Gln Tyr Thr Ser Lys Thr Cys Ser Asn Cys Gly Phe Thr
                805                 810                 815

Ile Thr Ser Ala Asp Tyr Asp Arg Val Leu Glu Lys Leu Lys Lys Thr
            820                 825                 830

Ala Thr Gly Trp Met Thr Thr Ile Asn Gly Lys Glu Leu Lys Val Glu
        835                 840                 845

Gly Gln Ile Thr Tyr Tyr Asn Arg Tyr Lys Arg Gln Asn Val Val Lys
    850                 855                 860

Asp Leu Ser Val Glu Leu Asp Arg Leu Ser Glu Glu Ser Val Asn Asn
865                 870                 875                 880

Asp Ile Ser Ser Trp Thr Lys Gly Arg Ser Gly Glu Ala Leu Ser Leu
                885                 890                 895

Leu Lys Lys Arg Phe Ser His Arg Pro Val Gln Glu Lys Phe Val Cys
            900                 905                 910

Leu Asn Cys Gly Phe Glu Thr His Ala Asp Glu Gln Ala Ala Leu Asn
        915                 920                 925

Ile Ala Arg Ser Trp Leu Phe Leu Arg Ser Gln Glu Tyr Lys Lys Tyr
    930                 935                 940

Gln Thr Asn Lys Thr Thr Gly Asn Thr Asp Lys Arg Ala Phe Val Glu
945                 950                 955                 960

Thr Trp Gln Ser Phe Tyr Arg Lys Lys Leu Lys Glu Val Trp Lys Pro
                965                 970                 975

Ala Val
```

<210> SEQ ID NO 3
<211> LENGTH: 855
<212> TYPE: PRT
<213> ORGANISM: unknown
<220> FEATURE:
<223> OTHER INFORMATION: identified from meta-transcriptomics
      sequence data from Candidatus Sungbacteria bacterium

<400> SEQUENCE: 3

Met Asp Asn Ala Asn Lys Pro Ser Thr Lys Ser Leu Val Asn Thr Thr
1               5                   10                  15

Arg Ile Ser Asp His Phe Gly Val Thr Pro Gly Gln Val Thr Arg Val
            20                  25                  30

Phe Ser Phe Gly Ile Ile Pro Thr Lys Arg Gln Tyr Ala Ile Ile Glu
        35                  40                  45

Arg Trp Phe Ala Ala Val Glu Ala Arg Glu Arg Leu Tyr Gly Met
    50                  55                  60

Leu Tyr Ala His Phe Gln Glu Asn Pro Pro Ala Tyr Leu Lys Glu Lys
65                  70                  75                  80

Phe Ser Tyr Glu Thr Phe Phe Lys Gly Arg Pro Val Leu Asn Gly Leu
                85                  90                  95

Arg Asp Ile Asp Pro Thr Ile Met Thr Ser Ala Val Phe Thr Ala Leu
            100                 105                 110

Arg His Lys Ala Glu Gly Ala Met Ala Ala Phe His Thr Asn His Arg
        115                 120                 125

Arg Leu Phe Glu Glu Ala Arg Lys Lys Met Arg Glu Tyr Ala Glu Cys
    130                 135                 140

Leu Lys Ala Asn Glu Ala Leu Leu Arg Gly Ala Ala Asp Ile Asp Trp
145                 150                 155                 160

Asp Lys Ile Val Asn Ala Leu Arg Thr Arg Leu Asn Thr Cys Leu Ala
                165                 170                 175

Pro Glu Tyr Asp Ala Val Ile Ala Asp Phe Gly Ala Leu Cys Ala Phe
            180                 185                 190

Arg Ala Leu Ile Ala Glu Thr Asn Ala Leu Lys Gly Ala Tyr Asn His
        195                 200                 205

Ala Leu Asn Gln Met Leu Pro Ala Leu Val Lys Val Asp Glu Pro Glu
    210                 215                 220

Glu Ala Glu Glu Ser Pro Arg Leu Arg Phe Asn Gly Arg Ile Asn
225                 230                 235                 240

Asp Leu Pro Lys Phe Pro Val Ala Glu Arg Glu Thr Pro Pro Asp Thr
                245                 250                 255

Glu Thr Ile Ile Arg Gln Leu Glu Asp Met Ala Arg Val Ile Pro Asp
            260                 265                 270

Thr Ala Glu Ile Leu Gly Tyr Ile His Arg Ile Arg His Lys Ala Ala
        275                 280                 285

Arg Arg Lys Pro Gly Ser Ala Val Pro Leu Pro Gln Arg Val Ala Leu
    290                 295                 300

Tyr Cys Ala Ile Arg Met Glu Arg Asn Pro Glu Glu Asp Pro Ser Thr
305                 310                 315                 320

Val Ala Gly His Phe Leu Gly Glu Ile Asp Arg Val Cys Glu Lys Arg
                325                 330                 335

Arg Gln Gly Leu Val Arg Thr Pro Phe Asp Ser Gln Ile Arg Ala Arg
            340                 345                 350

Tyr Met Asp Ile Ile Ser Phe Arg Ala Thr Leu Ala His Pro Asp Arg
        355                 360                 365

Trp Thr Glu Ile Gln Phe Leu Arg Ser Asn Ala Ala Ser Arg Arg Val
370                 375                 380

Arg Ala Glu Thr Ile Ser Ala Pro Phe Glu Gly Phe Ser Trp Thr Ser
385                 390                 395                 400

Asn Arg Thr Asn Pro Ala Pro Gln Tyr Gly Met Ala Leu Ala Lys Asp
            405                 410                 415

Ala Asn Ala Pro Ala Asp Ala Pro Glu Leu Cys Ile Cys Leu Ser Pro
            420                 425                 430

Ser Ser Ala Ala Phe Ser Val Arg Glu Lys Gly Gly Asp Leu Ile Tyr
            435                 440                 445

Met Arg Pro Thr Gly Gly Arg Gly Lys Asp Asn Pro Gly Lys Glu
450                 455                 460

Ile Thr Trp Val Pro Gly Ser Phe Asp Glu Tyr Pro Ala Ser Gly Val
465                 470                 475                 480

Ala Leu Lys Leu Arg Leu Tyr Phe Gly Arg Ser Gln Ala Arg Arg Met
            485                 490                 495

Leu Thr Asn Lys Thr Trp Gly Leu Leu Ser Asp Asn Pro Arg Val Phe
            500                 505                 510

Ala Ala Asn Ala Glu Leu Val Gly Lys Lys Arg Asn Pro Gln Asp Arg
            515                 520                 525

Trp Lys Leu Phe Phe His Met Val Ile Ser Gly Pro Pro Val Glu
530                 535                 540

Tyr Leu Asp Phe Ser Ser Asp Val Arg Ser Arg Ala Arg Thr Val Ile
545                 550                 555                 560

Gly Ile Asn Arg Gly Glu Val Asn Pro Leu Ala Tyr Ala Val Val Ser
            565                 570                 575

Val Glu Asp Gly Gln Val Leu Glu Glu Gly Leu Leu Gly Lys Lys Glu
            580                 585                 590

Tyr Ile Asp Gln Leu Ile Glu Thr Arg Arg Ile Ser Glu Tyr Gln
595                 600                 605

Ser Arg Glu Gln Thr Pro Pro Arg Asp Leu Arg Gln Arg Val Arg His
            610                 615                 620

Leu Gln Asp Thr Val Leu Gly Ser Ala Arg Ala Lys Ile His Ser Leu
625                 630                 635                 640

Ile Ala Phe Trp Lys Gly Ile Leu Ala Ile Glu Arg Leu Asp Asp Gln
            645                 650                 655

Phe His Gly Arg Glu Gln Lys Ile Ile Pro Lys Lys Thr Tyr Leu Ala
            660                 665                 670

Asn Lys Thr Gly Phe Met Asn Ala Leu Ser Phe Ser Gly Ala Val Arg
            675                 680                 685

Val Asp Lys Lys Gly Asn Pro Trp Gly Gly Met Ile Glu Ile Tyr Pro
690                 695                 700

Gly Gly Ile Ser Arg Thr Cys Thr Gln Cys Gly Thr Val Trp Leu Ala
705                 710                 715                 720

Arg Arg Pro Lys Asn Pro Gly His Arg Asp Ala Met Val Val Ile Pro
            725                 730                 735

Asp Ile Val Asp Asp Ala Ala Ala Thr Gly Phe Asp Asn Val Asp Cys
            740                 745                 750

Asp Ala Gly Thr Val Asp Tyr Gly Glu Leu Phe Thr Leu Ser Arg Glu
            755                 760                 765

Trp Val Arg Leu Thr Pro Arg Tyr Ser Arg Val Met Arg Gly Thr Leu
770                 775                 780

-continued

```
Gly Asp Leu Glu Arg Ala Ile Arg Gln Gly Asp Asp Arg Lys Ser Arg
785                 790                 795                 800

Gln Met Leu Glu Leu Ala Leu Glu Pro Gln Pro Gln Trp Gly Gln Phe
            805                 810                 815

Phe Cys His Arg Cys Gly Phe Asn Gly Gln Ser Asp Val Leu Ala Ala
        820                 825                 830

Thr Asn Leu Ala Arg Arg Ala Ile Ser Leu Ile Arg Arg Leu Pro Asp
            835                 840                 845

Thr Asp Thr Pro Pro Thr Pro
        850                 855

<210> SEQ ID NO 4
<211> LENGTH: 4
<212> TYPE: PRT
<213> ORGANISM: Artificial Sequence
<220> FEATURE:
<223> OTHER INFORMATION: Synthetic sequence

<400> SEQUENCE: 4

Ala Ala Ala Ala
1

<210> SEQ ID NO 5
<211> LENGTH: 4
<212> TYPE: PRT
<213> ORGANISM: Artificial Sequence
<220> FEATURE:
<223> OTHER INFORMATION: Synthetic sequence

<400> SEQUENCE: 5

Ala Ala Ala Ala
1

<210> SEQ ID NO 6
<211> LENGTH: 4
<212> TYPE: PRT
<213> ORGANISM: Artificial Sequence
<220> FEATURE:
<223> OTHER INFORMATION: Synthetic sequence

<400> SEQUENCE: 6

Ala Ala Ala Ala
1

<210> SEQ ID NO 7
<211> LENGTH: 4
<212> TYPE: PRT
<213> ORGANISM: Artificial Sequence
<220> FEATURE:
<223> OTHER INFORMATION: Synthetic sequence

<400> SEQUENCE: 7

Ala Ala Ala Ala
1

<210> SEQ ID NO 8
<211> LENGTH: 4
<212> TYPE: PRT
<213> ORGANISM: Artificial Sequence
<220> FEATURE:
<223> OTHER INFORMATION: Synthetic sequence

<400> SEQUENCE: 8

Ala Ala Ala Ala
1
```

<210> SEQ ID NO 9
<211> LENGTH: 4
<212> TYPE: PRT
<213> ORGANISM: Artificial Sequence
<220> FEATURE:
<223> OTHER INFORMATION: Synthetic sequence

<400> SEQUENCE: 9

Ala Ala Ala Ala
1

<210> SEQ ID NO 10
<211> LENGTH: 4
<212> TYPE: PRT
<213> ORGANISM: Artificial Sequence
<220> FEATURE:
<223> OTHER INFORMATION: Synthetic sequence

<400> SEQUENCE: 10

Ala Ala Ala Ala
1

<210> SEQ ID NO 11
<211> LENGTH: 23
<212> TYPE: RNA
<213> ORGANISM: Artificial sequence
<220> FEATURE:
<223> OTHER INFORMATION: Synthetic sequence

<400> SEQUENCE: 11
ccgauaagua aaacgcauca aag                                           23

<210> SEQ ID NO 12
<211> LENGTH: 37
<212> TYPE: RNA
<213> ORGANISM: Artificial sequence
<220> FEATURE:
<223> OTHER INFORMATION: Synthetic sequence

<400> SEQUENCE: 12
auuugaaggu aucuccgaua aguaaaacgc aucaaag                            37

<210> SEQ ID NO 13
<211> LENGTH: 26
<212> TYPE: RNA
<213> ORGANISM: Artificial sequence
<220> FEATURE:
<223> OTHER INFORMATION: Synthetic sequence

<400> SEQUENCE: 13
ucuccgauaa auaagaagca ucaaag                                        26

<210> SEQ ID NO 14
<211> LENGTH: 25
<212> TYPE: RNA
<213> ORGANISM: Artificial sequence
<220> FEATURE:
<223> OTHER INFORMATION: Synthetic sequence

<400> SEQUENCE: 14
guuuacacac ucccucucau agggu                                         25

<210> SEQ ID NO 15
<211> LENGTH: 25
<212> TYPE: RNA

<213> ORGANISM: Artificial sequence
<220> FEATURE:
<223> OTHER INFORMATION: Synthetic sequence

<400> SEQUENCE: 15
guuuacacac ucccucucau gaggu                                         25

<210> SEQ ID NO 16
<211> LENGTH: 25
<212> TYPE: RNA
<213> ORGANISM: Artificial sequence
<220> FEATURE:
<223> OTHER INFORMATION: Synthetic sequence

<400> SEQUENCE: 16
uuuuacauac ccccucucau gggau                                         25

<210> SEQ ID NO 17
<211> LENGTH: 25
<212> TYPE: RNA
<213> ORGANISM: Artificial sequence
<220> FEATURE:
<223> OTHER INFORMATION: Synthetic sequence

<400> SEQUENCE: 17
guuuacacac ucccucucau ggggg                                         25

<210> SEQ ID NO 18
<211> LENGTH: 10
<212> TYPE: RNA
<213> ORGANISM: Artificial sequence
<220> FEATURE:
<223> OTHER INFORMATION: Synthetic sequence

<400> SEQUENCE: 18
aaaaaaaaaa                                                          10

<210> SEQ ID NO 19
<211> LENGTH: 10
<212> TYPE: RNA
<213> ORGANISM: Artificial sequence
<220> FEATURE:
<223> OTHER INFORMATION: Synthetic sequence

<400> SEQUENCE: 19
aaaaaaaaaa                                                          10

<210> SEQ ID NO 20
<211> LENGTH: 10
<212> TYPE: RNA
<213> ORGANISM: Artificial sequence
<220> FEATURE:
<223> OTHER INFORMATION: Synthetic sequence

<400> SEQUENCE: 20
aaaaaaaaaa                                                          10

<210> SEQ ID NO 21
<211> LENGTH: 81
<212> TYPE: RNA
<213> ORGANISM: Artificial sequence
<220> FEATURE:
<223> OTHER INFORMATION: Synthetic sequence

<400> SEQUENCE: 21
acaucuggcg cguuuauucc auuacuuugg agccaguccc agcgacuaug ucguauggac   60

```
gaagcgcuua uuuaucggag a                                                      81

<210> SEQ ID NO 22
<211> LENGTH: 78
<212> TYPE: RNA
<213> ORGANISM: Artificial sequence
<220> FEATURE:
<223> OTHER INFORMATION: Synthetic sequence

<400> SEQUENCE: 22
acaucuggcg cguuuauucc auuacuuugg agccaguccc agcgacuaug ucguauggac           60
gaagcgcuua uuuaucgg                                                          78

<210> SEQ ID NO 23
<211> LENGTH: 65
<212> TYPE: RNA
<213> ORGANISM: Artificial sequence
<220> FEATURE:
<223> OTHER INFORMATION: Synthetic sequence

<400> SEQUENCE: 23
uuauuccauu acuuggagc cagcccagc gacuaugucg uaggacgaa gcgcuuauuu              60 aucgg                                                                       65

<210> SEQ ID NO 24
<211> LENGTH: 93
<212> TYPE: RNA
<213> ORGANISM: Artificial sequence
<220> FEATURE:
<223> OTHER INFORMATION: Synthetic sequence

<400> SEQUENCE: 24
aaguaguaaa uuacaucugg cgcguuuauu ccauuacuuu ggagccaguc ccagcgacua           60
ugucguaugg acgaagcgcu uauuuaucgg aga                                        93

<210> SEQ ID NO 25
<211> LENGTH: 68
<212> TYPE: RNA
<213> ORGANISM: Artificial sequence
<220> FEATURE:
<223> OTHER INFORMATION: Synthetic sequence

<400> SEQUENCE: 25
uuauuccauu acuuggagc cagcccagc gacuaugucg uaggacgaa gcgcuuauuu              60 aucggaga                                                                    68

<210> SEQ ID NO 26
<211> LENGTH: 69
<212> TYPE: RNA
<213> ORGANISM: Artificial sequence
<220> FEATURE:
<223> OTHER INFORMATION: Synthetic sequence

<400> SEQUENCE: 26
uuaucucauu acuuugagag ccaucaccag cgacuauguc guauggguaa agcgcuuauu           60
uaucggaga                                                                   69

<210> SEQ ID NO 27
<211> LENGTH: 66
<212> TYPE: RNA
<213> ORGANISM: Artificial sequence
<220> FEATURE:
```

<223> OTHER INFORMATION: Synthetic sequence

<400> SEQUENCE: 27
uuaucucauu acuugagag ccaucaccag cgacuauguc guauggguaa agcgcuuauu    60
uaucgg    66

<210> SEQ ID NO 28
<211> LENGTH: 230
<212> TYPE: RNA
<213> ORGANISM: Artificial sequence
<220> FEATURE:
<223> OTHER INFORMATION: Synthetic sequence

<400> SEQUENCE: 28
uaaauuuuuu gagcccuauc uccgcgagga agacagggcu cuuuucauga gaggaagcuu    60
uuauacccga ccgguaaucc ggucgggga uuggccguug aaacgauuuu aaagcggcca    120 augggcccu cuauauggau acuacuuaua uaaggagcuu ggggaagaag auagcuuaau    180
cccgcuaucu ugucaagggg uuggggagu aucaguaucc ggcaggcgcc    230

<210> SEQ ID NO 29
<211> LENGTH: 10
<212> TYPE: RNA
<213> ORGANISM: Artificial sequence
<220> FEATURE:
<223> OTHER INFORMATION: Synthetic sequence

<400> SEQUENCE: 29
aaaaaaaaaa    10

<210> SEQ ID NO 30
<211> LENGTH: 10
<212> TYPE: RNA
<213> ORGANISM: Artificial sequence
<220> FEATURE:
<223> OTHER INFORMATION: Synthetic sequence

<400> SEQUENCE: 30
aaaaaaaaaa    10

<210> SEQ ID NO 31
<211> LENGTH: 45
<212> TYPE: RNA
<213> ORGANISM: Artificial sequence
<220> FEATURE:
<223> OTHER INFORMATION: Synthetic sequence
<220> FEATURE:
<221> NAME/KEY: misc_feature
<222> LOCATION: (26)..(45)
<223> OTHER INFORMATION: n is a, c, g, or u

<400> SEQUENCE: 31
guuuacacac ucccucucau agggunnnnn nnnnnnnnnn nnnnn    45

<210> SEQ ID NO 32
<211> LENGTH: 45
<212> TYPE: RNA
<213> ORGANISM: Artificial sequence
<220> FEATURE:
<223> OTHER INFORMATION: Synthetic sequence
<220> FEATURE:
<221> NAME/KEY: misc_feature
<222> LOCATION: (26)..(45)
<223> OTHER INFORMATION: n is a, c, g, or u

<400> SEQUENCE: 32
guuuacacac ucccucucau gaggunnnnn nnnnnnnnnn nnnnn        45

<210> SEQ ID NO 33
<211> LENGTH: 45
<212> TYPE: RNA
<213> ORGANISM: Artificial sequence
<220> FEATURE:
<223> OTHER INFORMATION: Synthetic sequence
<220> FEATURE:
<221> NAME/KEY: misc_feature
<222> LOCATION: (26)..(45)
<223> OTHER INFORMATION: n is a, c, g, or u

<400> SEQUENCE: 33
uuuuacauac ccccucucau gggaunnnnn nnnnnnnnnn nnnnn        45

<210> SEQ ID NO 34
<211> LENGTH: 45
<212> TYPE: RNA
<213> ORGANISM: Artificial sequence
<220> FEATURE:
<223> OTHER INFORMATION: Synthetic sequence
<220> FEATURE:
<221> NAME/KEY: misc_feature
<222> LOCATION: (26)..(45)
<223> OTHER INFORMATION: n is a, c, g, or u

<400> SEQUENCE: 34
guuuacacac ucccucucau gggggnnnnn nnnnnnnnnn nnnnn        45

<210> SEQ ID NO 35
<211> LENGTH: 10
<212> TYPE: RNA
<213> ORGANISM: Artificial sequence
<220> FEATURE:
<223> OTHER INFORMATION: Synthetic sequence

<400> SEQUENCE: 35
aaaaaaaaaa        10

<210> SEQ ID NO 36
<211> LENGTH: 10
<212> TYPE: RNA
<213> ORGANISM: Artificial sequence
<220> FEATURE:
<223> OTHER INFORMATION: Synthetic sequence

<400> SEQUENCE: 36
aaaaaaaaaa        10

<210> SEQ ID NO 37
<211> LENGTH: 10
<212> TYPE: RNA
<213> ORGANISM: Artificial sequence
<220> FEATURE:
<223> OTHER INFORMATION: Synthetic sequence

<400> SEQUENCE: 37
aaaaaaaaaa        10

<210> SEQ ID NO 38
<211> LENGTH: 10
<212> TYPE: RNA
<213> ORGANISM: Artificial sequence
<220> FEATURE:
<223> OTHER INFORMATION: Synthetic sequence

```
<400> SEQUENCE: 38
aaaaaaaaaa                                                            10

<210> SEQ ID NO 39
<211> LENGTH: 10
<212> TYPE: RNA
<213> ORGANISM: Artificial sequence
<220> FEATURE:
<223> OTHER INFORMATION: Synthetic sequence

<400> SEQUENCE: 39
aaaaaaaaaa                                                            10

<210> SEQ ID NO 40
<211> LENGTH: 10
<212> TYPE: RNA
<213> ORGANISM: Artificial sequence
<220> FEATURE:
<223> OTHER INFORMATION: Synthetic sequence

<400> SEQUENCE: 40
aaaaaaaaaa                                                            10

<210> SEQ ID NO 41
<211> LENGTH: 92
<212> TYPE: RNA
<213> ORGANISM: Artificial sequence
<220> FEATURE:
<223> OTHER INFORMATION: Synthetic sequence

<400> SEQUENCE: 41
uuauuccauu acuuggagc cagucccagc gacuaugucg uauggacgaa gcgcuuauuu       60
aucgggaaac cgauaaguaa aacgcaucaa ag                                   92

<210> SEQ ID NO 42
<211> LENGTH: 108
<212> TYPE: RNA
<213> ORGANISM: Artificial sequence
<220> FEATURE:
<223> OTHER INFORMATION: Synthetic sequence

<400> SEQUENCE: 42
acaucuggcg cguuuauucc auuacuuugg agccaguccc agcgacuaug ucguauggac      60
gaagcgcuua uuuaucggag agaaaccgau aaguaaaacg caucaaag                 108

<210> SEQ ID NO 43
<211> LENGTH: 96
<212> TYPE: RNA
<213> ORGANISM: Artificial sequence
<220> FEATURE:
<223> OTHER INFORMATION: Synthetic sequence

<400> SEQUENCE: 43
uuaucucauu acuuugagag ccaucaccag cgacuauguc guauggguaa agcgcuuauu      60
uaucgggaaa ucuccgauaa auaagaagca ucaaag                               96

<210> SEQ ID NO 44
<211> LENGTH: 10
<212> TYPE: RNA
<213> ORGANISM: Artificial sequence
<220> FEATURE:
<223> OTHER INFORMATION: Synthetic sequence

<400> SEQUENCE: 44
```

```
aaaaaaaaaa                                                                10

<210> SEQ ID NO 45
<211> LENGTH: 10
<212> TYPE: RNA
<213> ORGANISM: Artificial sequence
<220> FEATURE:
<223> OTHER INFORMATION: Synthetic sequence

<400> SEQUENCE: 45
aaaaaaaaaa                                                                10

<210> SEQ ID NO 46
<211> LENGTH: 10
<212> TYPE: RNA
<213> ORGANISM: Artificial sequence
<220> FEATURE:
<223> OTHER INFORMATION: Synthetic sequence

<400> SEQUENCE: 46
aaaaaaaaaa                                                                10

<210> SEQ ID NO 47
<211> LENGTH: 10
<212> TYPE: RNA
<213> ORGANISM: Artificial sequence
<220> FEATURE:
<223> OTHER INFORMATION: Synthetic sequence

<400> SEQUENCE: 47
aaaaaaaaaa                                                                10

<210> SEQ ID NO 48
<211> LENGTH: 10
<212> TYPE: RNA
<213> ORGANISM: Artificial sequence
<220> FEATURE:
<223> OTHER INFORMATION: Synthetic sequence

<400> SEQUENCE: 48
aaaaaaaaaa                                                                10

<210> SEQ ID NO 49
<211> LENGTH: 10
<212> TYPE: RNA
<213> ORGANISM: Artificial sequence
<220> FEATURE:
<223> OTHER INFORMATION: Synthetic sequence

<400> SEQUENCE: 49
aaaaaaaaaa                                                                10

<210> SEQ ID NO 50
<211> LENGTH: 10
<212> TYPE: RNA
<213> ORGANISM: Artificial sequence
<220> FEATURE:
<223> OTHER INFORMATION: Synthetic sequence

<400> SEQUENCE: 50
aaaaaaaaaa                                                                10

<210> SEQ ID NO 51
<211> LENGTH: 25368
<212> TYPE: DNA
```

<213> ORGANISM: Artificial sequence
<220> FEATURE:
<223> OTHER INFORMATION: Synthetic sequence

<400> SEQUENCE: 51

```
ctggaaggac gcatggcaga aatcgttttt tactgttttt gccgataggg atagtttttg      60
cttcttgaca tgcttttttca tagatgacag attaaggact tttacaagag gctaacattg    120
ctttgttttt caaaaacaac ttaagaagat agtctatcat gcaaaaatct atagaggtta    180
ttgatgttat aaagatatac aagatgggag atgtagattt tccagcgctt caagggtttt    240
ctcttgagat agacaaaggg gaattcgtgg cagtaatggg gccgtcaggt tctggaaaat    300
ctacattcat gaacatcata ggctgtctcg atacgcctac tgccggaaaa tattggttgg    360
ataggcagga agtcgggcaa ttaagcaaag atgtgttggc aattatacgc aataaaaata    420
tagggtttgt atttcagagc tttaacctgc tgccaaggat aactgcaatg gaaaatgttg    480
aactccccct tttgtataac ggtttgccgt caagggagag aagacaaagg tctctttcag    540
cattgaggtc tgttgggctt gaagggaggg aatatcacaa atccaatcaa ttatcaggcg    600
ggcagcaaca gagggttgcc atagcaaggg cattggtaaa taatccatct ctcattctgg    660
ctgatgaacc aaccggcaat cttgattccc aaacaagcaa tgaacttatg acgcttttta    720
agcggctcaa taaggaaaac ggcataacta ttgttatggt aacccatgag gcagatgttg    780
cccggtatgc tgacaggcat attgttttta aggacggaag ggtggtaaaa gacgataaaa    840
ttacgaatta atcttgcaat tccctgtagc ttgctgcagg gttactttat agttccctcc    900
cccttgatgg gggagggtta gggtgggggt gatagaatgt tgtttccacc ctccccttg     960
tcccctcccg tcaagagagg ggagatttta ggatacccg cagcttgccg cggggaggtt   1020
cattaactac gaatttaaaa aaaccattc agatgtctta gcaggctgtt gaaaagtca    1080
tcaacagcct tgattacaca gattataaaa aatgattaca cagatatttc aaggagtttc   1140
aatctgtgta atccaatctt ttctctgtgt aatcagagat tgttgagttt ttcaacaatc   1200
tgttaatttt taattcttac ttcataattg cttttcctatg aacataatcg caaccattaa   1260
aatagccgcc aatgccctgg gcataaataa aatgaggtca ggcctaccaa tgcttggcat   1320
aataatcggc gtggccgctg ttatagccat gctctctgta ggctcaggcg caaggactca   1380
gatttctaaa gagattgcca gcctcggctc caacctttg ataattctgc ctggcgcgcc   1440
caccagcggc ggactcagaa tgggttttgg aacagcgccc acgttgacat ccgatgatgc   1500
aaaggcaata cctcaggaaa tatctaatgt tgcatttgca gcgccgattt taggcggcac   1560
agcgcagata gtatacggaa atcaaaactg gagcaccatt gtgacaggca caacaccggg   1620
tttttttgat atacgggaat ggcagcttga ctcaggcgct ctgtttaccc agaaggatgt   1680
tgatggcgca acaaaggttg cattggttgg ccagactgtt acggaaaacc ttttttggata   1740
tgaggaccca ttgggaaaga ttataagaat aaaaaagata ccatttagag tcatcggggt   1800
cttatccaga aaagggcagt ctcctattgg ccaggatcag gatgacagca tatatatacc   1860
ggtaacaact gcgcaaaaga ggcttttttgg cacaacattt cccggcatgg tgaggatgat   1920
aaccgtaaag gcgaaaacct ctgatgcaat caaagatgct gaaaaggaga ttgcggcatt   1980
actgagacag agacatcata ttacagccgg gagggacgaa gatgatttca gcgtccgcaa   2040
tcttagtgaa atgatggctg catctgaaca ggcggcaaaa atcatgtcca tcctcctcgg   2100
ctctattgcg tcggtatctt taatagtcgg cggcataggc attatgaaca tcatgcttgt   2160
ctctgtaaca gaaaggacaa gagagatagg catccgcatg gcagtcggcg caaggcccag   2220
```

```
agatatactc atgcagtttc ttatagaagc catagtcctt gctgtcattg gcggcagtat    2280
aggtattctg tgcggcgccg gaggctcatg gcttatttca tactttgccg gctgggagat    2340
agccatatcc tctgttgcta tagttcttgc attcggtttt tccgcgttag tcggaatatt    2400
cttcggtttt tatccggcca gaaaggcgtc ccgccttgcg ccggtggagt gtttgaggta    2460
tgaataagtt gtggtttgca ggcaaactcc attttcgttt tataatccgg agcggactgg    2520
gtttgtctgg ctgggttgcg gcattacaga ggaagtaaat ttgggaaact gttataaaaa    2580
aggttgaaat acatatctgt tctgcttata ataagaatat cagataatca gaaaggagga    2640
atttatatgc ctgttgtcaa aatgagggaa agggacaac taaccatccc atacgaatac    2700
aggaaagatc tcggcattgg caaggaagat atgctcaatg tcttaaaaat cggcgatgtg    2760
cttatccttg tgccgaaaca gcttgccgga gatatcgtat ccaagaaaat tgaagggacg    2820
atgaagaaaa aagggctgac acttgataac cttctaagca atctcaggga gcagagaaaa    2880
agatattcca aagagacata tgccaaagca aagacctaaa gttttcttg acacaagcgc    2940 attgattgcc ggcatagcat cttcaagggg cgcagcaagg gctgtgctgc agcttgctga    3000
aatcggtttg atacaggtct ttgtctcaag gcaggtcatt gtggaagcag acaggaatat    3060
tgaagaaaaa ctgccggaga tgctgaatga atacagagaa tttatcaaac tcctatcacc    3120
cgtgttagtt gatgacccaa gccacaagga agttgcaaaa tatttatcag taatcaattc    3180
ggatgacgcg cctatccttg cctctgcaat aacctcacac gctgatttcc ttatcacatg    3240
ggacagaaag catttcatcg gcaaaaatat ccgtatccac ttaaacctga aaatcgttac    3300
tccgggagat tttttgaagt atttcaggaa atatattgag taaaagccca cctctttggc    3360
aaagagggga atggcatttg tttgagggac gaggggactg tcccagacaa aataaaattat    3420 ttttaaccgt tttttggatg tgtgttatat tctgtgaata aggagggatt gccatggatg    3480
ataaagacaa ggatttaatg ctggaattta gaaaaaggct ttcatcggat ttagcaaatc    3540
atataacacg tctcatagta ttcgggtcaa gggcgaaagg tgaagtagca gaggattctg    3600
atcttgatgt aattgccata gttgatgaaa aaaactctgc gattgaaaaa agtcttgaag    3660
atatagcgta tcggattatg tgggatcatg acttcaggcc aatcatatca ctcaaagtgc    3720
tctctgaagc ccaattcagt gacgcccttc gtagagggtt ttcttttac aggcatgtgg    3780 aaaaagaggg ggttttggta tgaccgagga agtaaaaaag ctgattgaaa aagctgaaca    3840
cgcccttgag gtagccgaaa agttaatgaa tgacggttat ccatcagatg ccgcaagcaa    3900
aatctattat tcaatgtatt atgcagcaca tgccccttta aaatcagaag gaattgatgt    3960
catcaagcac tcagccgttg aatcagcctt cgggtattac tttgcgaaga ctggaaagat    4020
taatcccaaa caccacagga tgctaataga cgcaagaaag attcgtgaaa tagccgatta    4080
tgatattcag gaagagattg ttgagccaac tgcatcgcta aaaattaaag aggggaagtc    4140 tttttttgtct gcaatcagaa aaattcttgg cagcctgtag caatggactt gacaagcgaa    4200
gtgggactgt ccaggattta cggacagagc gaagcggagt cccgaatcca atggttgtgg    4260
tttgcgggca ggcattattt tcgtttata atctggaaag aaaaaaggaa aaccccttat    4320 ggaaagaga ataaacaaga tacgaaagaa actatcggcc gataatgcca caaagcctgt    4380
gagcaggagc ggccccatga aaacactcct tgtccgggtc atgacggacg acttgaaaaa    4440
aagactggag aagcgtcgga aaaagccgga agttatgccg caggttattt caaataacgc    4500
agcaaacaat cttagaatgc tccttgatga ctatacaaag atgaaggagg cgatactaca    4560
```

```
agtttactgg caggaattta aggacgacca tgtgggcttg atgtgcaaat ttgcccagcc    4620
tgcttccaaa aaaattgacc agaacaaact aaaaccggaa atggatgaaa aaggaaatct    4680
aacaactgcc ggttttgcat gttctcaatg cggtcagccg ctatttgttt ataagcttga    4740
acaggtgagt gaaaaaggca aggcttatac aaattacttc ggccggtgta atgtggccga    4800
gcatgagaaa ttgattcttc ttgctcaatt aaaacctgaa aaagacagtg acgaagcagt    4860
gacatactcc cttggcaaat tcggccagag ggcattggac ttttattcaa tccacgtaac    4920
aaaagaatcc acccatccag taaagcccct ggcacagatt gcgggcaacc gctatgcaag    4980
cggacctgtt ggcaaggccc tttccgatgc ctgtatgggc actatagcca gttttctttc    5040
gaaatatcaa gacatcatca tagaacatca aaaggttgtg aagggtaatc aaaagaggtt    5100
agagagtctc agggaattgg cagggaaaga aaatcttgag tacccatcgg ttacactgcc    5160
gccgcagccg catacgaaag aagggggttga cgcttataac gaagttattg caagggtacg    5220
tatgtgggtt aatcttaatc tgtggcaaaa gctgaagctc agccgtgatg acgcaaaacc    5280
gctactgcgg ctaaaaggat tcccatcttt ccctgttgtg gagcggcgtg aaaacgaagt    5340
tgactggtgg aatacgatta atgaagtaaa aaaactgatt gacgctaaac gagatatggg    5400
acgggtattc tggagcggcg ttaccgcaga aaagagaaat accatccttg aaggatacaa    5460
ctatctgcca aatgagaatg accataaaaa gagagagggc agtttggaaa accctaagaa    5520
gcctgccaaa cgccagtttg gagacctctt gctgtatctt gaaaagaaat atgccggaga    5580
ctggggaaag gtcttcgatg aggcatggga gaggatagat aagaaaatag ccggactcac    5640
aagccatata gagcgcgaag aagcaagaaa cgcggaagac gctcaatcca agccgtact    5700
tacagactgg ctaagggcaa aggcatcatt tgttcttgaa agactgaagg aaatggatga    5760
aaaggaattc tatgcgtgtg aaatccaact tcaaaaatgg tatggcgatc ttcgaggcaa    5820
cccgtttgcc gttgaagctg agaatagagt tgttgatata agcgggtttt ctatcggaag    5880
cgatggccat tcaatccaat acagaaatct ccttgcctgg aaatatctgg agaacggcaa    5940
gcgtgaattc tatctgttaa tgaattatgg caagaaaggg cgcatcagat ttacagatgg    6000
aacagatatt aaaaagagcg gcaaatggca gggactatta tatggcggtg caaggcaaa    6060
ggttattgat ctgactttcg accccgatga tgaacagttg ataatcctgc cgctggcctt    6120
tggcacaagg caaggccgcg agtttatctg gaacgatttg ctgagtcttg aaacaggcct    6180
gataaagctc gcaaacggaa gagttatcga aaaacaatc tataacaaaa aatagggcg    6240
ggatgaaccg gctctattcg ttgccttaac atttgagcgc cgggaagttg ttgatccatc    6300
aaatataaag cctgtaaacc ttataggcgt tgaccgcggc gaaaacatcc cggcggttat    6360
tgcattgaca gaccctgaag gttgtccttt accggaattc aaggattcat caggggccc    6420
aacagacatc ctgcgaatag gagaaggata taaggaaaag cagagggcta ttcaggcagc    6480
aaaggaggta gagcaaggc gggctggcgg ttattcacgg aagtttgcat ccaagtcgag    6540
gaacctggcg gacgacatgg tgagaaattc agcgcgagac cttttttacc atgccgttac    6600
ccacgatgcc gtccttgtct ttgaaaacct gagcaggggt tttggaaggc agggcaaaag    6660
gaccttcatg acggaaagac aatatacaaa gatggaagac tggctgacag cgaagctcgc    6720
atacgaaggt cttacgtcaa aaacctacct ttcaaagacg ctggcgcaat atacgtcaaa    6780
aacatgctcc aactgcgggt ttactataac gactgccgat tatgacggga tgttggtaag    6840
gcttaaaaag acttctgatg gatgggcaac taccctcaac aacaaagaat taaaagccga    6900
aggccagata acgtattata accggtataa aaggcaaacc gtggaaaaag aactctccgc    6960
```

```
agagcttgac aggctttcag aagagtcggg caataatgat atttctaagt ggaccaaggg    7020
tcgccgggac gaggcattat ttttgttaaa gaaaagattc agccatcggc ctgttcagga    7080
acagtttgtt tgcctcgatt gcggccatga agtccacgcc gatgaacagg cagccttgaa    7140
tattgcaagg tcatggcttt ttctaaactc aaattcaaca gaattcaaaa gttataaatc    7200
gggtaaacag cccttcgttg gtgcttggca ggccttttac aaaaggaggc ttaaagaggt    7260
atggaagccc aacgcctgat attgccgata agcaccgtaa tggaatccat ctactgcccg    7320
cgcaacgcat ggtatgcctt tgtgggcgag cggcggaata tggctaaaag cgttcacttt    7380
acggaggccg tccatgcaca cagggcggtg gatgaatcca cgcagagaat ccgcactgat    7440
tgcaagcaga ttacagggat gtatatttat agcaataagc ttggcctgac agggcgggcg    7500
gatacagttg agtggctgta tggaatccct ataccggttg agacaaagac cggcgcaatc    7560
agggattttg agaacttccg ggtacagatt gcattacagg ccttgtgcct ggaagagatg    7620
tttaatgtga acatcccata cggtgagata ttttctgtg aaaccatgcg gcggcacgaa    7680
atagctgtag acgaagacct tagaacgcat agcacggcaa ttgtggtgga gttgagagaa    7740
aggtttctgt cttttgacat caaccgcttc caaagggtaa atgaccatag atgcccaaag    7800
tgtcaatatt tggagtcatg ccttcctccg agtcttgagt tgtgaggttc ctttatgacg    7860
gcgataacag acaggataac cctttacatc acagcggatg aatccagcat ttcacgccga    7920
ggcgatgcat tcctgatcca aaaggcaggc gaggaaaaag gcaaaagat accagcgatg    7980
aaagtaaaag atatagtagt cgttggtcac gttacgcttg acagccgtct gattggactt    8040
tgcagggaag agtcaattcc gatccatttt ctaagcggaa ggtgggaata tcagggtagc    8100
cttcagttcg agccggtcaa gaatctattt atccgcaggg cgcagataaa aaaacatttc    8160
gacccggaaa agaaactgga tatatccaaa aaaatagtcg gtggaaaaat ccgaaatcag    8220
caggccatgc tggataaata ccggaaaaat ctgaagttgg cgtgcccgca aattgattca    8280
gtgggcgata tggaaaccct gcgagggatt gagggtgtgg tggcaaagga gtattacggc    8340
ttctatcccg ccataataaa aaattcggag ttcacgttta cacgcaggac aaagcgtccg    8400
ccggaggatg aaataaacgc gctcctaagc ctgctgtata ccctcatttt caacgagata    8460
cactctaccg cattgctcgt agggctggac ccggcctttg ggtatctcca cgacgtctat    8520
tacgacgac catcgttgat ttgcgatctt cttgaagaat ggcggccatt ggccgaccgg    8580
tttgtgctga atatgataaa caggaaagag gtcacaccgg aagatttcag gaaagagacc    8640
gaccaaaagg gcgtgtggtt aagcaaggac ggatatccaa aggtgataaa gaaatggcac    8700
cagttttttca agatggatga acaaaacaca agcattctga gccgcccat aacatatcaa    8760
cacgcaattg aaaggcaggt caggaccttc agccagtatc tcatggatga caaagacaat    8820
tataagacga tagagctttg ataatgcgcc atctcatctg ttatgacata gaggaggata    8880
aggtaagggc acggcttgta aagctcttgg aagcctacgg cgtcaggatt caatattctg    8940
tttttgaatt caacctttca aaggcgcgct ggacagacct taagctgaat ttgaaagaaa    9000
aagggttcct tgacggctcc attagcattg tcatctatcc attatccgca gaggcttatg    9060
agctggtgga acgttatggc gctgcctcta tatgggatga ggggatatg gttttcgatt    9120
gattttcttt gactgcaatc tgtcataagt agtaaattac atctggcgcg tttattccat    9180
tactttggag ccagtcccag cgactatgtc gtatggacga agcgcttatt tatcggagat    9240
agctccgggt gcaaactcgg agctgttttt ttacgaaaca gctaatttta gccaaaagtt    9300
```

```
ctttgaaaac ctgatattac ggttttttg tttgtaaaag ggtttacagt gcagatctcc    9360
ttataattat tgaaaatgtg tttcgttact cttaatattc gagaatttcg acttccggaa   9420
ctcattgata tatctgggtt gttggtattt gaaggtatct ccgataagta aaacgcatca   9480
aaggtctcac tcaagatgac gaggagatac ttgagaattt gaaggtatct ccgataagta   9540
aaacgcatca aagatccaga aaaatacggc cttctttacc atttcctatt tgaaggtatc   9600
tccgataagt aaaacgcatc aaagtacccc tgcacccatt agatttagat gcaggataat   9660
ttgaaggtat ctccgataag taaaacgcat caaagagctc tgctttgtag atgcctgctg   9720
caagggttga tttgaaggta tctccgataa gtaaaacgca tcaaagtcct gcagcagaaa   9780
atcaaagaca atgaatatta tttgaaggta tctccgataa gtaaaacgca tcaaaggccg   9840
ctctgaaaaa ggaaaagctc ggactaaaat tatatttggg cgggaagcaa cgtaaagcct   9900
tcttttcttg ctgcatctct cagttttgaa tcaaggcaga cgaaataatg accttttggc   9960
cttttttcctg cccatacgag cgcggcagat agttgcaagg catctgcggc acggagaggg  10020
tgcagcataa gaagtcttcc tgcaatatcc cgtatgtctt cgccgggttc aatctctgtc  10080
catgtatccg aaagaagggt gaggagatgc cgcacaccgt cttcttcctc aggtttgagg  10140
aatcccttgc gccgcaagcg ggcaaaggct gaacagcact ctatgaagct gccccaccat  10200
actgcaatag cgtgatcttt tctcacaagc tgttagacag cctttgtttg tggttcgtca  10260
atgcataatg ggatgatagc agaagaatcc cagaacatca tcttccttcc tcccgttccc  10320
gtaaaagggc attaagagcc cgtccttttt tatcctttgg tctgggcata ttccaaaaat  10380
ctgccggcag tctgcctgcg ccgatgcgga caagccctgc cttctccaac gttaatagat  10440
gcgccggtat ttcaatatct cctcttttca aaggaataat cttggctata ggctttcccc  10500
tgtcagtgac aagaacctct tctccagcct ttacctttga caggtattcg ctgatagatg  10560
cctttaattc agaaaccttt gcggtcttca tagggttatc ctccgtgact atatggatat  10620
gaccgatata gtcttattcc atagccctgt caaatgaaaa aaacgaataa cagttactt    10680
atcgtatgaa acataagctc agcatgattt aatgaaccgc ttttatcaag aatgagtttc   10740
aggagaaaag ggcgtcttgg cggaagcgag ttaaaccgca ggtcaaaata ttccaccata   10800
tatccttcgc cctcctcttt tacggttacc acaggaaatc tggcaaacca gagatatgtc   10860
tttacaatct ccagttttc aacctttca ataatgttat ttccctccgg tcctgatttt     10920
aagccttcag ggagatgctt tttctcaaag gaattaaatg gcgagatgct tttcagcgca   10980
tcaacatcaa cctgataaaa cctttttatca tcctctatat acacagacca tctgaaaggg  11040
gagaaggga ggggaattgc ctcaactctt ttgccggtta tgccaagttt ttgagcctcg     11100
gccttagcgc tttcaatagc aatggttctc catgtgtagg caatcccag atagattatt     11160
atacctgcaa cagaactcaa ggctataacc tttgtccatt cccgtttgaa ctttattatg   11220
accaatggga taagcatcaa ggcggtgaaa taaaatcta tgataaagac aaggtcaaga    11280
gagtatcttt tgtcggtgaa aggaaagaaa actaaagtcc cgtaagatgt gatgaggtca   11340
aggaagatat gggtgtatat gcctaataaa aacaggccaa aggttgttag atagcctaat   11400
ttttctctaa atcgttctat tgaacagaca atacctgcca tgatacgggc gattacaaaa   11460
ctgccgataa tggagtgcgt aaatccccga tggtatttga ataggcgag gggacctgca   11520
agcctcaggg ttaagtggtc aatatcaggt attagtgcgg caacaataaa gattatggtg   11580
gcaggtctgc caaatctctg atagaatcct gttctggaca gaacgacacc ggagaggccg   11640
tgtgttattg gatccatagg tttagataag tatattatat ataatggtat taaacaacag   11700
```

```
gggattttat cgttacccttt ttatgagaac aattaaaaga acagtttgtt cagcctttgt   11760
tttatttatc ttattctcgt cagatgctgt tgccgacctt tatcagtggc aggatgaaaa   11820
aggggatatc catgttgtag atgatatgct cctggttccg ccgcaatata aagataaggc   11880
aaagaaatta aaggcaaggc cttcaaggca aaccccttct ccccaacaaa atgttcaacc   11940
ccctgtgccg cctcaaacat cttcagaaca agaagagctg tatggggatt atcctttgag   12000
ttggtggaaa aatgagttca gcagtaaaaa aaacgagatt tctaaacttg aaaatactat   12060
aaaagagcag aaaaatttta tagctgatta tgaagaggg aggaggcttt atcgattata   12120
cagcaaggaa gatacggata aatacgaaac ctataaaaaa gagctgtctg ataatgagaa   12180
ccaattgaac aaactcaaaa cagatttgga cgaattcagg cgcaaggcgc aaatctacgg   12240
cgttccgagg gcaatcagag aatagtaatt aacaggctgt tgaaaaggc atcaacagcc   12300 ttgattacac agattaggaa aaacgattac acagatattt caatgagttt taatctgtga   12360
aatctaatct tttatccgtg taattgaagt ttgttgagtt tttcaacaaa ctgttaatat   12420
ggtaaaacct gttatcagtt gtagggcaag ccttcaggct tgcttatttg cagggctaaa   12480
gccctgccct acatcaagtt atttatcaag ttatttattg ccttcactat aatatggtaa   12540
aacctattat cagaaatagc attgcatatc tcttatgttt atgcctcctt taccccgtga   12600
ctaaggtttt tggtgtggat gacgatgcta taacaatagt ggcagcagga gacctttatc   12660
ttggaggctc tgccaatcca tacttaaaac agcgcggata ttcatatcca tttgaatcaa   12720
ccaaggatgt tttgcatagc gcggatatcg cagttgtcaa tctcgaagcg cccttgacca   12780
acaagacgga aatatttatg aataaagagt ttgtccttaa ggctaaccct gattcaagtg   12840
aggcgataaa ggctgtgggt tttgatgtgg cgacattggc aaataatcac attatggatt   12900
acgggcaaga gggattgaaa gatacgataa ccgcacttaa taagagaggg gtaagctata   12960
ctggcgcagg agaagactta aataatgcaa ggaagcctgc catccttaat gttaaaaata   13020
aaaagattgc ctttcttgca tattccaggg tctttccaga agaattctat gctaccgata   13080
tctctggcgg aacagcgccc ggtttatttg aatatataag ggacgatatt aaaaagataa   13140
agaaagatgc tgatattgtt gttgtttctt ttcactggag tgaagagctg ttgaaatatc   13200
ccaaagaata ccaaattaaa cttgcccatc ttgccattga cagcggggca aatctaatca   13260
taggccatca cccgcatgtg attcagggta tagagaaata taaaaacggc ctcatctttt   13320
acagtcttgg gaattttgcc tttggatcta tcagccaatc atcgccagag ggtatattgg   13380
ccgctgtccg gtttaagggt aaccaaatca tctcggctga gataattcca ttaaatgtca   13440
ataataaaga ggttttttttt cagccaaagg ttttggaagg agaaagggcg gaagttgcaa   13500
tgaggaatat tcaagaaata tcagacagat tcaaattaac cattatggct agggaaggaa   13560
agggctacat acagcttaac gaggagttaa aatcagcctc gcttccgtga ataggggttg   13620
ttgttacaag tagagttaag tcagatatta tgtaaacgtg tgatcccttg ctatgcaagt   13680
ttacataata tatcttatgc gacaataaaa tttagttagc cttaatggcc tgtttgggct   13740
aaaaatccct atattccatt cgttttgccc cctgttatct ttatcccgct tttctttatt   13800
gcgcttttta tcatctttag tttccaatcc ctatgcgcat taattgtaga gagaacctct   13860
ctggggttat cggttatttt aacgaggtct aaatcttccg gagatattgt atcttccttt   13920
aacatcgttg ttttcatcca gtggataaga ccattccaat aatccttgcc aaccagaatt   13980
aaaggcaatg gatatatctt atgagtctga acaagcgtaa gcgcctcaaa aaattcatca   14040
```

```
agggttccaa atccgccagg catacagaca tagcccatgg catactttat aaacatcacc   14100
tttctggcaa aaaagtattt aaaggttaat gatttattct gaaatgggtt cggcttctgc   14160
tcctttggca gaaggatgtt gagtcctacc gaacctccgc cattcttggc agcgcctctg   14220
ttggcagcct ccataatgcc gggaccgccg ccggttatga tggtatagcc atcctttgca   14280
agcagtgtgg ctatatcttc ggccattttg tagtatgtat gattttagg aaatcttgcg    14340
gagccgaata tagatacagc cggccctatg gcagaaagtt cttcaaaacc ctccacgaac   14400
tcgctcatta ttttaaatat acgccatgtt tcctgacctc ttaaatcttc aaccattttt   14460
atttactccc attctatagt actcgggggt tttgtgctga tatcataaac cacctgttg    14520
atgccgcgca cttcatttat aatccttgag gagatccttg ccattaaatc atagggaagc   14580
tttacccagt ctgccgtcat tccatccatg cttttctacag cccttattgc ggcaacattc  14640
tcatatgtcc tctcatcacc catgacaccc actgtcctta cgggcaaaag cactgcaaac   14700
gcctgccaca tctttgtgta aaggccggcc ttttttatct cttcaagcac aatactgtct   14760
gccttttctta gtatatcaca tctctctttt gtaacctcgc ctaaaattct tatagcaagg  14820
cctgggcctg gaaatgggtg tctgtttatt atttcctcag acatgccaag ttctttaccc   14880
agtatccgca cttcatcctt aaacaattcg cgaagaggtt cgacaagttt gagtttcatt   14940
ttttttagaa gaccgccgac attatggtgg cttttattg tcgctgaagg gcctttgaag    15000
gatacactct caatcacatc cggataaaga gtgccttgtc caagaaagct cacttcctgc   15060
cttttgcctc cgcctctggc ggatgaggcg gatgcccct gttttaactt catggcctct    15120
tcttcaaaga cccttacaaa ttcattgcct attattttc tcttcttttc agggtcctcg    15180
atacctttga gcttgtttaa aaatctttga gaggcgtcaa tacatttaaa attcatacga   15240
aaatgcttct ttaatgtctc ttcaaccttc tttgcctcac cctgcctcaa tacgccgttg   15300
tctacaaaga tacaggtaag tttgtttcct atggcttat gcattaatac cgctgcaact    15360
gctgaatcca cacccccgct tatgccgcat accaccccc tgcccctac cctttccctt    15420
atatccttta cagcagtgtc tacaaatgcc tccatggtcc agataggttt gcatccacat   15480
atcttgaaaa ggaaatttct aattatctgc aagccctttg gcgtatgaac tacttccgga   15540
tgaaactgca cgccaaagat ttttcttttg gcatccttca tagcacagat tggagaatta   15600
ctactgcggg caatagatgt gaatccatta ggcatctttc ttacacggtc gccgtggctc   15660
atccatacag gcgtgaggtg tgaggcgtaa ggcgtgaggc gtgacaacaa atcattacta   15720
tcatcaatta ccagttcagc gcttccgtat tctctgtgtg atgattttc aacctttccg    15780
cctaaaaggt aggctgtaag ctgcatgccg tagcatatgc cgaggattgg aatgtccaga   15840
ttgaagagtt cttttggaat aagaggggcg tttttatcgt agacgcttga cggcccgccg   15900
gagaggatta tgccttttgg gtgaaaagcc ctgatctttt caaggcctat attataagga   15960
tgtatctcgc agtagacctt tgttcccgc accctcctgg caataagctg ggtatattgg    16020
gaaccaaagt ctaaaataag gattttttgc tgatgtatgt tttgcattag gggaatatt    16080
tattaaagtt aaaaaaatat atcttaaaaa aaccaaatag acaatagaaa aatcatgcgt   16140
gtaaaaaacc tctttcttga cagtatccat tctgttatga taagaacagc tctttttta    16200
tacagaacaa gactgaatct tacgatagaa tcattaagca aatcatatag tttaataggt   16260
aggacacttc atgtttcaat ttgttaagat agcagcgcta tcctttataa taattatagc   16320
accttgggat tcatttaaac caacatataa tagcgatata tttcagttta taataacctc   16380
tttcagttca gttgacctgc catttgtatc aagcagtctg catagagagg aattggaaca   16440
```

```
agcctctgtc tttttggaagt atttctttct attaatctttt ttcctgtctg ttgatggatt   16500
caaaatattg attgaaattt ataaacgtcc ggtcttacgg acttatactt ccaaccctca   16560
ggatgtaaca gcattaatcg catgctacaa tagcgctaaa acaataaagt ttacgattga   16620
tgaccttcaa aagattttgt ctaatgatag gattattgtt gtggatgacg gcagcactga   16680
taatacattt aatattgcaa agaatatggg cgttcaggta tatcggtttg aaatgaataa   16740
aggaaaagtt gcagccatta attttggaat ctaccgtgtt aaaactaagt atactttgct   16800
attagatgat gatacaaggg taggcccttt gtctcctcca acctctttgc tggaggaagg   16860
gtacaccgga gtggcctta acctttacc ttgccgtaga acacgagact tgactaatgg   16920
gaaaaacttt gtaagctgcc ttcagagata cgagtacagt aaatccatgg agattggcaa   16980
aagattccaa gacggcgcat tgagcgtcag ctgcatatcc ggcgcagtag gcctgttttt   17040
gacttcacgg ctcaattctt tccatcattt acactcaacg gtatttcagg gagaagattt   17100
ggagagaacc ttaatagatt tattaaaagg cggaaaggtt gcctttgtaa atcaaaatgt   17160
ttggaccttt gccccggata actggttgag tctcacaaag caacggcttt ttaactggta   17220
ccctgggttt taccgcaata tagaccattt cttccatata ctctttgaca aacaacttcc   17280
gttaaggctc aaaggtgaaa tgttttataa catctttgta attctgactg atcctctaag   17340
gatatattca ttttttgccc tgtttattta taagcagtgg gctatgcttc ttttcgtata   17400 tctctttttat ttagctatag agatatacccc ctttattgta gtggaaaaat atcttcctgt   17460
cgcaagatat tatatgcccg ccctcatcgc atatcccata tatggaattt ataatacct   17520 attgcgctct cttgctttat tcgtatggtt gtataataga tttataacaa aacggatgag   17580
accaaaagga cgcccggggg atagaattgc ttaggaatgc cttttctgatt gctgtatttc   17640 tactatggct gccaaatgtt gtaatgggcg ctgacagctt aactatcaca aatgattata   17700
ttatagatat caaagatggc ggggataaaa catataacga cacatatatc cgcttagatt   17760
ataaacagct ctacgcagtg ggctatcttg gagagtggca gcatggcttt gaaataggcg   17820
ggtttataaa agatgaacgg atgtctgcgt atagcgcaat gttgcgggct cgtggaaatg   17880
atcagaccta tcaggtggga accgatcagg tgttaggaat gggttttgtg ggaaaggttg   17940
atttacgata catccatatt gaagaattag aaaaaaccgg agataaacac gacctttttg   18000
tttatggttt gggatttgat aaatattatg gtgattacaa ctatttgact gctgtgattt   18060
ataacgaccc ccggaagagt gatagattct ctgtagtcat cagtaacacc cttgccaatc   18120
agaactctta tctgagatta ggtgtcgttc cgagaagcga cggcacattg ggctattttg   18180
gaacaataaa ataccactgg attgtggccg gatatgccta tacgcgagaa tttgacttta   18240
ctacccttga taggaaggtt tttaccttag cgctccagat accctttgat ttaaagtgga   18300
acagagaaga acaataaccc gaaaagtgca taatgcctgt ctgcaaacaa ctactccacc   18360 acctataat tcggcgcctc ttttgtgatt acgacatcat ggacatgact ttcacgaagc   18420
cctgcaatgc ttattctgac taatttggca ttctttctaa gctcagaaat agtcctgcac   18480
ccgcaataac ccataccgga ttttaggccg cctataagct gaaatatact tgaagatacc   18540
ggccccttgt gaggcaccct cccctcaatg ccttccggca caagcttaag ctcgctctca   18600
acatcatcct gaaagtatct gtctttgctc cctttcttca tagcttcaat agatcccatt   18660
cctctataca tcttataggt tcgcccttga taaagaactg tctccccagg gctttcatct   18720
gtgcctgcaa ataaccctcc tatcataacc gaatcagcgc cggcagcgag ggcctttaca   18780
```

```
atatcgcctg aaaactttat gccgccgtcg gcaataaccg gtatgttctt ttttctggca   18840
acagccgcac aatccatgat ggctgttatc tgcggaacgc ctaccctgt cactatcctg    18900
gtggtgcata ttgagccggg gccaatgcca atctttacag catcaacgtc agcctttatc   18960
agagcatttg cgccatcgga tgtcccaaca ttgcctgcta tcagctggca ttttggaaag   19020
ttttcttgg tatctttaac agcggtgagc acccctttgc tgtggccgtg ggctgtatca    19080
ataacaataa catcagcgcc tgcctttaaa agcgcatcta tccttgcctc gcggtcaaat   19140
gatacgccaa ctgcagcgcc aaccattaat cgcccgagtt tatccttgca agagtttgga   19200
tattttccc gttttctat gtcagagatg gttatcaggc ctttcaactg cccattttta    19260
tcaattaacg gcagttttc tatcctgtgg cggtgaagca tatcctttgc cttttctatt    19320
gatgtgccgg ccggagctgt tacaagtttt tttgtcatta cctcggatat ttttttgtta   19380
gggttcttct caaatcttaa gtccctgttg gtaaggatgc cgaccaatac cccgttttta   19440
actatagga aactggatat ctgctctatt tttttaatct gcaatgcatc ggcaatgcgc    19500
tggtctggct ccagtgtcct tggtttcatt attacaacac tttcgtattt ttttactttg   19560
tcaacctcta tggcctgttc ttctatggtc aggtttttat ggattatgcc cataccgcct   19620
tcctgggcta ttgcaattgc catgcggat tccgttactg tatccatagc ggagcttaaa    19680
agaggtatat ttaatctgat ggtatttgta aggcgggtag aggtatctac atccctcggc   19740
aaagcttccg aaaatgccgg tatcagtaaa acatcgtcaa aggcaagacc ttgtttaata   19800
tttttttctg gcataaataa aacctccaac agaaattgat tgaggctgga ggcaagaggt   19860
gcgaggcaaa cgacactacc tccatcctcc aacctctaac ctgtcttctc caatagtatc   19920
ccttccaaaa gccccgcatc gcttaccgtc attttatcaa aaccaaaacc ttccattgcc   19980
tttaaaacaa tagctgcgcc tgggattatt atgtcttccc tcccctttc aagagagaga    20040
atttcctctc tctgttttaa aggcaataag gcaaggtgtt gatatatctt tctgatagcc   20100
tcataactta atatgtaatt gtttatcttg cctgactcat atttctcaag tccctgatca   20160
atagcagcaa gcgtggtaat agtacctgct gttcctacaa ataaggcgga ggctgaaggt   20220
aaacagccat ctcttttcat caaatccttt aaatctgcaa taacacctct tatctcattt   20280
tccattgcgt ctaactcact gtgagtcggc gggtctgtct tgagataatt ttctgtgaga   20340
tgcaccaccc ccatctcaag actccacgca ccaagcatcc ttccggcatc tgttgcaata   20400
aactcggtgc tccctccgcc aatatcaacg acaaggcatt tggggataga ttttaaatct   20460
gtccccactt ttatgactga cagaaccccca agcaaagaaa gccttgcctc ttcatcgcct   20520
gatattatct ttatctctat ccctgtcctt tcaggacac tgttcagaaa ttcttccctg    20580
ttctttgccc tgcgtaccac actggttgca actgccctta cctcttttat atcatactct   20640
tttatctttt cagaaaaaaa ctcaagcgcc tttattgtcc tttcctgagc cttcctgttt   20700
atgccaatat cttctttata accgccgcca agcttgtga tggttcgttt taagtaaaca    20760
ggctgaaggt ttttattatc tatctctgca atcagtaacc ttaaggtgtt tgtgccaata   20820
tcaatggagg cgtatttgt tgacatagct gtatcattgc ttaattcagt ttatgctcaa    20880
aaatatccca gatgcaaggc gccgaggagc gagcagcgga gcatacgccc tcaggtatgt   20940
gagcagcgca gtgacgaagg caacgtagca gatgggtatt tttcagcata aactatttcc   21000
tttccggctc tattgcgata gataacttct ctgccccggc gcgcttggca atatccaaaa   21060
cctttacaac tatgccgtgg agaacatctt tatctgcctt tattattacg attttatcag   21120
ctcgagatgt aatatctgtt tttatagcgt caaaaagcat ttctatgccg attgttttgt   21180
```

```
tgttaatata tataataccct cccggagcaa tggagatagt tatacccttc cctgtttcag   21240
tgtctgccgt aaccgccttt ggcagcttta ttttgaatga ttccattatc agaagcggcg   21300
ttgtcaccat aaaaatcaca agcaagacaa gcatgacatc agtcaatgga gtgatattta   21360
tctcagagat aatcttatcc ctattacctg caagactcca ttttttcatt tattgtcctc   21420
aaaaagcgca tcaataaatt ctgctgccct gccttctatt tcaactgccg cgctgtttat   21480
ttttcttgta aagtaattat atgcaataac cgccggcaca gccacaaaaa gacctgctgc   21540
ggttgccaca agggcctctg caatcccatc tgccacaaca gaaggccctg cccctctgc    21600
tatggcgagg tcatggaatg ccctgataat tccaagcact gtgccaaaga gccccacaaa   21660
gggggctgtg cttccagtgg ttccaagaac gcctaaatac cgctctaaat aaagaagctc   21720
ttgttttgct gccagctcca ttgcctctcc aaccgctgtt ttgccttctt tatatttgt    21780
aagccctgcc ttaaaaatcc ttgccagagg ttcttccttc ccgcagatgg taaatgccgc   21840
ctccctgtta ccatcccctta aagccttttc aatttgcaaa gaaatatttt tagaacctct   21900
tcggaattta aataaagccc aaagtctctc catcatcacg ccgacagaga gaacagaaaa   21960
gaaggcgagg acaattaccg taacgccgcc tttttgaagc agggatataa gaccaagatt   22020
atcaaacata tttatatttc taaacctaat gtaatctgcc gatttatcgg ctattcaaag   22080
ttacgcaata gaaatacgcc cataaatggg caactacctt ttatactcct tagaatattc   22140
aatgtagttt tttgcggatt tcaaaatcct tgccacttct tcatctttaa gctgtcggac   22200
aacctttccc ggcagcccca tgacaaggct tttcggcggg attatgctct tttcagtaac   22260
gagtgcgccc gctcctatga tggaatcttc gccgatggta acgccatcaa gtattattga   22320
acccatgccg atgaggcacc tatctttgat cacacagccg tgcagcgtaa cattgtgccc   22380
gacagtaata tcattgccaa gcatcacagg ccaaacacct tttgtgccgt gaaggacgca   22440
attatcctgg atatttgtcc ttgcgccaag cttaatatga tgaacatcgc ctctcagaac   22500
agcgttgcac caaatgctgg aatattcgcc tatctccaca tcgccgatta cctgggcgct   22560
gtcttcaata taggctgtag catgtatttt tggatttatg tttttgtaag gtcttatcat   22620
aagaaattac agattgtgat atgccttata aatatagtat aaggtctttt cttcggtaga   22680
tattctcttc attaacgccg ctcttattgc aataatgcca tttataaaac cggtttcgtc   22740
tgctgtaatg gcttttcat tttcatacct tgaaagaaaa tcaaaatat tcttggaaat    22800
atctttcatg ccgtctataa aaatatcaag cgcaggcagc agtgcgtctt gtttaagctc   22860
tatggccttt tgcctcatag cagggtaaaa cttattgtcc tcatcccgga gatgattaat   22920
gaggatagtt ttaagctgtt caataatttt caatacataa gcagtgtcac ggatgtcctt   22980
gttttctata ataggctcta atttcttgaa tgccttctct atcattgcat gttctttttc   23040
taaacccttta ataattttt catgctccat aacaatgccc ctctaaataa agacaccaat   23100
aaaggtgtaa aactataaca aaaacaccca tctttgcgca agattttgct gccacccaga   23160
aaatcaaagt ctatttttt gtatcacttt ctgggcgtct ttacagatgc gataaattca    23220
gcgctgaaaa gcaatataac tgccgaataa aatatccata aaagcattat cataatagcg   23280
ccaagagagc catacatctt attaaaactc ccaaagtgtg cgaggtataa ggcaaagagg   23340
tgttttgctg tctcccataa aacagagaat attacgctgc ctaaaatagc atgtcttgcc   23400
tttatgttct tcccggccat tattttgaat ataaggcga cggcaataat cataattaca   23460
actggcagga aatatttaaa ggttatactc tttgcaacat agtaggatat atctatgccc   23520
```

| | | | | |
|---|---|---|---|---|
| aagacagcta | tttttactct | gcctaaaatc | tctgcggcaa | tcggaagacc tatagaaata | 23580 |
| agaaaaactg | cgcaccagat | aaaaaataca | ccccatacaa | ctatcctggt ttttatgaag | 23640 |
| cccatcttct | ctgcttctcc | aaaaatgagg | ttcattgcat | cccttatcgc gagtattaca | 23700 |
| aactcagcgc | tccagatgag | cgtgataatg | ccaatccagc | caaaaacctt tctgttagct | 23760 |
| ataagccctt | taatatcatc | tacgatgctg | tcgctcaaat | atggaaggct ctcctttaca | 23820 |
| aattctaaaa | tccgttcaaa | aagccgtgtc | tccgttccga | aatagagcc tataaaagag | 23880 |
| aagagcagaa | acatgagcgg | gagcagagag | aataaggcat | aaaatgatat tgccgcagcc | 23940 |
| atagtaagac | aattatcata | agaaaatgcc | ctaatgctgt | cagttataat tacaaaaagt | 24000 |
| cgtttcataa | ttatttctgc | ctcttttctaa | aataaagccg | tatgacaacc ttatcaaggc | 24060 |
| caaaggcctc | tctcatttga | tttacaagga | accgttcata | ggaaaagtga atacccttccg | 24120 |
| ggtaattggc | aaagccgaca | aatgtaggcg | gttttatgtc | agtctgggtt atataataaa | 24180 |
| ttttcagcaa | tttccccta | tacatcggag | gctgatggtg | cttattgaag gtgctaaaaa | 24240 |
| atttgttaag | ctgtgcagtt | ggtatcctt | tcgtaagctg | cgccaatacc tcttctacca | 24300 |
| attcaaggat | tttaaaaaatc | ctctggcctg | taagcgctga | cacaaagatg acagggcga | 24360 |
| actgcaaaaa | ttttaccttc | caccgtatac | gttctgcata | ttgttttgcc gtgtttgtct | 24420 |
| cttttttcagg | caaatcccat | ttattgacaa | caataataca | tcccttaccc ctttcatagg | 24480 |
| caaggcctgc | tatcttttca | tcctgctctg | tcatgccgct | cattgcatct ataaccaata | 24540 |
| atgcaacatc | gcatctatca | atacacttga | ttgccgacat | aactgaatac tgttcaagcg | 24600 |
| ccatgcctat | ccttgccttt | tttcttatac | cggctgtatc | aacaagcaga taattttct | 24660 |
| tattataatt | gaattgcgta | tcaatggcat | ctctggttgt | gccaggaata tcgcttacca | 24720 |
| caaccctctc | atagccgaga | agcctgttaa | caagggaaga | cttgccgaca tttggtcttc | 24780 |
| caactactgc | caattttatc | ctctcttctt | tttcttcttt | gacagcagcc cttggaataa | 24840 |
| ggcttattgc | tttatctaat | aattcatcaa | ccccccttcc | ctgttcagat gaaacgagaa | 24900 |
| agagattttc | catgccgaga | ctgaagaaat | cagaaacccc | ctgttcttgc ttggtagtat | 24960 |
| ctattttatt | cacagcataa | actattggtt | tgccggattt | tctcagtatg tctgccacat | 25020 |
| ccctatctga | cggaagaaat | ccatctctgc | catccatgag | aagtataata acatcagcct | 25080 |
| cctcaatggc | gagcatggcc | tgctctctta | ccttggcagg | gatagttaaa tccctcctat | 25140 |
| caccctttct | ggggacagtc | cgcatttggc | ggatgaaatc | tgttcccata gggcgagcgg | 25200 |
| ggattgcctc | gaaaccgcct | gtgtcaataa | gggtaaatgt | tgttcctcgt tcaaccacat | 25260 |
| ccccataatt | caagtctctg | gttacaccag | gctcattttt | tacaatggcc tttcttttcc | 25320 |
| caatgagacg | gttgaagagg | gttgacttgc | cgacattcgg | cctgccta | 25368 |

<210> SEQ ID NO 52
<211> LENGTH: 7832
<212> TYPE: DNA
<213> ORGANISM: Artificial sequence
<220> FEATURE:
<223> OTHER INFORMATION: Synthetic sequence

<400> SEQUENCE: 52

| | | | | |
|---|---|---|---|---|
| gctatctta | atctcaattc | ttttcataca | cgcataatac | cataaatctg tattatgcgc | 60 |
| aatatattat | gtcgttatgt | ataataagct | gataaatacc | gatccgagac ccatttcatg | 120 |
| taaaaggca | catattttc | tttaactagt | ggcttctgaa | tgagatgctc tttaaaagcc | 180 |
| aaaagcataa | caggatcaaa | caattatcgt | aattcagtat | aataataaat atcctatttc | 240 |

```
ttatctaaaa tatctccaag ttttcaacat aatgctgtcg attttggatt gacatccgct    300
aagtaatacg atattcctta acacttcaat ctctttctga aaattttatc tctttatggt    360
cttgccattg ctctatactt tatctatttc tcattgcttg caattgaaat atgaaggtga    420
ccccaatctc ccgccatgaa aacttagtca aatatattta ttgcatggag atttcatctg    480
tagtaaaatc ctgaaaatgc tgggatgaaa gatatttatc gaattttgcc atctatttaa    540
atagccacca aactatatac ttattaaaga attgggggta aagatgcagg aaataaaaag    600
gataaataaa atacgaagga gattggtaaa ggatagcaac acgaaaaaag ccggcaaaac    660
cggccctatg aaaaccttgc tcgttcgggt tatgacacct gacctgagag aaaggttaga    720
gaatcttcgc aaaaagccgg aaaacattcc tcagcccatt tcaaatactt cacgtgcaaa    780
tttaaataaa ctcctcactg actatacgga aatgaagaaa gcaatcctgc atgtttattg    840
ggaagagttc caaaaagacc ctgtcggatt gatgagcagg gttgcacaac cagcgcccaa    900
gaatattgat cagagaaaat tgattccggt gaaggacgga aatgagagac taacaagttc    960
tggatttgcc tgttctcagt gctgtcaacc cctctatgtt tataagcttg aacaagtgaa   1020
tgacaagggt aagccccata caaattactt tggccgttgt aatgtctccg agcatgaacg   1080
tttgatattg ctctcgccgc ataaaccgga ggcaaatgac gagctagtaa cgtattcgtt   1140
ggggaagttc ggtcaaaggg cattggactt ttattcaatc cacgtaacaa gagaatcgaa   1200
ccatcctgta aagccgctag aacagatcgg tggcaatagc tgcgcaagtg gtcccgttgg   1260
taaggcttta tctgatgcct gtatgggagc agtagccagt ttccttacaa agtaccagga   1320
catcatcctc gaacaccaaa aggttataaa aaaaaacgaa aagagattgg caaatctaaa   1380
ggatatagca agtgcaaacg ggcttgcatt tcctaaaatc actcttccac cgcaaccgca   1440
tacaaaagaa gggattgaag cttataacaa tgttgttgct cagatagtga tctgggtaaa   1500
cctgaatctt tggcagaaac tcaaaattgg cagggatgag gcaaagcccct tacagcggct   1560 taagggtttt ccgtccttcc ctcttgttga acgccaggcg aatgaggttg attggtggga   1620
tatggtctgt aatgtcaaaa agttgattaa cgaaaagaaa gaggacggga aggtcttctg   1680
gcaaaatctt gctggatata aaaggcagga agccttgctt ccatatcttt cgtctgaaga   1740
agaccgtaaa aaaggaaaaa agtttgcgcg ttatcagttt ggtgacccttt tgcttcacct   1800 tgaaaagaaa cacggtgaag attggggcaa agtttatgat gaggcatggg aaagaataga   1860
taaaaaagtt gaaggtctga gtaagcacat aaagttggag gaagaaagaa ggtctgaaga   1920
tgctcaatca aaggctgccc tcactgattg gctcagggca aaggcctctt tgttattga    1980 agggctcaaa gaagctgata aggatgagtt ttgcaggtgt gagttaaagc ttcaaaagtg   2040
gtatggagat ttgagaggaa aaccatttgc tatagaagca gagaacagca ttttagatat   2100
aagcggattt tctaaacagt ataattgtgc atttatatgg cagaaagacg gcgtaaagaa   2160
gttaaatctt tatttaataa taaattactt caaaggtggt aagctacgct tcaaaaaaat   2220
caagccagaa gcttttgaag caaataggtt ttatacagta attaataaaa aaagcggtga   2280
gattgtgcct atggaggtca acttcaattt tgatgacccg aatttgataa ttctgccttt   2340
ggcctttgga aaaaggcagg ggaggagtt tatctggaac gacctattga gccttgagac   2400
gggttcattg aaactcgcca atggcagggt tattgaaaaa acgctctata acagaaggac   2460
gagacaggat gaaccagcac ttttttgttgc cctgacattt gaaagaagag aggtgcttga   2520
ctcatcgaat ataaaaccga tgaatctgat aggaatagac cggggagaaa atatcccggc   2580
```

```
agtcatagca ttaacagacc cggaaggatg ccccttgtca agattcaaag attcattggg    2640
caatccaacg catattttgc gaataggaga aagttataag gaaaaacaac ggactattca    2700
ggctgctaaa gaagttgaac aaaggcgggc aggcggatat tcgagaaaat atgcatcaaa    2760
ggcgaagaat ctggcggacg atatggtaag aaatacagct cgtgacctct tatattatgc    2820
tgttactcaa gatgcaatgc tcattttga aaatctttcc cgcggttttg gtagacaagg     2880
caagaggact tttatggcgg aaaggcagta cacgaggatg gaagactggc tgactgcaaa    2940
gcttgcctat gaaggtctgc catcaaaaac ctatctttca aagactctgg cacagtatac    3000
ctcaaagaca tgttctaatt gtggttttac aatcacaagt gcagattatg acagggtgct    3060
cgaaaagctc aagaagacgg ctactggatg gatgactaca atcaatggaa aagagttaaa    3120
agttgaagga cagataacat actataaccg gtataaaagg cagaatgtgg taaaagacct    3180
ctctgtagag ctggatagac tttcggaaga gtcggtaaat aatgatattt ctagttggac    3240
aaaaggccgc agtggtgaag ctttatctct gctaaaaaag agatttagtc acaggccggt    3300
gcaggaaaag tttgtttgcc tgaactgtgg ttttgaaacc catgcagacg aacaagcagc    3360
actgaatatt gcaaggtcgt ggctctttct ccgttctcaa gaatataaga agtatcaaac    3420
caataaaacg accggaaata ctgacaaaag ggcatttgtt gaaacatggc aatcctttta    3480
cagaaagaag ctcaagaag tatgaaaacc agccgtctga tattgcacat cagcacggta     3540
atggagtcaa tctattgtcc gcgcaatgca tggtatgcct tgttggaga acggcgtaat     3600 atggctaaga gcatccactt tacagaggcc atacacgcgc acaggcggt ggataaatca     3660 tcgcagagaa gctgccctga ttgtaagcag gtaacaggcg tgtatcttta cagcaataag    3720
ctcggtttgg caggccgggc agaccttatc gagtggaggg atgggatacc gattcctatc    3780
gaaacaaaga cagggaaggt aagggattt gagaacttcc acgttcagat tgggttacag     3840
gcaatttgcc ttgaagagat gtataatgtc aatataccag ttggtgaaat atttttctgt    3900
gaaacacgga gacggaaaga aattgttata gataaaaccc tgaaagtgcg ttgtgtagaa    3960
gttgttacaa atctgcgaga ctgcttcttg tcctttgata taagcaggtt tcccaaggtt    4020
gatgaccata ggtgtccgca gtgccagtat agtgaatcgt gtcttccttc aatacttggt    4080
tagaaaaata aaaggcttac tgatgaccgc tataaccgac aggataaccc tctatctcac    4140
gggtgatgaa ttcattttgg attgtcgtgg tcggcatttt ctcataaaaa aggacaatga    4200
agagaagggg cagaagattc ccgcaatgaa ggtaaaagat atcgtggtag ttggccgggt    4260
taccctcgat agccgtgtta ttagcctttg cagagaagaa tctataccga tacatttctt    4320
tagcggcaga tgggaatatc aagggagcct tcaatttgaa cccgtcaaaa atctgtttat    4380
tcgtcgggcg caaattcata agcattttga tccccacaaa aaacttgaaa ttgcaaaaag    4440
tatcgttgcc ggtaagatca aaaccagca atcattactt gataaatata gacttggttt      4500
gagaatcgag tgtaccgaaa tcaacgccgt cactgattta gagaccttgc gtggaataga    4560
aggcgcaaca acaaggcagt attatggcaa ttttcggct atcttaaagc atccaagctt     4620 tgttttgtg cgccgtacca agagacctcc tgaggatgaa atcaacgcca tgatgagcct      4680
tatctacacc ctcctgttca acgaaataca ttcgactgca ttactcgtcg ttttgaccc     4740 ggcctttggt tacttgcatg acgtctatta tggtcgtccc tctttaatat gcgatcttct    4800
ggaggagtgg cggccgttgg ctgaccgttt tgtgatcaat ttgataaata gaagggaagt    4860
ggatacagac gatttcagga agaaactga ccaaaaaggt gtttggctga ataaggatgc     4920
ctatccaaaa gtaatcaaaa aatggcatca attctttaag gtagatgagc agaaaaccaa    4980
```

```
tttacttatc caatcaataa cgtatcagca cgcagttgag cggcaggtta ggttgtttag   5040
ccagcatatt caagatgata gggaatgtta taagcctata gagctttaaa atgcgacatc   5100
tcatttgtta tgatattgaa gatgataagg tcagggcacg gttagttaaa cttctggaag   5160
cctatggtgt tcggattcaa tattctgtct ttgagtttaa cctttcaaaa gcaaggtggg   5220
ctgatctaaa gctcaacctt aaagaaaaag gatttatgga tggctctata agtctggtaa   5280
tttatcctct ctcagaggag atatatgaac ggatagaaag gtacgaagc gctgctattt    5340 ggaatgaagg ggatatggtc tttgattgat tttaagcttg acgaaaggat tgtgaatag    5400 taaattatta ctggcgcttt tatctcatta ctttgagagc catcaccagc gactatgtcg   5460
tatgggtaaa gcgcttattt atcggagagt tctggatgca aacccagagc tgttttttta   5520
gattcttata aattacataa gaagttcttt gaaaatctga tgttaaagct ttttgtgaga   5580
agaacaggtt tacagtgcgt aactctgcta aattattaaa ggtatcctcc gcaacttgta   5640
aaatattgaa aatacaattt ccagaagtca ttgaaaaatc tggatatgcg gggtttgaag   5700
atatctccga taaataagaa gcatcaaagt taatccccaa atagacgggc taaaatacgt   5760
atcgtttgaa gatatctccg ataaataaga agcatcaaag cttatatata tacaatcttt   5820
gcaggtttct gtgtttgaag atatctccga taaataagaa gcatcaaagt tatctaatct   5880
tgatgtcttt ctcaatacat tacgtttgaa gatatctccg ataaataaga agcatcaaag   5940
agccagaaga tatgcctgta aaatgggcaa tgtttgaaga tatctccgat aaataagaag   6000
catcaaagaa tattaatggt tcaccattgc catgttgatg gtgtttgaag atatctccga   6060
taaataagaa gcatcaaaga ataataggc gcataattcc acgatttcag tttgaagata    6120
tctccgataa ataagaagca tcaaagtatt aaatactcgt attgctgttc gattatgttt   6180
gaagatatct ccgataaata agaagcatca agaacaaag cagaatatat tacacggaca    6240
aatcatgtga ttaggaagat aaaggctttg gggtagatat aatgagcttt acacgagtag   6300
attgcctttc cttgattcaa aagatttcag aagagatagg cgctttgtgc cttaaatccc   6360
cagaatcaac aattcagaga cacgtggaaa aacccagccc cataaaaaat cctttagact   6420
tagccccatt aattgagcat accttattga aaccggaggc aacccatagg gatataacga   6480
ggctttgcga tgaggcaagg cgattccatt ttcgtggcgt ctgtgtgaat cctgtctttg   6540
ttaaagaagt ccaaaaccaa ttagcaggaa cagattgttt gattgttact gttgtgggtt   6600
tcccactagg tgctaattta acagctacaa aggttgagga aacgaaacat gttataaatc   6660
taggtgcgaa tgaggtggat atggttattg cactcggtgc attgaaagag ggcaattaca   6720
aaactgtcta taatgacatc cgtgcggtcg ttaaatctgt agaatcaata cctgttaagg   6780
taattgtaga ggcaggactt ctgaatgaaa gagaaaagat agccgcttgt ctgttagcag   6840
aacgggctgg cgcatcgttt gttaaaacct ctactggttt tactgcacgt agtgcgacgg   6900
taggagatgt cagattaatg aaggcagtag taggagacag actcggcata aaagccgcag   6960
gtgggatacg tgattttcag actgcctgcg ctatggtgga ggcaggggca gtgcgtttgg   7020
gctgttcggc atcggtagca attgtgacag aacacatata aaaaagcatt gtgagatatt   7080
tttgtatata atgtttaaca atagaatttt ttaaatattt ctgtttgttt actattttgg   7140
caagtttaag tatgtatctt ttgttatttc ttcttcgtgc tgaacaagct atattgacca   7200
tctttaaaac agtatgtccc tataacattg ggagcttctg gattttttaaa ggatatgaca   7260 aatttaagac gtgaataacc agcggtttca gatgaaggtt ctacctctac gtaggtcaag   7320
```

-continued

| | |
|---|---|
| tgcgccttat gctcaaggct aatgatattc cactgaattc ccttattatc gggaaactca | 7380 |
| gcttctgcca acctggtaat attgtctttc agaaacgatt ccctctttgc ctcttcgctg | 7440 |
| acaaaggttg tttcctgttt tggttgcaca atgtcgggct ttgcctcgct agtctgcgtt | 7500 |
| atttcttcag tagctttctg caaatcttcg gacttagtct gttcactgat tacggctgtt | 7560 |
| tcctcttttg gtggtgcgat atcagtattt acttcgccgg tctgtgttgt ttcttcaaga | 7620 |
| ccttcctgtg tattttcagc cattgccttt tctatttcct cgatgccttt cttgattccc | 7680 |
| tctcccacag ccttgccaag acctttcacc atctcaccca ctgcgcctcc aaacattgac | 7740 |
| atcattgtct tgtcagcatc aaccttccac tgtccgcctt cttttacaag aatagtctgc | 7800 |
| atctggactt caaattccgt tgtctcgtta tg | 7832 |

<210> SEQ ID NO 53
<211> LENGTH: 10
<212> TYPE: DNA
<213> ORGANISM: Artificial sequence
<220> FEATURE:
<223> OTHER INFORMATION: Synthetic sequence

<400> SEQUENCE: 53
aaaaaaaaaa                                                          10

<210> SEQ ID NO 54
<211> LENGTH: 25
<212> TYPE: DNA
<213> ORGANISM: Artificial sequence
<220> FEATURE:
<223> OTHER INFORMATION: Synthetic sequence

<400> SEQUENCE: 54
gtttacacac tccctctcat agggt                                         25

<210> SEQ ID NO 55
<211> LENGTH: 25
<212> TYPE: DNA
<213> ORGANISM: Artificial sequence
<220> FEATURE:
<223> OTHER INFORMATION: Synthetic sequence

<400> SEQUENCE: 55
gtttacacac tccctctcat gaggt                                         25

<210> SEQ ID NO 56
<211> LENGTH: 25
<212> TYPE: DNA
<213> ORGANISM: Artificial sequence
<220> FEATURE:
<223> OTHER INFORMATION: Synthetic sequence

<400> SEQUENCE: 56
ttttacatac cccctctcat gggat                                         25

<210> SEQ ID NO 57
<211> LENGTH: 25
<212> TYPE: DNA
<213> ORGANISM: Artificial sequence
<220> FEATURE:
<223> OTHER INFORMATION: Synthetic sequence

<400> SEQUENCE: 57
gtttacacac tccctctcat gggggg                                        25

```
<210> SEQ ID NO 58
<211> LENGTH: 10
<212> TYPE: DNA
<213> ORGANISM: Artificial sequence
<220> FEATURE:
<223> OTHER INFORMATION: Synthetic sequence

<400> SEQUENCE: 58
aaaaaaaaaa                                                                  10

<210> SEQ ID NO 59
<211> LENGTH: 10
<212> TYPE: DNA
<213> ORGANISM: Artificial sequence
<220> FEATURE:
<223> OTHER INFORMATION: Synthetic sequence

<400> SEQUENCE: 59
aaaaaaaaaa                                                                  10

<210> SEQ ID NO 60
<211> LENGTH: 10
<212> TYPE: DNA
<213> ORGANISM: Artificial sequence
<220> FEATURE:
<223> OTHER INFORMATION: Synthetic sequence

<400> SEQUENCE: 60
aaaaaaaaaa                                                                  10

<210> SEQ ID NO 61
<211> LENGTH: 43
<212> TYPE: RNA
<213> ORGANISM: Artificial sequence
<220> FEATURE:
<223> OTHER INFORMATION: Synthetic sequence
<220> FEATURE:
<221> NAME/KEY: misc_feature
<222> LOCATION: (24)..(43)
<223> OTHER INFORMATION: n is a, c, g, or u

<400> SEQUENCE: 61
ccgauaagua aaacgcauca aagnnnnnnn nnnnnnnnnn nnn                             43

<210> SEQ ID NO 62
<211> LENGTH: 70
<212> TYPE: RNA
<213> ORGANISM: Artificial sequence
<220> FEATURE:
<223> OTHER INFORMATION: Synthetic sequence
<220> FEATURE:
<221> NAME/KEY: misc_feature
<222> LOCATION: (38)..(70)
<223> OTHER INFORMATION: n is a, c, g, or u

<400> SEQUENCE: 62
auuugaaggu aucuccgaua aguaaaacgc aucaaagnnn nnnnnnnnnn nnnnnnnnnn           60 nnnnnnnnnn                                                                  70

<210> SEQ ID NO 63
<211> LENGTH: 174
<212> TYPE: RNA
<213> ORGANISM: Artificial sequence
<220> FEATURE:
<223> OTHER INFORMATION: Synthetic sequence
<220> FEATURE:
<221> NAME/KEY: misc_feature
<222> LOCATION: (142)..(174)
```

<223> OTHER INFORMATION: n is a, c, g, or u

<400> SEQUENCE: 63
aaguaguaaa uuacaucugg cgcguuuauu ccauuacuuu ggagccaguc ccagcgacua    60
ugucguaugg acgaagcgcu uauuuaucgg agauagcucc gaaaauuuga agguaucucc   120
gauaaguaaa acgcaucaaa gnnnnnnnnn nnnnnnnnnn nnnnnnnnnn nnnn         174

<210> SEQ ID NO 64
<211> LENGTH: 128
<212> TYPE: RNA
<213> ORGANISM: Artificial sequence
<220> FEATURE:
<223> OTHER INFORMATION: Synthetic sequence
<220> FEATURE:
<221> NAME/KEY: misc_feature
<222> LOCATION: (1)..(20)
<223> OTHER INFORMATION: n is a, c, g, or u

<400> SEQUENCE: 64
nnnnnnnnnn nnnnnnnnnn cuuugaugcg uuuuacuuau cgggaaaucu ccgauaaaua    60
agcgcuucgu ccaucgaca uagucgcugg gacuggcucc aaaguaaugg aauaaacgcg   120
ccagaugu                                                            128

<210> SEQ ID NO 65
<211> LENGTH: 171
<212> TYPE: RNA
<213> ORGANISM: Artificial sequence
<220> FEATURE:
<223> OTHER INFORMATION: Synthetic sequence
<220> FEATURE:
<221> NAME/KEY: misc_feature
<222> LOCATION: (1)..(30)
<223> OTHER INFORMATION: n is a, c, g, or u

<400> SEQUENCE: 65
nnnnnnnnnn nnnnnnnnnn nnnnnnnnnn cuuugaugcg uuuuacuuau cggagauacc    60
uucaaaugaa aggagcuauc uccgauaaau aagcgcuucg uccaucgac auagucgcug   120 ggacuggcuc caaaguaaug gaauaaacgc gccagaugua auuuacuacu u            171

<210> SEQ ID NO 66
<211> LENGTH: 65
<212> TYPE: RNA
<213> ORGANISM: Artificial sequence
<220> FEATURE:
<223> OTHER INFORMATION: Synthetic sequence

<400> SEQUENCE: 66
uuccauuacu uuggagccag ucccagcgac uaugucguau ggacgaagcg cuuauuuauc    60
ggaga                                                               65

<210> SEQ ID NO 67
<211> LENGTH: 46
<212> TYPE: RNA
<213> ORGANISM: Artificial sequence
<220> FEATURE:
<223> OTHER INFORMATION: Synthetic sequence

<400> SEQUENCE: 67
gucccagcga cuaugucgua uggacgaagc gcuuauuuau cggaga                   46

<210> SEQ ID NO 68
<211> LENGTH: 21

```
<212> TYPE: RNA
<213> ORGANISM: Artificial sequence
<220> FEATURE:
<223> OTHER INFORMATION: Synthetic sequence

<400> SEQUENCE: 68
gaagcgcuua uuuaucggag a                                               21

<210> SEQ ID NO 69
<211> LENGTH: 46
<212> TYPE: RNA
<213> ORGANISM: Artificial sequence
<220> FEATURE:
<223> OTHER INFORMATION: Synthetic sequence
<220> FEATURE:
<221> NAME/KEY: misc_feature
<222> LOCATION: (27)..(46)
<223> OTHER INFORMATION: n is a, c, g, or u

<400> SEQUENCE: 69
ucuccgauaa auaagaagca ucaaagnnnn nnnnnnnnnn nnnnnn                    46

<210> SEQ ID NO 70
<211> LENGTH: 10
<212> TYPE: RNA
<213> ORGANISM: Artificial sequence
<220> FEATURE:
<223> OTHER INFORMATION: Synthetic sequence

<400> SEQUENCE: 70
aaaaaaaaaa                                                            10

<210> SEQ ID NO 71
<211> LENGTH: 949
<212> TYPE: PRT
<213> ORGANISM: Unknown
<220> FEATURE:
<223> OTHER INFORMATION: Synthetic sequence

<400> SEQUENCE: 71
```

Met Arg Asp Ser Ile Thr Ala Pro Arg Tyr Ser Ser Ala Leu Ala Ala
1               5                   10                  15

Arg Ile Lys Glu Phe Asn Ser Ala Phe Lys Leu Gly Ile Asp Leu Gly
                20                  25                  30

Thr Lys Thr Gly Gly Val Ala Leu Val Lys Asp Asn Lys Val Leu Leu
            35                  40                  45

Ala Lys Thr Phe Leu Asp Tyr His Lys Gln Thr Leu Glu Glu Arg Arg
        50                  55                  60

Ile His Arg Arg Asn Arg Arg Ser Arg Leu Ala Arg Arg Lys Arg Ile
65                  70                  75                  80

Ala Arg Leu Arg Ser Trp Ile Leu Arg Gln Lys Ile Tyr Gly Lys Gln
                85                  90                  95

Leu Pro Asp Pro Tyr Lys Ile Lys Lys Met Gln Leu Pro Asn Gly Val
                100                 105                 110

Arg Lys Gly Glu Asn Trp Ile Asp Leu Val Val Ser Gly Arg Asp Leu
            115                 120                 125

Ser Pro Glu Ala Phe Val Arg Ala Ile Thr Leu Ile Phe Gln Lys Arg
        130                 135                 140

Gly Gln Arg Tyr Glu Glu Val Ala Lys Glu Ile Glu Glu Met Ser Tyr
145                 150                 155                 160

Lys Glu Phe Ser Thr His Ile Lys Ala Leu Thr Ser Val Thr Glu Glu
                165                 170                 175

```
Glu Phe Thr Ala Leu Ala Ala Glu Ile Glu Arg Arg Gln Asp Val Val
                180                 185                 190

Asp Thr Asp Lys Glu Ala Glu Arg Tyr Thr Gln Leu Ser Glu Leu Leu
            195                 200                 205

Ser Lys Val Ser Glu Ser Lys Ser Glu Ser Lys Asp Arg Ala Gln Arg
    210                 215                 220

Lys Glu Asp Leu Gly Lys Val Val Asn Ala Phe Cys Ser Ala His Arg
225                 230                 235                 240

Ile Glu Asp Lys Asp Lys Trp Cys Lys Glu Leu Met Lys Leu Leu Asp
                245                 250                 255

Arg Pro Val Arg His Ala Arg Phe Leu Asn Lys Val Leu Ile Arg Cys
            260                 265                 270

Asn Ile Cys Asp Arg Ala Thr Pro Lys Lys Ser Arg Pro Asp Val Arg
        275                 280                 285

Glu Leu Leu Tyr Phe Asp Thr Val Arg Asn Phe Leu Lys Ala Gly Arg
    290                 295                 300

Val Glu Gln Asn Pro Asp Val Ile Ser Tyr Tyr Lys Lys Ile Tyr Met
305                 310                 315                 320

Asp Ala Glu Val Ile Arg Val Lys Ile Leu Asn Lys Glu Lys Leu Thr
                325                 330                 335

Asp Glu Asp Lys Lys Gln Lys Arg Lys Leu Ala Ser Glu Leu Asn Arg
            340                 345                 350

Tyr Lys Asn Lys Glu Tyr Val Thr Asp Ala Gln Lys Lys Met Gln Glu
        355                 360                 365

Gln Leu Lys Thr Leu Leu Phe Met Lys Leu Thr Gly Arg Ser Arg Tyr
    370                 375                 380

Cys Met Ala His Leu Lys Glu Arg Ala Ala Gly Lys Asp Val Glu Glu
385                 390                 395                 400

Gly Leu His Gly Val Val Gln Lys Arg His Asp Arg Asn Ile Ala Gln
                405                 410                 415

Arg Asn His Asp Leu Arg Val Ile Asn Leu Ile Glu Ser Leu Leu Phe
            420                 425                 430

Asp Gln Asn Lys Ser Leu Ser Asp Ala Ile Arg Lys Asn Gly Leu Met
        435                 440                 445

Tyr Val Thr Ile Glu Ala Pro Glu Pro Lys Thr Lys His Ala Lys Lys
    450                 455                 460

Gly Ala Ala Val Val Arg Asp Pro Arg Lys Leu Lys Glu Lys Leu Phe
465                 470                 475                 480

Asp Asp Gln Asn Gly Val Cys Ile Tyr Thr Gly Leu Gln Leu Asp Lys
                485                 490                 495

Leu Glu Ile Ser Lys Tyr Glu Lys Asp His Ile Phe Pro Asp Ser Arg
            500                 505                 510

Asp Gly Pro Ser Ile Arg Asp Asn Leu Val Leu Thr Thr Lys Glu Ile
        515                 520                 525

Asn Ser Asp Lys Gly Asp Arg Thr Pro Trp Glu Trp Met His Asp Asn
    530                 535                 540

Pro Glu Lys Trp Lys Ala Phe Glu Arg Arg Val Ala Glu Phe Tyr Lys
545                 550                 555                 560

Lys Gly Arg Ile Asn Glu Arg Lys Arg Glu Leu Leu Leu Asn Lys Gly
                565                 570                 575

Thr Glu Tyr Pro Gly Asp Asn Pro Thr Glu Leu Ala Arg Gly Gly Ala
            580                 585                 590
```

Arg Val Asn Asn Phe Ile Thr Glu Phe Asn Asp Arg Leu Lys Thr His
    595                 600                 605

Gly Val Gln Glu Leu Gln Thr Ile Phe Glu Arg Asn Lys Pro Ile Val
610                 615                 620

Gln Val Val Arg Gly Glu Thr Gln Arg Leu Arg Arg Gln Trp Asn
625                 630                 635                 640

Ala Leu Asn Gln Asn Phe Ile Pro Leu Lys Asp Arg Ala Met Ser Phe
            645                 650                 655

Asn His Ala Glu Asp Ala Ala Ile Ala Ala Ser Met Pro Pro Lys Phe
            660                 665                 670

Trp Arg Glu Gln Ile Tyr Arg Thr Ala Trp His Phe Gly Pro Ser Gly
            675                 680                 685

Asn Glu Arg Pro Asp Phe Ala Leu Ala Glu Leu Ala Pro Gln Trp Asn
            690                 695                 700

Asp Phe Phe Met Thr Lys Gly Gly Pro Ile Ile Ala Val Leu Gly Lys
705                 710                 715                 720

Thr Lys Tyr Ser Trp Lys His Ser Ile Ile Asp Thr Ile Tyr Lys
            725                 730                 735

Pro Phe Ser Lys Ser Ala Tyr Tyr Val Gly Ile Tyr Lys Lys Pro Asn
            740                 745                 750

Ala Ile Thr Ser Asn Ala Ile Lys Val Leu Arg Pro Lys Leu Leu Asn
            755                 760                 765

Gly Glu His Thr Met Ser Lys Asn Ala Lys Tyr Tyr His Gln Lys Ile
            770                 775                 780

Gly Asn Glu Arg Phe Leu Met Lys Ser Gln Lys Gly Gly Ser Ile Ile
785                 790                 795                 800

Thr Val Lys Pro His Asp Gly Pro Glu Lys Val Leu Gln Ile Ser Pro
                805                 810                 815

Thr Tyr Glu Cys Ala Val Leu Thr Lys His Asp Gly Lys Ile Ile Val
                820                 825                 830

Lys Phe Lys Pro Ile Lys Pro Leu Arg Asp Met Tyr Ala Arg Gly Val
            835                 840                 845

Ile Lys Ala Met Asp Lys Glu Leu Glu Thr Ser Leu Ser Ser Met Ser
850                 855                 860

Lys His Ala Lys Tyr Lys Glu Leu His Thr His Asp Ile Ile Tyr Leu
865                 870                 875                 880

Pro Ala Thr Lys Lys His Val Asp Gly Tyr Phe Ile Ile Thr Lys Leu
                885                 890                 895

Ser Ala Lys His Gly Ile Lys Ala Leu Pro Glu Ser Met Val Lys Val
            900                 905                 910

Lys Tyr Thr Gln Ile Gly Ser Glu Asn Asn Ser Glu Val Lys Leu Thr
            915                 920                 925

Lys Pro Lys Pro Glu Ile Thr Leu Asp Ser Glu Asp Ile Thr Asn Ile
            930                 935                 940

Tyr Asn Phe Thr Arg
945

<210> SEQ ID NO 72
<211> LENGTH: 967
<212> TYPE: PRT
<213> ORGANISM: Unknown
<220> FEATURE:
<223> OTHER INFORMATION: Synthetic sequence

<400> SEQUENCE: 72

-continued

```
Met Leu Gly Ser Ser Arg Tyr Leu Arg Tyr Asn Leu Thr Ser Phe Glu
1               5                   10                  15
Gly Lys Glu Pro Phe Leu Ile Met Gly Tyr Tyr Lys Glu Tyr Asn Lys
            20                  25                  30
Glu Leu Ser Ser Lys Ala Gln Lys Glu Phe Asn Asp Gln Ile Ser Glu
        35                  40                  45
Phe Asn Ser Tyr Tyr Lys Leu Gly Ile Asp Leu Gly Asp Lys Thr Gly
    50                  55                  60
Ile Ala Ile Val Lys Gly Asn Lys Ile Ile Leu Ala Lys Thr Leu Ile
65                  70                  75                  80
Asp Leu His Ser Gln Lys Leu Asp Lys Arg Glu Ala Arg Arg Asn
                85                  90                  95
Arg Arg Thr Arg Leu Ser Arg Lys Lys Arg Leu Ala Arg Leu Arg Ser
            100                 105                 110
Trp Val Met Arg Gln Lys Val Gly Asn Gln Arg Leu Pro Asp Pro Tyr
            115                 120                 125
Lys Ile Met His Asp Asn Lys Tyr Trp Ser Ile Tyr Asn Lys Ser Asn
130                 135                 140
Ser Ala Asn Lys Lys Asn Trp Ile Asp Leu Leu Ile His Ser Asn Ser
145                 150                 155                 160
Leu Ser Ala Asp Asp Phe Val Arg Gly Leu Thr Ile Ile Phe Arg Lys
                165                 170                 175
Arg Gly Tyr Leu Ala Phe Lys Tyr Leu Ser Arg Leu Ser Asp Lys Glu
            180                 185                 190
Phe Glu Lys Tyr Ile Asp Asn Leu Lys Pro Pro Ile Ser Lys Tyr Glu
            195                 200                 205
Tyr Asp Glu Asp Leu Glu Glu Leu Ser Ser Arg Val Glu Asn Gly Glu
210                 215                 220
Ile Glu Glu Lys Lys Phe Glu Gly Leu Lys Asn Lys Leu Asp Lys Ile
225                 230                 235                 240
Asp Lys Glu Ser Lys Asp Phe Gln Val Lys Gln Arg Glu Glu Val Lys
                245                 250                 255
Lys Glu Leu Glu Asp Leu Val Asp Leu Phe Ala Lys Ser Val Asp Asn
            260                 265                 270
Lys Ile Asp Lys Ala Arg Trp Lys Arg Glu Leu Asn Asn Leu Leu Asp
            275                 280                 285
Lys Lys Val Arg Lys Ile Arg Phe Asp Asn Arg Phe Ile Leu Lys Cys
            290                 295                 300
Lys Ile Lys Gly Cys Asn Lys Asn Thr Pro Lys Lys Glu Lys Val Arg
305                 310                 315                 320
Asp Phe Glu Leu Lys Met Val Leu Asn Asn Ala Arg Ser Asp Tyr Gln
                325                 330                 335
Ile Ser Asp Glu Asp Leu Asn Ser Phe Arg Asn Glu Val Ile Asn Ile
            340                 345                 350
Phe Gln Lys Lys Glu Asn Leu Lys Lys Gly Glu Leu Lys Gly Val Thr
            355                 360                 365
Ile Glu Asp Leu Arg Lys Gln Leu Asn Lys Thr Phe Asn Lys Ala Lys
            370                 375                 380
Ile Lys Lys Gly Ile Arg Glu Gln Ile Arg Ser Ile Val Phe Glu Lys
385                 390                 395                 400
Ile Ser Gly Arg Ser Lys Phe Cys Lys Glu His Leu Lys Glu Phe Ser
                405                 410                 415
Glu Lys Pro Ala Pro Ser Asp Arg Ile Asn Tyr Gly Val Asn Ser Ala
```

-continued

```
                420                 425                 430
Arg Glu Gln His Asp Phe Arg Val Leu Asn Phe Ile Asp Lys Lys Ile
            435                 440                 445
Phe Lys Asp Lys Leu Ile Asp Pro Ser Lys Leu Arg Tyr Ile Thr Ile
            450                 455                 460
Glu Ser Pro Glu Pro Glu Thr Glu Lys Leu Glu Lys Gly Gln Ile Ser
465                 470                 475                 480
Glu Lys Ser Phe Glu Thr Leu Lys Glu Lys Leu Ala Lys Glu Thr Gly
                485                 490                 495
Gly Ile Asp Ile Tyr Thr Gly Glu Lys Leu Lys Lys Asp Phe Glu Ile
                500                 505                 510
Glu His Ile Phe Pro Arg Ala Arg Met Gly Pro Ser Ile Arg Glu Asn
            515                 520                 525
Glu Val Ala Ser Asn Leu Glu Thr Asn Lys Glu Lys Ala Asp Arg Thr
            530                 535                 540
Pro Trp Glu Trp Phe Gly Gln Asp Glu Lys Arg Trp Ser Glu Phe Glu
545                 550                 555                 560
Lys Arg Val Asn Ser Leu Tyr Ser Lys Lys Ile Ser Glu Arg Lys
                565                 570                 575
Arg Glu Ile Leu Leu Asn Lys Ser Asn Glu Tyr Pro Gly Leu Asn Pro
                580                 585                 590
Thr Glu Leu Ser Arg Ile Pro Ser Thr Leu Ser Asp Phe Val Glu Ser
            595                 600                 605
Ile Arg Lys Met Phe Val Lys Tyr Gly Tyr Glu Glu Pro Gln Thr Leu
            610                 615                 620
Val Gln Lys Gly Lys Pro Ile Ile Gln Val Val Arg Gly Arg Asp Thr
625                 630                 635                 640
Gln Ala Leu Arg Trp Arg Trp His Ala Leu Asp Ser Asn Ile Ile Pro
                645                 650                 655
Glu Lys Asp Arg Lys Ser Ser Phe Asn His Ala Glu Asp Ala Val Ile
                660                 665                 670
Ala Ala Cys Met Pro Pro Tyr Tyr Leu Arg Gln Lys Ile Phe Arg Glu
            675                 680                 685
Glu Ala Lys Ile Lys Arg Lys Val Ser Asn Lys Glu Lys Glu Val Thr
            690                 695                 700
Arg Pro Asp Met Pro Thr Lys Lys Ile Ala Pro Asn Trp Ser Glu Phe
705                 710                 715                 720
Met Lys Thr Arg Asn Glu Pro Val Ile Glu Val Ile Gly Lys Val Lys
                725                 730                 735
Pro Ser Trp Lys Asn Ser Ile Met Asp Gln Thr Phe Tyr Lys Tyr Leu
            740                 745                 750
Leu Lys Pro Phe Lys Asp Asn Leu Ile Lys Ile Pro Asn Val Lys Asn
            755                 760                 765
Thr Tyr Lys Trp Ile Gly Val Asn Gly Gln Thr Asp Ser Leu Ser Leu
            770                 775                 780
Pro Ser Lys Val Leu Ser Ile Ser Asn Lys Lys Val Asp Ser Ser Thr
785                 790                 795                 800
Val Leu Leu Val His Asp Lys Lys Gly Lys Arg Asn Trp Val Pro
                805                 810                 815
Lys Ser Ile Gly Gly Leu Leu Val Tyr Ile Thr Pro Lys Asp Gly Pro
                820                 825                 830
Lys Arg Ile Val Gln Val Lys Pro Ala Thr Gln Gly Leu Leu Ile Tyr
            835                 840                 845
```

-continued

```
Arg Asn Glu Asp Gly Arg Val Asp Ala Val Arg Glu Phe Ile Asn Pro
    850                 855                 860
Val Ile Glu Met Tyr Asn Asn Gly Lys Leu Ala Phe Val Glu Lys Glu
865                 870                 875                 880
Asn Glu Glu Glu Leu Leu Lys Tyr Phe Asn Leu Leu Glu Lys Gly Gln
                885                 890                 895
Lys Phe Glu Arg Ile Arg Arg Tyr Asp Met Ile Thr Tyr Asn Ser Lys
            900                 905                 910
Phe Tyr Tyr Val Thr Lys Ile Asn Lys Asn His Arg Val Thr Ile Gln
        915                 920                 925
Glu Glu Ser Lys Ile Lys Ala Glu Ser Asp Lys Val Lys Ser Ser Ser
    930                 935                 940
Gly Lys Glu Tyr Thr Arg Lys Glu Thr Glu Glu Leu Ser Leu Gln Lys
945                 950                 955                 960
Leu Ala Glu Leu Ile Ser Ile
                965

<210> SEQ ID NO 73
<211> LENGTH: 56
<212> TYPE: RNA
<213> ORGANISM: Artificial sequence
<220> FEATURE:
<223> OTHER INFORMATION: Synthetic sequence
<220> FEATURE:
<221> NAME/KEY: misc_feature
<222> LOCATION: (1)..(20)
<223> OTHER INFORMATION: n is a, c, g, or u

<400> SEQUENCE: 73
nnnnnnnnnn nnnnnnnnnn cuuacaaucg acacuuaaau aauuugcaug uguaag      56

<210> SEQ ID NO 74
<211> LENGTH: 56
<212> TYPE: RNA
<213> ORGANISM: Artificial sequence
<220> FEATURE:
<223> OTHER INFORMATION: Synthetic sequence
<220> FEATURE:
<221> NAME/KEY: misc_feature
<222> LOCATION: (1)..(20)
<223> OTHER INFORMATION: n is a, c, g, or u

<400> SEQUENCE: 74
nnnnnnnnnn nnnnnnnnnn cuuucaauaa acaaauaaau cuuaguaaua uguaac      56

<210> SEQ ID NO 75
<211> LENGTH: 36
<212> TYPE: RNA
<213> ORGANISM: Artificial sequence
<220> FEATURE:
<223> OTHER INFORMATION: Synthetic sequence

<400> SEQUENCE: 75
cuuacaaucg acacuuaaau aauuugcaug uguaag                             36

<210> SEQ ID NO 76
<211> LENGTH: 36
<212> TYPE: RNA
<213> ORGANISM: Artificial sequence
<220> FEATURE:
<223> OTHER INFORMATION: Synthetic sequence

<400> SEQUENCE: 76
```
cuuucaauaa acaaauaaau cuuaguaaua uguaac        36

<210> SEQ ID NO 77
<211> LENGTH: 180
<212> TYPE: RNA
<213> ORGANISM: Artificial sequence
<220> FEATURE:
<223> OTHER INFORMATION: Synthetic sequence

<400> SEQUENCE: 77
ggcauggacc auauccaggu guugauugua aacaccuagc ggggaaauua uauauguuug        60
uaauaucuuc acuauccaaa guuaucucug guuuugguuu gguaagcuuc acuucacuau       120
uguuuucacu cccaauuuga guaugguugg ggguaaggau gcuucgggg agugcuuuua        180

<210> SEQ ID NO 78
<211> LENGTH: 85
<212> TYPE: RNA
<213> ORGANISM: Artificial sequence
<220> FEATURE:
<223> OTHER INFORMATION: Synthetic sequence

<400> SEQUENCE: 78
aacuggcuau ugcuaauauu auuuguuuau ugaaagaagc cuagacguua ggguucgcgu        60
gcauguaggc uccagcaggu accuc                                              85

<210> SEQ ID NO 79
<211> LENGTH: 204
<212> TYPE: RNA
<213> ORGANISM: Artificial sequence
<220> FEATURE:
<223> OTHER INFORMATION: Synthetic sequence
<220> FEATURE:
<221> NAME/KEY: misc_feature
<222> LOCATION: (1)..(20)
<223> OTHER INFORMATION: n is a, c, g, or u

<400> SEQUENCE: 79
nnnnnnnnnn nnnnnnnnnn cuuacaaucg acacuuaaac aggguugau uguaaacacc         60 uagcggggaa auuauauaug uuuguaauau cuucacuauc caaaguuauc ucugguuuug       120
guuugguaag cuucacuuca cuauuguuuu cacucccaau uugaguaugg uuggggguaa       180
ggaugcuuuc ggggagugcu uuua                                              204

<210> SEQ ID NO 80
<211> LENGTH: 109
<212> TYPE: RNA
<213> ORGANISM: Artificial sequence
<220> FEATURE:
<223> OTHER INFORMATION: Synthetic sequence
<220> FEATURE:
<221> NAME/KEY: misc_feature
<222> LOCATION: (1)..(20)
<223> OTHER INFORMATION: n is a, c, g, or u

<400> SEQUENCE: 80
nnnnnnnnnn nnnnnnnnnn cuuucaauaa acaaauaaaa acuuauuugu uuauugaaag        60
aagccuagac guuagggguc gcgugcaugu aggcuccagc agguaccuc                   109

<210> SEQ ID NO 81
<211> LENGTH: 184
<212> TYPE: RNA
<213> ORGANISM: Artificial sequence
<220> FEATURE:
<223> OTHER INFORMATION: Synthetic sequence

<400> SEQUENCE: 81
cuuacaaucg acacuuaaac aggguguugau uguaaacacc uagcggggaa auuauauaug    60
uuuguaauau cuucacuauc caaaguuauc ucugguuuug guuugguaag cuucacuuca    120
cuauuguuuu cacucccaau uugaguaugg ugggggguaa ggaugcuuuc ggggagugcu    180
uuua    184

<210> SEQ ID NO 82
<211> LENGTH: 89
<212> TYPE: RNA
<213> ORGANISM: Artificial sequence
<220> FEATURE:
<223> OTHER INFORMATION: Synthetic sequence

<400> SEQUENCE: 82
cuuucaauaa acaaauaaaa acuuauuugu uauugaaag aagccuagac guuagguuc    60 gcgugcaugu aggcuccagc agguaccuc    89

<210> SEQ ID NO 83
<211> LENGTH: 84
<212> TYPE: PRT
<213> ORGANISM: Artificial Sequence
<220> FEATURE:
<223> OTHER INFORMATION: Synthetic sequence

<400> SEQUENCE: 83

Met Ala Ser Met Ile Ser Ser Ser Ala Val Thr Thr Val Ser Arg Ala
1               5                   10                  15

Ser Arg Gly Gln Ser Ala Ala Met Ala Pro Phe Gly Gly Leu Lys Ser
            20                  25                  30

Met Thr Gly Phe Pro Val Arg Lys Val Asn Thr Asp Ile Thr Ser Ile
        35                  40                  45

Thr Ser Asn Gly Gly Arg Val Lys Cys Met Gln Val Trp Pro Pro Ile
    50                  55                  60

Gly Lys Lys Lys Phe Glu Thr Leu Ser Tyr Leu Pro Pro Leu Thr Arg
65                  70                  75                  80

Asp Ser Arg Ala

<210> SEQ ID NO 84
<211> LENGTH: 57
<212> TYPE: PRT
<213> ORGANISM: Artificial Sequence
<220> FEATURE:
<223> OTHER INFORMATION: Synthetic sequence

<400> SEQUENCE: 84

Met Ala Ser Met Ile Ser Ser Ser Ala Val Thr Thr Val Ser Arg Ala
1               5                   10                  15

Ser Arg Gly Gln Ser Ala Ala Met Ala Pro Phe Gly Gly Leu Lys Ser
            20                  25                  30

Met Thr Gly Phe Pro Val Arg Lys Val Asn Thr Asp Ile Thr Ser Ile
        35                  40                  45

Thr Ser Asn Gly Gly Arg Val Lys Ser
    50                  55

<210> SEQ ID NO 85
<211> LENGTH: 85
<212> TYPE: PRT
<213> ORGANISM: Artificial Sequence
<220> FEATURE:
<223> OTHER INFORMATION: Synthetic sequence

<400> SEQUENCE: 85

Met Ala Ser Ser Met Leu Ser Ser Ala Thr Met Val Ala Ser Pro Ala
1               5                   10                  15

Gln Ala Thr Met Val Ala Pro Phe Asn Gly Leu Lys Ser Ser Ala Ala
                20                  25                  30

Phe Pro Ala Thr Arg Lys Ala Asn Asn Asp Ile Thr Ser Ile Thr Ser
            35                  40                  45

Asn Gly Gly Arg Val Asn Cys Met Gln Val Trp Pro Pro Ile Glu Lys
        50                  55                  60

Lys Lys Phe Glu Thr Leu Ser Tyr Leu Pro Asp Leu Thr Asp Ser Gly
65                  70                  75                  80

Gly Arg Val Asn Cys
                85

<210> SEQ ID NO 86
<211> LENGTH: 76
<212> TYPE: PRT
<213> ORGANISM: Artificial Sequence
<220> FEATURE:
<223> OTHER INFORMATION: Synthetic sequence

<400> SEQUENCE: 86

Met Ala Gln Val Ser Arg Ile Cys Asn Gly Val Gln Asn Pro Ser Leu
1               5                   10                  15

Ile Ser Asn Leu Ser Lys Ser Ser Gln Arg Lys Ser Pro Leu Ser Val
                20                  25                  30

Ser Leu Lys Thr Gln Gln His Pro Arg Ala Tyr Pro Ile Ser Ser Ser
            35                  40                  45

Trp Gly Leu Lys Lys Ser Gly Met Thr Leu Ile Gly Ser Glu Leu Arg
        50                  55                  60

Pro Leu Lys Val Met Ser Ser Val Ser Thr Ala Cys
65                  70                  75

<210> SEQ ID NO 87
<211> LENGTH: 76
<212> TYPE: PRT
<213> ORGANISM: Artificial Sequence
<220> FEATURE:
<223> OTHER INFORMATION: Synthetic sequence

<400> SEQUENCE: 87

Met Ala Gln Val Ser Arg Ile Cys Asn Gly Val Trp Asn Pro Ser Leu
1               5                   10                  15

Ile Ser Asn Leu Ser Lys Ser Ser Gln Arg Lys Ser Pro Leu Ser Val
                20                  25                  30

Ser Leu Lys Thr Gln Gln His Pro Arg Ala Tyr Pro Ile Ser Ser Ser
            35                  40                  45

Trp Gly Leu Lys Lys Ser Gly Met Thr Leu Ile Gly Ser Glu Leu Arg
        50                  55                  60

Pro Leu Lys Val Met Ser Ser Val Ser Thr Ala Cys
65                  70                  75

<210> SEQ ID NO 88
<211> LENGTH: 72
<212> TYPE: PRT
<213> ORGANISM: Artificial Sequence
<220> FEATURE:

<223> OTHER INFORMATION: Synthetic sequence

<400> SEQUENCE: 88

Met Ala Gln Ile Asn Asn Met Ala Gln Gly Ile Gln Thr Leu Asn Pro
1               5                   10                  15

Asn Ser Asn Phe His Lys Pro Gln Val Pro Lys Ser Ser Ser Phe Leu
            20                  25                  30

Val Phe Gly Ser Lys Lys Leu Lys Asn Ser Ala Asn Ser Met Leu Val
        35                  40                  45

Leu Lys Lys Asp Ser Ile Phe Met Gln Leu Phe Cys Ser Phe Arg Ile
    50                  55                  60

Ser Ala Ser Val Ala Thr Ala Cys
65                  70

<210> SEQ ID NO 89
<211> LENGTH: 69
<212> TYPE: PRT
<213> ORGANISM: Artificial Sequence
<220> FEATURE:
<223> OTHER INFORMATION: Synthetic sequence

<400> SEQUENCE: 89

Met Ala Ala Leu Val Thr Ser Gln Leu Ala Thr Ser Gly Thr Val Leu
1               5                   10                  15

Ser Val Thr Asp Arg Phe Arg Arg Pro Gly Phe Gln Gly Leu Arg Pro
            20                  25                  30

Arg Asn Pro Ala Asp Ala Ala Leu Gly Met Arg Thr Val Gly Ala Ser
        35                  40                  45

Ala Ala Pro Lys Gln Ser Arg Lys Pro His Arg Phe Asp Arg Arg Cys
    50                  55                  60

Leu Ser Met Val Val
65

<210> SEQ ID NO 90
<211> LENGTH: 77
<212> TYPE: PRT
<213> ORGANISM: Artificial Sequence
<220> FEATURE:
<223> OTHER INFORMATION: Synthetic sequence

<400> SEQUENCE: 90

Met Ala Ala Leu Thr Thr Ser Gln Leu Ala Thr Ser Ala Thr Gly Phe
1               5                   10                  15

Gly Ile Ala Asp Arg Ser Ala Pro Ser Ser Leu Leu Arg His Gly Phe
            20                  25                  30

Gln Gly Leu Lys Pro Arg Ser Pro Ala Gly Gly Asp Ala Thr Ser Leu
        35                  40                  45

Ser Val Thr Thr Ser Ala Arg Ala Thr Pro Lys Gln Gln Arg Ser Val
    50                  55                  60

Gln Arg Gly Ser Arg Arg Phe Pro Ser Val Val Val Cys
65                  70                  75

<210> SEQ ID NO 91
<211> LENGTH: 57
<212> TYPE: PRT
<213> ORGANISM: Artificial Sequence
<220> FEATURE:
<223> OTHER INFORMATION: Synthetic sequence

<400> SEQUENCE: 91

```
Met Ala Ser Ser Val Leu Ser Ala Ala Val Ala Thr Arg Ser Asn
1               5                   10                  15

Val Ala Gln Ala Asn Met Val Ala Pro Phe Thr Gly Leu Lys Ser Ala
            20                  25                  30

Ala Ser Phe Pro Val Ser Arg Lys Gln Asn Leu Asp Ile Thr Ser Ile
        35                  40                  45

Ala Ser Asn Gly Gly Arg Val Gln Cys
    50                  55
```

<210> SEQ ID NO 92
<211> LENGTH: 65
<212> TYPE: PRT
<213> ORGANISM: Artificial Sequence
<220> FEATURE:
<223> OTHER INFORMATION: Synthetic sequence

<400> SEQUENCE: 92

```
Met Glu Ser Leu Ala Ala Thr Ser Val Phe Ala Pro Ser Arg Val Ala
1               5                   10                  15

Val Pro Ala Ala Arg Ala Leu Val Arg Ala Gly Thr Val Val Pro Thr
            20                  25                  30

Arg Arg Thr Ser Ser Thr Ser Gly Thr Ser Gly Val Lys Cys Ser Ala
        35                  40                  45

Ala Val Thr Pro Gln Ala Ser Pro Val Ile Ser Arg Ser Ala Ala Ala
    50                  55                  60

Ala
65
```

<210> SEQ ID NO 93
<211> LENGTH: 72
<212> TYPE: PRT
<213> ORGANISM: Artificial Sequence
<220> FEATURE:
<223> OTHER INFORMATION: Synthetic sequence

<400> SEQUENCE: 93

```
Met Gly Ala Ala Ala Thr Ser Met Gln Ser Leu Lys Phe Ser Asn Arg
1               5                   10                  15

Leu Val Pro Pro Ser Arg Arg Leu Ser Pro Val Pro Asn Asn Val Thr
            20                  25                  30

Cys Asn Asn Leu Pro Lys Ser Ala Ala Pro Val Arg Thr Val Lys Cys
        35                  40                  45

Cys Ala Ser Ser Trp Asn Ser Thr Ile Asn Gly Ala Ala Ala Thr Thr
    50                  55                  60

Asn Gly Ala Ser Ala Ala Ser Ser
65                  70
```

<210> SEQ ID NO 94
<211> LENGTH: 20
<212> TYPE: PRT
<213> ORGANISM: Artificial Sequence
<220> FEATURE:
<223> OTHER INFORMATION: Synthetic sequence
<220> FEATURE:
<221> NAME/KEY: misc_feature
<222> LOCATION: (4)..(4)
<223> OTHER INFORMATION: Xaa can be any naturally occurring amino acid
<220> FEATURE:
<221> NAME/KEY: misc_feature
<222> LOCATION: (8)..(8)
<223> OTHER INFORMATION: Xaa can be any naturally occurring amino acid
<220> FEATURE:
<221> NAME/KEY: misc_feature

```
<222> LOCATION: (11)..(11)
<223> OTHER INFORMATION: Xaa can be any naturally occurring amino acid
<220> FEATURE:
<221> NAME/KEY: misc_feature
<222> LOCATION: (15)..(15)
<223> OTHER INFORMATION: Xaa can be any naturally occurring amino acid
<220> FEATURE:
<221> NAME/KEY: misc_feature
<222> LOCATION: (19)..(19)
<223> OTHER INFORMATION: Xaa can be any naturally occurring amino acid

<400> SEQUENCE: 94

Gly Leu Phe Xaa Ala Leu Leu Xaa Leu Leu Xaa Ser Leu Trp Xaa Leu
1               5                   10                  15

Leu Leu Xaa Ala
            20

<210> SEQ ID NO 95
<211> LENGTH: 20
<212> TYPE: PRT
<213> ORGANISM: Artificial Sequence
<220> FEATURE:
<223> OTHER INFORMATION: Synthetic sequence

<400> SEQUENCE: 95

Gly Leu Phe His Ala Leu Leu His Leu Leu His Ser Leu Trp His Leu
1               5                   10                  15

Leu Leu His Ala
            20

<210> SEQ ID NO 96
<211> LENGTH: 7
<212> TYPE: PRT
<213> ORGANISM: Artificial Sequence
<220> FEATURE:
<223> OTHER INFORMATION: Synthetic sequence

<400> SEQUENCE: 96

Pro Lys Lys Lys Arg Lys Val
1               5

<210> SEQ ID NO 97
<211> LENGTH: 16
<212> TYPE: PRT
<213> ORGANISM: Artificial Sequence
<220> FEATURE:
<223> OTHER INFORMATION: Synthetic sequence

<400> SEQUENCE: 97

Lys Arg Pro Ala Ala Thr Lys Lys Ala Gly Gln Ala Lys Lys Lys Lys
1               5                   10                  15

<210> SEQ ID NO 98
<211> LENGTH: 9
<212> TYPE: PRT
<213> ORGANISM: Artificial Sequence
<220> FEATURE:
<223> OTHER INFORMATION: Synthetic sequence

<400> SEQUENCE: 98

Pro Ala Ala Lys Arg Val Lys Leu Asp
1               5

<210> SEQ ID NO 99
<211> LENGTH: 11
<212> TYPE: PRT
<213> ORGANISM: Artificial Sequence
```

<220> FEATURE:
<223> OTHER INFORMATION: Synthetic sequence

<400> SEQUENCE: 99

Arg Gln Arg Arg Asn Glu Leu Lys Arg Ser Pro
1               5                   10

<210> SEQ ID NO 100
<211> LENGTH: 38
<212> TYPE: PRT
<213> ORGANISM: Artificial Sequence
<220> FEATURE:
<223> OTHER INFORMATION: Synthetic sequence

<400> SEQUENCE: 100

Asn Gln Ser Ser Asn Phe Gly Pro Met Lys Gly Gly Asn Phe Gly Gly
1               5                   10                  15

Arg Ser Ser Gly Pro Tyr Gly Gly Gly Gln Tyr Phe Ala Lys Pro
            20                  25                  30

Arg Asn Gln Gly Gly Tyr
        35

<210> SEQ ID NO 101
<211> LENGTH: 42
<212> TYPE: PRT
<213> ORGANISM: Artificial Sequence
<220> FEATURE:
<223> OTHER INFORMATION: Synthetic sequence

<400> SEQUENCE: 101

Arg Met Arg Ile Glx Phe Lys Asn Lys Gly Lys Asp Thr Ala Glu Leu
1               5                   10                  15

Arg Arg Arg Arg Val Glu Val Ser Val Glu Leu Arg Lys Ala Lys Lys
            20                  25                  30

Asp Glu Gln Ile Leu Lys Arg Arg Asn Val
        35                  40

<210> SEQ ID NO 102
<211> LENGTH: 8
<212> TYPE: PRT
<213> ORGANISM: Artificial Sequence
<220> FEATURE:
<223> OTHER INFORMATION: Synthetic sequence

<400> SEQUENCE: 102

Val Ser Arg Lys Arg Pro Arg Pro
1               5

<210> SEQ ID NO 103
<211> LENGTH: 8
<212> TYPE: PRT
<213> ORGANISM: Artificial Sequence
<220> FEATURE:
<223> OTHER INFORMATION: Synthetic sequence

<400> SEQUENCE: 103

Pro Pro Lys Lys Ala Arg Glu Asp
1               5

<210> SEQ ID NO 104
<211> LENGTH: 8
<212> TYPE: PRT
<213> ORGANISM: Artificial Sequence
<220> FEATURE:
<223> OTHER INFORMATION: Synthetic sequence

```
<400> SEQUENCE: 104

Pro Gln Pro Lys Lys Lys Pro Leu
1               5

<210> SEQ ID NO 105
<211> LENGTH: 12
<212> TYPE: PRT
<213> ORGANISM: Artificial Sequence
<220> FEATURE:
<223> OTHER INFORMATION: Synthetic sequence

<400> SEQUENCE: 105

Ser Ala Leu Ile Lys Lys Lys Lys Lys Met Ala Pro
1               5                   10

<210> SEQ ID NO 106
<211> LENGTH: 5
<212> TYPE: PRT
<213> ORGANISM: Artificial Sequence
<220> FEATURE:
<223> OTHER INFORMATION: Synthetic sequence

<400> SEQUENCE: 106

Asp Arg Leu Arg Arg
1               5

<210> SEQ ID NO 107
<211> LENGTH: 7
<212> TYPE: PRT
<213> ORGANISM: Artificial Sequence
<220> FEATURE:
<223> OTHER INFORMATION: Synthetic sequence

<400> SEQUENCE: 107

Pro Lys Gln Lys Lys Arg Lys
1               5

<210> SEQ ID NO 108
<211> LENGTH: 10
<212> TYPE: PRT
<213> ORGANISM: Artificial Sequence
<220> FEATURE:
<223> OTHER INFORMATION: Synthetic sequence

<400> SEQUENCE: 108

Arg Lys Leu Lys Lys Lys Ile Lys Lys Leu
1               5                   10

<210> SEQ ID NO 109
<211> LENGTH: 10
<212> TYPE: PRT
<213> ORGANISM: Artificial Sequence
<220> FEATURE:
<223> OTHER INFORMATION: Synthetic sequence

<400> SEQUENCE: 109

Arg Glu Lys Lys Lys Phe Leu Lys Arg Arg
1               5                   10

<210> SEQ ID NO 110
<211> LENGTH: 20
<212> TYPE: PRT
<213> ORGANISM: Artificial Sequence
<220> FEATURE:
<223> OTHER INFORMATION: Synthetic sequence
```

```
<400> SEQUENCE: 110

Lys Arg Lys Gly Asp Glu Val Asp Gly Val Asp Glu Val Ala Lys Lys
1               5                   10                  15

Lys Ser Lys Lys
            20

<210> SEQ ID NO 111
<211> LENGTH: 17
<212> TYPE: PRT
<213> ORGANISM: Artificial Sequence
<220> FEATURE:
<223> OTHER INFORMATION: Synthetic sequence

<400> SEQUENCE: 111

Arg Lys Cys Leu Gln Ala Gly Met Asn Leu Glu Ala Arg Lys Thr Lys
1               5                   10                  15

Lys

<210> SEQ ID NO 112
<211> LENGTH: 11
<212> TYPE: PRT
<213> ORGANISM: Artificial Sequence
<220> FEATURE:
<223> OTHER INFORMATION: Synthetic sequence

<400> SEQUENCE: 112

Tyr Gly Arg Lys Lys Arg Arg Gln Arg Arg Arg
1               5                   10

<210> SEQ ID NO 113
<211> LENGTH: 12
<212> TYPE: PRT
<213> ORGANISM: Artificial Sequence
<220> FEATURE:
<223> OTHER INFORMATION: Synthetic sequence

<400> SEQUENCE: 113

Arg Arg Gln Arg Arg Thr Ser Lys Leu Met Lys Arg
1               5                   10

<210> SEQ ID NO 114
<211> LENGTH: 27
<212> TYPE: PRT
<213> ORGANISM: Artificial Sequence
<220> FEATURE:
<223> OTHER INFORMATION: Synthetic sequence

<400> SEQUENCE: 114

Gly Trp Thr Leu Asn Ser Ala Gly Tyr Leu Leu Gly Lys Ile Asn Leu
1               5                   10                  15

Lys Ala Leu Ala Ala Leu Ala Lys Lys Ile Leu
            20                  25

<210> SEQ ID NO 115
<211> LENGTH: 33
<212> TYPE: PRT
<213> ORGANISM: Artificial Sequence
<220> FEATURE:
<223> OTHER INFORMATION: Synthetic sequence

<400> SEQUENCE: 115

Lys Ala Leu Ala Trp Glu Ala Lys Leu Ala Lys Ala Leu Ala Lys Ala
1               5                   10                  15

Leu Ala Lys His Leu Ala Lys Ala Leu Ala Lys Ala Leu Lys Cys Glu
```

```
                20                  25                  30

Ala

<210> SEQ ID NO 116
<211> LENGTH: 16
<212> TYPE: PRT
<213> ORGANISM: Artificial Sequence
<220> FEATURE:
<223> OTHER INFORMATION: Synthetic sequence

<400> SEQUENCE: 116

Arg Gln Ile Lys Ile Trp Phe Gln Asn Arg Arg Met Lys Trp Lys Lys
1               5                   10                  15

<210> SEQ ID NO 117
<211> LENGTH: 11
<212> TYPE: PRT
<213> ORGANISM: Artificial Sequence
<220> FEATURE:
<223> OTHER INFORMATION: Synthetic sequence

<400> SEQUENCE: 117

Tyr Gly Arg Lys Lys Arg Arg Gln Arg Arg Arg
1               5                   10

<210> SEQ ID NO 118
<211> LENGTH: 9
<212> TYPE: PRT
<213> ORGANISM: Artificial Sequence
<220> FEATURE:
<223> OTHER INFORMATION: Synthetic sequence

<400> SEQUENCE: 118

Arg Lys Lys Arg Arg Gln Arg Arg Arg
1               5

<210> SEQ ID NO 119
<211> LENGTH: 11
<212> TYPE: PRT
<213> ORGANISM: Artificial Sequence
<220> FEATURE:
<223> OTHER INFORMATION: Synthetic sequence

<400> SEQUENCE: 119

Tyr Gly Arg Lys Lys Arg Arg Gln Arg Arg
1               5                   10

<210> SEQ ID NO 120
<211> LENGTH: 8
<212> TYPE: PRT
<213> ORGANISM: Artificial Sequence
<220> FEATURE:
<223> OTHER INFORMATION: Synthetic sequence

<400> SEQUENCE: 120

Arg Lys Lys Arg Arg Gln Arg Arg
1               5

<210> SEQ ID NO 121
<211> LENGTH: 11
<212> TYPE: PRT
<213> ORGANISM: Artificial Sequence
<220> FEATURE:
<223> OTHER INFORMATION: Synthetic sequence

<400> SEQUENCE: 121
```

Tyr Ala Arg Ala Ala Ala Arg Gln Ala Arg Ala
1               5                   10

<210> SEQ ID NO 122
<211> LENGTH: 11
<212> TYPE: PRT
<213> ORGANISM: Artificial Sequence
<220> FEATURE:
<223> OTHER INFORMATION: Synthetic sequence

<400> SEQUENCE: 122

Thr His Arg Leu Pro Arg Arg Arg Arg Arg Arg
1               5                   10

<210> SEQ ID NO 123
<211> LENGTH: 11
<212> TYPE: PRT
<213> ORGANISM: Artificial Sequence
<220> FEATURE:
<223> OTHER INFORMATION: Synthetic sequence

<400> SEQUENCE: 123

Gly Gly Arg Arg Ala Arg Arg Arg Arg Arg Arg
1               5                   10

<210> SEQ ID NO 124
<211> LENGTH: 5
<212> TYPE: PRT
<213> ORGANISM: Artificial Sequence
<220> FEATURE:
<223> OTHER INFORMATION: Synthetic sequence

<400> SEQUENCE: 124

Gly Ser Gly Gly Ser
1               5

<210> SEQ ID NO 125
<211> LENGTH: 6
<212> TYPE: PRT
<213> ORGANISM: Artificial Sequence
<220> FEATURE:
<223> OTHER INFORMATION: Synthetic sequence

<400> SEQUENCE: 125

Gly Gly Ser Gly Gly Ser
1               5

<210> SEQ ID NO 126
<211> LENGTH: 4
<212> TYPE: PRT
<213> ORGANISM: Artificial Sequence
<220> FEATURE:
<223> OTHER INFORMATION: Synthetic sequence

<400> SEQUENCE: 126

Gly Gly Gly Ser
1

<210> SEQ ID NO 127
<211> LENGTH: 4
<212> TYPE: PRT
<213> ORGANISM: Artificial Sequence
<220> FEATURE:
<223> OTHER INFORMATION: Synthetic sequence

<400> SEQUENCE: 127

Gly Gly Ser Gly
1

```
<210> SEQ ID NO 128
<211> LENGTH: 5
<212> TYPE: PRT
<213> ORGANISM: Artificial Sequence
<220> FEATURE:
<223> OTHER INFORMATION: Synthetic sequence

<400> SEQUENCE: 128

Gly Gly Ser Gly Gly
1               5

<210> SEQ ID NO 129
<211> LENGTH: 5
<212> TYPE: PRT
<213> ORGANISM: Artificial Sequence
<220> FEATURE:
<223> OTHER INFORMATION: Synthetic sequence

<400> SEQUENCE: 129

Gly Ser Gly Ser Gly
1               5

<210> SEQ ID NO 130
<211> LENGTH: 5
<212> TYPE: PRT
<213> ORGANISM: Artificial Sequence
<220> FEATURE:
<223> OTHER INFORMATION: Synthetic sequence

<400> SEQUENCE: 130

Gly Ser Gly Gly Gly
1               5

<210> SEQ ID NO 131
<211> LENGTH: 5
<212> TYPE: PRT
<213> ORGANISM: Artificial Sequence
<220> FEATURE:
<223> OTHER INFORMATION: Synthetic sequence

<400> SEQUENCE: 131

Gly Gly Gly Ser Gly
1               5

<210> SEQ ID NO 132
<211> LENGTH: 5
<212> TYPE: PRT
<213> ORGANISM: Artificial Sequence
<220> FEATURE:
<223> OTHER INFORMATION: Synthetic sequence

<400> SEQUENCE: 132

Gly Ser Ser Ser Gly
1               5

<210> SEQ ID NO 133
<211> LENGTH: 16
<212> TYPE: PRT
<213> ORGANISM: Artificial Sequence
<220> FEATURE:
<223> OTHER INFORMATION: Synthetic sequence

<400> SEQUENCE: 133

Arg Gln Ile Lys Ile Trp Phe Gln Asn Arg Arg Met Lys Trp Lys Lys
1               5                   10                  15
```

<210> SEQ ID NO 134
<211> LENGTH: 11
<212> TYPE: PRT
<213> ORGANISM: Artificial Sequence
<220> FEATURE:
<223> OTHER INFORMATION: Synthetic sequence

<400> SEQUENCE: 134

Tyr Gly Arg Lys Lys Arg Arg Gln Arg Arg Arg
1               5                   10

<210> SEQ ID NO 135
<211> LENGTH: 1067
<212> TYPE: PRT
<213> ORGANISM: Unknown
<220> FEATURE:
<223> OTHER INFORMATION: sequence from metagenomic data -
      from unidentified Lindow bacteria

<400> SEQUENCE: 135

Val Ser Ala Thr Arg Lys Gly Gln Gly Ser Gly Ala Pro Ile Ser Arg
1               5                   10                  15

Thr Glu Ala Pro Gln Ile Ala Leu Met Ala Thr Glu Leu Glu Gln Arg
                20                  25                  30

Leu Asn Glu Phe Leu Asp Ser Leu Arg Leu Gly Ile Asp Phe Gly Glu
            35                  40                  45

Asp Tyr Gly Gly Ile Ala Leu Val Gln Ala Asn Arg Val Leu His Ala
        50                  55                  60

Glu Thr Phe Val Asp Phe His Gln Ala Thr Leu Lys Asp Arg Arg Arg
65                  70                  75                  80

Asn Arg Arg Gly Arg Thr Arg His Ala Arg Lys Met Arg Leu Ala
                85                  90                  95

Arg Leu Arg Ser Trp Ile Leu Arg Gln Lys Leu Pro Gly Gly Gln Arg
                100                 105                 110

Leu Pro Asp Pro Tyr Gly Val Met His Trp Pro Phe Lys Thr Lys Lys
            115                 120                 125

Gly His Thr Ile Lys Thr Gly Leu Ala Ser Arg Gln Asp Gly Lys Arg
        130                 135                 140

Thr Ile Ile Gln Lys Cys Lys Ile Gly Thr Ala Thr Pro Glu Glu Phe
145                 150                 155                 160

Val Cys Ser Leu Thr Leu Leu Phe Gln Lys Arg Gly Phe Val Trp Glu
                165                 170                 175

Gly Ser Asp Leu Cys Glu Leu Ser Asp Gln Glu Leu Ala Glu Glu Leu
            180                 185                 190

Met Thr Val Arg Ile Thr Glu Ala Val Ala Ala Ile Lys Glu Glu
        195                 200                 205

Ile Glu Arg Arg Lys Lys Glu Pro Glu Asp Asn Lys Glu Gly Glu Ile
        210                 215                 220

Glu Asn Leu Glu Thr Val Leu Cys Asp Ala Val Lys Arg Ala Arg Ser
225                 230                 235                 240

Pro Arg Thr Pro Glu His Arg Ser Ile Val Glu Ser Asp Leu Lys Asp
                245                 250                 255

Ile Val Asp Gly Trp Thr Arg Lys Asn Cys Pro Gln Met Thr Asp Met
            260                 265                 270

Trp Lys Lys Glu Leu Ser Cys Leu Leu Asn Lys His Val Arg Pro Ala
        275                 280                 285

```
Arg Phe Glu Asn Arg Ile Val Ala Gly Cys Ser Trp Cys Gly Lys Met
    290                 295                 300
Val Pro Arg Lys Ser Lys Val Arg Glu Leu Ala Tyr Lys Val Val
305                 310                 315                 320
Lys Asn Ile Arg Val Glu Asp Phe Thr Ser Arg Gln Pro Leu Thr Ala
                325                 330                 335
Gln Glu Ala Glu Tyr Phe Ser Gln Leu Trp Val Asp Lys Glu Ala Lys
            340                 345                 350
Pro Pro Ala Arg Thr Ala Ile Glu Asn Lys Leu Lys Lys Leu Lys Ala
                355                 360                 365
Ser Pro Lys Met Ala Asn Gln Leu Tyr Glu Leu Leu Ala Pro Ser Glu
370                 375                 380
Pro Lys Gly His Thr Asn Leu Cys Gln Gln His Leu Glu Met Ala Ala
385                 390                 395                 400
Arg Gly Ala Phe Met Cys Asn Arg His His Ala Ile Cys Glu Asn Asn
                405                 410                 415
Asn Gly Asp His Gln Thr Ile Asp Ser Val Lys Glu Gly Arg Lys Arg
                420                 425                 430
Ala Gly Pro Arg Asn Pro Cys Arg Glu Asp Arg Asp Arg Arg Met Ile
            435                 440                 445
Arg Arg Leu Glu Gln Ile Leu Phe Glu Thr Pro Gly Lys Pro Gly Lys
450                 455                 460
Pro Ser His Ser Ile Pro Arg Leu Ile Thr Ile Glu Phe Pro Lys Pro
465                 470                 475                 480
Asn Thr Ala Gln Thr Ala Gly Cys Pro His Cys Lys Glu Lys Leu Ser
                485                 490                 495
Leu Asp Ala Arg Val Arg Trp Lys Met Ala Arg Pro Met Lys Leu Glu
            500                 505                 510
Ala Ser Asn Asp Ser Thr Pro Phe Phe Cys Pro Ser Cys Ala Ala Gly
            515                 520                 525
Ile Lys Ile Thr Leu Tyr Lys Lys Met Arg Ile Lys Glu Lys Glu Ile
530                 535                 540
Val Gln Lys Tyr Ser Pro Lys Asp Thr Asp Val Leu Val Arg Lys Thr
545                 550                 555                 560
Ala Ala Gly Gly Leu Lys Lys Leu Lys Tyr Asp Met Tyr Leu Lys Glu
                565                 570                 575
Thr Asp Gly Thr Cys Val Tyr Cys Gly Thr Ser Ile Gly Ser Gly Gln
                580                 585                 590
Ile Asp His Ile Phe Pro Gln Ser Arg Gly Gly Pro Asn Ile Asp Tyr
            595                 600                 605
Asn Leu Ile Ser Cys Cys Arg Thr Cys Asn Gly Asn Leu Lys Lys Asn
            610                 615                 620
Lys Ser Pro Trp Glu Trp Phe Gly Asn Ile Asp Gln Arg Trp Arg Glu
625                 630                 635                 640
Phe Glu Asp Arg Val Lys Lys Leu Pro Ala Pro Gln Lys Lys Ala
                645                 650                 655
Ile Leu Leu Ser Arg Glu Ser Ala Tyr Pro Glu Asn Pro Thr Ala Leu
                660                 665                 670
Ala Arg Val Gly Ala Arg Thr Lys Glu Phe Ile Gly Arg Ile Lys Gln
            675                 680                 685
Met Leu Leu Ala Asn Gly Val Lys Glu Asn Glu Ile Ala Asp Asn Tyr
690                 695                 700
Glu Lys Asp Lys Ile Val Ile Gln Thr Ile Asp Gly Trp Met Thr Ser
```

|   |   |   |   |   |   |   |   |   |   |   |   |   |   |   |   |
|---|---|---|---|---|---|---|---|---|---|---|---|---|---|---|---|
| 705 | | | | | 710 | | | | | 715 | | | | | 720 |

Arg Leu Arg Gly Cys Trp Arg Thr Phe Pro Asp Gly Thr Ala Asn Phe
                725                        730                      735

Pro Pro Lys Asn Asp Ala Asp Lys Arg Asn His Ala Gln Asp Ala Val
                740                        745                      750

Leu Ile Ala Ala Cys Pro Pro His Thr Trp Arg Glu Arg Ile Phe Thr
                755                        760                      765

Trp Lys Pro Glu Asn Pro Tyr Phe Ser Val Leu Gln Lys Ile Ala Pro
770                      775                      780

Arg Trp Lys Asp His Gln Ala Thr Met Lys Ile Leu Gly Arg Tyr Phe
785                      790                      795                      800

Pro Arg Trp His Asn Gln Asn Ser Asp Ile Gln Phe Val His Gln His
                805                        810                      815

Lys Thr Gln Asn Gly Thr Ser Tyr Thr Met Arg Asp Thr Val Glu Ser
                820                        825                      830

Ile Asp Val Gly Thr Asp Lys Lys Gly Gly Ser Ile Glu Arg Ile Tyr
                835                        840                      845

Ser Lys Ser Phe Arg Asp Phe Phe Ser Arg Thr Phe Lys Ser Leu Gly
    850                      855                      860

Ile Lys Met Ala Met Asn Glu Ile Pro Lys Leu Lys Ser Gln Trp Leu
865                      870                      875                      880

Asn Glu Arg Arg Ala Ala Trp Met Lys Lys Asn Pro Ala Thr Pro Val
                885                        890                      895

Pro Asn Gln Arg Glu Arg Ala Trp Glu Ala Ser Phe Pro Arg Arg Leu
                900                        905                      910

Gln Phe Asp Met Gly Tyr Gly Glu Asp Val Ala Glu Val Asn Pro Lys
                915                        920                      925

Asn Gly Pro Ser Arg Phe Val Arg Ala Gln Pro Val Asn Asp Arg Ile
    930                      935                      940

Glu Val Trp Thr Asn Asp Val Arg Gln Ala Gln Ile Arg Thr Val Lys
945                      950                      955                      960

Asn Arg Ile Leu Phe Arg His Ile Gln Asp Asn Ser Pro Gln Gly Arg
                965                        970                      975

Thr Leu Glu Arg Ile Phe Arg Arg Asn Asp Met Ile Gln Leu Asp Ala
                980                        985                      990

Val Gln Lys Arg Gly Arg Lys Gly Ile Thr Gly Lys Ser Tyr Glu Ala
                995                      1000                    1005

Gly Glu Tyr Met Val Val Lys Ile Glu Lys Gly Lys Phe Thr
1010                      1015                    1020

Ala Val Pro Ala His Arg Gly Lys Gly Arg Glu Asn Gln Arg Gln
1025                      1030                    1035

Val Ser Gln Arg Glu Ile Ala Lys Leu Cys Gly Val Ser Leu Ser
1040                      1045                    1050

Pro Lys Arg Arg Lys Pro Ser Arg Ser Thr Ser Glu Ser Gly
1055                      1060                    1065

<210> SEQ ID NO 136
<211> LENGTH: 990
<212> TYPE: PRT
<213> ORGANISM: Unknown
<220> FEATURE:
<223> OTHER INFORMATION: sequence from metagenomic data -
     from unidentified Delta proteobacteria

<400> SEQUENCE: 136

-continued

```
Val Ala Ala Ala Ser Leu Ile Leu Gln Arg Gly Gly Leu Val Ala Leu
 1               5                  10                  15

His Pro Arg Leu Glu Arg Lys Ile Lys Glu Phe Leu Pro Thr Tyr Arg
             20                  25                  30

Leu Gly Val Asp Leu Gly Glu Ala Ala Gly Gly Leu Ala Leu Ile His
             35                  40                  45

Asn Asn Asn Ile Leu His Ala Glu Thr Phe Thr Asp Phe His Glu Ala
 50                  55                  60

Thr Leu Glu Thr Lys Arg Ala Leu Arg Arg Gly Arg Arg Thr Arg His
 65                  70                  75                  80

Ala Lys Lys Met Arg Leu Ala Arg Leu Arg Ser Trp Ile Leu Arg Gln
                 85                  90                  95

Cys Ile Pro Ala His Val Thr Gly Ala Glu Ile Lys Asp Ser Tyr Ser
             100                 105                 110

Arg Leu Pro Asp Pro Tyr Arg Leu Met Lys Asp Lys Tyr Gln Thr
             115                 120                 125

Leu Pro Gly Phe Tyr Glu Val Lys Gly Gln Asn Pro Glu Lys Ser Pro
             130                 135                 140

Thr Trp Ile Asp Lys Ala Lys Ala Gly Glu Val Asp Ala Glu Gly Phe
145                 150                 155                 160

Val Ile Ala Leu Thr His Ile Leu Gln Lys Arg Gly Tyr Lys Tyr Asp
                 165                 170                 175

Gly Lys Glu Phe Ser Asp Tyr Asp Ser Arg Leu Ile Asp Phe Ile
             180                 185                 190

Asp Ser Cys Ala Met Leu Ala Glu Ala Pro Glu Met Arg Lys Ala Leu
         195                 200                 205

Glu Asp Glu Ile Met Arg Arg Glu Val Gly Glu Lys Glu Lys Pro Lys
         210                 215                 220

Leu His Glu Ala Phe Asp Asn Ala Leu Asn Arg Gln Arg Glu Arg Lys
225                 230                 235                 240

Lys Ala Leu Pro Arg Gln Val Arg Glu Lys Asp Met Glu Asp Met Val
                 245                 250                 255

Asp Val Phe Gly Arg Arg Trp Gln Leu Ser Gln Glu Ile Ile Ala Asn
             260                 265                 270

Trp Lys Ser Gln Leu Thr Gly Leu Leu Asn Lys Val Val Arg Glu Ala
             275                 280                 285

Arg Tyr Asp Asn Arg Leu Lys Ser Gly Cys Ser Trp Cys Gly Lys Lys
             290                 295                 300

Thr Pro Arg Leu Ala Lys Pro Glu Ile Arg Glu Leu Ala Phe Glu Ala
305                 310                 315                 320

Ala Val Gly Asn Leu Arg Ile Arg Glu Arg Asp Gly Arg Asp Arg Pro
                 325                 330                 335

Ile Ser Asp Glu Glu Arg Asn Pro Leu Arg Gly Trp Phe Gln Arg Arg
             340                 345                 350

Arg Glu Asn His Asp Tyr Ser Arg Ala Thr Lys Asn Thr Pro Ile Glu
             355                 360                 365

Glu Arg Ala Pro Ser Glu Asp Asn Ile Arg Thr Tyr Leu Glu Gln Ile
         370                 375                 380

Gly Val Lys Lys Ala Trp Ile Arg Lys Lys Gly Lys Glu Lys Trp
385                 390                 395                 400

Lys Phe Asp Phe Ala Met Leu Pro Gln Leu Asp Asn Leu Ile Asn Lys
                 405                 410                 415

Glu Ala Arg Lys Gly Arg Ala Arg Leu Cys Val Glu His Met Arg Met
```

-continued

```
                420             425             430
Gln Ala Glu Gly Lys Thr Met Lys Asp Ala Asp Val Asp Trp Gln Ser
            435                 440                 445
Met Arg Lys Arg Asn Ala Pro Asn Pro Arg Glu Gln His Asp Ala
450                 455                 460
Arg Val Leu Lys Arg Ile Glu Arg Leu Ile Phe Asn Arg Gly Lys Lys
465                 470                 475                 480
Gly Thr Asp Ala Trp Arg His Gly Pro Ile Ala Val Ile Thr Leu Glu
                485                 490                 495
Val Pro Met Pro Val Asp Leu Glu Arg Ala Arg Glu Lys Glu Gln Val
            500                 505                 510
Glu Arg Lys Pro Leu Asn Leu Arg Gln Arg Leu His Ala Glu Thr Glu
            515                 520                 525
Gly Val Cys Ile Tyr Cys Gly Glu Asn Val His Asp Arg Thr Met His
            530                 535                 540
Leu Glu His Ile Val Pro Gln Ala Lys Gly Gly Pro Asp Val Gln Met
545                 550                 555                 560
Asn Arg Ile Ala Ser Cys Pro Lys Cys Asn Ala Asp Arg Asp Thr Gly
                565                 570                 575
Lys Lys Asp Met Leu Pro Ser Glu Trp Leu Thr Gly Asp Lys Trp Asn
                580                 585                 590
Val Phe Lys Ser Arg Val Met Ser Leu Asn Leu Pro Pro Leu Lys Lys
            595                 600                 605
Gln Leu Leu Leu Glu Pro Gly Ser Lys Tyr Pro Asn Asp Pro Thr
            610                 615                 620
Pro Leu Ala Arg Val Ser Ala Arg Trp Arg Ala Phe Ala Ala Asp Ile
625                 630                 635                 640
Met Trp Leu Phe Asp Glu Tyr Ser Val Pro Val Pro Thr Leu Asn Tyr
                645                 650                 655
Glu Lys Asp Lys Pro His Ile Gln Val Val Arg Gly Asn Leu Thr Ser
                660                 665                 670
Arg Leu Arg Arg Asp Trp Arg Trp Lys Asp His Glu Ala Thr Val Glu
            675                 680                 685
Asn Phe Pro Asp Lys Arg Arg Thr Asp Leu Tyr Asn His Ala Gln Asp
            690                 695                 700
Ala Ala Ile Leu Ala Ala Ile Pro Pro His Thr Trp Gln Glu Gln Ile
705                 710                 715                 720
Phe Ser Asp Met Ala Val Arg Pro Cys Ala Lys Lys Asp Glu Gln Gly
                725                 730                 735
Asn Ile Leu Lys Asn Glu Lys Glu Met Arg Pro Arg Pro Gly Ile Ala
            740                 745                 750
Ala Leu Ala Leu Ala Pro Glu Trp Ala Asp Tyr Glu Arg Thr Gln Lys
            755                 760                 765
Glu Leu Lys Arg Pro Met Val His Thr Leu Gly Lys Leu Lys Ala Thr
            770                 775                 780
Trp Arg Arg Gln Ile Met Asp Leu Ser Phe Tyr Gln Asn Pro Thr Asp
785                 790                 795                 800
Asn Asp Gly Pro Leu Phe Ile Arg Lys Val Asp Ala Lys Thr Gly Lys
                805                 810                 815
Arg Glu Thr Lys Glu Val Gln Lys Gly Gly Leu Val Val Gln Val Pro
            820                 825                 830
His Tyr Asp Gly Thr Ser Gly Lys Arg Lys Val Gln Ile Lys Pro Ile
            835                 840                 845
```

```
Gln Ser Asn Ala Ile Ile Leu Trp His Asp Pro Ser Gly Arg Lys Asp
    850                 855                 860

Asn Leu Asn Ile Ser Ile Glu Arg Pro Ala Ala Ile Lys Lys Phe Val
865                 870                 875                 880

Lys His Pro Val Asp Pro Ile Ala Ser Asp Ala Ile Ile Leu Gly
                885                 890                 895

Arg Ile Glu Arg Ala Ser Thr Leu Trp Leu Arg Glu Gly Lys Gly Thr
            900                 905                 910

Val Glu Leu Lys Ala Asp Lys Lys Ser Val Arg Ser Ser Val Val Met
            915                 920                 925

Pro Glu Gly Ile Tyr Arg Val Lys Glu Leu Gly Ser Asn Gly Val Ile
            930                 935                 940

Val Val Gln Glu Asn Ala Val Ser Lys Glu Leu Ala Asn Lys Leu Gly
945                 950                 955                 960

Ile Ser Asp Asp Gln Phe Ser Lys Val Pro Glu Arg Ala Leu Gly Lys
                965                 970                 975

Lys Glu Leu Ala Glu Tyr Phe Lys Gly Asn Gln Arg Ser Gly
            980                 985                 990
```

<210> SEQ ID NO 137
<211> LENGTH: 988
<212> TYPE: PRT
<213> ORGANISM: unknown
<220> FEATURE:
<223> OTHER INFORMATION: Deltaproteobacter

<400> SEQUENCE: 137

```
Met Glu Ile Ile Lys Arg Ile Asn Lys Ile Arg Lys Lys Leu Ser Ala
1               5                   10                  15

Asp Asn Ala Thr Lys Pro Val Ser Arg Ser Gly Pro Met Lys Thr Leu
            20                  25                  30

Leu Val Arg Val Met Thr Asp Asp Leu Lys Lys Arg Leu Glu Lys Arg
            35                  40                  45

Arg Lys Lys Pro Glu Val Met Pro Gln Val Ile Ser Asn Asn Ala Ala
50                  55                  60

Asn Asn Leu Arg Met Leu Leu Asp Asp Tyr Thr Lys Met Lys Glu Ala
65                  70                  75                  80

Ile Leu Gln Val Tyr Trp Gln Glu Phe Lys Asp Asp His Val Gly Leu
                85                  90                  95

Met Cys Lys Phe Ala Gln Pro Ala Ser Lys Ile Asp Gln Asn Lys
            100                 105                 110

Leu Lys Pro Glu Met Asp Glu Lys Gly Asn Leu Thr Thr Ala Gly Phe
            115                 120                 125

Ala Cys Ser Gln Cys Gly Gln Pro Leu Phe Val Tyr Lys Leu Glu Gln
130                 135                 140

Val Ser Glu Lys Gly Lys Ala Tyr Thr Asn Tyr Phe Gly Arg Cys Asn
145                 150                 155                 160

Val Ala Glu His Glu Lys Leu Ile Leu Leu Ala Gln Leu Lys Pro Glu
                165                 170                 175

Lys Asp Ser Asp Glu Ala Val Thr Tyr Ser Leu Gly Lys Phe Gly Gln
            180                 185                 190

Arg Ala Leu Asp Phe Tyr Ser Ile His Val Thr Lys Glu Ser Thr His
            195                 200                 205

Pro Val Lys Pro Leu Ala Gln Ile Ala Gly Asn Arg Tyr Ala Ser Gly
210                 215                 220
```

```
Pro Val Gly Lys Ala Leu Ser Asp Ala Cys Met Gly Thr Ile Ala Ser
225                 230                 235                 240

Phe Leu Ser Lys Tyr Gln Asp Ile Ile Ile Glu His Gln Lys Val Val
            245                 250                 255

Lys Gly Asn Gln Lys Arg Leu Glu Ser Leu Arg Glu Leu Ala Gly Lys
            260                 265                 270

Glu Asn Leu Glu Tyr Pro Ser Val Thr Leu Pro Pro Gln Pro His Thr
            275                 280                 285

Lys Glu Gly Val Asp Ala Tyr Asn Glu Val Ile Ala Arg Val Arg Met
290                 295                 300

Trp Val Asn Leu Asn Leu Trp Gln Lys Leu Lys Leu Ser Arg Asp Asp
305                 310                 315                 320

Ala Lys Pro Leu Leu Arg Leu Lys Gly Phe Pro Ser Phe Pro Val Val
            325                 330                 335

Glu Arg Arg Glu Asn Glu Val Asp Trp Trp Asn Thr Ile Asn Glu Val
            340                 345                 350

Lys Lys Leu Ile Asp Ala Lys Arg Asp Met Gly Arg Val Phe Trp Ser
            355                 360                 365

Gly Val Thr Ala Glu Lys Arg Asn Thr Ile Leu Glu Gly Tyr Asn Tyr
370                 375                 380

Leu Pro Asn Glu Asn Asp His Lys Lys Arg Glu Gly Ser Leu Glu Asn
385                 390                 395                 400

Pro Lys Lys Pro Ala Lys Arg Gln Phe Gly Asp Leu Leu Tyr Leu
            405                 410                 415

Glu Lys Lys Tyr Ala Gly Asp Trp Gly Lys Val Phe Asp Glu Ala Trp
            420                 425                 430

Glu Arg Ile Asp Lys Lys Ile Ala Gly Leu Thr Ser His Ile Glu Arg
            435                 440                 445

Glu Glu Ala Arg Asn Ala Glu Asp Ala Gln Ser Lys Ala Val Leu Thr
            450                 455                 460

Asp Trp Leu Arg Ala Lys Ala Ser Phe Val Leu Glu Arg Leu Lys Glu
465                 470                 475                 480

Val Asp Glu Lys Glu Phe Tyr Ala Cys Glu Ile Gln Leu Gln Lys Trp
            485                 490                 495

Tyr Gly Asp Leu Arg Gly Asn Pro Phe Ala Val Glu Ala Glu Asn Arg
            500                 505                 510

Val Val Asp Ile Ser Gly Phe Ser Ile Gly Ser Asp Gly His Ser Ile
            515                 520                 525

Gln Tyr Arg Asn Leu Leu Ala Trp Lys Tyr Leu Glu Asn Gly Lys Arg
            530                 535                 540

Glu Phe Tyr Leu Leu Met Asn Tyr Gly Lys Lys Gly Arg Ile Arg Phe
545                 550                 555                 560

Thr Asp Gly Thr Asp Ile Lys Lys Ser Gly Lys Trp Gln Gly Leu Leu
            565                 570                 575

Tyr Gly Gly Gly Lys Ala Lys Val Ile Asp Leu Thr Phe Asp Pro Asp
            580                 585                 590

Asp Glu Gln Leu Ile Ile Leu Pro Leu Ala Phe Gly Thr Arg Gln Gly
            595                 600                 605

Arg Glu Phe Ile Trp Asn Asp Leu Leu Ser Leu Glu Thr Gly Leu Ile
            610                 615                 620

Lys Leu Ala Asn Gly Arg Val Ile Glu Lys Thr Ile Tyr Asn Lys Lys
625                 630                 635                 640
```

Ile Gly Arg Asp Glu Pro Ala Leu Phe Val Ala Leu Thr Phe Glu Arg
                645                 650                 655

Arg Glu Val Val Asp Pro Ser Asn Ile Lys Pro Val Asn Leu Ile Gly
            660                 665                 670

Val Asp Arg Gly Glu Asn Ile Pro Ala Val Ile Ala Leu Thr Asp Pro
        675                 680                 685

Glu Gly Cys Pro Leu Pro Glu Phe Lys Asp Ser Ser Gly Ser Pro Thr
    690                 695                 700

Asp Ile Leu Arg Ile Gly Gly Tyr Lys Glu Lys Gln Arg Ala Ile
705                 710                 715                 720

Gln Ala Ala Lys Glu Val Glu Gln Arg Arg Ala Gly Gly Tyr Ser Arg
                725                 730                 735

Lys Phe Ala Ser Lys Ser Arg Asn Leu Ala Asp Asp Met Val Arg Asn
            740                 745                 750

Ser Ala Arg Asp Leu Phe Tyr His Ala Val Thr His Asp Ala Val Leu
        755                 760                 765

Val Phe Glu Asn Leu Ser Arg Gly Phe Gly Arg Gln Gly Lys Arg Thr
    770                 775                 780

Phe Met Thr Glu Arg Gln Tyr Thr Lys Met Glu Asp Trp Leu Thr Ala
785                 790                 795                 800

Lys Leu Ala Tyr Glu Gly Leu Thr Ser Lys Thr Tyr Leu Ser Lys Thr
                805                 810                 815

Leu Ala Gln Tyr Thr Ser Lys Thr Cys Ser Asn Cys Gly Phe Thr Ile
            820                 825                 830

Thr Thr Ala Asp Tyr Asp Gly Met Leu Val Arg Leu Lys Lys Thr Ser
        835                 840                 845

Asp Gly Trp Ala Thr Thr Leu Asn Asn Lys Glu Leu Lys Ala Glu Gly
    850                 855                 860

Gln Ile Thr Tyr Tyr Asn Arg Tyr Lys Arg Gln Thr Val Glu Lys Glu
865                 870                 875                 880

Leu Ser Ala Glu Leu Asp Arg Leu Ser Glu Ser Gly Asn Asn Asp
                885                 890                 895

Ile Ser Lys Trp Thr Lys Gly Arg Arg Asp Glu Ala Leu Phe Leu Leu
            900                 905                 910

Lys Lys Arg Phe Ser His Arg Pro Val Gln Glu Gln Phe Val Cys Leu
        915                 920                 925

Asp Cys Gly His Glu Val His Ala Asp Glu Gln Ala Ala Leu Asn Ile
    930                 935                 940

Ala Arg Ser Trp Leu Phe Leu Asn Ser Asn Ser Thr Glu Phe Lys Ser
945                 950                 955                 960

Tyr Lys Ser Gly Lys Gln Pro Phe Val Gly Ala Trp Gln Ala Phe Tyr
                965                 970                 975

Lys Arg Arg Leu Lys Glu Val Trp Lys Pro Asn Ala
            980                 985

<210> SEQ ID NO 138
<211> LENGTH: 50
<212> TYPE: DNA
<213> ORGANISM: Artificial Sequence
<220> FEATURE:
<223> OTHER INFORMATION: Synthetic sequence
<220> FEATURE:
<221> NAME/KEY: misc_feature
<222> LOCATION: (11)..(30)
<223> OTHER INFORMATION: n is a, c, g, or t

<400> SEQUENCE: 138
cgggatttca nnnnnnnnnn nnnnnnnnnn gttcgattat tcggcgtaaa        50

<210> SEQ ID NO 139
<211> LENGTH: 50
<212> TYPE: DNA
<213> ORGANISM: Artificial Sequence
<220> FEATURE:
<223> OTHER INFORMATION: Synthetic sequence
<220> FEATURE:
<221> NAME/KEY: misc_feature
<222> LOCATION: (11)..(30)
<223> OTHER INFORMATION: n is a, c, g, or t

<400> SEQUENCE: 139
gccctaaagt nnnnnnnnnn nnnnnnnnnn caagctaata agccgcattt        50

<210> SEQ ID NO 140
<211> LENGTH: 112
<212> TYPE: DNA
<213> ORGANISM: Artificial Sequence
<220> FEATURE:
<223> OTHER INFORMATION: Synthetic sequence
<220> FEATURE:
<221> NAME/KEY: misc_feature
<222> LOCATION: (93)..(112)
<223> OTHER INFORMATION: n is a, c, g, t or u

<400> SEQUENCE: 140
uuauuccauu acuuggagc cagucccagc gacuaugucg uauggacgaa gcgcuuauuu        60
aucgggaaac cgauaaguaa aacgcaucaa agnnnnnnnn nnnnnnnnnn nn        112

<210> SEQ ID NO 141
<211> LENGTH: 50
<212> TYPE: DNA
<213> ORGANISM: Artificial Sequence
<220> FEATURE:
<223> OTHER INFORMATION: Synthetic sequence

<400> SEQUENCE: 141
cgggatttca tattaaatac tcgtattgct gttcgattat tcggcgtaaa        50

<210> SEQ ID NO 142
<211> LENGTH: 50
<212> TYPE: DNA
<213> ORGANISM: Artificial Sequence
<220> FEATURE:
<223> OTHER INFORMATION: Synthetic sequence

<400> SEQUENCE: 142
gccctaaagt ataatttatg agcataacga caagctaata agccgcattt        50

<210> SEQ ID NO 143
<211> LENGTH: 57
<212> TYPE: RNA
<213> ORGANISM: Artificial Sequence
<220> FEATURE:
<223> OTHER INFORMATION: Synthetic sequence
<220> FEATURE:
<221> NAME/KEY: misc_feature
<222> LOCATION: (38)..(57)
<223> OTHER INFORMATION: n is a, c, g, or u

<400> SEQUENCE: 143
auuugaagcu aucuccgaua aguaaaacgc aucaaagnnn nnnnnnnnn nnnnnnn        57

<210> SEQ ID NO 144

```
<211> LENGTH: 70
<212> TYPE: RNA
<213> ORGANISM: Artificial Sequence
<220> FEATURE:
<223> OTHER INFORMATION: Synthetic sequence

<400> SEQUENCE: 144
uuauuccauu acuuggagc cagucccagc gacuaugucg uauggacgaa gcgcuuauuu    60
aucggagaua                                                          70

<210> SEQ ID NO 145
<211> LENGTH: 56
<212> TYPE: RNA
<213> ORGANISM: Artificial Sequence
<220> FEATURE:
<223> OTHER INFORMATION: Synthetic sequence
<220> FEATURE:
<221> NAME/KEY: misc_feature
<222> LOCATION: (1)..(20)
<223> OTHER INFORMATION: n is a, c, g, or u

<400> SEQUENCE: 145
nnnnnnnnnn nnnnnnnnnn cuuacaaucg acacuuaaau aauuugcaug uguaag       56

<210> SEQ ID NO 146
<211> LENGTH: 181
<212> TYPE: RNA
<213> ORGANISM: Artificial Sequence
<220> FEATURE:
<223> OTHER INFORMATION: Synthetic sequence

<400> SEQUENCE: 146
auuuucguga ggggcuuucg uaggaaugg gguuggauag aguuuaaccc ucacuuugu     60 uaucacuuca cuucgaaugg uuuggutuug gucucuauug aaaccuauca cuucuauau   120 guuuguauau auuaaagugg gcgauccaca aauguuaguu guggaccuau accagguacg   180
g                                                                   181

<210> SEQ ID NO 147
<211> LENGTH: 204
<212> TYPE: RNA
<213> ORGANISM: Artificial Sequence
<220> FEATURE:
<223> OTHER INFORMATION: Synthetic sequence
<220> FEATURE:
<221> NAME/KEY: misc_feature
<222> LOCATION: (1)..(20)
<223> OTHER INFORMATION: n is a, c, g, or u

<400> SEQUENCE: 147
nnnnnnnnnn nnnnnnnnnn cuuacaaucg acacuuggca ggguugauu guaaacaccu    60 agcggugaa auuauauaug uuuguaauau cuucacuauc caaaguuauc ucugutuug    120 guugguaag cuucacuuca cuauuguuu cacucccaau uugaguaugg uugggguaa     180 ggaugcuuuc ggggagugcu uuua                                         204

<210> SEQ ID NO 148
<211> LENGTH: 56
<212> TYPE: RNA
<213> ORGANISM: Artificial Sequence
<220> FEATURE:
<223> OTHER INFORMATION: Synthetic sequence
<220> FEATURE:
<221> NAME/KEY: misc_feature
<222> LOCATION: (1)..(20)
<223> OTHER INFORMATION: n is a, c, g, or u
```

<400> SEQUENCE: 148
nnnnnnnnnn nnnnnnnnnn cuuucaauaa acaaauaaau cuuaguaaua uguaac          56

<210> SEQ ID NO 149
<211> LENGTH: 86
<212> TYPE: RNA
<213> ORGANISM: Artificial Sequence
<220> FEATURE:
<223> OTHER INFORMATION: Synthetic sequence

<400> SEQUENCE: 149
cuccauggac gaccucggau uguacgugcg cuugggauug cagauccgaa gaaaguuauu          60
uguuuauuau aaucguuauc ggucaa                                              86

<210> SEQ ID NO 150
<211> LENGTH: 110
<212> TYPE: RNA
<213> ORGANISM: Artificial Sequence
<220> FEATURE:
<223> OTHER INFORMATION: Synthetic sequence
<220> FEATURE:
<221> NAME/KEY: misc_feature
<222> LOCATION: (1)..(20)
<223> OTHER INFORMATION: n is a, c, g, or u

<400> SEQUENCE: 150
nnnnnnnnnn nnnnnnnnnn cuuucaauaa acaaauaaaa acuuauuugu uuauugaaag          60
aagccuagac guuagggaguc gcgugcaugu uaggcuccag cagguaccuc                  110

<210> SEQ ID NO 151
<211> LENGTH: 946
<212> TYPE: PRT
<213> ORGANISM: Artificial Sequence
<220> FEATURE:
<223> OTHER INFORMATION: Synthetic sequence

<400> SEQUENCE: 151

Met Arg Asp Ser Ile Thr Ala Pro Arg Tyr Ser Ser Ala Leu Ala Ala
1               5                   10                  15

Arg Ile Lys Glu Phe Asn Ser Ala Lys Gln Leu Pro Asp Pro Tyr Lys
            20                  25                  30

Ile Lys Lys Met Gln Leu Pro Asn Gly Val Glu Arg Arg Gln Asp Val
        35                  40                  45

Val Asp Thr Asp Lys Glu Ala Glu Arg Tyr Thr Gln Leu Ser Glu Leu
    50                  55                  60

Leu Ser Lys Val Ser Glu Ser Lys Ser Glu Ser Lys Leu Tyr Phe Asp
65                  70                  75                  80

Thr Val Arg Asn Phe Leu Lys Ala Gly Arg Val Glu Gln Asn Pro Asp
                85                  90                  95

Val Ile Ser Tyr Tyr Lys Lys Ile Tyr Met Asp Ala Phe Lys Leu Gly
            100                 105                 110

Ile Asp Leu Gly Thr Lys Thr Gly Gly Val Ala Leu Val Lys Asp Asn
        115                 120                 125

Lys Val Leu Leu Ala Lys Thr Phe Leu Asp Tyr His Lys Gln Thr Leu
    130                 135                 140

Glu Glu Arg Arg Ile His Arg Arg Asn Arg Arg Ser Arg Leu Ala Arg
145                 150                 155                 160

Arg Lys Arg Ile Ala Arg Leu Arg Ser Trp Ile Leu Arg Gln Lys Ile
                165                 170                 175

Tyr Gly Arg Lys Gly Glu Asn Trp Ile Asp Leu Val Val Ser Gly Arg
            180                 185                 190

Asp Leu Ser Pro Glu Ala Phe Val Arg Ala Ile Thr Leu Ile Phe Gln
            195                 200                 205

Lys Arg Gly Gln Arg Tyr Glu Glu Val Ala Lys Glu Ile Glu Glu Met
    210                 215                 220

Ser Tyr Lys Glu Phe Ser Thr His Ile Lys Ala Leu Thr Ser Val Thr
225                 230                 235                 240

Glu Glu Glu Phe Thr Ala Leu Ala Ala Glu Ile Asp Arg Ala Gln Arg
                245                 250                 255

Lys Glu Asp Leu Gly Lys Val Val Asn Ala Phe Cys Ser Ala His Arg
            260                 265                 270

Ile Glu Asp Lys Asp Lys Trp Cys Lys Glu Leu Met Lys Leu Leu Asp
            275                 280                 285

Arg Pro Val Arg His Ala Arg Phe Leu Asn Lys Val Leu Ile Arg Cys
            290                 295                 300

Asn Ile Cys Asp Arg Ala Thr Pro Lys Lys Ser Arg Pro Asp Val Arg
305                 310                 315                 320

Glu Leu Glu Val Ile Arg Val Lys Ile Leu Asn Lys Glu Lys Leu Thr
                325                 330                 335

Asp Glu Asp Lys Lys Gln Lys Arg Lys Leu Ala Ser Glu Leu Asn Arg
            340                 345                 350

Tyr Lys Asn Lys Glu Tyr Val Thr Asp Ala Gln Lys Lys Met Gln Glu
            355                 360                 365

Gln Leu Lys Thr Leu Leu Phe Met Lys Leu Thr Gly Arg Ser Arg Tyr
            370                 375                 380

Cys Met Ala His Leu Lys Glu Arg Ala Ala Gly Lys Asp Val Glu Glu
385                 390                 395                 400

Gly Leu His Gly Val Val Gln Lys Arg Lys Glu Ile Asn Ser Asp Lys
                405                 410                 415

Gly Asp Arg Thr Pro Trp Glu Trp Met His Asp Asn Pro Glu Lys Trp
            420                 425                 430

Lys Ala Phe Glu Arg Arg Val Ala Glu Phe Tyr Lys Arg Leu Arg Arg
            435                 440                 445

Gln Trp Asn Ala Leu Asn Gln Asn Phe Ile Pro Leu Lys Asp Arg Ala
            450                 455                 460

Met Ser Phe Asn His Ala Glu Asp Ala Ala Ile Ala Ala Asn Ile Ala
465                 470                 475                 480

Gln Arg Asn His Asp Leu Arg Val Ile Asn Leu Ile Glu Ser Leu Leu
                485                 490                 495

Phe Asp Gln Asn Lys Ser Leu Ser Asp Ala Ile Arg Lys Asn Gly Leu
            500                 505                 510

Met Tyr Val Thr Ile Glu Ala Pro Glu Pro Lys Thr Lys His Ala Lys
            515                 520                 525

Lys Gly Ala Ala Val Val Arg Asp Pro Arg Lys Leu Lys Glu Lys Leu
            530                 535                 540

Phe Asp Asp Gln Asn Gly Val Cys Ile Tyr Thr Gly Leu Gln Leu Asp
545                 550                 555                 560

Lys Leu Glu Ile Ser Lys Tyr Glu Lys Asp His Ile Phe Pro Asp Ser
                565                 570                 575

Arg Asp Gly Pro Ser Ile Arg Asp Asn Leu Val Leu Thr Thr Lys Gly
            580                 585                 590

Arg Ile Asn Glu Arg Lys Arg Glu Leu Leu Leu Asn Lys Gly Thr Glu
    595                 600                 605

Tyr Pro Gly Asp Asn Pro Thr Glu Leu Ala Arg Gly Gly Ala Arg Val
610                 615                 620

Asn Asn Phe Ile Thr Glu Phe Asn Asp Arg Leu Lys Thr His Gly Val
625                 630                 635                 640

Gln Glu Leu Gln Thr Ile Phe Glu Arg Asn Lys Pro Ile Val Gln Val
            645                 650                 655

Val Arg Gly Glu Glu Thr Gln Ser Met Pro Pro Lys Phe Trp Arg Glu
        660                 665                 670

Gln Ile Tyr Arg Thr Ala Trp His Phe Gly Pro Ser Gly Asn Glu Arg
    675                 680                 685

Pro Asp Phe Ala Leu Ala Glu Leu Ala Pro Gln Trp Asn Asp Phe Phe
690                 695                 700

Met Thr Lys Gly Gly Pro Ile Ile Ala Val Leu Gly Lys Thr Lys Tyr
705                 710                 715                 720

Ser Trp Lys His Ser Ile Ile Asp Asp Thr Ile Tyr Lys Pro Phe Ser
            725                 730                 735

Lys Ser Ala Tyr Tyr Gly Gly Ser Ile Ile Thr Val Lys Pro His Asp
        740                 745                 750

Gly Pro Glu Lys Val Leu Gln Ile Ser Pro Lys Tyr Lys Glu Leu His
    755                 760                 765

Thr His Asp Ile Ile Tyr Leu Pro Ala Thr Lys Lys His Val Asp Gly
770                 775                 780

Tyr Phe Ile Ile Thr Lys Leu Val Gly Ile Tyr Lys Lys Pro Asn Ala
785                 790                 795                 800

Ile Thr Ser Asn Ala Ile Lys Val Leu Arg Pro Lys Leu Leu Asn Gly
            805                 810                 815

Glu His Thr Met Ser Lys Asn Ala Lys Tyr Tyr His Gln Lys Ile Gly
        820                 825                 830

Asn Glu Arg Phe Leu Met Lys Ser Gln Lys Tyr Glu Cys Ala Val Leu
    835                 840                 845

Thr Lys His Asp Gly Lys Ile Ile Val Lys Phe Lys Pro Ile Lys Pro
850                 855                 860

Leu Arg Asp Met Tyr Ala Arg Gly Val Ile Lys Ala Met Asp Lys Glu
865                 870                 875                 880

Leu Glu Thr Ser Leu Ser Ser Met Ser Lys His Ala Ser Ala Lys His
            885                 890                 895

Gly Ile Leu Lys Ala Leu Pro Glu Ser Met Val Lys Val Lys Tyr Thr
        900                 905                 910

Gln Ile Gly Ser Glu Asn Asn Ser Glu Val Lys Leu Thr Lys Pro Lys
    915                 920                 925

Pro Glu Ile Thr Leu Asp Ser Glu Asp Ile Thr Asn Ile Tyr Asn Phe
930                 935                 940

Thr Arg
945

<210> SEQ ID NO 152
<211> LENGTH: 943
<212> TYPE: PRT
<213> ORGANISM: Artificial Sequence
<220> FEATURE:
<223> OTHER INFORMATION: Synthetic sequence

<400> SEQUENCE: 152

-continued

```
Met Gly Tyr Tyr Lys Glu Tyr Asn Lys Glu Leu Ser Ser Lys Ala Gln
1               5                   10                  15

Lys Glu Phe Asn Asp Gln Ile Ser Glu Phe Asn Ser Tyr Gln Arg Leu
            20                  25                  30

Pro Asp Pro Tyr Lys Ile Met His Asp Asn Lys Tyr Trp Ser Ile Tyr
        35                  40                  45

Asn Lys Ser Asn Ser Ser Arg Val Glu Asn Gly Glu Ile Glu Glu
    50              55                  60

Lys Lys Phe Glu Gly Leu Lys Asn Lys Leu Lys Ile Asp Lys Glu
65                  70                  75                  80

Ser Lys Asp Phe Gln Val Lys Glu Leu Lys Met Val Leu Asn Asn Ala
                85                  90                  95

Arg Ser Asp Tyr Gln Ile Ser Asp Glu Asp Leu Tyr Lys Leu Gly Ile
            100                 105                 110

Asp Leu Gly Asp Lys Thr Gly Ile Ala Ile Val Lys Gly Asn Lys Ile
        115                 120                 125

Ile Leu Ala Lys Thr Leu Ile Asp Leu His Ser Gln Lys Leu Asp Lys
    130                 135                 140

Arg Arg Glu Ala Arg Arg Asn Arg Arg Thr Arg Leu Ser Arg Lys Lys
145                 150                 155                 160

Arg Leu Ala Arg Leu Arg Ser Trp Val Met Arg Gln Lys Val Gly Asn
            165                 170                 175

Ala Asn Lys Lys Asn Trp Ile Asp Leu Leu Ile His Ser Asn Ser Leu
        180                 185                 190

Ser Ala Asp Asp Phe Val Arg Gly Leu Thr Ile Ile Phe Arg Lys Arg
    195                 200                 205

Gly Tyr Leu Ala Phe Lys Tyr Leu Ser Arg Leu Ser Asp Lys Glu Phe
210                 215                 220

Glu Lys Tyr Ile Asp Asn Leu Lys Pro Pro Ile Ser Lys Tyr Glu Tyr
225                 230                 235                 240

Asp Glu Asp Leu Glu Glu Leu Gln Arg Glu Val Lys Lys Glu Leu
            245                 250                 255

Glu Asp Leu Val Asp Leu Phe Ala Lys Ser Val Asp Asn Lys Ile Asp
        260                 265                 270

Lys Ala Arg Trp Lys Arg Glu Leu Asn Asn Leu Leu Asp Lys Lys Val
    275                 280                 285

Arg Lys Ile Arg Phe Asp Asn Arg Phe Ile Leu Lys Cys Lys Ile Lys
    290                 295                 300

Gly Cys Asn Lys Asn Thr Pro Lys Lys Glu Lys Val Arg Asp Phe Asn
305                 310                 315                 320

Ser Phe Arg Asn Glu Val Ile Asn Ile Phe Gln Lys Lys Glu Asn Leu
            325                 330                 335

Lys Lys Gly Glu Leu Lys Gly Val Thr Ile Glu Asp Leu Arg Lys Gln
        340                 345                 350

Leu Asn Lys Thr Phe Asn Lys Ala Lys Ile Lys Lys Gly Ile Arg Glu
    355                 360                 365

Gln Ile Arg Ser Ile Val Phe Glu Lys Ile Ser Gly Arg Ser Lys Phe
370                 375                 380

Cys Lys Glu His Leu Lys Glu Phe Ser Glu Lys Pro Ala Pro Ser Asp
385                 390                 395                 400

Arg Ile Asn Ser Glu Thr Asn Lys Glu Lys Ala Asp Arg Thr Pro Trp
            405                 410                 415

Glu Trp Phe Gly Gln Asp Glu Lys Arg Trp Ser Glu Phe Glu Lys Arg
```

-continued

```
                420             425             430
Val Asn Ser Leu Tyr Ser Ala Leu Arg Trp Arg Trp His Ala Leu Asp
            435                 440                 445
Ser Asn Ile Ile Pro Glu Lys Asp Arg Lys Ser Ser Phe Asn His Ala
            450                 455                 460
Glu Asp Ala Val Ile Ala Ala Tyr Gly Val Asn Ser Ala Arg Glu Gln
465                 470                 475                 480
His Asp Phe Arg Val Leu Asn Phe Ile Asp Lys Lys Ile Phe Lys Asp
                485                 490                 495
Lys Leu Ile Asp Pro Ser Lys Leu Arg Tyr Ile Thr Ile Glu Ser Pro
                500                 505                 510
Glu Pro Glu Thr Glu Lys Leu Glu Lys Gly Gln Ile Ser Glu Lys Ser
                515                 520                 525
Phe Glu Thr Leu Lys Glu Lys Leu Ala Lys Glu Thr Gly Gly Ile Asp
                530                 535                 540
Ile Tyr Thr Gly Glu Lys Leu Lys Lys Asp Phe Glu Ile Glu His Ile
545                 550                 555                 560
Phe Pro Arg Ala Arg Val Gly Pro Ser Ile Arg Glu Asn Glu Val Ala
                565                 570                 575
Ser Asn Lys Lys Lys Ile Ser Glu Arg Lys Arg Glu Ile Leu Leu Asn
                580                 585                 590
Lys Ser Asn Glu Tyr Pro Gly Leu Asn Pro Thr Glu Leu Ser Arg Ile
                595                 600                 605
Pro Ser Thr Leu Ser Asp Phe Val Glu Ser Ile Arg Lys Met Phe Val
                610                 615                 620
Lys Tyr Gly Tyr Glu Glu Pro Gln Thr Leu Val Gln Lys Gly Lys Pro
625                 630                 635                 640
Ile Ile Gln Val Val Arg Gly Arg Asp Thr Gln Cys Met Pro Pro Tyr
                645                 650                 655
Tyr Leu Arg Gln Lys Ile Phe Arg Glu Glu Ala Lys Ile Lys Arg Lys
                660                 665                 670
Val Ser Asn Lys Glu Lys Glu Val Thr Arg Pro Asp Met Pro Thr Lys
                675                 680                 685
Lys Ile Ala Pro Asn Trp Ser Glu Phe Met Lys Thr Arg Asn Glu Pro
                690                 695                 700
Val Ile Glu Val Ile Gly Lys Val Lys Pro Ser Trp Lys Asn Ser Ile
705                 710                 715                 720
Met Asp Gln Thr Phe Tyr Lys Tyr Leu Leu Lys Pro Phe Lys Asp Asn
                725                 730                 735
Leu Ile Lys Ile Pro Asn Val Lys Asn Thr Tyr Lys Trp Gly Gly Leu
                740                 745                 750
Leu Val Tyr Ile Thr Pro Lys Asp Gly Pro Lys Arg Ile Val Gln Val
                755                 760                 765
Lys Pro Lys Phe Glu Arg Ile Arg Arg Tyr Asp Met Ile Thr Tyr Ser
                770                 775                 780
Lys Phe Tyr Tyr Val Thr Lys Ile Ile Gly Val Asn Gly Gln Thr Asp
785                 790                 795                 800
Ser Leu Ser Leu Pro Ser Lys Val Leu Ser Ile Ser Asn Lys Lys Val
                805                 810                 815
Asp Ser Ser Thr Val Leu Leu Val His Asp Lys Lys Gly Gly Lys Arg
                820                 825                 830
Asn Trp Val Pro Lys Ser Ile Ala Thr Gln Gly Leu Leu Ile Tyr Arg
                835                 840                 845
```

```
Asn Glu Asp Gly Arg Val Asp Ala Val Arg Glu Phe Ile Asn Pro Val
            850                 855                 860

Ile Glu Met Tyr Asn Asn Gly Lys Leu Ala Phe Val Glu Lys Glu Asn
865                 870                 875                 880

Glu Glu Glu Leu Leu Lys Tyr Phe Asn Leu Leu Glu Lys Gly Gln Asn
                885                 890                 895

Lys Asn His Arg Val Thr Ile Gln Glu Ser Lys Ile Lys Ala Glu
            900                 905                 910

Ser Asp Lys Val Lys Ser Ser Gly Lys Glu Tyr Thr Arg Lys Glu
            915                 920                 925

Thr Glu Glu Leu Ser Leu Gln Lys Leu Ala Glu Leu Ile Ser Ile
930                 935                 940
```

<210> SEQ ID NO 153
<211> LENGTH: 1029
<212> TYPE: PRT
<213> ORGANISM: Unknown
<220> FEATURE:
<223> OTHER INFORMATION: sequence from metagenomic data -
      from unidentified Deltaproteobacteria

<400> SEQUENCE: 153

```
Val Ala Ala Ala Ser Leu Ile Leu Gln Arg Gly Gly Leu Val Ala Leu
1               5                   10                  15

His Pro Arg Leu Glu Arg Lys Ile Lys Glu Phe Leu Pro Thr Glu Ile
                20                  25                  30

Lys Asp Ser Tyr Ser Arg Leu Pro Asp Pro Tyr Arg Leu Met Lys Asp
            35                  40                  45

Lys Lys Tyr Gln Thr Leu Pro Gly Phe Tyr Glu Val Lys Gly Gln Asn
50                  55                  60

Pro Met Arg Arg Glu Val Gly Glu Lys Glu Pro Lys Leu His Glu
65                  70                  75                  80

Ala Phe Asp Asn Ala Leu Asn Arg Gln Arg Lys Lys Ala Leu
                85                  90                  95

Ala Phe Glu Ala Ala Val Gly Asn Leu Arg Ile Arg Glu Arg Asp Gly
                100                 105                 110

Arg Asp Arg Pro Ile Ser Asp Glu Glu Arg Asn Pro Leu Arg Gly Trp
            115                 120                 125

Phe Gln Arg Arg Glu Asn Tyr Arg Leu Gly Val Asp Leu Gly Glu
            130                 135                 140

Ala Ala Gly Gly Leu Ala Leu Ile His Asn Asn Asn Ile Leu His Ala
145                 150                 155                 160

Glu Thr Phe Thr Asp Phe His Glu Ala Thr Leu Glu Thr Lys Arg Ala
                165                 170                 175

Leu Arg Arg Gly Arg Arg Thr Arg His Ala Lys Lys Met Arg Leu Ala
            180                 185                 190

Arg Leu Arg Ser Trp Ile Leu Arg Gln Cys Ile Pro Ala His Val Thr
            195                 200                 205

Gly Ala Glu Lys Ser Pro Thr Trp Ile Asp Lys Ala Lys Ala Gly Glu
            210                 215                 220

Val Asp Ala Glu Gly Phe Val Ile Ala Leu Thr His Ile Leu Gln Lys
225                 230                 235                 240

Arg Gly Tyr Lys Tyr Asp Gly Lys Glu Phe Ser Asp Tyr Asp Asp Ser
                245                 250                 255

Arg Leu Ile Asp Phe Ile Asp Ser Cys Ala Met Leu Ala Glu Ala Pro
```

```
                260                 265                 270
Glu Met Arg Lys Ala Leu Glu Asp Glu Ile Pro Arg Gln Val Arg Glu
            275                 280                 285
Lys Asp Met Glu Asp Met Val Asp Val Phe Gly Arg Arg Trp Gln Leu
            290                 295                 300
Ser Gln Glu Ile Ile Ala Asn Trp Lys Ser Gln Leu Thr Gly Leu Leu
305                 310                 315                 320
Asn Lys Val Val Arg Glu Ala Arg Tyr Asp Asn Arg Leu Lys Ser Gly
                325                 330                 335
Cys Ser Trp Cys Gly Lys Lys Thr Pro Arg Leu Ala Lys Pro Glu Ile
            340                 345                 350
Arg Glu Leu His Asp Tyr Ser Arg Ala Thr Lys Asn Thr Pro Ile Glu
            355                 360                 365
Glu Arg Ala Pro Ser Glu Asp Asn Ile Arg Thr Tyr Leu Glu Gln Ile
            370                 375                 380
Gly Val Lys Lys Ala Trp Ile Arg Lys Lys Gly Lys Glu Lys Trp
385                 390                 395                 400
Lys Phe Asp Phe Ala Met Leu Pro Gln Leu Asp Asn Leu Ile Asn Lys
                405                 410                 415
Glu Ala Arg Lys Gly Arg Ala Arg Leu Cys Val Glu His Met Arg Met
            420                 425                 430
Gln Ala Glu Gly Lys Thr Met Lys Asp Ala Asp Val Asp Trp Gln Ser
            435                 440                 445
Met Arg Lys Arg Ala Arg Pro Met Lys Leu Glu Ala Ser Asn Asp Ser
450                 455                 460
Thr Pro Phe Phe Cys Pro Ser Cys Ala Ala Gly Ile Lys Ile Thr Leu
465                 470                 475                 480
Tyr Lys Lys Met Arg Ile Lys Glu Lys Glu Ile Pro Lys Cys Asn Ala
                485                 490                 495
Asp Arg Asp Thr Gly Lys Lys Asp Met Leu Pro Ser Glu Trp Leu Thr
            500                 505                 510
Gly Asp Lys Trp Asn Val Phe Lys Ser Arg Val Met Ser Leu Arg Leu
            515                 520                 525
Arg Arg Asp Trp Arg Trp Lys Asp His Glu Ala Thr Val Glu Asn Phe
            530                 535                 540
Pro Asp Lys Arg Arg Thr Asp Leu Tyr Asn His Ala Gln Asp Ala Ala
545                 550                 555                 560
Ile Leu Ala Asn Ala Pro Asn Pro Arg Arg Glu Gln His Asp Ala Arg
                565                 570                 575
Val Leu Lys Arg Ile Glu Arg Leu Ile Phe Asn Arg Gly Lys Lys Gly
            580                 585                 590
Thr Asp Ala Trp Arg His Gly Pro Ile Ala Val Ile Thr Leu Glu Val
            595                 600                 605
Pro Val Pro Val Asp Leu Glu Arg Ala Arg Glu Lys Glu Gln Val Glu
            610                 615                 620
Arg Lys Pro Leu Asn Leu Arg Gln Arg Leu His Ala Glu Thr Glu Gly
625                 630                 635                 640
Val Cys Ile Tyr Cys Gly Glu Asn Val His Asp Arg Thr Met His Leu
                645                 650                 655
Glu His Ile Val Pro Gln Ala Lys Gly Gly Pro Asp Val Gln Val Asn
            660                 665                 670
Arg Ile Ala Ser Cys Asn Leu Pro Pro Leu Lys Lys Gln Leu Leu Leu
            675                 680                 685
```

```
Leu Glu Pro Gly Ser Lys Tyr Pro Asn Asp Pro Thr Pro Leu Ala Arg
            690                 695                 700

Val Ser Ala Arg Trp Arg Ala Phe Ala Ala Asp Ile Met Trp Leu Phe
705                 710                 715                 720

Asp Glu Tyr Ser Val Pro Val Pro Thr Leu Asn Tyr Glu Lys Asp Lys
                    725                 730                 735

Pro His Ile Gln Val Val Arg Gly Asn Leu Thr Ser Ala Ile Pro Pro
            740                 745                 750

His Thr Trp Gln Glu Gln Ile Phe Ser Asp Met Ala Val Arg Pro Cys
        755                 760                 765

Ala Lys Lys Asp Glu Gln Gly Asn Ile Leu Lys Asn Glu Lys Glu Met
770                 775                 780

Arg Pro Arg Pro Gly Ile Ala Ala Leu Ala Leu Ala Pro Glu Trp Ala
785                 790                 795                 800

Asp Tyr Glu Arg Thr Gln Lys Glu Leu Lys Arg Pro Met Val His Thr
                805                 810                 815

Leu Gly Lys Leu Lys Ala Thr Trp Arg Arg Gln Ile Met Asp Leu Ser
            820                 825                 830

Phe Tyr Gln Asn Pro Thr Asp Asn Gly Gly Leu Val Val Gln Val Pro
        835                 840                 845

His Tyr Asp Gly Thr Ser Gly Lys Arg Lys Val Gln Ile Lys Pro Asp
850                 855                 860

Lys Lys Ser Val Arg Ser Ser Val Val Met Pro Gly Ile Tyr Arg
865                 870                 875                 880

Val Lys Glu Leu Asp Gly Pro Leu Phe Ile Arg Lys Val Asp Ala Lys
                885                 890                 895

Thr Gly Lys Arg Glu Thr Lys Glu Val Gln Lys Ile Gln Ser Asn Ala
            900                 905                 910

Ile Ile Leu Trp His Asp Pro Ser Gly Arg Lys Asp Asn Leu Asn Ile
        915                 920                 925

Ser Ile Glu Arg Pro Ala Ala Ile Lys Lys Phe Val Lys His Pro Val
930                 935                 940

Asp Pro Pro Ile Ala Ser Asp Ala Ile Ile Leu Gly Arg Ile Glu Arg
945                 950                 955                 960

Ala Ser Thr Leu Trp Leu Arg Glu Gly Lys Gly Thr Val Glu Leu Lys
                965                 970                 975

Ala Gly Ser Asn Gly Val Ile Val Gln Glu Asn Ala Val Ser Lys
            980                 985                 990

Glu Leu Ala Asn Lys Leu Gly Ile Ser Asp Asp Gln Phe Ser Lys Val
        995                 1000                1005

Pro Glu Arg Ala Leu Gly Lys Lys Glu Leu Ala Glu Tyr Phe Lys
    1010                1015                1020

Gly Asn Gln Arg Ser Gly
1025

<210> SEQ ID NO 154
<211> LENGTH: 1067
<212> TYPE: PRT
<213> ORGANISM: Unknown
<220> FEATURE:
<223> OTHER INFORMATION: sequence from metagenomic data - from
      unidentified Lindow bacteria

<400> SEQUENCE: 154

Cys Ser Ala Thr Arg Lys Gly Gln Gly Ser Gly Ala Pro Ile Ser Arg
```

-continued

```
1               5                   10                  15
Thr Glu Ala Pro Gln Ile Ala Leu Met Ala Thr Glu Leu Glu Gln Arg
                20                  25                  30
Leu Asn Glu Phe Leu Asp Ser Gln Arg Leu Pro Asp Pro Tyr Gly Val
                35                  40                  45
Met His Trp Pro Phe Lys Thr Lys Lys Gly His Thr Ile Lys Thr Gly
                50                  55                  60
Leu Ala Ser Arg Gln Glu Arg Arg Lys Glu Pro Glu Asp Asn Lys
65                  70                  75                  80
Glu Gly Glu Ile Glu Asn Leu Glu Thr Val Leu Cys Asp Ala Val Lys
                85                  90                  95
Arg Ala Arg Ser Pro Arg Thr Pro Glu Ala Tyr Lys Val Val Lys
                100                 105                 110
Asn Ile Arg Val Glu Asp Phe Thr Ser Arg Gln Pro Leu Thr Ala Gln
                115                 120                 125
Glu Ala Glu Tyr Phe Ser Gln Leu Trp Val Asp Lys Leu Arg Leu Gly
                130                 135                 140
Ile Asp Phe Gly Glu Asp Tyr Gly Gly Ile Ala Leu Val Gln Ala Asn
145                 150                 155                 160
Arg Val Leu His Ala Glu Thr Phe Val Asp Phe His Gln Ala Thr Leu
                165                 170                 175
Lys Asp Arg Arg Arg Asn Arg Gly Arg Arg Thr Arg His Ala Arg
                180                 185                 190
Lys Met Arg Leu Ala Arg Leu Arg Ser Trp Ile Leu Arg Gln Lys Leu
                195                 200                 205
Pro Gly Gly Asp Gly Lys Arg Thr Ile Ile Gln Lys Cys Lys Ile Gly
                210                 215                 220
Thr Ala Thr Pro Glu Glu Phe Val Cys Ser Leu Thr Leu Leu Phe Gln
225                 230                 235                 240
Lys Arg Gly Phe Val Trp Glu Gly Ser Asp Leu Cys Glu Leu Ser Asp
                245                 250                 255
Gln Glu Leu Ala Glu Glu Leu Met Thr Val Arg Ile Thr Glu Ala Val
                260                 265                 270
Ala Ala Ala Ile Lys Glu Glu Ile His Arg Ser Ile Val Glu Ser Asp
                275                 280                 285
Leu Lys Asp Ile Val Asp Gly Trp Thr Arg Lys Asn Cys Pro Gln Met
                290                 295                 300
Thr Asp Met Trp Lys Lys Glu Leu Ser Cys Leu Leu Asn Lys His Val
305                 310                 315                 320
Arg Pro Ala Arg Phe Glu Asn Arg Ile Val Ala Gly Cys Ser Trp Cys
                325                 330                 335
Gly Lys Met Val Pro Arg Lys Ser Lys Val Arg Glu Leu Glu Ala Lys
                340                 345                 350
Pro Pro Ala Arg Thr Ala Ile Glu Asn Lys Leu Lys Lys Leu Lys Ala
                355                 360                 365
Ser Pro Lys Met Ala Asn Gln Leu Tyr Glu Leu Leu Ala Pro Ser Glu
                370                 375                 380
Pro Lys Gly His Thr Asn Leu Cys Gln Gln His Leu Glu Met Ala Ala
385                 390                 395                 400
Arg Gly Ala Phe Met Cys Asn Arg His His Ala Ile Cys Glu Asn Asn
                405                 410                 415
Asn Gly Asp His Gln Thr Ile Asp Ser Val Lys Glu Gly Arg Lys Arg
                420                 425                 430
```

```
Ala Arg Pro Met Lys Leu Glu Ala Ser Asn Asp Ser Thr Pro Phe Phe
        435                 440                 445

Cys Pro Ser Cys Ala Ala Gly Ile Lys Ile Thr Leu Tyr Lys Lys Met
        450                 455                 460

Arg Ile Lys Glu Lys Glu Ile Arg Thr Cys Asn Gly Asn Leu Lys Lys
465                 470                 475                 480

Asn Lys Ser Pro Trp Glu Trp Phe Gly Asn Ile Asp Gln Arg Trp Arg
                485                 490                 495

Glu Phe Glu Asp Arg Val Lys Lys Leu Arg Leu Arg Gly Cys Trp Arg
                500                 505                 510

Thr Phe Pro Asp Gly Thr Ala Asn Phe Pro Pro Lys Asn Asp Ala Asp
            515                 520                 525

Lys Arg Asn His Ala Gln Asp Ala Val Leu Ile Ala Ala Gly Pro Arg
        530                 535                 540

Asn Pro Cys Arg Glu Asp Arg Asp Arg Arg Met Ile Arg Arg Leu Glu
545                 550                 555                 560

Gln Ile Leu Phe Glu Thr Pro Gly Lys Pro Gly Lys Pro Ser His Ser
                565                 570                 575

Ile Pro Arg Leu Ile Thr Ile Glu Phe Pro Lys Pro Asn Thr Ala Gln
            580                 585                 590

Thr Ala Gly Cys Pro His Cys Lys Glu Lys Leu Ser Leu Asp Ala Arg
        595                 600                 605

Val Arg Trp Lys Met Val Gln Lys Tyr Ser Pro Lys Asp Thr Asp Val
        610                 615                 620

Leu Val Arg Lys Thr Ala Ala Gly Gly Leu Lys Lys Leu Lys Tyr Asp
625                 630                 635                 640

Met Tyr Leu Lys Glu Thr Asp Gly Thr Cys Val Tyr Cys Gly Thr Ser
                645                 650                 655

Ile Gly Ser Gly Gln Ile Asp His Ile Phe Pro Gln Ser Arg Gly Gly
                660                 665                 670

Pro Asn Ile Asp Tyr Asn Leu Ile Ser Cys Cys Pro Ala Pro Gln Arg
            675                 680                 685

Lys Lys Ala Ile Leu Leu Ser Arg Glu Ser Ala Tyr Pro Glu Asn Pro
        690                 695                 700

Thr Ala Leu Ala Arg Val Gly Ala Arg Thr Lys Glu Phe Ile Gly Arg
705                 710                 715                 720

Ile Lys Gln Met Leu Leu Ala Asn Gly Val Lys Glu Asn Glu Ile Ala
                725                 730                 735

Asp Asn Tyr Glu Lys Asp Lys Ile Val Ile Gln Thr Ile Asp Gly Trp
            740                 745                 750

Met Thr Ser Ala Cys Pro Pro His Thr Trp Arg Glu Arg Ile Phe Thr
        755                 760                 765

Trp Lys Pro Glu Asn Pro Tyr Phe Ser Val Leu Gln Lys Ile Ala Pro
770                 775                 780

Arg Trp Lys Asp His Gln Ala Thr Met Lys Ile Leu Gly Arg Tyr Phe
785                 790                 795                 800

Pro Arg Trp His Asn Gln Asn Ser Asp Ile Gln Phe Val His Gln His
                805                 810                 815

Lys Thr Gln Asn Gly Thr Ser Tyr Thr Met Arg Ala Trp Glu Ala Ser
            820                 825                 830

Phe Pro Arg Arg Leu Gln Phe Asp Met Gly Tyr Gly Glu Asp Val Ala
        835                 840                 845
```

```
                        -continued
Glu Val Asn Pro Lys Asn Gly Pro Ser Arg Phe Val Arg Ala Gln Pro
        850                 855                 860

Leu Glu Arg Ile Phe Arg Arg Asn Asp Met Ile Gln Leu Asp Ala Val
865                 870                 875                 880

Gln Lys Arg Gly Arg Lys Gly Ile Thr Gly Lys Ser Tyr Glu Ala Gly
                    885                 890                 895

Glu Tyr Val Val Val Lys Ile Asp Thr Val Glu Ser Ile Asp Val Gly
                900                 905                 910

Thr Asp Lys Lys Gly Gly Ser Ile Glu Arg Ile Tyr Ser Lys Ser Phe
            915                 920                 925

Arg Asp Phe Phe Ser Arg Thr Phe Lys Ser Leu Gly Ile Lys Met Ala
        930                 935                 940

Met Asn Glu Ile Pro Lys Leu Lys Ser Gln Trp Leu Asn Glu Arg Arg
945                 950                 955                 960

Ala Ala Trp Met Lys Lys Asn Pro Ala Thr Pro Val Pro Asn Gln Arg
                965                 970                 975

Glu Arg Val Asn Asp Arg Ile Glu Val Trp Thr Asn Asp Val Arg Gln
                980                 985                 990

Ala Gln Ile Arg Thr Val Lys Asn  Arg Ile Leu Phe Arg  His Ile Gln
            995                 1000                1005

Asp Asn  Ser Pro Gln Gly Arg  Thr Glu Lys Gly Gly  Lys Phe Thr
    1010                1015                1020

Ala Val  Pro Ala His Arg Gly  Lys Gly Arg Glu Asn  Gln Arg Gln
    1025                1030                1035

Val Ser  Gln Arg Glu Ile Ala  Lys Leu Cys Gly Val  Ser Leu Ser
    1040                1045                1050

Pro Lys  Arg Arg Lys Pro Ser  Arg Ser Thr Ser Glu  Ser Gly
    1055                1060                1065
```